(12) United States Patent
Sheppard et al.

(10) Patent No.: US 12,344,600 B2
(45) Date of Patent: Jul. 1, 2025

(54) c-MYC mRNA TRANSLATION MODULATORS AND USES THEREOF IN THE TREATMENT OF CANCER

(71) Applicant: Anima Biotech Inc., Bernardsville, NJ (US)

(72) Inventors: David William Sheppard, Ramat Gan (IL); Jason Paul Tierney, Ramat Gan (IL); Aviad Mandabi, Ramat Gan (IL); Iris Alroy, Ramat Gan (IL); Rina Wassermann, Ramat Gan (IL); Yoni Sheinberger, Ramat Gan (IL)

(73) Assignee: ANIMA BIOTECH INC., NJ (US)

( * ) Notice: Subject to any disclaimer, the term of this patent is extended or adjusted under 35 U.S.C. 154(b) by 0 days.

(21) Appl. No.: 18/838,246

(22) PCT Filed: Mar. 15, 2023

(86) PCT No.: PCT/US2023/015237
§ 371 (c)(1),
(2) Date: Aug. 14, 2024

(87) PCT Pub. No.: WO2023/177700
PCT Pub. Date: Sep. 21, 2023

(65) Prior Publication Data
US 2025/0109128 A1    Apr. 3, 2025

(30) Foreign Application Priority Data
Mar. 16, 2022 (IL) .......................................... 291418

(51) Int. Cl.
| C07D 413/14 | (2006.01) |
| A61K 31/4245 | (2006.01) |
| A61K 31/454 | (2006.01) |
| A61K 31/4545 | (2006.01) |
| C07D 401/14 | (2006.01) |
| C07D 413/12 | (2006.01) |

(52) U.S. Cl.
CPC ........ *C07D 413/14* (2013.01); *A61K 31/4245* (2013.01); *A61K 31/454* (2013.01); *A61K 31/4545* (2013.01); *C07D 401/14* (2013.01); *C07D 413/12* (2013.01)

(58) Field of Classification Search
CPC .............. C07D 413/14; A61K 31/4245; A61K 31/454; A61K 31/4545
USPC ....................................................... 514/318
See application file for complete search history.

(56) References Cited

U.S. PATENT DOCUMENTS

| 7,851,473 B2 | 12/2010 | Matsumoto et al. |
| 8,389,736 B2 | 5/2013 | Kurth et al. |
| 8,785,119 B2 | 7/2014 | Cooperman et al. |
| 9,150,561 B2 | 6/2015 | Quattropani et al. |
| 2009/0163545 A1 | 6/2009 | Goldfarb |
| 2009/0197897 A1 | 8/2009 | Bugada et al. |
| 2011/0183974 A1 | 7/2011 | Dessole et al. |
| 2013/0195879 A1 | 8/2013 | Bylock |
| 2017/0340636 A1 | 11/2017 | Goldsmith et al. |
| 2019/0374526 A1 | 12/2019 | Fischer et al. |
| 2020/0010462 A1 | 1/2020 | Lucas et al. |
| 2020/0262828 A1 | 8/2020 | Lucas et al. |
| 2020/0345700 A1 | 11/2020 | Wu et al. |
| 2020/0347043 A1 | 11/2020 | Martin et al. |

FOREIGN PATENT DOCUMENTS

| WO | WO 2007/118149 A2 | 10/2007 |
| WO | WO 2008/070692 A2 | 6/2008 |
| WO | WO 2008/130581 A1 | 10/2008 |
| WO | WO 2010/013037 A1 | 2/2010 |
| WO | WO 2011/147951 A1 | 12/2011 |
| WO | WO 2012/024150 A1 | 2/2012 |
| WO | WO 2012/077655 A1 | 6/2012 |
| WO | WO 2017/175068 A1 | 10/2017 |
| WO | WO 2018/081167 A1 | 5/2018 |
| WO | WO 2019/018795 A1 | 1/2019 |

OTHER PUBLICATIONS

International Search Report for PCT Application No. P-599641-PC dated Sep. 14, 2023.
Muraglia et al. "N-(2-alkylaminoethyl)-4-(1, 2, 4-oxadiazol-5-yl) piperazine-1-carboxamides as highly potent smoothened antagonists" Bioorganic & medicinal chemistry letters. Sep. 15, 2011;21(18):5283-8.
Allen-Petersen et al. "Mission possible: advances in MYC therapeutic targeting in cancer" BioDrugs. Oct. 2019;33(5):539-53.
Benz et al. "Identification of novel quadruplex ligands from small molecule libraries by FRET-based high-throughput screening" Chembiochem: a European journal of chemical biology. Jun. 14, 2011; 12(9):1422-6.
Brvar et al. "Structure-based discovery of substituted 4, 5'-bithiazoles as novel DNA gyrase inhibitors" Journal of medicinal chemistry. Jul. 26, 2012;55(14):6413-26.
Cancer Facts & Figures American Cancer Society: Atlanta, GA (2008).
Coffman et al. "Constrained Bithiazoles: Small Molecule Correctors of Defective ΔF508-CFTR Protein Trafficking" Journal of Medicinal Chemistry. Aug. 8, 2014;57(15):6729.
Dang CV "MYC on the path to cancer" Cell. Mar. 30, 2012;149(1):22-35.
Loo et al. "Bithiazole correctors rescue CFTR mutants by two different mechanisms" Biochemistry. Aug. 6, 2013;52(31):5161-3.
Piala et al. "Discovery of novel TAOK2 inhibitor scaffolds from high-throughput screening" Bioorganic & medicinal chemistry letters. Aug. 15, 2016;26(16):3923-7.

(Continued)

*Primary Examiner* — Kahsay Habte
(74) *Attorney, Agent, or Firm* — Mark S. Cohen; PEARL COHEN ZEDEK LATZER BARATZ LLP

(57) ABSTRACT

The present invention relates to novel c-Myc mRNA translation modulators, composition and methods of preparation CA thereof, and uses thereof in the treatment of cancer.

17 Claims, 4 Drawing Sheets
Specification includes a Sequence Listing.

(56) References Cited

OTHER PUBLICATIONS

Product Name: C066-5012-N-(3,4-dimethoxyphenyl)-1-[3-(3,4-dimethoxyphenyl)-1,2,4-oxadiazol-5-yl]piperidine-4-carboxamide.
Sayers et al. "Identification and characterization of a potent activator of p53-independent cellular senescence via a small-molecule screen for modifiers of the integrated stress response" Molecular pharmacology. Mar. 2013; 83(3):594-604.
Soucek et al. "Modelling Myc inhibition as a cancer therapy" Nature. Oct. 2, 2008;455(7213):679-83.
Whitfield et al. "Strategies to Inhibit Myc and Their Clinical Applicability" Frontiers in Cell and Developmental Biology. 2017;5.
Woodland et al. "From On-Target to Off-Target Activity: Identification and Optimisation of Trypanosoma brucei GSK3 Inhibitors and Their Characterisation as Anti-Trypanosoma brucei Drug Discovery Lead Molecules" Chemmedchem. Jul. 2013;8(7): 1127.
Yoo et al. "4'-Methyl-4, 5'-bithiazole-based correctors of defective ΔF508-CFTR cellular processing" Bioorganic & medicinal chemistry letters. Apr. 4, 2008;18(8):2610.

SEQUENCE LISTING

```
Sequence total quantity: 3
SEQ ID NO: 1            moltype = DNA  length = 52
FEATURE                 Location/Qualifiers
source                  1..52
                        mol_type = other DNA
                        organism = synthetic construct
misc_feature            1..52
                        note = Description of sequence: cDNA RTqT
SEQUENCE: 1
ccagtgagca gagtgacgag gactcgagct caagcttttt tttttttttt tt          52

SEQ ID NO: 2            moltype = DNA  length = 18
FEATURE                 Location/Qualifiers
source                  1..18
                        mol_type = other DNA
                        organism = synthetic construct
misc_feature            1..18
                        note = Description of sequence: PCR Qi (reverse primer)
SEQUENCE: 2
gaggactcga gctcaagc                                                18
```

```
SEQ ID NO: 3          moltype = DNA   length = 20
FEATURE               Location/Qualifiers
source                1..20
                      mol_type = other DNA
                      organism = synthetic construct
misc_feature          1..20
                      note = Description of sequence: Myc_RACE-F3 (Forward primer)
SEQUENCE: 3
tagcagttac acagaatttc                                                      20
```

c-MYC mRNA TRANSLATION MODULATORS AND USES THEREOF IN THE TREATMENT OF CANCER

CROSS-REFERENCE TO RELATED APPLICATIONS

This application is a National Phase Application of PCT International Application No. PCT/US23/15237, International Filing Date Mar. 15, 2023, claiming priority of Israel Patent Application No. 291418, filed Mar. 16, 2022, both of which are hereby incorporated by reference.

SEQUENCE LISTING STATEMENT

This instant application contains a Sequence Listing which has been submitted electronically in XML format and is hereby incorporated by reference in its entirety. Said XML copy created on Jul. 12, 2023, is named P-599641-PC_SL.xml and is 4.91 kilobytes in size.

The present invention relates to novel c-Myc mRNA translation modulators, composition and methods of preparation thereof, and uses thereof in the treatment of cancer.

BACKGROUND OF THE INVENTION

Cancer is the second most common cause of death in the United States, exceeded only by heart disease. In the United States, cancer accounts for 1 of every 4 deaths. The 5-year relative survival rate for all cancer patients diagnosed in 1996-2003 is 66%, up from 50% in 1975-1977 (*Cancer Facts & Figures* American Cancer Society: Atlanta, GA (2008)). The rate of new cancer cases decreased by an average 0.6% per year among men between 2000 and 2009 and stayed the same for women. From 2000 through 2009, death rates from all cancers combined decreased on average 1.8% per year among men and 1.4% per year among women. This improvement in survival reflects progress in diagnosing at an earlier stage and improvements in treatment. Discovering highly effective anticancer agents with low toxicity is a primary goal of cancer research.

The Myc family includes three major members, the proto-oncogene c-Myc (cellular Myelocytomatosis, short Myc), as well as L-Myc and N-Myc. These three Myc homologs are involved in the early stages of carcinogenesis and metastatic spread in most human cancers. In most types of tumors Myc gene is not mutated or duplicated, but its mRNA and/or protein levels are increased, indicating that in cancer Myc overexpression is induced at the level of transcription, mRNA steady state levels and translation. Indeed, Myc gene expression normally depends on growth factor signaling and both Myc mRNA and Myc protein have very short half-lives (of 30 and 20 min respectively) [Dang, C. V. (2012). *Myc on the path to cancer. Cell* 149, 22-35]. In tumor cells however, the cellular levels of Myc become independent from such signaling and regulation, and the resulting exacerbated Myc function drives intracellular and extracellular transcription programs that allow tumors to grow and thrive. However, Myc does not necessarily need to be overexpressed in order for a cancer to be highly dependent upon its activity. A study from Soucek et al. (*Nature* (2008) 455(7213):679-83) shows that tumors that express c-Myc at endogenous levels exhibit tumor regression upon Myc inhibition via a genetically engineered system. Therefore, treatment with a Myc inhibitor is not necessarily limited to cancers that overexpress Myc. Compounds according to this invention may also be used to regulate the translation of Myc mRNA, wherein the direct target for the compounds is a protein or RNA which regulate Myc mRNA translation, and as such any tumor which is Myc dependent will benefit from the therapeutic utility if these compounds.

Due to its extensive pathogenic significance, Myc is an important anticancer target. Deregulated Myc gene is found in a wide range of human hematological malignancies and solid tumors, especially in breast cancer, ovarian carcinoma, acute myeloid leukemia, chronic myelogenous leukemia, Hodgkin's and Burkitt's lymphoma, diffuse large Bcell lymphoma, prostate cancer, colon cancer, gastric cancer, primary central nervous system lymphoma, glioblastoma, medulloblastoma, melanoma, non-small cell lung carcinoma, germinal center-derived lymphomas, esophageal squamous cell carcinoma, osteosarcoma, bladder cancer, pancreatic cancer and lung adenocarcinoma. Recent studies also indicate that deregulation of c-Myc is related to the occurrence of BRAF V600E thyroid cancers, choroid plexus carcinoma, and colitis-associated cancer. In addition, amplification of the Myc gene was found in a significant number of epithelial ovarian cancer cases. In TCGA datasets, the amplification of Myc occurs in several cancer types, including breast, colorectal, pancreatic, gastric, and uterine cancers.

Although Myc gene is a very important oncogene and considered as a driver in carcinogenesis and Myc protein is a key transcription factor broadly targeting various genes, rational designing a direct Myc inhibitor is still challenging. This is mainly because Myc protein lacks structural regions amenable to therapeutic inhibition by small molecules and is considered an undruggable target [BioDrugs (2019) 33:539-553].

Designing and developing Myc modulators is challenging, primarily because the Myc protein has a disordered structure which lacks a pocket or groove that can act as a binding site for modulators.

Interfering with the Myc transcription, blocking the protein-protein interaction (PPI) of Myc and its cofactors, and influencing on signaling pathways related to Myc were used in the past as potential modulatory targets, but failed to be developed as drug candidates. Myc PPI inhibitors failed to show sufficient efficacy in cell-based assays and animal models due to the requirement of high target occupancy to drive efficacy. Modulators of signaling pathways upstream to Myc, for example mTOR modulators, failed due lack of target specificity.

Nevertheless, a therapeutic approach to target c-Myc has remained elusive. The absence of a clear ligand-binding domain establishes a formidable obstacle toward direct inhibition, which is a challenging feature shared among many compelling transcriptional targets in cancer. Thus, alternative modalities that target Myc are required, as outlined herein, namely compounds which regulate Myc mRNA translation.

SUMMARY OF THE INVENTION

This invention provides a compound or its pharmaceutically acceptable salt, stereoisomer, tautomer, hydrate, N-oxide, reverse amide analog, prodrug, isotopic variants (e.g., deuterated analog), PROTAC, pharmaceutical product or any combination thereof, represented by the structure of formula I, I(a), I(a(i)), I(a(ii)), I(a(iii)), I(b), I(b(i)), I(b(ii)), I(b(iii)), II and by the structures listed in Table 1, as defined herein below. In various embodiments, the compound is c-Myc mRNA translation modulator. In various embodiments, the compound is a c-Myc mRNA transcription regulator. In various embodiments, the compound is a c-Myc inhibitor. In various embodiments, the compound is any combination of a c-Myc mRNA transcription regulator, c-Myc mRNA transcription regulator and c-Myc inhibitor.

This invention further provides a pharmaceutical composition comprising a compound or its pharmaceutically acceptable salt, stereoisomer, tautomer, hydrate, N-oxide, prodrug, isotopic variants (e.g., deuterated analog), PROTAC, pharmaceutical product or any combination thereof, represented by the structure of formula I, I(a), I(a(i)), I(a(ii)), I(a(iii)), I(b), I(b(i)), I(b(ii)), I(b(iii)), II and by the structures listed in Table 1, as defined herein below, and a pharmaceutically acceptable carrier.

This invention further provides a method of treating, suppressing, reducing the severity, reducing the risk of developing or inhibiting cancer in a subject, comprising administering a compound represented by the structure of formula I, I(a), I(a(i)), I(a(ii)), I(a(iii)), I(b), I(b(i)), I(b(ii)), I(b(iii)), II and by the structures listed in Table 1, as defined herein below, to a subject suffering from cancer under conditions effective to treat, suppress, reduce the severity, reduce the risk of developing, or inhibit cancer in said subject.

This invention further provides a method of modulating c-Myc mRNA translation in a cell, comprising contacting a compound represented by the structure of formula I, I(a), I(a(i)), I(a(ii)), I(a(iii)), I(b), I(b(i)), I(b(ii)), I(b(iii)), II and by the structures listed in Table 1, as defined herein below, with a cell, thereby modulating c-Myc mRNA translation in said cell.

This invention further provides a method of regulating c-Myc mRNA transcription in a cell, comprising contacting a compound represented by the structure of formula I, I(a), I(a(i)), I(a(ii)), I(a(iii)), I(b), I(b(i)), I(b(ii)), I(b(iii)), II and by the structures listed in Table 1, as defined herein below, with a cell, thereby regulating c-Myc mRNA transcription in said cell.

In some embodiments, this invention is directed to a compound represented by the structure of formula (I):

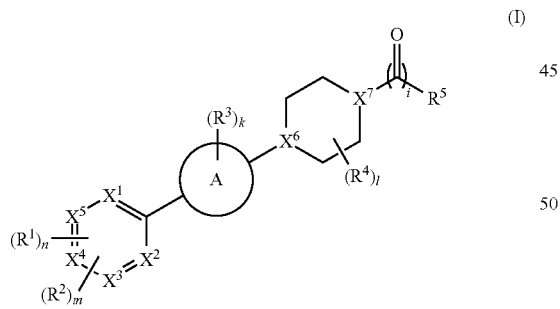

(I)

wherein
A ring is a single aromatic or heteroaromatic ring (e.g., oxadiazole);
$R^1$ and $R^2$ are each independently F, Cl, Br, I, OH, O—$R^{20}$, $R^6$—OH, —$R^6$—O—$R^7$, $CF_3$, $OCH_3$, CN, $NO_2$, —$CH_2CN$, —$R^6CN$, $C_1$-$C_5$ linear or branched, substituted or unsubstituted alkyl, $C_1$-$C_5$ linear or branched, or $C_3$-$C_8$ cyclic haloalkyl (e.g., $CF_3$), substituted or unsubstituted $C_1$-$C_5$ linear or branched, or $C_3$-$C_8$ cyclic alkoxy, $C_1$-$C_5$ linear or branched haloalkoxy, $C_1$-$C_5$ linear or branched alkoxyalkyl, NH—C(O)—$R^7$ (e.g., NHC(O)—$CH_3$);
or $R^2$ and $R^1$ are joint together to form a 5 or 6 membered substituted or unsubstituted, aliphatic or aromatic, carbocyclic or heterocyclic ring;
wherein
$R^6$ is absent or O, C=O, C(=O)—$[CH_2]_p$, $[CH_2]_p$—C(=O), $[CH_2]_p$ (e.g., $CH_2$, $CH_2$—$CH_2$—$CH_2$), $[CHR^{21}]_p$, $[C(R^{21})_2]_p$ or $[CH_2]_{pa}$—O—$[CH_2]_{pb}$, or $[CH_2]_p$—O;
wherein
each p is independently an integer between 1 and 10 (e.g., 1, 3); and
each pa and pb is independently an integer between 1 and 5;
$R^{21}$ is H, F, Cl, Br, I, OH, $CF_3$, CN, $NO_2$, $C_1$-$C_5$ linear or branched, substituted or unsubstituted alkyl, $C_1$-$C_5$ linear or branched alkoxy, $C_1$-$C_5$ linear or branched haloalkyl, $R^6$-aryl, $R^6$—N(alkyl)$_2$, $R^6$—NH(alkyl), ($R^6$—NH(cycloalkyl), ($R^6$—NH(aryl), substituted or unsubstituted aryl, substituted or unsubstituted heteroaryl, substituted or unsubstituted $C_3$-$C_8$ cycloalkyl, substituted or unsubstituted 3-8 membered heterocyclic ring, $R^6$-(substituted or unsubstituted heterocycle) or C(O)-(alkyl);
or wherein two geminal or vicinal $R^2$ substituents are joined to form a substituted or unsubstituted $C_3$-$C_8$ cycloalkyl;
$R^7$ is H, $C_1$-$C_5$ substituted or unsubstituted linear or branched alkyl, $C_1$-$C_5$ linear or branched alkoxy, C(O)R, or $S(O)_2R$;
wherein
R is H, F, Cl, Br, I, OH, $CF_3$, CN, $NO_2$, $C_1$-$C_5$ linear or branched, substituted or unsubstituted alkyl, $C_1$-$C_5$ linear or branched alkoxy, $C_1$-$C_5$ linear or branched haloalkyl, $R^6$-aryl, $R^6$—N(alkyl)$_2$, $R^6$—NH(alkyl), ($R^6$—NH(cycloalkyl), ($R^6$—NH(aryl), substituted or unsubstituted aryl, substituted or unsubstituted heteroaryl, substituted or unsubstituted $C_3$-$C_8$ cycloalkyl, substituted or unsubstituted 3-8 membered heterocyclic ring, $R^6$-(substituted or unsubstituted heterocycle)(e.g., $CH_2$-benzoxazole, $CH_2$-benzimidazole, $CH_2$-indole), or C(O)-(alkyl);
$R^{20}$ is represented by the following structure:

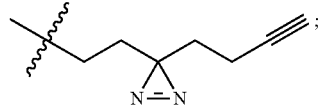 [SMILES: *CCC1(CCC#C)N=N1]

$R^3$ and $R^4$ are each independently H, F, Cl, Br, I, OH, $CF_3$, CN, $NO_2$, $C_1$-$C_5$ linear or branched, substituted or unsubstituted alkyl, $C_1$-$C_5$ linear or branched, or $C_3$-$C_8$ cyclic haloalkyl;
wherein substitutions include: F, Cl, Br, I, $C_1$-$C_5$ linear, cyclic or branched alkyl, OH, alkoxy, $NH_2$, N(alkyl)$_2$, NH(alkyl), NH(cycloalkyl), NH(aryl), NH(benzyl), N(cycloalkyl)$_2$, N(aryl)$_2$, N(alkyl)(aryl), N(alkyl)(cycloalkyl), N(aryl)(cycloalkyl), $CF_3$, aryl, phenyl, heteroaryl, $C_3$-$C_8$ cycloalkyl, halophenyl, (benzyloxy)phenyl, CN, $NO_2$ or any combination thereof);
$R^5$ is OH, $C_1$-$C_5$ linear or branched, substituted or unsubstituted alkyl, $C_1$-$C_5$ linear or branched, or $C_3$-$C_8$ cyclic haloalkyl, N($R^a$)($R^b$), NHR, $NH_2$, N(alkyl)$_2$, NH(alkyl), NH(cycloalkyl), NH(aryl) (e.g., NH-1-methylindole), NH(benzyl), N(cycloalkyl)$_2$, N(aryl)$_2$, N(alkyl)(aryl), N(alkyl)(cycloalkyl), N(aryl)(cycloalkyl), substituted or unsubstituted aryl, substituted or unsubstituted heteroaryl, substituted or unsubstituted $C_3$-$C_8$ cycloalkyl, substituted or unsubstituted single or fused 3-8 membered heterocyclic ring system, NH—$R^{20}$, NH—$R^6$—NH(alkyl), NH—$R^6$—NH$_2$, NH—$R^6$—N(alkyl)$_2$, NH—$R^6$—N(alkyl)(cycloalkyl), NH—$R^6$—NH(cycloalkyl), NH—$R^6$—NH(aryl), NH—$R^6$—N(alkyl)(aryl), NH—$R^6$—OH, NH—$R^6$—O(alkyl), NH—$R^6$—O(aryl) or NH—$R^6$—O(cycloalkyl);

or $R^5$ is represented by any one of the following structures:

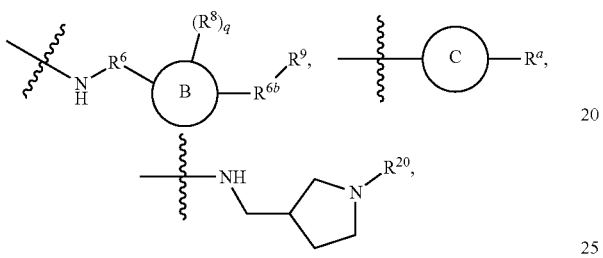

wherein q is an integer between 0 and 4;

$R^{6b}$ is absent or O, C=O, C(=O)—[CH$_2$]$_p$, [CH$_2$]$_p$—C(=O), [CH$_2$]$_p$ (e.g., CH$_2$), [CHR$^{21}$]$_p$, [C(R$^{21}$)$_2$]$_p$ or [CH$_2$]$_{pa}$—O—[CH$_2$]$_{pb}$, or [CH$_2$]$_p$—O;

$R^8$ is H, F, Cl, Br, I, OH, CF$_3$, CN, NO$_2$, $C_1$-$C_5$ linear or branched, substituted or unsubstituted alkyl, $C_1$-$C_5$ linear or branched, or $C_3$-$C_8$ cyclic haloalkyl;

$R^9$ is H, $C_1$-$C_5$ linear or branched alkoxy, $C_1$-$C_5$ linear or branched haloalkoxy, $C_1$-$C_5$ linear or branched alkyl (e.g., isopentyl), $C_1$-$C_5$ linear or branched alkenyl, $R^6$—OH, a substituted or unsubstituted aryl (e.g., phenyl, tolyl, 2-fluoro-phenyl), substituted or unsubstituted heteroaryl (e.g., pyridine, 3-methylpyridine, thiazolyl, oxazolyl thiophenyl, furanyl), substituted or unsubstituted $C_3$-$C_8$ cycloalkyl (e.g., cyclohexyl, cyclopentyl, cyclopropyl), substituted or unsubstituted $C_3$-$C_8$ cycloalkenyl (e.g., cyclohexenyl), $C_1$-$C_5$ linear or branched, or $C_3$-$C_8$ cyclic haloalkyl, substituted or unsubstituted 3-8 membered heterocyclic ring (e.g., tetrahydropyran, tetrahydrothiopyran), NH$_2$, N(alkyl)$_2$, NH(alkyl) or $R^{20}$;

$R^a$ is $R^{101}$-$R^{102}$, $R^{20}$, $R^6$—NH(alkyl), $R^6$—NH$_2$, $R^6$—N(alkyl)$_2$, $R^6$—N(alkyl)(cycloalkyl), $R^6$—NH(cycloalkyl), $R^6$—NH(aryl), $R^6$—OH, $R^6$—O(alkyl), $R^6$—O(aryl) or $R^6$—O(cycloalkyl)

or $R^a$ is represented by the following structures:

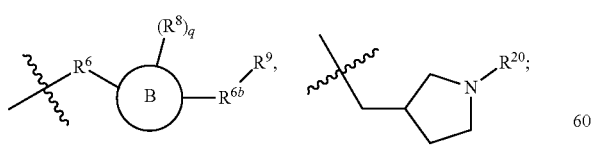

$R^b$ is $R^{103}$-$R^{104}$;

wherein $R^{101}$ and $R^{103}$ are each independently absent or O, C=O, C(=O)—[CH$_2$]$_p$, [CH$_2$]$_p$—C(=O), [CH$_2$]$_p$, [CHR$^{21}$]$_p$, [C(R$^{21}$)$_2$]$_p$ or [CH$_2$]$_{pa}$—O—[CH$_2$]$_{pb}$, or [CH$_2$]$_p$—O, substituted or unsubstituted arylene, substituted or unsubstituted heteroarylene, substituted or unsubstituted heterocycloalkylene or substituted or unsubstituted cycloalkylene wherein p is an integer between 0 and 10;

$R^{102}$ and $R^{104}$ are each independently H, F, Cl, Br, I, OH, CF$_3$, CN, NO$_2$, $C_1$-$C_5$ linear or branched, substituted or unsubstituted alkyl, $C_1$-$C_5$ linear or branched alkoxy, $C_1$-$C_5$ linear or branched haloalkyl, $R^6$-aryl, $R^6$—N(alkyl)$_2$, $R^6$—NH(alkyl), ($R^6$—NH(cycloalkyl), ($R^6$—NH(aryl), substituted or unsubstituted aryl, substituted or unsubstituted heteroaryl, substituted or unsubstituted $C_3$-$C_8$ cycloalkyl, substituted or unsubstituted 3-8 membered heterocyclic ring (e.g., piperidine), $R^6$-(substituted or unsubstituted heterocycle) (e.g., CH$_2$-piperidine) or C(O)-(alkyl);

or $R^a$ and $R^b$ are joined to form a substituted or unsubstituted 3-8 membered heterocyclic ring;

B ring is a substituted or unsubstituted saturated, unsaturated or aromatic, single, fused or spiro, carbocyclic or heterocyclic 3-12 membered ring (e.g., piperidine, pyrrolidine, 2-pyrrolidone, indole, phenyl, pyridine, pyrimidine, piperazine, thiophene, tetrahydrofuran, cyclobutyl, cyclohexyl, 2,5-dihydrothiazole);

C ring is a 5-10 membered heterocyclic, aryl or heteroaryl ring (e.g., phenyl);

$X^1$-$X^5$ are each independently C, CH or N;

$X^6$-$X^7$ are each independently CH or N;

m, n, l and k are each independently an integer between 0 and 4;

wherein m+n=1 or m+n>2;

i is 0 or 1;

or its pharmaceutically acceptable salt, optical isomer, tautomer, hydrate, N-oxide, reverse amide analog, prodrug, isotopic variant, PROTAC, pharmaceutical product or any combination thereof.

In some embodiments, the compound is represented by the structure of formula (I(a)):

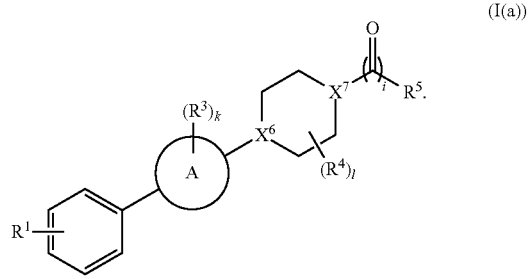

In some embodiments, A is oxadiazole.

In some embodiments, the compound is represented by the structure of formula (I(a(i))):

(I(a(i)))

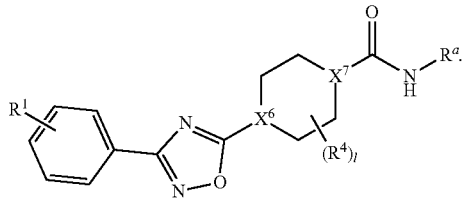

In some embodiments, the compound is represented by the structure of formula (I(a(ii))):

(I(a(ii)))

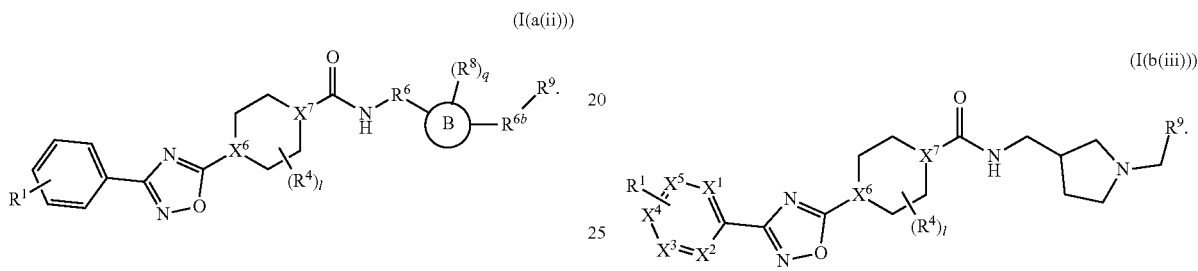

In some embodiments, the compound is represented by the structure of formula (I(a(iii))):

(I(a(iii)))

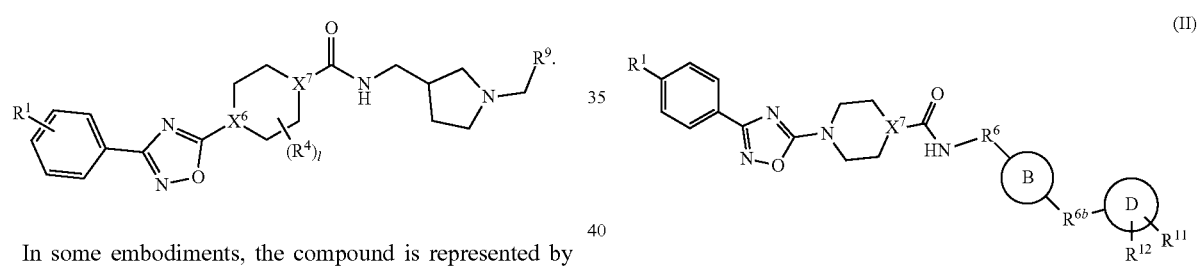

In some embodiments, the compound is represented by the structure of formula (I(b)):

(I(b))

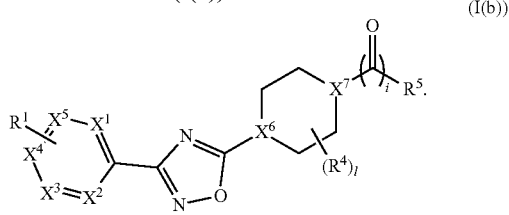

In some embodiments, the compound is represented by the structure of formula (I(b(i))):

(I(b(i)))

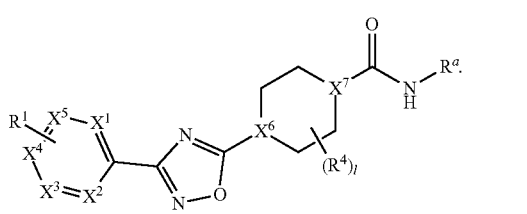

In some embodiments, the compound is represented by the structure of formula (I(b(ii))):

(I(b(ii)))

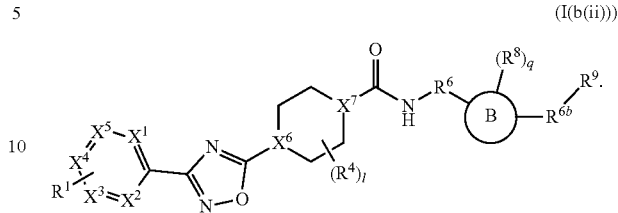

In some embodiments, the compound is represented by the structure of formula (I(b(iii))):

(I(b(iii)))

In some embodiments, the compound is represented by the structure of formula (II):

(II)

wherein $R^1$ is H, F, Cl, Br, I, OH, $CF_3$, $OCH_3$, CN, $NO_2$, $C_1$-$C_5$ linear or branched, substituted or unsubstituted alkyl (e.g., methyl, ethyl), $C_1$-$C_5$ linear or branched, or $C_3$-$C_8$ cyclic haloalkyl (e.g., $CHF_2$), $C_1$-$C_5$ substituted or unsubstituted, linear or branched, or $C_3$-$C_8$ cyclic alkoxy (e.g. methoxy, O—$(CH_2)_2$—OH), $C_1$-$C_5$ linear or branched haloalkoxy (e.g., $OCF_3$, $OCHF_2$), NH—C(O)—$R^7$ (e.g., NHC(O)—$CH_3$), or $C_1$-$C_5$ linear or branched alkoxyalkyl;

wherein $R^7$ is H, $C_1$-$C_5$ substituted or unsubstituted linear or branched alkyl (e.g., methyl, ethyl, $CH_2$—$CH_2$—O—$CH_3$), $C_1$-$C_5$ linear or branched alkoxy (e.g., O—$CH_3$), C(O)R, or $S(O)_2R$;

$R^6$ is absent or O, C=O, C(=O)—$[CH_2]_p$, $[CH_2]_p$—C(=O), $[CH_2]_p$ (e.g. $CH_2$, $CH_2CH_2$, $CH_2CH_2CH_2$, $CH_2CH_2CH_2CH_2$), $[CHR^{21}]_p$ (e.g. CHF, CH—$CH_3$), $[C(R^{21})_2]_p$ (e.g. $CF_2$) or $[CH_2]_{pa}$—O—$[CH_2]_{pb}$ (e.g. $CH_2OCH_2$), or $[CH_2]_p$—O (e.g., $CH_2CH_2O$);

$R^{6b}$ is absent or O, C=O, C(=O)—$[CH_2]_p$, $[CH_2]_p$—C(=O), $[CH_2]_p$ (e.g. $CH_2$, $CH_2CH_2$, $CH_2CH_2CH_2$, $CH_2CH_2CH_2CH_2$), $[CHR^{21}]_p$ (e.g. CHF, CH—$CH_3$), $[C(R^{21})_2]_p$ (e.g. $CF_2$) or $[CH_2]_{pa}$—O—$[CH_2]_{pb}$ (e.g. $CH_2OCH_2$), or $[CH_2]_p$—O (e.g., $CH_2CH_2O$);

wherein
p is an integer between 1 and 10; and
each pa and pb is independently an integer between 1 and 5;
$R^{21}$ is H, F, Cl, Br, I, OH, $CF_3$, CN, $NO_2$, $C_1$-$C_5$ linear or branched, substituted or unsubstituted alkyl (e.g., methyl, ethyl, propyl, isopropyl, isobutyl), $C_1$-$C_5$ linear or branched alkoxy (e.g. methoxy), $C_1$-$C_5$ linear or branched haloalkyl (e.g., $CHF_2$, $CF_3$, $CH_2$-Ph, $CH_2$-Ph-ethyl, substituted or unsubstituted aryl (e.g., phenyl, ethylphenyl), substituted or unsubstituted heteroaryl (e.g., pyridine (2, 3, and 4-pyridine) or benzimidazole), substituted or unsubstituted $C_3$-$C_8$ cycloalkyl (e.g., cyclopropyl), substituted or unsubstituted 3-8 membered heterocyclic ring (e.g., piperidine, pyrrolidine), $(CH_2)_3$-piperidine or C(O)-(alkyl) (e.g. C(O)—$CH_3$);
or wherein two geminal or vicinal $R^2$ substituents are joined to form a substituted or unsubstituted $C_3$-$C_8$ cycloalkyl (e.g., cyclopropyl);
B ring is a substituted or unsubstituted saturated, unsaturated or aromatic, single, fused or spiro, 3-12 membered heterocyclic ring (e.g., piperidine, pyrrolidine, piperazine, 2-pyrrolidone, indole) or substituted or unsubstituted saturated or unsaturated single, fused or spiro, 3-12 membered cycloalkyl ring;
D ring is a saturated, unsaturated or aromatic, single, fused or spiro, heterocyclic 3-12 membered ring (e.g., 2, 3, or 4-pyridine, furan, thiophene, pyrrol, thiazole, isothiazole, tetrahydrofuran, piperidine, azepane, oxepane, 2-oxaspiro[3.3]heptane, azetidine, tetrahydro-2H-thiopyran 1,1-dioxide, tetrahydrothiopyran, tetrahydropyran, pyrrolidine, oxetane, diazirine) or a saturated, unsaturated, single, fused or spiro, aliphatic carbocyclic 3-12 membered ring (e.g., cyclopropyl, cyclobutyl, cyclopentyl, cyclohexyl, cyclohexenyl);
$R^{11}$ and $R^{12}$ are each independently H, F, Cl, Br, I, OH, $CF_3$, $OCH_3$, CN, $NO_2$, $C_1$-$C_5$ linear or branched, substituted or unsubstituted alkyl (e.g., methyl, ethyl, ethylacetylene, 1-butyne), $C_1$-$C_5$ linear or branched, or $C_3$-$C_8$ cyclic haloalkyl (e.g., $CHF_2$), $C_1$-$C_5$ substituted or unsubstituted, linear or branched, or $C_3$-$C_8$ cyclic alkoxy (e.g. methoxy, O—$(CH_2)_2$—OH), $C_1$-$C_5$ linear or branched haloalkoxy (e.g., $OCF_3$, $OCHF_2$), $C_1$-$C_5$ linear or branched alkoxyalkyl, $R^{20}$, $NH_2$, NHR, $NR_2$;
wherein
R is H, F, Cl, Br, I, OH, $CF_3$, CN, $NO_2$, $C_1$-$C_5$ linear or branched, substituted or unsubstituted alkyl, $C_1$-$C_5$ linear or branched alkoxy, $C_1$-$C_5$ linear or branched haloalkyl, $R^6$-aryl, $R^6$—$N(alkyl)_2$, $R^6$—NH(alkyl), ($R^6$—NH(cycloalkyl), ($R^6$—NH(aryl), substituted or unsubstituted aryl, substituted or unsubstituted heteroaryl, substituted or unsubstituted $C_3$-$C_8$ cycloalkyl, substituted or unsubstituted 3-8 membered heterocyclic ring, $R^6$-(substituted or unsubstituted heterocycle) (e.g., $(CH_2)_3$-piperidine, $CH_2$-benzoxazole, $CH_2$-benzimidazole, $CH_2$-indole) or C(O)-(alkyl);
$X^7$ is CH or N;
$R^{20}$ is represented by the following structure:

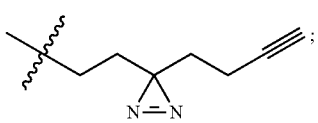 [SMILES: *CCC1(CCC#C)N=N1]

or its pharmaceutically acceptable salt, optical isomer, tautomer, hydrate, N-oxide, reverse amide analog, prodrug, isotopic variant (e.g., deuterated analog), PROTAC, pharmaceutical product or any combination thereof In some embodiments, $R^1$ is Cl, O—$R^{20}$, $OCH_3$, —$R^6$CN, $C_1$-$C_5$ linear or branched, or $C_3$-$C_8$ cyclic haloalkyl, $CF_3$, $C_1$-$C_5$ linear or branched haloalkoxy, $OCF_3$, or $OCHF_2$. In some embodiments, $R^6$ is absent or is $[CH_2]_p$, $CH_2$, or $CH_2$—$CH_2$—$CH_2$. In some embodiments, $R^5$ is NH(aryl), substituted or unsubstituted single or fused 3-8 membered heterocyclic ring system, or $R^5$ is represented by the following structure:

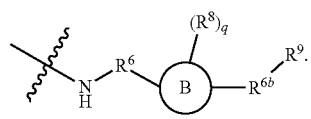

In some embodiments, $R^{6b}$ is absent, O, C=O, $[CH_2]_p$ or $CH_2$. In some embodiments, $R^9$ is H, $R^{20}$, $C_1$-$C_5$ linear or branched alkyl (e.g., isopentyl), a substituted or unsubstituted aryl, phenyl, tolyl, 2-fluoro-phenyl, substituted or unsubstituted heteroaryl, pyridine, 3-methyl-pyridine, thiazolyl, oxazolyl thiophenyl, furanyl, substituted or unsubstituted $C_3$-$C_8$ cycloalkyl, cyclohexyl, cyclopentyl, cyclopropyl, substituted or unsubstituted $C_3$-$C_8$ cycloalkenyl, cyclohexenyl, substituted or unsubstituted 3-8 membered heterocyclic ring, tetrahydropyran, or tetrahydrothiopyran. In some embodiments, $R^a$ is represented by the following structure:

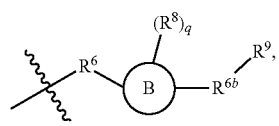

wherein B ring is piperidine, pyrrolidine, 2-pyrrolidone, or indole.

In some embodiments, the compound is a c-Myc mRNA translation modulator, a c-Myc mRNA transcription regulator, a c-Myc inhibitor or any combination thereof.

In some embodiments, this invention is directed to a pharmaceutical composition comprising the compound of this invention and a pharmaceutically acceptable carrier.

In some embodiments, this invention is directed to a compound as described herein above, for use in treating, suppressing, reducing the severity, reducing the risk of developing or inhibiting cancer in a subject suffering from cancer.

In some embodiments, the cancer is selected from the list of: breast cancer, ovarian carcinoma, acute myeloid leukemia, chronic myelogenous leukemia, Hodgkin's and Burkitt's lymphoma, diffuse large Bcell lymphoma, prostate cancer, colon cancer, gastric cancer, primary central nervous system lymphoma, glioblastoma, medulloblastoma, melanoma, non-small cell lung carcinoma, germinal center-derived lymphomas, esophageal squamous cell carcinoma, osteosarcoma, bladder cancer, pancreatic cancer, lung adenocarcinoma, BRAF V600E thyroid cancer, choroid plexus carcinoma, colitis-associated cancer, epithelial ovarian cancer, colorectal cancer, pancreatic cancer and uterine cancer.

In some embodiments, the cancer is early cancer, advanced cancer, invasive cancer, metastatic cancer, drug resistant cancer or any combination thereof.

In some embodiments, the subject has been previously treated with chemotherapy, immunotherapy, radiotherapy, biological therapy, surgical intervention, or any combination thereof.

In some embodiments, the compound is administered in combination with an anti-cancer therapy.

In some embodiments, the anti-cancer therapy is chemotherapy, immunotherapy, radiotherapy, biological therapy, surgical intervention, or any combination thereof.

In some embodiments, this invention is directed to a compound as described herein above, for use in suppressing, reducing or inhibiting tumor growth in a subject suffering from cancer.

In some embodiments, this invention is directed to a method of modulating c-Myc mRNA translation in a cell, comprising contacting a compound according to this invention as described hereinabove, with a cell, thereby modulating c-Myc mRNA translation in said cell.

In some embodiments, this invention is directed to a method of regulating c-Myc mRNA transcription in a cell, comprising contacting a compound according to this invention as described hereinabove, with a cell, thereby regulating c-Myc mRNA transcription in said cell.

In some embodiments, the method is carried out
(a) by regulating c-Myc mRNA splicing (inclusion or exclusion of untranslated region or alternative usage of exons);
(b) by regulation of c-Myc mRNA modifications;
(c) by regulation of the interaction of RNA binding protein with c-Myc mRNA thereby changing mRNA localization;
(d) by regulating c-Myc mRNA localization in the cytoplasm;
(e) by regulating ribosomes or ribosome accessory factor to c-Myc mRNA;
(f) by reducing the amount of c-Myc protein in the cell;
or any combination thereof.

BRIEF DESCRIPTION OF THE DRAWINGS

FIG. 4A depicts representative images from compound 207. Images were taken with ×20 objective in Operetta machine (Perkin-Elmer). Cell nuclei stained with DAPI and c-Myc protein are signed on the images. FIG. 4B depicts pIC50 of toxicity in A549 cells plotted against $pIC_{50}$ of toxicity in SK-N-F1 cells expressing very low c-Myc protein level. Dashed lines represent ×10 or ×100 toxicity window between two cell types.

DETAILED DESCRIPTION OF THE INVENTION

Figure 1:
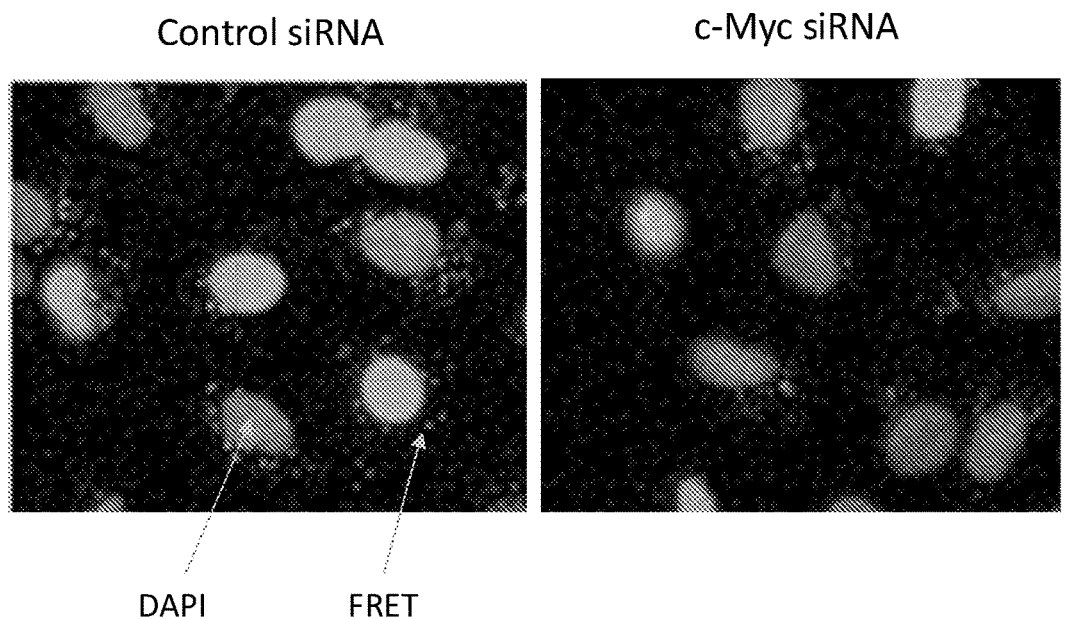
FIG. 1 demonstrates how protein synthesis monitoring (PSM) specifically monitors c-Myc synthesis. The assay system comprises human non-small cell lung carcinoma cell line A549, which is expressing high level of c-Myc. Two tRNAs (di-tRNA) which decode one specific glutamine codon and one specific serine codon were transfected with control RNAi or an RNAi directed to c-Myc. The FRET signal specifically monitors c-Myc translation, as the FRET signal in c-Myc siRNA treated cells was inhibited. Cell nuclei stained with DAPI and FRET signals from tRNA pair which decodes glutamine-serine di-codons are signed on the images.

In various embodiments, this invention is directed to a compound represented by the structure of formula (I):

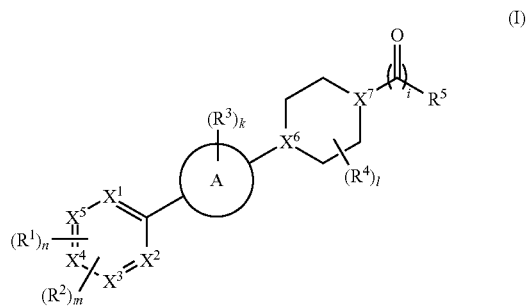

wherein

A ring is a single aromatic or heteroaromatic ring (e.g. phenyl, pyrimidine, 2-, 3- or 4-pyridine, pyridazine, pyrazine, isothiazole, thiadiazole, imidazole, triazole, thiazole, oxazole, isoxazole, 1-methylimidazole, pyrrole, furan, thiophene, oxadiazole, or pyrazole);

$R^1$ and $R^2$ are each independently H, F, Cl, Br, I, OH, O—$R^{20}$, $R^6$—OH, —$R^6$—O—$R^7$, $CF_3$, $OCH_3$, CN, $NO_2$, —$CH_2CN$, —$R^6CN$, $C_1$-$C_5$ linear or branched, substituted or unsubstituted alkyl (e.g., methyl, ethyl, isopropyl), $C_1$-$C_5$ linear or branched, or $C_3$-$C_8$ cyclic haloalkyl (e.g., $CHF_2$), substituted or unsubstituted $C_1$-$C_5$ linear or branched, or $C_3$-$C_8$ cyclic alkoxy (e.g. methoxy, O—$(CH_2)_2$—OH, O—$CH_2$—CH(OH)—$CH_2$—OH), $C_1$-$C_5$ linear or branched haloalkoxy (e.g., $OCF_3$, $OCHF_2$), NH—C(O)—$R^7$ (e.g., NHC(O)—$CH_3$), or $C_1$-$C_5$ linear or branched alkoxyalkyl;

or $R^2$ and $R^1$ are joint together to form a 5 or 6 membered substituted or unsubstituted, aliphatic or aromatic, carbocyclic or heterocyclic ring;

wherein $R^6$ is absent or O, C=O, C(=O)—$[CH_2]_p$, $[CH_2]_p$—C(=O), $[CH_2]_p$ (e.g. $CH_2$, $CH_2CH_2$, $CH_2CH_2CH_2$, $CH_2CH_2CH_2CH_2$), $[CHR^{21}]_p$ (e.g. CHF, CH—$CH_3$), $[C(R^{21})_2]_p$ (e.g. $CF_2$) or $[CH_2]_{pa}$—O—$[CH_2]_{pb}$ (e.g. $CH_2OCH_2$), or $[CH_2]_p$—O (e.g., $CH_2CH_2O$);

wherein
p is an integer between 1 and 10; and
each pa and pb is independently an integer between 1 and 5;

$R^{21}$ is H, F, Cl, Br, I, OH, $CF_3$, CN, $NO_2$, $C_1$-$C_5$ linear or branched, substituted or unsubstituted alkyl (e.g., methyl, ethyl, propyl, isopropyl, isobutyl), $C_1$-$C_5$ linear or branched alkoxy (e.g. methoxy), $C_1$-$C_5$ linear or branched haloalkyl (e.g., $CHF_2$, $CF_3$, $R^6$-aryl (e.g., $CH_2$-Ph, $CH_2$-Ph-ethyl), $R^6$—N(alkyl)$_2$, $R^6$—NH(alkyl), ($R^6$—NH(cycloalkyl), ($R^6$—NH(aryl), substituted or unsubstituted aryl (e.g., phenyl, ethylphenyl), substituted or unsubstituted heteroaryl (e.g., pyridine (2, 3, and 4-pyridine) or benzimidazole), substituted or unsubstituted $C_3$-$C_8$ cycloalkyl (e.g., cyclopropyl), substituted or unsubstituted 3-8 membered heterocyclic ring (e.g., piperidine, pyrrolidine), $R^6$-(substituted or unsubstituted heterocycle) (e.g., $(CH_2)_3$-piperidine) or C(O)-(alkyl) (e.g. C(O)—$CH_3$);
or wherein two geminal or vicinal $R^2$ substituents are joined to form a substituted or unsubstituted $C_3$-$C_8$ cycloalkyl (e.g., cyclopropyl);

$R^7$ is H, $C_1$-$C_5$ substituted or unsubstituted linear or branched alkyl (e.g., methyl, ethyl, $CH_2$—$CH_2$—O—$CH_3$), $C_1$-$C_5$ linear or branched alkoxy (e.g., O—$CH_3$), C(O)R, or $S(O)_2R$;
wherein
R is H, F, Cl, Br, I, OH, $CF_3$, CN, $NO_2$, $C_1$-$C_5$ linear or branched, substituted or unsubstituted alkyl (e.g., methyl, ethyl, propyl, isopropyl, isobutyl), $C_1$-$C_5$ linear or branched alkoxy (e.g. methoxy), $C_1$-$C_5$ linear or branched haloalkyl (e.g., $CHF_2$, $CF_3$, $R^6$-aryl (e.g., $CH_2$-Ph, $CH_2$-Ph-ethyl), $R^6$—N(alkyl)$_2$, $R^6$—NH(alkyl), ($R^6$—NH(cycloalkyl), ($R^6$—NH(aryl), substituted or unsubstituted aryl (e.g., phenyl, ethylphenyl), substituted or unsubstituted heteroaryl (e.g., pyridine (2, 3, and 4-pyridine) or benzimidazole), substituted or unsubstituted $C_3$-$C_8$ cycloalkyl (e.g., cyclopropyl), substituted or unsubstituted 3-8 membered heterocyclic ring (e.g., piperidine, pyrrolidine), $R^6$-(substituted or unsubstituted heterocycle) (e.g., $(CH_2)_3$-piperidine, $CH_2$-benzoxazole, $CH_2$-benzimidazole, $CH_2$-indole) or C(O)-(alkyl) (e.g. C(O)—$CH_3$);

$R^{20}$ is represented by the following structure:

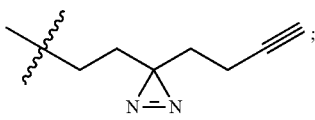 [SMILES: *CCC1(CCC#C)N=N1]

$R^3$ and $R^4$ are each independently H, F, Cl, Br, I, OH, $CF_3$, CN, $NO_2$, $C_1$-$C_5$ linear or branched, substituted or unsubstituted alkyl (e.g., methyl, ethyl, tert-butyl, $CH_2CH_2CH(CH_3)_2$, $CH_2$—$C(CH_3)_3$), $C_1$-$C_5$ linear or branched, or $C_3$-$C_8$ cyclic haloalkyl;

$R^5$ is OH, $C_1$-$C_5$ linear or branched, substituted or unsubstituted alkyl (e.g., methyl, ethyl), $C_1$-$C_5$ linear or branched, or $C_3$-$C_8$ cyclic haloalkyl, $N(R^a)(R^b)$, NHR, $NH_2$, N(alkyl)$_2$ (e.g. $N(CH_3)_2$, $N(CH_2CH_3)_2$, $N(CH_3)(CH_2CH_3)$) NH(alkyl) (e.g. $NHCH_3$, $NHCH_2CH_3$, $NHCH_2CH_2CH_3$) NH(cycloalkyl) (e.g. NH(cyclohexyl), NH(cylopentyl)), NH(aryl) (e.g. NH(phenyl), NH(pyridiny), NH-1-methyl-indole), NH(benzyl), N(cycloalkyl)$_2$ (e.g. N(cyclohexyl)$_2$, N(cylopentyl)$_2$), N(aryl)$_2$ (e.g. N(phenyl)$_2$, N(pyridiny)$_2$), N(alkyl)(aryl) (e.g. N(methyl)(phenyl), N(methyl)(pyridinyl)), N(alkyl)(cycloalkyl) (e.g. N(methyl)(cyclopropyl), N(methyl)(cyclohexyl), N(methyl)(cyclopentyl)), N(aryl)(cycloalkyl) (e.g. N(phenyl)(cyclohexyl), N(pyridinyl)(cyclohexyl)), substituted or unsubstituted aryl, substituted or unsubstituted heteroaryl, substituted or unsubstituted $C_3$-$C_8$ cycloalkyl (e.g., cyclopropyl), substituted or unsubstituted 3-8 membered heterocyclic ring (e.g., pyrrolidine, piperidine, morpholine, tetrahydropyran), NH—$R^{20}$, NH—$R^6$—NH(alkyl), NH—$R^6$—$NH_2$, NH—$R^6$—N(alkyl)$_2$ (e.g. $NH(CH_2)_3N(CH_2CH_2CH_2CH_3)(CH_2CH_3)$, $NH(CH_2)_2N(CH_3)_2$), $NH(CH_2)_3N(CH_2CH_3)_2$, $NH(CH_2)_2N(CH_2CH_3)_2$, $NHCH_2CH(C_6H_5)N(CH_3)_2$), NH—$R^6$—N(alkyl)(cycloalkyl), NH—$R^6$—NH(cycloalkyl), NH—$R^6$—NH(aryl), NH—$R^6$—N(alkyl)(aryl) (e.g. $NH(CH_2)_3(C_6H_5)(CH_3)$), NH—$R^6$—OH, NH—$R^6$—O(alkyl) (e.g. $NH(CH_2)_3OCH_3$), NH—$R^6$—O(aryl) or NH—$R^6$—O(cycloalkyl);
or $R^5$ is represented by any one of the following structures:

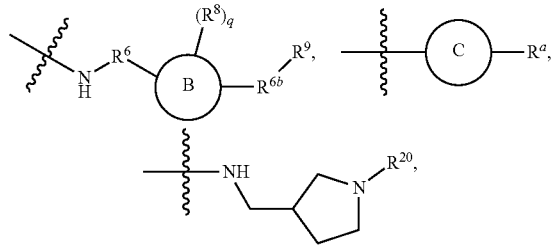

wherein
q is an integer between 0 and 4 (e.g., 0, 1 or 2);
$R^{6b}$ is absent or O, C=O, C(=O)—$[CH_2]_p$, $[CH_2]_p$—C(=O), $[CH_2]_p$ (e.g. $CH_2$, $CH_2CH_2$, $CH_2CH_2CH_2$, $CH_2CH_2CH_2CH_2$), $[CHR^{21}]_p$ (e.g. CHF, CH—$CH_3$), $[C(R^{21})_2]_p$ (e.g. $CF_2$) or $[CH_2]_{pa}$—O—$[CH_2]_{pb}$ (e.g. $CH_2OCH_2$), or $[CH_2]_p$—O (e.g., $CH_2CH_2O$);
$R^8$ is H, F, Cl, Br, I, OH, $CF_3$, CN, $NO_2$, $C_1$-$C_5$ linear or branched, substituted or unsubstituted alkyl (e.g., methyl, ethyl, tert-butyl, $CH_2CH_2CH(CH_3)_2$, $CH_2$—$C(CH_3)_3$), $C_1$-$C_5$ linear or branched, or $C_3$-$C_8$ cyclic haloalkyl;
$R^9$ is H, substituted or unsubstituted $C_1$-$C_5$ linear or branched alkyl, substituted or unsubstituted $C_1$-$C_5$ linear or branched alkenyl, $C_1$-$C_5$ linear or branched alkoxy (e.g., O—$CH_3$), $C_1$-$C_5$ linear or branched haloalkoxy (e.g., $OCF_3$, $OCHF_2$), $R^6$—OH, a substituted or unsubstituted aryl (e.g., phenyl, tolyl, fluorophenyl, cyanophenyl), substituted or unsubstituted heteroaryl (e.g., pyridine (2, 3, and 4-pyridine), furan, thiazole, isothiazole, thiophene, pyrrole, methylthiophene, methylfuran, methylpyridine, methylthiazole, indole, benzimidazole, pyrrolopyridine, benzoxazole), substituted or unsubstituted $C_3$-$C_8$ cycloalkyl (e.g., cyclopropyl, methylcyclopropyl, cyclobutyl, cyclohexyl, cyclohexenyl, cyclopentyl), $C_1$-$C_5$ linear or branched, or $C_3$-$C_8$ cyclic haloalkyl (e.g. $CF_3$, $CHF_2$), substituted or unsubstituted 3-8 membered heterocyclic ring (e.g. oxetane, azetidine, methyloxetane, tetrahydrofuran, methyltetrahydropyran, pyrrolidine, methylpyrrolidine, tetrahydropyran, tetrahydrothiopyran, piperidine, methylpiperidine, azepane, oxepane, 2H-thiopyran-tetrahydro-1,1-dioxide), $NH_2$, $N(alkyl)_2$ (e.g. $N(CH_3)_2$, $N(CH_2CH_3)_2$, $N(CH_3)(CH_2CH_3)$) NH(alkyl) (e.g. $NHCH_3$, $NHCH_2CH_3$, $NHCH_2CH_2CH_3$), or $R^{20}$;

$R^a$ is $R^{101}$-$R^{102}$, $R^{20}$, $R^6$—NH(alkyl), $R^6$—$NH_2$, $R^6$—N(alkyl)$_2$, $R^6$—N(alkyl)(cycloalkyl), $R^6$—NH(cycloalkyl), $R^6$—NH(aryl), $R^6$—OH, $R^6$—O(alkyl), $R^6$—O(aryl) or $R^6$—O(cycloalkyl)

or $R^a$ is represented by the following structures:

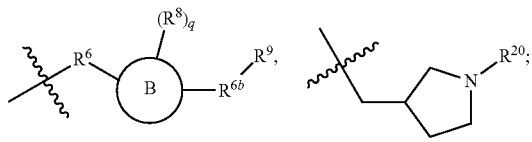

$R^b$ is $R^{103}$-$R^{104}$;

wherein $R^{101}$ and $R^{103}$ are each independently absent or O, C=O, C(=O)—$[CH_2]_p$, $[CH_2]_p$—C(=O), $[CH_2]_p$ (e.g. $CH_2$, $CH_2CH_2$, $CH_2CH_2CH_2$, $CH_2CH_2CH_2CH_2$), $[CHR^{21}]_p$ (e.g. CHF), $[C(R^{21})_2]_p$ (e.g. $CF_2$) or $[CH_2]_{pa}$—O—$[CH_2]_{pb}$ (e.g. $CH_2OCH_2$), or $[CH_2]_p$—O (e.g., $CH_2CH_2O$), substituted or unsubstituted arylene, substituted or unsubstituted heteroarylene, substituted or unsubstituted heterocycloalkylene or substituted or unsubstituted cycloalkylene wherein p is an integer between 0 and 10;

$R^{102}$ and $R^{104}$ are each independently H, F, Cl, Br, I, OH, $CF_3$, CN, $NO_2$, $C_1$-$C_5$ linear or branched, substituted or unsubstituted alkyl (e.g., methyl, ethyl, propyl, isopropyl, isobutyl), $C_1$-$C_5$ linear or branched alkoxy (e.g. methoxy), $C_1$-$C_5$ linear or branched haloalkyl (e.g., $CHF_2$, $CF_3$, $R^6$-aryl (e.g., $CH_2$-Ph, $CH_2$-Ph-ethyl), $R^6$—N(alkyl)$_2$, $R^6$—NH(alkyl), ($R^6$—NH(cycloalkyl), ($R^6$—NH(aryl), substituted or unsubstituted aryl (e.g., phenyl, ethylphenyl), substituted or unsubstituted heteroaryl (e.g., pyridine (2, 3, and 4-pyridine) or benzimidazole), substituted or unsubstituted $C_3$-$C_8$ cycloalkyl (e.g., cyclopropyl), substituted or unsubstituted 3-8 membered heterocyclic ring (e.g., piperidine, pyrrolidine), $R^6$-(substituted or unsubstituted heterocycle) (e.g., $(CH_2)_3$-piperidine) or C(O)-(alkyl) (e.g. C(O)—$CH_3$);

or $R^a$ and $R^b$ are joined to form a substituted or unsubstituted 3-8 membered heterocyclic ring (e,g, morpholine, piperidine);

B ring is a substituted or unsubstituted saturated, unsaturated or aromatic, single, fused or spiro, carbocyclic or heterocyclic 3-12 membered ring, including a single or fused $C_3$-$C_{12}$ aromatic or heteroaromatic ring (e.g. phenyl, pyrimidine, 2-, 3- or 4-pyridine, pyridazine, pyrazine, isothiazole, thiadiazole, imidazole, triazole, thiazole, oxazole, isoxazole, 1-methylimidazole, pyrrole, furan, thiophene, oxadiazole, indole, indane, benzodihydrofuran, tetrahydroquinoline, or pyrazole), saturated or unsaturated 3-8 membered heterocyclic ring (e.g. tetrahydropyran, tetrahydrofuran, pyrrolidine, piperidine, piperazine, 2-oxopyrrolidine, 2-pyrrolidone, 2,5-dioxopyrrolidine, 2,5-dioxoimidazolidine, 2,5-dihydrothiazole, oxetane, chromane), $C_3$-$C_8$ cycloalkyl (e.g. cyclobutyl, cyclohexyl, cyclopentyl, cyclooctyl), $C_3$-$C_8$ cycloalkenyl or a spiro ring system (e.g.

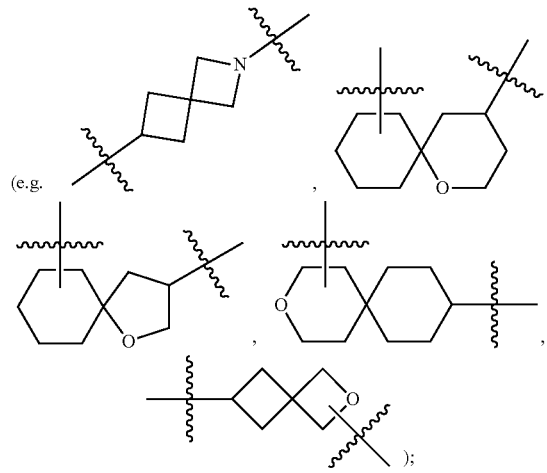

C ring is a 5-10 membered heterocyclic, aryl or heteroaryl ring (e.g. benzene, benzopyrrolidine, piperazine, pyrrolidine, piperidine, morpholine, tetrahydropyran or thiomorpholine-1,1-dioxide);

$X^1$-$X^5$ are each independently C, CH or N;

$X^6$-$X^7$ are each independently CH or N;

m, n, l and k are each independently an integer between 0 and 4 (e.g., 0, 1 or 2);

i is 0 or 1;

or its pharmaceutically acceptable salt, optical isomer, tautomer, hydrate, N-oxide, reverse amide analog, prodrug, isotopic variant (e.g., deuterated analog), PROTAC, pharmaceutical product or any combination thereof.

In some embodiments, each of the variables R-$R^{104}$ (R, $R^1$, $R^2$, $R^3$, $R^4$, $R^5$, $R^7$, $R^8$, $R^9$, $R^{21}$, $R^{101}$, $R^{102}$, $R^{103}$ and $R^{104}$) of formula I may be further substituted with at least one substitution selected from: F, Cl, Br, I, OH, SH, $C_1$-$C_5$ linear alkyne (e.g., acetylene), diazirine, $C_1$-$C_5$ linear, cyclic or branched alkyl (e.g. methyl, ethyl, propyl, isopropyl or cyclopropyl), substituted or unsubstituted benzyl (e.g., benzyl, methylbenzyl), substituted or unsubstituted aryl (e.g., phenyl, fluorophenyl), heteroaryl (e.g., indole, tetrahydropyran, pyridine (2, 3, and 4-pyridine)), $C_3$-$C_8$ cycloalkyl (e.g., cyclopropyl), $C_1$-$C_5$ linear or branched alkyl-OH (e.g., $C(CH_3)_2CH_2$—OH, $CH_2CH_2$—OH), 3-8 membered heterocyclic ring (e.g., piperidine), alkoxy (e.g. methoxy, ethoxy, propyloxy, isopropyloxy), $NH_2$, $N(alkyl)_2$ (e.g. $N(CH_3)_2$, $N(CH_2CH_3)_2$, $N(CH_3)(CH_2CH_3)$), NH(alkyl) (e.g. $NHCH_3$, $NHCH_2CH_3$, $NHCH_2CH_2CH_3$) NH(cycloalkyl) (e.g. NH(cyclohexyl), NH(cylopentyl)), NH(aryl) (e.g. NH(phenyl), NH(pyridiny)), NH(benzyl), N(cycloalkyl)$_2$ (e.g. N(cyclohexyl)$_2$, N(cylopentyl)$_2$), N(aryl)$_2$ (e.g. N(phenyl)$_2$, N(pyridiny)$_2$), N(alkyl)(aryl) (e.g. N(methyl)(phenyl), N(methyl)(pyridinyl)), N(alkyl)(cycloalkyl) (e.g. N(methyl)(cyclopropyl), N(methyl)(cyclohexyl), N(methyl)(cyclopentyl)), N(aryl)(cycloalkyl) (e.g. N(phenyl)(cyclohexyl), N(pyridinyl)(cyclohexyl)), NHC(O)(alkyl) (e.g. NHC(O)$CH_3$), $CF_3$, aryl, phenyl, heteroaryl, $C_3$-$C_8$ cycloalkyl, halophenyl, (benzyloxy)phenyl, CN and $NO_2$.

In some embodiments, in formula (I): m+n=1. In other embodiments, m=0 and n=1. In other embodiments, m=1 and n=0. In other embodiments, m+n>2. In other embodiments, m+n=1 or m+n>2.

In various embodiments, this invention is directed to a compound represented by the structure of formula (I(a)):

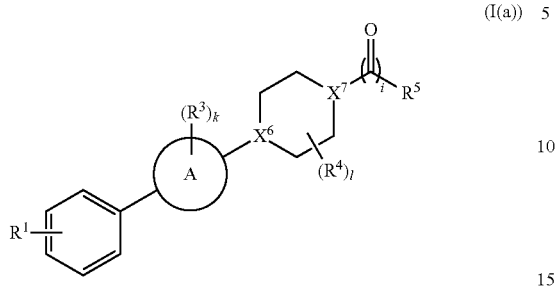

wherein

A ring is a single aromatic or heteroaromatic ring (e.g. phenyl, pyrimidine, 2-, 3- or 4-pyridine, pyridazine, pyrazine, isothiazole, thiadiazole, imidazole, triazole, thiazole, oxazole, isoxazole, 1-methylimidazole, pyrrole, furan, thiophene, oxadiazole, or pyrazole)

$R^1$ is H, F, Cl, Br, I, OH, $R^6$—OH, —$R^6$—O—$R^7$, O—$R^{20}$, $CF_3$, $OCH_3$, CN, $NO_2$, —$CH_2CN$, —$R^6CN$, $C_1$-$C_5$ linear or branched, substituted or unsubstituted alkyl (e.g., methyl, ethyl), $C_1$-$C_5$ linear or branched, or $C_3$-$C_8$ cyclic haloalkyl (e.g., $CHF_2$), $C_1$-$C_5$ substituted or unsubstituted, linear or branched, or $C_3$-$C_8$ cyclic alkoxy (e.g. methoxy, O—$(CH_2)_2$—OH), $C_1$-$C_5$ linear or branched haloalkoxy (e.g., $OCF_3$, $OCHF_2$), NH—C(O)—$R^7$ (e.g., NHC(O)—$CH_3$), $C_1$-$C_5$ linear or branched alkoxyalkyl;

wherein $R^6$ is absent or O, C=O, C(=O)—$[CH_2]_p$, $[CH_2]_p$—C(=O), $[CH_2]_p$ (e.g. $CH_2$, $CH_2CH_2$, $CH_2CH_2CH_2$, $CH_2CH_2CH_2CH_2$), $[CHR^{21}]_p$ (e.g. CHF, CH—$CH_3$), $[C(R^{21})_2]_p$ (e.g. $CF_2$) or $[CH_2]_{pa}$—O—$[CH_2]_{pb}$ (e.g. $CH_2OCH_2$), or $[CH_2]_p$—O (e.g., $CH_2CH_2O$);

wherein p is an integer between 1 and 10; and each pa and pb is independently an integer between 1 and 5;

$R^{21}$ is H, F, Cl, Br, I, OH, $CF_3$, CN, $NO_2$, $C_1$-$C_5$ linear or branched, substituted or unsubstituted alkyl (e.g., methyl, ethyl, propyl, isopropyl, isobutyl), $C_1$-$C_5$ linear or branched alkoxy (e.g. methoxy), $C_1$-$C_5$ linear or branched haloalkyl (e.g., $CHF_2$, $CF_3$, $R^6$-aryl (e.g., $CH_2$-Ph, $CH_2$-Ph-ethyl), $R^6$—N(alkyl)$_2$, $R^6$—NH(alkyl), ($R^6$—NH (cycloalkyl), ($R^6$—NH(aryl), substituted or unsubstituted aryl (e.g., phenyl, ethylphenyl), substituted or unsubstituted heteroaryl (e.g., pyridine (2, 3, and 4-pyridine) or benzimidazole), substituted or unsubstituted $C_3$-$C_8$ cycloalkyl (e.g., cyclopropyl), substituted or unsubstituted 3-8 membered heterocyclic ring (e.g., piperidine, pyrrolidine), $R^6$-(substituted or unsubstituted heterocycle) (e.g., $(CH_2)_3$-piperidine) or C(O)-(alkyl) (e.g. C(O)—$CH_3$);

or wherein two geminal or vicinal $R^2$ substituents are joined to form a substituted or unsubstituted $C_3$-$C_8$ cycloalkyl (e.g., cyclopropyl);

$R^7$ is H, $C_1$-$C_5$ substituted or unsubstituted linear or branched alkyl (e.g., methyl, ethyl, $CH_2$—$CH_2$—O—$CH_3$), $C_1$-$C_5$ linear or branched alkoxy (e.g., O—$CH_3$), C(O)R, or $S(O)_2R$;

wherein

R is H, F, Cl, Br, I, OH, $CF_3$, CN, $NO_2$, $C_1$-$C_5$ linear or branched, substituted or unsubstituted alkyl (e.g., methyl, ethyl, propyl, isopropyl, isobutyl), $C_1$-$C_5$ linear or branched alkoxy (e.g. methoxy), $C_1$-$C_5$ linear or branched haloalkyl (e.g., $CHF_2$, $CF_3$, $R^6$-aryl (e.g., $CH_2$-Ph, $CH_2$-Ph-ethyl), $R^6$—N(alkyl)$_2$, $R^6$—NH(alkyl), ($R^6$—NH(cycloalkyl), ($R^6$—NH(aryl), substituted or unsubstituted aryl (e.g., phenyl, ethylphenyl), substituted or unsubstituted heteroaryl (e.g., pyridine (2, 3, and 4-pyridine) or benzimidazole), substituted or unsubstituted $C_3$-$C_8$ cycloalkyl (e.g., cyclopropyl), substituted or unsubstituted 3-8 membered heterocyclic ring (e.g., piperidine, pyrrolidine), $R^6$-(substituted or unsubstituted heterocycle) (e.g., $(CH_2)_3$-piperidine, $CH_2$-benzoxazole, $CH_2$-benzimidazole, $CH_2$-indole) or C(O)-(alkyl) (e.g. C(O)—$CH_3$);

$R^{20}$ is represented by the following structure:

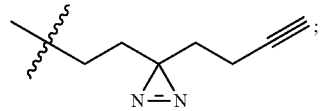 [SMILES: *CCC1(CCC#C)N=N1]

$R^3$ and $R^4$ are each independently H, F, Cl, Br, I, OH, $CF_3$, CN, $NO_2$, $C_1$-$C_5$ linear or branched, substituted or unsubstituted alkyl (e.g., methyl, ethyl, tert-butyl, $CH_2CH_2CH(CH_3)_2$, $CH_2$—$C(CH_3)_3$), $C_1$-$C_5$ linear or branched, or $C_3$-$C_8$ cyclic haloalkyl;

$R^5$ is OH, $C_1$-$C_5$ linear or branched, substituted or unsubstituted alkyl (e.g., methyl, ethyl), $C_1$-$C_5$ linear or branched, or $C_3$-$C_8$ cyclic haloalkyl, $N(R^a)(R^b)$, NHR, $NH_2$, N(alkyl)$_2$ (e.g. $N(CH_3)_2$, $N(CH_2CH_3)_2$, $N(CH_3)(CH_2CH_3)$)) NH(alkyl) (e.g. $NHCH_3$, $NHCH_2CH_3$, $NHCH_2CH_2CH_3$) NH(cycloalkyl) (e.g. NH(cyclohexyl), NH(cylopentyl)), NH(aryl) (e.g. NH(phenyl), NH(pyridiny), (e.g., NH-1-methyl-indole)), NH(benzyl), N(cycloalkyl)$_2$ (e.g. N(cyclohexyl)$_2$, N(cylopentyl)$_2$), N(aryl)$_2$ (e.g. N(phenyl)$_2$, N(pyridiny)$_2$), N(alkyl)(aryl) (e.g. N(methyl)(phenyl), N(methyl)(pyridinyl)), N(alkyl)(cycloalkyl) (e.g. N(methyl)(cyclopropyl), N(methyl)(cyclohexyl), N(methyl)(cyclopentyl)), N(aryl)(cycloalkyl) (e.g. N(phenyl)(cyclohexyl), N(pyridinyl)(cyclohexyl)), substituted or unsubstituted aryl, substituted or unsubstituted heteroaryl, substituted or unsubstituted $C_3$-$C_8$ cycloalkyl (e.g., cyclopropyl), substituted or unsubstituted 3-8 membered heterocyclic ring (e.g., pyrrolidine, piperidine, morpholine, tetrahydropyran), NH—$R^{20}$, NH—$R^6$—NH(alkyl), NH—$R^6$—$NH_2$, NH—$R^6$—N(alkyl)$_2$ (e.g. $NH(CH_2)_3N(CH_2CH_2CH_2CH_3)$ $(CH_2CH_3)$, $NH(CH_2)_2N(CH_3)_2$), $NH(CH_2)_3N$ $(CH_2CH_3)_2$, $NH(CH_2)_2N(CH_2CH_3)_2$, $NHCH_2CH$ $(C_6H_5)N(CH_3)_2$), NH—$R^6$—N(alkyl)(cycloalkyl), NH—$R^6$—NH(cycloalkyl), NH—$R^6$—NH(aryl), NH—$R^6$—N(alkyl)(aryl) (e.g. $NH(CH_2)_3(C_6H_5)$ $(CH_3)$), NH—$R^6$—OH, NH—$R^6$—O(alkyl) (e.g. $NH(CH_2)_3OCH_3$), NH—$R^6$—O(aryl) or NH—$R^6$—O (cycloalkyl);

or $R^5$ is represented by any one of the following structures:

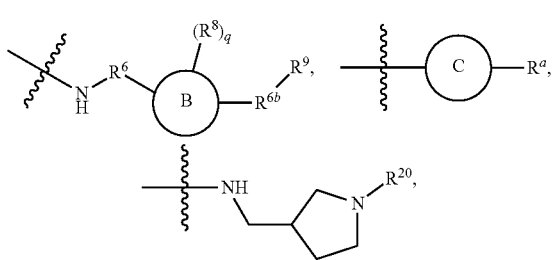

wherein
q is an integer between 0 and 4 (e.g., 0, 1 or 2);
$R^{6b}$ is absent or O, C=O, C(=O)—$[CH_2]_p$, $[CH_2]_p$—C(=O), $[CH_2]_p$ (e.g. $CH_2$, $CH_2CH_2$, $CH_2CH_2CH_2$, $CH_2CH_2CH_2CH_2$), $[CHR^{21}]_p$ (e.g. CHF, CH—$CH_3$), $[C(R^{21})_2]_p$ (e.g. $CF_2$) or $[CH_2]_{pa}$—O—$[CH_2]_{pb}$ (e.g. $CH_2OCH_2$), or $[CH_2]_p$—O (e.g., $CH_2CH_2O$);
$R^8$ is H, F, Cl, Br, I, OH, $CF_3$, CN, $NO_2$, $C_1$-$C_5$ linear or branched, substituted or unsubstituted alkyl (e.g., methyl, ethyl, tert-butyl, $CH_2CH_2CH(CH_3)_2$, $CH_2$—$C(CH_3)_3$), $C_1$-$C_5$ linear or branched, or $C_3$-$C_8$ cyclic haloalkyl;
$R^9$ is H, substituted or unsubstituted $C_1$-$C_5$ linear or branched alkyl, substituted or unsubstituted $C_1$-$C_5$ linear or branched alkenyl, $C_1$-$C_5$ linear or branched alkoxy (e.g., O—$CH_3$), $C_1$-$C_5$ linear or branched haloalkoxy (e.g., $OCF_3$, $OCHF_2$), $R^6$—OH, a substituted or unsubstituted aryl (e.g., phenyl, tolyl, fluorophenyl, cyanophenyl), substituted or unsubstituted heteroaryl (e.g., pyridine (2, 3, and 4-pyridine), furan, thiazole, isothiazole, thiophene, pyrrole, methylthiophene, methylfuran, methylpyridine, methylthiazole, indole, benzimidazole, pyrrolopyridine, benzoxazole), substituted or unsubstituted $C_3$-$C_8$ cycloalkyl (e.g., cyclopropyl, methylcyclopropyl, cyclobutyl, cyclohexyl, cyclohexenyl, cyclopentyl), $C_1$-$C_5$ linear or branched, or $C_3$-$C_8$ cyclic haloalkyl (e.g. $CF_3$, $CHF_2$), substituted or unsubstituted 3-8 membered heterocyclic ring (e.g. oxetane, azetidine, methyloxetane, tetrahydrofuran, methyltetrahydropyran, pyrrolidine, methylpyrrolidine, tetrahydropyran, tetrahydrothiopyran, piperidine, methylpiperidine, azepane, oxepane, 2H-Thiopyran-tetrahydro-1,1-dioxide), $NH_2$, $N(alkyl)_2$ (e.g. $N(CH_3)_2$, $N(CH_2CH_3)_2$, $N(CH_3)(CH_2CH_3)$) NH(alkyl) (e.g. $NHCH_3$, $NHCH_2CH_3$, $NHCH_2CH_2CH_3$) or $R^{20}$;
$R^a$ is $R^{101}$-$R^{102}$, $R^{20}$, $R^6$—NH(alkyl), $R^6$—$NH_2$, $R^6$—$N(alkyl)_2$, $R^6$—N(alkyl)(cycloalkyl), $R^6$—NH(cycloalkyl), $R^6$—NH(aryl), $R^6$—OH, $R^6$—O(alkyl), $R^6$—O(aryl) or $R^6$—O(cycloalkyl);
or $R^a$ is represented by any one of the following structures:

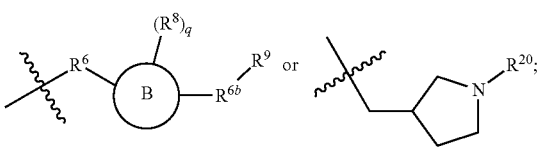

$R^b$ is $R^{103}$-$R^{104}$;
wherein
$R^{101}$ and $R^{103}$ are each independently absent or O, C=O, C(=O)—$[CH_2]_p$, $[CH_2]_p$—C(=O),
$[CH_2]_p$ (e.g. $CH_2$, $CH_2CH_2$, $CH_2CH_2CH_2$, $CH_2CH_2CH_2CH_2$), $[CHR^{21}]_p$ (e.g. CHF), $[C(R^{21})_2]_p$ (e.g. $CF_2$) or $[CH_2]_{pa}$—O—$[CH_2]_{pb}$ (e.g. $CH_2OCH_2$), or $[CH_2]_p$—O (e.g., $CH_2CH_2O$), substituted or unsubstituted arylene, substituted or unsubstituted heteroarylene, substituted or unsubstituted heterocycloalkylene or substituted or unsubstituted cycloalkylene;
wherein p is an integer between 0 and 10;
$R^{102}$ and $R^{104}$ are each independently H, F, Cl, Br, I, OH, $CF_3$, CN, $NO_2$, $C_1$-$C_5$ linear or branched, substituted or unsubstituted alkyl (e.g., methyl, ethyl, propyl, isopropyl, isobutyl), $C_1$-$C_5$ linear or branched alkoxy (e.g. methoxy), $C_1$-$C_5$ linear or branched haloalkyl (e.g., $CHF_2$, $CF_3$, $R^6$-aryl (e.g., $CH_2$-Ph, $CH_2$-Ph-ethyl), $R^6$—$N(alkyl)_2$, $R^6$—NH(alkyl), ($R^6$—NH(cycloalkyl), ($R^6$—NH (aryl), substituted or unsubstituted aryl (e.g., phenyl, ethylphenyl), substituted or unsubstituted heteroaryl (e.g., pyridine (2, 3, and 4-pyridine) or benzimidazole), substituted or unsubstituted $C_3$-$C_8$ cycloalkyl (e.g., cyclopropyl), substituted or unsubstituted 3-8 membered heterocyclic ring (e.g., piperidine, pyrrolidine), $R^6$-(substituted or unsubstituted heterocycle) (e.g., $(CH_2)_3$-piperidine) or C(O)-(alkyl) (e.g. C(O)—$CH_3$);
or $R^a$ and $R^b$ are joined to form a substituted or unsubstituted 3-8 membered heterocyclic ring (e.g., morpholine, piperidine);
B ring is a substituted or unsubstituted saturated, unsaturated or aromatic, single, fused or spiro, carbocyclic or heterocyclic 3-12 membered ring, including a single or fused $C_3$-$C_{12}$ aromatic or heteroaromatic ring (e.g. phenyl, pyrimidine, 2-, 3- or 4-pyridine, pyridazine, pyrazine, isothiazole, thiadiazole, imidazole, triazole, thiazole, oxazole, isoxazole, 1-methylimidazole, pyrrole, furan, thiophene, oxadiazole, indole, indane, benzodihydrofuran, tetrahydroquinoline, or pyrazole), a 3-8 membered saturated or unsaturated heterocyclic ring (e.g. tetrahydropyran, tetrahydrofuran, pyrrolidine, piperidine, piperazine, 2-oxopyrrolidine, 2,5-dioxopyrrolidine, 2,5-dioxoimidazolidine, oxetane, chromane), a $C_3$-$C_8$ cycloalkyl ring (e.g. cyclobutyl, cyclohexyl, cyclopentyl, cyclooctyl) a $C_3$-$C_8$ cycloalkenyl ring, or a spiro ring system (e.g.

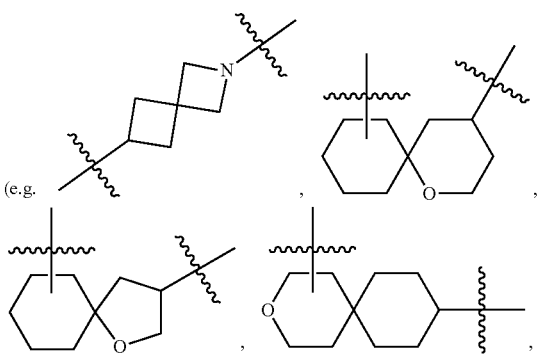

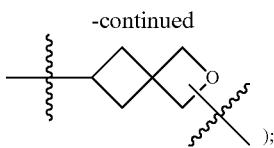

C ring is a 5-10 membered heterocyclic, aryl or heteroaryl ring (e.g. benzene, benzopyrrolidine, piperazine, pyrrolidine, piperidine, morpholine, tetrahydropyran or thiomorpholine-1,1-dioxide);

$X^6$-$X^7$ are each independently CH or N;

l and k are each independently an integer between 0 and 4 (e.g., 0, 1 or 2);

i is 0 or 1;

or its pharmaceutically acceptable salt, optical isomer, tautomer, hydrate, N-oxide, reverse amide analog, prodrug, isotopic variant (e.g., deuterated analog), PROTAC, pharmaceutical product or any combination thereof.

In some embodiments, each of the variables R-$R^{104}$ of formula I(a) may be further substituted with at least one substitution selected from: F, Cl, Br, I, OH, SH, $C_1$-$C_5$ linear alkyne, diazirine, $C_1$-$C_5$ linear, cyclic or branched alkyl (e.g. methyl, ethyl, propyl, isopropyl or cyclopropyl), substituted or unsubstituted benzyl (e.g., benzyl, methylbenzyl), substituted or unsubstituted aryl (e.g., phenyl, fluorophenyl), heteroaryl (e.g., indole, tetrahydropyran, pyridine (2, 3, and 4-pyridine)), $C_3$-$C_8$ cycloalkyl (e.g., cyclopropyl), $C_1$-$C_5$ linear or branched alkyl-OH (e.g., $C(CH_3)_2CH_2$—OH, $CH_2CH_2$—OH), 3-8 membered heterocyclic ring (e.g., piperidine), alkoxy (e.g. methoxy, ethoxy, propyloxy, isopropyloxy), $NH_2$, $N(alkyl)_2$ (e.g. $N(CH_3)_2$, $N(CH_2CH_3)_2$, $N(CH_3)(CH_2CH_3)$), NH(alkyl) (e.g. $NHCH_3$, $NHCH_2CH_3$, $NHCH_2CH_2CH_3$) NH(cycloalkyl) (e.g. NH(cyclohexyl), NH(cylopentyl)), NH(aryl) (e.g. NH(phenyl), NH(pyridiny)), NH(benzyl), $N(cycloalkyl)_2$ (e.g. $N(cyclohexyl)_2$, $N(cylopentyl)_2$), $N(aryl)_2$ (e.g. $N(phenyl)_2$, $N(pyridiny)_2$), N(alkyl)(aryl) (e.g. N(methyl)(phenyl), N(methyl)(pyridinyl)), N(alkyl)(cycloalkyl) (e.g. N(methyl)(cyclopropyl), N(methyl)(cyclohexyl), N(methyl)(cyclopentyl)), N(aryl)(cycloalkyl) (e.g. N(phenyl)(cyclohexyl), N(pyridinyl)(cyclohexyl)), NHC(O)(alkyl) (e.g. $NHC(O)CH_3$), $CF_3$, aryl, phenyl, heteroaryl, $C_3$-$C_8$ cycloalkyl, halophenyl, (benzyloxy)phenyl, CN and $NO_2$.

In various embodiments, this invention is directed to a compound represented by the structure of formula (I(a(i))):

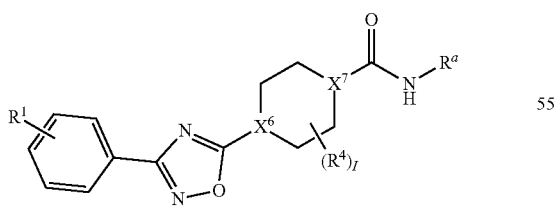

(I(a(i)))

wherein $R^1$ is H, F, Cl, Br, I, OH, $R^6$—OH, O—$R^{20}$, —$R^6$—O—$R^7$, $CF_3$, $OCH_3$, CN, $NO_2$, —$CH_2CN$, —$R^6CN$, $C_1$-$C_5$ linear or branched, substituted or unsubstituted alkyl (e.g., methyl, ethyl), $C_1$-$C_5$ linear or branched, or $C_3$-$C_8$ cyclic haloalkyl (e.g., $CHF_2$), $C_1$-$C_5$ substituted or unsubstituted, linear or branched, or $C_3$-$C_8$ cyclic alkoxy (e.g. methoxy, O—$(CH_2)_2$—OH), $C_1$-$C_5$ linear or branched haloalkoxy (e.g., $OCF_3$, $OCHF_2$), NH—C(O)—$R^7$ (e.g., NHC(O)—$CH_3$), $C_1$-$C_5$ linear or branched alkoxyalkyl;

wherein $R^6$ is absent or O, C=O, C(=O)—$[CH_2]_p$, $[CH_2]_p$—C(=O), $[CH_2]_p$ (e.g. $CH_2$, $CH_2CH_2$, $CH_2CH_2CH_2$, $CH_2CH_2CH_2CH_2$), $[CHR^{21}]_p$ (e.g. CHF, CH—$CH_3$), $[C(R^{21})_2]_p$ (e.g. $CF_2$) or $[CH_2]_{pa}$—O—$[CH_2]_{pb}$ (e.g. $CH_2OCH_2$), or $[CH_2]_p$—O (e.g., $CH_2CH_2O$);

wherein p is an integer between 1 and 10; and each pa and pb is independently an integer between 1 and 5;

$R^{21}$ is H, F, Cl, Br, I, OH, $CF_3$, CN, $NO_2$, $C_1$-$C_5$ linear or branched, substituted or unsubstituted alkyl (e.g., methyl, ethyl, propyl, isopropyl, isobutyl), $C_1$-$C_5$ linear or branched alkoxy (e.g. methoxy), $C_1$-$C_5$ linear or branched haloalkyl (e.g., $CHF_2$, $CF_3$, $R^6$-aryl (e.g., $CH_2$-Ph, $CH_2$-Ph-ethyl), $R^6$—$N(alkyl)_2$, $R^6$—NH(alkyl), ($R^6$—NH(cycloalkyl), ($R^6$—NH(aryl), substituted or unsubstituted aryl (e.g., phenyl, ethylphenyl), substituted or unsubstituted heteroaryl (e.g., pyridine (2, 3, and 4-pyridine) or benzimidazole), substituted or unsubstituted $C_3$-$C_8$ cycloalkyl (e.g., cyclopropyl), substituted or unsubstituted 3-8 membered heterocyclic ring (e.g., piperidine, pyrrolidine), $R^6$-(substituted or unsubstituted heterocycle) (e.g., $(CH_2)_3$-piperidine) or C(O)-(alkyl) (e.g. C(O)—$CH_3$);

or wherein two geminal or vicinal $R^{21}$ substituents are joined to form a substituted or unsubstituted $C_3$-$C_8$ cycloalkyl (e.g., cyclopropyl);

$R^7$ is H, $C_1$-$C_5$ substituted or unsubstituted linear or branched alkyl (e.g., methyl, ethyl, $CH_2$—$CH_2$—O—$CH_3$), $C_1$-$C_5$ linear or branched alkoxy (e.g., O—$CH_3$), C(O)R, or $S(O)_2R$;

wherein

R is H, F, Cl, Br, I, OH, $CF_3$, CN, $NO_2$, $C_1$-$C_5$ linear or branched, substituted or unsubstituted alkyl (e.g., methyl, ethyl, propyl, isopropyl, isobutyl), $C_1$-$C_5$ linear or branched alkoxy (e.g. methoxy), $C_1$-$C_5$ linear or branched haloalkyl (e.g., $CHF_2$, $CF_3$, $R^6$-aryl (e.g., $CH_2$-Ph, $CH_2$-Ph-ethyl), $R^6$—$N(alkyl)_2$, $R^6$—NH(alkyl), ($R^6$—NH(cycloalkyl), ($R^6$—NH(aryl), substituted or unsubstituted aryl (e.g., phenyl, ethylphenyl), substituted or unsubstituted heteroaryl (e.g., pyridine (2, 3, and 4-pyridine) or benzimidazole), substituted or unsubstituted $C_3$-$C_8$ cycloalkyl (e.g., cyclopropyl), substituted or unsubstituted 3-8 membered heterocyclic ring (e.g., piperidine, pyrrolidine), $R^6$-(substituted or unsubstituted heterocycle) (e.g., $(CH_2)_3$-piperidine, $CH_2$-benzoxazole, $CH_2$-benzimidazole, $CH_2$-indole) or C(O)-(alkyl) (e.g. C(O)—$CH_3$);

$R^{20}$ is represented by the following structure:

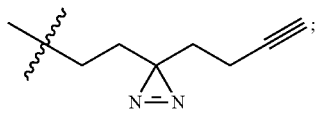 [SMILES: *CCC1(CCC#C)N=N1]

$R^4$ is H, F, Cl, Br, I, OH, $CF_3$, CN, $NO_2$, $C_1$-$C_5$ linear or branched, substituted or unsubstituted alkyl (e.g., methyl, ethyl, tert-butyl, $CH_2CH_2CH(CH_3)_2$, $CH_2$—C$(CH_3)_3$), $C_1$-$C_5$ linear or branched, or $C_3$-$C_8$ cyclic haloalkyl;

$R^a$ is $R^{101}$-$R^{102}$, $R^{20}$, $R^6$—NH(alkyl), $R^6$—$NH_2$, $R^6$—N(alkyl)$_2$, $R^6$—N(alkyl)(cycloalkyl), $R^6$—NH(cycloalkyl), $R^6$—NH(aryl), $R^6$—OH, $R^6$—O(alkyl), $R^6$—O(aryl) or $R^6$—O(cycloalkyl);

or $R^a$ is represented by the following structures:

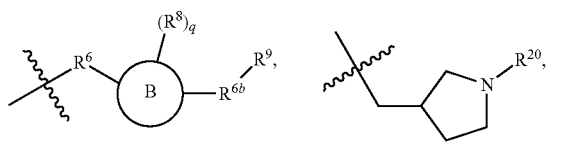

wherein
q is an integer between 0 and 4 (e.g., 0, 1 or 2);

$R^{6b}$ is absent or O, C=O, C(=O)—$[CH_2]_p$, $[CH_2]_p$—C(=O), $[CH_2]_p$ (e.g. $CH_2$, $CH_2CH_2$, $CH_2CH_2CH_2$, $CH_2CH_2CH_2CH_2$), $[CHR^{21}]_p$ (e.g. CHF, CH—$CH_3$), $[C(R^{21})_2]_p$ (e.g. $CF_2$) or $[CH_2]_{pa}$—O—$[CH_2]_{pb}$ (e.g. $CH_2OCH_2$), or $[CH_2]_p$—O (e.g., $CH_2CH_2O$);

$R^8$ is H, F, Cl, Br, I, OH, $CF_3$, CN, $NO_2$, $C_1$-$C_5$ linear or branched, substituted or unsubstituted alkyl (e.g., methyl, ethyl, tert-butyl, $CH_2CH_2CH(CH_3)_2$, $CH_2$—C$(CH_3)_3$), $C_1$-$C_5$ linear or branched, or $C_3$-$C_8$ cyclic haloalkyl;

$R^9$ is H, substituted or unsubstituted $C_1$-$C_5$ linear or branched alkyl, substituted or unsubstituted $C_1$-$C_5$ linear or branched alkenyl, $C_1$-$C_5$ linear or branched alkoxy (e.g., O—$CH_3$), $C_1$-$C_5$ linear or branched haloalkoxy (e.g., $OCF_3$, $OCHF_2$), $R^6$—OH, a substituted or unsubstituted aryl (e.g., phenyl, tolyl, fluorophenyl, cyanophenyl), substituted or unsubstituted heteroaryl (e.g., pyridine (2, 3, and 4-pyridine), furan, thiazole, isothiazole, thiophene, pyrrole, methylthiophene, methylfuran, methylpyridine, methylthiazole, indole, benzimidazole, pyrrolopyridine, benzoxazole), substituted or unsubstituted $C_3$-$C_8$ cycloalkyl (e.g., cyclopropyl, methylcyclopropyl, cyclobutyl, cyclohexyl, cyclohexenyl, cyclopentyl), $C_1$-$C_5$ linear or branched, or $C_3$-$C_8$ cyclic haloalkyl (e.g. $CF_3$, $CHF_2$), substituted or unsubstituted 3-8 membered heterocyclic ring (e.g. oxetane, azetidine, methyloxetane, tetrahydrofuran, methyltetrahydropyran, pyrrolidine, methylpyrrolidine, tetrahydropyran, tetrahydrothiopyran, piperidine, methylpiperidine, azepane, oxepane, 2H-Thiopyrantetrahydro-1,1-dioxide), $NH_2$, N(alkyl)$_2$ (e.g. N$(CH_3)_2$, N$(CH_2CH_3)_2$, N$(CH_3)(CH_2CH_3)$) NH(alkyl) (e.g. $NHCH_3$, $NHCH_2CH_3$, $NHCH_2CH_2CH_3$) or $R^{20}$;

$R^{101}$ is absent or O, C=O, C(=O)—$[CH_2]_p$, $[CH_2]_p$—C(=O), $[CH_2]_p$ (e.g. $CH_2$, $CH_2CH_2$, $CH_2CH_2CH_2$, $CH_2CH_2CH_2CH_2$), $[CHR^{21}]_p$ (e.g. CHF), $[C(R^{21})_2]_p$ (e.g. $CF_2$) or $[CH_2]_{pa}$—O—$[CH_2]_{pb}$ (e.g. $CH_2OCH_2$), or $[CH_2]_p$—O (e.g., $CH_2CH_2O$), substituted or unsubstituted arylene, substituted or unsubstituted heteroarylene, substituted or unsubstituted heterocycloalkylene or substituted or unsubstituted cycloalkylene;

wherein p is an integer between 0 and 10;

$R^2$ is H, F, Cl, Br, I, OH, $CF_3$, CN, $NO_2$, $C_1$-$C_5$ linear or branched, substituted or unsubstituted alkyl (e.g., methyl, ethyl, propyl, isopropyl, isobutyl), $C_1$-$C_5$ linear or branched alkoxy (e.g. methoxy), $C_1$-$C_5$ linear or branched haloalkyl (e.g., $CHF_2$, $CF_3$, $R^6$-aryl (e.g., $CH_2$-Ph, $CH_2$-Ph-ethyl), $R^6$—N(alkyl)$_2$, $R^6$—NH(alkyl), ($R^6$—NH(cycloalkyl), ($R^6$—NH(aryl), substituted or unsubstituted aryl (e.g., phenyl, ethylphenyl), substituted or unsubstituted heteroaryl (e.g., pyridine (2, 3, and 4-pyridine) or benzimidazole), substituted or unsubstituted $C_3$-$C_8$ cycloalkyl (e.g., cyclopropyl), substituted or unsubstituted 3-8 membered heterocyclic ring (e.g., piperidine, pyrrolidine), $R^6$-(substituted or unsubstituted heterocycle) (e.g., $(CH_2)_3$-piperidine) or C(O)-(alkyl) (e.g. C(O)—$CH_3$);

B ring is a substituted or unsubstituted saturated, unsaturated or aromatic, single, fused or spiro, carbocyclic or heterocyclic 3-12 membered ring, including a single or fused $C_3$-$C_{12}$ aromatic or heteroaromatic ring (e.g. phenyl, pyrimidine, 2-, 3- or 4-pyridine, pyridazine, pyrazine, isothiazole, thiadiazole, imidazole, triazole, thiazole, oxazole, isoxazole, 1-methylimidazole, pyrrole, furan, thiophene, oxadiazole, indole, indane, benzodihydrofuran, tetrahydroquinoline, or pyrazole), a 3-8 membered saturated or unsaturated heterocyclic ring (e.g. tetrahydropyran, tetrahydrofuran, pyrrolidine, piperidine, piperazine, 2-oxopyrrolidine, 2,5-dioxopyrrolidine, 2,5-dioxoimidazolidine, oxetane, chromane), a $C_3$-$C_8$ cycloalkyl ring (e.g. cyclobutyl, cyclohexyl, cyclopentyl, cyclooctyl) a $C_3$-$C_8$ cycloalkenyl ring, or a spiro ring system

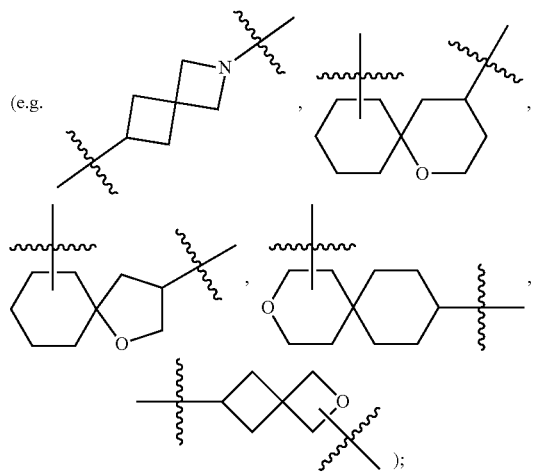

$X^6$-$X^7$ are each independently CH or N;
l is an integer between 0 and 4 (e.g., 0, 1 or 2);
or its pharmaceutically acceptable salt, optical isomer, tautomer, hydrate, N-oxide, reverse amide analog, prodrug, isotopic variant (e.g., deuterated analog), PROTAC, pharmaceutical product or any combination thereof.

In some embodiments, each of the variables R-$R^{104}$ of formula I(a(i)) may be further substituted with at least one substitution selected from: F, Cl, Br, I, OH, SH, $C_1$-$C_5$ linear alkyne, diazirine, $C_1$-$C_5$ linear, cyclic or branched alkyl (e.g. methyl, ethyl, propyl, isopropyl or cyclopropyl), substituted or unsubstituted benzyl (e.g., benzyl, methylbenzyl), substituted or unsubstituted aryl (e.g., phenyl, fluorophenyl), heteroaryl (e.g., indole, tetrahydropyran, pyridine (2, 3, and 4-pyridine)), $C_3$-$C_8$ cycloalkyl (e.g., cyclopropyl), $C_1$-$C_5$ linear or branched alkyl-OH (e.g., $C(CH_3)_2CH_2$—OH, $CH_2CH_2$—OH), 3-8 membered heterocyclic ring (e.g., piperidine), alkoxy (e.g. methoxy, ethoxy, propyloxy, isopropyloxy), $NH_2$, $N(alkyl)_2$ (e.g. $N(CH_3)_2$, $N(CH_2CH_3)_2$, $N(CH_3)(CH_2CH_3)$), NH(alkyl) (e.g. $NHCH_3$, $NHCH_2CH_3$, $NHCH_2CH_2CH_3$) NH(cycloalkyl) (e.g. NH(cyclohexyl), NH(cylopentyl)), NH(aryl) (e.g. NH(phenyl), NH(pyridiny)), NH(benzyl), $N(cycloalkyl)_2$ (e.g. $N(cyclohexyl)_2$, $N(cylopentyl)_2$), $N(aryl)_2$ (e.g. $N(phenyl)_2$, $N(pyridiny)_2$), N(alkyl)(aryl) (e.g. N(methyl)(phenyl), N(methyl)(pyridinyl)), N(alkyl)(cycloalkyl) (e.g. N(methyl)(cyclopropyl), N(methyl)(cyclohexyl), N(methyl)(cyclopentyl)), N(aryl)(cycloalkyl) (e.g. N(phenyl)(cyclohexyl), N(pyridinyl)(cyclohexyl)), NHC(O)(alkyl) (e.g. $NHC(O)CH_3$), $CF_3$, aryl, phenyl, heteroaryl, $C_3$-$C_8$ cycloalkyl, halophenyl, (benzyloxy)phenyl, CN and $NO_2$.

In various embodiments, this invention is directed to a compound represented by the structure of formula (I(a(ii))):

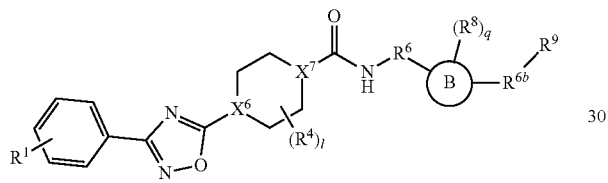

(I(a(ii)))

wherein
B ring is a substituted or unsubstituted saturated, unsaturated or aromatic, single, fused or spiro, carbocyclic or heterocyclic 3-12 membered ring, including a single or fused 3-12 membered aromatic or heteroaromatic ring (e.g. phenyl, pyrimidine, 2-, 3- or 4-pyridine, pyridazine, pyrazine, isothiazole, thiadiazole, imidazole, triazole, thiazole, oxazole, isoxazole, 1-methylimidazole, pyrrole, furan, thiophene, oxadiazole, indole, indane, benzodihydrofuran, tetrahydroquinoline, or pyrazole), a 3-8 membered saturated or unsaturated heterocyclic ring (e.g. tetrahydropyran, tetrahydrofuran, pyrrolidine, piperidine, piperazine, 2-oxopyrrolidine, 2,5-dioxopyrrolidine, 2,5-dioxoimidazolidine, oxetane, chromane), a $C_3$-$C_8$ cycloalkyl ring (e.g. cyclobutyl, cyclohexyl, cyclopentyl, cyclooctyl) a $C_3$-$C_8$ cycloalkenyl ring, or a spiro ring system

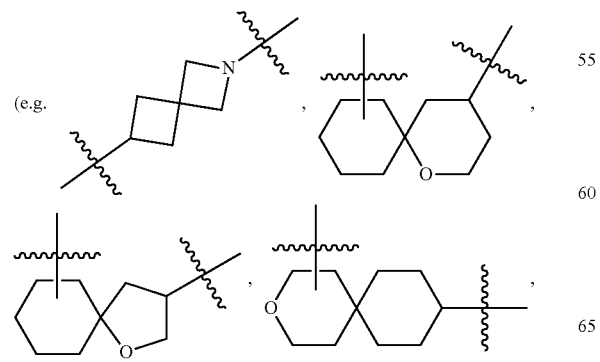

(e.g.

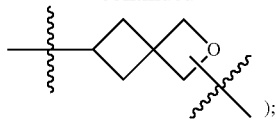

);

$R^1$ is H, F, Cl, Br, I, OH, $R^6$—OH, O—$R^{20}$, —$R^6$—O—$R^7$, $CF_3$, $OCH_3$, CN, $NO_2$, —$CH_2CN$, —$R^6CN$, $C_1$-$C_5$ linear or branched, substituted or unsubstituted alkyl (e.g., methyl, ethyl), $C_1$-$C_5$ linear or branched, or $C_3$-$C_8$ cyclic haloalkyl (e.g., $CHF_2$), $C_1$-$C_5$ substituted or unsubstituted, linear or branched, or $C_3$-$C_8$ cyclic alkoxy (e.g. methoxy, O—$(CH_2)_2$—OH), $C_1$-$C_5$ linear or branched haloalkoxy (e.g., $OCF_3$, $OCHF_2$), NH—C(O)—$R^7$ (e.g., NHC(O)—$CH_3$), $C_1$-$C_5$ linear or branched alkoxyalkyl;

wherein
$R^7$ is H, $C_1$-$C_5$ substituted or unsubstituted linear or branched alkyl (e.g., methyl, ethyl, $CH_2$—$CH_2$—O—$CH_3$), $C_1$-$C_5$ linear or branched alkoxy (e.g., O—$CH_3$), C(O)R, or $S(O)_2R$;

wherein
R is H, F, Cl, Br, I, OH, $CF_3$, CN, $NO_2$, $C_1$-$C_5$ linear or branched, substituted or unsubstituted alkyl (e.g., methyl, ethyl, propyl, isopropyl, isobutyl), $C_1$-$C_5$ linear or branched alkoxy (e.g. methoxy), $C_1$-$C_5$ linear or branched haloalkyl (e.g., $CHF_2$, $CF_3$, $R^6$-aryl (e.g., $CH_2$-Ph, $CH_2$-Ph-ethyl), $R^6$—$N(alkyl)_2$, $R^6$—NH(alkyl), ($R^6$—NH(cycloalkyl), ($R^6$—NH(aryl), substituted or unsubstituted aryl (e.g., phenyl, ethylphenyl), substituted or unsubstituted heteroaryl (e.g., pyridine (2, 3, and 4-pyridine) or benzimidazole), substituted or unsubstituted $C_3$-$C_8$ cycloalkyl (e.g., cyclopropyl), substituted or unsubstituted 3-8 membered heterocyclic ring (e.g., piperidine, pyrrolidine), $R^6$-(substituted or unsubstituted heterocycle) (e.g., $(CH_2)_3$-piperidine, $CH_2$-benzoxazole, $CH_2$-benzimidazole, $CH_2$-indole) or C(O)-(alkyl) (e.g. C(O)—$CH_3$);

$R^{20}$ is represented by the following structure:

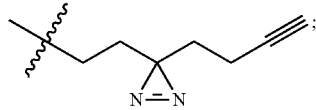 [SMILES: *CCC1(CCC#C)N=N1]

$R^4$ and $R^8$ are each independently H, F, Cl, Br, I, OH, $CF_3$, CN, $NO_2$, $C_1$-$C_5$ linear or branched, substituted or unsubstituted alkyl (e.g., methyl, ethyl, tert-butyl, $CH_2CH_2CH(CH_3)_2$, $CH_2$—$C(CH_3)_3$), $C_1$-$C_5$ linear or branched, or $C_3$-$C_8$ cyclic haloalkyl;

each $R^6$ and $R^{6b}$ is independently absent or O, C=O, C(=O)—$[CH_2]_p$, $[CH_2]_p$—C(=O), $[CH_2]_p$ (e.g. $CH_2$, $CH_2CH_2$, $CH_2CH_2CH_2$, $CH_2CH_2CH_2CH_2$), $[CHR^{21}]_p$ (e.g. CHF, CH—$CH_3$), $[C(R^{21})_2]_p$ (e.g. $CF_2$) or $[CH_2]_{pa}$—O—$[CH_2]_{pb}$ (e.g. $CH_2OCH_2$), or $[CH_2]_p$—O (e.g., $CH_2CH_2O$);

wherein
p is an integer between 1 and 10; and
each pa and pb is independently an integer between 1 and 5;
$R^{21}$ is H, F, Cl, Br, I, OH, $CF_3$, CN, $NO_2$, $C_1$-$C_5$ linear or branched, substituted or unsubstituted alkyl (e.g., methyl, ethyl, propyl, isopropyl, isobutyl), $C_1$-$C_5$ linear or branched alkoxy (e.g. methoxy), $C_1$-$C_5$ linear or branched haloalkyl (e.g., $CHF_2$, $CF_3$, $R^6$-aryl (e.g., $CH_2$-Ph, $CH_2$-Ph-ethyl), $R^6$—N(alkyl)$_2$, $R^6$—NH(alkyl), ($R^6$—NH(cycloalkyl), ($R^6$—NH(aryl), substituted or unsubstituted aryl (e.g., phenyl, ethylphenyl), substituted or unsubstituted heteroaryl (e.g., pyridine (2, 3, and 4-pyridine) or benzimidazole), substituted or unsubstituted $C_3$-$C_8$ cycloalkyl (e.g., cyclopropyl), substituted or unsubstituted 3-8 membered heterocyclic ring (e.g., piperidine, pyrrolidine), $R^6$-(substituted or unsubstituted heterocycle) (e.g., $(CH_2)_3$-piperidine) or C(O)-(alkyl) (e.g. C(O)—$CH_3$);

or wherein two geminal or vicinal $R^2$ substituents are joined to form a substituted or unsubstituted $C_3$-$C_8$ cycloalkyl (e.g., cyclopropyl);

$R^9$ is H, substituted or unsubstituted $C_1$-$C_5$ linear or branched alkyl, substituted or unsubstituted $C_1$-$C_5$ linear or branched alkenyl, $C_1$-$C_5$ linear or branched alkoxy (e.g., O—$CH_3$), $C_1$-$C_5$ linear or branched haloalkoxy (e.g., $OCF_3$, $OCHF_2$), $R^6$—OH, a substituted or unsubstituted aryl (e.g., phenyl, tolyl, fluorophenyl, cyanophenyl), substituted or unsubstituted heteroaryl (e.g., pyridine (2, 3, and 4-pyridine), furan, thiazole, isothiazole, thiophene, pyrrole, methylthiophene, methylfuran, methylpyridine, methylthiazole, indole, benzimidazole, pyrrolopyridine, benzoxazole), substituted or unsubstituted $C_3$-$C_8$ cycloalkyl (e.g., cyclopropyl, methylcyclopropyl, cyclobutyl, cyclohexyl, cyclohexenyl, cyclopentyl), $C_1$-$C_5$ linear or branched, or $C_3$-$C_8$ cyclic haloalkyl (e.g. $CF_3$, $CHF_2$), substituted or unsubstituted 3-8 membered heterocyclic ring (e.g. oxetane, azetidine, methyloxetane, tetrahydrofuran, methyltetrahydropyran, pyrrolidine, methylpyrrolidine, tetrahydropyran, tetrahydrothiopyran, piperidine, methylpiperidine, azepane, oxepane, 2H-thiopyran-tetrahydro-1,1-dioxide), $NH_2$, N(alkyl)$_2$ (e.g. N($CH_3$)$_2$, N($CH_2CH_3$)$_2$, N($CH_3$)($CH_2CH_3$)) NH(alkyl) (e.g. $NHCH_3$, $NHCH_2CH_3$, $NHCH_2CH_2CH_3$) or $R^{20}$;

$X^6$-$X^7$ are each independently CH or N;

l and q are each independently an integer between 0 and 4 (e.g., 0, 1 or 2);

or its pharmaceutically acceptable salt, optical isomer, tautomer, hydrate, N-oxide, reverse amide analog, prodrug, isotopic variant (e.g., deuterated analog), PROTAC, pharmaceutical product or any combination thereof.

In some embodiments, each of the variables R-$R^{104}$ of formula I(a(ii)) may be further substituted with at least one substitution selected from: F, Cl, Br, I, OH, SH, $C_1$-$C_5$ linear alkyne, diazirine, $C_1$-$C_5$ linear, cyclic or branched alkyl (e.g. methyl, ethyl, propyl, isopropyl or cyclopropyl), substituted or unsubstituted benzyl (e.g., benzyl, methylbenzyl), substituted or unsubstituted aryl (e.g., phenyl, fluorophenyl), heteroaryl (e.g., indole, tetrahydropyran, pyridine (2, 3, and 4-pyridine)), $C_3$-$C_8$ cycloalkyl (e.g., cyclopropyl), $C_1$-$C_5$ linear or branched alkyl-OH (e.g., C($CH_3$)$_2$$CH_2$—OH, $CH_2CH_2$—OH), 3-8 membered heterocyclic ring (e.g., piperidine), alkoxy (e.g. methoxy, ethoxy, propyloxy, isopropyloxy), $NH_2$, N(alkyl)$_2$ (e.g. N($CH_3$)$_2$, N($CH_2CH_3$)$_2$, N($CH_3$)($CH_2CH_3$)), NH(alkyl) (e.g. $NHCH_3$, $NHCH_2CH_3$, $NHCH_2CH_2CH_3$) NH(cycloalkyl) (e.g. NH(cyclohexyl), NH(cylopentyl)), NH(aryl) (e.g. NH(phenyl), NH(pyridiny)), NH(benzyl), N(cycloalkyl)$_2$ (e.g. N(cyclohexyl)$_2$, N(cylopentyl)$_2$), N(aryl)$_2$ (e.g. N(phenyl)$_2$, N(pyridiny)$_2$), N(alkyl)(aryl) (e.g. N(methyl)(phenyl), N(methyl)(pyridinyl)), N(alkyl)(cycloalkyl) (e.g. N(methyl)(cyclopropyl), N(methyl)(cyclohexyl), N(methyl)(cyclopentyl)), N(aryl)(cycloalkyl) (e.g. N(phenyl)(cyclohexyl), N(pyridinyl)(cyclohexyl)), NHC(O)(alkyl) (e.g. NHC(O)$CH_3$), $CF_3$, aryl, phenyl, heteroaryl, $C_3$-$C_8$ cycloalkyl, halophenyl, (benzyloxy)phenyl, CN and $NO_2$.

In various embodiments, this invention is directed to a compound represented by the structure of formula (I(a(iii))):

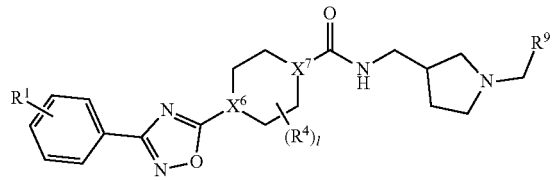

(I(a(iii)))

wherein $R^1$ is H, F, Cl, Br, I, OH, $R^6$—OH, O—$R^{20}$, —$R^6$—O—$R^7$, $CF_3$, $OCH_3$, CN, $NO_2$, —$CH_2CN$, —$R^6CN$, $C_1$-$C_5$ linear or branched, substituted or unsubstituted alkyl (e.g., methyl, ethyl), $C_1$-$C_5$ linear or branched, or $C_3$-$C_8$ cyclic haloalkyl (e.g., $CHF_2$), $C_1$-$C_5$ substituted or unsubstituted, linear or branched, or $C_3$-$C_8$ cyclic alkoxy (e.g. methoxy, O—$(CH_2)_2$—OH), $C_1$-$C_5$ linear or branched haloalkoxy (e.g., $OCF_3$, $OCHF_2$), NH—C(O)—$R^7$ (e.g., NHC(O)—$CH_3$), $C_1$-$C_5$ linear or branched alkoxyalkyl;

wherein $R^6$ is absent or O, C=O, C(=O)—[$CH_2$]$_p$, [$CH_2$]$_p$—C(=O), [$CH_2$]$_p$ (e.g. $CH_2$, $CH_2CH_2$, $CH_2CH_2CH_2$, $CH_2CH_2CH_2CH_2$), [$CHR^{21}$]$_p$ (e.g. CHF, CH—$CH_3$), [C($R^{21}$)$_2$]$_p$ (e.g. $CF_2$) or [$CH_2$]$_{pa}$—O—[$CH_2$]$_{pb}$ (e.g. $CH_2OCH_2$), or [$CH_2$]$_p$—O (e.g., $CH_2CH_2O$);

wherein p is an integer between 1 and 10; and each pa and pb is independently an integer between 1 and 5;

$R^{21}$ is H, F, Cl, Br, I, OH, $CF_3$, CN, $NO_2$, $C_1$-$C_5$ linear or branched, substituted or unsubstituted alkyl (e.g., methyl, ethyl, propyl, isopropyl, isobutyl), $C_1$-$C_5$ linear or branched alkoxy (e.g. methoxy), $C_1$-$C_5$ linear or branched haloalkyl (e.g., $CHF_2$, $CF_3$, $R^6$-aryl (e.g., $CH_2$-Ph, $CH_2$-Ph-ethyl), $R^6$—N(alkyl)$_2$, $R^6$—NH(alkyl), ($R^6$—NH(cycloalkyl), ($R^6$—NH(aryl), substituted or unsubstituted aryl (e.g., phenyl, ethylphenyl), substituted or unsubstituted heteroaryl (e.g., pyridine (2, 3, and 4-pyridine) or benzimidazole), substituted or unsubstituted $C_3$-$C_8$ cycloalkyl (e.g., cyclopropyl), substituted or unsubstituted 3-8 membered heterocyclic ring (e.g., piperidine, pyrrolidine), $R^6$-(substituted or unsubstituted heterocycle) (e.g., $(CH_2)_3$-piperidine) or C(O)-(alkyl) (e.g. C(O)—$CH_3$);

or wherein two geminal or vicinal $R^{21}$ substituents are joined to form a substituted or unsubstituted $C_3$-$C_8$ cycloalkyl (e.g., cyclopropyl);

$R^7$ is H, $C_1$-$C_5$ substituted or unsubstituted linear or branched alkyl (e.g., methyl, ethyl, $CH_2$—$CH_2$—O—$CH_3$), $C_1$-$C_5$ linear or branched alkoxy (e.g., O—$CH_3$), C(O)R, or S(O)$_2$R;

wherein
R is H, F, Cl, Br, I, OH, $CF_3$, CN, $NO_2$, $C_1$-$C_5$ linear or branched, substituted or unsubstituted alkyl (e.g., methyl, ethyl, propyl, isopropyl, isobutyl), $C_1$-$C_5$ linear or branched alkoxy (e.g. methoxy), $C_1$-$C_5$ linear or branched haloalkyl (e.g., $CHF_2$, $CF_3$), $R^6$-aryl (e.g., $CH_2$-Ph, $CH_2$-Ph-ethyl), $R^6$—$N(alkyl)_2$, $R^6$—NH(alkyl), ($R^6$—NH(cycloalkyl), ($R^6$—NH(aryl), substituted or unsubstituted aryl (e.g., phenyl, ethylphenyl), substituted or unsubstituted heteroaryl (e.g., pyridine (2, 3, and 4-pyridine) or benzimidazole), substituted or unsubstituted $C_3$-$C_8$ cycloalkyl (e.g., cyclopropyl), substituted or unsubstituted 3-8 membered heterocyclic ring (e.g., piperidine, pyrrolidine), $R^6$-(substituted or unsubstituted heterocycle) (e.g., $(CH_2)_3$-piperidine, $CH_2$-benzoxazole, $CH_2$-benzimidazole, $CH_2$-indole) or C(O)-(alkyl) (e.g. C(O)—$CH_3$);

$R^{20}$ is represented by the following structure:

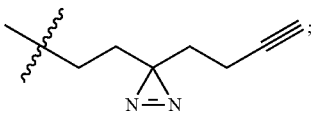 [SMILES: *CCC1(CCC#C)N=N1]

$R^4$ is H, F, Cl, Br, I, OH, $CF_3$, CN, $NO_2$, $C_1$-$C_5$ linear or branched, substituted or unsubstituted alkyl (e.g., methyl, ethyl, tert-butyl, $CH_2CH_2CH(CH_3)_2$, $CH_2$—C$(CH_3)_3$), $C_1$-$C_5$ linear or branched, or $C_3$-$C_5$ cyclic haloalkyl;

$R^9$ is H, substituted or unsubstituted $C_1$-$C_5$ linear or branched alkyl, substituted or unsubstituted $C_1$-$C_5$ linear or branched alkenyl, $C_1$-$C_5$ linear or branched alkoxy (e.g., O—$CH_3$), $C_1$-$C_5$ linear or branched haloalkoxy (e.g., $OCF_3$, $OCHF_2$), $R^6$—OH, a substituted or unsubstituted aryl (e.g., phenyl, tolyl, fluorophenyl, cyanophenyl), substituted or unsubstituted heteroaryl (e.g., pyridine (2, 3, and 4-pyridine), furan, thiazole, isothiazole, thiophene, pyrrole, methylthiophene, methylfuran, methylpyridine, methylthiazole, indole, benzimidazole, pyrrolopyridine, benzoxazole), substituted or unsubstituted $C_3$-$C_5$ cycloalkyl (e.g., cyclopropyl, methylcyclopropyl, cyclobutyl, cyclohexyl, cyclohexenyl, cyclopentyl), $C_1$-$C_5$ linear or branched, or $C_3$-$C_8$ cyclic haloalkyl (e.g. $CF_3$, $CHF_2$), substituted or unsubstituted 3-8 membered heterocyclic ring (e.g. oxetane, azetidine, methyloxetane, tetrahydrofuran, methyltetrahydropyran, pyrrolidine, methylpyrrolidine, tetrahydropyran, tetrahydrothiopyran, piperidine, methylpiperidine, azepane, oxepane, 2H-thiopyran-tetrahydro-1,1-dioxide), $NH_2$, $N(alkyl)_2$ (e.g. $N(CH_3)_2$, $N(CH_2CH_3)_2$, $N(CH_3)(CH_2CH_3)$) NH(alkyl) (e.g. $NHCH_3$, $NHCH_2CH_3$, $NHCH_2CH_2CH_3$) or $R^{20}$;

$X^6$-$X^7$ are each independently CH or N;

l is an integer between 0 and 4 (e.g., 0, 1 or 2);

or its pharmaceutically acceptable salt, optical isomer, tautomer, hydrate, N-oxide, reverse amide analog, prodrug, isotopic variant (e.g., deuterated analog), PROTAC, pharmaceutical product or any combination thereof.

In some embodiments, each of the variables R-$R^{104}$ of formula I(a(iii)) may be further substituted with at least one substitution selected from: F, Cl, Br, I, OH, SH, $C_1$-$C_5$ linear alkyne, diazirine, $C_1$-$C_5$ linear, cyclic or branched alkyl (e.g. methyl, ethyl, propyl, isopropyl or cyclopropyl), substituted or unsubstituted benzyl (e.g., benzyl, methylbenzyl), substituted or unsubstituted aryl (e.g., phenyl, fluorophenyl), heteroaryl (e.g., indole, tetrahydropyran, pyridine (2, 3, and 4-pyridine)), $C_3$-$C_8$ cycloalkyl (e.g., cyclopropyl), $C_1$-$C_5$ linear or branched alkyl-OH (e.g., $C(CH_3)_2CH_2$—OH, $CH_2CH_2$—OH), 3-8 membered heterocyclic ring (e.g., piperidine), alkoxy (e.g. methoxy, ethoxy, propyloxy, isopropyloxy), $NH_2$, $N(alkyl)_2$ (e.g. $N(CH_3)_2$, $N(CH_2CH_3)_2$, $N(CH_3)(CH_2CH_3)$), NH(alkyl) (e.g. $NHCH_3$, $NHCH_2CH_3$, $NHCH_2CH_2CH_3$) NH(cycloalkyl) (e.g. NH(cyclohexyl), NH(cylopentyl)), NH(aryl) (e.g. NH(phenyl), NH(pyridiny)), NH(benzyl), $N(cycloalkyl)_2$ (e.g. $N(cyclohexyl)_2$, $N(cylopentyl)_2$), $N(aryl)_2$ (e.g. $N(phenyl)_2$, $N(pyridiny)_2$), N(alkyl)(aryl) (e.g. N(methyl)(phenyl), N(methyl)(pyridinyl)), N(alkyl)(cycloalkyl) (e.g. N(methyl)(cyclopropyl), N(methyl)(cyclohexyl), N(methyl)(cyclopentyl)), N(aryl)(cycloalkyl) (e.g. N(phenyl)(cyclohexyl), N(pyridinyl)(cyclohexyl)), NHC(O)(alkyl) (e.g. $NHC(O)CH_3$), $CF_3$, aryl, phenyl, heteroaryl, $C_3$-$C_8$ cycloalkyl, halophenyl, (benzyloxy)phenyl, CN and $NO_2$.

In various embodiments, this invention is directed to a compound represented by the structure of formula (I(b)):

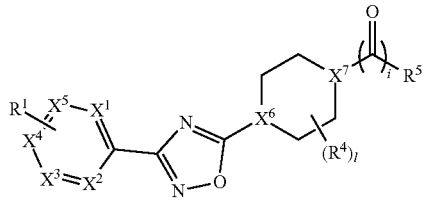

(I(b))

wherein
$R^1$ is H, F, Cl, Br, I, OH, $R^6$—OH, O—$R^{20}$, —$R^6$—O—$R^7$, $CF_3$, $OCH_3$, CN, $NO_2$, —$CH_2CN$, —$R^6CN$, $C_1$-$C_5$ linear or branched, substituted or unsubstituted alkyl (e.g., methyl, ethyl), $C_1$-$C_5$ linear or branched, or $C_3$-$C_8$ cyclic haloalkyl (e.g., $CHF_2$), $C_1$-$C_5$ substituted or unsubstituted, linear or branched, or $C_3$-$C_8$ cyclic alkoxy (e.g. methoxy, O—$(CH_2)_2$—OH), $C_1$-$C_5$ linear or branched haloalkoxy (e.g., $OCF_3$, $OCHF_2$), NH—C(O)—$R^7$ (e.g., NHC(O)—$CH_3$), $C_1$-$C_5$ linear or branched alkoxyalkyl;

wherein
$R^6$ is absent or O, C=O, C(=O)—$[CH_2]_p$, $[CH_2]_p$—C(=O), $[CH_2]_p$ (e.g. $CH_2$, $CH_2CH_2$, $CH_2CH_2CH_2$, $CH_2CH_2CH_2CH_2$), $[CHR^{21}]_p$ (e.g. CHF, CH—$CH_3$), $[C(R^{21})_2]_p$ (e.g. $CF_2$) or $[CH_2]_{pa}$—O—$[CH_2]_{pb}$ (e.g. $CH_2OCH_2$), or $[CH_2]_p$—O (e.g., $CH_2CH_2O$);

wherein
p is an integer between 1 and 10; and
each pa and pb is independently an integer between 1 and 5;

$R^{21}$ is H, F, Cl, Br, I, OH, $CF_3$, CN, $NO_2$, $C_1$-$C_5$ linear or branched, substituted or unsubstituted alkyl (e.g., methyl, ethyl, propyl, isopropyl, isobutyl), $C_1$-$C_5$ linear or branched alkoxy (e.g. methoxy), $C_1$-$C_5$ linear or branched haloalkyl (e.g., $CHF_2$, $CF_3$, $R^6$-aryl (e.g., $CH_2$-Ph, $CH_2$-Ph-ethyl), $R^6$—$N(alkyl)_2$, $R^6$—NH(alkyl), ($R^6$—NH (cycloalkyl), ($R^6$—NH(aryl), substituted or unsubstituted aryl (e.g., phenyl, ethylphenyl), substituted or unsubstituted heteroaryl (e.g., pyridine (2, 3, and 4-pyridine) or benzimidazole), substituted or unsubstituted $C_3$-$C_8$ cycloalkyl (e.g., cyclopropyl), substituted or unsubstituted 3-8 membered heterocyclic ring (e.g., piperidine, pyrrolidine), $R^6$-(substituted or unsubstituted heterocycle) (e.g., $(CH_2)_3$-piperidine) or C(O)-(alkyl) (e.g. C(O)—$CH_3$);

or wherein two geminal or vicinal $R^{21}$ substituents are joined to form a substituted or unsubstituted $C_3$-$C_8$ cycloalkyl (e.g., cyclopropyl);

$R^7$ is H, $C_1$-$C_5$ substituted or unsubstituted linear or branched alkyl (e.g., methyl, ethyl, $CH_2$—$CH_2$—O—$CH_3$), $C_1$-$C_5$ linear or branched alkoxy (e.g., O—$CH_3$), C(O)R, or $S(O)_2R$;

wherein

R is H, F, Cl, Br, I, OH, $CF_3$, CN, $NO_2$, $C_1$-$C_5$ linear or branched, substituted or unsubstituted alkyl (e.g., methyl, ethyl, propyl, isopropyl, isobutyl), $C_1$-$C_5$ linear or branched alkoxy (e.g. methoxy), $C_1$-$C_5$ linear or branched haloalkyl (e.g., $CHF_2$, $CF_3$), $R^6$-aryl (e.g., $CH_2$-Ph, $CH_2$-Ph-ethyl), $R^6$—N(alkyl)$_2$, $R^6$—NH(alkyl), ($R^6$—NH(cycloalkyl), ($R^6$—NH(aryl), substituted or unsubstituted aryl (e.g., phenyl, ethylphenyl), substituted or unsubstituted heteroaryl (e.g., pyridine (2, 3, and 4-pyridine) or benzimidazole), substituted or unsubstituted $C_3$-$C_8$ cycloalkyl (e.g., cyclopropyl), substituted or unsubstituted 3-8 membered heterocyclic ring (e.g., piperidine, pyrrolidine), $R^6$-(substituted or unsubstituted heterocycle) (e.g., $(CH_2)_3$-piperidine, $CH_2$-benzoxazole, $CH_2$-benzimidazole, $CH_2$-indole) or C(O)-(alkyl) (e.g. C(O)—$CH_3$);

$R^{20}$ is represented by the following structure:

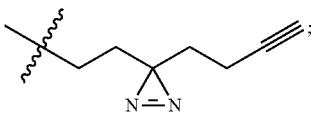 [SMILES: *CCC1(CCC#C)N=N1]

$R^4$ is H, F, Cl, Br, I, OH, $CF_3$, CN, $NO_2$, $C_1$-$C_5$ linear or branched, substituted or unsubstituted alkyl (e.g., methyl, ethyl, tert-butyl, $CH_2CH_2CH(CH_3)_2$, $CH_2$—C($CH_3$)$_3$), $C_1$-$C_5$ linear or branched, or $C_3$-$C_8$ cyclic haloalkyl;

$R^5$ is OH, $C_1$-$C_5$ linear or branched, substituted or unsubstituted alkyl (e.g., methyl, ethyl), $C_1$-$C_5$ linear or branched, or $C_3$-$C_8$ cyclic haloalkyl, $N(R^a)(R^b)NHR$, $NH_2$, N(alkyl)$_2$ (e.g. $N(CH_3)_2$, $N(CH_2CH_3)_2$, $N(CH_3)(CH_2CH_3)$) NH(alkyl) (e.g. $NHCH_3$, $NHCH_2CH_3$, $NHCH_2CH_2CH_3$) NH(cycloalkyl) (e.g. NH(cyclohexyl), NH(cylopentyl)), NH(aryl) (e.g. NH(phenyl), NH(pyridiny), (e.g., NH-1-methyl-indole)), NH(benzyl), N(cycloalkyl)$_2$ (e.g. N(cyclohexyl)$_2$, N(cylopentyl)$_2$), N(aryl)$_2$ (e.g. N(phenyl)$_2$, N(pyridiny)$_2$), N(alkyl)(aryl) (e.g. N(methyl)(phenyl), N(methyl)(pyridinyl)), N(alkyl)(cycloalkyl) (e.g. N(methyl)(cyclopropyl), N(methyl)(cyclohexyl), N(methyl)(cyclopentyl)), N(aryl)(cycloalkyl) (e.g. N(phenyl)(cyclohexyl), N(pyridinyl)(cyclohexyl)), substituted or unsubstituted aryl, substituted or unsubstituted heteroaryl, substituted or unsubstituted $C_3$-$C_8$ cycloalkyl (e.g., cyclopropyl), substituted or unsubstituted 3-8 membered heterocyclic ring (e.g., pyrrolidine, piperidine, morpholine, tetrahydropyran), NH—$R^{20}$, NH—$R^6$—NH(alkyl), NH—$R^6$—$NH_2$, NH—$R^6$—N(alkyl)$_2$ (e.g. $NH(CH_2)_3N(CH_2CH_2CH_3)$($CH_2CH_3$), $NH(CH_2)_2N(CH_3)_2$), $NH(CH_2)_3N(CH_2CH_3)_2$, $NH(CH_2)_2N(CH_2CH_3)_2$, $NHCH_2CH(C_6H_5)N(CH_3)_2$), NH—$R^6$—N(alkyl)(cycloalkyl), NH—$R^6$—NH(cycloalkyl), NH—$R^6$—NH(aryl), NH—$R^6$—N(alkyl)(aryl) (e.g. $NH(CH_2)_3(C_6H_5)$($CH_3$)), NH—$R^6$—OH, NH—$R^6$—O(alkyl) (e.g. $NH(CH_2)_3OCH_3$), NH—$R^6$—O(aryl) or NH—$R^6$—O(cycloalkyl);

or $R_5$ is represented by any one of the following structures:

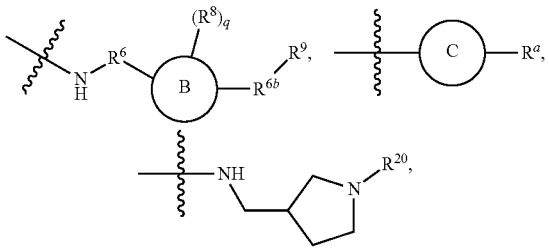

wherein q is an integer between 0 and 4 (e.g., 0, 1 or 2);

$R^{6b}$ is absent or O, C=O, C(=O)—[$CH_2$]$_p$, [$CH_2$]$_p$—C(=O), [$CH_2$]$_p$ (e.g. $CH_2$, $CH_2CH_2$, $CH_2CH_2CH_2$, $CH_2CH_2CH_2CH_2$), [$CHR^{21}$]$_p$ (e.g. CHF, CH—$CH_3$), [C($R^{21}$)$_2$]$_p$ (e.g. $CF_2$) or [$CH_2$]$_{pa}$—O—[$CH_2$]$_{pb}$ (e.g. $CH_2OCH_2$), or [$CH_2$]$_p$—O (e.g., $CH_2CH_2O$);

$R^8$ is H, F, Cl, Br, I, OH, $CF_3$, CN, $NO_2$, $C_1$-$C_5$ linear or branched, substituted or unsubstituted alkyl (e.g., methyl, ethyl, tert-butyl, $CH_2CH_2CH(CH_3)_2$, $CH_2$—C($CH_3$)$_3$), $C_1$-$C_5$ linear or branched, or $C_3$-$C_8$ cyclic haloalkyl;

$R^8$ is H, F, Cl, Br, I, OH, $CF_3$, CN, $NO_2$, $C_1$-$C_5$ linear or branched, substituted or unsubstituted alkyl (e.g., methyl, ethyl, tert-butyl, $CH_2CH_2CH(CH_3)_2$, $CH_2$—C($CH_3$)$_3$), $C_1$-$C_5$ linear or branched, or $C_3$-$C_8$ cyclic haloalkyl;

$R^9$ is H, substituted or unsubstituted $C_1$-$C_5$ linear or branched alkyl, substituted or unsubstituted $C_1$-$C_5$ linear or branched alkenyl, $C_1$-$C_5$ linear or branched alkoxy (e.g., O—$CH_3$), $C_1$-$C_5$ linear or branched haloalkoxy (e.g., $OCF_3$, $OCHF_2$), $R^6$—OH, a substituted or unsubstituted aryl (e.g., phenyl, tolyl, fluorophenyl, cyanophenyl), substituted or unsubstituted heteroaryl (e.g., pyridine (2, 3, and 4-pyridine), furan, thiazole, isothiazole, thiophene, pyrrole, methylthiophene, methylfuran, methylpyridine, methylthiazole, indole, benzimidazole, pyrrolopyridine, benzoxazole), substituted or unsubstituted $C_3$-$C_8$ cycloalkyl (e.g., cyclopropyl, methylcyclopropyl, cyclobutyl, cyclohexyl, cyclohexenyl, cyclopentyl), $C_1$-$C_5$ linear or branched, or $C_3$-$C_8$ cyclic haloalkyl (e.g. $CF_3$, $CHF_2$), substituted or unsubstituted 3-8 membered heterocyclic ring (e.g. oxetane, azetidine, methyloxetane, tetrahydrofuran, methyltetrahydrofuran, pyrrolidine, methylpyrrolidine, tetrahydropyran, tetrahydrothiopyran, piperidine, methylpiperidine, azepane, oxepane, 2H-thiopyran-tetrahydro-1,1-dioxide), $NH_2$, N(alkyl)$_2$ (e.g. $N(CH_3)_2$, $N(CH_2CH_3)_2$, $N(CH_3)(CH_2CH_3)$) NH(alkyl) (e.g. $NHCH_3$, $NHCH_2CH_3$, $NHCH_2CH_2CH_3$) or $R^{20}$;

$R^a$ is $R^{101}$-$R^{102}$, $R^{20}$, $R^6$—NH(alkyl), $R^6$—$NH_2$, $R^6$—$N(alkyl)_2$, $R^6$—N(alkyl)(cycloalkyl), $R^6$—NH(cycloalkyl), $R^6$—NH(aryl), $R^6$—OH, $R^6$—O(alkyl), $R^6$—O(aryl) or $R^6$—O(cycloalkyl)

or $R^a$ is represented by the following structures:

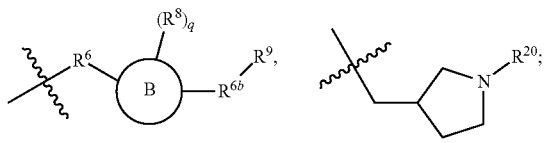

$R^b$ is $R^{103}$-$R^{104}$ wherein $R^{101}$ and $R^{103}$ are each independently absent or O, C=O, C(=O)—$[CH_2]_p$, $[CH_2]_p$—C(=O), $[CH_2]_p$ (e.g. $CH_2$, $CH_2CH_2$, $CH_2CH_2CH_2$, $CH_2CH_2CH_2CH_2$), $[CHR^{21}]_p$ (e.g. CHF), $[C(R^{21})_2]_p$ (e.g. $CF_2$) or $[CH_2]_{pa}$—O—$[CH_2]_{pb}$ (e.g. $CH_2OCH_2$), or $[CH_2]_p$—O (e.g., $CH_2CH_2O$), substituted or unsubstituted arylene, substituted or unsubstituted heteroarylene, substituted or unsubstituted heterocycloalkylene or substituted or unsubstituted cycloalkylene;

wherein p is an integer between 0 and 10;

$R^{102}$ and $R^{104}$ are each independently H, F, Cl, Br, I, OH, $CF_3$, CN, $NO_2$, $C_1$-$C_5$ linear or branched, substituted or unsubstituted alkyl (e.g., methyl, ethyl, propyl, isopropyl, isobutyl), $C_1$-$C_5$ linear or branched alkoxy (e.g. methoxy), $C_1$-$C_5$ linear or branched haloalkyl (e.g., $CHF_2$, $CF_3$, $R^6$-aryl (e.g., $CH_2$-Ph, $CH_2$-Ph-ethyl), $R^6$—$N(alkyl)_2$, $R^6$—NH(alkyl), ($R^6$—NH(cycloalkyl), ($R^6$—NH(aryl), substituted or unsubstituted aryl (e.g., phenyl, ethylphenyl), substituted or unsubstituted heteroaryl (e.g., pyridine (2, 3, and 4-pyridine) or benzimidazole), substituted or unsubstituted $C_3$-$C_5$ cycloalkyl (e.g., cyclopropyl), substituted or unsubstituted 3-8 membered heterocyclic ring (e.g., piperidine, pyrrolidine), $R^6$-(substituted or unsubstituted heterocycle) (e.g., $(CH_2)_3$-piperidine) or C(O)-(alkyl) (e.g. C(O)—$CH_3$);

or $R^a$ and $R^b$ are joined to form a substituted or unsubstituted 3-8 membered heterocyclic ring (e.g, morpholine, piperidine);

B ring is a substituted or unsubstituted saturated, unsaturated or aromatic, single, fused or spiro, carbocyclic or heterocyclic 3-12 membered ring, including a single or fused $C_3$-$C_{12}$ aromatic or heteroaromatic ring (e.g. phenyl, pyrimidine, 2-, 3- or 4-pyridine, pyridazine, pyrazine, isothiazole, thiadiazole, imidazole, triazole, thiazole, oxazole, isoxazole, 1-methylimidazole, pyrrole, furan, thiophene, oxadiazole, indole, indane, benzodihydrofuran, tetrahydroquinoline, or pyrazole), a 3-8 membered saturated or unsaturated heterocyclic ring (e.g. tetrahydropyran, tetrahydrofuran, pyrrolidine, piperidine, piperazine, 2-oxopyrrolidine, 2,5-dioxopyrrolidine, 2,5-dioxoimidazolidine, oxetane, chromane), a $C_3$-$C_8$ cycloalkyl ring (e.g. cyclobutyl, cyclohexyl, cyclopentyl, cyclooctyl) a $C_3$-$C_8$ cycloalkenyl ring, or a spiro ring system (e.g. 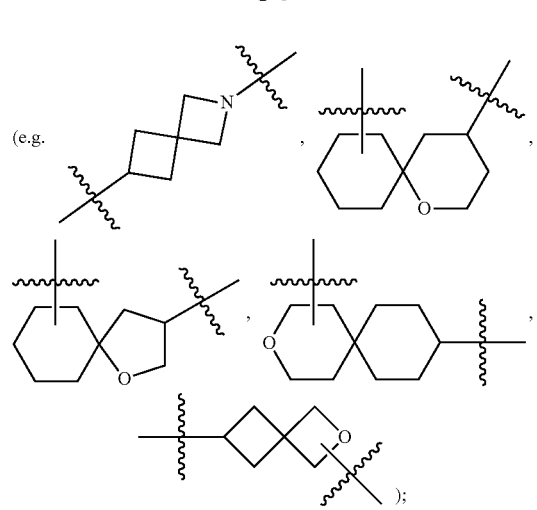);

C ring is a 5-10 membered heterocyclic, aryl or heteroaryl ring (e.g. benzene, benzopyrrolidine, piperazine, pyrrolidine, piperidine, morpholine, tetrahydropyran or thiomorpholine-1,1-dioxide);

$X^1$-$X^5$ are each independently C, CH or N;

$X^6$-$X^7$ are each independently CH or N;

l is an integer between 0 and 4 (e.g., 0, 1 or 2);

i is 0 or 1;

or its pharmaceutically acceptable salt, optical isomer, tautomer, hydrate, N-oxide, reverse amide analog, prodrug, isotopic variant (e.g., deuterated analog), PROTAC, pharmaceutical product or any combination thereof.

In some embodiments, each of the variables R-$R^{104}$ of formula I(b) may be further substituted with at least one substitution selected from: F, Cl, Br, I, OH, SH, $C_1$-$C_5$ linear alkyne, diazirine, $C_1$-$C_5$ linear, cyclic or branched alkyl (e.g. methyl, ethyl, propyl, isopropyl or cyclopropyl), substituted or unsubstituted benzyl (e.g., benzyl, methylbenzyl), substituted or unsubstituted aryl (e.g., phenyl, fluorophenyl), heteroaryl (e.g., indole, tetrahydropyran, pyridine (2, 3, and 4-pyridine)), $C_3$-$C_8$ cycloalkyl (e.g., cyclopropyl), $C_1$-$C_5$ linear or branched alkyl-OH (e.g., $C(CH_3)_2CH_2$—OH, $CH_2CH_2$—OH), 3-8 membered heterocyclic ring (e.g., piperidine), alkoxy (e.g. methoxy, ethoxy, propyloxy, isopropyloxy), $NH_2$, $N(alkyl)_2$ (e.g. $N(CH_3)_2$, $N(CH_2CH_3)_2$, $N(CH_3)(CH_2CH_3)$), NH(alkyl) (e.g. $NHCH_3$, $NHCH_2CH_3$, $NHCH_2CH_2CH_3$) NH(cycloalkyl) (e.g. NH(cyclohexyl), NH(cylopentyl)), NH(aryl) (e.g. NH(phenyl), NH(pyridiny)), NH(benzyl), $N(cycloalkyl)_2$ (e.g. $N(cyclohexyl)_2$, $N(cylopentyl)_2$), $N(aryl)_2$ (e.g. $N(phenyl)_2$, $N(pyridiny)_2$), N(alkyl)(aryl) (e.g. N(methyl)(phenyl), N(methyl)(pyridinyl)), N(alkyl)(cycloalkyl) (e.g. N(methyl)(cyclopropyl), N(methyl)(cyclohexyl), N(methyl)(cyclopentyl)), N(aryl)(cycloalkyl) (e.g. N(phenyl)(cyclohexyl), N(pyridinyl)(cyclohexyl)), NHC(O)(alkyl) (e.g. NHC(O)$CH_3$), $CF_3$, aryl, phenyl, heteroaryl, $C_3$-$C_8$ cycloalkyl, halophenyl, (benzyloxy)phenyl, CN and $NO_2$.

In various embodiments, this invention is directed to a compound represented by the structure of formula (I(b(i))):

(I(b(i)))

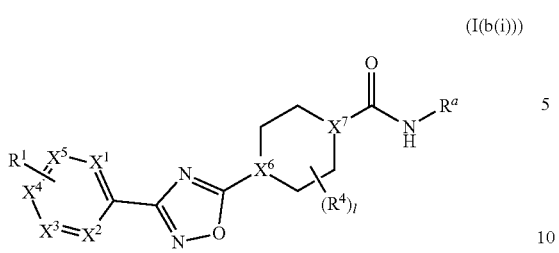

wherein
R[1] is H, F, Cl, Br, I, OH, R[6]—OH, O—R[20], —R[6]—O—R[7], CF$_3$, OCH$_3$, CN, NO$_2$, —CH$_2$CN, —R[6]CN, C$_1$-C$_5$ linear or branched, substituted or unsubstituted alkyl (e.g., methyl, ethyl), C$_1$-C$_5$ linear or branched, or C$_3$-C$_8$ cyclic haloalkyl (e.g., CHF$_2$), C$_1$-C$_5$ substituted or unsubstituted, linear or branched, or C$_3$-C$_8$ cyclic alkoxy (e.g. methoxy, O—(CH$_2$)$_2$—OH), C$_1$-C$_5$ linear or branched haloalkoxy (e.g., OCF$_3$, OCHF$_2$), NH—C(O)—R[7] (e.g., NHC(O)—CH$_3$), C$_1$-C$_5$ linear or branched alkoxyalkyl;
wherein
R[6] is absent or O, C═O, C(═O)—[CH$_2$]$_p$, [CH$_2$]$_p$—C(═O), [CH$_2$]$_p$ (e.g. CH$_2$, CH$_2$CH$_2$, CH$_2$CH$_2$CH$_2$, CH$_2$CH$_2$CH$_2$CH$_2$), [CHR[21]]$_p$ (e.g. CHF, CH—CH$_3$), [C(R[21])$_2$]$_p$ (e.g. CF$_2$) or [CH$_2$]$_{pa}$—O—[CH$_2$]$_{pb}$ (e.g. CH$_2$OCH$_2$), or [CH$_2$]$_p$—O (e.g., CH$_2$CH$_2$O);
wherein
p is an integer between 1 and 10; and
each pa and pb is independently an integer between 1 and 5;
R[21] is H, F, Cl, Br, I, OH, CF$_3$, CN, NO$_2$, C$_1$-C$_5$ linear or branched, substituted or unsubstituted alkyl (e.g., methyl, ethyl, propyl, isopropyl, isobutyl), C$_1$-C$_5$ linear or branched alkoxy (e.g. methoxy), C$_1$-C$_5$ linear or branched haloalkyl (e.g., CHF$_2$, CF$_3$, R[6]-aryl (e.g., CH$_2$-Ph, CH$_2$-Ph-ethyl), R[6]—N(alkyl)$_2$, R[6]—NH(alkyl), (R[6]—NH(cycloalkyl), (R[6]—NH(aryl), substituted or unsubstituted aryl (e.g., phenyl, ethylphenyl), substituted or unsubstituted heteroaryl (e.g., pyridine (2, 3, and 4-pyridine) or benzimidazole), substituted or unsubstituted C$_3$-C$_8$ cycloalkyl (e.g., cyclopropyl), substituted or unsubstituted 3-8 membered heterocyclic ring (e.g., piperidine, pyrrolidine), R[6]-(substituted or unsubstituted heterocycle) (e.g., (CH$_2$)$_3$-piperidine or C(O)-(alkyl) (e.g. C(O)—CH$_3$);
or wherein two geminal or vicinal R[2] substituents are joined to form a substituted or unsubstituted C$_3$-C$_8$ cycloalkyl (e.g., cyclopropyl);
R[7] is H, C$_1$-C$_5$ substituted or unsubstituted linear or branched alkyl (e.g., methyl, ethyl, CH$_2$—CH$_2$—O—CH$_3$), C$_1$-C$_5$ linear or branched alkoxy (e.g., O—CH$_3$), C(O)R, or S(O)$_2$R;
wherein
R is H, F, Cl, Br, I, OH, CF$_3$, CN, NO$_2$, C$_1$-C$_5$ linear or branched, substituted or unsubstituted alkyl (e.g., methyl, ethyl, propyl, isopropyl, isobutyl), C$_1$-C$_5$ linear or branched alkoxy (e.g. methoxy), C$_1$-C$_5$ linear or branched haloalkyl (e.g., CHF$_2$, CF$_3$, R[6]-aryl (e.g., CH$_2$-Ph, CH$_2$-Ph-ethyl), R[6]—N(alkyl)$_2$, R[6]—NH(alkyl), (R[6]—NH(cycloalkyl), (R[6]—NH(aryl), substituted or unsubstituted aryl (e.g., phenyl, ethylphenyl), substituted or unsubstituted heteroaryl (e.g., pyridine (2, 3, and 4-pyridine) or benzimidazole), substituted or unsubstituted C$_3$-C$_8$ cycloalkyl (e.g., cyclopropyl), substituted or unsubstituted 3-8 membered heterocyclic ring (e.g., piperidine, pyrrolidine), R[6]-(substituted or unsubstituted heterocycle) (e.g., (CH$_2$)$_3$-piperidine, CH$_2$-benzoxazole, CH$_2$-benzimidazole, CH$_2$-indole) or C(O)-(alkyl) (e.g. C(O)—CH$_3$);
R[20] is represented by the following structure:

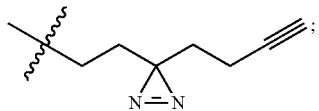 [SMILES: *CCC1(CCC#C)N=N1]

R[4] is H, F, Cl, Br, I, OH, CF$_3$, CN, NO$_2$, C$_1$-C$_5$ linear or branched, substituted or unsubstituted alkyl (e.g., methyl, ethyl, tert-butyl, CH$_2$CH$_2$CH(CH$_3$)$_2$, CH$_2$—C(CH$_3$)$_3$), C$_1$-C$_5$ linear or branched, or C$_3$-C$_5$ cyclic haloalkyl;
R[a] is R[101]-R[102], R[20], R[6]—NH(alkyl), R[6]—NH$_2$, R[6]—N(alkyl)$_2$, R[6]—N(alkyl)(cycloalkyl), R[6]—NH(cycloalkyl), R[6]—NH(aryl), R[6]—OH, R[6]—O(alkyl), R[6]—O(aryl) or R[6]—O(cycloalkyl);
or R[a] is represented by the following structures:

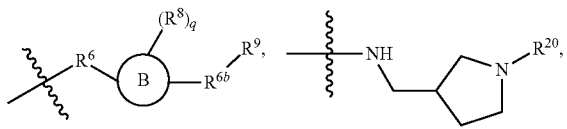

wherein
q is an integer between 0 and 4 (e.g., 0, 1 or 2);
R[6b] is absent or O, C═O, C(═O)—[CH$_2$]$_p$, [CH$_2$]$_p$—C(═O), [CH$_2$]$_p$ (e.g. CH$_2$, CH$_2$CH$_2$, CH$_2$CH$_2$CH$_2$, CH$_2$CH$_2$CH$_2$CH$_2$), [CHR[21]]$_p$ (e.g. CHF, CH—CH$_3$), [C(R[21])$_2$]$_p$ (e.g. CF$_2$) or [CH$_2$]$_{pa}$—O—[CH$_2$]$_{pb}$ (e.g. CH$_2$OCH$_2$), or [CH$_2$]$_p$—O (e.g., CH$_2$CH$_2$O);
R[8] is H, F, Cl, Br, I, OH, CF$_3$, CN, NO$_2$, C$_1$-C$_5$ linear or branched, substituted or unsubstituted alkyl (e.g., methyl, ethyl, tert-butyl, CH$_2$CH$_2$CH(CH$_3$)$_2$, CH$_2$—C(CH$_3$)$_3$), C$_1$-C$_5$ linear or branched, or C$_3$-C$_8$ cyclic haloalkyl;
R[9] is H, substituted or unsubstituted C$_1$-C$_5$ linear or branched alkyl, substituted or unsubstituted C$_1$-C$_5$ linear or branched alkenyl, C$_1$-C$_5$ linear or branched alkoxy (e.g., O—CH$_3$), C$_1$-C$_5$ linear or branched haloalkoxy (e.g., OCF$_3$, OCHF$_2$), R[6]—OH, a substituted or unsubstituted aryl (e.g., phenyl, tolyl, fluorophenyl, cyanophenyl), substituted or unsubstituted heteroaryl (e.g., pyridine (2, 3, and 4-pyridine), furan, thiazole, isothiazole, thiophene, pyrrole, methylthiophene, methylfuran, methylpyridine, methylthiazole, indole, benzimidazole, pyrrolopyridine, benzoxazole), substituted or unsubstituted C$_3$-C$_8$ cycloalkyl (e.g., cyclopropyl, methylcyclopropyl, cyclobutyl, cyclohexyl, cyclohexenyl, cyclopentyl), C$_1$-C$_5$ linear or branched, or C$_3$-C$_8$ cyclic haloalkyl (e.g. CF$_3$, CHF$_2$), substituted or unsubstituted 3-8 membered heterocyclic ring (e.g. oxetane, azetidine, methyloxetane, tetrahydrofuran, methyltetrahydropyran, pyrrolidine, methylpyrrolidine, tetrahydropyran, tetrahydrothiopyran, piperidine, methylpiperidine, azepane, oxepane, 2H-thiopyran-tetrahydro-1,1-dioxide), $NH_2$, $N(alkyl)_2$ (e.g. $N(CH_3)_2$, $N(CH_2CH_3)_2$, $N(CH_3)(CH_2CH_3)$) NH(alkyl) (e.g. $NHCH_3$, $NHCH_2CH_3$, $NHCH_2CH_2CH_3$) or $R^{20}$;

$R^{101}$ is absent or O, C=O, C(=O)—$[CH_2]_p$, $[CH_2]_p$—C(=O), $[CH_2]_p$ (e.g. $CH_2$, $CH_2CH_2$, $CH_2CH_2CH_2$, $CH_2CH_2CH_2CH_2$), $[CHR^{21}]_p$ (e.g. CHF), $[C(R^{21})_2]_p$ (e.g. $CF_2$) or $[CH_2]_{pa}$—O—$[CH_2]_{pb}$ (e.g. $CH_2OCH_2$), or $[CH_2]_p$—O (e.g., $CH_2CH_2O$), substituted or unsubstituted arylene, substituted or unsubstituted heteroarylene, substituted or unsubstituted heterocycloalkylene or substituted or unsubstituted cycloalkylene;

wherein p is an integer between 0 and 10;

$R^{102}$ is H, F, Cl, Br, I, OH, $CF_3$, CN, $NO_2$, $C_1$-$C_5$ linear or branched, substituted or unsubstituted alkyl (e.g., methyl, ethyl, propyl, isopropyl, isobutyl), $C_1$-$C_5$ linear or branched alkoxy (e.g. methoxy), $C_1$-$C_5$ linear or branched haloalkyl (e.g., $CHF_2$, $CF_3$, $R^6$-aryl (e.g., $CH_2$-Ph, $CH_2$-Ph-ethyl), $R^6$—N(alkyl)$_2$, $R^6$—NH(alkyl), ($R^6$—NH(cycloalkyl), ($R^6$—NH(aryl), substituted or unsubstituted aryl (e.g., phenyl, ethylphenyl), substituted or unsubstituted heteroaryl (e.g., pyridine (2, 3, and 4-pyridine) or benzimidazole), substituted or unsubstituted $C_3$-$C_8$ cycloalkyl (e.g., cyclopropyl), substituted or unsubstituted 3-8 membered heterocyclic ring (e.g., piperidine, pyrrolidine), $R^6$-(substituted or unsubstituted heterocycle) (e.g., $(CH_2)_3$-piperidine) or C(O)-(alkyl) (e.g. C(O)—$CH_3$);

B ring is a substituted or unsubstituted saturated, unsaturated or aromatic, single, fused or spiro, carbocyclic or heterocyclic 3-12 membered ring, including a single or fused $C_3$-$C_{12}$ aromatic or heteroaromatic ring (e.g. phenyl, pyrimidine, 2-, 3- or 4-pyridine, pyridazine, pyrazine, isothiazole, thiadiazole, imidazole, triazole, thiazole, oxazole, isoxazole, 1-methylimidazole, pyrrole, furan, thiophene, oxadiazole, indole, indane, benzodihydrofuran, tetrahydroquinoline, or pyrazole), a 3-8 membered saturated or unsaturated heterocyclic ring (e.g. tetrahydropyran, tetrahydrofuran, pyrrolidine, piperidine, piperazine, 2-oxopyrrolidine, 2,5-dioxopyrrolidine, 2,5-dioxoimidazolidine, oxetane, chromane), a $C_3$-$C_8$ cycloalkyl ring (e.g. cyclobutyl, cyclohexyl, cyclopentyl, cyclooctyl) a $C_3$-$C_8$ cycloalkenyl ring, or a spiro ring system

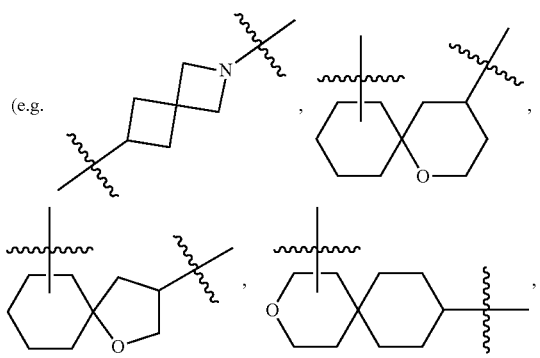

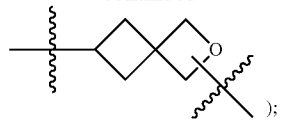

$X^1$-$X^5$ are each independently C, CH or N;

$X^6$-$X^7$ are each independently CH or N;

l is an integer between 0 and 4 (e.g., 0, 1 or 2);

or its pharmaceutically acceptable salt, optical isomer, tautomer, hydrate, N-oxide, reverse amide analog, prodrug, isotopic variant (e.g., deuterated analog), PROTAC, pharmaceutical product or any combination thereof.

In some embodiments, each of the variables R-$R^{104}$ of formula I(b(i)) may be further substituted with at least one substitution selected from: F, Cl, Br, I, OH, SH, $C_1$-$C_5$ linear alkyne, diazirine, $C_1$-$C_5$ linear, cyclic or branched alkyl (e.g. methyl, ethyl, propyl, isopropyl or cyclopropyl), substituted or unsubstituted benzyl (e.g., benzyl, methylbenzyl), substituted or unsubstituted aryl (e.g., phenyl, fluorophenyl), heteroaryl (e.g., indole, tetrahydropyran, pyridine (2, 3, and 4-pyridine)), $C_3$-$C_8$ cycloalkyl (e.g., cyclopropyl), $C_1$-$C_5$ linear or branched alkyl-OH (e.g., $C(CH_3)_2CH_2$—OH, $CH_2CH_2$—OH), 3-8 membered heterocyclic ring (e.g., piperidine), alkoxy (e.g. methoxy, ethoxy, propyloxy, isopropyloxy), $NH_2$, $N(alkyl)_2$ (e.g. $N(CH_3)_2$, $N(CH_2CH_3)_2$, $N(CH_3)(CH_2CH_3)$), NH(alkyl) (e.g. $NHCH_3$, $NHCH_2CH_3$, $NHCH_2CH_2CH_3$) NH(cycloalkyl) (e.g. NH(cyclohexyl), NH(cylopentyl)), NH(aryl) (e.g. NH(phenyl), NH(pyridiny)), NH(benzyl), N(cycloalkyl)$_2$ (e.g. N(cyclohexyl)$_2$, N(cylopentyl)$_2$), N(aryl)$_2$ (e.g. N(phenyl)$_2$, N(pyridiny)$_2$), N(alkyl)(aryl) (e.g. N(methyl)(phenyl), N(methyl)(pyridinyl)), N(alkyl)(cycloalkyl) (e.g. N(methyl)(cyclopropyl), N(methyl)(cyclohexyl), N(methyl)(cyclopentyl)), N(aryl)(cycloalkyl) (e.g. N(phenyl)(cyclohexyl), N(pyridinyl)(cyclohexyl)), NHC(O)(alkyl) (e.g. NHC(O)$CH_3$), $CF_3$, aryl, phenyl, heteroaryl, $C_3$-$C_8$ cycloalkyl, halophenyl, (benzyloxy)phenyl, CN and $NO_2$.

In various embodiments, this invention is directed to a compound represented by the structure of formula (I(b(ii))):

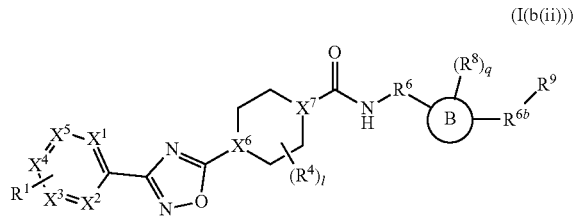

(I(b(ii)))

wherein

B ring is a substituted or unsubstituted saturated, unsaturated or aromatic, single, fused or spiro, carbocyclic or heterocyclic 3-12 membered ring, including a single or fused 3-12 membered aromatic or heteroaromatic ring (e.g. phenyl, pyrimidine, 2-, 3- or 4-pyridine, pyridazine, pyrazine, isothiazole, thiadiazole, imidazole, triazole, thiazole, oxazole, isoxazole, 1-methylimidazole, pyrrole, furan, thiophene, oxadiazole, indole, indane, benzodihydrofuran, tetrahydroquinoline, or pyrazole), a 3-8 membered saturated or unsaturated heterocyclic ring (e.g. tetrahydropyran, tetrahydrofuran, pyrrolidine, piperidine, piperazine, 2-oxopyrrolidine, 2,5-dioxopyrrolidine, 2,5-dioxoimidazolidine, oxetane, chromane), a $C_3$-$C_8$ cycloalkyl ring (e.g. cyclobutyl, cyclohexyl, cyclopentyl, cyclooctyl) a $C_3$-$C_8$ cycloalkenyl ring, or a spiro ring system

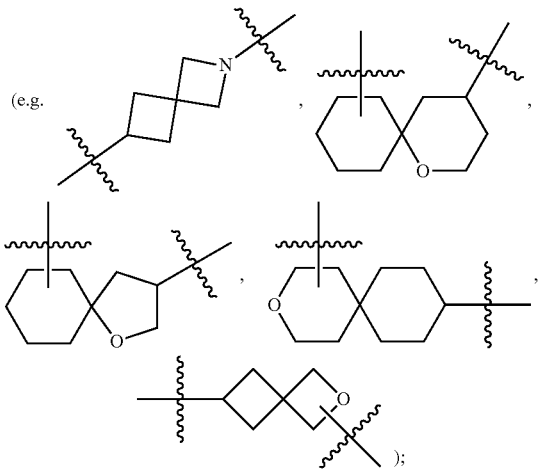

$R^1$ is H, F, Cl, Br, I, OH, $R^6$—OH, O—$R^{20}$, —$R^6$—O—$R^7$, $CF_3$, $OCH_3$, CN, $NO_2$, —$CH_2CN$, —$R^6CN$, $C_1$-$C_5$ linear or branched, substituted or unsubstituted alkyl (e.g., methyl, ethyl), $C_1$-$C_5$ linear or branched, or $C_3$-$C_8$ cyclic haloalkyl (e.g., $CHF_2$), $C_1$-$C_5$ substituted or unsubstituted, linear or branched, or $C_3$-$C_8$ cyclic alkoxy (e.g. methoxy, O—$(CH_2)_2$—OH), $C_1$-$C_5$ linear or branched haloalkoxy (e.g., $OCF_3$, $OCHF_2$), NH—C(O)—$R^7$ (e.g., NHC(O)—$CH_3$), $C_1$-$C_5$ linear or branched alkoxyalkyl;

wherein
$R^7$ is H, $C_1$-$C_5$ substituted or unsubstituted linear or branched alkyl (e.g., methyl, ethyl, $CH_2$—$CH_2$—O—$CH_3$), $C_1$-$C_5$ linear or branched alkoxy (e.g., O—$CH_3$), C(O)R, or $S(O)_2R$;

wherein
R is H, F, Cl, Br, I, OH, $CF_3$, CN, $NO_2$, $C_1$-$C_5$ linear or branched, substituted or unsubstituted alkyl (e.g., methyl, ethyl, propyl, isopropyl, isobutyl), $C_1$-$C_5$ linear or branched alkoxy (e.g. methoxy), $C_1$-$C_5$ linear or branched haloalkyl (e.g., $CHF_2$, $CF_3$, $R^6$-aryl (e.g., $CH_2$-Ph, $CH_2$-Ph-ethyl), $R^6$—N(alkyl)$_2$, $R^6$—NH(alkyl), ($R^6$—NH(cycloalkyl), ($R^6$—NH(aryl), substituted or unsubstituted aryl (e.g., phenyl, ethylphenyl), substituted or unsubstituted heteroaryl (e.g., pyridine (2, 3, and 4-pyridine) or benzimidazole), substituted or unsubstituted $C_3$-$C_8$ cycloalkyl (e.g., cyclopropyl), substituted or unsubstituted 3-8 membered heterocyclic ring (e.g., piperidine, pyrrolidine), $R^6$-(substituted or unsubstituted heterocycle) (e.g., $(CH_2)_3$-piperidine, $CH_2$-benzoxazole, $CH_2$-benzimidazole, $CH_2$-indole) or C(O)-(alkyl) (e.g. C(O)—$CH_3$);

$R^{20}$ is represented by the following structure:

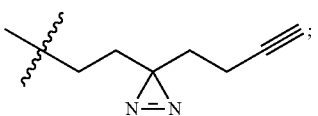 [SMILES: *CCC1(CCC#C)N=N1]

$R^4$ and $R^8$ are each independently H, F, Cl, Br, I, OH, $CF_3$, CN, $NO_2$, $C_1$-$C_5$ linear or branched, substituted or unsubstituted alkyl (e.g., methyl, ethyl, tert-butyl, $CH_2CH_2CH(CH_3)_2$, $CH_2$—$C(CH_3)_3$), $C_1$-$C_5$ linear or branched, or $C_3$-$C_8$ cyclic haloalkyl;

each $R^6$ and $R^{6b}$ is independently absent or O, C=O, C(=O)—$[CH_2]_p$, $[CH_2]_p$—C(=O), $[CH_2]_p$ (e.g. $CH_2$, $CH_2CH_2$, $CH_2CH_2CH_2$, $CH_2CH_2CH_2CH_2$), $[CHR^{21}]_p$ (e.g. CHF, CH—$CH_3$), $[C(R^{21})_2]_p$ (e.g. $CF_2$) or $[CH_2]_{pa}$—O—$[CH_2]_{pb}$ (e.g. $CH_2OCH_2$), or $[CH_2]_p$—O (e.g., $CH_2CH_2O$);

wherein
p is an integer between 1 and 10; and
each pa and pb is independently an integer between 1 and 5;

$R^{21}$ is H, F, Cl, Br, I, OH, $CF_3$, CN, $NO_2$, $C_1$-$C_5$ linear or branched, substituted or unsubstituted alkyl (e.g., methyl, ethyl, propyl, isopropyl, isobutyl), $C_1$-$C_5$ linear or branched alkoxy (e.g. methoxy), $C_1$-$C_5$ linear or branched haloalkyl (e.g., $CHF_2$, $CF_3$, $R^6$-aryl (e.g., $CH_2$-Ph, $CH_2$-Ph-ethyl), $R^6$—N(alkyl)$_2$, $R^6$—NH(alkyl), ($R^6$—NH(cycloalkyl), ($R^6$—NH(aryl), substituted or unsubstituted aryl (e.g., phenyl, ethylphenyl), substituted or unsubstituted heteroaryl (e.g., pyridine (2, 3, and 4-pyridine) or benzimidazole), substituted or unsubstituted $C_3$-$C_8$ cycloalkyl (e.g., cyclopropyl), substituted or unsubstituted 3-8 membered heterocyclic ring (e.g., piperidine, pyrrolidine), $R^6$-(substituted or unsubstituted heterocycle) (e.g., $(CH_2)_3$-piperidine) or C(O)-(alkyl) (e.g. C(O)—$CH_3$);

or wherein two geminal or vicinal $R^2$ substituents are joined to form a substituted or unsubstituted $C_3$-$C_8$ cycloalkyl (e.g., cyclopropyl);

$R^9$ is H, substituted or unsubstituted $C_1$-$C_5$ linear or branched alkyl, substituted or unsubstituted $C_1$-$C_5$ linear or branched alkenyl, $C_1$-$C_5$ linear or branched alkoxy (e.g., O—$CH_3$), $C_1$-$C_5$ linear or branched haloalkoxy (e.g., $OCF_3$, $OCHF_2$), $R^6$—OH, a substituted or unsubstituted aryl (e.g., phenyl, tolyl, fluorophenyl, cyanophenyl), substituted or unsubstituted heteroaryl (e.g., pyridine (2, 3, and 4-pyridine), furan, thiazole, isothiazole, thiophene, pyrrole, methylthiophene, methylfuran, methylpyridine, methylthiazole, indole, benzimidazole, pyrrolopyridine, benzoxazole), substituted or unsubstituted $C_3$-$C_8$ cycloalkyl (e.g., cyclopropyl, methylcyclopropyl, cyclobutyl, cyclohexyl, cyclohexenyl, cyclopentyl), $C_1$-$C_5$ linear or branched, or $C_3$-$C_8$ cyclic haloalkyl (e.g. $CF_3$, $CHF_2$), substituted or unsubstituted 3-8 membered heterocyclic ring (e.g. oxetane, azetidine, methyloxetane, tetrahydrofuran, methyltetrahydropyran, pyrrolidine, methylpyrrolidine, tetrahydropyran, tetrahydrothiopyran, piperidine, methylpiperidine, azepane, oxepane, 2H-thiopyran-tetrahydro-1,1-dioxide), $NH_2$, N(alkyl)$_2$ (e.g. N($CH_3$)$_2$, N($CH_2CH_3$)$_2$, N($CH_3$)($CH_2CH_3$)) NH(alkyl) (e.g. $NHCH_3$, $NHCH_2CH_3$, $NHCH_2CH_2CH_3$) or $R^{20}$;

$X^1$-$X^5$ are each independently C, CH or N;
$X^6$-$X^7$ are each independently CH or N;
l and q are each independently an integer between 0 and 4 (e.g., 0, 1 or 2);

or its pharmaceutically acceptable salt, optical isomer, tautomer, hydrate, N-oxide, reverse amide analog, prodrug, isotopic variant (e.g., deuterated analog), PROTAC, pharmaceutical product or any combination thereof.

In some embodiments, each of the variables R-R$^{104}$ of formula I(b(iii)) may be further substituted with at least one substitution selected from: F, Cl, Br, I, OH, SH, $C_1$-$C_5$ linear alkyne, diazirine, $C_1$-$C_5$ linear, cyclic or branched alkyl (e.g. methyl, ethyl, propyl, isopropyl or cyclopropyl), substituted or unsubstituted benzyl (e.g., benzyl, methylbenzyl), substituted or unsubstituted aryl (e.g., phenyl, fluorophenyl), heteroaryl (e.g., indole, tetrahydropyran, pyridine (2, 3, and 4-pyridine)), $C_3$-$C_8$ cycloalkyl (e.g., cyclopropyl), $C_1$-$C_5$ linear or branched alkyl-OH (e.g., $C(CH_3)_2CH_2$—OH, $CH_2CH_2$—OH), 3-8 membered heterocyclic ring (e.g., piperidine), alkoxy (e.g. methoxy, ethoxy, propyloxy, isopropyloxy), $NH_2$, $N(alkyl)_2$ (e.g. $N(CH_3)_2$, $N(CH_2CH_3)_2$, $N(CH_3)(CH_2CH_3)$), NH(alkyl) (e.g. $NHCH_3$, $NHCH_2CH_3$, $NHCH_2CH_2CH_3$) NH(cycloalkyl) (e.g. NH(cyclohexyl), NH(cylopentyl)), NH(aryl) (e.g. NH(phenyl), NH(pyridiny)), NH(benzyl), N(cycloalkyl)$_2$ (e.g. N(cyclohexyl)$_2$, N(cylopentyl)$_2$), N(aryl)$_2$ (e.g. N(phenyl)$_2$, N(pyridiny)$_2$), N(alkyl)(aryl) (e.g. N(methyl)(phenyl), N(methyl)(pyridinyl)), N(alkyl)(cycloalkyl) (e.g. N(methyl)(cyclopropyl), N(methyl)(cyclohexyl), N(methyl)(cyclopentyl)), N(aryl)(cycloalkyl) (e.g. N(phenyl)(cyclohexyl), N(pyridinyl)(cyclohexyl)), NHC(O)(alkyl) (e.g. $NHC(O)CH_3$), $CF_3$, aryl, phenyl, heteroaryl, $C_3$-$C_8$ cycloalkyl, halophenyl, (benzyloxy)phenyl, CN and $NO_2$.

In various embodiments, this invention is directed to a compound represented by the structure of formula (I(b(iii))):

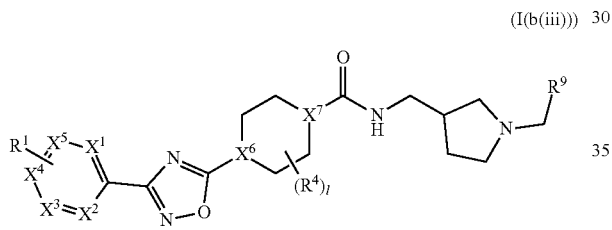

(I(b(iii)))

wherein
  $R^1$ is H, F, Cl, Br, I, OH, $R^6$—OH, O—$R^{20}$, —$R^6$—O—$R^7$, $CF_3$, $OCH_3$, CN, $NO_2$, —$CH_2CN$, —$R^6CN$, $C_1$-$C_5$ linear or branched, substituted or unsubstituted alkyl (e.g., methyl, ethyl), $C_1$-$C_5$ linear or branched, or $C_3$-$C_8$ cyclic haloalkyl (e.g., $CHF_2$), $C_1$-$C_5$ substituted or unsubstituted, linear or branched, or $C_3$-$C_8$ cyclic alkoxy (e.g. methoxy, O—$(CH_2)_2$—OH), $C_1$-$C_5$ linear or branched haloalkoxy (e.g., $OCF_3$, $OCHF_2$), NH—C(O)—$R^7$ (e.g., $NHC(O)$—$CH_3$), $C_1$-$C_5$ linear or branched alkoxyalkyl;
  wherein
    $R^6$ is absent or O, C=O, C(=O)—$[CH_2]_p$, $[CH_2]_p$—C(=O), $[CH_2]_p$ (e.g. $CH_2$, $CH_2CH_2$, $CH_2CH_2CH_2$, $CH_2CH_2CH_2CH_2$), $[CHR^{21}]_p$ (e.g. CHF, CH—$CH_3$), $[C(R^{21})_2]_p$ (e.g. $CF_2$) or $[CH_2]_{pa}$—O—$[CH_2]_{pb}$ (e.g. $CH_2OCH_2$), or $[CH_2]_p$—O (e.g., $CH_2CH_2O$);
      wherein
        p is an integer between 1 and 10; and
        each pa and pb is independently an integer between 1 and 5;
  $R^{21}$ is H, F, Cl, Br, I, OH, $CF_3$, CN, $NO_2$, $C_1$-$C_5$ linear or branched, substituted or unsubstituted alkyl (e.g., methyl, ethyl, propyl, isopropyl, isobutyl), $C_1$-$C_5$ linear or branched alkoxy (e.g. methoxy), $C_1$-$C_5$ linear or branched haloalkyl (e.g., $CHF_2$, $CF_3$, $R^6$-aryl (e.g., $CH_2$-Ph, $CH_2$-Ph-ethyl), $R^6$—N(alkyl)$_2$, $R^6$—NH(alkyl), ($R^6$—NH(cycloalkyl), ($R^6$—NH(aryl), substituted or unsubstituted aryl (e.g., phenyl, ethylphenyl), substituted or unsubstituted heteroaryl (e.g., pyridine (2, 3, and 4-pyridine) or benzimidazole), substituted or unsubstituted $C_3$-$C_8$ cycloalkyl (e.g., cyclopropyl), substituted or unsubstituted 3-8 membered heterocyclic ring (e.g., piperidine, pyrrolidine), $R^6$-(substituted or unsubstituted heterocycle) (e.g., $(CH_2)_3$-piperidine) or C(O)-(alkyl) (e.g. C(O)—$CH_3$);
  or wherein two geminal or vicinal $R^{21}$ substituents are joined to form a substituted or unsubstituted $C_3$-$C_8$ cycloalkyl (e.g., cyclopropyl);
  $R^7$ is H, $C_1$-$C_5$ substituted or unsubstituted linear or branched alkyl (e.g., methyl, ethyl, $CH_2$—$CH_2$—O—$CH_3$), $C_1$-$C_5$ linear or branched alkoxy (e.g., O—$CH_3$), C(O)R, or $S(O)_2R$;
  wherein
    R is H, F, Cl, Br, I, OH, $CF_3$, CN, $NO_2$, $C_1$-$C_5$ linear or branched, substituted or unsubstituted alkyl (e.g., methyl, ethyl, propyl, isopropyl, isobutyl), $C_1$-$C_5$ linear or branched alkoxy (e.g. methoxy), $C_1$-$C_5$ linear or branched haloalkyl (e.g., $CHF_2$, $CF_3$, $R^6$-aryl (e.g., $CH_2$-Ph, $CH_2$-Ph-ethyl), $R^6$—N(alkyl)$_2$, $R^6$—NH(alkyl), ($R^6$—NH(cycloalkyl), ($R^6$—NH(aryl), substituted or unsubstituted aryl (e.g., phenyl, ethylphenyl), substituted or unsubstituted heteroaryl (e.g., pyridine (2, 3, and 4-pyridine) or benzimidazole), substituted or unsubstituted $C_3$-$C_8$ cycloalkyl (e.g., cyclopropyl), substituted or unsubstituted 3-8 membered heterocyclic ring (e.g., piperidine, pyrrolidine), $R^6$-(substituted or unsubstituted heterocycle) (e.g., $(CH_2)_3$-piperidine, $CH_2$-benzoxazole, $CH_2$-benzimidazole, $CH_2$-indole) or C(O)-(alkyl) (e.g. C(O)—$CH_3$);
  $R^{20}$ is represented by the following structure:

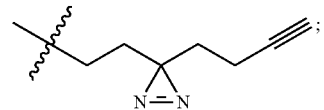 [SMILES: *CCC1(CCC#C)N=N1]

$R^4$ is H, F, Cl, Br, I, OH, $CF_3$, CN, $NO_2$, $C_1$-$C_5$ linear or branched, substituted or unsubstituted alkyl (e.g., methyl, ethyl, tert-butyl, $CH_2CH_2CH(CH_3)_2$, $CH_2$—$C(CH_3)_3$), $C_1$-$C_5$ linear or branched, or $C_3$-$C_5$ cyclic haloalkyl;
  $R^9$ is H, substituted or unsubstituted $C_1$-$C_5$ linear or branched alkyl, substituted or unsubstituted $C_1$-$C_5$ linear or branched alkenyl, $C_1$-$C_5$ linear or branched alkoxy (e.g., O—$CH_3$), $C_1$-$C_5$ linear or branched haloalkoxy (e.g., $OCF_3$, $OCHF_2$), $R^6$—OH, a substituted or unsubstituted aryl (e.g., phenyl, tolyl, fluorophenyl, cyanophenyl), substituted or unsubstituted heteroaryl (e.g., pyridine (2, 3, and 4-pyridine), furan, thiazole, isothiazole, thiophene, pyrrole, methylthiophene, methylfuran, methylpyridine, methylthiazole, indole, benzimidazole, pyrrolopyridine, benzoxazole), substituted or unsubstituted $C_3$-$C_5$ cycloalkyl (e.g., cyclopropyl, methylcyclopropyl, cyclobutyl, cyclohexyl, cyclohexenyl, cyclopentyl), $C_1$-$C_5$ linear or branched, or $C_3$-$C_8$ cyclic haloalkyl (e.g. $CF_3$, $CHF_2$), substituted or unsubstituted 3-8 membered heterocyclic ring (e.g. oxetane, azetidine, methyloxetane, tetrahydrofuran, methyltetrahydropyran, pyrrolidine, methylpyrrolidine, tetrahydropyran, tetrahydrothiopyran, piperidine, methylpiperidine, azepane, oxepane, 2H-thiopyran-tetrahydro-1,1-dioxide), $NH_2$, $N(alkyl)_2$ (e.g. $N(CH_3)_2$, $N(CH_2CH_3)_2$, $N(CH_3)(CH_2CH_3)$) NH(alkyl) (e.g. $NHCH_3$, $NHCH_2CH_3$, $NHCH_2CH_2CH_3$) or $R^{20}$;

$X^1$-$X^5$ are each independently C, CH or N;

$X^6$-$X^7$ are each independently CH or N;

l is an integer between 0 and 4 (e.g., 0, 1 or 2);

or its pharmaceutically acceptable salt, optical isomer, tautomer, hydrate, N-oxide, reverse amide analog, prodrug, isotopic variant (e.g., deuterated analog), PROTAC, pharmaceutical product or any combination thereof.

In various embodiments, this invention is directed to a compound represented by the structure of formula (II):

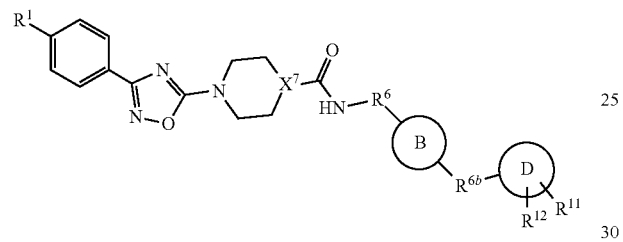

(II)

wherein $R^1$ is H, F, Cl, Br, I, OH, $CF_3$, $OCH_3$, CN, $NO_2$, $C_1$-$C_5$ linear or branched, substituted or unsubstituted alkyl (e.g., methyl, ethyl), $C_1$-$C_5$ linear or branched, or $C_3$-$C_8$ cyclic haloalkyl (e.g., $CHF_2$), $C_1$-$C_5$ substituted or unsubstituted, linear or branched, or $C_3$-$C_8$ cyclic alkoxy (e.g. methoxy, O—$(CH_2)_2$—OH), $C_1$-$C_5$ linear or branched haloalkoxy (e.g., $OCF_3$, $OCHF_2$), NH—C(O)—$R^7$ (e.g., NHC(O)—$CH_3$), $C_1$-$C_5$ linear or branched alkoxyalkyl;

$R^6$ and $R^{6b}$ are each independently absent or O, C=O, C(=O)—$[CH_2]_p$, $[CH_2]_p$—C(=O), $[CH_2]_p$ (e.g. $CH_2$, $CH_2CH_2$, $CH_2CH_2CH_2$, $CH_2CH_2CH_2CH_2$), $[CHR^{21}]_p$ (e.g. CHF, CH—$CH_3$), $[C(R^{21})_2]_p$ (e.g. $CF_2$) or $[CH_2]_{pa}$—O—$[CH_2]_{pb}$ (e.g. $CH_2OCH_2$), or $[CH_2]_p$—O (e.g., $CH_2CH_2O$);

wherein p is an integer between 1 and 10; and each pa and pb is independently an integer between 1 and 5;

$R^2$ is H, F, Cl, Br, I, OH, $CF_3$, CN, $NO_2$, $C_1$-$C_5$ linear or branched, substituted or unsubstituted alkyl (e.g., methyl, ethyl, propyl, isopropyl, isobutyl), $C_1$-$C_5$ linear or branched alkoxy (e.g. methoxy), $C_1$-$C_5$ linear or branched haloalkyl (e.g., $CHF_2$, $CF_3$, $R^6$-aryl (e.g., $CH_2$-Ph, $CH_2$-Ph-ethyl), $R^6$—N(alkyl)$_2$, $R^6$—NH(alkyl), ($R^6$—NH(cycloalkyl), ($R^6$—NH(aryl), substituted or unsubstituted aryl (e.g., phenyl, ethylphenyl), substituted or unsubstituted heteroaryl (e.g., pyridine (2, 3, and 4-pyridine) or benzimidazole), substituted or unsubstituted $C_3$-$C_8$ cycloalkyl (e.g., cyclopropyl), substituted or unsubstituted 3-8 membered heterocyclic ring (e.g., piperidine, pyrrolidine), $R^{18}$-(substituted or unsubstituted heterocycle) (e.g., $(CH_2)_3$-piperidine) or C(O)-(alkyl) (e.g. C(O)—$CH_3$);

or wherein two geminal or vicinal $R^2$ substituents are joined to form a substituted or unsubstituted $C_3$-$C_8$ cycloalkyl (e.g., cyclopropyl);

B ring is a substituted or unsubstituted saturated, unsaturated or aromatic, single, fused or spiro, carbocyclic or heterocyclic 3-12 membered ring (e.g., piperidine, pyrrolidine, 2-pyrrolidone, indole);

D ring is a saturated, unsaturated or aromatic, single, fused or spiro, carbocyclic or heterocyclic 3-12 membered ring (e.g., cyclopropyl, cyclobutyl, cyclopentyl, cyclohexyl, cyclohexenyl, 2, 3, or 4-pyridine, furan, thiophene, pyrrol, thiazole, isothiazole, tetrahydrofuran, piperidine, azepane, oxepane, 2-oxaspiro[3.3]heptane, tetrahydro-2H-thiopyran 1,1-dioxide, tetrahydrothiopyran, tetrahydropyran, pyrrolidine, oxetane, diazirine);

$R^{11}$ and $R^{12}$ are each independently H, F, Cl, Br, I, OH, $CF_3$, $OCH_3$, CN, $NO_2$, $C_1$-$C_5$ linear or branched, substituted or unsubstituted alkyl (e.g., methyl, ethyl), $C_1$-$C_5$ linear or branched, or $C_3$-$C_8$ cyclic haloalkyl (e.g., $CHF_2$), $C_1$-$C_5$ substituted or unsubstituted, linear or branched, or $C_3$-$C_8$ cyclic alkoxy (e.g. methoxy, O—$(CH_2)_2$—OH), $C_1$-$C_5$ linear or branched haloalkoxy (e.g., $OCF_3$, $OCHF_2$), $C_1$-$C_5$ linear or branched alkoxyalkyl, $R^{20}$, $NH_2$, NHR, $NR_2$;

wherein

R is H, F, Cl, Br, I, OH, $CF_3$, CN, $NO_2$, $C_1$-$C_5$ linear or branched, substituted or unsubstituted alkyl, $C_1$-$C_5$ linear or branched alkoxy, $C_1$-$C_5$ linear or branched haloalkyl, $R^6$-aryl, $R^6$—N(alkyl)$_2$, $R^6$—NH(alkyl), ($R^6$—NH(cycloalkyl), ($R^6$—NH(aryl), substituted or unsubstituted aryl, substituted or unsubstituted heteroaryl, substituted or unsubstituted $C_3$-$C_8$ cycloalkyl, substituted or unsubstituted 3-8 membered heterocyclic ring, $R^6$-(substituted or unsubstituted heterocycle) or C(O)-(alkyl);

$X^7$ is CH or N;

$R^{20}$ is represented by the following structure:

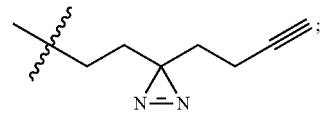 [SMILES: *CCC1(CCC#C)N=N1]

or its pharmaceutically acceptable salt, optical isomer, tautomer, hydrate, N-oxide, reverse amide analog, prodrug, isotopic variant (e.g., deuterated analog), PROTAC, pharmaceutical product or any combination thereof.

In some embodiments, D ring is saturated, unsaturated or aromatic, single, fused or spiro, carbocyclic or heterocyclic 3-12 membered ring; each represent a separate embodiment according to this invention. In some embodiments, D ring is a saturated, unsaturated or aromatic, single, fused or spiro, heterocyclic 3-12 membered ring. In some embodiments, D ring is 2, 3, or 4-pyridine, furan, thiophene, pyrrol, thiazole, isothiazole, tetrahydrofuran, piperidine, azepane, oxepane, 2-oxaspiro[3.3]heptane, azetidine, tetrahydro-2H-thiopyran 1,1-dioxide, tetrahydrothiopyran, tetrahydropyran, pyrrolidine, oxetane or diazirine; each represents a separate embodiment according to this invention. In some embodiments, D ring is an aliphatic ring. In some embodiments, D ring is a saturated aliphatic ring. In some embodiments, D ring is an unsaturated aliphatic ring. In some embodiments, D ring is a saturated, unsaturated, single, fused or spiro, aliphatic carbocyclic 3-12 membered ring. In some embodiments, D ring is a saturated, single, 3-8 membered cycloalkyl ring. In some embodiments, D ring is an unsaturated, single, 3-8 membered cycloalkenyl ring. In some embodiments, D ring is a cyclopropyl, cyclobutyl, cyclopentyl, cyclohexyl or cyclohexenyl; each represents a separate embodiment according to this invention. In some embodiments, D ring is aromatic, single, carbocyclic 3-12 membered ring. In some embodiments, D ring is phenyl. In some embodiments, D ring is aromatic, single or fused, heterocyclic 3-12 membered ring. In some embodiments, D ring is 3-8 membered heteroaryl. In some embodiments, D ring is pyridine (2, 3, and 4-pyridine), furan, thiazole, isothiazole, thiophene, pyrrole, indole, benzimidazole, pyrrolopyridine, benzoxazole; each represent a separate embodiment according to this invention. In some embodiments, D ring is saturated or unsaturated, single, fused or spiro, aliphatic carbocyclic 3-12 membered ring. In some embodiments, D ring is $C_3$-$C_8$ cycloalkyl. In some embodiments, D ring is cyclopropyl, methylcyclopropyl, cyclobutyl, cyclohexyl, cyclohexenyl, cyclopentyl; each represent a separate embodiment according to this invention. In some embodiments, D ring is saturated, single, 3-8 membered heterocyclic ring. In some embodiments, D ring is oxetane, azetidine, tetrahydrofuran, tetrahydropyran, pyrrolidine, tetrahydrothiopyran, piperidine, azepane, oxepane, 2H-thiopyran-tetrahydro-1,1-dioxide); each represent a separate embodiment according to this invention.

In some embodiments, each of the variables R-$R^{104}$ of formula I(b(iii)) may be further substituted with at least one substitution selected from: F, Cl, Br, I, OH, SH, $C_1$-$C_5$ linear alkyne, diazirine, $C_1$-$C_5$ linear, cyclic or branched alkyl (e.g. methyl, ethyl, propyl, isopropyl or cyclopropyl), substituted or unsubstituted benzyl (e.g., benzyl, methylbenzyl), substituted or unsubstituted aryl (e.g., phenyl, fluorophenyl), heteroaryl (e.g., indole, tetrahydropyran, pyridine (2, 3, and 4-pyridine)), $C_3$-$C_8$ cycloalkyl (e.g., cyclopropyl), $C_1$-$C_5$ linear or branched alkyl-OH (e.g., $C(CH_3)_2CH_2$—OH, $CH_2CH_2$—OH), 3-8 membered heterocyclic ring (e.g., piperidine), alkoxy (e.g. methoxy, ethoxy, propyloxy, isopropyloxy), $NH_2$, $N(alkyl)_2$ (e.g. $N(CH_3)_2$, $N(CH_2CH_3)_2$, $N(CH_3)(CH_2CH_3)$), NH(alkyl) (e.g. $NHCH_3$, $NHCH_2CH_3$, $NHCH_2CH_2CH_3$) NH(cycloalkyl) (e.g. NH(cyclohexyl), NH(cylopentyl)), NH(aryl) (e.g. NH(phenyl), NH(pyridiny)), NH(benzyl), N(cycloalkyl)$_2$ (e.g. N(cyclohexyl)$_2$, N(cylopentyl)$_2$), N(aryl)$_2$ (e.g. N(phenyl)$_2$, N(pyridiny)$_2$), N(alkyl)(aryl) (e.g. N(methyl)(phenyl), N(methyl)(pyridinyl)), N(alkyl)(cycloalkyl) (e.g. N(methyl)(cyclopropyl), N(methyl)(cyclohexyl), N(methyl)(cyclopentyl)), N(aryl)(cycloalkyl) (e.g. N(phenyl)(cyclohexyl), N(pyridinyl)(cyclohexyl)), NHC(O)(alkyl) (e.g. NHC(O)$CH_3$), $CF_3$, aryl, phenyl, heteroaryl, $C_3$-$C_8$ cycloalkyl, halophenyl, (benzyloxy)phenyl, CN and $NO_2$.

In some embodiments, A of formula I, and/or I(a) is a is a single aromatic ring. In other embodiments, A is a single heteroaromatic ring. In other embodiments, A is phenyl. In other embodiments, A is pyridinyl. In other embodiments, A is 2-pyridinyl. In other embodiments, A is 3-pyridinyl. In other embodiments, A is 4-pyridinyl. In other embodiments, A is pyrimidine. In other embodiments, A is pyridazine. In other embodiments, A is pyrazine. In other embodiments, A is pyrazole. In other embodiments, A is thiazole. In other embodiments, A is imidazole. In other embodiments, A is 1-methylimidazole. In other embodiments, A is thiophene. In other embodiments, A is isothiazolyl. In other embodiments, A is thiadiazolyl. In other embodiments, A is triazolyl. In other embodiments, A is thiazolyl. In other embodiments, A is oxazolyl. In other embodiments, A is isoxazolyl. In other embodiments, A is pyrrolyl. In other embodiments, A is furanyl. In other embodiments, A is oxadiazolyl. In other embodiments, A is 1,2,3-, 1,2,4-, 1,2,5- or 1,3,4-oxadiazolyl; each is a separate embodiment of this invention.

In some embodiments, B of formula I, I(a), I(a(i), I(a(ii)), I(b), I(b(i)), and/or I(b(ii)) is a substituted or unsubstituted saturated, unsaturated or aromatic, single, fused or spiro, carbocyclic or heterocyclic 3-12 membered ring. In other embodiments, B is an unsubstituted saturated, single, 3-12 membered heterocyclic ring. In other embodiments, B is piperidine, pyrrolidine, or piperazine; each represents a separate embodiment according to this invention. In some embodiments, B is a substituted saturated, single, 3-12 membered heterocyclic ring. In some embodiments, B is an unsaturated, single, 3-12 membered heterocyclic ring. In some embodiments, B is 2-pyrrolidone or indole. In other embodiments, B is an aromatic, single, 3-12 membered carbocyclic ring. In other embodiments, B is phenyl. In other embodiments, B is a saturated, single, 3-12 membered carbocyclic ring. In other embodiments, B is a substituted or unsubstituted $C_3$-$C_{12}$ cycloalkyl ring. In other embodiments, B is a $C_3$-$C_{12}$ single or fused aromatic ring. In other embodiments, B is a substituted or unsubstituted 3-12 membered heterocyclic ring. In other embodiments, B is a substituted or unsubstituted 3-12 membered heteroaromatic ring. In other embodiments, B is pyridinyl. In other embodiments, B is 2-pyridinyl. In other embodiments, B is 3-pyridinyl. In other embodiments, B is 4-pyridinyl. In other embodiments, B is pyrimidine. In other embodiments, B is pyridazine. In other embodiments, B is pyrazine. In other embodiments, B is pyrazole. In other embodiments, B is thiazole. In other embodiments, B is imidazole. In other embodiments, B is 1-methylimidazole. In other embodiments, B is thiophene. In other embodiments, B is isothiazolyl. In other embodiments, B is thiadiazolyl. In other embodiments, B is triazolyl. In other embodiments, B is thiazolyl. In other embodiments, B is oxazolyl. In other embodiments, B is isoxazolyl. In other embodiments, B is pyrrolyl. In other embodiments, B is furanyl. In other embodiments, B is indole. In other embodiments, B is indane. In other embodiments, B is benzodihydrofuran. In other embodiments, B is tetrahydroquinoline. In other embodiments, B is tetrahydropyran. In other embodiments, B is tetrahydrofuran. In other embodiments, B is 1,2,3-, 1,2,4-, 1,2,5- or 1,3,4-oxadiazolyl. In other embodiments, B is oxadiazolyl. In other embodiments, B is pyrrolidine. In other embodiments, B is piperazine. In other embodiments, B is. In other embodiments, B is 2-oxopyrrolidine. In other embodiments, B is 2-pyrrolidone. In other embodiments, B is 2,5-dioxopyrrolidine. In other embodiments, B is 2,5-dioxoimidazolidine. In other embodiments, B is 2,5-dihydrothiazole. In other embodiments, B is oxetane. In other embodiments, B is chromane. In other embodiments, B is piperidine. In other embodiments, B is cyclohexyl. In other embodiments, B is cyclooctyl. In other embodiments, B is cyclopropyl. In other embodiments, B is cyclopentyl. In other embodiments, B is cyclobutyl. In other embodiments, B is a spiro ring system. In other embodiments, B is

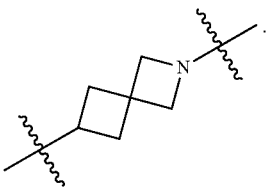 [SMILES: *C1CC2(C1)CN(*)C2]

In other embodiments, B is

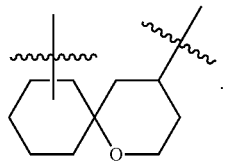

In other embodiments, B is

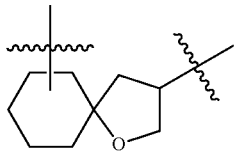

In other embodiments, B is

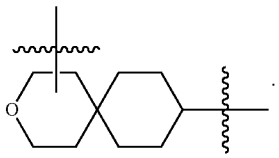

In other embodiments, B is

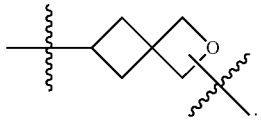

Each possibility is a separate embodiment of this invention. In some embodiments, B ring is a single or fused 3-8 membered heterocyclic ring (e.g., piperidine), $C_3$-$C_8$ saturated or unsaturated cycloalkyl or a spiro ring system. In some embodiments, B ring is a substituted or unsubstituted saturated, unsaturated or aromatic, single, fused or spiro, carbocyclic or heterocyclic 3-12 membered ring. In some embodiments, B ring is a single or fused $C_3$-$C_{12}$ aromatic ring. In some embodiments, B ring is a single or fused 3-12 membered heteroaromatic ring (e.g. phenyl, pyrimidine, 2—, 3- or 4-pyridine, pyridazine, pyrazine, isothiazole, thiadiazole, imidazole, triazole, thiazole, oxazole, isoxazole, 1-methylimidazole, pyrrole, furan, thiophene, oxadiazole, indole, indane, benzodihydrofuran, tetrahydroquinoline, or pyrazole). In some embodiments, B ring is a 3-8 membered saturated or unsaturated heterocyclic ring (e.g. tetrahydropyran, tetrahydrofuran, pyrrolidine, piperidine, piperazine, 2-oxopyrrolidine, 2,5-dioxopyrrolidine, 2,5-dioxoimidazolidine, oxetane, chromane). In some embodiments, B ring is a $C_3$-$C_8$ cycloalkyl ring (e.g. cyclobutyl, cyclohexyl, cyclopentyl, cyclooctyl). In some embodiments, B ring is a $C_3$-$C_8$ cycloalkenyl ring. In some embodiments, B ring is a spiro ring system.

In some embodiments, C of formula I, I(a), and/or I(b) is a 5-10 membered heterocyclic ring. In other embodiments, C is heteroaryl ring. In other embodiments, C is aryl ring. In other embodiments, C is benzene ring. In other embodiments, C is benzopyrrolidine. In other embodiments, C is piperazine. In other embodiments, C is pyrrolidine. In other embodiments, C is piperidine. In other embodiments, C is morpholine. In other embodiments, C is tetrahydropyran. In other embodiments, C is thiomorpholine-1,1-dioxide. Each possibility is a separate embodiment of this invention In some embodiments, D ring of formula II is a saturated, unsaturated or aromatic, single, fused or spiro, carbocyclic or heterocyclic 3-12 membered ring. In some embodiments, D ring is not an aromatic carbocyclic ring. In some embodiments, D ring is not an aryl. In some embodiments, D ring is a saturated, unsaturated or aromatic, single, fused or spiro, heterocyclic 3-12 membered ring. In some embodiments, D ring is 2, 3, or 4-pyridine, furan, thiophene, pyrrol, thiazole, isothiazole, tetrahydrofuran, piperidine, azepane, oxepane, 2-oxaspiro[3.3]heptane, azetidine, tetrahydro-2H-thiopyran 1,1-dioxide, tetrahydrothiopyran, tetrahydropyran, pyrrolidine, oxetane or diazirine; each represents a separate embodiment according to this invention. In some embodiments, D ring is an aliphatic ring. In some embodiments, D ring is a saturated aliphatic ring. In some embodiments, D ring is an unsaturated aliphatic ring. In some embodiments, D ring is a saturated, unsaturated, single, fused or spiro, aliphatic carbocyclic 3-12 membered ring. In some embodiments, D ring is a saturated, single, 3-8 membered cycloalkyl ring. In some embodiments, D ring is an unsaturated, single, 3-8 membered cycloalkenyl ring. In some embodiments, D ring is a cyclopropyl, cyclobutyl, cyclopentyl, cyclohexyl or cyclohexenyl; each represents a separate embodiment according to this invention. In some embodiments, D ring is a saturated, single, 3-12 membered carbocyclic ring. In some embodiments, D ring is cyclopropyl, cyclobutyl, cyclopentyl, cyclohexyl; each represents a separate embodiment of this invention. In some embodiments, D ring is an unsaturated, single, 3-12 membered carbocyclic ring. In some embodiments, D ring is cyclohexenyl. In some embodiments, D ring is an aromatic, single, 3-12 membered heterocyclic ring. In some embodiments, D ring is 2, 3, or 4-pyridine, furan, thiophene, pyrrol, thiazole, isothiazole, diazirine; each possibility is a separate embodiment of this invention. In some embodiments, D ring is a saturated, single, 3-12 membered heterocyclic ring. In some embodiments, D ring is tetrahydrofuran, piperidine, azepane, oxepane, 2-oxaspiro[3.3]heptane, azetidine, tetrahydro-2H-thiopyran 1,1-dioxide, tetrahydrothiopyran, tetrahydropyran, pyrrolidine, oxetane; each possibility is a separate embodiment of this invention. In some embodiments, D ring is cyclopropyl. In some embodiments, D ring is cyclobutyl. In some embodiments, D ring is cyclopentyl. In some embodiments, D ring is cyclohexyl. In some embodiments, D ring is cyclohexenyl. In some embodiments, D ring is 2, 3, or 4-pyridine. In some embodiments, D ring is furan. In some embodiments, D ring is thiophene. In some embodiments, D ring is pyrrol. In some embodiments, D ring is thiazole. In some embodiments, D ring is isothiazole. In some embodiments, D ring is tetrahydrofuran. In some embodiments, D ring is piperidine. In some embodiments, D ring is azepane. In some embodiments, D ring is oxepane. In some embodiments, D ring is 2-oxaspiro[3.3]heptane. In some embodiments, D ring is azetidine. In some embodiments, D ring is tetrahydro-2H-thiopyran 1,1-dioxide. In some embodiments, D ring is tetrahydrothiopyran. In some embodiments, D ring is tetrahydropyran. In some embodiments, D ring is pyrrolidine. In some embodiments, D ring is oxetane. In some embodiments, D ring is diazirine.

In some embodiments, $X^1$ of compound of formula I, I(b), I(b(i)), I(b(ii)) and/or I(b(iii)) is C. In other embodiments, $X^1$ is N. In other embodiments, $X^1$ is CH.

In some embodiments, $X^2$ of compound of formula I, I(b), I(b(i)), I(b(ii)) and/or I(b(iii)) is C. In other embodiments, $X^2$ is N. In other embodiments, $X^2$ is CH.

In some embodiments, $X^3$ of compound of formula I, I(b), I(b(i)), I(b(ii)) and/or I(b(iii)) is C. In other embodiments, $X^3$ is N. In other embodiments, $X^3$ is CH.

In some embodiments, $X^4$ of compound of formula I, I(b), I(b(i)), I(b(ii)) and/or I(b(iii)) is C. In other embodiments, $X^4$ is N. In other embodiments, $X^4$ is CH.

In some embodiments, $X^5$ of compound of formula I, I(b), I(b(i)), I(b(ii)) and/or I(b(iii)) is C. In other embodiments, $X^5$ is N. In other embodiments, $X^5$ is CH.

In some embodiments, $X^6$ of compound of formula I, I(a), I(a(i)), I(a(ii)), I(a(iii)), I(b), I(b(i)), I(b(ii)) and/or I(b(iii)) is CH. In other embodiments, $X^6$ is N.

In some embodiments, $X^7$ of compound of formula I, I(a), I(a(i)), I(a(ii)), I(a(iii)), I(b), I(b(i)), I(b(ii)), I(b(iii)) and/or II is CH. In other embodiments, $X^7$ is N.

In some embodiments, all of $X_1$-$X_5$ are C. In some embodiments, at least one of $X_1$-$X_5$ is N. In some embodiments, at least two of $X_1$-$X_5$ are N. In some embodiments, both of $X^6$ and $X^7$ are N. In some embodiments, $X^6$ is CH and $X^7$ is N. In some embodiments, $X^6$ is N and $X^7$ is CH. In some embodiments, $X^6$ is N and $X^7$ is CH or N. Each possibility is a separate embodiment of this invention.

In some embodiments, $R^1$ of formula formula I, I(a), I(a(i)), I(a(ii)), I(a(iii)), I(b), I(b(i)), I(b(ii)), I(b(iii)) and/or II is H. In some embodiments, $R^1$ is $C_1$-$C_5$ linear or branched, substituted or unsubstituted alkyl. In other embodiments, $R^1$ is methyl. In other embodiments, $R^1$ is ethyl. In other embodiments, $R^1$ is iso-propyl. In other embodiments, $R^1$ is t-Bu. In other embodiments, $R^1$ is iso-butyl. In other embodiments, $R^1$ is pentyl. In other embodiments, $R^1$ is propyl. In other embodiments, $R^1$ is O—$R^{20}$. In other embodiments, $R^1$ is F. In other embodiments, $R^1$ is Cl. In other embodiments, $R^1$ is Br. In other embodiments, $R^1$ is I. In other embodiments, $R^1$ is benzyl. In other embodiments, $R^1$ is in the ortho position. In other embodiments, $R^1$ is an ortho-methyl. In other embodiments, $R^1$ is OH. In other embodiments, $R^1$ is $R^6$—OH. In other embodiments, $R^1$ is —$R^6$—O—$R^7$. In other embodiments, $R^1$ is $OCH_3$. In other embodiments, $R^1$ is CN. In other embodiments, $R^1$ is $NO_2$. In other embodiments, $R^1$ is $CH_2CN$. In other embodiments, $R^1$ is $R_6CN$. In other embodiments, $R^1$ is $C_1$-$C_5$ linear or branched, or $C_3$-$C_8$ cyclic haloalkyl. In other embodiments, $R^1$ is $CF_3$. In other embodiments, $R^1$ is $CHF_2$. In other embodiments, $R^1$ is $C_1$-$C_5$ substituted or unsubstituted, linear or branched, or $C_3$-$C_8$ cyclic alkoxy. In other embodiments, $R^1$ is methoxy. In other embodiments, $R^1$ is O—$(CH_2)_2$—OH. In other embodiments, $R^1$ is $C_1$-$C_5$ linear or branched haloalkoxy. In other embodiments, $R^1$ is $OCF_3$. In other embodiments, $R^1$ is $OCHF_2$. In other embodiments, $R^1$ is NH—C(O)—$R^7$. In other embodiments, $R^1$ is NHC(O)—$CH_3$. In other embodiments, $R^1$ is $C_1$-$C_5$ linear or branched alkoxyalkyl. Each possibility is a separate embodiment of this invention. In some embodiments, $R^1$ of compound of formula (I), (I(a)), (I(a(i))), (I(a(ii))), (I(a(iii))), (I(b)), (I(b(i))), (I(b(ii))), or (I(b(iii))), is in the para position. In some embodiments, $R^1$ is in the ortho position. In some embodiments, $R^1$ is in the meta position. In some embodiments, $R^1$ is F, Cl, Br, I, OH, $CF_3$, $OCH_3$, CN, $NO_2$, —$CH_2CN$, $C_1$-$C_5$ linear or branched, substituted or unsubstituted alkyl, $C_1$-$C_5$ linear or branched, or $C_3$-$C_8$ cyclic haloalkyl (e.g., $CHF_2$, $CF_3$), substituted or unsubstituted $C_1$-$C_5$ linear or branched, or $C_3$-$C_8$ cyclic alkoxy, $C_1$-$C_5$ linear or branched haloalkoxy, NH—C(O)—$R^7$, NHC(O)—$CH_3$ or $C_1$-$C_5$ linear or branched alkoxyalkyl. In some embodiments, $R^1$ is Cl, O—$R^{20}$, $OCH_3$, —$R^6CN$, $C_1$-$C_5$ linear or branched, or $C_3$-$C_8$ cyclic haloalkyl, $CF_3$, $C_1$-$C_5$ linear or branched haloalkoxy, $OCF_3$, or $OCHF_2$. In some embodiments, $R^1$ is F, Cl, Br, I, $CF_3$, $OCH_3$, CN, $C_1$-$C_5$ linear or branched, or $C_3$-$C_8$ cyclic haloalkyl, $CHF_2$, substituted or unsubstituted $C_1$-$C_5$ linear or branched, or $C_3$-$C_8$ cyclic alkoxy, $C_1$-$C_5$ linear or branched haloalkoxy, $OCF_3$, or $OCHF_2$.

In some embodiments, $R^2$ of formula formula I is $C_1$-$C_5$ linear or branched, substituted or unsubstituted alkyl. In other embodiments, $R^2$ is methyl. In other embodiments, $R^2$ is ethyl. In other embodiments, $R^2$ is iso-propyl. In other embodiments, $R^2$ is t-Bu. In other embodiments, $R^2$ is iso-butyl. In other embodiments, $R^2$ is pentyl. In other embodiments, $R^2$ is propyl. In other embodiments, $R^2$ is O—$R^{20}$. In other embodiments, $R^2$ is F. In other embodiments, $R^2$ is Cl. In other embodiments, $R^2$ is Br. In other embodiments, $R^2$ is I. In other embodiments, $R^2$ is benzyl. In other embodiments, $R^2$ is in the ortho position. In other embodiments, $R^2$ is an ortho-methyl. In other embodiments, $R^2$ is OH. In other embodiments, $R^2$ is $R^6$—OH. In other embodiments, $R^2$ is —$R^6$—O—$R^7$. In other embodiments, $R^2$ is $CF_3$. In other embodiments, $R^2$ is $OCH_3$. In other embodiments, $R^2$ is CN. In other embodiments, $R^2$ is $NO_2$. In other embodiments, $R^2$ is $CH_2CN$. In other embodiments, $R^2$ is $R_6CN$. In other embodiments, $R^2$ is $C_1$-$C_5$ linear or branched, or $C_3$-$C_8$ cyclic haloalkyl. In other embodiments, $R^2$ is $CHF_2$. In other embodiments, $R^2$ is $C_1$-$C_5$ substituted or unsubstituted, linear or branched, or $C_3$-$C_8$ cyclic alkoxy. In other embodiments, $R^2$ is methoxy. In other embodiments, $R^2$ is O—$(CH_2)_2$—OH. In other embodiments, $R^2$ is $C_1$-$C_5$ linear or branched haloalkoxy. In other embodiments, $R^2$ is $OCF_3$. In other embodiments, $R^2$ is $OCHF_2$. In other embodiments, $R^2$ is $C_1$-$C_5$ linear or branched alkoxyalkyl. Each possibility is a separate embodiment of this invention.

In some embodiments, $R^1$ and $R^2$ of formula I are joint together to form a pyrrol ring. In some embodiments, $R^1$ and $R^2$ are joint together to form a [1,3]dioxole ring. In some embodiments, $R^1$ and $R^2$ are joint together to form a furanone ring (e.g., furan-2(3H)-one). In some embodiments, $R^1$ and $R^2$ are joint together to form a benzene ring. In some embodiments, $R^1$ and $R^2$ are joint together to form a pyridine ring. In some embodiments, $R^1$ and $R^2$ are joint together to form an oxazine ring. In some embodiments, $R^1$ and $R^2$ are joint together to form a pyrimidine ring. Each possibility is a separate embodiment of this invention.

In some embodiments, $R^3$ of formula I, and/or I(a) is H. In other embodiments, $R^3$ is Cl. In other embodiments, $R^3$ is I. In other embodiments, $R^3$ is F. In other embodiments, $R^3$ is Br. In other embodiments, $R^3$ is OH. In other embodiments, $R^3$ is $C_1$-$C_5$ linear or branched, substituted or unsubstituted alkyl. In other embodiments, $R^3$ is methyl. In other embodiments, $R^3$ is ethyl. In other embodiments, $R^3$ is propyl. In other embodiments, $R^3$ is iso-propyl. In other embodiments, $R^3$ is t-Bu. In other embodiments, $R^3$ is iso-butyl. In other embodiments, $R^3$ is pentyl. In other embodiments, $R^3$ is $C_1$-$C_5$ linear or branched, or $C_3$-$C_8$ cyclic haloalkyl. In other embodiments, $R^3$ is $CF_2CH_3$. In other embodiments, $R^3$ is $CF_2$-cyclobutyl. In other embodiments, $R^3$ is $CH_2CF_3$. In other embodiments, $R^3$ is $CF_2CH_2CH_3$. In other embodiments, $R^3$ is $CF_3$. In other embodiments, $R^3$ is $CF_2CH_2CH_3$. In other embodiments, $R^3$ is $CH_2CH_2CF_3$. In other embodiments, $R^3$ is $CF_2CH(CH_3)_2$. In other embodiments, $R^3$ is $CF(CH_3)$—$CH(CH_3)_2$. Each possibility represents a separate embodiment of this invention.

In some embodiments, $R^4$ of formula I, I(a), I(a(i)), I(a(ii)), I(a(iii)), I(b), I(b(i)), I(b(ii)), and/or I(b(iii)) is H. In other embodiments, $R^4$ is Cl. In other embodiments, $R^4$ is I. In other embodiments, $R^4$ is F. In other embodiments, $R^4$ is Br. In other embodiments, $R^4$ is OH. In other embodiments, $R^4$ is $C_1$-$C_5$ linear or branched, substituted or unsubstituted alkyl. In other embodiments, $R^4$ is methyl. In other embodiments, $R^4$ is ethyl. In other embodiments, $R^4$ is propyl. In other embodiments, $R^4$ is iso-propyl. In other embodiments, $R^4$ is t-Bu. In other embodiments, $R^4$ is iso-butyl. In other embodiments, $R^4$ is pentyl. In other embodiments, $R^4$ is $CH_2$—$C(CH_3)_3$. In other embodiments, $R^4$ is $CH_2CH_2CH(CH_3)_2$. In other embodiments, $R^4$ is $C_1$-$C_5$ linear or branched, or $C_3$-$C_8$ cyclic haloalkyl. In other embodiments, $R^4$ is $CF_2CH_3$. In other embodiments, $R^4$ is $CF_2$-cyclobutyl. In other embodiments, $R^4$ is $CH_2CF_3$. In other embodiments, $R^4$ is $CF_2CH_2CH_3$. In other embodiments, $R^4$ is $CF_3$. In other embodiments, $R^4$ is $CF_2CH_2CH_3$. In other embodiments, $R^4$ is $CH_2CH_2CF_3$. In other embodiments, $R^4$ is $CF_2CH(CH_3)_2$. In other embodiments, $R^4$ is $CF(CH_3)$—$CH(CH_3)_2$. Each possibility represents a separate embodiment of this invention.

In some embodiments, $R^5$ of compound of formula I, I(a) and/or I(b) is OH. In other embodiments, $R^5$ is $C_1$-$C_5$ linear or branched, substituted or unsubstituted alkyl. In other embodiments, $R^5$ is $C_1$-$C_5$ linear or branched, or $C_3$-$C_8$ cyclic haloalkyl. In other embodiments, $R^5$ is $N(R^a)(R^b)$. In other embodiments, $R^5$ is NHR. In other embodiments, $R^5$ is $NH_2$. In other embodiments, $R^5$ is $N(alkyl)_2$. In other embodiments, $R^5$ is $N(CH_3)_2$. In other embodiments, $R^5$ is $N(CH_2CH_3)_2$. In other embodiments, $R^5$ is $N(CH_3)(CH_2CH_3)$. In other embodiments, $R^5$ is NH(alkyl). In other embodiments, $R^5$ is $NHCH_3$. In other embodiments, $R^5$ is $NHCH_2CH_3$. In other embodiments, $R^5$ is $NHCH_2CH_2CH_3$. In other embodiments, $R^5$ is NH(cycloalkyl). In other embodiments, $R^5$ is NH(cyclohexyl). In other embodiments, $R^5$ is NH(cylopentyl). In other embodiments, $R^5$ is NH(aryl). In other embodiments, $R^5$ is NH(phenyl). In other embodiments, $R^5$ is NH(pyridiny). In other embodiments, $R^5$ is NH-1-methyl-indole. In other embodiments, $R^5$ is NH(benzyl). In other embodiments, $R^5$ is $N(cycloalkyl)_2$. In other embodiments, $R^5$ is $N(cyclohexyl)_2$. In other embodiments, $R^5$ is $N(cylopentyl)_2$. In other embodiments, $R^5$ is $N(aryl)_2$. In other embodiments, $R^5$ is $N(phenyl)_2$. In other embodiments, $R^5$ is $N(pyridiny)_2$. In other embodiments, $R^5$ is N(alkyl)(aryl). In other embodiments, $R^5$ is N(methyl)(phenyl). In other embodiments, $R^5$ is N(methyl)(pyridinyl). In other embodiments, $R^5$ is N(alkyl)(cycloalkyl). In other embodiments, $R^5$ is N(methyl)(cyclopropyl). In other embodiments, $R^5$ is N(methyl)(cyclohexyl). In other embodiments, $R^5$ is N(methyl)(cyclopentyl). In other embodiments, $R^5$ is N(aryl)(cycloalkyl). In other embodiments, $R^5$ is N(phenyl)(cyclohexyl). In other embodiments, $R^5$ is N(pyridinyl)(cyclohexyl). In other embodiments, $R^5$ is NHR. In other embodiments, $R^5$ is substituted or unsubstituted aryl. In other embodiments, $R^5$ is substituted or unsubstituted heteroaryl. In other embodiments, $R^5$ is substituted or unsubstituted $C_3$-$C_8$ cycloalkyl. In other embodiments, $R^5$ is substituted or unsubstituted 3-8 membered heterocyclic ring. In other embodiments, $R^5$ is pyrrolidine. In other embodiments, $R^5$ is piperidine. In other embodiments, $R^5$ is morpholine. In other embodiments, $R^5$ is tetrahydropyran. In other embodiments, $R^5$ is

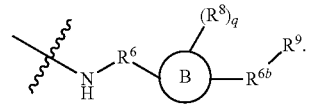

In other embodiments, $R^5$ is

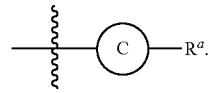

In other embodiments, $R^5$ is

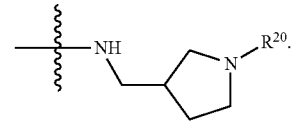

In other embodiments, $R^5$ is NH—$R^{20}$. In other embodiments, R is NH—$R^6$—NH(alkyl). In other embodiments, $R^5$ is NH—$R^6$—$NH_2$. In other embodiments, $R^5$ is NH—$R^6$—$N(alkyl)_2$. In other embodiments, $R^5$ is $NH(CH_2)_3N(CH_2CH_2CH_3)(CH_2CH_3)$. In other embodiments, $R^5$ is $NH(CH_2)_2N(CH_3)_2$. In other embodiments, $R^5$ is $NH(CH_2)_3N(CH_2CH_3)_2$. In other embodiments, $R^5$ is $NH(CH_2)_2N(CH_2CH_3)_2$. In other embodiments, $R^5$ is $NHCH_2CH(C_6H_5)N(CH_3)_2$. In other embodiments, $R^5$ is NH—$R^6$—N(alkyl)(cycloalkyl). In other embodiments, $R^5$ is NH—$R^6$—NH(cycloalkyl). In other embodiments, $R^5$ is NH—$R^6$—NH(aryl). In other embodiments, $R^5$ is NH—$R^6$—N(alkyl)(aryl). In other embodiments, $R^5$ is $NH(CH_2)_3(C_6H_5)(CH_3)$. In other embodiments, $R^5$ is NH—$R^6$—OH. In other embodiments, $R^5$ is NH—$R^6$—O(alkyl). In other embodiments, $R^5$ is NH—$R^6$—O(aryl). $NH(CH_2)_3OCH_3)$. In other embodiments, $R^5$ is NH—$R^6$—O(cycloalkyl). Each possibility is a separate embodiment of this invention.

In some embodiments, $R^6$ of formula I, I(a), I(a(i)), I(a(ii)), I(a(iii)), I(b), I(b(i)), I(b(ii)), I(b(iii)) and/or II is absent. In other embodiments, $R^6$ is $[CH_2]_p$ wherein p is an integer between 1 and 10. In other embodiments, $R^6$ is O. In other embodiments, $R^6$ is C=O. In other embodiments, $R^6$ is C(=O)—$[CH_2]_p$. In other embodiments, $R^6$ is $[CH_2]_p$—C(=O). In other embodiments, $R^6$ is $[CHR^{21}]_p$. In other embodiments, $R^6$ is CHF. In other embodiments, $R^6$ is CH—$CH_3$. In other embodiments, $R^6$ is $[C(R^{21})_2]p$. In other embodiments, $R^6$ is $CF_2$. In other embodiments, $R^6$ is $[CH_2]_p$—O. In other embodiments, $R^6$ is $CH_2CH_2O$. In other embodiments, $R^6$ is $CH_2$. In other embodiments, $R^6$ is $CH_2CH_2$. In other embodiments, $R^6$ is $CH_2CH_2CH_2$. In other embodiments, $R^6$ is $CH_2CH_2CH_2CH_2$. In other embodiments, $R^6$ is $C(CH_2CH_2)CH(C_6H_5)$. In other embodiments, $R^6$ is $CH_2C(CH_3)(C_6H_5)$. In other embodiments, $R^6$ is $CH(thiophenyl)CH_2$. In other embodiments, $R^6$ is $CH(CH_3)CH_2$. In other embodiments, $R^6$ is $C(=O)CH_2$ In other embodiments, $R^6$ is $CH_2C(=O)$. In other embodiments, $R^6$ is $CH(C_6H_5)CH_2$. In other embodiments, $R^6$ is $CH(CH_3)$. In other embodiments, $R^6$ is $CH_2CH(CH_3)$. In other embodiments, $R^6$ is $CH(cyclopropyl)$. In other embodiments, $R^6$ is $CH(CH_3)C(CH_3)_2$. In other embodiments, $R^6$ is $CH(CH_2CF_3)CH_2$. In other embodiments, $R^6$ is $CH_2CHC_6H_5$. In other embodiments, $R^6$ is $CH_2CHOHCH_2$. In other embodiments, $R^6$ is $CH(isopropyl)CH_2CH_2$. In other embodiments, $R^6$ is $CF_2$. In other embodiments, $R^6$ is $CH_2(C(CH_2)_2)CH_2$. In other embodiments, $R^6$ is $CH(CH_2)CH$. In other embodiments, each $R^6$ is independently $[CH_2]_{pa}$—O—$[CH_2]_{pb}$, wherein each pa and pb is independently an integer between 1 and 5. In other embodiments, $R^6$ is $CH_2OCH_2$. Each possibility is a separate embodiment of this invention. In some embodiments, $R^6$ is $[CH_2]_p$ (e.g., $CH_2$—$CH_2$—$CH_2$), $[CH_2]_{pa}$—O—$[CH_2]_{pb}$, or $[CH_2]_p$—O. In some embodiments, $R^6$ is $[CH_2]_p$ (e.g., $CH_2$—$CH_2$—$CH_2$), $[CH_2]_{pa}$—O—$[CH_2]_{pb}$, or $[CH_2]_p$—O, wherein p is 1, 2 or 3; and each pa and pb is independently an integer between 1 and 5. In some embodiments, $R^6$ is absent or is 0, C=O, or $[CH_2]_p$ (e.g., $CH_2$).

In some embodiments, $R^{6b}$ of formula I, I(a), I(a(i)), I(a(ii)), I(a(iii)), I(b), I(b(i)), I(b(ii)), I(b(iii)) and/or II is absent. In other embodiments, $R^{6b}$ is $[CH_2]_p$ wherein p is an integer between 1 and 10. In other embodiments, $R^{6b}$ is O. In other embodiments, $R^{6b}$ is C=O. In other embodiments, $R^{6b}$ is C(=O)—$[CH_2]_p$. In other embodiments, $R^{6b}$ is $[CH_2]_p$—C(=O). In other embodiments, $R^{6b}$ is $[CHR^{21}]_p$. In other embodiments, $R^{6b}$ is CHF. In other embodiments, $R^{6b}$ is CH—$CH_3$. In other embodiments, $R^{6b}$ is $[C(R^{21})_2]_p$. In other embodiments, $R^{6b}$ is $CF_2$. In other embodiments, $R^{6b}$ is $[CH_2]_p$—O. In other embodiments, $R^{6b}$ is $CH_2CH_2O$. In other embodiments, $R^{6b}$ is $CH_2$. In other embodiments, $R^{6b}$ is $CH_2CH_2$. In other embodiments, $R^{6b}$ is $CH_2CH_2CH_2$. In other embodiments, $R^{6b}$ is $CH_2CH_2CH_2CH_2$. In other embodiments, $R^{6b}$ is $C(CH_2CH_2)CH(C_6H_5)$. In other embodiments, $R^{6b}$ is $CH_2C(CH_3)(C_6H_5)$. In other embodiments, $R^{6b}$ is $CH(thiophenyl)CH_2$. In other embodiments, $R^{6b}$ is $CH(CH_3)CH_2$. In other embodiments, $R^{6b}$ is $C(=O)CH_2$ In other embodiments, $R^6$ and/or $R^{6b}$ is $CH_2C(=O)$. In other embodiments, $R^{6b}$ is $CH(C_6H_5)CH_2$. In other embodiments, $R^{6b}$ is $CH(CH_3)$. In other embodiments, $R^{6b}$ is $CH_2CH(CH_3)$. In other embodiments, $R^{6b}$ is $CH(cyclopropyl)$. In other embodiments, $R^{6b}$ is $CH(CH_3)C(CH_3)_2$. In other embodiments, $R^{6b}$ is $CH(CH_2CF_3)CH_2$. In other embodiments, $R^{6b}$ is $CH_2CHC_6H_5$. In other embodiments, $R^{6b}$ is $CH_2CHOHCH_2$. In other embodiments, $R^{6b}$ is $CH(isopropyl)CH_2CH_2$. In other embodiments, $R^{6b}$ is $CF_2$. In other embodiments, $R^{6b}$ is $CH_2(C(CH_2)_2)CH_2$. In other embodiments, $R^{6b}$ is $CH(CH_2)CH$. In other embodiments, each $R^{6b}$ is independently $[CH_2]_{pa}$—O—$[CH_2]_{pb}$, wherein each pa and pb is independently an integer between 1 and 5. In other embodiments, $R^{6b}$ is $CH_2OCH_2$. Each possibility is a separate embodiment of this invention. In some embodiments, $R^{6b}$ is $[CH_2]_p$ (e.g., $CH_2$—$CH_2$—$CH_2$), $[CH_2]_{pa}$—O—$[CH_2]_{pb}$, or $[CH_2]_p$—O. In some embodiments, $R^{6b}$ is $[CH_2]_p$ (e.g., $CH_2$—$CH_2$—$CH_2$), $[CH_2]_{pa}$—O—$[CH_2]_{pb}$, or $[CH_2]_p$—O, wherein p is 1, 2 or 3; and each pa and pb is independently an integer between 1 and 5. In some embodiments, $R^{6b}$ is absent or is 0, C=O, or $[CH_2]_p$ (e.g., $CH_2$).

In some embodiments, $R^7$ of formula I, I(a), I(a(i)), I(a(ii)), I(a(iii)), I(b), I(b(i)), I(b(ii)), and/or I(b(iii)) is H. $C_1$-$C_5$ substituted or unsubstituted linear or branched alkyl. In other embodiments, $R^7$ is methyl. In other embodiments, $R^7$ is ethyl. In other embodiments, $R^7$ is $CH_2CH_2OCH_3$. In other embodiments, $R^7$ is C(O)R. In other embodiments, $R^7$ is $C_1$-$C_5$ linear or branched alkoxy. In other embodiments, $R^7$ is methoxy. In other embodiments, $R^7$ is $S(O)_2R$. Each possibility is a separate embodiment of this invention.

In some embodiments, $R^8$ of compound of formula I, I(a), I(a(i)), I(a(ii)), I(a(iii)), I(b), I(b(i)), I(b(ii)), and/or I(b(iii)) is H. In other embodiments, $R^8$ is Cl. In other embodiments, $R^8$ is I. In other embodiments, $R^8$ is F. In other embodiments, $R^8$ is Br. In other embodiments, $R^8$ is OH. In other embodiments, $R^8$ is $C_1$-$C_5$ linear or branched, substituted or unsubstituted alkyl. In other embodiments, $R^8$ is methyl. In other embodiments, $R^8$ is ethyl. In other embodiments, $R^8$ is propyl. In other embodiments, $R^8$ is iso-propyl. In other embodiments, $R^5$ is t-Bu. In other embodiments, $R^8$ is iso-butyl. In other embodiments, $R^4$ is pentyl. In other embodiments, $R^8$ is $CH_2$—$C(CH_3)_3$. In other embodiments, $R^8$ is $CH_2CH_2CH(CH_3)_2$. In other embodiments, $R^8$ is $C_1$-$C_5$ linear or branched, or $C_3$-$C_8$ cyclic haloalkyl. In other embodiments, $R^8$ is $CF_2CH_3$. In other embodiments, $R^8$ is $CF_2$-cyclobutyl. In other embodiments, $R^8$ is $CH_2CF_3$. In other embodiments, $R^8$ is $CF_2CH_2CH_3$. In other embodiments, $R^8$ is $CF_3$. In other embodiments, $R^1$ is $CF_2CH_2CH_3$. In other embodiments, $R^8$ is $CH_2CH_2CF_3$. In other embodiments, $R^8$ is $CF_2CH(CH_3)_2$. In other embodiments, $R^8$ is $CF(CH_3)$—$CH(CH_3)_2$. Each possibility represents a separate embodiment of this invention. In some embodiments, $R^8$ is H, F, Cl, Br, I, OH, $CF_3$, CN, $NO_2$, $C_1$-$C_5$ linear or branched, substituted or unsubstituted alkyl, $C_1$-$C_5$ linear or branched, or $C_3$-$C_8$ cyclic haloalkyl.

In some embodiments, $R^9$ of formula I, I(a), I(a(i)), I(a(ii)), I(a(iii)), I(b), I(b(i)), I(b(ii)), and/or I(b(iii)) is substituted or unsubstituted aryl. In other embodiments, $R^9$ is phenyl. In other embodiments, $R^9$ is tolyl. In other embodiments, $R^9$ is fluorophenyl. In other embodiments, $R^9$ is cyanophenyl. In other embodiments, $R^9$ is H. In other embodiments, $R^9$ is substituted or unsubstituted $C_1$-$C_5$ linear or branched alkyl. In other embodiments, $R^9$ is neopentyl. In other embodiments, $R^9$ is methyl, ethyl, propyl, isopropyl, butyl, isobutyl, t-butyl, pentyl, neopentyl, isopentyl, or hexyl; each represents a separate embodiment according to this invention. In other embodiments, $R^9$ is substituted or unsubstituted $C_1$-$C_5$ linear or branched alkenyl. In other embodiments, $R^9$ is isopentenyl. In other embodiments, $R^9$ is neopentenyl. In other embodiments, $R^9$ is $C_1$-$C_5$ linear or branched alkoxy. In other embodiments, $R^9$ is $OCH_3$. In other embodiments, $R^9$ is $C_1$-$C_5$ linear or branched haloalkoxy. In other embodiments, $R^9$ is $OCF_3$. In other embodiments, $R^9$ is $OCHF_2$. In other embodiments, $R^9$ is $R^6$—OH. In other embodiments, $R^9$ is substituted or unsubstituted heteroaryl. In some embodiments, $R^9$ is substituted heteroaryl. In other embodiments, $R^9$ is 2, 3 or 4 pyridine. In other embodiments, $R^9$ is methyl-pyridine. In other embodiments, $R^9$ is fluoro-pyridine. In other embodiments, $R^9$ is furan. In other embodiments, $R^9$ is pyrrol. In other embodiments, $R^9$ is methyl-pyrrol. In other embodiments, $R^9$ is thiazole. In other embodiments, $R^9$ is isothiazole. In other embodiments, $R^9$ is thiophene. In other embodiments, $R^9$ is methylthiophene. In other embodiments, $R^9$ is methylfuran. In other embodiments, $R^9$ is methylpyridine. In other embodiments, $R^9$ is methylthiazole. In other embodiments, $R^9$ is substituted or unsubstituted $C_3$-$C_8$ cycloalkyl. In other embodiments, $R^9$ is cyclopropyl. In other embodiments, $R^9$ is methylcyclopropyl. In other embodiments, $R^9$ is dimethylcyclopropyl. In other embodiments, $R^9$ is cyclobutyl. In other embodiments, $R^9$ is cyclohexyl. In other embodiments, $R^9$ is cyclopentyl. In other embodiments, $R^9$ is substituted or unsubstituted unsaturated $C_3$-$C_8$ cycloalkyl. In other embodiments, $R^9$ is substituted or unsubstituted $C_3$-$C_8$ cycloalkenyl. In other embodiments, $R^9$ is cyclohexenyl. In other embodiments, $R^9$ is substituted or unsubstituted, saturated or unsaturated 3-8 membered heterocyclic ring. In other embodiments, $R^9$ is substituted or unsubstituted, saturated 3-8 membered heterocyclic ring. In other embodiments, $R^9$ is oxetane. In other embodiments, $R^9$ is azetidine. In other embodiments, $R^9$ is methyloxetane. In other embodiments, $R^9$ is tetrahydrofuran. In other embodiments, $R^9$ is methyltetrahydropyran. In other embodiments, $R^9$ is pyrrolidine. In other embodiments, $R^9$ is methylpyrrolidine. In other embodiments, $R^9$ is tetrahydropyran. In other embodiments, $R^9$ is tetrahydrothiopyran. In other embodiments, $R^9$ is piperidine. In other embodiments, $R^9$ is methylpiperidine. In other embodiments, $R^9$ is azepane. In other embodiments, $R^9$ is oxepane. In other embodiments, $R^9$ is 2H-Thiopyran-tetrahydro-1,1-dioxide. In other embodiments, $R^9$ is substituted or unsubstituted, unsaturated 3-8 membered heterocyclic ring. In other embodiments, $R^9$ is $C_1$-$C_5$ linear or branched, or $C_3$-$C_8$ cyclic haloalkyl. In other embodiments, $R^9$ is $CF_3$. In other embodiments, $R^9$ is $CHF_2$. In other embodiments, $R^9$ is $NH_2$. In other embodiments, $R^9$ is $N(alkyl)_2$. In other embodiments, $R^9$ is $N(CH_3)_2$. In other embodiments, $R^9$ is $N(CH_2CH_3)_2$. In other embodiments, $R^9$ is NH(alkyl). In other embodiments, $R^9$ is $NHCH_3$. In other embodiments, $R^9$ is $N(CH_3)(CH_2CH_3)$. In other embodiments, $R^9$ is $NHCH_2CH_3$. In other embodiments, $R^9$ is $NHCH_2CH_2CH_3$. Each possibility is a separate embodiment of this invention. In some embodiments, $R^9$ is substituted or unsubstituted heteroaryl, pyridine, 3-methyl-pyridine, thiazolyl, oxazolyl thiophenyl, furanyl, substituted or unsubstituted saturated $C_3$-$C_8$ cycloalkyl, cyclohexyl, cyclopentyl, cyclopropyl, substituted or unsubstituted $C_3$-$C_8$ cycloalkenyl, cyclohexenyl, substituted or unsubstituted 3-8 membered heterocyclic ring, tetrahydropyran, or tetrahydrothiopyran. In some embodiments, $R^9$ is substituted or unsubstituted saturated $C_3$-$C_8$ cycloalkyl (e.g., cyclohexyl, cyclopentyl, cyclopropyl), substituted or unsubstituted $C_3$-$C_8$ cycloalkenyl (e.g., cyclohexenyl), or substituted or unsubstituted saturated or unsaturated 3-8 membered heterocyclic ring (e.g., methyl-piperidine, tetrahydropyran, tetrahydrothiopyran). In some embodiments, $R^9$ is $R^{20}$. In some embodiments, $R^9$ may be further substituted with at least one substitution selected from: F, Cl, Br, I, OH, SH, $C_1$-$C_5$ linear alkyne (e.g., acetylene), diazirine, $C_1$-$C_5$ linear, cyclic or branched alkyl (e.g. methyl, ethyl, propyl, isopropyl or cyclopropyl), substituted or unsubstituted benzyl (e.g., benzyl, methylbenzyl), substituted or unsubstituted aryl (e.g., phenyl, fluorophenyl), heteroaryl (e.g., indole, tetrahydropyran, pyridine (2, 3, and 4-pyridine)), $C_3$-$C_8$ cycloalkyl (e.g., cyclopropyl), $C_1$-$C_5$ linear or branched alkyl-OH (e.g., $C(CH_3)_2CH_2$—OH, $CH_2CH_2$—OH), 3-8 membered heterocyclic ring (e.g., piperidine), alkoxy (e.g. methoxy, ethoxy, propyloxy, isopropyloxy), $NH_2$, $N(alkyl)_2$ (e.g. $N(CH_3)_2$, $N(CH_2CH_3)_2$, $N(CH_3)(CH_2CH_3)$), NH(alkyl) (e.g. $NHCH_3$, $NHCH_2CH_3$, $NHCH_2CH_2CH_3$) NH(cycloalkyl) (e.g. NH(cyclohexyl), NH(cylopentyl)), NH(aryl) (e.g. NH(phenyl), NH(pyridiny)), NH(benzyl), $N(cycloalkyl)_2$ (e.g. $N(cyclohexyl)_2$, $N(cylopentyl)_2$), $N(aryl)_2$ (e.g. $N(phenyl)_2$, $N(pyridiny)_2$), N(alkyl)(aryl) (e.g. N(methyl) (phenyl), N(methyl)(pyridinyl)), N(alkyl)(cycloalkyl) (e.g. N(methyl)(cyclopropyl), N(methyl)(cyclohexyl), N(methyl) (cyclopentyl)), N(aryl)(cycloalkyl) (e.g. N(phenyl)(cyclohexyl), N(pyridinyl)(cyclohexyl)), NHC(O)(alkyl) (e.g. $NHC(O)CH_3$), $CF_3$, aryl, phenyl, heteroaryl, $C_3$-$C_8$ cycloalkyl, halophenyl, (benzyloxy)phenyl, CN and $NO_2$.

In some embodiments, $R^{20}$ of formula I, I(a), I(a(i)), I(a(ii)), I(a(iii)), I(b), I(b(i)), I(b(ii)), I(b(iii)) and/or II is represented by the following structure:

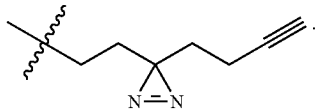 [SMILES: *CCC1(CCC#C)N=N1]

In some embodiments, $R^{21}$ of compound of formula I, I(a), I(a(i)), I(a(ii)), I(a(iii)), I(b), I(b(i)), I(b(ii)), I(b(iii)) and/or II is H. In other embodiments, $R^{21}$ is F. In other embodiments, $R^{21}$ is Cl. In other embodiments, $R^{21}$ is Br. In other embodiments, $R^{21}$ is I. In other embodiments, $R^{21}$ is OH. In other embodiments, $R^{21}$ is $CF_3$. In other embodiments, $R^{21}$ is CN. In other embodiments, $R^{21}$ is $NO_2$. In other embodiments, $R^{21}$ is $N(R^a)(R^b)$. In other embodiments, $R^{21}$ is $C_1$-$C_5$ linear or branched, substituted or unsubstituted alkyl. In other embodiments, $R^{21}$ is methyl. In other embodiments, $R^{21}$ is ethyl. In other embodiments, $R^{21}$ is propyl. In other embodiments, $R^{21}$ is isobutyl. In other embodiments, $R^{21}$ is isopropyl. In other embodiments, $R^{21}$ is $C_1$-$C_5$ linear or branched alkoxy. In other embodiments, $R^{21}$ is methoxy. In other embodiments, $R^{21}$ is $C_1$-$C_5$ linear or branched haloalkyl. In other embodiments, $R^{21}$ is $CHF_2$. In other embodiments, $R^{21}$ is $CF_3$. In other embodiments, $R^{21}$ is $R^6$-aryl. In other embodiments, $R^{21}$ is $CH_2$-Ph. In other embodiments, $R^{21}$ is $CH_2$-Ph-ethyl. In other embodiments, $R^{21}$ is $R^6$—N(alkyl)_2. In other embodiments, $R^{21}$ is $R^6$—NH(alkyl). In other embodiments, $R^{21}$ is ($R^6$—NH(cycloalkyl). In other embodiments, $R^{21}$ is ($R^6$—NH(aryl). In other embodiments, $R^{21}$ is substituted or unsubstituted aryl. In other embodiments, $R^{21}$ is phenyl. In other embodiments, $R^{21}$ is ethylphenyl. In other embodiments, $R^{21}$ is substituted or unsubstituted heteroaryl. In other embodiments, $R^{21}$ is 2, 3, or 4 pyridine. In other embodiments, $R^{21}$ is benzimidazole. In other embodiments, $R^{21}$ is substituted or unsubstituted $C_3$-$C_8$ cycloalkyl. In other embodiments, $R^{21}$ is cyclopropyl. In other embodiments, $R^{21}$ is substituted or unsubstituted 3-8 membered heterocyclic ring. In other embodiments, $R^{21}$ is piperidine. In other embodiments, $R^{21}$ is pyrrolidine. In other embodiments, $R^{21}$ is $R^6$-(substituted or unsubstituted heterocycle). In other embodiments, $R^{21}$ is $(CH_2)_3$-piperidine. In other embodiments, $R^{21}$ is C(O)-(alkyl). In other embodiments, $R^{21}$ is C(O)—$(CH_3)$. Each possibility is a separate embodiment of this invention.

In some embodiments, R of compound of formula I, I(a), I(a(i)), I(a(ii)), I(a(iii)), I(b), I(b(i)), I(b(ii)), I(b(iii)) and/or II is H. In other embodiments, R is F. In other embodiments, R is Cl. In other embodiments, R is Br. In other embodiments, R is I. In other embodiments, R is OH. In other embodiments, R is $CF_3$. In other embodiments, R is CN. In other embodiments, R is $NO_2$. In other embodiments, R is $N(R^a)(R^b)$. In other embodiments, R is $C_1$-$C_5$ linear or branched, substituted or unsubstituted alkyl. In other embodiments, R is methyl. In other embodiments, R is ethyl. In other embodiments, R is propyl. In other embodiments, R is isobutyl. In other embodiments, R is isopropyl. In other embodiments, R is $C_1$-$C_5$ linear or branched alkoxy. In other embodiments, R is methoxy. In other embodiments, R is $C_1$-$C_5$ linear or branched haloalkyl. In other embodiments, R is $CHF_2$. In other embodiments, R is $CF_3$. In other embodiments, R is $R^6$-aryl. In other embodiments, R is $CH_2$-Ph. In other embodiments, R is $CH_2$-Ph-ethyl. In other embodiments, R is $R^6$—N(alkyl)_2. In other embodiments, R is $R^6$—NH(alkyl). In other embodiments, R is ($R^6$—NH(cycloalkyl). In other embodiments, R is ($R^6$—NH(aryl). In other embodiments, R is substituted or unsubstituted aryl. In other embodiments, R is phenyl. In other embodiments, R is ethylphenyl. In other embodiments, R is substituted or unsubstituted heteroaryl. In other embodiments, R is 2, 3, or 4 pyridine. In other embodiments, R is benzimidazole. In other embodiments, R is substituted or unsubstituted $C_3$-$C_8$ cycloalkyl. In other embodiments, R is cyclopropyl. In other embodiments, R is substituted or unsubstituted 3-8 membered heterocyclic ring. In other embodiments, R is piperidine. In other embodiments, R is pyrrolidine. In other embodiments, R is $R^6$-(substituted or unsubstituted heterocycle). In other embodiments, R is $(CH_2)_3$-piperidine. In other embodiments, R is C(O)-(alkyl). In other embodiments, R is C(O)—($CH_3$). Each possibility is a separate embodiment of this invention. In other embodiments, R is F, Cl, Br, I, OH, $CF_3$, CN, $NO_2$, $C_1$-$C_5$ linear or branched, substituted or unsubstituted alkyl, $C_1$-$C_5$ linear or branched alkoxy, $C_1$-$C_5$ linear or branched haloalkyl, $R^6$-aryl, $R^6$—N(alkyl)$_2$, $R^6$—NH(alkyl), ($R^6$—NH(cycloalkyl), ($R^6$—NH (aryl), substituted or unsubstituted aryl, substituted or unsubstituted heteroaryl, substituted or unsubstituted $C_3$-$C_8$ cycloalkyl, substituted or unsubstituted 3-8 membered heterocyclic ring, $R^6$-(substituted or unsubstituted heterocycle) or C(O)-(alkyl).

In some embodiments, $R^a$ of compound of formula I, I(a), I(a(i)), I(b) and/or I(b(i)) is $R^{101}$-$R^{102}$. In other embodiments, $R^a$ is

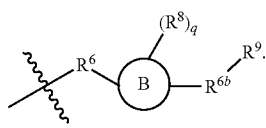

In other embodiments, $R^a$ is

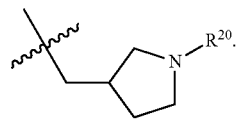

In other embodiments, $R^a$ is $R^{20}$. In other embodiments, $R^a$ is $R^6$—NH(alkyl). In other embodiments, $R^a$ is $R^6$—$NH_2$. In other embodiments, $R^a$ is $R^6$—N(alkyl)$_2$. In other embodiments, $R^a$ is $R^6$—N(alkyl)(cycloalkyl). In other embodiments, $R^a$ is $R^6$—NH(cycloalkyl). In other embodiments, $R^a$ is $R^6$—NH(aryl). In other embodiments, $R^a$ is $R^6$—OH. In other embodiments, $R^a$ is $R^6$—O(alkyl). In other embodiments, $R^a$ is $R^6$—O(aryl). In other embodiments, $R^a$ is $R^6$—O(cycloalkyl). Each possibility is a separate embodiment of this invention.

In some embodiments, $R^b$ of compound of formula I, I(a) and/or I(b) is $R^{103}$-$R^{104}$.

In some embodiments, $R^{101}$ of compound of formula I, I(a), I(a(i)), I(b), and/or I(b(i)) is absent. In other embodiments, $R^{101}$ is —O—. In other embodiments, $R^{101}$ is C=O. In other embodiments, $R^{101}$ is C(=O)—[$CH_2$]$_p$. In other embodiments, $R^{101}$ is [$CH_2$]$_p$—C(=O). In other embodiments, $R^{101}$ is, [$CHR^{21}$]$_p$. In other embodiments, $R^{101}$ is CHF. In other embodiments, $R^{101}$ is [$C(R^{21})_2$]$_p$. In other embodiments, $R^{101}$ is $CF_2$). In other embodiments, $R^{101}$ is [$CH_2$]$_p$—O. In other embodiments, $R^{101}$ is $CH_2CH_2O$. In other embodiments, $R^{101}$ is [$CH_2$]$_p$. In other embodiments, $R^{101}$ is substituted or unsubstituted [$CH_2$]$_{pa}$—O—[$CH_2$]$_{pb}$. In other embodiments, $R^{101}$ is $CH_2OCH_2$. In other embodiments, $R^{101}$ is substituted or unsubstituted arylene. In other embodiments, $R^{101}$ is substituted or unsubstituted heteroarylene. In other embodiments, $R^{101}$ is substituted or unsubstituted heterocycloalkylene. In other embodiments, $R^{101}$ is substituted or unsubstituted cycloalkylene. Each possibility represents a separate embodiment of this invention.

In some embodiments, $R^{103}$ of compound of I, I(a) and/or I(b) is absent. In other embodiments, $R^{103}$ is —O—. In other embodiments, $R^{103}$ is C=O. In other embodiments, $R^{103}$ is C(=O)—[$CH_2$]$_p$. In other embodiments, $R^{103}$ is [$CH_2$]$_p$—C(=O). In other embodiments, $R^{103}$ is, [$CHR^{21}$]$_p$. In other embodiments, $R^{103}$ is CHF. In other embodiments, $R^{103}$ is [$C(R^{21})_2$]$_p$. In other embodiments, $R^{103}$ is $CF_2$). In other embodiments, $R^{103}$ is [$CH_2$]$_p$—O. In other embodiments, $R^{103}$ is $CH_2CH_2O$. In other embodiments, $R^{103}$ is [$CH_2$]$_p$. In other embodiments, $R^{103}$ is substituted or unsubstituted [$CH_2$]$_{pa}$—O—[$CH_2$]$_{pb}$. In other embodiments, $R^{103}$ is $CH_2OCH_2$. In other embodiments, $R^{103}$ is substituted or unsubstituted arylene. In other embodiments, $R^{103}$ is substituted or unsubstituted heteroarylene. In other embodiments, $R^{103}$ is substituted or unsubstituted heterocycloalkylene. In other embodiments, $R^{103}$ is substituted or unsubstituted cycloalkylene. Each possibility represents a separate embodiment of this invention.

In some embodiments, $R^{102}$ of compound of formula I, I(a), I(a(i)), I(b), and/or I(b(i)) is H. In other embodiments, $R^{102}$ is F. In other embodiments, $R^{102}$ is Cl. In other embodiments, $R^{102}$ is Br. In other embodiments, $R^{102}$ is I. In other embodiments, $R^{102}$ is OH. In other embodiments, $R^{102}$ is $CF_3$. In other embodiments, $R^{102}$ is CN. In other embodiments, $R^{102}$ is $NO_2$. In other embodiments, $R^{102}$ is N($R^a$)($R^b$). In other embodiments, $R^{102}$ is $C_1$-$C_5$ linear or branched, substituted or unsubstituted alkyl. In other embodiments, $R^{102}$ is methyl. In other embodiments, $R^{102}$ is ethyl. In other embodiments, $R^{102}$ is propyl. In other embodiments, $R^{102}$ is isobutyl. In other embodiments, $R^{102}$ is cyclopropyl. In other embodiments, $R^{102}$ is isopropyl. In other embodiments, $R^{102}$ is $C_1$-$C_5$ linear or branched alkoxy. In other embodiments, $R^{102}$ is methoxy. In other embodiments, $R^{102}$ is $C_1$-$C_5$ linear or branched haloalkyl. In other embodiments, $R^{102}$ is $CHF_2$. In other embodiments, $R^{102}$ is $CF_3$. In other embodiments, $R^{102}$ is $R^6$-aryl. In other embodiments, $R^{102}$ is $CH_2$-Ph. In other embodiments, $R^{102}$ is $CH_2$-Ph-ethyl. In other embodiments, $R^{102}$ is $R^6$—N(alkyl)$_2$. In other embodiments, $R^{102}$ is $R^6$—NH(alkyl). In other embodiments, $R^{102}$ is ($R^6$—NH(cycloalkyl). In other embodiments, $R^{102}$ is ($R^6$—NH(aryl). In other embodiments, $R^{102}$ is substituted or unsubstituted aryl. In other embodiments, $R^{102}$ is phenyl. In other embodiments, $R^{102}$ is ethylphenyl. In other embodiments, $R^{102}$ is substituted or unsubstituted heteroaryl. In other embodiments, $R^{102}$ is 2, 3, or 4 pyridine. In other embodiments, $R^{102}$ is benzimidazole. In other embodiments, $R^{102}$ is substituted or unsubstituted $C_3$-$C_8$ cycloalkyl. In other embodiments, $R^{102}$ is cyclopropyl. In other embodiments, $R^{102}$ is substituted or unsubstituted 3-8 membered heterocyclic ring. In other embodiments, $R^{102}$ is piperidine. In other embodiments, $R^{102}$ is pyrrolidine. In other embodiments, $R^{102}$ is $R^6$-(substituted or unsubstituted heterocycle). In other embodiments, $R^{102}$ is $(CH_2)_3$-piperidine. In other embodiments, R is C(O)-(alkyl). In other embodiments, $R^{102}$ is C(O)—($CH_3$). Each possibility is a separate embodiment of this invention.

In some embodiments, $R^{104}$ of compound of formula I, I(a) and/or I(b) is H. In other embodiments, $R^{104}$ is F. In other embodiments, $R^{104}$ is Cl. In other embodiments, $R^{104}$ is Br. In other embodiments, $R^{104}$ is I. In other embodiments, $R^{104}$ is OH. In other embodiments, $R^{104}$ is $CF_3$. In other embodiments, $R^{104}$ is CN. In other embodiments, $R^{104}$ is $NO_2$. In other embodiments, $R^{104}$ is $N(R^a)(R^b)$. In other embodiments, $R^{104}$ is $C_1$-$C_5$ linear or branched, substituted or unsubstituted alkyl. In other embodiments, $R^{104}$ is methyl. In other embodiments, $R^{104}$ is ethyl. In other embodiments, $R^{104}$ is propyl. In other embodiments, $R^{104}$ is cyclopropyl. In other embodiments, $R^{104}$ is isopropyl. In other embodiments, $R^{104}$ is isobutyl. In other embodiments, $R^{104}$ is $C_1$-$C_5$ linear or branched alkoxy. In other embodiments, $R^{104}$ is methoxy. In other embodiments, $R^{104}$ is $C_1$-$C_5$ linear or branched haloalkyl. In other embodiments, $R^{104}$ is $CHF_2$. In other embodiments, $R^{104}$ is $CF_3$. In other embodiments, $R^{104}$ is $R^6$-aryl. In other embodiments, $R^{104}$ is $CH_2$-Ph. In other embodiments, $R^{104}$ is $CH_2$-Ph-ethyl. In other embodiments, $R^{104}$ is $R^6$—$N(alkyl)_2$. In other embodiments, $R^{104}$ is $R^6$—NH(alkyl). In other embodiments, $R^{104}$ is ($R^6$—NH(cycloalkyl). In other embodiments, $R^{104}$ is ($R^6$—NH(aryl). In other embodiments, $R^{104}$ is substituted or unsubstituted aryl. In other embodiments, $R^{104}$ is phenyl. In other embodiments, $R^{104}$ is ethylphenyl. In other embodiments, $R^{104}$ is substituted or unsubstituted heteroaryl. In other embodiments, $R^{104}$ is 2, 3, or 4 pyridine. In other embodiments, $R^{104}$ is benzimidazole. In other embodiments, $R^{104}$ is substituted or unsubstituted $C_3$-$C_8$ cycloalkyl. In other embodiments, $R^{104}$ is cyclopropyl. In other embodiments, $R^{104}$ is substituted or unsubstituted 3-8 membered heterocyclic ring. In other embodiments, $R^{104}$ is piperidine. In other embodiments, $R^{104}$ is pyrrolidine. In other embodiments, $R^{104}$ is $R^6$-(substituted or unsubstituted heterocycle). In other embodiments, $R^{104}$ is $(CH_2)_3$-piperidine. In other embodiments, $R^{104}$ is C(O)-(alkyl). In other embodiments, $R^{104}$ is C(O)—($CH_3$). Each possibility is a separate embodiment of this invention.

In some embodiments, $R^a$ and $R^b$ of compound of formula I, I(a) and/or I(b) are joined to form a substituted or unsubstituted 3-8 membered heterocyclic ring. In some embodiments, $R^a$ and $R^b$ are joined to form an unsubstituted 3-8 membered heterocyclic ring. In some embodiments, $R^a$ and $R^b$ are joined to form an unsubstituted morpholine ring. In some embodiments, $R^a$ and $R^b$ are joined to form an unsubstituted piperidine ring. In some embodiments, $R^a$ and $R^b$ are joined to form an unsubstituted piperazine ring.

In some embodiments, m of formula I is 0. In other embodiments, m is 1. In other embodiments, m is 2. In other embodiments, m is 3. In other embodiments, m is 4. Each possibility is a separate embodiment of this invention.

In some embodiments, n of formula I is 0. In other embodiments, n is 1. In other embodiments, n is 2. In other embodiments, n is 3. In other embodiments, n is 4. Each possibility is a separate embodiment of this invention.

In some embodiments, m+n=1, in formula I. In other embodiments, m=0 and n=1. In other embodiments, m=1 and n=0. In other embodiments, m+n>2. In other embodiments, m+n=1 or m+n>2.

In some embodiments, l of formula I, I(a), I(a(i)), I(a(ii)), I(a(iii)), I(b), I(b(i)), I(b(ii)) and/or I(b(iii)) is an integer between 0 and 4. In other embodiments, l is between 0 and 3. In other embodiments, l is between 1 and 4. In other embodiments, l is 0. In other embodiments, l is 1. In other embodiments, l is 2. In other embodiments, l is 3. In other embodiments, l is 4. Each possibility is a separate embodiment of this invention.

In some embodiments, q of formula I, I(a), I(a(i)), I(a(ii)), I(b), I(b(i)) and/or I(b(ii)) is an integer between 0 and 4. In other embodiments, q is between 0 and 3. In other embodiments, q is between 1 and 4. In other embodiments, q is 0. In other embodiments, q is 1. In other embodiments, q is 2. In other embodiments, q is 3. In other embodiments, q is 4. Each possibility is a separate embodiment of this invention.

In some embodiments, p of formula I, I(a), I(a(i)), I(a(ii)), I(a(iii)), I(b), I(b(i)), I(b(ii)) I(b(iii)) and/or II is 1. In other embodiments, p is 2. In other embodiments, p is 3. In other embodiments, p is 4.

In other embodiments, p is 5. In other embodiments, p is 6. In other embodiments, p is 7. In other embodiments, p is 8. In other embodiments, p is 9. In other embodiments, p is 10. In other embodiments, p is between 1 and 5. In other embodiments, p is between 1 and 3. In other embodiments, p is between 3 and 5. In other embodiments, p is between 5 and 10 Each possibility is a separate embodiment of this invention.

In some embodiments, $p^a$ of formula I, I(a), I(a(i)), I(a(ii)), I(a(iii)), I(b), I(b(i)), I(b(ii)) I(b(iii)) and/or II is 0. In other embodiments, $p^a$ is 1. In other embodiments, $p^a$ is 2. In other embodiments, $p^a$ is 3. In other embodiments, $p^a$ is 4. In other embodiments, $p^a$ is 5. In other embodiments, $p^a$ is 6. In other embodiments, $p^a$ is 7. In other embodiments, $p^a$ is 8. In other embodiments, $p^a$ is 9. In other embodiments, $p^a$ is 10. Each possibility is a separate embodiment of this invention.

In some embodiments, $p^b$ of formula I, I(a), I(a(i)), I(a(ii)), I(a(iii)), I(b), I(b(i)), I(b(ii)) I(b(iii)) and/or II is 0. In other embodiments, $p^b$ is 1. In other embodiments, $p^b$ is 2. In other embodiments, $p^b$ is 3. In other embodiments, $p^b$ is 4. In other embodiments, $p^b$ is 5. In other embodiments, $p^b$ is 6. In other embodiments, $p^b$ is 7. In other embodiments, $p^b$ is 8. In other embodiments, $p^b$ is 9. In other embodiments, $p^b$ is 10. Each possibility is a separate embodiment of this invention.

In some embodiments, k of formula I and/or I(a) is 0. In other embodiments, k is 1. In other embodiments, k is 2. In other embodiments, k is 3. In other embodiments, k is 4. Each possibility is a separate embodiment of this invention.

In some embodiments, i of formula I, I(a) and/or I(b) is 1. In other embodiments i is 0.

In various embodiments, this invention is directed to the compounds presented in Table 1, pharmaceutical compositions and/or method of use thereof, each represents a separate embodiment according to this invention:

TABLE 1

| Compound number | Compound Name |
|---|---|
| 101 | 1-(3-(4-methoxyphenyl)-1,2,4-oxadiazol-5-yl)-N-(3-(piperidin-1-yl)propyl)piperidine-4-carboxamide |
| 102 | N-(3-(butyl(ethyl)amino)propyl)-1-(3-(4-methoxyphenyl)-1,2,4-oxadiazol-5-yl)piperidine-4-carboxamide |

TABLE 1-continued

| Compound number | Compound Name |
|---|---|
| 103 | 1-(3-(4-chlorophenyl)-1,2,4-oxadiazol-5-yl)-N-(4-ethylbenzyl)piperidine-4-carboxamide |
| 104 | (1-(3-(4-methoxyphenyl)-1,2,4-oxadiazol-5-yl)piperidin-4-yl)(4-propylpiperazin-1-yl)methanone |
| 105 | 1-(3-(4-methoxyphenyl)-1,2,4-oxadiazol-5-yl)-N-((1-(4-methylbenzyl)pyrrolidin-3-yl)methyl)piperidine-4-carboxamide |
| 106 | (R)-1-(3-(4-methoxyphenyl)-1,2,4-oxadiazol-5-yl)-N-((1-(4-methylbenzyl)pyrrolidin-3-yl)methyl)piperidine-4-carboxamide |
| 107 | (S)-1-(3-(4-methoxyphenyl)-1,2,4-oxadiazol-5-yl)-N-((1-(4-methylbenzyl)pyrrolidin-3-yl)methyl)piperidine-4-carboxamide |
| 109 | (1-(3-(4-methoxyphenyl)-1,2,4-oxadiazol-5-yl)piperidin-4-yl)(pyrrolidin-1-yl)methanone |
| 110 | (1-(3-(4-methoxyphenyl)-1,2,4-oxadiazol-5-yl)piperidin-4-yl)(4-methylpiperidin-1-yl)methanone |
| 111 | N-(2-(dimethylamino)ethyl)-1-(3-(4-methoxyphenyl)-1,2,4-oxadiazol-5-yl)piperidine-4-carboxamide |
| 112 | 1-(3-(4-methoxyphenyl)-1,2,4-oxadiazol-5-yl)-N-(3-methoxypropyl)piperidine-4-carboxamide |
| 113 | N-(3-(diethylamino)propyl)-1-(3-(4-methoxyphenyl)-1,2,4-oxadiazol-5-yl)piperidine-4-carboxamide |
| 114 | N-(2-(diethylamino)ethyl)-1-(3-(4-methoxyphenyl)-1,2,4-oxadiazol-5-yl)piperidine-4-carboxamide |
| 115 | 1-(3-(4-methoxyphenyl)-1,2,4-oxadiazol-5-yl)-N-(pyridin-2-ylmethyl)piperidine-4-carboxamide |
| 116 | 1-(3-(4-methoxyphenyl)-1,2,4-oxadiazol-5-yl)-N-(pyridin-3-ylmethyl)piperidine-4-carboxamide |
| 117 | 1-(3-(4-methoxyphenyl)-1,2,4-oxadiazol-5-yl)-N-(3-(4-methylpiperazin-1-yl)propyl)piperidine-4-carboxamide |
| 119 | N-(2-(butyl(ethyl)amino)ethyl)-1-(3-(4-methoxyphenyl)-1,2,4-oxadiazol-5-yl)piperidine-4-carboxamide |
| 120 | 1-(3-(4-methoxyphenyl)-1,2,4-oxadiazol-5-yl)-N-(thiophen-2-ylmethyl)piperidine-4-carboxamide |
| 121 | N-(3-methoxybenzyl)-1-(3-(4-methoxyphenyl)-1,2,4-oxadiazol-5-yl)piperidine-4-carboxamide |
| 122 | N-(3-chlorobenzyl)-1-(3-(4-methoxyphenyl)-1,2,4-oxadiazol-5-yl)piperidine-4-carboxamide |
| 123 | N-(4-chlorobenzyl)-1-(3-(4-methoxyphenyl)-1,2,4-oxadiazol-5-yl)piperidine-4-carboxamide |
| 124 | 1-(3-(4-methoxyphenyl)-1,2,4-oxadiazol-5-yl)-N-(3-(3-methylpiperidin-1-yl)propyl)piperidine-4-carboxamide |
| 125 | N-(3-(4-benzylpiperidin-1-yl)propyl)-3-(4-methoxyphenyl)-1,2,4-oxadiazol-5-amine |
| 126 | N-(4-ethylbenzyl)-1-(3-(4-methoxyphenyl)-1,2,4-oxadiazol-5-yl)piperidine-4-carboxamide |
| 127 | 1-(3-(4-methoxyphenyl)-1,2,4-oxadiazol-5-yl)-N-propylpiperidine-4-carboxamide |
| 128 | 1-(3-(4-methoxyphenyl)-1,2,4-oxadiazol-5-yl)-N-phenethylpiperidine-4-carboxamide |
| 129 | 1-(3-(4-methoxyphenyl)-1,2,4-oxadiazol-5-yl)-N-(3-phenylpropyl)piperidine-4-carboxamide |
| 130 | 1-(3-(4-methoxyphenyl)-1,2,4-oxadiazol-5-yl)-N-(3-(methyl(phenyl)amino)propyl)piperidine-4-carboxamide |
| 131 | (4-benzylpiperazin-1-yl)(1-(3-phenyl-1,2,4-oxadiazol-5-yl)piperidin-4-yl)methanone |
| 132 | 1-(3-(4-chlorophenyl)-1,2,4-oxadiazol-5-yl)-N-(3-(3-methylpiperidin-1-yl)propyl)piperidine-4-carboxamide |
| 133 | 1-(3-(4-isopropylphenyl)-1,2,4-oxadiazol-5-yl)-N-(4-methoxybenzyl)piperidine-4-carboxamide |
| 134 | (1-(3-(4-methoxyphenyl)-1,2,4-oxadiazol-5-yl)piperidin-4-yl)(4-methoxypiperidin-1-yl)methanone |
| 135 | 3-(4-methoxyphenyl)-5-(4-phenoxypiperidin-1-yl)-1,2,4-oxadiazole |
| 136 | 3-(4-methoxyphenyl)-5-(4-phenylpiperidin-1-yl)-1,2,4-oxadiazole |
| 137 | 1-(3-(4-methoxyphenyl)-1,2,4-oxadiazol-5-yl)-N-methylpiperidine-4-carboxamide |
| 138 | 3-(4-methoxyphenyl)-5-(piperazin-1-yl)-1,2,4-oxadiazole |
| 139 | (1-(3-(4-methoxyphenyl)-1,2,4-oxadiazol-5-yl)piperidin-4-yl)(morpholino)methanone |
| 140 | 1-(3-(4-methoxyphenyl)-1,2,4-oxadiazol-5-yl)-N-(3-(4-methylpiperidin-1-yl)propyl)piperidine-4-carboxamide |
| 141 | (S)-1-(3-(4-methoxyphenyl)-1,2,4-oxadiazol-5-yl)-N-(3-(3-methylpiperidin-1-yl)propyl)piperidine-4-carboxamide |
| 142 | (R)-1-(3-(4-methoxyphenyl)-1,2,4-oxadiazol-5-yl)-N-(3-(3-methylpiperidin-1-yl)propyl)piperidine-4-carboxamide |
| 143 | 1-(3-(4-methoxyphenyl)-1,2,4-oxadiazol-5-yl)-N-phenylpiperidine-4-carboxamide |
| 144 | (4-(3-(4-methoxyphenyl)-1,2,4-oxadiazol-5-yl)piperazin-1-yl)(morpholino)methanone |
| 145 | (4-(3-(4-methoxyphenyl)-1,2,4-oxadiazol-5-yl)piperazin-1-yl)(4-methylpiperidin-1-yl)methanone |
| 146 | (1,1-dioxidothiomorpholino)(4-(3-(4-methoxyphenyl)-1,2,4-oxadiazol-5-yl)piperazin-1-yl)methanone |
| 147 | 1-(4-(3-(4-methoxyphenyl)-1,2,4-oxadiazol-5-yl)piperazin-1-yl)ethan-1-one |
| 148 | (4-(3-(4-methoxyphenyl)-1,2,4-oxadiazol-5-yl)piperazin-1-yl)(tetrahydro-2H-pyran-4-yl)methanone |
| 149 | (R)-3-(3-(4-methoxyphenyl)-1,2,4-oxadiazol-5-yl)-N-((1-(4-methylbenzyl)pyrrolidin-3-yl)methyl)propanamide |

TABLE 1-continued

| Compound number | Compound Name |
|---|---|
| 150 | (S)-3-(3-(4-methoxyphenyl)-1,2,4-oxadiazol-5-yl)-N-((1-(4-methylbenzyl)pyrrolidin-3-yl)methyl)propanamide |
| 151 | N-(3-(4-benzylpiperidin-1-yl)propyl)-3-(3-(4-methoxyphenyl)-1,2,4-oxadiazol-5-yl)propanamide |
| 152 | N-(3-(4-benzylpiperidin-1-yl)propyl)-1-(3-(4-methoxyphenyl)-1,2,4-oxadiazol-5-yl)piperidine-4-carboxamide |
| 153 | (3-(3-(4-methoxyphenyl)-1,2,4-oxadiazol-5-yl)azetidin-1-yl)(4-methylpiperidin-1-yl)methanone |
| 154 | 1-(3-(4-chlorophenyl)-1,2,4-oxadiazol-5-yl)-N-((1-(4-methylbenzyl)pyrrolidin-3-yl)methyl)piperidine-4-carboxamide |
| 155 | 1-(3-(3-chlorophenyl)-1,2,4-oxadiazol-5-yl)-N-((1-(4-methylbenzyl)pyrrolidin-3-yl)methyl)piperidine-4-carboxamide |
| 156 | 1-(3-(2-chlorophenyl)-1,2,4-oxadiazol-5-yl)-N-((1-(4-methylbenzyl)pyrrolidin-3-yl)methyl)piperidine-4-carboxamide |
| 157 | 1-(6-(4-methoxyphenyl)pyridin-2-yl)-N-((1-(4-methylbenzyl)pyrrolidin-3-yl)methyl)piperidine-4-carboxamide |
| 158 | 1-(3-(4-cyanophenyl)-1,2,4-oxadiazol-5-yl)-N-((1-(4-methylbenzyl)pyrrolidin-3-yl)methyl)piperidine-4-carboxamide |
| 159 | 1-(3-(6-methoxypyridin-3-yl)-1,2,4-oxadiazol-5-yl)-N-((1-(4-methylbenzyl)pyrrolidin-3-yl)methyl)piperidine-4-carboxamide |
| 160 | 1-(4-(4-methoxyphenyl)thiazol-2-yl)-N-((1-(4-methylbenzyl)pyrrolidin-3-yl)methyl)piperidine-4-carboxamide |
| 161 | 1-(3-(4-methoxyphenyl)-1,2,4-oxadiazol-5-yl)-N-(pyridin-4-ylmethyl)piperidine-4-carboxamide |
| 162 | 1-(3-(4-methoxyphenyl)-1,2,4-oxadiazol-5-yl)-N-(pyrimidin-5-ylmethyl)piperidine-4-carboxamide |
| 163 | 1-(3-(4-chlorophenyl)-1,2,4-oxadiazol-5-yl)-N-(pyridin-3-ylmethyl)piperidine-4-carboxamide |
| 164 | (1-(3-(2-chlorophenyl)-1,2,4-oxadiazol-5-yl)piperidin-4-yl)(morpholino)methanone |
| 165 | (1-(3-(3-chlorophenyl)-1,2,4-oxadiazol-5-yl)piperidin-4-yl)(morpholino)methanone |
| 166 | (1-(3-(4-chlorophenyl)-1,2,4-oxadiazol-5-yl)piperidin-4-yl)(morpholino)methanone |
| 167 | (S)-1-(3-(4-chlorophenyl)-1,2,4-oxadiazol-5-yl)-N-((1-(4-methylbenzyl)pyrrolidin-3-yl)methyl)piperidine-4-carboxamide |
| 168 | (R)-1-(3-(4-chlorophenyl)-1,2,4-oxadiazol-5-yl)-N-((1-(4-methylbenzyl)pyrrolidin-3-yl)methyl)piperidine-4-carboxamide |
| 169 | 1-(3-(4-methoxyphenyl)-1H-1,2,4-triazol-5-yl)-N-((1-(4-methylbenzyl)pyrrolidin-3-yl)methyl)piperidine-4-carboxamide |
| 170 | 1-(3-(4-hydroxyphenyl)-1,2,4-oxadiazol-5-yl)-N-((1-(4-methylbenzyl)pyrrolidin-3-yl)methyl)piperidine-4-carboxamide |
| 171 | 1-(4'-methoxy-[1,1'-biphenyl]-3-yl)-N-((1-(4-methylbenzyl)pyrrolidin-3-yl)methyl)piperidine-4-carboxamide |
| 172 | (1s,4s)-N-((1-benzylpyrrolidin-3-yl)methyl)-4-(3-(4-methoxyphenyl)-1,2,4-oxadiazol-5-yl)cyclohexane-1-carboxamide |
| 173 | (1s,4s)-4-(3-(4-methoxyphenyl)-1,2,4-oxadiazol-5-yl)cyclohexane-1-carboxylic acid |
| 174 | (1r,4r)-N-((1-benzylpyrrolidin-3-yl)methyl)-4-(3-(4-methoxyphenyl)-1,2,4-oxadiazol-5-yl)cyclohexane-1-carboxamide |
| 175 | (1r,4r)-4-(3-(4-methoxyphenyl)-1,2,4-oxadiazol-5-yl)cyclohexane-1-carboxylic acid |
| 176 | (1s,4s)-N-((1-benzyl-5-oxopyrrolidin-3-yl)methyl)-4-(3-(4-methoxyphenyl)-1,2,4-oxadiazol-5-yl)cyclohexane-1-carboxamide |
| 177 | (1r,4r)-N-((1-benzyl-5-oxopyrrolidin-3-yl)methyl)-4-(3-(4-methoxyphenyl)-1,2,4-oxadiazol-5-yl)cyclohexane-1-carboxamide |
| 178 | 1-(3-(4-hydroxyphenyl)-1,2,4-oxadiazol-5-yl)-N-(pyridin-3-ylmethyl)piperidine-4-carboxamide |
| 179 | 1-(3-(2-methoxyphenyl)-1,2,4-oxadiazol-5-yl)-N-(pyridin-3-ylmethyl)piperidine-4-carboxamide |
| 180 | 1-(3-(3-methoxyphenyl)-1,2,4-oxadiazol-5-yl)-N-(pyridin-3-ylmethyl)piperidine-4-carboxamide |
| 181 | 1-(3-(4-methoxyphenyl)isoxazol-5-yl)-N-(pyridin-3-ylmethyl)piperidine-4-carboxamide |
| 182 | (1-(3-(4-hydroxyphenyl)-1,2,4-oxadiazol-5-yl)piperidin-4-yl)(morpholino)methanone |
| 183 | (1-(3-(4-methoxyphenyl)isoxazol-5-yl)piperidin-4-yl)(morpholino)methanone |
| 184 | 1-(3-(4-acetamidophenyl)-1,2,4-oxadiazol-5-yl)-N-((1-(4-methylbenzyl)pyrrolidin-3-yl)methyl)piperidine-4-carboxamide |
| 185 | 1-(3-(5-methoxypyridin-2-yl)-1,2,4-oxadiazol-5-yl)-N-((1-(4-methylbenzyl)pyrrolidin-3-yl)methyl)piperidine-4-carboxamide |
| 186 | N-((1-(4-methylbenzyl)pyrrolidin-3-yl)methyl)-1-(3-(m-tolyl)-1,2,4-oxadiazol-5-yl)piperidine-4-carboxamide |
| 187 | 1-(3-(3-methoxyphenyl)-1,2,4-oxadiazol-5-yl)-N-((1-(4-methylbenzyl)pyrrolidin-3-yl)methyl)piperidine-4-carboxamide |
| 188 | N-((1-(4-methylbenzyl)pyrrolidin-3-yl)methyl)-1-(3-(o-tolyl)-1,2,4-oxadiazol-5-yl)piperidine-4-carboxamide |
| 189 | 1-(3-(2-methoxyphenyl)-1,2,4-oxadiazol-5-yl)-N-((1-(4-methylbenzyl)pyrrolidin-3-yl)methyl)piperidine-4-carboxamide |
| 190 | (4-(3-(4-methoxyphenyl)-1,2,4-oxadiazol-5-yl)piperazin-1-yl)(4-methoxypiperidin-1-yl)methanone |
| 191 | 4-(3-(4-methoxyphenyl)-1,2,4-oxadiazol-5-yl)-N-methylpiperazine-1-carboxamide |
| 192 | N-(4-chlorophenyl)-1-(3-(4-methoxyphenyl)-1,2,4-oxadiazol-5-yl)piperidine-4-carboxamide |

TABLE 1-continued

| Compound number | Compound Name |
|---|---|
| 193 | N-(4-chlorophenyl)-4-(3-(4-methoxyphenyl)-1,2,4-oxadiazol-5-yl)piperazine-1-carboxamide |
| 194 | N-(3-chlorophenyl)-4-(3-(4-methoxyphenyl)-1,2,4-oxadiazol-5-yl)piperazine-1-carboxamide |
| 195 | N-(2-chlorophenyl)-4-(3-(4-methoxyphenyl)-1,2,4-oxadiazol-5-yl)piperazine-1-carboxamide |
| 196 | 1-(4-(4-methoxyphenyl)oxazol-2-yl)-N-((1-(4-methylbenzyl)pyrrolidin-3-yl)methyl)piperidine-4-carboxamide |
| 197 | (1r,4r)-N-((1-(2-hydroxyethyl)pyrrolidin-3-yl)methyl)-4-(3-(4-methoxyphenyl)-1,2,4-oxadiazol-5-yl)cyclohexane-1-carboxamide |
| 198 | 1-(3-(3-cyanophenyl)-1,2,4-oxadiazol-5-yl)-N-((1-(4-methylbenzyl)pyrrolidin-3-yl)methyl)piperidine-4-carboxamide |
| 199 | 1-(3-(3-hydroxyphenyl)-1,2,4-oxadiazol-5-yl)-N-((1-(4-methylbenzyl)pyrrolidin-3-yl)methyl)piperidine-4-carboxamide |
| 200 | N-(pyridin-3-ylmethyl)-1-(3-(pyridin-4-yl)-1,2,4-oxadiazol-5-yl)piperidine-4-carboxamide |
| 201 | 1-(4-(4-methoxyphenyl)oxazol-2-yl)-N-(pyridin-3-ylmethyl)piperidine-4-carboxamide |
| 202 | morpholino(1-(3-(pyridin-4-yl)-1,2,4-oxadiazol-5-yl)piperidin-4-yl)methanone |
| 203 | (1-(4-(4-methoxyphenyl)oxazol-2-yl)piperidin-4-yl)(morpholino)methanone |
| 204 | (1-(3-(4-methoxyphenyl)-1,2,4-oxadiazol-5-yl)piperidin-4-yl)(4-methylpiperazin-1-yl)methanone |
| 205 | (1-(3-(4-methoxyphenyl)-1,2,4-oxadiazol-5-yl)piperidin-4-yl)(4-phenylpiperazin-1-yl)methanone |
| 206 | 4-(3-(4-methoxyphenyl)-1,2,4-oxadiazol-5-yl)-N-((1-methylpyrrolidin-3-yl)methyl)piperazine-1-carboxamide |
| 207 | N-(3-(4-benzylpiperidin-1-yl)propyl)-4-(3-(4-methoxyphenyl)-1,2,4-oxadiazol-5-yl)piperazine-1-carboxamide |
| 208 | 4-(3-(4-methoxyphenyl)-1,2,4-oxadiazol-5-yl)-N-(3-(4-methylpiperidin-1-yl)propyl)piperazine-1-carboxamide |
| 209 | 4-(3-(4-methoxyphenyl)-1,2,4-oxadiazol-5-yl)-N-phenylpiperazine-1-carboxamide |
| 210 | 1-(3-(4-methoxyphenyl)-1,2,4-oxadiazol-5-yl)-N-(p-tolyl)piperidine-4-carboxamide |
| 211 | 1-(3-(4-methoxyphenyl)-1,2,4-oxadiazol-5-yl)-N-(m-tolyl)piperidine-4-carboxamide |
| 212 | N-(3-chlorophenyl)-1-(3-(4-methoxyphenyl)-1,2,4-oxadiazol-5-yl)piperidine-4-carboxamide |
| 213 | 1-(3-(4-methoxyphenyl)-1,2,4-oxadiazol-5-yl)-N-(o-tolyl)piperidine-4-carboxamide |
| 214 | 5-(4-(1H-benzo[d]imidazol-2-yl)piperidin-1-yl)-3-(4-methoxyphenyl)-1,2,4-oxadiazole |
| 215 | (1s,4s)-N-((1-(2-hydroxyethyl)pyrrolidin-3-yl)methyl)-4-(3-(4-methoxyphenyl)-1,2,4-oxadiazol-5-yl)cyclohexane-1-carboxamide |
| 216 | (4-(3-(4-methoxyphenyl)-1,2,4-oxadiazol-5-yl)piperazin-1-yl)(4-phenoxypiperidin-1-yl)methanone |
| 217 | 1-(3-(4-methoxyphenyl)-1,2,4-oxadiazol-5-yl)-N-((1-methylpiperidin-4-yl)methyl)piperidine-4-carboxamide |
| 218 | 1-(3-(4-methoxyphenyl)-1,2,4-oxadiazol-5-yl)-N-(1-methylpiperidin-4-yl)piperidine-4-carboxamide |
| 219 | 1-(3-(4-methoxyphenyl)-1,2,4-oxadiazol-5-yl)-N-((1-methylpyrrolidin-3-yl)methyl)piperidine-4-carboxamide |
| 220 | N-((1-(cyclopropylmethyl)pyrrolidin-3-yl)methyl)-1-(3-(4-methoxyphenyl)-1,2,4-oxadiazol-5-yl)piperidine-4-carboxamide |
| 221 | N-((1-(cyclopropylmethyl)pyrrolidin-3-yl)methyl)-4-(3-(4-methoxyphenyl)-1,2,4-oxadiazol-5-yl)piperazine-1-carboxamide |
| 222 | 1-(3-(4-methoxyphenyl)-1,2,4-oxadiazol-5-yl)-N-((1-(4-methylbenzoyl)pyrrolidin-3-yl)methyl)piperidine-4-carboxamide |
| 223 | 1-(3-(4-methoxyphenyl)-1,2,4-oxadiazol-5-yl)-N-((1-((5-methylpyridin-2-yl)methyl)pyrrolidin-3-yl)methyl)piperidine-4-carboxamide |
| 224 | N-(2-chlorophenyl)-1-(3-(4-methoxyphenyl)-1,2,4-oxadiazol-5-yl)piperidine-4-carboxamide |
| 225 | 1-(4-(4-(3-(4-methoxyphenyl)-1,2,4-oxadiazol-5-yl)piperazine-1-carbonyl)piperazin-1-yl)ethan-1-one |
| 226 | (3-isobutylpiperidin-1-yl)(4-(3-(4-methoxyphenyl)-1,2,4-oxadiazol-5-yl)piperazin-1-yl)methanone |
| 227 | (1-isobutylpiperidin-3-yl)(4-(3-(4-methoxyphenyl)-1,2,4-oxadiazol-5-yl)piperazin-1-yl)methanone |
| 228 | N-(3-(4-benzoylpiperazin-1-yl)propyl)-1-(3-(4-methoxyphenyl)-1,2,4-oxadiazol-5-yl)piperidine-4-carboxamide |
| 229 | (1r,4r)-4-(3-(4-methoxyphenyl)-1,2,4-oxadiazol-5-yl)-N-((1-methyl-5-oxopyrrolidin-3-yl)methyl)cyclohexane-1-carboxamide |
| 230 | 1-(3-(3-acetamidophenyl)-1,2,4-oxadiazol-5-yl)-N-((1-(4-methylbenzyl)pyrrolidin-3-yl)methyl)piperidine-4-carboxamide |
| 231 | 1-(3-(2-chloro-4-methoxyphenyl)-1,2,4-oxadiazol-5-yl)-N-((1-(4-methylbenzyl)pyrrolidin-3-yl)methyl)piperidine-4-carboxamide |
| 232 | 1-(3-(2-methoxypyrimidin-5-yl)-1,2,4-oxadiazol-5-yl)-N-((1-(4-methylbenzyl)pyrrolidin-3-yl)methyl)piperidine-4-carboxamide |
| 233 | 1-(3-(5-methoxypyrazin-2-yl)-1,2,4-oxadiazol-5-yl)-N-((1-(4-methylbenzyl)pyrrolidin-3-yl)methyl)piperidine-4-carboxamide |
| 234 | 1-(3-(4-methoxyphenyl)-1,2,4-oxadiazol-5-yl)-N-((1-phenylpyrrolidin-3-yl)methyl)piperidine-4-carboxamide |

TABLE 1-continued

| Compound number | Compound Name |
|---|---|
| 235 | 5-(4-(1H-benzo[d]imidazol-2-yl)piperazin-1-yl)-3-(4-methoxyphenyl)-1,2,4-oxadiazole |
| 236 | (4-(3-(4-methoxyphenyl)-1,2,4-oxadiazol-5-yl)piperazin-1-yl)(3-(piperidin-1-ylmethyl)phenyl)methanone |
| 237 | N-((1-(4-methylbenzyl)pyrrolidin-3-yl)methyl)-1-(3-(4-(trifluoromethoxy)phenyl)-1,2,4-oxadiazol-5-yl)piperidine-4-carboxamide |
| 238 | 1-(3-(4-(difluoromethoxy)phenyl)-1,2,4-oxadiazol-5-yl)-N-((1-(4-methylbenzyl)pyrrolidin-3-yl)methyl)piperidine-4-carboxamide |
| 239 | N-(3-(4-benzylpiperidin-1-yl)propyl)-1-(3-(4-(trifluoromethoxy)phenyl)-1,2,4-oxadiazol-5-yl)piperidine-4-carboxamide |
| 240 | N-(3-(4-benzylpiperidin-1-yl)propyl)-1-(3-(4-(difluoromethoxy)phenyl)-1,2,4-oxadiazol-5-yl)piperidine-4-carboxamide |
| 241 | N-(3-(4-benzylpiperidin-1-yl)propyl)-1-(3-(4-cyanophenyl)-1,2,4-oxadiazol-5-yl)piperidine-4-carboxamide |
| 242 | 1-(3-(4-methoxyphenyl)-1,2,4-oxadiazol-5-yl)-N-((1-(5-methylpicolinoyl)pyrrolidin-3-yl)methyl)piperidine-4-carboxamide |
| 243 | 1-(3-(4-chlorophenyl)-1,2,4-oxadiazol-5-yl)-N-((1-((5-methylpyridin-2-yl)methyl)pyrrolidin-3-yl)methyl)piperidine-4-carboxamide |
| 244 | 1-(3-(4-cyanophenyl)-1,2,4-oxadiazol-5-yl)-N-((1-((5-methylpyridin-2-yl)methyl)pyrrolidin-3-yl)methyl)piperidine-4-carboxamide |
| 245 | 4-(3-(4-methoxyphenyl)-1,2,4-oxadiazol-5-yl)-N-(3-(4-phenoxypiperidin-1-yl)propyl)piperazine-1-carboxamide |
| 246 | N-(2-(3-(but-3-yn-1-yl)-3H-diazirin-3-yl)ethyl)-4-(3-(4-methoxyphenyl)-1,2,4-oxadiazol-5-yl)piperazine-1-carboxamide |
| 247 | 1-(3-(5-methoxypyrimidin-2-yl)-1,2,4-oxadiazol-5-yl)-N-((1-(4-methylbenzyl)pyrrolidin-3-yl)methyl)piperidine-4-carboxamide |
| 248 | 4-(3-(4-methoxyphenyl)-1,2,4-oxadiazol-5-yl)-N-(3-(4-(pyridin-2-ylmethyl)piperidin-1-yl)propyl)piperazine-1-carboxamide |
| 249 | N-((1-(dimethylamino)cyclohexyl)methyl)-1-(3-(4-methoxyphenyl)-1,2,4-oxadiazol-5-yl)piperidine-4-carboxamide |
| 250 | N-((1-(tert-butyl)pyrrolidin-3-yl)methyl)-1-(3-(4-methoxyphenyl)-1,2,4-oxadiazol-5-yl)piperidine-4-carboxamide |
| 251 | 1-(3-(4-methoxyphenyl)-1,2,4-oxadiazol-5-yl)-N-(1-propylpiperidin-4-yl)piperidine-4-carboxamide |
| 252 | (R)-1-(3-(4-methoxyphenyl)-1,2,4-oxadiazol-5-yl)-N-((1-methylpyrrolidin-2-yl)methyl)piperidine-4-carboxamide |
| 253 | (R)-1-(3-(4-methoxyphenyl)-1,2,4-oxadiazol-5-yl)-N-((1-methylpyrrolidin-3-yl)methyl)piperidine-4-carboxamide |
| 254 | 1-(3-(4-methoxyphenyl)-1,2,4-oxadiazol-5-yl)-N-(tetrahydro-2H-pyran-4-yl)piperidine-4-carboxamide |
| 255 | 1-(3-(4-methoxyphenyl)-1,2,4-oxadiazol-5-yl)-N-((tetrahydrofuran-3-yl)methyl)piperidine-4-carboxamide |
| 256 | N-((1s,3s)-3-methoxycyclobutyl)-1-(3-(4-methoxyphenyl)-1,2,4-oxadiazol-5-yl)piperidine-4-carboxamide |
| 257 | 1-(3-(4-methoxyphenyl)-1,2,4-oxadiazol-5-yl)-N-(2-(pyrrolidin-1-yl)benzyl)piperidine-4-carboxamide |
| 258 | N-(1-(hydroxy(phenyl)methyl)cyclopropyl)-1-(3-(4-methoxyphenyl)-1,2,4-oxadiazol-5-yl)piperidine-4-carboxamide |
| 259 | N-((1S,2R)-2-hydroxy-2,3-dihydro-1H-inden-1-yl)-1-(3-(4-methoxyphenyl)-1,2,4-oxadiazol-5-yl)piperidine-4-carboxamide |
| 260 | N-(2-hydroxy-2-phenylpropyl)-1-(3-(4-methoxyphenyl)-1,2,4-oxadiazol-5-yl)piperidine-4-carboxamide |
| 261 | N-(4,5-dihydrothiazol-2-yl)-1-(3-(4-methoxyphenyl)-1,2,4-oxadiazol-5-yl)piperidine-4-carboxamide |
| 262 | N-(2-hydroxy-1-(thiophen-2-yl)ethyl)-1-(3-(4-methoxyphenyl)-1,2,4-oxadiazol-5-yl)piperidine-4-carboxamide |
| 263 | 1-(3-(4-methoxyphenyl)-1,2,4-oxadiazol-5-yl)-N-(1-(pyridin-2-yl)propan-2-yl)piperidine-4-carboxamide |
| 264 | 1-(3-(4-methoxyphenyl)-1,2,4-oxadiazol-5-yl)-N-(1-phenylcyclopropyl)piperidine-4-carboxamide |
| 265 | (R)-N-(2-hydroxy-1-phenylethyl)-1-(3-(4-methoxyphenyl)-1,2,4-oxadiazol-5-yl)piperidine-4-carboxamide |
| 266 | (S)-N-(1-(2-fluorophenyl)ethyl)-1-(3-(4-methoxyphenyl)-1,2,4-oxadiazol-5-yl)piperidine-4-carboxamide |
| 267 | 1-(3-(4-cyanophenyl)-1,2,4-oxadiazol-5-yl)-N-((1-(4-methylbenzyl)-5-oxopyrrolidin-3-yl)methyl)piperidine-4-carboxamide |
| 268 | 4-(3-(4-cyanophenyl)-1,2,4-oxadiazol-5-yl)-N-((1-(4-methylbenzyl)-5-oxopyrrolidin-3-yl)methyl)piperazine-1-carboxamide |
| 269 | N-(2-(2,2-dimethylpyrrolidin-1-yl)ethyl)-1-(3-(4-methoxyphenyl)-1,2,4-oxadiazol-5-yl)piperidine-4-carboxamide |
| 270 | N-((1-hydroxycyclohexyl)methyl)-1-(3-(4-methoxyphenyl)-1,2,4-oxadiazol-5-yl)piperidine-4-carboxamide |
| 271 | 1-(3-(4-methoxyphenyl)-1,2,4-oxadiazol-5-yl)-N-(2-methyl-2-azaspiro[3.3]heptan-6-yl)piperidine-4-carboxamide |
| 272 | (R)-N-((4,4-dimethyloxetan-2-yl)methyl)-1-(3-(4-methoxyphenyl)-1,2,4-oxadiazol-5-yl)piperidine-4-carboxamide |
| 273 | 1-(3-(4-methoxyphenyl)-1,2,4-oxadiazol-5-yl)-N-((4-phenyltetrahydro-2H-pyran-4-yl)methyl)piperidine-4-carboxamide |

TABLE 1-continued

| Compound number | Compound Name |
|---|---|
| 274 | N-((1R,3S)-3-hydroxycyclopentyl)-1-(3-(4-methoxyphenyl)-1,2,4-oxadiazol-5-yl)piperidine-4-carboxamide |
| 275 | N-(3,3-difluorocyclopentyl)-1-(3-(4-methoxyphenyl)-1,2,4-oxadiazol-5-yl)piperidine-4-carboxamide |
| 276 | (S)-1-(3-(4-methoxyphenyl)-1,2,4-oxadiazol-5-yl)-N-(2-methoxypropyl)piperidine-4-carboxamide |
| 277 | N-(3-benzyloxetan-3-yl)-1-(3-(4-methoxyphenyl)-1,2,4-oxadiazol-5-yl)piperidine-4-carboxamide |
| 278 | N-(chroman-2-ylmethyl)-1-(3-(4-methoxyphenyl)-1,2,4-oxadiazol-5-yl)piperidine-4-carboxamide |
| 279 | (S)-N-(sec-butyl)-1-(3-(4-methoxyphenyl)-1,2,4-oxadiazol-5-yl)piperidine-4-carboxamide |
| 280 | N-(cyclopropyl(pyridin-2-yl)methyl)-1-(3-(4-methoxyphenyl)-1,2,4-oxadiazol-5-yl)piperidine-4-carboxamide |
| 281 | N-((2,3-dihydrobenzofuran-5-yl)methyl)-1-(3-(4-methoxyphenyl)-1,2,4-oxadiazol-5-yl)piperidine-4-carboxamide |
| 282 | 1-(3-(4-methoxyphenyl)-1,2,4-oxadiazol-5-yl)-N-(2-phenoxyethyl)piperidine-4-carboxamide |
| 283 | N-(2,3-dihydrobenzofuran-3-yl)-1-(3-(4-methoxyphenyl)-1,2,4-oxadiazol-5-yl)piperidine-4-carboxamide |
| 284 | N-(2-(difluoromethoxy)benzyl)-1-(3-(4-methoxyphenyl)-1,2,4-oxadiazol-5-yl)piperidine-4-carboxamide |
| 285 | N-((1H-indol-2-yl)methyl)-1-(3-(4-methoxyphenyl)-1,2,4-oxadiazol-5-yl)piperidine-4-carboxamide |
| 286 | N-((1-(2-(3-(but-3-yn-1-yl)-3H-diazirin-3-yl)ethyl)pyrrolidin-3-yl)methyl)-1-(3-(4-methoxyphenyl)-1,2,4-oxadiazol-5-yl)piperidine-4-carboxamide |
| 287 | 1-(3-(4-(2-(3-(but-3-yn-1-yl)-3H-diazirin-3-yl)ethoxy)phenyl)-1,2,4-oxadiazol-5-yl)-N-((1-(4-methylbenzyl)pyrrolidin-3-yl)methyl)piperidine-4-carboxamide |
| 288 | 1-(3-(3-(2-(3-(but-3-yn-1-yl)-3H-diazirin-3-yl)ethoxy)phenyl)-1,2,4-oxadiazol-5-yl)-N-((1-(4-methylbenzyl)pyrrolidin-3-yl)methyl)piperidine-4-carboxamide |
| 289 | 1-(3-(4-methoxyphenyl)-1,2,4-oxadiazol-5-yl)-N-(1-oxaspiro[5.5]undecan-4-yl)piperidine-4-carboxamide |
| 290 | 1-(3-(4-methoxyphenyl)-1,2,4-oxadiazol-5-yl)-N-(1-oxaspiro[4.5]decan-3-yl)piperidine-4-carboxamide |
| 291 | N-(4-cyclopropyltetrahydro-2H-pyran-4-yl)-1-(3-(4-methoxyphenyl)-1,2,4-oxadiazol-5-yl)piperidine-4-carboxamide |
| 292 | N-(1-cyclohexylcyclopropyl)-1-(3-(4-methoxyphenyl)-1,2,4-oxadiazol-5-yl)piperidine-4-carboxamide |
| 293 | N-(((1S,2R)-2-hydroxycyclohexyl)methyl)-1-(3-(4-methoxyphenyl)-1,2,4-oxadiazol-5-yl)piperidine-4-carboxamide |
| 294 | N-(3-hydroxy-2,2-dimethylcyclobutyl)-1-(3-(4-methoxyphenyl)-1,2,4-oxadiazol-5-yl)piperidine-4-carboxamide |
| 295 | 1-(3-(4-methoxyphenyl)-1,2,4-oxadiazol-5-yl)-N-((1R,5S,6s)-3-methyl-3-azabicyclo[3.1.0]hexan-6-yl)piperidine-4-carboxamide |
| 296 | N-((2-(dimethylamino)-2,3-dihydro-1H-inden-2-yl)methyl)-1-(3-(4-methoxyphenyl)-1,2,4-oxadiazol-5-yl)piperidine-4-carboxamide |
| 297 | N-(3-hydroxy-3-methylbutan-2-yl)-1-(3-(4-methoxyphenyl)-1,2,4-oxadiazol-5-yl)piperidine-4-carboxamide |
| 298 | 1-(3-(4-methoxyphenyl)-1,2,4-oxadiazol-5-yl)-N-(1-(4-methylthiazol-2-yl)cyclobutyl)piperidine-4-carboxamide |
| 299 | 1-(3-(4-methoxyphenyl)-1,2,4-oxadiazol-5-yl)-N-(4,4,4-trifluoro-1-hydroxybutan-2-yl)piperidine-4-carboxamide |
| 300 | N-(3-isopropoxybenzyl)-1-(3-(4-methoxyphenyl)-1,2,4-oxadiazol-5-yl)piperidine-4-carboxamide |
| 301 | 1-(3-(4-methoxyphenyl)-1,2,4-oxadiazol-5-yl)-N-((5,6,7,8-tetrahydroquinolin-8-yl)methyl)piperidine-4-carboxamide |
| 302 | 1-(3-(4-methoxyphenyl)-1,2,4-oxadiazol-5-yl)-N-(1-methyl-1,2,3,4-tetrahydroquinolin-4-yl)piperidine-4-carboxamide |
| 303 | N-(isochroman-1-ylmethyl)-1-(3-(4-methoxyphenyl)-1,2,4-oxadiazol-5-yl)piperidine-4-carboxamide |
| 304 | N-(2-(dimethylamino)-2-phenylethyl)-1-(3-(4-methoxyphenyl)-1,2,4-oxadiazol-5-yl)piperidine-4-carboxamide |
| 305 | N-(2-hydroxy-3-phenylpropyl)-1-(3-(4-methoxyphenyl)-1,2,4-oxadiazol-5-yl)piperidine-4-carboxamide |
| 306 | 1-(3-(4-methoxyphenyl)-1,2,4-oxadiazol-5-yl)-N-(4-(oxetan-3-yl)phenyl)piperidine-4-carboxamide |
| 307 | N-((1-(2,4-difluorophenyl)cyclopropyl)methyl)-1-(3-(4-methoxyphenyl)-1,2,4-oxadiazol-5-yl)piperidine-4-carboxamide |
| 308 | N-(4-methoxy-3-(trifluoromethyl)benzyl)-1-(3-(4-methoxyphenyl)-1,2,4-oxadiazol-5-yl)piperidine-4-carboxamide |
| 309 | 1-(3-(4-methoxyphenyl)-1,2,4-oxadiazol-5-yl)-N-(2-(6-(trifluoromethyl)pyridin-2-yl)ethyl)piperidine-4-carboxamide |
| 310 | N-(1-(1H-indol-3-yl)propan-2-yl)-1-(3-(4-methoxyphenyl)-1,2,4-oxadiazol-5-yl)piperidine-4-carboxamide |
| 311 | N-(2-fluoro-5-methylbenzyl)-1-(3-(4-methoxyphenyl)-1,2,4-oxadiazol-5-yl)piperidine-4-carboxamide |

TABLE 1-continued

| Compound number | Compound Name |
|---|---|
| 312 | 1-(3-(4-methoxyphenyl)-1,2,4-oxadiazol-5-yl)-N-(3-oxaspiro[5.5]undecan-9-yl)piperidine-4-carboxamide |
| 313 | 1-(3-(4-methoxyphenyl)-1,2,4-oxadiazol-5-yl)-N-(1-(tetrahydro-2H-pyran-2-yl)ethyl)piperidine-4-carboxamide |
| 314 | N-(2-(cyclopropyl(methyl)amino)ethyl)-1-(3-(4-methoxyphenyl)-1,2,4-oxadiazol-5-yl)piperidine-4-carboxamide |
| 315 | (S)-N-(1-hydroxy-4-methylpentan-3-yl)-1-(3-(4-methoxyphenyl)-1,2,4-oxadiazol-5-yl)piperidine-4-carboxamide |
| 316 | (S)-N-(1-benzylpyrrolidin-3-yl)-1-(3-(4-methoxyphenyl)-1,2,4-oxadiazol-5-yl)piperidine-4-carboxamide |
| 317 | 1-(3-(4-methoxyphenyl)-1,2,4-oxadiazol-5-yl)-N-(2-(6-methyl-1H-indol-3-yl)ethyl)piperidine-4-carboxamide |
| 318 | 1-(3-(4-methoxyphenyl)-1,2,4-oxadiazol-5-yl)-N-((2-(trifluoromethyl)thiazol-5-yl)methyl)piperidine-4-carboxamide |
| 319 | N-(4,5-dichloropyridin-2-yl)-1-(3-(4-methoxyphenyl)-1,2,4-oxadiazol-5-yl)piperidine-4-carboxamide |
| 320 | N-((1-(furan-2-ylmethyl)pyrrolidin-3-yl)methyl)-1-(3-(4-methoxyphenyl)-1,2,4-oxadiazol-5-yl)piperidine-4-carboxamide |
| 321 | N-((1-(2-hydroxybenzyl)pyrrolidin-3-yl)methyl)-1-(3-(4-methoxyphenyl)-1,2,4-oxadiazol-5-yl)piperidine-4-carboxamide |
| 322 | 1-(3-(4-methoxyphenyl)-1,2,4-oxadiazol-5-yl)-N-((1-(pyridin-4-ylmethyl)pyrrolidin-3-yl)methyl)piperidine-4-carboxamide |
| 323 | N-((1-(cyclopentylmethyl)pyrrolidin-3-yl)methyl)-1-(3-(4-methoxyphenyl)-1,2,4-oxadiazol-5-yl)piperidine-4-carboxamide |
| 324 | N-((1-(3-ethynylbenzyl)pyrrolidin-3-yl)methyl)-1-(3-(4-methoxyphenyl)-1,2,4-oxadiazol-5-yl)piperidine-4-carboxamide |
| 325 | N-((1-((1H-pyrrol-3-yl)methyl)pyrrolidin-3-yl)methyl)-1-(3-(4-methoxyphenyl)-1,2,4-oxadiazol-5-yl)piperidine-4-carboxamide |
| 326 | 1-(3-(4-methoxyphenyl)-1,2,4-oxadiazol-5-yl)-N-((1-((4-methylpyridin-2-yl)methyl)pyrrolidin-3-yl)methyl)piperidine-4-carboxamide |
| 327 | 1-(3-(4-methoxyphenyl)-1,2,4-oxadiazol-5-yl)-N-((1-neopentylpyrrolidin-3-yl)methyl)piperidine-4-carboxamide |
| 328 | 1-(3-(4-methoxyphenyl)-1,2,4-oxadiazol-5-yl)-N-((1-(2-methylbenzyl)pyrrolidin-3-yl)methyl)piperidine-4-carboxamide |
| 329 | 1-(3-(4-methoxyphenyl)-1,2,4-oxadiazol-5-yl)-N-((1-((4-methylpyridin-3-yl)methyl)pyrrolidin-3-yl)methyl)piperidine-4-carboxamide |
| 330 | N-((1-(furan-3-ylmethyl)pyrrolidin-3-yl)methyl)-1-(3-(4-methoxyphenyl)-1,2,4-oxadiazol-5-yl)piperidine-4-carboxamide |
| 331 | N-((1-(4-fluorobenzyl)pyrrolidin-3-yl)methyl)-1-(3-(4-methoxyphenyl)-1,2,4-oxadiazol-5-yl)piperidine-4-carboxamide |
| 332 | N-((1-(3-fluorobenzyl)pyrrolidin-3-yl)methyl)-1-(3-(4-methoxyphenyl)-1,2,4-oxadiazol-5-yl)piperidine-4-carboxamide |
| 333 | N-((1-((5-fluoropyridin-3-yl)methyl)pyrrolidin-3-yl)methyl)-1-(3-(4-methoxyphenyl)-1,2,4-oxadiazol-5-yl)piperidine-4-carboxamide |
| 334 | N-((1-((3-fluoropyridin-2-yl)methyl)pyrrolidin-3-yl)methyl)-1-(3-(4-methoxyphenyl)-1,2,4-oxadiazol-5-yl)piperidine-4-carboxamide |
| 335 | N-((1-((5-fluoropyridin-2-yl)methyl)pyrrolidin-3-yl)methyl)-1-(3-(4-methoxyphenyl)-1,2,4-oxadiazol-5-yl)piperidine-4-carboxamide |
| 336 | N-((1-(cyclobutylmethyl)pyrrolidin-3-yl)methyl)-1-(3-(4-methoxyphenyl)-1,2,4-oxadiazol-5-yl)piperidine-4-carboxamide |
| 337 | N-((1-((2,2-dimethylcyclopropyl)methyl)pyrrolidin-3-yl)methyl)-1-(3-(4-methoxyphenyl)-1,2,4-oxadiazol-5-yl)piperidine-4-carboxamide |
| 338 | N-((1-(cyclohexylmethyl)pyrrolidin-3-yl)methyl)-1-(3-(4-methoxyphenyl)-1,2,4-oxadiazol-5-yl)piperidine-4-carboxamide |
| 339 | N-((1-(4-hydroxybenzyl)pyrrolidin-3-yl)methyl)-1-(3-(4-methoxyphenyl)-1,2,4-oxadiazol-5-yl)piperidine-4-carboxamide |
| 340 | 1-(3-(4-methoxyphenyl)-1,2,4-oxadiazol-5-yl)-N-((1-(pyridin-2-ylmethyl)pyrrolidin-3-yl)methyl)piperidine-4-carboxamide |
| 341 | 1-(3-(4-methoxyphenyl)-1,2,4-oxadiazol-5-yl)-N-((1-(thiazol-5-ylmethyl)pyrrolidin-3-yl)methyl)piperidine-4-carboxamide |
| 342 | N-((1-benzylpyrrolidin-3-yl)methyl)-1-(3-(4-methoxyphenyl)-1,2,4-oxadiazol-5-yl)piperidine-4-carboxamide |
| 343 | 1-(3-(4-methoxyphenyl)-1,2,4-oxadiazol-5-yl)-N-((1-(2,2,2-trifluoroethyl)pyrrolidin-3-yl)methyl)piperidine-4-carboxamide |
| 344 | 1-(3-(3-(2-(3-(but-3-yn-1-yl)-3H-diazirin-3-yl)ethoxy)-4-methoxyphenyl)-1,2,4-oxadiazol-5-yl)-N-((1-(4-methylbenzyl)pyrrolidin-3-yl)methyl)piperidine-4-carboxamide |
| 345 | 4-(3-(4-methoxyphenyl)-1,2,4-oxadiazol-5-yl)-N-((1-phenylpyrrolidin-3-yl)methyl)piperazine-1-carboxamide |
| 346 | 1-(3-(4-methoxyphenyl)-1,2,4-oxadiazol-5-yl)-N-(1-phenylpyrrolidin-3-yl)piperidine-4-carboxamide |
| 347 | 1-(3-(4-methoxyphenyl)-1,2,4-oxadiazol-5-yl)-N-((1-((tetrahydrofuran-3-yl)methyl)pyrrolidin-3-yl)methyl)piperidine-4-carboxamide |
| 348 | 1-(3-(4-methoxyphenyl)-1,2,4-oxadiazol-5-yl)-N-((1-((3-methylpyridin-4-yl)methyl)pyrrolidin-3-yl)methyl)piperidine-4-carboxamide |
| 349 | 1-(3-(4-methoxyphenyl)-1,2,4-oxadiazol-5-yl)-N-((1-(3-methylbenzyl)pyrrolidin-3-yl)methyl)piperidine-4-carboxamide |

TABLE 1-continued

| Compound number | Compound Name |
|---|---|
| 350 | 1-(3-(4-methoxyphenyl)-1,2,4-oxadiazol-5-yl)-N-((1-((3-methylpyridin-2-yl)methyl)pyrrolidin-3-yl)methyl)piperidine-4-carboxamide |
| 351 | 1-(3-(4-methoxyphenyl)-1,2,4-oxadiazol-5-yl)-N-((1-((6-methylpyridin-3-yl)methyl)pyrrolidin-3-yl)methyl)piperidine-4-carboxamide |
| 352 | N-((1-(isothiazol-5-ylmethyl)pyrrolidin-3-yl)methyl)-1-(3-(4-methoxyphenyl)-1,2,4-oxadiazol-5-yl)piperidine-4-carboxamide |
| 353 | 1-(3-(4-methoxyphenyl)-1,2,4-oxadiazol-5-yl)-N-((1-((1-methylpiperidin-4-yl)methyl)pyrrolidin-3-yl)methyl)piperidine-4-carboxamide |
| 354 | 1-(3-(4-methoxyphenyl)-1,2,4-oxadiazol-5-yl)-N-((1-((tetrahydro-2H-thiopyran-4-yl)methyl)pyrrolidin-3-yl)methyl)piperidine-4-carboxamide |
| 355 | 1-(3-(4-methoxyphenyl)-1,2,4-oxadiazol-5-yl)-N-((1-((tetrahydro-2H-pyran-4-yl)methyl)pyrrolidin-3-yl)methyl)piperidine-4-carboxamide |
| 356 | 1-(3-(4-methoxyphenyl)-1,2,4-oxadiazol-5-yl)-N-((1-(pyridin-3-ylmethyl)pyrrolidin-3-yl)methyl)piperidine-4-carboxamide |
| 357 | 1-(3-(4-methoxyphenyl)-1,2,4-oxadiazol-5-yl)-N-((1-(thiophen-3-ylmethyl)pyrrolidin-3-yl)methyl)piperidine-4-carboxamide |
| 358 | N-((1-(2-fluorobenzyl)pyrrolidin-3-yl)methyl)-1-(3-(4-methoxyphenyl)-1,2,4-oxadiazol-5-yl)piperidine-4-carboxamide |
| 359 | N-((1-((3-fluoropyridin-4-yl)methyl)pyrrolidin-3-yl)methyl)-1-(3-(4-methoxyphenyl)-1,2,4-oxadiazol-5-yl)piperidine-4-carboxamide |
| 360 | 1-(3-(4-methoxyphenyl)-1,2,4-oxadiazol-5-yl)-N-((1-(thiazol-4-ylmethyl)pyrrolidin-3-yl)methyl)piperidine-4-carboxamide |
| 361 | 1-(3-(4-methoxyphenyl)-1,2,4-oxadiazol-5-yl)-N-((1-((tetrahydro-2H-pyran-2-yl)methyl)pyrrolidin-3-yl)methyl)piperidine-4-carboxamide |
| 362 | N-((1-(2-hydroxyethyl)pyrrolidin-3-yl)methyl)-1-(3-(4-methoxyphenyl)-1,2,4-oxadiazol-5-yl)piperidine-4-carboxamide |
| 363 | 1-(3-(4-methoxyphenyl)-1,2,4-oxadiazol-5-yl)-N-((1-((1-methyl-1H-pyrrol-2-yl)methyl)pyrrolidin-3-yl)methyl)piperidine-4-carboxamide |
| 364 | 1-(3-(4-methoxyphenyl)-1,2,4-oxadiazol-5-yl)-N-((1-(thiazol-2-ylmethyl)pyrrolidin-3-yl)methyl)piperidine-4-carboxamide |
| 365 | 1-(3-(4-methoxyphenyl)-1,2,4-oxadiazol-5-yl)-N-((1-((5-methylpyridin-3-yl)methyl)pyrrolidin-3-yl)methyl)piperidine-4-carboxamide |
| 366 | N-((1-(2-fluoroethyl)pyrrolidin-3-yl)methyl)-1-(3-(4-methoxyphenyl)-1,2,4-oxadiazol-5-yl)piperidine-4-carboxamide |
| 367 | N-((1-(2,2-difluoroethyl)pyrrolidin-3-yl)methyl)-1-(3-(4-methoxyphenyl)-1,2,4-oxadiazol-5-yl)piperidine-4-carboxamide |
| 368 | 1-(3-(4-methoxyphenyl)-1,2,4-oxadiazol-5-yl)-N-((1-((2-methylcyclopropyl)methyl)pyrrolidin-3-yl)methyl)piperidine-4-carboxamide |
| 369 | 1-(3-(4-methoxyphenyl)-1,2,4-oxadiazol-5-yl)-N-((1-(((S)-1-methylpyrrolidin-2-yl)methyl)pyrrolidin-3-yl)methyl)piperidine-4-carboxamide |
| 370 | 1-(3-(4-methoxyphenyl)-1,2,4-oxadiazol-5-yl)-N-((1-(tetrahydrofuran-3-yl)pyrrolidin-3-yl)methyl)piperidine-4-carboxamide |
| 371 | 1-(3-(4-methoxyphenyl)-1,2,4-oxadiazol-5-yl)-N-((1-((3-methyloxetan-3-yl)methyl)pyrrolidin-3-yl)methyl)piperidine-4-carboxamide |
| 372 | 1-(3-(4-methoxyphenyl)-1,2,4-oxadiazol-5-yl)-N-((1-(thiophen-2-ylmethyl)pyrrolidin-3-yl)methyl)piperidine-4-carboxamide |
| 373 | N-((1-(isothiazol-4-ylmethyl)pyrrolidin-3-yl)methyl)-1-(3-(4-methoxyphenyl)-1,2,4-oxadiazol-5-yl)piperidine-4-carboxamide |
| 374 | N-((1-isobutylpyrrolidin-3-yl)methyl)-1-(3-(4-methoxyphenyl)-1,2,4-oxadiazol-5-yl)piperidine-4-carboxamide |
| 375 | 1-(3-(4-methoxyphenyl)-1,2,4-oxadiazol-5-yl)-N-((1-((tetrahydro-2H-pyran-3-yl)methyl)pyrrolidin-3-yl)methyl)piperidine-4-carboxamide |
| 376 | N-((1-ethylpyrrolidin-3-yl)methyl)-1-(3-(4-methoxyphenyl)-1,2,4-oxadiazol-5-yl)piperidine-4-carboxamide |
| 377 | 1-(3-(4-methoxyphenyl)-1,2,4-oxadiazol-5-yl)-N-((1-((4-methyltetrahydro-2H-pyran-4-yl)methyl)pyrrolidin-3-yl)methyl)piperidine-4-carboxamide |
| 378 | N-((1-(4-ethynylbenzyl)pyrrolidin-3-yl)methyl)-1-(3-(4-methoxyphenyl)-1,2,4-oxadiazol-5-yl)piperidine-4-carboxamide |
| 379 | 1-(3-(4-methoxyphenyl)-1,2,4-oxadiazol-5-yl)-N-((1-((5-methylfuran-2-yl)methyl)pyrrolidin-3-yl)methyl)piperidine-4-carboxamide |
| 380 | 1-(3-(4-methoxyphenyl)-1,2,4-oxadiazol-5-yl)-N-((1-((2-methylpyridin-3-yl)methyl)pyrrolidin-3-yl)methyl)piperidine-4-carboxamide |
| 381 | 1-(3-(4-methoxyphenyl)-1,2,4-oxadiazol-5-yl)-N-((1-((3-methylthiophen-2-yl)methyl)pyrrolidin-3-yl)methyl)piperidine-4-carboxamide |
| 382 | 1-(3-(4-methoxyphenyl)-1,2,4-oxadiazol-5-yl)-N-((1-((4-methylfuran-2-yl)methyl)pyrrolidin-3-yl)methyl)piperidine-4-carboxamide |
| 383 | 1-(3-(4-methoxyphenyl)-1,2,4-oxadiazol-5-yl)-N-((1-((2-methylthiazol-4-yl)methyl)pyrrolidin-3-yl)methyl)piperidine-4-carboxamide |
| 384 | 1-(3-(4-methoxyphenyl)-1,2,4-oxadiazol-5-yl)-N-((1-((4-methylthiazol-2-yl)methyl)pyrrolidin-3-yl)methyl)piperidine-4-carboxamide |
| 385 | 1-(3-(4-methoxyphenyl)-1,2,4-oxadiazol-5-yl)-N-((1-((5-methylthiophen-2-yl)methyl)pyrrolidin-3-yl)methyl)piperidine-4-carboxamide |
| 386 | 1-(3-(4-methoxyphenyl)-1,2,4-oxadiazol-5-yl)-N-((1-propylpyrrolidin-3-yl)methyl)piperidine-4-carboxamide |
| 387 | 1-(3-(4-methoxyphenyl)-1,2,4-oxadiazol-5-yl)-N-((1-((6-methylpyridin-2-yl)methyl)pyrrolidin-3-yl)methyl)piperidine-4-carboxamide |

TABLE 1-continued

| Compound number | Compound Name |
|---|---|
| 388 | 1-(3-(4-methoxyphenyl)-1,2,4-oxadiazol-5-yl)-N-((1-((2-methylthiazol-5-yl)methyl)pyrrolidin-3-yl)methyl)piperidine-4-carboxamide |
| 389 | N-((1-((1H-pyrrol-2-yl)methyl)pyrrolidin-3-yl)methyl)-1-(3-(4-methoxyphenyl)-1,2,4-oxadiazol-5-yl)piperidine-4-carboxamide |
| 390 | N-((1-(3-hydroxybenzyl)pyrrolidin-3-yl)methyl)-1-(3-(4-methoxyphenyl)-1,2,4-oxadiazol-5-yl)piperidine-4-carboxamide |
| 391 | N-((1-(azepan-4-ylmethyl)pyrrolidin-3-yl)methyl)-1-(3-(4-methoxyphenyl)-1,2,4-oxadiazol-5-yl)piperidine-4-carboxamide |
| 392 | 1-(3-(4-methoxyphenyl)-1,2,4-oxadiazol-5-yl)-N-((1-(((S)-pyrrolidin-2-yl)methyl)pyrrolidin-3-yl)methyl)piperidine-4-carboxamide |
| 393 | N-((1-((3,3-difluorocyclobutyl)methyl)pyrrolidin-3-yl)methyl)-1-(3-(4-methoxyphenyl)-1,2,4-oxadiazol-5-yl)piperidine-4-carboxamide |
| 394 | N-((1-(((1s,3s)-3-aminocyclobutyl)methyl)pyrrolidin-3-yl)methyl)-1-(3-(4-methoxyphenyl)-1,2,4-oxadiazol-5-yl)piperidine-4-carboxamide |
| 395 | 1-(3-(4-methoxyphenyl)-1,2,4-oxadiazol-5-yl)-N-((1-(oxetan-2-ylmethyl)pyrrolidin-3-yl)methyl)piperidine-4-carboxamide |
| 396 | 1-(3-(4-methoxyphenyl)-1,2,4-oxadiazol-5-yl)-N-((1-(tetrahydro-2H-pyran-3-yl)pyrrolidin-3-yl)methyl)piperidine-4-carboxamide |
| 397 | N-((1-(1-hydroxypropan-2-yl)pyrrolidin-3-yl)methyl)-1-(3-(4-methoxyphenyl)-1,2,4-oxadiazol-5-yl)piperidine-4-carboxamide |
| 398 | 1-(3-(4-methoxyphenyl)-1,2,4-oxadiazol-5-yl)-N-((1-(tetrahydro-2H-pyran-4-yl)pyrrolidin-3-yl)methyl)piperidine-4-carboxamide |
| 399 | N-((1-(2-oxaspiro[3.3]heptan-6-yl)pyrrolidin-3-yl)methyl)-1-(3-(4-methoxyphenyl)-1,2,4-oxadiazol-5-yl)piperidine-4-carboxamide |
| 400 | 1-(3-(4-methoxyphenyl)-1,2,4-oxadiazol-5-yl)-N-((1-(oxepan-4-yl)pyrrolidin-3-yl)methyl)piperidine-4-carboxamide |
| 401 | 1-(3-(4-methoxyphenyl)-1,2,4-oxadiazol-5-yl)-N-((1-(oxetan-3-yl)pyrrolidin-3-yl)methyl)piperidine-4-carboxamide |
| 402 | 1-(3-(4-methoxyphenyl)-1,2,4-oxadiazol-5-yl)-N-((1-(2-methyltetrahydro-2H-pyran-4-yl)pyrrolidin-3-yl)methyl)piperidine-4-carboxamide |
| 403 | 1-(3-(4-methoxyphenyl)-1,2,4-oxadiazol-5-yl)-N-(1-methylindolin-5-yl)piperidine-4-carboxamide |
| 404 | 1-(3-(4-methoxyphenyl)-1,2,4-oxadiazol-5-yl)-N-((1-((4-methylthiazol-5-yl)methyl)pyrrolidin-3-yl)methyl)piperidine-4-carboxamide |
| 405 | 1-(3-(4-methoxyphenyl)-1,2,4-oxadiazol-5-yl)-N-((1-((tetrahydrofuran-2-yl)methyl)pyrrolidin-3-yl)methyl)piperidine-4-carboxamide |
| 406 | 1-(3-(4-methoxyphenyl)-1,2,4-oxadiazol-5-yl)-N-((1-((3-methylfuran-2-yl)methyl)pyrrolidin-3-yl)methyl)piperidine-4-carboxamide |
| 407 | 1-(3-(4-methoxyphenyl)-1,2,4-oxadiazol-5-yl)-N-((1-((5-methylthiazol-2-yl)methyl)pyrrolidin-3-yl)methyl)piperidine-4-carboxamide |
| 408 | 1-(3-(4-methoxyphenyl)-1,2,4-oxadiazol-5-yl)-N-((1-(oxetan-3-ylmethyl)pyrrolidin-3-yl)methyl)piperidine-4-carboxamide |
| 409 | N-((1-(cyclohex-1-en-1-ylmethyl)pyrrolidin-3-yl)methyl)-1-(3-(4-methoxyphenyl)-1,2,4-oxadiazol-5-yl)piperidine-4-carboxamide |
| 410 | 1-(3-(4-methoxyphenyl)-1,2,4-oxadiazol-5-yl)-N-((1-(3-methylbut-2-en-1-yl)pyrrolidin-3-yl)methyl)piperidine-4-carboxamide |
| 411 | N-((1-isopentylpyrrolidin-3-yl)methyl)-1-(3-(4-methoxyphenyl)-1,2,4-oxadiazol-5-yl)piperidine-4-carboxamide |
| 412 | 1-(3-(4-methoxyphenyl)-1,2,4-oxadiazol-5-yl)-N-((1-(((R)-piperidin-3-yl)methyl)pyrrolidin-3-yl)methyl)piperidine-4-carboxamide |
| 413 | N-((1-(((R)-azetidin-2-yl)methyl)pyrrolidin-3-yl)methyl)-1-(3-(4-methoxyphenyl)-1,2,4-oxadiazol-5-yl)piperidine-4-carboxamide |
| 414 | 1-(3-(4-methoxyphenyl)-1,2,4-oxadiazol-5-yl)-N-((1-(((R)-1-methylpiperidin-2-yl)methyl)pyrrolidin-3-yl)methyl)piperidine-4-carboxamide |
| 415 | 1-(3-(4-methoxyphenyl)-1,2,4-oxadiazol-5-yl)-N-((1-(((R)-piperidin-2-yl)methyl)pyrrolidin-3-yl)methyl)piperidine-4-carboxamide |
| 416 | 1-(3-(4-methoxyphenyl)-1,2,4-oxadiazol-5-yl)-N-((1-(1-(tetrahydro-2H-pyran-4-yl)ethyl)pyrrolidin-3-yl)methyl)piperidine-4-carboxamide |
| 417 | N-((1H-indol-2-yl)methyl)-4-(3-(4-methoxyphenyl)-1,2,4-oxadiazol-5-yl)piperazine-1-carboxamide |
| 418 | N-((1H-pyrrolo[2,3-b]pyridin-2-yl)methyl)-1-(3-(4-methoxyphenyl)-1,2,4-oxadiazol-5-yl)piperidine-4-carboxamide |
| 419 | N-((1H-benzo[d]imidazol-2-yl)methyl)-1-(3-(4-methoxyphenyl)-1,2,4-oxadiazol-5-yl)piperidine-4-carboxamide |
| 420 | N-(benzo[d]oxazol-2-ylmethyl)-1-(3-(4-methoxyphenyl)-1,2,4-oxadiazol-5-yl)piperidine-4-carboxamide |
| 421 | N-((1-(cyclohexylmethyl)pyrrolidin-3-yl)methyl)-4-(3-(4-methoxyphenyl)-1,2,4-oxadiazol-5-yl)piperazine-1-carboxamide |
| 422 | 1-(3-(4-methoxyphenyl)-1,2,4-oxadiazol-5-yl)-N-((1-(((S)-1-methylpiperidin-3-yl)methyl)pyrrolidin-3-yl)methyl)piperidine-4-carboxamide |
| 423 | N-((1-(((1s,4s)-4-aminocyclohexyl)methyl)pyrrolidin-3-yl)methyl)-1-(3-(4-methoxyphenyl)-1,2,4-oxadiazol-5-yl)piperidine-4-carboxamide |
| 424 | N-((1-(1-hydroxy-2-methylpropan-2-yl)pyrrolidin-3-yl)methyl)-1-(3-(4-methoxyphenyl)-1,2,4-oxadiazol-5-yl)piperidine-4-carboxamide |
| 425 | N-((1-((1,1-dioxidotetrahydro-2H-thiopyran-4-yl)methyl)pyrrolidin-3-yl)methyl)-4-(3-(4-methoxyphenyl)-1,2,4-oxadiazol-5-yl)piperazine-1-carboxamide |

TABLE 1-continued

| Compound number | Compound Name |
|---|---|
| 426 | 4-(3-(4-methoxyphenyl)-1,2,4-oxadiazol-5-yl)-N-(3-(4-(trifluoromethyl)piperidin-1-yl)propyl)piperazine-1-carboxamide |
| 427 | 1-(3-(4-methoxyphenyl)-1,2,4-oxadiazol-5-yl)-N-(1-methyl-1H-indol-5-yl)piperidine-4-carboxamide |
| 428 | N-(3-(4-phenoxypiperidin-1-yl)propyl)-4-(3-(4-(trifluoromethoxy)phenyl)-1,2,4-oxadiazol-5-yl)piperazine-1-carboxamide |
| 429 | N-(3-(4-(2-fluorobenzyl)piperidin-1-yl)propyl)-4-(3-(4-(trifluoromethoxy)phenyl)-1,2,4-oxadiazol-5-yl)piperazine-1-carboxamide |
| 430 | 4-(3-(4-fluorophenyl)-1,2,4-oxadiazol-5-yl)-N-(3-(4-(pyridin-2-ylmethyl)piperidin-1-yl)propyl)piperazine-1-carboxamide |
| 431 | 4-(3-(4-cyanophenyl)-1,2,4-oxadiazol-5-yl)-N-(3-(4-(pyridin-2-ylmethyl)piperidin-1-yl)propyl)piperazine-1-carboxamide |
| 432 | 4-(3-(4-methoxyphenyl)-1,2,4-oxadiazol-5-yl)-N-((1-((tetrahydro-2H-pyran-4-yl)methyl)pyrrolidin-3-yl)methyl)piperazine-1-carboxamide |
| 433 | (R)-1-(3-(4-methoxyphenyl)-1,2,4-oxadiazol-5-yl)-N-((1-((1-methylpiperidin-4-yl)methyl)pyrrolidin-3-yl)methyl)piperidine-4-carboxamide |
| 434 | (S)-1-(3-(4-methoxyphenyl)-1,2,4-oxadiazol-5-yl)-N-((1-((1-methylpiperidin-4-yl)methyl)pyrrolidin-3-yl)methyl)piperidine-4-carboxamide |
| 435 | N-(3-(4-(pyridin-2-ylmethyl)piperidin-1-yl)propyl)-1-(3-(4-(trifluoromethoxy)phenyl)-1,2,4-oxadiazol-5-yl)piperidine-4-carboxamide |
| 436 | N-(3-(4-(pyridin-2-ylmethyl)piperidin-1-yl)propyl)-4-(3-(4-(trifluoromethoxy)phenyl)-1,2,4-oxadiazol-5-yl)piperazine-1-carboxamide |
| 437 | 4-(3-(4-(difluoromethoxy)phenyl)-1,2,4-oxadiazol-5-yl)-N-(3-(4-(pyridin-2-ylmethyl)piperidin-1-yl)propyl)piperazine-1-carboxamide |
| 438 | 4-(3-(4-(difluoromethoxy)phenyl)-1,2,4-oxadiazol-5-yl)-N-(3-(4-(2-fluorobenzyl)piperidin-1-yl)propyl)piperazine-1-carboxamide |
| 439 | N-(3-(4-(difluoromethyl)piperidin-1-yl)propyl)-4-(3-(4-methoxyphenyl)-1,2,4-oxadiazol-5-yl)piperazine-1-carboxamide |
| 440 | N-(3-(4-fluoro-4-(pyridin-2-yl)piperidin-1-yl)propyl)-4-(3-(4-methoxyphenyl)-1,2,4-oxadiazol-5-yl)piperazine-1-carboxamide |
| 441 | 4-(3-(4-methoxyphenyl)-1,2,4-oxadiazol-5-yl)-N-(3-(4-(pyridin-2-ylmethyl)piperazin-1-yl)propyl)piperazine-1-carboxamide |
| 442 | 1-(2-(4-methoxyphenyl)-1H-imidazol-4-yl)-N-((1-(4-methylbenzyl)pyrrolidin-3-yl)methyl)piperidine-4-carboxamide |
| 443 | N-((1-benzyl-2,5-dioxopyrrolidin-3-yl)methyl)-4-(3-(4-methoxyphenyl)-1,2,4-oxadiazol-5-yl)cyclohexane-1-carboxamide |
| 447 | N-(((3R)-1-(fluoro(p-tolyl)methyl)pyrrolidin-3-yl)methyl)-1-(3-(4-methoxyphenyl)-1,2,4-oxadiazol-5-yl)piperidine-4-carboxamide |
| 448 | (R)-N-((1-(difluoro(p-tolyl)methyl)pyrrolidin-3-yl)methyl)-1-(3-(4-methoxyphenyl)-1,2,4-oxadiazol-5-yl)piperidine-4-carboxamide |
| 449 | 1-(3-(4-methoxyphenyl)-1,2,4-oxadiazol-5-yl)-N-((3-(4-methylbenzyl)-2,5-dioxoimidazolidin-1-yl)methyl)piperidine-4-carboxamide |
| 450 | N-((1-((4-(pyridin-2-ylmethyl)piperidin-1-yl)methyl)cyclopropyl)methyl)-4-(3-(4-(trifluoromethoxy)phenyl)-1,2,4-oxadiazol-5-yl)piperazine-1-carboxamide |
| 451 | N-(((4-(pyridin-2-ylmethyl)piperidin-1-yl)methoxy)methyl)-4-(3-(4-(trifluoromethoxy)phenyl)-1,2,4-oxadiazol-5-yl)piperazine-1-carboxamide |
| 452 | N-(((4-(pyridin-2-yloxy)piperidin-1-yl)methoxy)methyl)-4-(3-(4-(trifluoromethoxy)phenyl)-1,2,4-oxadiazol-5-yl)piperazine-1-carboxamide |
| 453 | 1-(3-(4-(difluoromethoxy)phenyl)-1,2,4-oxadiazol-5-yl)-N-(3-(4-(pyridin-2-ylmethyl)piperidin-1-yl)propyl)piperidine-4-carboxamide |
| 454 | N-(2-(4-(pyridin-2-ylmethyl)piperidin-1-yl)cyclopropyl)-1-(3-(4-(trifluoromethoxy)phenyl)-1,2,4-oxadiazol-5-yl)piperidine-4-carboxamide |
| 455 | 1-(3-(4-(difluoromethoxy)phenyl)-1,2,4-oxadiazol-5-yl)-N-(2-(4-(pyridin-2-ylmethyl)piperidin-1-yl)cyclopropyl)piperidine-4-carboxamide |
| 456 | 1-(3-(4-methoxyphenyl)-1,2,4-oxadiazol-5-yl)-N-(2-((1-(pyridin-2-ylmethyl)piperidin-4-yl)oxy)ethyl)piperidine-4-carboxamide |
| 457 | 4-(3-(4-methoxyphenyl)-1,2,4-oxadiazol-5-yl)-N-(2-((1-(pyridin-2-ylmethyl)piperidin-4-yl)oxy)ethyl)piperazine-1-carboxamide |
| 458 | 4-(3-(4-chlorophenyl)-1,2,4-oxadiazol-5-yl)-N-(3-(4-(pyridin-2-ylmethyl)piperidin-1-yl)propyl)piperazine-1-carboxamide |
| 459 | N-(3-(4-(pyridin-2-ylmethyl)piperidin-1-yl)propyl)-4-(3-(4-(trifluoromethyl)phenyl)-1,2,4-oxadiazol-5-yl)piperazine-1-carboxamide |
| 460 | 4-(3-(4-(difluoromethyl)phenyl)-1,2,4-oxadiazol-5-yl)-N-(3-(4-(pyridin-2-ylmethyl)piperidin-1-yl)propyl)piperazine-1-carboxamide |
| 461 | N-(3-(4-fluoro-4-(pyridin-2-ylmethyl)piperidin-1-yl)propyl)-4-(3-(4-methoxyphenyl)-1,2,4-oxadiazol-5-yl)piperazine-1-carboxamide |
| 462 | 4-(3-(4-(2-hydroxyethoxy)phenyl)-1,2,4-oxadiazol-5-yl)-N-((1-(4-methylbenzyl)pyrrolidin-3-yl)methyl)piperazine-1-carboxamide |
| 463 | 1-(3-(4-(2-hydroxyethoxy)phenyl)-1,2,4-oxadiazol-5-yl)-N-((1-(4-methylbenzyl)pyrrolidin-3-yl)methyl)piperidine-4-carboxamide |
| 464 | 1-(3-(4-methoxyphenyl)-1,2,4-oxadiazol-5-yl)-N-((1-(((R)-1-methylpiperidin-3-yl)methyl)pyrrolidin-3-yl)methyl)piperidine-4-carboxamide |
| 465 | 1-(3-(4-methoxyphenyl)-1,2,4-oxadiazol-5-yl)-N-(((R)-1-(((S)-1-methylpiperidin-3-yl)methyl)pyrrolidin-3-yl)methyl)piperidine-4-carboxamide |
| 466 | 1-(3-(4-methoxyphenyl)-1,2,4-oxadiazol-5-yl)-N-(((S)-1-(((S)-1-methylpiperidin-3-yl)methyl)pyrrolidin-3-yl)methyl)piperidine-4-carboxamide |

TABLE 1-continued

| Compound number | Compound Name |
|---|---|
| 467 | 1-(3-(4-cyanophenyl)-1,2,4-oxadiazol-5-yl)-N-((1-(((S)-1-methylpiperidin-3-yl)methyl)pyrrolidin-3-yl)methyl)piperidine-4-carboxamide |
| 468 | 1-(3-(4-chlorophenyl)-1,2,4-oxadiazol-5-yl)-N-((1-(((S)-1-methylpiperidin-3-yl)methyl)pyrrolidin-3-yl)methyl)piperidine-4-carboxamide |
| 470 | 1-(3-(4-chlorophenyl)-1,2,4-oxadiazol-5-yl)-N-(((S)-1-(((S)-1-methylpiperidin-3-yl)methyl)pyrrolidin-3-yl)methyl)piperidine-4-carboxamide |
| 471 | 1-(3-(4-chlorophenyl)-1,2,4-oxadiazol-5-yl)-N-(((R)-1-(((S)-1-methylpiperidin-3-yl)methyl)pyrrolidin-3-yl)methyl)piperidine-4-carboxamide |
| 472 | 1-(3-(4-(2,3-dihydroxypropoxy)phenyl)-1,2,4-oxadiazol-5-yl)-N-((1-(4-methylbenzyl)pyrrolidin-3-yl)methyl)piperidine-4-carboxamide |
| 473 | 4-(3-(4-(2,3-dihydroxypropoxy)phenyl)-1,2,4-oxadiazol-5-yl)-N-((1-(4-methylbenzyl)pyrrolidin-3-yl)methyl)piperazine-1-carboxamide |
| 474 | 1-(3-(4-chlorophenyl)-1,2,4-oxadiazol-5-yl)-N-(((S)-1-(((R)-1-methylpiperidin-3-yl)methyl)pyrrolidin-3-yl)methyl)piperidine-4-carboxamide |
| 475 | 1-(3-(4-chlorophenyl)-1,2,4-oxadiazol-5-yl)-N-(((R)-1-(((R)-1-methylpiperidin-3-yl)methyl)pyrrolidin-3-yl)methyl)piperidine-4-carboxamide |

It is well understood that in structures presented in this invention wherein the carbon atom has less than 4 bonds, H atoms are present to complete the valence of the carbon. It is well understood that in structures presented in this invention wherein the nitrogen atom has less than 3 bonds, H atoms are present to complete the valence of the nitrogen.

In some embodiments, this invention is directed to the compounds listed hereinabove, pharmaceutical compositions and/or method of use thereof, wherein the compound is pharmaceutically acceptable salt, stereoisomer, tautomer, hydrate, N-oxide, reverse amide analog, prodrug, isotopic variant (deuterated analog), PROTAC, pharmaceutical product or any combination thereof. In some embodiments, the compounds are c-Myc mRNA translation modulators. In some embodiments, the compounds are c-Myc mRNA translation inhibitors. In some embodiments, the compounds are c-Myc inhibitors. In various embodiments, the compounds are a c-Myc mRNA transcription regulators. In various embodiments, the compounds are any combination of c-Myc mRNA transcription regulators, c-Myc mRNA transcription regulators and c-Myc inhibitors.

In various embodiments, A of formula I, and/or I(a) is a single aromatic or heteroaromatic ring (e.g. phenyl, pyridinyl, 2-pyridinyl, 3-pyridinyl, 4-pyridinyl, pyrimidine, pyridazine, pyrazine, pyrazole, thiazole, imidazole, 1-methylimidazole, thiophene, isothiazolyl, thiadiazolyl, triazolyl, thiazolyl, oxazolyl, isoxazolyl, pyrrolyl, furanyl, 1,2,3-, 1,2,4-, 1,2,5- or 1,3,4-oxadiazolyl). Each possibility is a separate embodiment of this invention.

In various embodiments, B of formula I, I(a), I(a(i)), I(a(ii)), I(b), I(b(i)), I(b(ii)) and/or II is a single or fused $C_3$-$C_{12}$ aromatic, heteroaromatic (e.g. phenyl, pyrimidine, 2-, 3- or 4-pyridine, pyridazine, pyrazine, isothiazole, thiadiazole, imidazole, triazole, thiazole, oxazole, isoxazole, 1-methylimidazole, pyrrole, furan, thiophene, 1,2,3-, 1,2,4-, 1,2,5- or 1,3,4-oxadiazole, indole, indane, benzodihydrofuran, tetrahydroquinoline or pyrazole), heterocyclic (e.g. tetrahydropyran, tetrahydrofuran, pyrrolidine, piperidine, piperazine, 2-oxopyrrolidine, 2,5-dioxopyrrolidine, 2,5-dioxoimidazolidine, oxetane, chromane), cycloalkyl (e.g. cyclopropyl, cyclobutyl, cyclohexyl, cyclopentyl, cyclooctyl) ring or a spiro ring system

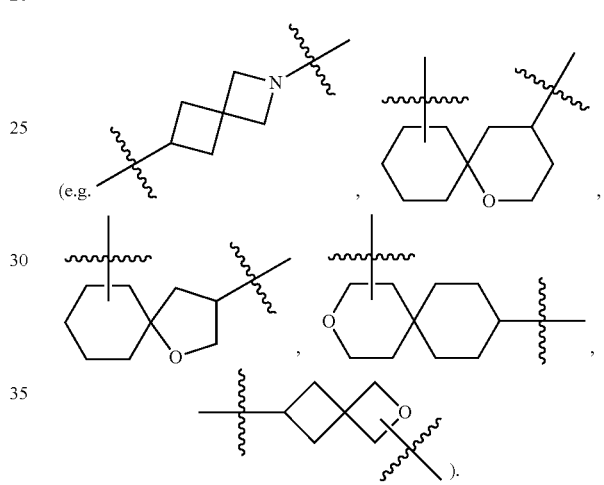

(e.g.

).

Each possibility is a separate embodiment of this invention.

In various embodiments, C ring of I, I(a) and/or I(b) is a 5-10 membered heterocyclic, aryl or heteroaryl ring (e.g. benzene, benzopyrrolidine, piperazine, pyrrolidine, piperidine, morpholine, tetrahydropyran or thiomorpholine-1,1-dioxide). Each possibility is a separate embodiment of this invention.

In various embodiments, D ring of formula I, I(a), I(a(i)), I(a(ii)), I(b), I(b(i)), I(b(ii)) and/or II is a saturated, unsaturated or aromatic, single, fused or spiro, carbocyclic or heterocyclic 3-12 membered ring; each possibility is a separate embodiment of this invention. In various embodiments, D ring is saturated, single, 3-8 membered carbocyclic ring. In various embodiments, D ring is $C_3$-$C_8$ cycloalkyl. In various embodiments, D ring is cyclopropyl, cyclobutyl, cyclopentyl, cyclohexyl; each possibility is a separate embodiment of this invention. In various embodiments, D ring is unsaturated, single, 3-8 membered carbocyclic ring. In various embodiments, D ring is $C_3$-$C_8$ cycloalkenyl. In various embodiments, D ring is cyclohexenyl. In various embodiments, D ring is saturated, unsaturated or aromatic, single, 3-8 membered heterocyclic ring. In various embodiments, D ring is unsaturated or aromatic, single, heterocyclic 3-8 membered ring. In various embodiments, D ring is 2, 3, or 4-pyridine, furan, thiophene, pyrrol, thiazole, isothiazole, or diazirine; each possibility is a separate embodiment of this invention. In various embodiments, D ring is saturated, single, 3-8 membered heterocyclic ring. In various embodiments, D ring is tetrahydrofuran, piperidine, azepane, oxepane, 2-oxaspiro[3.3]heptane, tetrahydro-2H-thiopyran 1,1-dioxide, tetrahydropyran, tetrahydrothiopyran, pyrrolidine, or oxetane; each possibility is a separate embodiment of this invention. In some embodiments, D ring is not an aromatic carbocyclic ring. In some embodiments, D ring is not an aryl. In some embodiments, D ring is a saturated, unsaturated or aromatic, single, fused or spiro, heterocyclic 3-12 membered ring. In some embodiments, D ring is 2, 3, or 4-pyridine, furan, thiophene, pyrrol, thiazole, isothiazole, tetrahydrofuran, piperidine, azepane, oxepane, 2-oxaspiro[3.3]heptane, azetidine, tetrahydro-2H-thiopyran 1,1-dioxide, tetrahydrothiopyran, tetrahydropyran, pyrrolidine, oxetane or diazirine; each represents a separate embodiment according to this invention. In some embodiments, D ring is an aliphatic ring. In some embodiments, D ring is a saturated aliphatic ring. In some embodiments, D ring is an unsaturated aliphatic ring. In some embodiments, D ring is a saturated, unsaturated, single, fused or spiro, aliphatic carbocyclic 3-12 membered ring. In some embodiments, D ring is a saturated, single, 3-8 membered cycloalkyl ring. In some embodiments, D ring is an unsaturated, single, 3-8 membered cycloalkenyl ring. In some embodiments, D ring is a cyclopropyl, cyclobutyl, cyclopentyl, cyclohexyl or cyclohexenyl; each represents a separate embodiment according to this invention.

In various embodiments, $R_1$ and/or $R_2$ of I, I(a), I(a(i)), I(a(ii)), I(a(iii)), I(b), I(b(i)), I(b(ii)), I(b(iii)) and/or II are each independently F, Cl, Br, I, OH, O—$R^{20}$, $R^6$—OH, —$R^6$—O—$R^7$, $CF_3$, $OCH_3$, CN, $NO_2$, —$CH_2CN$, —$R^6CN$, $C_1$-$C_5$ linear or branched, substituted or unsubstituted alkyl (e.g., methyl, ethyl), $C_1$-$C_5$ linear or branched, or $C_3$-$C_8$ cyclic haloalkyl (e.g., $CHF_2$), $C_1$-$C_5$ substituted or unsubstituted, linear or branched, or $C_3$-$C_8$ cyclic alkoxy (e.g. methoxy, O—$(CH_2)_2$—OH), $C_1$-$C_5$ linear or branched haloalkoxy (e.g., $OCF_3$, $OCHF_2$), $C_1$-$C_5$ linear or branched alkoxyalkyl (wherein substitutions include: F, Cl, Br, I, $C_1$-$C_5$ linear alkyne, diazirine, $C_1$-$C_5$ linear, cyclic or branched alkyl (e.g. methyl, ethyl, propyl, isopropyl or cyclopropyl), OH, alkoxy, $NH_2$, $N(alkyl)_2$ (e.g. $N(CH_3)_2$, $N(CH_2CH_3)_2$, $N(CH_3)(CH_2CH_3)$), NH(alkyl) (e.g. $NHCH_3$, $NHCH_2CH_3$, $NHCH_2CH_2CH_3$) NH(cycloalkyl) (e.g. NH(cyclohexyl), NH(cylopentyl)), NH(aryl) (e.g. NH(phenyl), NH(pyridiny)), NH(benzyl), $N(cycloalkyl)_2$ (e.g. $N(cyclohexyl)_2$, $N(cylopentyl)_2$), $N(aryl)_2$ (e.g. $N(phenyl)_2$, $N(pyridiny)_2$), N(alkyl)(aryl) (e.g. N(methyl)(phenyl), N(methyl)(pyridinyl)), N(alkyl)(cycloalkyl) (e.g. N(methyl)(cyclopropyl), N(methyl)(cyclohexyl), N(methyl)(cyclopentyl)), N(aryl)(cycloalkyl) (e.g. N(phenyl)(cyclohexyl), N(pyridinyl)(cyclohexyl)) NHC(O)(alkyl) (e.g. $NHC(O)CH_3$), $CF_3$, aryl, phenyl, heteroaryl, $C_3$-$C_8$ cycloalkyl, halophenyl, (benzyloxy)phenyl, CN, $NO_2$ or any combination thereof). Each possibility represents a separate embodiment of this invention.

In some embodiments, $R_1$ and $R_2$ are joint together to form a 5 or 6 membered substituted or unsubstituted, aliphatic or aromatic, carbocyclic or heterocyclic ring. Each possibility represents a separate embodiment of this invention.

In various embodiments, $R_3$ and $R_4$ of formula I, I(a), I(a(i)), I(a(ii)), I(a(iii)), I(b), I(b(i)), I(b(ii)) and/or I(b(iii)) are each independently H, F, Cl, Br, I, OH, $CF_3$, CN, $NO_2$, $C_1$-$C_5$ linear or branched, substituted or unsubstituted alkyl (e.g., methyl, ethyl, tert-butyl, $CH_2CH_2CH(CH_3)_2$, $CH_2$—$C(CH_3)_3$), $C_1$-$C_5$ linear or branched, or $C_3$-$C_8$ cyclic haloalkyl (wherein substitutions include: F, Cl, Br, I, $C_1$-$C_5$ linear, cyclic or branched alkyl (e.g. methyl, ethyl, propyl, isopropyl or cyclopropyl), OH, alkoxy, $NH_2$, $N(alkyl)_2$ (e.g. $N(CH_3)_2$, $N(CH_2CH_3)_2$, $N(CH_3)(CH_2CH_3)$) NH(alkyl) (e.g. $NHCH_3$, $NHCH_2CH_3$, $NHCH_2CH_2CH_3$) NH(cycloalkyl) (e.g. NH(cyclohexyl), NH(cylopentyl)), NH(aryl) (e.g. NH(phenyl), NH(pyridiny)), NH(benzyl), $N(cycloalkyl)_2$ (e.g. $N(cyclohexyl)_2$, $N(cylopentyl)_2$), $N(aryl)_2$ (e.g. $N(phenyl)_2$, $N(pyridiny)_2$), N(alkyl)(aryl) (e.g. N(methyl)(phenyl), N(methyl)(pyridinyl)), N(alkyl)(cycloalkyl) (e.g. N(methyl)(cyclopropyl), N(methyl)(cyclohexyl), N(methyl)(cyclopentyl)), N(aryl)(cycloalkyl) (e.g. N(phenyl)(cyclohexyl), N(pyridinyl)(cyclohexyl)), $CF_3$, aryl, phenyl, heteroaryl, $C_3$-$C_8$ cycloalkyl, halophenyl, (benzyloxy)phenyl, CN, $NO_2$ or any combination thereof); each represents a separate embodiment of this invention.

In various embodiments, $R_5$ of formula I, I(a) and/or I(b) is OH, $C_1$-$C_5$ linear or branched, substituted or unsubstituted alkyl (e.g., methyl, ethyl), $C_1$-$C_5$ linear or branched, or $C_3$-$C_8$ cyclic haloalkyl, $N(R^a)(R^b)$, NHR, $NH_2$, $N(alkyl)_2$ (e.g. $N(CH_3)_2$, $N(CH_2CH_3)_2$, $N(CH_3)(CH_2CH_3)$) NH(alkyl) (e.g. $NHCH_3$, $NHCH_2CH_3$, $NHCH_2CH_2CH_3$) NH(cycloalkyl) (e.g. NH(cyclohexyl), NH(cylopentyl)), NH(aryl) (e.g. NH(phenyl), NH(pyridiny)), NH(benzyl), $N(cycloalkyl)_2$ (e.g. $N(cyclohexyl)_2$, $N(cylopentyl)_2$), $N(aryl)_2$ (e.g. $N(phenyl)_2$, $N(pyridiny)_2$), N(alkyl)(aryl) (e.g. N(methyl)(phenyl), N(methyl)(pyridinyl)), N(alkyl)(cycloalkyl) (e.g. N(methyl)(cyclopropyl), N(methyl)(cyclohexyl), N(methyl)(cyclopentyl)), N(aryl)(cycloalkyl) (e.g. N(phenyl)(cyclohexyl), N(pyridinyl)(cyclohexyl)), substituted or unsubstituted aryl, substituted or unsubstituted heteroaryl, substituted or unsubstituted $C_3$-$C_5$ cycloalkyl (e.g., cyclopropyl), substituted or unsubstituted 3-8 membered heterocyclic ring (e.g., pyrrolidine, piperidine, morpholine, tetrahydropyran), NH—$R^{20}$, NH—$R^6$—NH(alkyl), NH—$R^6$—$NH_2$, NH—$R^6$—$N(alkyl)_2$ (e.g. $NH(CH_2)_3N(CH_2CH_2CH_2CH_3)(CH_2CH_3)$, $NH(CH_2)_2N(CH_3)_2$), $NH(CH_2)_3N(CH_2CH_3)_2$, $NH(CH_2)_2N(CH_2CH_3)_2$, $NHCH_2CH(C_6H_5)N(CH_3)_2$), NH—$R^6$—N(alkyl)(cycloalkyl), NH—$R^6$—NH(cycloalkyl), NH—$R^6$—NH(aryl), NH—$R^6$—N(alkyl)(aryl) (e.g. $NH(CH_2)_3(C_6H_5)(CH_3)$), NH—$R^6$—OH, NH—$R^6$—O(alkyl) (e.g. $NH(CH_2)_3OCH_3$), NH—$R^6$—O(aryl) or NH—$R^6$—O(cycloalkyl), or $R_5$ is represented by any one of the following structures:

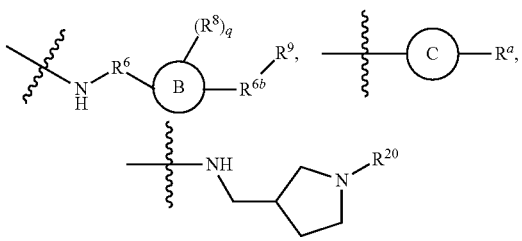

(wherein substitutions include: F, Cl, Br, I, $C_1$-$C_5$ linear, cyclic or branched alkyl (e.g. methyl, ethyl, propyl, isopropyl or cyclopropyl), OH, alkoxy, $NH_2$, $N(alkyl)_2$ (e.g. $N(CH_3)_2$, $N(CH_2CH_3)_2$, $N(CH_3)(CH_2CH_3)$) NH(alkyl) (e.g. $NHCH_3$, $NHCH_2CH_3$, $NHCH_2CH_2CH_3$) NH(cycloalkyl) (e.g. NH(cyclohexyl), NH(cylopentyl)), NH(aryl) (e.g. NH(phenyl), NH(pyridiny)), NH(benzyl), $N(cycloalkyl)_2$ (e.g. $N(cyclohexyl)_2$, $N(cylopentyl)_2$), $N(aryl)_2$ (e.g. $N(phenyl)_2$, $N(pyridiny)_2$), N(alkyl)(aryl) (e.g. N(methyl)(phenyl), N(methyl)(pyridinyl)), N(alkyl)(cycloalkyl) (e.g. N(methyl)

(cyclopropyl), N(methyl)(cyclohexyl), N(methyl)(cyclopentyl)), N(aryl)(cycloalkyl) (e.g. N(phenyl)(cyclohexyl), N(pyridinyl)(cyclohexyl))$CF_3$, aryl, phenyl, heteroaryl, 3-8 membered heterocyclic ring $C_3$-$C_8$ cycloalkyl, $C_1$-$C_5$ linear alkyne, diazirine, halophenyl, (benzyloxy)phenyl, CN, $NO_2$ or any combination thereof); each represents a separate embodiment of this invention.

In various embodiments, $R^6$ of formula I, I(a), I(a(i)), I(a(ii)), I(a(iii)), I(b), I(b(i)), I(b(ii)), I(b(iii)) and/or II is absent or O, C=O, C(=O)—[CH$_2$]$_p$, [CH$_2$]$_p$—C(=O), [CH$_2$]$_p$ (e.g. $CH_2$, $CH_2CH_2$, $CH_2CH_2CH_2$, $CH_2CH_2CH_2CH_2$), [CHR$^{21}$]$_p$ (e.g. CHF), [C(R$^{21}$)$_2$]$_p$ (e.g. $CF_2$) or [CH$_2$]$_{pa}$—O—[CH$_2$]$_{pb}$ (e.g. $CH_2OCH_2$), or [CH$_2$]$_p$—O (e.g., $CH_2CH_2O$); each represents a separate embodiment of this invention. In other embodiments, $R^6$ is $CH_2$. In other embodiments, $R^6$ is $CH_2CH_2$. In other embodiments, $R^6$ is $CH_2CH_2CH_2$. In other embodiments, $R^6$ is $CH_2CH_2CH_2CH_2$. In other embodiments, $R^6$ is $C(CH_2CH_2)CH(C_6H_5)$, C(=O), C(=O)$CH_2$, $CH_2C$(=O), $CH_2C(CH_3)(C_6H_5)$, CH(thiophenyl)$CH_2$, $CH(CH_3)CH_2$, $CH(C_6H_5)CH_2$, $CH(CH_3)$, $CH_2CH(CH_3)$, CH(cyclopropyl), $CH(CH_3)C(CH_3)_2$, $CH(CH_2CF_3)CH_2$, $CH_2CHC_6H_5$, $CH_2CHOHCH_2$, CH(isopropyl)$CH_2CH_2$, $CF_2$, $CH_2C(CH_2)_2)CH_2$, or $CH(CH_2)CH$. Each possibility represents a separate embodiment of this invention.

In various embodiments, $R^{6b}$ of formula I, I(a), I(a(i)), I(a(ii)), I(a(iii)), I(b), I(b(i)), I(b(ii)), I(b(iii)) and/or II is absent or O, C=O, C(=O)—[CH$_2$]$_p$, [CH$_2$]$_p$—C(=O), [CH$_2$]$_p$ (e.g. $CH_2$, $CH_2CH_2$, $CH_2CH_2CH_2$, $CH_2CH_2CH_2CH_2$), [CHR$^{21}$]$_p$ (e.g. CHF), [C(R$^{21}$)$_2$]$_p$ (e.g. $CF_2$) or [CH$_2$]$_{pa}$—O—[CH$_2$]$_{pb}$ (e.g. $CH_2OCH_2$), or [CH$_2$]$_p$—O (e.g., $CH_2CH_2O$); each represents a separate embodiment of this invention. In other embodiments, $R^{6b}$ is $CH_2$. In other embodiments, $R^{6b}$ is $CH_2CH_2$. In other embodiments, $R^{6b}$ is $CH_2CH_2CH_2$. In other embodiments, $R^{6b}$ is $CH_2CH_2CH_2CH_2$. In other embodiments, $R^{6b}$ is $C(CH_2CH_2)CH(C_6H_5)$, C(=O), C(=O)$CH_2$, $CH_2C$(=O), $CH_2C(CH_3)(C_6H_5)$, CH(thiophenyl)$CH_2$, $CH(CH_3)CH_2$, $CH(C_6H_5)CH_2$, $CH(CH_3)$, $CH_2CH(CH_3)$, CH(cyclopropyl), $CH(CH_3)C(CH_3)_2$, $CH(CH_2CF_3)CH_2$, $CH_2CHC_6H_5$, $CH_2CHOHCH_2$, CH(isopropyl)$CH_2CH_2$, $CF_2$, $CH_2C(CH_2)_2)CH_2$, or $CH(CH_2)CH$. Each possibility represents a separate embodiment of this invention.

In some embodiments, both $R^6$ and $R^{6b}$ are $CH_2$. In other embodiments, $R^6$ is $CH_2$ and $R^{6b}$ is absent. In other embodiments, $R^{6b}$ is $CH_2$ and $R^6$ is absent. In other embodiments, $R^6$ is $CH_2CH_2$ and $R^{6b}$ is absent. In other embodiments, $R^{6b}$ is $CH_2CH_2$ and $R^6$ is absent. In other embodiments, $R^6$ is $CH_2CH_2$ and $R^{6b}$ is $CH_2$. In other embodiments, $R^{6b}$ is $CH_2CH_2$ and $R^6$ is $CH_2$. In other embodiments, $R^6$ is $CH_2OCH_2$ and $R^{6b}$ is $CH_2$. In other embodiments, $R^{6b}$ is $CH_2OCH_2$ and $R^6$ is $CH_2$. In other embodiments, $R^6$ is $CH_2OCH_2$ and $R^{6b}$ is O. In other embodiments, $R^{6b}$ is $CH_2OCH_2$ and $R^6$ is O.

In various embodiments, $R^7$ of I, I(a), I(a(i)), I(a(ii)), I(a(iii)), I(b), I(b(i)), I(b(ii)) and/or I(b(iii)) is H, $C_1$-$C_5$ substituted or unsubstituted linear or branched alkyl (e.g., methyl, ethyl, $CH_2$—$CH_2$—O—$CH_3$), $C_1$-$C_5$ linear or branched alkoxy (e.g., O—$CH_3$), C(O)R, or S(O)$_2$R (wherein substitutions include: F, Cl, Br, I, OH, $C_1$-$C_5$ linear, cyclic or branched alkyl (e.g. methyl, ethyl, propyl, isopropyl or cyclopropyl), $C_1$-$C_5$ linear or branched alkyl-OH (e.g., C(CH$_3$)$_2$CH$_2$—OH, $CH_2CH_2$—OH), 3-8 membered heterocyclic ring (e.g., piperidine), alkoxy, $NH_2$, N(alkyl)$_2$ (e.g. N(CH$_3$)$_2$, N(CH$_2$CH$_3$)$_2$, N(CH$_3$)(CH$_2$CH$_3$)) NH(alkyl) (e.g. NHCH$_3$, NHCH$_2$CH$_3$, NHCH$_2$CH$_2$CH$_3$) NH(cycloalkyl) (e.g. NH(cyclohexyl), NH(cylopentyl)), NH(aryl) (e.g. NH(phenyl), NH(pyridiny)), NH(benzyl), N(cycloalkyl)$_2$ (e.g. N(cyclohexyl)$_2$, N(cylopentyl)$_2$), N(aryl)$_2$ (e.g. N(phenyl)$_2$, N(pyridiny)$_2$), N(alkyl)(aryl) (e.g. N(methyl)(phenyl), N(methyl)(pyridinyl)), N(alkyl)(cycloalkyl) (e.g. N(methyl)(cyclopropyl), N(methyl)(cyclohexyl), N(methyl)(cyclopentyl)), N(aryl)(cycloalkyl) (e.g. N(phenyl)(cyclohexyl), N(pyridinyl)(cyclohexyl)), $CF_3$, aryl, phenyl, halophenyl, (benzyloxy)phenyl, CN, $NO_2$ or any combination thereof); each represents a separate embodiment of this invention. In various embodiments, $R^8$ of formula I, I(a), I(a(i)), I(a(ii)), I(a(iii)), I(b), I(b(i)), I(b(ii)), and/or I(b(iii)) is H, F, Cl, Br, I, OH, $CF_3$, CN, $NO_2$, $C_1$-$C_5$ linear or branched, substituted or unsubstituted alkyl (e.g., methyl, ethyl, t-Bu, $CH_2$—C(CH$_3$)$_3$, $CH_2CH_2CH(CH_3)_2$), $C_1$-$C_5$ linear or branched, or $C_3$-$C_8$ cyclic haloalkyl (wherein substitutions include: F, Cl, Br, I, $C_1$-$C_5$ linear, cyclic or branched alkyl (e.g. methyl, ethyl, propyl, isopropyl or cyclopropyl), OH, alkoxy, (e.g. methoxy, ethoxy, propyloxy, isopropyloxy), $NH_2$, N(alkyl)$_2$ (e.g. N(CH$_3$)$_2$, N(CH$_2$CH$_3$)$_2$, N(CH$_3$)(CH$_2$CH$_3$)) NH(alkyl) (e.g. NHCH$_3$, NHCH$_2$CH$_3$, NHCH$_2$CH$_2$CH$_3$), NH(cycloalkyl) (e.g. NH(cyclohexyl), NH(cylopentyl)), NH(aryl) (e.g. NH(phenyl), NH(pyridiny)), NH(benzyl), N(cycloalkyl)$_2$ (e.g. N(cyclohexyl)$_2$, N(cylopentyl)$_2$), N(aryl)$_2$ (e.g. N(phenyl)$_2$, N(pyridiny)$_2$), N(alkyl)(aryl) (e.g. N(methyl)(phenyl), N(methyl)(pyridinyl)), N(alkyl)(cycloalkyl) (e.g. N(methyl)(cyclopropyl), N(methyl)(cyclohexyl), N(methyl)(cyclopentyl)), N(aryl)(cycloalkyl) (e.g. N(phenyl)(cyclohexyl), N(pyridinyl)(cyclohexyl)), $CF_3$, aryl, phenyl, heteroaryl, $C_3$-$C_8$ cycloalkyl, halophenyl, (benzyloxy)phenyl, CN, $NO_2$ or any combination thereof); each represents a separate embodiment of this invention.

In various embodiments, $R^9$ of formula I I, I(a), I(a(i)), I(a(ii)), I(a(iii)), I(b), I(b(i)), I(b(ii)), and/or I(b(iii)) is substituted or unsubstituted aryl (e.g., phenyl, tolyl, fluorophenyl, cyanophenyl), $C_1$-$C_5$ linear or branched alkyl, $C_1$-$C_5$ linear or branched alkenyl, substituted or unsubstituted heteroaryl (e.g., pyridine (2, 3, and 4-pyridine), furan, thiazole, isothiazole, thiophene, pyrrole, methylthiophene, methylfuran, methylpyridine, methylthiazole, indole, benzimidazole, pyrrolopyridine, benzoxazole), substituted or unsubstituted $C_3$-$C_8$ cycloalkyl (e.g., cyclopropyl, methylcyclopropyl, cyclobutyl, cyclohexyl, cyclohexenyl, cyclopentyl), $C_1$-$C_5$ linear or branched, or $C_3$-$C_8$ cyclic haloalkyl (e.g. $CF_3$, $CHF_2$), $NH_2$, N(alkyl)$_2$ (e.g. N(CH$_3$)$_2$, N(CH$_2$CH$_3$)$_2$, N(CH$_3$)(CH$_2$CH$_3$)), NH(alkyl) (e.g. NHCH$_3$, NHCH$_2$CH$_3$, NHCH$_2$CH$_2$CH$_3$) or substituted or unsubstituted 3-8 membered heterocyclic ring (e.g. oxetane, azetidine, methyloxetane, tetrahydrofuran, methyltetrahydropyran, pyrrolidine, methylpyrrolidine, tetrahydropyran, tetrahydrothiopyran, piperidine, methylpiperidine, azepane, oxepane, 2H-Thiopyran-tetrahydro-1,1-dioxide) (wherein substitutions include: F, Cl, Br, I, OH, SH, diazirine, $C_1$-$C_5$ linear alkyne, $C_1$-$C_5$ linear, cyclic or branched alkyl (e.g. methyl, ethyl, propyl, isopropyl or cyclopropyl), aryl (e.g., phenyl), heteroaryl (e.g., pyridine (2, 3, and 4-pyridine)), $C_3$-$C_8$ cycloalkyl (e.g., cyclopropyl), $C_1$-$C_5$ linear alkyne, diazirine, 3-8 membered heterocyclic ring, alkoxy, $NH_2$, N(alkyl)$_2$ (e.g. N(CH$_3$)$_2$, N(CH$_2$CH$_3$)$_2$, N(CH$_3$)(CH$_2$CH$_3$)) NH(alkyl) (e.g. NHCH$_3$, NHCH$_2$CH$_3$, NHCH$_2$CH$_2$CH$_3$) NH(cycloalkyl) (e.g. NH(cyclohexyl), NH(cylopentyl)), NH(aryl) (e.g. NH(phenyl), NH(pyridiny)), NH(benzyl), N(cycloalkyl)$_2$ (e.g. N(cyclohexyl)$_2$, N(cylopentyl)$_2$), N(aryl)$_2$ (e.g. N(phenyl)$_2$, N(pyridiny)$_2$), N(alkyl)(aryl) (e.g. N(methyl)(phenyl), N(methyl)(pyridinyl)), N(alkyl)(cycloalkyl) (e.g. N(methyl)(cyclopropyl), N(methyl)(cyclohexyl), N(methyl)(cyclopentyl)), N(aryl)(cycloalkyl) (e.g. N(phenyl)(cyclohexyl), N(pyridinyl)(cyclohexyl)), $CF_3$, phenyl, halophenyl, (benzyloxy)phenyl, CN, NO$_2$ or any combination thereof); each possibility is a separate embodiment of this invention.

In various embodiments, R$^{11}$ of formula II is H, F, Cl, Br, I, OH, CF$_3$, O—R$^{20}$, CF$_3$, OCH$_3$, CN, NO$_2$, —CH$_2$CN, C$_1$-C$_5$ linear or branched, substituted or unsubstituted alkyl, methyl, ethyl, C$_1$-C$_5$ linear or branched, or C$_3$-C$_8$ cyclic haloalkyl, CHF$_2$, C$_1$-C$_5$ substituted or unsubstituted, linear or branched, or C$_3$-C$_8$ cyclic alkoxy, methoxy, O—(CH$_2$)$_2$—OH, C$_1$-C$_5$ linear or branched haloalkoxy, OCF$_3$, OCHF$_2$, C$_1$-C$_5$ linear or branched alkoxyalkyl, R$^{20}$, NH$_2$, NHR, or NR$_2$; each possibility is a separate embodiment of this invention. In various embodiments, R$^{11}$ is H. In various embodiments, R$^{11}$ is alkyl. In various embodiments, R$^{11}$ is methyl. In various embodiments, R$^{11}$ is ethyl. In various embodiments, R$^{11}$ is ethylacetylene. In various embodiments, R$^{11}$ is 1-butyne. In various embodiments, R$^{11}$ is NH$_2$. In various embodiments, R$^{11}$ is F. In various embodiments, R$^{11}$ is Cl. In various embodiments, R$^{11}$ is Br. In various embodiments, R$^{11}$ is I.

In various embodiments, R$^{12}$ of formula II is H, F, Cl, Br, I, OH, CF$_3$, O—R$^{20}$, CF$_3$, OCH$_3$, CN, NO$_2$, —CH$_2$CN, C$_1$-C$_5$ linear or branched, substituted or unsubstituted alkyl, methyl, ethyl, C$_1$-C$_5$ linear or branched, or C$_3$-C$_8$ cyclic haloalkyl, CHF$_2$, C$_1$-C$_5$ substituted or unsubstituted, linear or branched, or C$_3$-C$_8$ cyclic alkoxy, methoxy, O—(CH$_2$)$_2$—OH, C$_1$-C$_5$ linear or branched haloalkoxy, OCF$_3$, OCHF$_2$, C$_1$-C$_5$ linear or branched alkoxyalkyl, R$^{20}$, NH$_2$, NHR, or NR$_2$; each possibility is a separate embodiment of this invention. In various embodiments, R$^{12}$ is H. In various embodiments, R$^{12}$ is alkyl. In various embodiments, R$^{12}$ is methyl. In various embodiments, R$^{12}$ is ethyl. In various embodiments, R$^{12}$ is ethylacetylene. In various embodiments, R$^{12}$ is 1-butyne. In various embodiments, R$^{12}$ is NH$_2$. In various embodiments, R$^{12}$ is F. In various embodiments, R$^{12}$ is Cl. In various embodiments, R$^{12}$ is Br. In various embodiments, R$^{12}$ is I.

In various embodiments, R$^{20}$ of formula I, I(a), I(a(i)), I(a(ii)), I(a(iii)), I(b), I(b(i)), I(b(ii)), and/or I(b(iii)) is represented by the following structure:

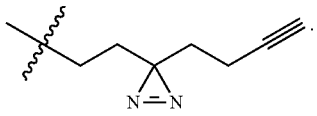 [SMILES: *CCC1(CCC#C)N=N1]

In various embodiments, R$^{21}$ of formula I, I(a), I(a(i)), I(a(ii)), I(a(iii)), I(b), I(b(i)), I(b(ii)), I(b(iii)) and/or II is H, F, Cl, Br, I, OH, CF$_3$, CN, NO$_2$, C$_1$-C$_5$ linear or branched, substituted or unsubstituted alkyl (e.g., methyl, ethyl, propyl, isopropyl, isobutyl), C$_1$-C$_5$ linear or branched alkoxy (e.g. methoxy), C$_1$-C$_5$ linear or branched haloalkyl (e.g., CHF$_2$, CF$_3$, R$^6$-aryl (e.g., CH$_2$-Ph, CH$_2$-Ph-ethyl), R$^6$—N(alkyl)$_2$, R$^6$—NH(alkyl), (R$^6$—NH(cycloalkyl), (R$^6$—NH (aryl), substituted or unsubstituted aryl (e.g., phenyl, ethylphenyl), substituted or unsubstituted heteroaryl (e.g., pyridine (2, 3, and 4-pyridine) or benzimidazole), substituted or unsubstituted C$_3$-C$_8$ cycloalkyl (e.g., cyclopropyl), substituted or unsubstituted 3-8 membered heterocyclic ring (e.g., piperidine, pyrrolidine), R$^6$-(substituted or unsubstituted heterocycle) (e.g., (CH$_2$)$_3$-piperidine) or C(O)-(alkyl) (e.g. C(O)—CH$_3$); (wherein substitutions include: F, Cl, Br, I, OH, SH, diazirine, C$_1$-C$_5$ linear alkyne, C$_1$-C$_5$ linear, cyclic or branched alkyl (e.g. methyl, ethyl, propyl, isopropyl or cyclopropyl), substituted or unsubstituted benzyl (e.g., benzyl, methylbenzyl), substituted or unsubstituted aryl (e.g., phenyl, fluorophenyl), heteroaryl (e.g., indole, tetrahydropyran, pyridine (2, 3, and 4-pyridine)), C$_3$-C$_8$ cycloalkyl (e.g., cyclopropyl), 3-8 membered heterocyclic ring, alkoxy, NH$_2$, N(alkyl)$_2$ (e.g. N(CH$_3$)$_2$, N(CH$_2$CH$_3$)$_2$, N(CH$_3$)(CH$_2$CH$_3$)), NH(alkyl) (e.g. NHCH$_3$, NHCH$_2$CH$_3$, NHCH$_2$CH$_2$CH$_3$) NH(cycloalkyl) (e.g. NH(cyclohexyl), NH(cylopentyl)), NH(aryl) (e.g. NH(phenyl), NH(pyridiny)), NH(benzyl), N(cycloalkyl)$_2$ (e.g. N(cyclohexyl)$_2$, N(cylopentyl)$_2$), N(aryl)$_2$ (e.g. N(phenyl)$_2$, N(pyridiny)$_2$), N(alkyl)(aryl) (e.g. N(methyl)(phenyl), N(methyl)(pyridinyl)), N(alkyl)(cycloalkyl) (e.g. N(methyl)(cyclopropyl), N(methyl)(cyclohexyl), N(methyl)(cyclopentyl)), N(aryl) (cycloalkyl) (e.g. N(phenyl)(cyclohexyl), N(pyridinyl)(cyclohexyl)), CF$_3$, phenyl, halophenyl, substituted or unsubstituted benzyl (e.g., methylbenzyl), (benzyloxy)phenyl, CN, NO$_2$ or any combination thereof); or wherein two geminal or vicinal R$^{21}$ substituents are joined to form a substituted or unsubstituted C$_3$-C$_5$ cycloalkyl (e.g., cyclopropyl). Each possibility represents a separate embodiment of this invention.

In various embodiments, R of formula I, I(a), I(a(i)), I(a(ii)), I(a(iii)), I(b), I(b(i)), I(b(ii)), I(b(iii)) and/or II is H, F, Cl, Br, I, OH, CF$_3$, CN, NO$_2$, C$_1$-C$_5$ linear or branched, substituted or unsubstituted alkyl (e.g., methyl, ethyl, propyl, isopropyl, isobutyl or cyclopropyl), C$_1$-C$_5$ linear or branched alkoxy(e.g. methoxy), C$_1$-C$_5$ linear or branched haloalkyl (e.g., CHF$_2$, CF$_3$, R$^6$-aryl (e.g., CH$_2$-Ph, CH$_2$-Ph-ethyl), R$^6$—N(alkyl)$_2$, R$^6$—NH(alkyl), (R$^6$—NH(cycloalkyl), (R$^6$—NH(aryl), substituted or unsubstituted aryl (e.g., phenyl, ethylphenyl), substituted or unsubstituted heteroaryl (e.g., pyridine (2, 3, and 4-pyridine), benzimidazole), substituted or unsubstituted C$_3$-C$_8$ cycloalkyl (e.g., cyclopropyl), substituted or unsubstituted 3-8 membered heterocyclic ring, R$^6$-(substituted or unsubstituted heterocycle) (e.g. (CH$_2$)$_3$-piperidine), or C(O)-(alkyl) (e.g. C(O)(CH$_3$) (wherein substitutions include: F, Cl, Br, I, OH, SH, diazirine, C$_1$-C$_5$ linear alkyne, C$_1$-C$_5$ linear, cyclic or branched alkyl (e.g. methyl, ethyl, propyl, isopropyl, isobutyl or cyclopropyl), substituted or unsubstituted benzyl (e.g., benzyl, methylbenzyl), aryl (e.g., phenyl, flourophenyl), heteroaryl (e.g., pyridine (2, 3, and 4-pyridine), indole, tetrahydropyran), C$_3$-C$_8$ cycloalkyl (e.g., cyclopropyl), 3-8 membered heterocyclic ring (e.g. piperidine, pyrrolidine), alkoxy, NH$_2$, N(alkyl)$_2$ (e.g. N(CH$_3$)$_2$, N(CH$_2$CH$_3$)$_2$, N(CH$_3$)(CH$_2$CH$_3$)) NH(alkyl) (e.g. NHCH$_3$, NHCH$_2$CH$_3$, NHCH$_2$CH$_2$CH$_3$) NH(cycloalkyl) (e.g. NH(cyclohexyl), NH(cylopentyl)), NH(aryl) (e.g. NH(phenyl), NH(pyridiny)), NH(benzyl), N(cycloalkyl)$_2$ (e.g. N(cyclohexyl)$_2$, N(cylopentyl)$_2$), N(aryl)$_2$ (e.g. N(phenyl)$_2$, N(pyridiny)$_2$), N(alkyl)(aryl) (e.g. N(methyl)(phenyl), N(methyl)(pyridinyl)), N(alkyl)(cycloalkyl) (e.g. N(methyl)(cyclopropyl), N(methyl)(cyclohexyl), N(methyl)(cyclopentyl)), N(aryl) (cycloalkyl) (e.g. N(phenyl)(cyclohexyl), N(pyridinyl)(cyclohexyl)), CF$_3$, phenyl, halophenyl, (benzyloxy)phenyl, CN, NO$_2$ or any combination thereof); each represents a separate embodiment of this invention.

In various embodiments, R$^a$ of compound of formula I, I(a), I(a(i)), I(b) and/or I(b(i)) is R$^{101}$-R$^{102}$,

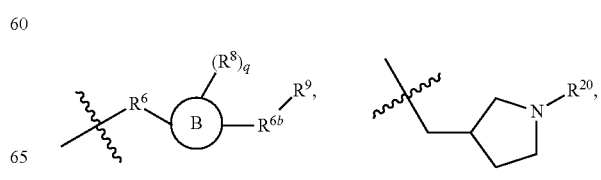

$R^{20}$, $R^6$—NH(alkyl), $R^6$—NH$_2$, $R^6$—N(alkyl)$_2$, $R^6$—N(alkyl)(cycloalkyl), $R^6$—NH(cycloalkyl), $R^6$—NH(aryl), $R^6$—OH, $R^6$—O(alkyl), $R^6$—O(aryl) or $R^6$—O(cycloalkyl); each represents a separate embodiment of this invention.

In various embodiments, $R^b$ of compound of formula I, I(a) and/or I(b) is $R^{103}$-$R^{104}$.

In various embodiments, $R^{101}$ of compound of formula I, I(a), I(a(i)), I(b) and/or I(b(i)) is independently absent or O, C=O, C(=O)—[CH$_2$]$_p$, [CH$_2$]$_p$—C(=O), [CH$_2$]$_p$ (e.g. CH$_2$, CH$_2$CH$_2$, CH$_2$CH$_2$CH$_2$, CH$_2$CH$_2$CH$_2$CH$_2$), [CHR$^{21}$]$_p$ (e.g. CHF), [C(R$^{21}$)$_2$]$_p$ (e.g. CF$_2$) or [CH$_2$]$_{pa}$—O—[CH$_2$]$_{pb}$ (e.g. CH$_2$OCH$_2$), or [CH$_2$]$_p$—O (e.g., CH$_2$CH$_2$O), substituted or unsubstituted arylene, substituted or unsubstituted heteroarylene, substituted or unsubstituted heterocycloalkylene or substituted or unsubstituted cycloalkylene (wherein substitutions include: F, Cl, Br, I, OH, C$_1$-C$_5$ linear, cyclic or branched alkyl (e.g. methyl, ethyl, propyl, isopropyl, isobutyl or cyclopropyl), C$_1$-C$_5$ linear or branched alkyl-OH (e.g., C(CH$_3$)$_2$CH$_2$—OH, CH$_2$CH$_2$—OH), 3-8 membered heterocyclic ring (e.g., piperidine), alkoxy, NH$_2$, N(alkyl)$_2$ (e.g. N(CH$_3$)$_2$, N(CH$_2$CH$_3$)$_2$, N(CH$_3$)(CH$_2$CH$_3$)) NH(alkyl) (e.g. NHCH$_3$, NHCH$_2$CH$_3$, NHCH$_2$CH$_2$CH$_3$) NH(cycloalkyl) (e.g. NH(cyclohexyl), NH(cylopentyl)), NH(aryl) (e.g. NH(phenyl), NH(pyridiny)), NH(benzyl), N(cycloalkyl)$_2$ (e.g. N(cyclohexyl)$_2$, N(cylopentyl)$_2$), N(aryl)$_2$ (e.g. N(phenyl)$_2$, N(pyridiny)$_2$), N(alkyl)(aryl) (e.g. N(methyl)(phenyl), N(methyl)(pyridinyl)), N(alkyl)(cycloalkyl) (e.g. N(methyl)(cyclopropyl), N(methyl)(cyclohexyl), N(methyl)(cyclopentyl)), N(aryl)(cycloalkyl) (e.g. N(phenyl)(cyclohexyl), N(pyridinyl)(cyclohexyl)), CF$_3$, aryl, phenyl, halophenyl, (benzyloxy)phenyl, CN, NO$_2$ or any combination thereof); each represents a separate embodiment of this invention.

In various embodiments, $R^{103}$ of compound of formula I, I(a) and/or I(b) is independently absent or O, C=O, C(=O)—[CH$_2$]$_p$, [CH$_2$]$_p$—C(=O), [CH$_2$]$_p$ (e.g. CH$_2$, CH$_2$CH$_2$, CH$_2$CH$_2$CH$_2$, CH$_2$CH$_2$CH$_2$CH$_2$), [CHR$^{21}$]$_p$ (e.g. CHF), [C(R$^{21}$)$_2$]$_p$ (e.g. CF$_2$) or [CH$_2$]$_{pa}$—O—[CH$_2$]$_{pb}$ (e.g. CH$_2$OCH$_2$), or [CH$_2$]$_p$—O (e.g., CH$_2$CH$_2$O), substituted or unsubstituted arylene, substituted or unsubstituted heteroarylene, substituted or unsubstituted heterocycloalkylene or substituted or unsubstituted cycloalkylene (wherein substitutions include: F, Cl, Br, I, OH, C$_1$-C$_5$ linear, cyclic or branched alkyl (e.g. methyl, ethyl, propyl, isopropyl or cyclopropyl), C$_1$-C$_5$ linear or branched alkyl-OH (e.g., C(CH$_3$)$_2$CH$_2$—OH, CH$_2$CH$_2$—OH), 3-8 membered heterocyclic ring (e.g., piperidine), alkoxy, NH$_2$, N(alkyl)$_2$ (e.g. N(CH$_3$)$_2$, N(CH$_2$CH$_3$)$_2$, N(CH$_3$)(CH$_2$CH$_3$)) NH(alkyl) (e.g. NHCH$_3$, NHCH$_2$CH$_3$, NHCH$_2$CH$_2$CH$_3$) NH(cycloalkyl) (e.g. NH(cyclohexyl), NH(cylopentyl)), NH(aryl) (e.g. NH(phenyl), NH(pyridiny)), NH(benzyl), N(cycloalkyl)$_2$ (e.g. N(cyclohexyl)$_2$, N(cylopentyl)$_2$), N(aryl)$_2$ (e.g. N(phenyl)$_2$, N(pyridiny)$_2$), N(alkyl)(aryl) (e.g. N(methyl)(phenyl), N(methyl)(pyridinyl)), N(alkyl)(cycloalkyl) (e.g. N(methyl)(cyclopropyl), N(methyl)(cyclohexyl), N(methyl)(cyclopentyl)), N(aryl)(cycloalkyl) (e.g. N(phenyl)(cyclohexyl), N(pyridinyl)(cyclohexyl)), CF$_3$, aryl, phenyl, halophenyl, (benzyloxy)phenyl, CN, NO$_2$ or any combination thereof); each represents a separate embodiment of this invention.

In various embodiments, $R^{102}$ of formula I I, I(a), I(a(i)), I(b) and/or I(b(i)) is H, F, Cl, Br, I, OH, CF$_3$, CN, NO$_2$, C$_1$-C$_5$ linear or branched, substituted or unsubstituted alkyl (e.g., methyl, ethyl), C$_1$-C$_5$ linear or branched alkoxy(e.g. methoxy), C$_1$-C$_5$ linear or branched haloalkyl (e.g., CHF$_2$, CF$_3$, R$^6$-aryl (e.g., CH$_2$-Ph, CH$_2$-Ph-ethyl), R$^6$—N(alkyl)$_2$, R$^6$—NH(alkyl), (R$^6$—NH(cycloalkyl), (R$^6$—NH(aryl), substituted or unsubstituted aryl (e.g., phenyl, ethylphenyl), substituted or unsubstituted heteroaryl (e.g., pyridine (2, 3, and 4-pyridine), benzimidazole), substituted or unsubstituted C$_3$-C$_8$ cycloalkyl (e.g., cyclopropyl), substituted or unsubstituted 3-8 membered heterocyclic ring (e.g. piperidine, pyrrolidine), R$^6$-(substituted or unsubstituted heterocycle), (e.g. (CH$_2$)$_3$-piperidine), or C(O)-(alkyl) (e.g. C(O)(CH$_3$) (wherein substitutions include: F, Cl, Br, I, OH, SH, diazirine, C$_1$-C$_5$ linear alkyne, C$_1$-C$_5$ linear, cyclic or branched alkyl (e.g. methyl, ethyl, propyl, isopropyl or cyclopropyl), substituted or unsubstituted benzyl (e.g., benzyl, methylbenzyl), aryl (e.g., phenyl), heteroaryl (e.g., pyridine (2, 3, and 4-pyridine), indole, tetrahydropyran), C$_3$-C$_8$ cycloalkyl (e.g., cyclopropyl), 3-8 membered heterocyclic ring (e.g. piperidine, pyrrolidine), alkoxy, NH$_2$, N(alkyl)$_2$ (e.g. N(CH$_3$)$_2$, N(CH$_2$CH$_3$)$_2$, N(CH$_3$)(CH$_2$CH$_3$)) NH(alkyl) (e.g. NHCH$_3$, NHCH$_2$CH$_3$, NHCH$_2$CH$_2$CH$_3$) NH(cycloalkyl) (e.g. NH(cyclohexyl), NH(cylopentyl)), NH(aryl) (e.g. NH(phenyl), NH(pyridiny)), NH(benzyl), N(cycloalkyl)$_2$ (e.g. N(cyclohexyl)$_2$, N(cylopentyl)$_2$), N(aryl)$_2$ (e.g. N(phenyl)$_2$, N(pyridiny)$_2$), N(alkyl)(aryl) (e.g. N(methyl)(phenyl), N(methyl)(pyridinyl)), N(alkyl)(cycloalkyl) (e.g. N(methyl)(cyclopropyl), N(methyl)(cyclohexyl), N(methyl)(cyclopentyl)), N(aryl)(cycloalkyl) (e.g. N(phenyl)(cyclohexyl), N(pyridinyl)(cyclohexyl)), CF$_3$, phenyl, halophenyl, (benzyloxy)phenyl, CN, NO$_2$ or any combination thereof); each represents a separate embodiment of this invention.

In various embodiments, $R^{104}$ of I, I(a) and/or I(b) is H, F, Cl, Br, I, OH, CF$_3$, CN, NO$_2$, C$_1$-C$_5$ linear or branched, substituted or unsubstituted alkyl (e.g., methyl, ethyl), C$_1$-C$_5$ linear or branched alkoxy (e.g. methoxy), C$_1$-C$_5$ linear or branched haloalkyl (e.g., CHF$_2$, CF$_3$, R$^6$-aryl (e.g., CH$_2$-Ph, CH$_2$-Ph-ethyl), R$^6$—N(alkyl)$_2$, R$^6$—NH(alkyl), (R$^6$—NH (cycloalkyl), (R$^6$—NH(aryl), substituted or unsubstituted aryl (e.g., phenyl, ethylphenyl), substituted or unsubstituted heteroaryl (e.g., pyridine (2, 3, and 4-pyridine), benzimidazole), substituted or unsubstituted C$_3$-C$_8$ cycloalkyl (e.g., cyclopropyl), substituted or unsubstituted 3-8 membered heterocyclic ring, R$^6$-(substituted or unsubstituted heterocycle) (e.g. (CH$_2$)$_3$-piperidine), or C(O)-(alkyl) (e.g. C(O)(CH$_3$) (wherein substitutions include: F, Cl, Br, I, OH, SH, diazirine, C$_1$-C$_5$ linear alkyne, C$_1$-C$_5$ linear, cyclic or branched alkyl (e.g. methyl, ethyl, propyl, isopropyl or cyclopropyl), substituted or unsubstituted benzyl (e.g., benzyl, methylbenzyl), aryl (e.g., phenyl), heteroaryl (e.g., pyridine (2, 3, and 4-pyridine), indole, tetrahydropyran), C$_3$-C$_8$ cycloalkyl (e.g., cyclopropyl), 3-8 membered heterocyclic ring (e.g. piperidine, pyrrolidine), alkoxy, NH$_2$, N(alkyl)$_2$ (e.g. N(CH$_3$)$_2$, N(CH$_2$CH$_3$)$_2$, N(CH$_3$)(CH$_2$CH$_3$)) NH(alkyl) (e.g. NHCH$_3$, NHCH$_2$CH$_3$, NHCH$_2$CH$_2$CH$_3$) NH(cycloalkyl) (e.g. NH(cyclohexyl), NH(cylopentyl)), NH(aryl) (e.g. NH(phenyl), NH(pyridiny)), NH(benzyl), N(cycloalkyl)$_2$ (e.g. N(cyclohexyl)$_2$, N(cylopentyl)$_2$), N(aryl)$_2$ (e.g. N(phenyl)$_2$, N(pyridiny)$_2$), N(alkyl)(aryl) (e.g. N(methyl)(phenyl), N(methyl)(pyridinyl)), N(alkyl)(cycloalkyl) (e.g. N(methyl)(cyclopropyl), N(methyl)(cyclohexyl), N(methyl)(cyclopentyl)), N(aryl)(cycloalkyl) (e.g. N(phenyl)(cyclohexyl), N(pyridinyl)(cyclohexyl)), CF$_3$, phenyl, halophenyl, (benzyloxy)phenyl, CN, NO$_2$ or any combination thereof); each represents a separate embodiment of this invention.

In some embodiments, $R^a$ and $R^b$ of compound of formula I, I(a) and/or I(b) are joined to form a 3-8 membered substituted or unsubstituted heterocyclic ring. In some embodiments, $R^a$ and $R^b$ are joined to form an unsubstituted 3-8 membered heterocyclic ring. In some embodiments, $R^a$ and $R^b$ are joined to form an unsubstituted morpholine ring.

In some embodiments, $R^a$ and $R^b$ are joined to form an unsubstituted piperidine ring. In some embodiments, $R^a$ and $R^b$ are joined to form an unsubstituted piperazine ring.

In various embodiments, $X^1$-$X^5$ of formula I, I(b), I(b(i)), I(b(ii)) and/or I(b(iii)) are each independently C, CH or N; each represents a separate embodiment of this invention.

In various embodiments, $X^6$-$X^7$ of formula I, I(a), I(a(i)), I(a(ii)), I(a(iii)), I(b), I(b(i)), I(b(ii)), I(b(iii)) and/or II are each independently CH or N; each represents a separate embodiment of this invention.

In some embodiments, m of formula I is 0. In other embodiments, m is 1. In other embodiments, m is 2. In other embodiments, m is 3. In other embodiments, m is between 1 and 3. In other embodiments, m is between 0 and 3. In other embodiments, m is between 0 and 4. In other embodiments, m is between 2 and 4. In other embodiments, m is between 1 and 4. In other embodiments, m is 4. Each possibility is a separate embodiment of this invention.

In some embodiments, n of formula I is 0. In other embodiments, n is 1. In other embodiments, n is 2. In other embodiments, n is 3. In other embodiments, n is 4. In other embodiments, n is between 1 and 3. In other embodiments, n is between 0 and 3. In other embodiments, n is between 0 and 4. In other embodiments, n is between 2 and 4. In other embodiments, n is between 1 and 4. Each possibility is a separate embodiment of this invention.

In some embodiments, m+n=1, in formula I. In other embodiments, m=0 and n=1. In other embodiments, m=1 and n=0. In other embodiments, m+n>2. In other embodiments, m+n=1 or m+n>2.

In some embodiments, 1 of formula I, I(a), I(a(i)), I(a(ii)), I(a(iii)), I(b), I(b(i)), I(b(ii) and/or I(b(iii))) is 0. In other embodiments, 1 is 1. In other embodiments, 1 is 2. In other embodiments, 1 is 3.

In other embodiments, 1 is 4. In other embodiments, 1 is between 1 and 3. In other embodiments, 1 is between 0 and 3. In other embodiments, 1 is between 0 and 4. In other embodiments, 1 is between 2 and 4. In other embodiments, 1 is between 1 and 4. Each possibility is a separate embodiment of this invention.

In some embodiments, q of formula I, I(a), I(a(i)), I(a(ii)), I(b), I(b(i)) and/or I(b(ii) is 0. In other embodiments, q is 1. In other embodiments, q is 2. In other embodiments, q is 3. In other embodiments, q is 4. In other embodiments, q is between 1 and 3. In other embodiments, q is between 0 and 3. In other embodiments, q is between 0 and 4. In other embodiments, q is between 2 and 4. In other embodiments, q is between q and 4. Each possibility is a separate embodiment of this invention.

In some embodiments, p of formula I, I(a), I(a(i)), I(a(ii)), I(a(iii)), I(b), I(b(i)), I(b(ii) and/or I(b(iii)) is 1. In other embodiments, p is 2. In other embodiments, p is 3. In other embodiments, p is 4. In other embodiments, p is 5. In other embodiments, p is 6. In other embodiments, p is 7. In other embodiments, p is 8. In other embodiments, p is 9. In other embodiments, p is 10. In other embodiments, p is between 1 and 5. In other embodiments, p is between 1 and 3. In other embodiments, p is between 3 and 5. In other embodiments, p is between 5 and 10. Each possibility is a separate embodiment of this invention.

In some embodiments, $p^a$ of formula formula I, I(a), I(a(i)), I(a(ii)), I(a(iii)), I(b), I(b(i)), I(b(ii)), I(b(iii)) and/or II is 0. In other embodiments, $p^a$ is 1. In other embodiments, $p^a$ is 2. In other embodiments, $p^a$ is 3. In other embodiments, $p^a$ is 4. In other embodiments, $p^a$ is 5. In other embodiments, $p^a$ is 6. In other embodiments, $p^a$ is 7. In other embodiments, $p^a$ is 8. In other embodiments, $p^a$ is 9. In other embodiments, $p^a$ is 10. In other embodiments, $p^a$ is between 0 and 5. In other embodiments, $p^a$ is between 0 and 3. In other embodiments, $p^a$ is between 5 and 10. Each possibility is a separate embodiment of this invention.

In some embodiments, $p^b$ of formula I, I(a), I(a(i)), I(a(ii)), I(a(iii)), I(b), I(b(i)), I(b(ii)), I(b(iii)) and/or II is 0. In other embodiments, $p^b$ is 1. In other embodiments, $p^b$ is 2. In other embodiments, $p^b$ is 3. In other embodiments, $p^b$ is 4. In other embodiments, $p^b$ is 5. In other embodiments, $p^b$ is 6. In other embodiments, $p^b$ is 7. In other embodiments, $p^b$ is 8. In other embodiments, $p^b$ is 9. In other embodiments, $p^b$ is 10. In other embodiments, $p^b$ is between 0 and 5. In other embodiments, $p^b$ is between 0 and 3. In other embodiments, $p^b$ is between 5 and 10. Each possibility is a separate embodiment of this invention.

In some embodiments, k of formula I and/or I(a) is 0. In other embodiments, k is 1. In other embodiments, k is 2. In other embodiments, k is 3. In other embodiments, k is between 1 and 3. In other embodiments, k is between 0 and 3. In other embodiments, k is between 0 and 4. In other embodiments, k is between 2 and 4. In other embodiments, k is between 1 and 4. In other embodiments, k is 4. Each possibility is a separate embodiment of this invention.

In some embodiments, in formula I: m+n=1. In other embodiments, m=0 and n=1.

In some embodiments, i of formula I, I(a) and/or I(b) is 1. In other embodiments i is 0.

It is understood that for heterocyclic, aryl or cycloalkyl rings, n, m, 1 and/or k are limited to the number of available positions for substitution, i.e. to the number of CH or NH groups minus one.

As used herein, "single aromatic or heteroaromatic ring" can be any such ring, including but not limited to phenyl, pyridinyl, (2-, 3-, and 4-pyridinyl), pyrimidinyl, pyridazinyl, pyrazinyl, triazinyl, tetrazinyl, thiazolyl, isothiazolyl, oxazolyl, isoxazolyl, imidazolyl, 1-methylimidazole, pyrazolyl, pyrrolyl, furanyl, thiophene-yl, triazolyl, thiadiazolyl, 1,2,3-, 1,2,4-, 1,2,5- or 1,3,4-oxadiazolyl, 3-methyl-4H-1,2,4-triazole, 5-methyl-1,2,4-oxadiazole etc. Each possibility is a separate embodiment of this invention. As used herein, "single or fused aliphatic or aromatic heterocyclic ring" can be any such ring, including but not limited to: phenyl, naphthyl, pyridinyl, (2-, 3-, and 4-pyridinyl), quinolinyl, pyrimidinyl, pyridazinyl, pyrazinyl, triazinyl, tetrazinyl, thiazolyl, isothiazolyl, oxazolyl, isoxazolyl, imidazolyl, 1-methylimidazole, pyrazolyl, pyrrolyl, furanyl, thiophene-yl, quinolinyl, isoquinolinyl, 2,3-dihydroindenyl, indenyl, tetrahydronaphthyl, 3,4-dihydro-2H-benzo[b][1,4]dioxepine, benzodioxolyl, benzo[d][1,3]dioxole, tetrahydronaphthyl, indolyl, 1H-indole, isoindolyl, anthracenyl, benzimidazolyl, 2,3-dihydro-1H-benzo[d]imidazolyl, indazolyl, 2H-indazole, triazolyl, 4,5,6,7-tetrahydro-2H-indazole, 3H-indol-3-one, purinyl, benzoxazolyl, 1,3-benzoxazolyl, benzisoxazolyl, benzothiazolyl, 1,3-benzothiazole, 4,5,6,7-tetrahydro-1,3-benzothiazole, quinazolinyl, quinoxalinyl, 1,2,3,4-tetrahydroquinoxaline, 1-(pyridin-1(2H)-yl) ethanone, cinnolinyl, phthalazinyl, quinolinyl, isoquinolinyl, acridinyl, benzofuranyl, 1-benzofuran, isobenzofuranyl, benzofuran-2(3H)-one, benzothiophenyl, benzoxadiazole, benzo[c][1,2,5]oxadiazolyl, benzo[c]thiophenyl, benzodioxolyl, thiadiazolyl, [1,3]oxazolo[4,5-b]pyridine, 1,2,3-, 1,2,4-, 1,2,5- or 1,3,4-oxadiazolyl, imidazo[2,1-b][1,3]thiazole, 4H,5H,6H-cyclopenta[d][1,3]thiazole, 5H,6H,7H,8H-imidazo[1,2-a]pyridine, 7-oxo-6H,7H-[1,3]thiazolo[4,5-d]pyrimidine, [1,3]thiazolo[5,4-b]pyridine, 2H,3H-imidazo[2,1-b][1,3]thiazole, thieno[3,2-d]pyrimidin-4(3H)-one, 4-oxo-4H-thieno[3,2-d][1,3]thiazin, imidazo[1,2-a]pyridine, 1H-imidazo[4,5-b]pyridine, 1H-imidazo[4,5-c]pyridine, 3H-imidazo[4,5-c]pyridine, pyrazolo[1,5-a]pyridine, imidazo[1,2-a]pyrazine, imidazo[1,2-a]pyrimidine, 1H-pyrrolo[2,3-b]pyridine, pyrido[2,3-b]pyrazine, pyrido[2,3-b]pyrazin-3(4H)-one, 4H-thieno[3,2-b]pyrrole, quinoxalin-2(1H)-one, 1H-pyrrolo[3,2-b]pyridine, 7H-pyrrolo[2,3-d]pyrimidine, oxazolo[5,4-b]pyridine, thiazolo[5,4-b]pyridine, thieno[3,2-c]pyridine, 3-methyl-4H-1,2,4-triazole, 5-methyl-1,2,4-oxadiazole, methylthiophene, methylfuran, methylpyridine, methylthiazole, indole, indane, benzimidazole, pyrrolopyridine, benzoxazole, oxetane, azetidine, methyloxetane, tetrahydrofuran, methyltetrahydropyran, pyrrolidine, methylpyrrolidine, tetrahydropyran, tetrahydrothiopyran, methylpiperidine, azepane, oxepane, 2H-thiopyran-tetrahydro-1,1-dioxide, 1-methylimidazole, pyrrole, furan, thiophene, oxadiazole, indole, indane, benzodihydrofuran, tetrahydroquinoline, tetrahydrofuran, piperidine, morpholine, thiomorpholine-1,1-dioxide, benzopyrrolidine, piperazine, 2-oxopyrrolidine, 2,5-dioxopyrrolidine, 2,5-dioxoimidazolidine, chromane, cyclobutyl, cyclohexyl, cyclopentyl, cyclooctyl etc. or a spiro ring system

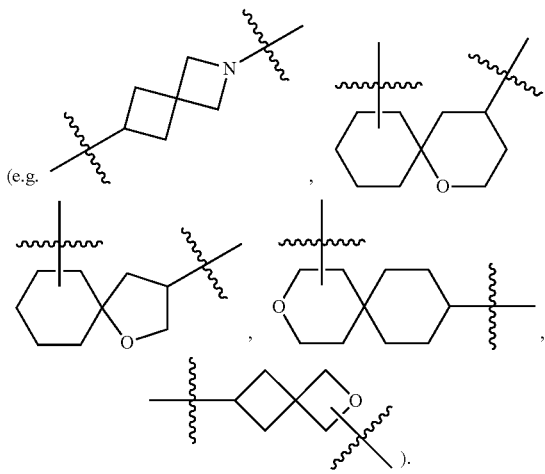

(e.g.

).

As used herein, the term "alkyl" can be any straight- or branched-chain alkyl group containing up to about 30 carbons unless otherwise specified. In various embodiments, an alkyl includes $C_1$-$C_5$ carbons. In some embodiments, an alkyl includes $C_1$-$C_6$ carbons. In some embodiments, an alkyl includes $C_1$-$C_8$ carbons. In some embodiments, an alkyl includes $C_1$-$C_{10}$ carbons. In some embodiments, an alkyl is a $C_1$-$C_{12}$ carbons. In some embodiments, an alkyl is a $C_1$-$C_{20}$ carbons. In some embodiments, branched alkyl is an alkyl substituted by alkyl side chains of 1 to 5 carbons. In various embodiments, the alkyl group may be unsubstituted. In some embodiments, the alkyl group may be substituted by a heteroaryl, aryl, cycloalkyl, heterocyclic ring, halogen, haloalkyl, hydroxyl, alkoxy, carbonyl, amido, alkylamido, dialkylamido, cyano, nitro, $CO_2H$, amino, alkylamino, dialkylamino, carboxyl, thio, thioalkyl, $C_1$-$C_5$ linear or branched haloalkoxy, $CF_3$, phenyl, halophenyl, (benzyloxy)phenyl, —$CH_2CN$, $NH_2$, NH-alkyl, N(alkyl)$_2$, —OC(O)CF$_3$, —OCH$_2$Ph, —NHCO-alkyl, —C(O)Ph, C(O)O-alkyl, C(O)H, —C(O)NH$_2$ or any combination thereof. In some embodiments, 1-3 carbon atoms of the alkyl chain/backbone form a heterocyclic, aromatic, heteroaryl or a cycloalkyl ring, e.g. with cyclopropyl the alkyl is for example —CH$_2$—CH$_2$—CH(CH$_2$)CH—CH$_3$ (2 carbon atoms of cyclopropyl within the alkyl backbone) or —CH$_2$—CH$_2$—C(CH$_2$)$_2$—CH$_3$ (1 carbon atom of cyclopropyl within the alkyl backbone). Each possibility is a separate embodiment of this invention.

The alkyl group can be a sole substituent, or it can be a component of a larger substituent, such as in an alkoxy, alkoxyalkyl, haloalkyl, arylalkyl, alkylamino, dialkylamino, alkylamido, alkylurea, etc. Preferred alkyl groups are methyl, ethyl, and propyl, and thus halomethyl, dihalomethyl, trihalomethyl, haloethyl, dihaloethyl, trihaloethyl, halopropyl, dihalopropyl, trihalopropyl, methoxy, ethoxy, propoxy, arylmethyl, arylethyl, arylpropyl, methylamino, ethylamino, propylamino, dimethylamino, diethylamino, methylamido, acetamido, propylamido, halomethylamido, haloethylamido, halopropylamido, methyl-urea, ethyl-urea, propyl-urea, 2, 3, or 4-CH$_2$—C$_6$H$_4$—Cl, C(OH)(CH$_3$)(Ph), etc. Each possibility is a separate embodiment of this invention.

As used herein, the term "aryl" refers to any aromatic ring that is directly bonded to another group and can be either substituted or unsubstituted. The aryl group can be a sole substituent, or the aryl group can be a component of a larger substituent, such as in an arylalkyl, arylamino, arylamido, etc. In some embodiments, the term aryl according to this invention, includes also heteroaryl. Exemplary aryl groups include, without limitation, phenyl, tolyl, xylyl, furanyl, naphthyl, pyridinyl, pyrimidinyl, pyridazinyl, pyrazinyl, triazinyl, thiazolyl, oxazolyl, isooxazolyl, pyrazolyl, imidazolyl, thiophene-yl, pyrrolyl, indolyl, benzimidazolyl, phenylmethyl, phenylethyl, indane, phenylamino, phenylamido, 3-methyl-4H-1,2,4-triazolyl, oxadiazolyl, 5-methyl-1,2,4-oxadiazolyl, isothiazolyl, thiadiazolyl, triazolyl, methylthiophene, methylfuran, methylpyridine, methylthiazole, indole, indane, benzimidazole, pyrrolopyridine, benzoxazole, 1-methylimidazole, pyrrole, furan, thiophene, oxadiazole, indane, benzodihydrofuran, tetrahydroquinoline, benzopyrrolidine, chromane, etc. Substitutions include but are not limited to: heteroaryl, aryl, cycloalkyl, heterocyclic ring, F, Cl, Br, I, $C_1$-$C_5$ linear or branched alkyl, heterocyclyl, $C_1$-$C_5$ linear or branched haloalkyl, $C_1$-$C_5$ linear or branched alkoxy, $C_1$-$C_5$ linear or branched haloalkoxy, $CF_3$, phenyl, halophenyl, CN, NO$_2$, —CH$_2$CN, NH$_2$, NH-alkyl, N(alkyl)$_2$, hydroxyl, —OC(O)CF$_3$, —OCH$_2$Ph, —NHCO-alkyl, COOH, —C(O)Ph, C(O)O-alkyl, C(O)H, —C(O)NH$_2$ or any combination thereof. The term "arylene" or a "heteroarylene" refers to "aryl" or "heteroaryl" as described hereinabove, where the aryl or heteroaryl is directly bonded to at least two other groups, e.g. phenyl connected at the left hand side to an alkyl backbone and to halide at the left hand side, when the alkyl and halide are for example para to each other (i.e. the compound is 1-alkyl-4-halophenyl). Each possibility is a separate embodiment of this invention.

As used herein, the term "alkoxy" refers to an ether group substituted by an alkyl group as defined above. Alkoxy refers both to linear and to branched alkoxy groups. Non-limiting examples of alkoxy groups are methoxy, ethoxy, propoxy, iso-propoxy, tert-butoxy. Each possibility is a separate embodiment of this invention. In some embodiments, the alkoxy may be substituted, unsubstituted, linear, branched or cyclic; each represents a separate embodiment according to this invention. In some embodiments the alkoxy is a linear or branched $C_1$-$C_5$ alkoxy. In some embodiments the alkoxy is a linear or branched $C_2$-$C_7$ alkoxy. In some embodiments the alkoxy is a linear or branched $C_2$-$C_5$ alkoxy. In some embodiments the alkoxy is a cyclic $C_3$-$C_8$ alkoxy. In some embodiments the alkoxy is a cyclic $C_5$-$C_7$ alkoxy.

As used herein, the term "aminoalkyl" refers to an amine group substituted by an alkyl group as defined above. Aminoalkyl refers to monoalkylamine, dialkylamine or trialkylamine. Nonlimiting examples of aminoalkyl groups are —N(Me)$_2$, —NHMe, —NH$_3$. Each possibility is a separate embodiment of this invention.

A "haloalkyl" group refers, in some embodiments, to an alkyl group as defined above, which is substituted by one or more halogen atoms, e.g. by F, Cl, Br or I. The term "haloalkyl" include but is not limited to fluoroalkyl, i.e., to an alkyl group bearing at least one fluorine atom. Nonlimiting examples of haloalkyl groups are CF$_3$, CF$_2$CF$_3$, CF$_2$CH$_3$, CH$_2$CF$_3$, CF$_2$CH$_2$CH$_3$, CH$_2$CH$_2$CF$_3$, CF$_2$CH(CH$_3$)$_2$ and CF(CH$_3$)—CH(CH$_3$)$_2$. Each possibility is a separate embodiment of this invention. In some embodiments, the haloalkyl may be linear, branched or cyclic; each represents a separate embodiment according to this invention. In some embodiments the haloalkyl is a linear or branched C$_1$-C$_5$ haloalkyl. In some embodiments the haloalkyl is a linear or branched C$_2$-C$_7$ haloalkyl. In some embodiments the haloalkyl is a linear or branched C$_2$-C$_5$ haloalkyl. In some embodiments the haloalkyl is a cyclic C$_3$-C$_8$ haloalkyl. In some embodiments the haloalkyl is a cyclic C$_5$-C$_7$ haloalkyl.

A "halophenyl" group refers, in some embodiments, to a phenyl substituent which is substituted by one or more halogen atoms, e.g. by F, Cl, Br or I. In one embodiment, the halophenyl is 4-chlorophenyl. Each possibility is a separate embodiment of this invention.

A "haloalkoxy" group refers, in some embodiments, to an alkoxy group as defined above, which is substituted by one or more halogen atoms, e.g. by F, Cl, Br or I. The term "haloalkoxy" include but is not limited to fluoroalkoxy, i.e., to an alkoxy group bearing at least one fluorine atom. Nonlimiting examples of haloalkoxy groups are OCF$_3$, OCF$_2$CF$_3$, OCF$_2$CH$_3$, OCH$_2$CF$_3$, OCF$_2$CH$_2$CH$_3$, OCH$_2$CH$_2$CF$_3$, OCF$_2$CH(CH$_3$)$_2$ and OCF(CH$_3$)—CH(CH$_3$)$_2$. Each possibility is a separate embodiment of this invention. In some embodiments, the haloalkoxy may be substituted, unsubstituted, linear, branched or cyclic; each represents a separate embodiment according to this invention. In some embodiments the haloalkoxy is a linear or branched C$_1$-C$_5$ haloalkoxy. In some embodiments the haloalkoxy is a linear or branched C$_2$-C$_7$ haloalkoxy. In some embodiments the haloalkoxy is a linear or branched C$_2$-C$_5$ haloalkoxy. In some embodiments the haloalkoxy is a cyclic C$_3$-C$_8$ haloalkoxy. In some embodiments the haloalkoxy is a cyclic C$_5$-C$_7$ haloalkoxy.

An "alkoxyalkyl" group refers, in some embodiments, to an alkyl group as defined above, which is substituted by alkoxy group as defined above, e.g. by methoxy, ethoxy, propoxy, i-propoxy, t-butoxy etc. Nonlimiting examples of alkoxyalkyl groups are —CH$_2$—O—CH$_3$, —CH$_2$—O—CH(CH$_3$)$_2$, —CH$_2$—O—C(CH$_3$)$_3$, —CH$_2$—CH$_2$—O—CH$_3$, —CH$_2$—CH$_2$—O—CH(CH$_3$)$_2$, —CH$_2$—CH$_2$—O—C(CH$_3$)$_3$. Each possibility is a separate embodiment of this invention. In some embodiments, the alkoxyalkyl may be substituted, unsubstituted, linear, branched or cyclic; each represents a separate embodiment according to this invention. In some embodiments the alkoxyalkyl is a linear or branched C$_1$-C$_5$ alkoxyalkyl. In some embodiments the alkoxyalkyl is a linear or branched C$_2$-C$_7$ alkoxyalkyl. In some embodiments the alkoxyalkyl is a linear or branched C$_2$-C$_5$ alkoxyalkyl. In some embodiments the alkoxyalkyl is a cyclic C$_3$-C$_8$ alkoxyalkyl. In some embodiments the alkoxyalkyl is a cyclic C$_5$-C$_7$ alkoxyalkyl.

A "cycloalkyl" or "carbocyclic" group refers, in various embodiments, to a ring structure comprising carbon atoms as ring atoms, which may be either saturated or unsaturated, substituted or unsubstituted, single or fused. In some embodiments the cycloalkyl is saturated. In some embodiments the cycloalkyl is unsaturated. In some embodiments the cycloalkyl is substituted. In some embodiments the cycloalkyl is unsubstituted. In some embodiments the cycloalkyl is a single ring. In some embodiments the cycloalkyl is a fused ring system. In some embodiments the cycloalkyl is a 3-10 membered ring. In some embodiments the cycloalkyl is a 3-12 membered ring. In some embodiments the cycloalkyl is a 6 membered ring. In some embodiments the cycloalkyl is a 5-7 membered ring. In some embodiments the cycloalkyl is a 3-8 membered ring. In some embodiments, the cycloalkyl group may be unsubstituted or substituted by a heteroaryl, aryl, cycloalkyl, heterocyclic ring, halogen, alkyl, haloalkyl, hydroxyl, alkoxy, carbonyl, amido, alkylamido, dialkylamido, cyano, nitro, CO$_2$H, amino, alkylamino, dialkylamino, carboxyl, thio, thioalkyl, C$_1$-C$_5$ linear or branched haloalkoxy, CF$_3$, phenyl, halophenyl, (benzyloxy)phenyl, —CH$_2$CN, NH$_2$, NH-alkyl, N(alkyl)$_2$, —OC(O)CF$_3$, —OCH$_2$Ph, —NHCO— alkyl, —C(O)Ph, C(O)O-alkyl, C(O)H, —C(O)NH$_2$ or any combination thereof. In some embodiments, the cycloalkyl ring may be fused to another saturated or unsaturated cycloalkyl or heterocyclic 3-8 membered ring. In some embodiments, the cycloalkyl ring is a saturated ring. In some embodiments, the cycloalkyl ring is an unsaturated ring. Non limiting examples of a cycloalkyl group comprise cyclohexyl, cyclohexenyl, cyclopropyl, cyclopropenyl, cyclopentyl, cyclopentenyl, cyclopentadienyl, cyclobutyl, cyclobutenyl, cycloctyl, cycloctadienyl (COD), cycloctaene (COE) etc. The term "cycloalkylene" refers to "cyclolkyl" as described hereinabove, where the cycloalkyl is directly bonded to at least two other groups, e.g. cyclohexyl connected at the left hand side to an alkyl backbone and to halide at the left hand side, when the alkyl and halide are for example connected at the 1,4 positions. Each possibility is a separate embodiment of this invention.

A "heterocycle" or "heterocyclic" group refers, in various embodiments, to a ring structure comprising in addition to carbon atoms, sulfur, oxygen, nitrogen or any combination thereof, as part of the ring. A "heteroaromatic ring" refers in various embodiments, to an aromatic ring structure comprising in addition to carbon atoms, sulfur, oxygen, nitrogen or any combination thereof, as part of the ring. In some embodiments the heterocycle or heteroaromatic ring is a 3-10 membered ring. In some embodiments the heterocycle or heteroaromatic ring is a 3-12 membered ring. In some embodiments the heterocycle or heteroaromatic ring is a 6 membered ring. In some embodiments the heterocycle or heteroaromatic ring is a 5-7 membered ring. In some embodiments the heterocycle or heteroaromatic ring is a 3-8 membered ring. In some embodiments, the heterocycle group or heteroaromatic ring may be unsubstituted or substituted by an aryl, heteroaryl, heterocyclic ring, cycloalkyl, halogen, alkyl, haloalkyl, hydroxyl, alkoxy, carbonyl, amido, alkylamido, dialkylamido, cyano, nitro, CO$_2$H, amino, alkylamino, dialkylamino, carboxyl, thio, thioalkyl, C$_1$-C$_5$ linear or branched haloalkoxy, CF$_3$, phenyl, halophenyl, (benzyloxy)phenyl, —CH$_2$CN, NH$_2$, NH-alkyl, N(alkyl)$_2$, —OC(O)CF$_3$, —OCH$_2$Ph, —NHCO— alkyl, —C(O)Ph, C(O)O-alkyl, C(O)H, —C(O)NH$_2$ or any combination thereof. In some embodiments, the heterocycle ring or heteroaromatic ring may be fused to another saturated or unsaturated cycloalkyl or heterocyclic 3-8 membered ring.

In some embodiments, the heterocyclic ring is a saturated ring. In some embodiments, the heterocyclic ring is an unsaturated ring. Non limiting examples of a heterocyclic ring or heteroaromatic ring systems comprise pyridine, piperidine, morpholine, piperazine, thiophene, pyrrole, benzodioxole, benzofuran-2(3H)-one, benzo[d][1,3]dioxole, indole, oxazole, isoxazole, imidazole and 1-methylimidazole, furan, triazole, pyrimidine, pyrazine, oxacyclobutane (1 or 2-oxacyclobutane), naphthalene, tetrahydrothiophene 1,1-dioxide, thiazole, benzimidazole, piperidine, 1-methylpiperidine, isoquinoline, 1,3-dihydroisobenzofuran, benzofuran, 3-methyl-4H-1,2,4-triazole, oxadiazolyl, 5-methyl-1,2,4-oxadiazole, pyrazole, isothiazole, thiadiazole, tetrahydrofuran, oxazolone, oxazolidone, thiazolone, isothiazolinone, isoxazolidinone, imidazolidinone, pyrazolone, 2H-pyrrol-2-one, furanone, thiophenone, thiane 1,1-dioxide, triazolopyrimidine, 6,7-dihydro-5H-pyrazolo[5,1-b][1,3] oxazine, methylthiophene, methylfuran, methylpyridine, methylthiazole, indole, benzimidazole, pyrrolopyridine, benzoxazole, oxetane, azetidine, methyloxetane, tetrahydrofuran, methyltetrahydropyran, pyrrolidine, methylpyrrolidine, tetrahydropyran, tetrahydrothiopyran, piperidine, methylpiperidine, azepane, oxepane, 2H-Thiopyran-tetrahydro-1,1-dioxide, 1-methylimidazole, furan, thiophene, oxadiazole, indole, benzodihydrofuran, tetrahydroquinoline, tetrahydrofuran, morpholine, thiomorpholine-1,1-dioxide, piperazine, benzopyrrolidine, 2-oxopyrrolidine, 2,5-dioxopyrrolidine, 2,5-dioxoimidazolidine, chromane, or indole. The term "heterocycloalkylene" refers to "heterocyclic ring" as described hereonabove, where the heterocyclic ring is directly bonded to at least two other groups, e.g. piperazine connected at the left hand side to an alkyl backbone and to halide at the left hand side, when the alkyl and halide are for example connected at the 1,4 or 2,5 positions. Each possibility is a separate embodiment of this invention.

In some embodiments, "heterocyclic ring" according to this invention refers to substituted or unsubstituted, 3 to 12 membered, saturated, unsaturated, aliphatic or aromatic, single, fused or spiro rings, which comprise at least one heteroatom selected from: N, O or S. In some embodiments, the heterocyclic ring may be substituted, unsubstituted, saturated, unsaturated, aliphatic, aromatic, single, fused or spiro ring; each represent a separate embodiment according to this invention. In some embodiments, the heterocyclic ring may be substituted. In some embodiments, the heterocyclic ring may be unsubstituted. In some embodiments, the heterocyclic ring may be saturated. In some embodiments, the heterocyclic ring may be unsaturated. In some embodiments, the heterocyclic ring may be aliphatic. In some embodiments, the heterocyclic ring may be aromatic. In some embodiments, the heterocyclic ring may be single ring. In some embodiments, the heterocyclic ring may be fused ring. In some embodiments, the heterocyclic ring may be spiro ring. In some embodiments, the heterocyclic ring may be any combination of: substituted, unsubstituted, saturated, unsaturated, aliphatic, aromatic, single, fused or spiro ring. The heterocyclic ring(s) may be 3-12; 3-10; 3-9; 3-8; 3-7; 3-6; 3-5; 4-6; 4-7; 4-8; 4-9; 5-6; 5-7; 5-8; 5-10 or 5-9 membered ring(s); each represents a separate embodiment according to this invention. Examples of heterocyclic rings include, but not limited to: pyran, tetrahydropyran, pyrrazole, imidazole, furan, tetrahydrofuran, dioxane, oxetane, azetidine, pyridine, pyridazine, pyrimidine, piperidine, piperazine, triazole, oxadiazole, tetrahydrofuran (THF), piperidine, tetrahydrofurane, morpholine, thiomorpholine 1,1-dioxide, oxa-azaspirodecane, azaspiroheptane, 5-azaspiro[2.4] heptane, 2-azaspiro[3.3]heptane, oxa-azaspiroheptane, 2-oxa-6-azaspiro[3.3]heptane pyrrol, pyrrolidine, pyrrolidine-2-one, 2-oxo-pyrrolidine, pyrrolidinone, quinuclidine, oxetane, azepane, azepan-2-one, azabicyclohexane, 2-azabicyclo[2.1.1]hexane, 3-azabicyclo[3.1.0]hexane, 1-oxa-8-azaspiro[4.5]decane, diazabicyclo[2.2.1]heptane, 2,5-diazabicyclo[2.2.1]heptane, thiomorpholine 1,1-dioxide. In some embodiments, the heterocyclic ring may be further substituted with at least one group selected from: F, Cl, Br, I, $CF_3$, $C_1$-$C_5$ linear or branched alkyl (e.g., methyl, ethyl, propyl), alkyleneamine (e.g., $CH_2$—$NH_2$), $C_1$-$C_5$ linear or branched haloalkyl, OH, alkoxy (e.g., $OCH_3$), alkylene-OH (e.g., $CH_2$—OH), amide, alkylene-amide (e.g., $CH_2$—C(O) $NH_2$), C(O)-heterocyclic ring, amine (e.g., $NH_2$), alkylamine (e.g., $NH(CH_3)$), dialkylamine (e.g., $N(CH_3)_2$), $CF_3$, aryl, phenyl, halophenyl, heteroaryl, $C_3$-$C_8$ cycloalkyl (e.g., cyclopropyl), saturated, unsaturated, aromatic, single fused or spiral 3-8 membered heterocyclic ring, CN, and $NO_2$; each is a separate embodiment according to this invention.

In some embodiments, "single or fused saturated, unsaturated or aromatic heterocyclic ring" or "saturated, unsaturated, aromatic, single, fused or spiro heterocyclic ring" can be any such ring(s), which comprise at least one heteroatom selected from: N, O or S. The heterocyclic ring may be 3-12; 3-10; 3-9; 3-8; 3-7; 3-6; 3-5; 4-6; 4-7; 4-8; 4-9; 5-6; 5-7; 5-8; 5-10 or 5-9 membered ring(s); each represents a separate embodiment according to this invention. In some embodiments, the heterocyclic ring may be substituted. In some embodiments, the heterocyclic ring may be unsubstituted. In some embodiments, the heterocyclic ring may be saturated. In some embodiments, the heterocyclic ring may be unsaturated. In some embodiments, the heterocyclic ring may be aliphatic. In some embodiments, the heterocyclic ring may be aromatic. In some embodiments, the heterocyclic ring may be single ring. In some embodiments, the heterocyclic ring may be fused ring. In some embodiments, the heterocyclic ring may be spiro ring. In some embodiments, the heterocyclic ring may be any combination of: substituted, unsubstituted, saturated, unsaturated, aromatic, single, fused or spiro ring. Examples of such heterocyclic rings according to this invention include but not limited to: pyridinyl, (2-, 3-, and 4-pyridinyl), quinolinyl, pyrimidinyl, pyridazinyl, pyrazinyl, triazinyl, tetrazinyl, thiazolyl, isothiazolyl, oxazolyl, isoxazolyl, imidazolyl, 1-methylimidazole, pyrazolyl, pyrrolyl, furanyl, thiophene-yl, quinolinyl, isoquinolinyl, 2,3-dihydroindenyl, indenyl, tetrahydronaphthyl, 3,4-dihydro-2H-benzo[b][1,4]dioxepine, benzodioxolyl, benzo[d] [1,3]dioxole, tetrahydronaphthyl, indolyl, 1H-indole, isoindolyl, anthracenyl, benzimidazolyl, 2,3-dihydro-1H-benzo [d]imidazolyl, indazolyl, 2H-indazole, triazolyl, 4,5,6,7-tetrahydro-2H-indazole, 3H-indol-3-one, purinyl, benzoxazolyl, 1,3-benzoxazolyl, benzisoxazolyl, benzothiazolyl, 1,3-benzothiazole, 4,5,6,7-tetrahydro-1,3-benzothiazole, quinazolinyl, quinoxalinyl, 1,2,3,4-tetrahydroquinoxaline, 1-(pyridin-1(2H)-yl)ethanone, cinnolinyl, phthalazinyl, quinolinyl, isoquinolinyl, acridinyl, benzofuranyl, 1-benzofuran, isobenzofuranyl, benzofuran-2(3H)-one, benzothiophenyl, benzoxadiazole, benzo[c][1,2,5]oxadiazolyl, benzo[c]thiophenyl, benzodioxolyl, thiadiazolyl, [1,3]oxazolo[4,5-b]pyridine, 1,2,3-, 1,2,4-, 1,2,5- or 1,3,4-oxadiazolyl, imidazo[2,1-b][1,3]thiazole, 4H,5H,6H-cyclopenta[d][1,3]thiazole, 5H,6H,7H,8H-imidazo[1,2-a]pyridine, 7-oxo-6H,7H-[1,3]thiazolo[4,5-d]pyrimidine, [1,3] thiazolo[5,4-b]pyridine, 2H,3H-imidazo[2,1-b][1,3] thiazole, thieno[3,2-d]pyrimidin-4(3H)-one, 4-oxo-4H-thieno[3,2-d][1,3]thiazin, imidazo[1,2-a]pyridine, 1H-imidazo[4,5-b]pyridine, 1H-imidazo[4,5-c]pyridine, 3H-imidazo[4,5-c]pyridine, pyrazolo[1,5-a]pyridine, imidazo[1,2-a]pyrazine, imidazo[1,2-a]pyrimidine, 1H-pyrrolo[2,3-b]pyridine, pyrido[2,3-b]pyrazine, pyrido[2,3-b]pyrazin-3(4H)-one, 4H-thieno[3,2-b]pyrrole, quinoxalin-2 (1H)-one, 1H-pyrrolo[3,2-b]pyridine, 7H-pyrrolo[2,3-d] pyrimidine, oxazolo[5,4-b]pyridine, thiazolo[5,4-b] pyridine, thieno[3,2-c]pyridine, 3-methyl-4H-1,2,4-triazole, 5-methyl-1,2,4-oxadiazole etc. In some embodiments, the heterocyclic ring according to this invention includes: pyran, tetrahydropyran, pyrrazole, imidazole, furan, tetrahydrofuran, dioxane, oxetane, azetidine, pyridine, pyridazine, pyrimidine, piperidine, piperazine, triazole, oxadiazole, tetrahydrofuran (THF), piperidine, tetrahydrofurane, morpholine, thiomorpholine 1,1-dioxide, oxa-azaspirodecane, azaspiroheptane, 5-azaspiro[2.4]heptane, 2-azaspiro[3.3] heptane, oxa-azaspiroheptane, pyrrol, pyrrolidine, pyrrolidine-2-one, 2-oxo-pyrrolidine, pyrrolidinone, quinuclidine, oxetane, azepane, azepan-2-one, azabicyclohexane, 2-azabicyclo[2.1.1]hexane, 3-azabicyclo[3.1.0]hexane, 1-oxa-8-azaspiro[4.5]decane, and/or diazabicyclo[2.2.1]heptane; each represent a separate embodiment according to this invention. In some embodiments, the heterocyclic ring may be further substituted with at least one group selected from: F, Cl, Br, I, $CF_3$, $C_1$-$C_5$ linear or branched alkyl (e.g., methyl, ethyl, propyl), alkyleneamine (e.g., $CH_2$—$NH_2$), $C_1$-$C_5$ linear or branched haloalkyl, OH, alkoxy (e.g., $OCH_3$), alkylene-OH (e.g., CH—OH), amide, alkylene-amide (e.g., $CH_2$—$C(O)NH_2$), C(O)-heterocyclic ring, amine (e.g., $NH_2$), alkylamine (e.g., $NH(CH_3)$), dialkylamine (e.g., $N(CH_3)_2$), $CF_3$, aryl, phenyl, halophenyl, heteroaryl, $C_3$-$C_8$ cycloalkyl (e.g., cyclopropyl), saturated, unsaturated, aromatice, single fused or spiral 3-8 membered heterocyclic ring, CN, and $NO_2$; each is a separate embodiment according to this invention.

In some embodiments, when a chemical term/group (e.g. alkyl, aryl, heteroaryl, cycloalkyl, amino, alkoxy, etc.) is said to be substituted, non-limiting examples of the substitutent or substituents include the following: F, Cl, Br, I, OH, SH, diazirine, $C_1$-$C_5$ linear alkyne, $C_1$-$C_5$ linear or branched alkyl, aryl (e.g., phenyl, fluorophenyl), heteroaryl (e.g., pyridine (2, 3, and 4-pyridine), thiophene, indole, tetrahydropyran), cycloalkyl (e.g., cyclopropyl, cyclobutyl, cyclohexyl, cyclopentyl), heterocyclic ring, alkoxy (e.g. methoxy, ethoxy, propyloxy, isopropyloxy), $C_1$-$C_5$ linear, cyclic or branched alkyl (e.g. methyl, ethyl, propyl, isopropyl, butyl, isobutyl or cyclopropyl), OH, alkoxy, $NH_2$, $N(alkyl)_2$ (e.g. $N(CH_3)_2$, $N(CH_2CH_3)_2$, $N(CH_3)(CH_2CH_3)$), NH(alkyl) (e.g. $NHCH_3$, $NHCH_2CH_3$, $NHCH_2CH_2CH_3$) NH(cycloalkyl) (e.g. NH(cyclohexyl), NH(cylopentyl)), NH(aryl) (e.g. NH(phenyl), NH(pyridiny)), NH(benzyl), $N(cycloalkyl)_2$ (e.g. $N(cyclohexyl)_2$, $N(cylopentyl)_2$), $N(aryl)_2$ (e.g. $N(phenyl)_2$, $N(pyridiny)_2$), N(alkyl)(aryl) (e.g. N(methyl)(phenyl), N(methyl)(pyridinyl)), N(alkyl)(cycloalkyl) (e.g. N(methyl) (cyclopropyl), N(methyl)(cyclohexyl), N(methyl)(cyclopentyl)), N(aryl)(cycloalkyl) (e.g. N(phenyl)(cyclohexyl), N(pyridinyl)(cyclohexyl)) NHC(O)(alkyl) (e.g. NHC(O) $CH_3$), $CF_3$, phenyl, halophenyl, (benzyloxy)phenyl, CN, $NO_2$, haloalkyl, carbonyl, amido, alkylamido, dialkylamido, $CO_2H$, carboxyl, thio, thioalkyl, $C_1$-$C_5$ linear or branched haloalkoxy, $CF_3$, phenyl, (benzyloxy)phenyl, —$CH_2CN$, —$OC(O)CF_3$, —$OCH_2Ph$, —NHCO-alkyl, —C(O)Ph, C(O)O-alkyl, C(O)H, —$C(O)NH_2$, substituted or unsubstituted benzyl (e.g., benzyl, methylbenzyl), oxo (i.e. =O, forming with the substituted carbon a carbonyl), haloalkyl (e.g. $CF_3$, $CH_2CF_3$), cycloalkyl (e.g. cyclopropyl), $C_1$-$C_5$ linear or branched haloalkoxy (e.g., $OCF_3$, $OCHF_2$), 3-8 membered heterocyclic ring (e.g., piperidine), $C_1$-$C_5$ linear or branched alkoxyalkyl (e.g. $CH_3OCH_2$), $C_1$-$C_5$ linear or branched alkyl-OH (e.g., $C(CH_3)_2CH_2$—OH, $CH_2CH_2$—OH), or any combination thereof In various embodiments, this invention provides a compound of this invention or its isomer, metabolite, pharmaceutically acceptable salt, pharmaceutical product, tautomer, hydrate, N-oxide, reverse amide analog, prodrug, isotopic variant (deuterated analog), PROTAC, polymorph, or crystal or combinations thereof. In various embodiments, this invention provides an isomer of the compound of this invention. In some embodiments, this invention provides a metabolite of the compound of this invention. In some embodiments, this invention provides a pharmaceutically acceptable salt of the compound of this invention. In some embodiments, this invention provides a pharmaceutical product of the compound of this invention. In some embodiments, this invention provides a tautomer of the compound of this invention. In some embodiments, this invention provides a hydrate of the compound of this invention. In some embodiments, this invention provides an N-oxide of the compound of this invention. In some embodiments, this invention provides a reverse amide analog of the compound of this invention. In some embodiments, this invention provides a prodrug of the compound of this invention. In some embodiments, this invention provides an isotopic variant (including but not limited to deuterated analog) of the compound of this invention. In some embodiments, this invention provides a PROTAC (proteolysis targeting chimera) of the compound of this invention. In some embodiments, this invention provides a polymorph of the compound of this invention. In some embodiments, this invention provides a crystal of the compound of this invention. In some embodiments, this invention provides composition comprising a compound of this invention, as described herein, or, In some embodiments, a combination of an isomer, metabolite, pharmaceutically acceptable salt, pharmaceutical product, tautomer, hydrate, N-oxide, reverse amide analog, prodrug, isotopic variant (deuterated analog), PROTAC, polymorph, or crystal of the compound of this invention.

In various embodiments, the term "isomer" includes, but is not limited to, stereoisomers including optical isomers and analogs, structural isomers and analogs, conformational isomers and analogs, and the like. In some embodiments, the isomer is a stereoisomer. In another embodiment, the isomer is an optical isomer.

Certain compounds of the present invention may exist in particular geometric or stereoisomeric forms. The present invention contemplates all such compounds, including cis- and trans-isomers, R- and S-enantiomers, diastereomers, the racemic mixtures thereof, and other mixtures thereof, as falling within the scope of the invention. Additional asymmetric carbon atoms may be present in a substituent such as an alkyl group. All such isomers, as well as mixtures thereof, are included in this invention.

In various embodiments, this invention encompasses the use of various stereoisomers of the compounds of the invention. It will be appreciated by those skilled in the art that the compounds of the present invention may contain at least one chiral center. Accordingly, the compounds used in the methods of the present invention may exist in, and be isolated in, optically-active or racemic forms. The compounds according to this invention may further exist as stereoisomers which may be also optically-active isomers (e.g., enantiomers such as (R) or (S)), as enantiomerically enriched mixtures, racemic mixtures, or as single diastereomers, diastereomeric mixtures, or any other stereoisomers, including but not limited to: (R)(R), (R)(S), (S)(S), (S)(R), (R)(R)(R), (R)(R)(S), (R)(S)(R), (S)(R)(R), (R)(S)(S), (S)(R)(S), (S)(S)(R) or (S)(S)(S) stereoisomers. Some compounds may also exhibit polymorphism. It is to be understood that the present invention encompasses any racemic, optically-active, polymorphic, or stereoisomeric form, or mixtures thereof, which form possesses properties useful in the treatment of the various conditions described herein.

It is well known in the art how to prepare optically active forms (for example, by resolution of the racemic form by recrystallization techniques, by synthesis from optically-active starting materials, by chiral synthesis, or by chromatographic separation using a chiral stationary phase).

The compounds of the present invention can also be present in the form of a racemic mixture, containing substantially equivalent amounts of stereoisomers. In some embodiments, the compounds of the present invention can be prepared or otherwise isolated, using known procedures, to obtain a stereoisomer substantially free of its corresponding stereoisomer (i.e., substantially pure). By substantially pure, it is intended that a stereoisomer is at least about 90% pure, more preferably at least about 95% pure, even more preferably at least about 98% pure, most preferably at least about 99% pure. In various embodiments, the compound according to the invention comprises a substantially pure stereoisomer. In some embodiments, the substantially pure stereoisomer is at least 70%; 75%; 80%; 85%; 90%; 93%; 95%; 97%; 98%; 99%; 99.5% pure; each represents a separate embodiment according to this invention.

In various embodiments, the compound comprises a single stereoisomer in a purity of >80%; >85%; >90%; >91%; >92%; >93%; >94%; >95%; >96%; >97%; >98%; >99%; >99.5% enantiomeric excess (ee); each represents a separate embodiment according to this invention. In various embodiments, the compound comprises a single stereoisomer in a purity >80%; >85%; >90%; >91%; >92%; >93%; >94%; >95%; >96%; >97%; >98%; >99%; >99.5% enantiomeric ratio (er); each represents a separate embodiment according to this invention. In various embodiments, the compound comprises a single stereoisomer in a purity higher than 80%; 85%; 90%; 91%; 92%; 93%; 94%; 95%; 96%; 97%; 98%; 99%; 99.5%; each represents a separate embodiment according to this invention. In some embodiments, the compound is compound 369, 392, 412, 413, 414, 415, 422, 433, 434, 464, 465, 466, 467, 468, 469, 470, 471, 474 or 475; each represents a separate embodiment according to this invention.

In various embodiments, the compound is a substantially pure single enantiomer. In various embodiments, the compound comprises a mixture of enantiomers. In various embodiments, the compound is a racemate.

In various embodiments, the compound has two chiral centers. In various embodiments, the compound comprises a mixture of stereoisomers. In various embodiments, the compound comprises a mixture of 2, 3, or 4 stereoisomers; each represents a separate embodiment according to this invention.

In various embodiments, the compound is a single stereoisomer. In various embodiments, the compound is a substantially pure single stereoisomer. In various embodiments, the substantially pure stereoisomer has at least 80%, 85%, 90%, 95%, 97%, 98%, 99% purity; each represents a separate embodiment according to this invention. In various embodiments, the compound is the substantially pure RR stereoisomer. In various embodiments, the compound is the substantially pure SS stereoisomer. In various embodiments, the compound is the substantially pure RS stereoisomer. In various embodiments, the compound is the substantially pure SR stereoisomer.

Compounds of the present invention can also be in the form of a hydrate, which means that the compound further includes a stoichiometric or non-stoichiometric amount of water bound by non-covalent intermolecular forces.

As used herein, when some chemical functional group (e.g., alkyl or aryl) is said to be "substituted", it is herein defined that one or more substitutions are possible.

Compounds of the present invention may exist in the form of one or more of the possible tautomers and depending on the conditions it may be possible to separate some or all of the tautomers into individual and distinct entities. It is to be understood that all of the possible tautomers, including all additional enol and keto tautomers and/or isomers are hereby covered. For example, the following tautomers, but not limited to these, are included:

Tautomerization of the Imidazole Ring

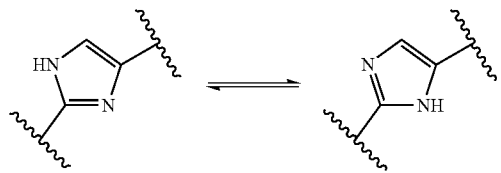 [SMILES: *c1c[nH]c(*)n1 ; *c1cnc(*)[nH]1]

Tautomerization of the Pyrazolone Ring:

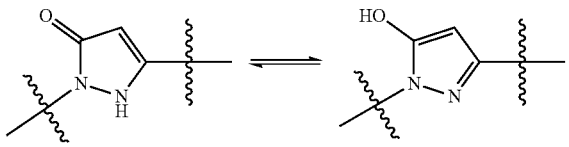 [SMILES: *c1cc(=O)n(*)[nH]1 ; *c1cc(O)n(*)n1]

The invention includes "pharmaceutically acceptable salts" of the compounds of this invention, which may be produced, by reaction of a compound of this invention with an acid or base. Certain compounds, particularly those possessing acid or basic groups, can also be in the form of a salt, preferably a pharmaceutically acceptable salt. The term "pharmaceutically acceptable salt" refers to those salts that retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcysteine and the like. Other salts are known to those of skill in the art and can readily be adapted for use in accordance with the present invention.

Suitable pharmaceutically acceptable salts of amines of compounds the compounds of this invention may be prepared from an inorganic acid or from an organic acid. In various embodiments, examples of inorganic salts of amines are bisulfates, borates, bromides, chlorides, hemisulfates, hydrobromates, hydrochlorates, 2-hydroxyethylsulfonates (hydroxyethanesulfonates), iodates, iodides, isothionates, nitrates, persulfates, phosphate, sulfates, sulfamates, sulfanilates, sulfonic acids (alkylsulfonates, arylsulfonates, halogen substituted alkylsulfonates, halogen substituted arylsulfonates), sulfonates and thiocyanates.

In various embodiments, examples of organic salts of amines may be selected from aliphatic, cycloaliphatic, aromatic, araliphatic, heterocyclic, carboxylic and sulfonic classes of organic acids, examples of which are acetates, arginines, aspartates, ascorbates, adipates, anthranilates, algenates, alkane carboxylates, substituted alkane carboxylates, alginates, benzenesulfonates, benzoates, bisulfates, butyrates, bicarbonates, bitartrates, citrates, camphorates, camphorsulfonates, cyclohexylsulfamates, cyclopentanepropionates, calcium edetates, camsylates, carbonates, clavulanates, cinnamates, dicarboxylates, digluconates, dodecylsulfonates, dihydrochlorides, decanoates, enanthuates, ethanesulfonates, edetates, edisylates, estolates, esylates, fumarates, formates, fluorides, galacturonates gluconates, glutamates, glycolates, glucorate, glucoheptanoates, glycerophosphates, gluceptates, glycollylarsanilates, glutarates, glutamate, heptanoates, hexanoates, hydroxymaleates, hydroxycarboxlic acids, hexylresorcinates, hydroxybenzoates, hydroxynaphthoates, hydrofluorates, lactates, lactobionates, laurates, malates, maleates, methylenebis(beta-oxynaphthoate), malonates, mandelates, mesylates, methane sulfonates, methylbromides, methylnitrates, methylsulfonates, monopotassium maleates, mucates, monocarboxylates, naphthalenesulfonates, 2-naphthalenesulfonates, nicotinates, nitrates, napsylates, N-methylglucamines, oxalates, octanoates, oleates, pamoates, phenylacetates, picrates, phenylbenzoates, pivalates, propionates, phthalates, phenylacetate, pectinates, phenylpropionates, palmitates, pantothenates, polygalacturates, pyruvates, quinates, salicylates, succinates, stearates, sulfanilate, subacetates, tartrates, theophyllineacetates, p-toluenesulfonates (tosylates), trifluoroacetates, terephthalates, tannates, teoclates, trihaloacetates, triethiodide, tricarboxylates, undecanoates and valerates.

In various embodiments, examples of inorganic salts of carboxylic acids or hydroxyls may be selected from ammonium, alkali metals to include lithium, sodium, potassium, cesium; alkaline earth metals to include calcium, magnesium, aluminium; zinc, barium, cholines, quaternary ammoniums.

In some embodiments, examples of organic salts of carboxylic acids or hydroxyl may be selected from arginine, organic amines to include aliphatic organic amines, alicyclic organic amines, aromatic organic amines, benzathines, t-butylamines, benethamines (N-benzylphenethylamine), dicyclohexylamines, dimethylamines, diethanolamines, ethanolamines, ethylenediamines, hydrabamines, imidazoles, lysines, methylamines, meglamines, N-methyl-D-glucamines, N,N'-dibenzylethylenediamines, nicotinamides, organic amines, ornithines, pyridines, picolies, piperazines, procain, tris(hydroxymethyl)methylamines, triethylamines, triethanolamines, trimethylamines, tromethamines and ureas.

In various embodiments, the salts may be formed by conventional means, such as by reacting the free base or free acid form of the product with one or more equivalents of the appropriate acid or base in a solvent or medium in which the salt is insoluble or in a solvent such as water, which is removed in vacuo or by freeze drying or by exchanging the ions of an existing salt for another ion or suitable ion-exchange resin.

Pharmaceutical Composition

Another aspect of the present invention relates to a pharmaceutical composition including a pharmaceutically acceptable carrier and a compound according to the aspects of the present invention. The pharmaceutical composition can contain one or more of the above-identified compounds of the present invention. Typically, the pharmaceutical composition of the present invention will include a compound of the present invention or its pharmaceutically acceptable salt, as well as a pharmaceutically acceptable carrier. The term "pharmaceutically acceptable carrier" refers to any suitable adjuvants, carriers, excipients, or stabilizers, and can be in solid or liquid form such as, tablets, capsules, powders, solutions, suspensions, or emulsions.

Typically, the composition will contain from about 0.01 to 99 percent, preferably from about 20 to 75 percent of active compound(s), together with the adjuvants, carriers and/or excipients. While individual needs may vary, determination of optimal ranges of effective amounts of each component is within the skill of the art. Typical dosages comprise about 0.01 to about 100 mg/kg body wt. The preferred dosages comprise about 0.1 to about 100 mg/kg body wt. The most preferred dosages comprise about 1 to about 100 mg/kg body wt. Treatment regimen for the administration of the compounds of the present invention can also be determined readily by those with ordinary skill in art. That is, the frequency of administration and size of the dose can be established by routine optimization, preferably while minimizing any side effects.

The solid unit dosage forms can be of the conventional type. The solid form can be a capsule and the like, such as an ordinary gelatin type containing the compounds of the present invention and a carrier, for example, lubricants and inert fillers such as, lactose, sucrose, or cornstarch. In some embodiments, these compounds are tabulated with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

The tablets, capsules, and the like can also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it can contain, in addition to materials of the above type, a liquid carrier such as a fatty oil.

Various other materials may be present as coatings or to modify the physical form of the dosage unit. For instance, tablets can be coated with shellac, sugar, or both. A syrup can contain, in addition to active ingredient, sucrose as a sweetening agent, methyl and propylparabens as preservatives, a dye, and flavoring such as cherry or orange flavor.

For oral therapeutic administration, these active compounds can be incorporated with excipients and used in the form of tablets, capsules, elixirs, suspensions, syrups, and the like. Such compositions and preparations should contain at least 0.1% of active compound. The percentage of the compound in these compositions can, of course, be varied and can conveniently be between about 2% to about 60% of the weight of the unit. The amount of active compound in such therapeutically useful compositions is such that a suitable dosage will be obtained. Preferred compositions according to the present invention are prepared so that an oral dosage unit contains between about 1 mg and 800 mg of active compound.

The active compounds of the present invention may be orally administered, for example, with an inert diluent, or with an assimilable edible carrier, or they can be enclosed in hard- or soft-shell capsules, or they can be compressed into tablets, or they can be incorporated directly with the food of the diet.

The pharmaceutical forms suitable for injectable use include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds or pharmaceutical compositions of the present invention may also be administered in injectable dosages by solution or suspension of these materials in a physiologically acceptable diluent with a pharmaceutical adjuvant, carrier or excipient. Such adjuvants, carriers and/or excipients include, but are not limited to, sterile liquids, such as water and oils, with or without the addition of a surfactant and other pharmaceutically and physiologically acceptable components. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

These active compounds may also be administered parenterally. Solutions or suspensions of these active compounds can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

In various embodiments, the compounds of this invention are administered in combination with an anti-cancer therapy. Examples of such therapies include but are not limited to: chemotherapy, immunotherapy, radiotherapy, biological therapy, surgical intervention, and combinations thereof. In various embodiments, the compound is administered in combination with an anti-cancer agent by administering the compounds as herein described, alone or in combination with other agents.

When administering the compounds of the present invention, they can be administered systemically or, alternatively, they can be administered directly to a specific site where cancer is present. Thus, administering can be accomplished in any manner effective for delivering the compounds or the pharmaceutical compositions to the cancerous cells. Exemplary modes of administration include, without limitation, administering the compounds or compositions orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

Biological Activity

In various embodiments, the invention provides compounds and compositions, including any embodiment described herein, for use in any of the methods of this invention. In various embodiments, use of a compound of this invention or a composition comprising the same, will have utility in inhibiting, suppressing, enhancing, or stimulating a desired response in a subject, as will be understood by one skilled in the art. In some embodiments, the compositions may further comprise additional active ingredients, whose activity is useful for the particular application for which the compound of this invention is being administered.

The invention relates to the treatment, inhibition, and reduction of cancer, employing the use of a compound according to this invention or a pharmaceutically acceptable salt thereof. Accordingly, in various embodiments, this invention is directed to a method of treating, suppressing, reducing the severity, reducing the risk of developing or inhibiting cancer in a subject, comprising administering a compound according to this invention, to a subject suffering from cancer under conditions effective to treat, suppress, reduce the severity, reduce the risk of developing, or inhibit cancer in said subject. In some embodiments, the compound is a c-Myc mRNA translation modulator. In some embodiments, the compound is a c-Myc mRNA translation inhibitor. In some embodiments, the compound is a c-Myc inhibitor. In some embodiments, the compound is a c-Myc mRNA transcription regulator. In some embodiments, the compound is any combination of a c-Myc mRNA transcription regulator, a c-Myc mRNA transcription regulator and a c-Myc inhibitor. In some embodiments, the compound is any one of the compounds listed in Table 1; each compound represents a separate embodiment according to this invention. In some embodiments, the cancer is early cancer. In some embodiments, the cancer is advanced cancer. In some embodiments, the cancer is invasive cancer. In some embodiments, the cancer is metastatic cancer. In some embodiments, the cancer is drug resistant cancer.

In some embodiments, the cancer is selected from the following list: bladder cancer (urothelial carcinoma), myelodysplasia, breast cancer, cervix cancer, endometrium cancer, esophagus cancer, head and neck cancer (squamous cell carcinoma), kidney cancer (e.g., renal cell carcinoma, clear cell renal cell carcinoma), liver cancer (hepatocellular carcinoma), lung cancer (e.g., metastatic, non-small cell, NSCLC, squamous cell carcinoma, small cell (SCLC)), metastatic cancer (e.g., to brain), nasopharynx cancer, solid tumor cancer, stomach cancer, adrenocortical carcinoma, Glioblastoma multiforme, acute myeloid leukemia, chronic lymphocytic leukemia, lymphoma (e.g., Hodgkin's (classical), diffuse large B-cell, primary central nervous system), malignant melanoma, uveal melanoma, meningioma, multiple myeloma, breast cancer, metastatic breast cancer, anus cancer (e.g. squamous cell), biliary cancer, bladder cancer, muscle invasive urothelial carcinoma, colorectal cancer, metastatic colorectal cancer, fallopian tube cancer, gastroesophageal junction cancer (e.g., adenocarcinoma), larynx cancer (e.g., squamous cell), merkel cell cancer, mouth cancer, ovary cancer (e.g., epithelial), pancreas cancer (e.g., adenocarcinoma, metastatic), penis cancer (e.g., squamous cell carcinoma), peritoneum cancer, prostate cancer (e.g., castration-resistant, metastatic), rectum cancer, skin cancer (e.g., basal cell carcinoma, squamous cell carcinoma), small intestine cancer (e.g., adenocarcinoma), testic cancer, thymus cancer, anaplastic thyroid cancer, cholangiocarcinoma, chordoma, cutaneous T-cell lymphoma, digestive-gastrointestinal cancer, familial pheochromocytoma-paraganglioma, Glioma, HTLV-1-associated adult T-cell leukemia-lymphoma, hematologic-blood cancer, hepatitis C (HCV), papillomaviral respiratory Infection, uterine leiomyosarcoma, acute lymphocytic leukemia, chronic myeloid leukemia, T-cell Lymphoma, follicular lymphoma, primary mediastinal large B-cell lymphoma, diffuse large B-cell testicular lymphoma, melanoma, malignant mesothelioma, pleural mesothelioma, mycosis fungoides, neuroendocrine cancer, oral epithelial dysplasia, Sarcoma, severe sepsis, sezary syndrome, smoldering myeloma, soft tissue sarcoma, nasal natural killer (NK) cell T-cell lymphoma, peripheral T-cell lymphoma.

In some embodiments, the cancer is selected from a list including but not limited to: breast cancer, ovarian carcinoma, acute myeloid leukemia, chronic myelogenous leukemia, Hodgkin's and Burkitt's lymphoma, diffuse large Bcell lymphoma, prostate cancer, colon cancer, gastric cancer, primary central nervous system lymphoma, glioblastoma, medulloblastoma, melanoma, non-small cell lung carcinoma, germinal center-derived lymphomas, esophageal squamous cell carcinoma, osteosarcoma, bladder cancer, pancreatic cancer, lung adenocarcinoma, BRAF V600E thyroid cancer, choroid plexus carcinoma, colitis-associated cancer, epithelial ovarian cancer, colorectal cancer, pancreatic cancer and uterine cancer.

In some embodiments, the cancer may be selected from solid tumors and non-solid tumors.

In various embodiments, this invention is directed to a method for suppressing, reducing or inhibiting tumor growth in a subject, comprising administering a compound of this invention, to a subject under conditions effective to suppress, reduce or inhibit tumor growth in said subject.

In some embodiments, the tumor may be a solid tumor or a non-solid tumor.

In some embodiments, the solid tumor cancer is selected from a list including but not limited to: breast cancer, ovarian carcinoma, prostate cancer, colon cancer, gastric cancer, glioblastoma, medulloblastoma, melanoma, non-small cell lung carcinoma, esophageal squamous cell carcinoma, osteosarcoma, bladder cancer, pancreatic cancer, lung adenocarcinoma, BRAF V600E thyroid cancer, choroid plexus carcinoma, colitis-associated cancer, epithelial ovarian cancer, colorectal cancer, pancreatic cancer and uterine cancer.

In some embodiments, the non-solid tumors include but not limited to: hematological malignancies including leukemia, lymphoma or myeloma and inherited cancers such as retinoblastoma and Wilm's tumor.

In some embodiments, the non-solid tumor cancer is selected from a list including but not limited to: acute myeloid leukemia, chronic myelogenous leukemia, Hodgkin's and Burkitt's lymphoma, diffuse large Bcell lymphoma, primary central nervous system lymphoma, glioblastoma, medulloblastoma, germinal center-derived lymphomas, myeloma, retinoblastoma and Wilm's tumor.

Therefore, and in various embodiments, this invention is directed to a method of treating, suppressing, reducing the severity, reducing the risk of developing or inhibiting cancer comprising administering a compound of this invention to a subject suffering from cancer under conditions effective to treat, suppress, reduce the severity, reduce the risk of developing, or inhibit the cancer. In some embodiments, the cancer is early cancer. In some embodiments, the cancer is advanced cancer. In some embodiments, the cancer is invasive cancer. In some embodiments, the cancer is metastatic cancer. In some embodiments, the cancer is drug resistant cancer. In some embodiments, the compound is a c-Myc mRNA translation modulator. In some embodiments, the compound is a c-Myc mRNA translation inhibitor. In some embodiments, the compound is a c-Myc mRNA transcription regulator. In some embodiments, the compound is selective to c-Myc. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting breast cancer comprising administering a compound of this invention to a subject suffering from breast cancer under conditions effective to treat, suppress, reduce the severity, reduce the risk of developing, or inhibit the breast cancer. In some embodiments, the breast cancer is early breast cancer. In some embodiments, the breast cancer is advanced breast cancer. In some embodiments, the breast cancer is invasive breast cancer. In some embodiments, the breast cancer is metastatic breast cancer. In some embodiments, the breast cancer is drug resistant breast cancer. In some embodiments, the compound is a c-Myc mRNA translation modulator. In some embodiments, the compound is a c-Myc mRNA translation inhibitor. In some embodiments, the compound is a c-Myc mRNA transcription regulator. In some embodiments, the compound is selective to c-Myc. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting ovarian carcinoma comprising administering a compound of this invention to a subject suffering from ovarian carcinoma under conditions effective to treat, suppress, reduce the severity, reduce the risk of developing, or inhibit the ovarian carcinoma. In some embodiments, the ovarian carcinoma is early ovarian carcinoma. In some embodiments, the ovarian carcinoma is advanced ovarian carcinoma. In some embodiments, the ovarian carcinoma is invasive ovarian carcinoma. In some embodiments, the ovarian carcinoma is metastatic ovarian carcinoma. In some embodiments, the ovarian carcinoma is drug resistant ovarian carcinoma. In some embodiments, the compound is a c-Myc mRNA translation modulator. In some embodiments, the compound is a c-Myc mRNA translation inhibitor. In some embodiments, the compound is a c-Myc mRNA transcription regulator. In some embodiments, the compound is selective to c-Myc. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting acute myeloid leukemia comprising administering a compound of this invention to a subject suffering from acute myeloid leukemia under conditions effective to treat, suppress, reduce the severity, reduce the risk of developing, or inhibit the acute myeloid leukemia. In some embodiments, the acute myeloid leukemia is early acute myeloid leukemia. In some embodiments, the acute myeloid leukemia is advanced acute myeloid leukemia. In some embodiments, the acute myeloid leukemia is invasive acute myeloid leukemia. In some embodiments, the acute myeloid leukemia is metastatic acute myeloid leukemia. In some embodiments, the acute myeloid leukemia is drug resistant acute myeloid leukemia. In some embodiments, the compound is a c-Myc mRNA translation modulator. In some embodiments, the compound is a c-Myc mRNA translation inhibitor. In some embodiments, the compound is a c-Myc mRNA transcription regulator. In some embodiments, the compound is selective to c-Myc. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting chronic myelogenous leukemia comprising administering a compound of this invention to a subject suffering from chronic myelogenous leukemia under conditions effective to treat, suppress, reduce the severity, reduce the risk of developing, or inhibit the chronic myelogenous leukemia. In some embodiments, the chronic myelogenous leukemia is early chronic myelogenous leukemia. In some embodiments, the chronic myelogenous leukemia is advanced chronic myelogenous leukemia. In some embodiments, the chronic myelogenous leukemia is invasive chronic myelogenous leukemia. In some embodiments, the chronic myelogenous leukemia is metastatic chronic myelogenous leukemia. In some embodiments, the chronic myelogenous leukemia is drug resistant chronic myelogenous leukemia. In some embodiments, the compound is a c-Myc mRNA translation modulator. In some embodiments, the compound is a c-Myc mRNA translation inhibitor. In some embodiments, the compound is a c-Myc mRNA transcription regulator. In some embodiments, the compound is selective to c-Myc. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting Hodgkin's and/or Burkitt's lymphoma comprising administering a compound of this invention to a subject suffering from Hodgkin's and/or Burkitt's lymphoma under conditions effective to treat, suppress, reduce the severity, reduce the risk of developing, or inhibit the Hodgkin's and/or Burkitt's lymphoma. In some embodiments, the Hodgkin's and/or Burkitt's lymphoma is early Hodgkin's and/or Burkitt's lymphoma. In some embodiments, the Hodgkin's and/or Burkitt's lymphoma is advanced Hodgkin's and/or Burkitt's lymphoma. In some embodiments, the Hodgkin's and/or Burkitt's lymphoma is invasive Hodgkin's and/or Burkitt's lymphoma. In some embodiments, the cancer is metastatic Hodgkin's and/or Burkitt's lymphoma. In some embodiments, the Hodgkin's and/or Burkitt's lymphoma is drug resistant Hodgkin's and/or Burkitt's lymphoma. In some embodiments, the compound is a c-Myc mRNA translation modulator. In some embodiments, the compound is a c-Myc mRNA translation inhibitor. In some embodiments, the compound is a c-Myc mRNA transcription regulator. In some embodiments, the compound is selective to c-Myc. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting diffuse large Bcell lymphoma comprising administering a compound of this invention to a subject suffering from diffuse large Bcell lymphoma under conditions effective to treat, suppress, reduce the severity, reduce the risk of developing, or inhibit the diffuse large Bcell lymphoma. In some embodiments, the diffuse large Bcell lymphoma is early diffuse large Bcell lymphoma. In some embodiments, the diffuse large Bcell lymphoma is advanced diffuse large Bcell lymphoma. In some embodiments, the diffuse large Bcell lymphoma is invasive diffuse large Bcell lymphoma. In some embodiments, the diffuse large Bcell lymphoma is metastatic diffuse large Bcell lymphoma. In some embodiments, the diffuse large Bcell lymphoma is drug resistant diffuse large Bcell lymphoma. In some embodiments, the compound is a c-Myc mRNA translation modulator. In some embodiments, the compound is a c-Myc mRNA translation inhibitor. In some embodiments, the compound is a c-Myc mRNA transcription regulator. In some embodiments, the compound is selective to c-Myc. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting prostate cancer comprising administering a compound of this invention to a subject suffering from prostate cancer under conditions effective to treat, suppress, reduce the severity, reduce the risk of developing, or inhibit the prostate cancer. In some embodiments, the prostate cancer is early prostate cancer. In some embodiments, the prostate cancer is advanced prostate cancer. In some embodiments, the prostate cancer is invasive prostate cancer. In some embodiments, the prostate cancer is metastatic prostate cancer. In some embodiments, the prostate cancer is drug resistant prostate cancer. In some embodiments, the compound is a c-Myc mRNA translation modulator. In some embodiments, the compound is a c-Myc mRNA translation inhibitor. In some embodiments, the compound is a c-Myc mRNA transcription regulator. In some embodiments, the compound is selective to c-Myc. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting colon cancer comprising administering a compound of this invention to a subject suffering from colon cancer under conditions effective to treat, suppress, reduce the severity, reduce the risk of developing, or inhibit the colon cancer. In some embodiments, the colon cancer is early colon cancer. In some embodiments, the colon cancer is advanced colon cancer. In some embodiments, the colon cancer is invasive colon cancer. In some embodiments, the colon cancer is metastatic colon cancer. In some embodiments, the colon cancer is drug resistant colon cancer. In some embodiments, the compound is a c-Myc mRNA translation modulator. In some embodiments, the compound is a c-Myc mRNA translation inhibitor. In some embodiments, the compound is a c-Myc mRNA transcription regulator. In some embodiments, the compound is selective to c-Myc. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting gastric cancer comprising administering a compound of this invention to a subject suffering from gastric cancer under conditions effective to treat, suppress, reduce the severity, reduce the risk of developing, or inhibit the gastric cancer. In some embodiments, the gastric cancer is early gastric cancer. In some embodiments, the gastric cancer is advanced gastric cancer. In some embodiments, the gastric cancer is invasive gastric cancer. In some embodiments, the gastric cancer is metastatic gastric cancer. In some embodiments, the gastric cancer is drug resistant gastric cancer. In some embodiments, the compound is a c-Myc mRNA translation modulator. In some embodiments, the compound is a c-Myc mRNA translation inhibitor. In some embodiments, the compound is a c-Myc mRNA transcription regulator. In some embodiments, the compound is selective to c-Myc. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting lymphoma comprising administering a compound of this invention to a subject suffering from lymphoma under conditions effective to treat, suppress, reduce the severity, reduce the risk of developing, or inhibit the lymphoma. In some embodiments, the lymphoma is early lymphoma. In some embodiments, the lymphoma is advanced lymphoma. In some embodiments, the lymphoma is invasive lymphoma. In some embodiments, the lymphoma is metastatic lymphoma. In some embodiments, the lymphoma is drug resistant lymphoma. In some embodiments, the lymphoma is primary central nervous system lymphoma. In some embodiments, the lymphoma is germinal center-derived lymphoma. In some embodiments, the lymphoma is Hodgkin's lymphoma. In some embodiments, the lymphoma is Burkitt's lymphoma. In some embodiments, the lymphoma is diffuse large B-cell lymphoma. In some embodiments, the compound is a c-Myc mRNA translation modulator. In some embodiments, the compound is a c-Myc mRNA translation inhibitor. In some embodiments, the compound is a c-Myc mRNA transcription regulator. In some embodiments, the compound is selective to c-Myc. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting glioblastoma comprising administering a compound of this invention to a subject suffering from glioblastoma under conditions effective to treat, suppress, reduce the severity, reduce the risk of developing, or inhibit the glioblastoma. In some embodiments, the glioblastoma is early glioblastoma. In some embodiments, the glioblastoma is advanced glioblastoma. In some embodiments, the glioblastoma is invasive glioblastoma. In some embodiments, the glioblastoma is metastatic glioblastoma. In some embodiments, the glioblastoma is drug resistant glioblastoma. In some embodiments, the compound is a c-Myc mRNA translation modulator. In some embodiments, the compound is a c-Myc mRNA translation inhibitor. In some embodiments, the compound is a c-Myc mRNA transcription regulator. In some embodiments, the compound is selective to c-Myc. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting medulloblastoma comprising administering a compound of this invention to a subject suffering from medulloblastoma under conditions effective to treat, suppress, reduce the severity, reduce the risk of developing, or inhibit the medulloblastoma. In some embodiments, the medulloblastoma is early medulloblastoma. In some embodiments, the medulloblastoma is advanced medulloblastoma. In some embodiments, the medulloblastoma is invasive medulloblastoma. In some embodiments, the medulloblastoma is metastatic medulloblastoma. In some embodiments, the medulloblastoma is drug resistant medulloblastoma. In some embodiments, the compound is a c-Myc mRNA translation modulator. In some embodiments, the compound is a c-Myc mRNA translation inhibitor. In some embodiments, the compound is a c-Myc mRNA transcription regulator. In some embodiments, the compound is selective to c-Myc. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting melanoma comprising administering a compound of this invention to a subject suffering from melanoma under conditions effective to treat, suppress, reduce the severity, reduce the risk of developing, or inhibit the melanoma. In some embodiments, the melanoma is early melanoma. In some embodiments, the melanoma is advanced melanoma. In some embodiments, the melanoma is invasive melanoma. In some embodiments, the melanoma is metastatic melanoma. In some embodiments, the melanoma is drug resistant melanoma. In some embodiments, the compound is a c-Myc mRNA translation modulator. In some embodiments, the compound is a c-Myc mRNA translation inhibitor. In some embodiments, the compound is a c-Myc mRNA transcription regulator. In some embodiments, the compound is selective to c-Myc. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting non-small cell lung carcinoma comprising administering a compound of this invention to a subject suffering from non-small cell lung carcinoma under conditions effective to treat, suppress, reduce the severity, reduce the risk of developing, or inhibit the non-small cell lung carcinoma. In some embodiments, the non-small cell lung carcinoma is early non-small cell lung carcinoma. In some embodiments, the non-small cell lung carcinoma is advanced non-small cell lung carcinoma. In some embodiments, the non-small cell lung carcinoma is invasive non-small cell lung carcinoma. In some embodiments, the non-small cell lung carcinoma is metastatic non-small cell lung carcinoma. In some embodiments, the non-small cell lung carcinoma is drug resistant non-small cell lung carcinoma. In some embodiments, the compound is a c-Myc mRNA translation modulator. In some embodiments, the compound is a c-Myc mRNA translation inhibitor. In some embodiments, the compound is a c-Myc mRNA transcription regulator. In some embodiments, the compound is selective to c-Myc. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting esophageal squamous cell carcinoma comprising administering a compound of this invention to a subject suffering from esophageal squamous cell carcinoma under conditions effective to treat, suppress, reduce the severity, reduce the risk of developing, or inhibit the esophageal squamous cell carcinoma. In some embodiments, the esophageal squamous cell carcinoma is early esophageal squamous cell carcinoma. In some embodiments, the esophageal squamous cell carcinoma is advanced esophageal squamous cell carcinoma. In some embodiments, the esophageal squamous cell carcinoma is invasive esophageal squamous cell carcinoma. In some embodiments, the esophageal squamous cell carcinoma is metastatic esophageal squamous cell carcinoma. In some embodiments, the esophageal squamous cell carcinoma is drug resistant esophageal squamous cell carcinoma. In some embodiments, the compound is a c-Myc mRNA translation modulator. In some embodiments, the compound is a c-Myc mRNA translation inhibitor. In some embodiments, the compound is a c-Myc mRNA transcription regulator. In some embodiments, the compound is selective to c-Myc. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting osteosarcoma comprising administering a compound of this invention to a subject suffering from osteosarcoma under conditions effective to treat, suppress, reduce the severity, reduce the risk of developing, or inhibit the osteosarcoma. In some embodiments, the osteosarcoma is early osteosarcoma. In some embodiments, the osteosarcoma is advanced osteosarcoma. In some embodiments, the osteosarcoma is invasive osteosarcoma. In some embodiments, the osteosarcoma is metastatic osteosarcoma. In some embodiments, the osteosarcoma is drug resistant osteosarcoma. In some embodiments, the compound is a c-Myc mRNA translation modulator. In some embodiments, the compound is a c-Myc mRNA translation inhibitor. In some embodiments, the compound is a c-Myc mRNA transcription regulator. In some embodiments, the compound is selective to c-Myc. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting bladder cancer comprising administering a compound of this invention to a subject suffering from bladder cancer under conditions effective to treat, suppress, reduce the severity, reduce the risk of developing, or inhibit the bladder cancer. In some embodiments, the bladder cancer is early bladder cancer. In some embodiments, the bladder cancer is advanced bladder cancer. In some embodiments, the bladder cancer is invasive bladder cancer. In some embodiments, the bladder cancer is metastatic bladder cancer. In some embodiments, the bladder cancer is drug resistant bladder cancer. In some embodiments, the compound is a c-Myc mRNA translation modulator. In some embodiments, the compound is a c-Myc mRNA translation inhibitor. In some embodiments, the compound is a c-Myc mRNA transcription regulator. In some embodiments, the compound is selective to c-Myc. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting pancreatic cancer comprising administering a compound of this invention to a subject suffering from pancreatic cancer under conditions effective to treat, suppress, reduce the severity, reduce the risk of developing, or inhibit the pancreatic cancer. In some embodiments, the pancreatic cancer is early pancreatic cancer. In some embodiments, the pancreatic cancer is advanced pancreatic cancer. In some embodiments, the pancreatic cancer is invasive pancreatic cancer. In some embodiments, the pancreatic cancer is metastatic pancreatic cancer. In some embodiments, the pancreatic cancer is drug resistant pancreatic cancer. In some embodiments, the compound is a c-Myc mRNA translation modulator. In some embodiments, the compound is a c-Myc mRNA translation inhibitor. In some embodiments, the compound is a c-Myc mRNA transcription regulator. In some embodiments, the compound is selective to c-Myc. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting lung adenocarcinoma comprising administering a compound of this invention to a subject suffering from lung adenocarcinoma under conditions effective to treat, suppress, reduce the severity, reduce the risk of developing, or inhibit the lung adenocarcinoma. In some embodiments, the lung adenocarcinoma is early lung adenocarcinoma. In some embodiments, the lung adenocarcinoma is advanced lung adenocarcinoma. In some embodiments, the lung adenocarcinoma is invasive lung adenocarcinoma. In some embodiments, the lung adenocarcinoma is metastatic lung adenocarcinoma. In some embodiments, the lung adenocarcinoma is drug resistant lung adenocarcinoma. In some embodiments, the compound is a c-Myc mRNA translation modulator. In some embodiments, the compound is a c-Myc mRNA translation inhibitor. In some embodiments, the compound is a c-Myc mRNA transcription regulator. In some embodiments, the compound is selective to c-Myc. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting thyroid cancer comprising administering a compound of this invention to a subject suffering from thyroid cancer under conditions effective to treat, suppress, reduce the severity, reduce the risk of developing, or inhibit the thyroid cancer. In some embodiments, the thyroid cancer is early thyroid cancer. In some embodiments, the thyroid cancer is advanced thyroid cancer. In some embodiments, the thyroid cancer is invasive thyroid cancer. In some embodiments, the thyroid cancer is metastatic thyroid cancer. In some embodiments, the thyroid cancer is drug resistant thyroid cancer. In some embodiments, the thyroid cancer is BRAF V600E thyroid cancer. In some embodiments, the compound is a c-Myc mRNA translation modulator. In some embodiments, the compound is a c-Myc mRNA translation inhibitor. In some embodiments, the compound is a c-Myc mRNA transcription regulator. In some embodiments, the compound is selective to c-Myc. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting choroid plexus carcinoma comprising administering a compound of this invention to a subject suffering from choroid plexus carcinoma under conditions effective to treat, suppress, reduce the severity, reduce the risk of developing, or inhibit the choroid plexus carcinoma. In some embodiments, the choroid plexus carcinoma is early choroid plexus carcinoma. In some embodiments, the choroid plexus carcinoma is advanced choroid plexus carcinoma. In some embodiments, the choroid plexus carcinoma is invasive choroid plexus carcinoma. In some embodiments, the choroid plexus carcinoma is metastatic choroid plexus carcinoma. In some embodiments, the choroid plexus carcinoma is drug resistant choroid plexus carcinoma. In some embodiments, the compound is a c-Myc mRNA translation modulator. In some embodiments, the compound is a c-Myc mRNA translation inhibitor. In some embodiments, the compound is a c-Myc mRNA transcription regulator. In some embodiments, the compound is selective to c-Myc. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting colitis-associated cancer comprising administering a compound of this invention to a subject suffering from colitis-associated cancer under conditions effective to treat, suppress, reduce the severity, reduce the risk of developing, or inhibit the colitis-associated cancer. In some embodiments, the colitis-associated cancer is early colitis-associated cancer. In some embodiments, the colitis-associated cancer is advanced colitis-associated cancer. In some embodiments, the colitis-associated cancer is invasive colitis-associated cancer. In some embodiments, the colitis-associated cancer is metastatic colitis-associated cancer. In some embodiments, the cancer is drug resistant colitis-associated cancer. In some embodiments, the compound is a c-Myc mRNA translation modulator. In some embodiments, the compound is a c-Myc mRNA translation inhibitor. In some embodiments, the compound is a c-Myc mRNA transcription regulator. In some embodiments, the compound is selective to c-Myc. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting ovarian cancer comprising administering a compound of this invention to a subject suffering from ovarian cancer under conditions effective to treat, suppress, reduce the severity, reduce the risk of developing, or inhibit the ovarian cancer. In some embodiments, the ovarian cancer is early ovarian cancer. In some embodiments, the ovarian cancer is advanced ovarian cancer. In some embodiments, the ovarian cancer is invasive ovarian cancer. In some embodiments, the ovarian cancer is metastatic ovarian cancer. In some embodiments, the ovarian cancer is drug resistant ovarian cancer. In some embodiments, the ovarian cancer is epithelial ovarian cancer. In some embodiments, the compound is a c-Myc mRNA translation modulator. In some embodiments, the compound is a c-Myc mRNA translation inhibitor. In some embodiments, the compound is a c-Myc mRNA transcription regulator. In some embodiments, the compound is selective to c-Myc. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting colorectal cancer comprising administering a compound of this invention to a subject suffering from colorectal cancer under conditions effective to treat, suppress, reduce the severity, reduce the risk of developing, or inhibit the colorectal cancer. In some embodiments, the colorectal cancer is early colorectal cancer. In some embodiments, the colorectal cancer is advanced colorectal cancer. In some embodiments, the colorectal cancer is invasive colorectal cancer. In some embodiments, the colorectal cancer is metastatic colorectal cancer. In some embodiments, the colorectal cancer is drug resistant colorectal cancer. In some embodiments, the compound is a c-Myc mRNA translation modulator. In some embodiments, the compound is a c-Myc mRNA translation inhibitor. In some embodiments, the compound is a c-Myc mRNA transcription regulator. In some embodiments, the compound is selective to c-Myc. In some embodiments, the compound reduces the amount of c-Myc protein in a cell. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting uterine cancer comprising administering a compound of this invention to a subject suffering from uterine cancer under conditions effective to treat, suppress, reduce the severity, reduce the risk of developing, or inhibit the uterine cancer. In some embodiments, the uterine cancer is early uterine cancer. In some embodiments, the uterine cancer is advanced uterine cancer. In some embodiments, the uterine cancer is invasive uterine cancer. In some embodiments, the uterine cancer is metastatic uterine cancer. In some embodiments, the uterine cancer is drug resistant uterine cancer. In some embodiments, the compound is a c-Myc mRNA translation modulator. In some embodiments, the compound is a c-Myc mRNA translation inhibitor. In some embodiments, the compound is a c-Myc mRNA transcription regulator. In some embodiments, the compound is selective to c-Myc. In some embodiments, the compound reduces the amount of c-Myc protein in a cell. In some embodiments, the compound is any one of the compounds listed in Table 1; each compound represents a separate embodiment according to this invention.

In various embodiments, this invention provides methods for increasing the survival of a subject suffering from metastatic cancer comprising the step of administering to said subject a compound of this invention and/or an isomer, metabolite, pharmaceutically acceptable salt, pharmaceutical product, tautomer, hydrate, N-oxide, reverse amide analog, prodrug, isotopic variant (e.g., deuterated analog), PROTAC, polymorph, or crystal of said compound, or any combination thereof. In some embodiments, the compound is a c-Myc mRNA translation modulator. In some embodiments, the compound is a c-Myc mRNA translation inhibitor. In some embodiments, the compound is a c-Myc mRNA transcription regulator. In some embodiments, the compound is selective to c-Myc. In some embodiments, the compound reduces the amount of c-Myc protein in a cell. In some embodiments, the cancer is breast cancer, ovarian carcinoma, acute myeloid leukemia, chronic myelogenous leukemia, Hodgkin's and Burkitt's lymphoma, diffuse large Bcell lymphoma, prostate cancer, colon cancer, gastric cancer, primary central nervous system lymphoma, glioblastoma, medulloblastoma, melanoma, non-small cell lung carcinoma, germinal center-derived lymphomas, esophageal squamous cell carcinoma, osteosarcoma, bladder cancer, pancreatic cancer, lung adenocarcinoma, thyroid cancer, choroid plexus carcinoma, colitis-associated cancer, colorectal cancer, or uterine cancer; each represents a separate embodiment according to this invention.

In various embodiments, this invention provides methods for treating, suppressing, reducing the severity, reducing the risk, or inhibiting advanced cancer comprising the step of administering to said subject a compound of this invention and/or an isomer, metabolite, pharmaceutically acceptable salt, pharmaceutical product, tautomer, hydrate, N-oxide, reverse amide analog, prodrug, isotopic variant (e.g., deuterated analog), PROTAC, polymorph, or crystal of said compound, or any combination thereof. In some embodiments, the compound is a c-Myc mRNA translation modulator. In some embodiments, the compound is a c-Myc mRNA translation inhibitor. In some embodiments, the compound is a c-Myc mRNA transcription regulator. In some embodiments, the compound is selective to c-Myc. In some embodiments, the compound reduces the amount of c-Myc protein in a cell. In some embodiments, the cancer is breast cancer, ovarian carcinoma, acute myeloid leukemia, chronic myelogenous leukemia, Hodgkin's and Burkitt's lymphoma, diffuse large Bcell lymphoma, prostate cancer, colon cancer, gastric cancer, primary central nervous system lymphoma, glioblastoma, medulloblastoma, melanoma, non-small cell lung carcinoma, germinal center-derived lymphomas, esophageal squamous cell carcinoma, osteosarcoma, bladder cancer, pancreatic cancer, lung adenocarcinoma, thyroid cancer, choroid plexus carcinoma, colitis-associated cancer, colorectal cancer, or uterine cancer; each represents a separate embodiment according to this invention.

The compounds of the present invention are useful in the treatment, reducing the severity, reducing the risk, or inhibition of cancer, metastatic cancer, advanced cancer, drug resistant cancer, and various forms of cancer. In a preferred embodiment the cancer is breast cancer, ovarian carcinoma, acute myeloid leukemia, chronic myelogenous leukemia, Hodgkin's and Burkitt's lymphoma, diffuse large Bcell lymphoma, prostate cancer, colon cancer, gastric cancer, primary central nervous system lymphoma, glioblastoma, medulloblastoma, melanoma, non-small cell lung carcinoma, germinal center-derived lymphomas, esophageal squamous cell carcinoma, osteosarcoma, bladder cancer, pancreatic cancer, lung adenocarcinoma, thyroid cancer, choroid plexus carcinoma, colitis-associated cancer, colorectal cancer, or uterine cancer; each represents a separate embodiment according to this invention. Based upon their believed mode of action, it is believed that other forms of cancer will likewise be treatable or preventable upon administration of the compounds or compositions of the present invention to a patient. Preferred compounds of the present invention are selectively disruptive to cancer cells, causing ablation of cancer cells but preferably not normal cells. Significantly, harm to normal cells is minimized because the cancer cells are susceptible to disruption at much lower concentrations of the compounds of the present invention.

In various embodiments, other types of cancers that may be treatable with the c-Myc mRNA translation modulators according to this invention include: adrenocortical carcinoma, anal cancer, bladder cancer, brain tumor, brain stem tumor, breast cancer, glioma, cerebellar astrocytoma, cerebral astrocytoma, ependymoma, medulloblastoma, supratentorial primitive neuroectodermal, pineal tumors, hypothalamic glioma, carcinoid tumor, carcinoma, cervical cancer, colon cancer, central nervous system (CNS) cancer, endometrial cancer, esophageal cancer, extrahepatic bile duct cancer, Ewing's family of tumors (Pnet), extracranial germ cell tumor, eye cancer, intraocular melanoma, gallbladder cancer, gastric cancer, germ cell tumor, extragonadal, gestational trophoblastic tumor, head and neck cancer, hypopharyngeal cancer, islet cell carcinoma, laryngeal cancer, leukemia, acute lymphoblastic, leukemia, oral cavity cancer, liver cancer, lung cancer, non-small cell lung cancer, small cell, lymphoma, AIDS-related lymphoma, central nervous system (primary), lymphoma, cutaneous T-cell, lymphoma, Hodgkin's disease, non-Hodgkin's disease, malignant mesothelioma, melanoma, Merkel cell carcinoma, metastatic squamous carcinoma, multiple myeloma, plasma cell neoplasms, Mycosis fungoides, myelodysplastic syndrome, myeloproliferative disorders, nasopharyngeal cancer, neuroblastoma, oropharyngeal cancer, osteosarcoma, ovarian cancer, ovarian epithelial cancer, ovarian germ cell tumor, ovarian low malignant potential tumor, pancreatic cancer, exocrine, pancreatic cancer, islet cell carcinoma, paranasal sinus and nasal cavity cancer, parathyroid cancer, penile cancer, pheochromocytoma cancer, pituitary cancer, plasma cell neoplasm, prostate cancer, rhabdomyosarcoma, rectal cancer, renal cancer, renal cell cancer, salivary gland cancer, Sezary syndrome, skin cancer, cutaneous T-cell lymphoma, skin cancer, Kaposi's sarcoma, skin cancer, melanoma, small intestine cancer, soft tissue sarcoma, soft tissue sarcoma, testicular cancer, thymoma, malignant, thyroid cancer, urethral cancer, uterine cancer, sarcoma, unusual cancer of childhood, vaginal cancer, vulvar cancer, Wilms' tumor, hepatocellular cancer, hematological cancer or any combination thereof. In some embodiments the cancer is invasive. In some embodiments the cancer is metastatic cancer. In some embodiments the cancer is advanced cancer. In some embodiments the cancer is drug resistant cancer.

In various embodiments "metastatic cancer" refers to a cancer that spread (metastasized) from its original site to another area of the body. Virtually all cancers have the potential to spread. Whether metastases develop depends on the complex interaction of many tumor cell factors, including the type of cancer, the degree of maturity (differentiation) of the tumor cells, the location and how long the cancer has been present, as well as other incompletely understood factors. Metastases spread in three ways—by local extension from the tumor to the surrounding tissues, through the bloodstream to distant sites or through the lymphatic system to neighboring or distant lymph nodes. Each kind of cancer may have a typical route of spread. The tumor is called by the primary site (ex. breast cancer that has spread to the brain is called metastatic breast cancer to the brain).

In various embodiments "drug-resistant cancer" refers to cancer cells that acquire resistance to chemotherapy. Cancer cells can acquire resistance to chemotherapy by a range of mechanisms, including the mutation or overexpression of the drug target, inactivation of the drug, or elimination of the drug from the cell. Tumors that recur after an initial response to chemotherapy may be resistant to multiple drugs (they are multidrug resistant). In the conventional view of drug resistance, one or several cells in the tumor population acquire genetic changes that confer drug resistance. Accordingly, the reasons for drug resistance, inter alia, are: a) some of the cells that are not killed by the chemotherapy mutate (change) and become resistant to the drug. Once they multiply, there may be more resistant cells than cells that are sensitive to the chemotherapy; b) Gene amplification. A cancer cell may produce hundreds of copies of a particular gene. This gene triggers an overproduction of protein that renders the anticancer drug ineffective; c) cancer cells may pump the drug out of the cell as fast as it is going in using a molecule called p-glycoprotein; d) cancer cells may stop taking in the drugs because the protein that transports the drug across the cell wall stops working; e) the cancer cells may learn how to repair the DNA breaks caused by some anti-cancer drugs; f) cancer cells may develop a mechanism that inactivates the drug. One major contributor to multidrug resistance is overexpression of P-glycoprotein (P-gp). This protein is a clinically important transporter protein belonging to the ATP-binding cassette family of cell membrane transporters. It can pump substrates including anticancer drugs out of tumor cells through an ATP-dependent mechanism; g) Cells and tumors with activating RAS mutations are relatively resistant to most anti-cancer agents. Thus, the resistance to anticancer agents used in chemotherapy is the main cause of treatment failure in malignant disorders, provoking tumors to become resistant. Drug resistance is the major cause of cancer chemotherapy failure.

In various embodiments "resistant cancer" refers to drug-resistant cancer as described herein above. In some embodiments "resistant cancer" refers to cancer cells that acquire resistance to any treatment such as chemotherapy, radiotherapy or biological therapy.

In various embodiments, this invention is directed to treating, suppressing, reducing the severity, reducing the risk, or inhibiting cancer in a subject, wherein the subject has been previously treated with chemotherapy, radiotherapy or biological therapy.

In various embodiments "Chemotherapy" refers to chemical treatment for cancer such as drugs that kill cancer cells directly. Such drugs are referred as "anti-cancer" drugs or "antineoplastics." Today's therapy uses more than 100 drugs to treat cancer. To cure a specific cancer. Chemotherapy is used to control tumor growth when cure is not possible; to shrink tumors before surgery or radiation therapy; to relieve symptoms (such as pain); and to destroy microscopic cancer cells that may be present after the known tumor is removed by surgery (called adjuvant therapy). Adjuvant therapy is given to prevent a possible cancer reoccurrence.

In various embodiments, "Radiotherapy" (also referred herein as "Radiation therapy") refers to high energy x-rays and similar rays (such as electrons) to treat disease. Many people with cancer will have radiotherapy as part of their treatment. This can be given either as external radiotherapy from outside the body using x-rays or from within the body as internal radiotherapy. Radiotherapy works by destroying the cancer cells in the treated area. Although normal cells can also be damaged by the radiotherapy, they can usually repair themselves. Radiotherapy treatment can cure some cancers and can also reduce the chance of a cancer coming back after surgery. It may be used to reduce cancer symptoms.

In various embodiments "Biological therapy" refers to substances that occur naturally in the body to destroy cancer cells. There are several types of treatment including: monoclonal antibodies, cancer growth inhibitors, vaccines and gene therapy. Biological therapy is also known as immunotherapy.

When the compounds or pharmaceutical compositions of the present invention are administered to treat, suppress, reduce the severity, reduce the risk, or inhibit a cancerous condition, the pharmaceutical composition can also contain, or can be administered in conjunction with, other therapeutic agents or treatment regimen presently known or hereafter developed for the treatment of various types of cancer. Examples of other therapeutic agents or treatment regimen include, without limitation, radiation therapy, immunotherapy, chemotherapy, surgical intervention, and combinations thereof.

In various embodiments, the compound according to this invention, is administered in combination with an anti-cancer therapy. Examples of such therapies include but are not limited to: chemotherapy, immunotherapy, radiotherapy, biological therapy, surgical intervention, and combinations thereof.

In various embodiments, the compound is administered in combination with an anti-cancer agent by administering the compounds as herein described, alone or in combination with other agents.

In various embodiments, the composition for cancer treatment of the present invention can be used together with existing chemotherapy drugs or be made as a mixture with them. Such a chemotherapy drug includes, for example, alkylating agents, nitrosourea agents, antimetabolites, antitumor antibiotics, alkaloids derived from plant, topoisomerase inhibitors, hormone therapy medicines, hormone antagonists, aromatase inhibitors, P-glycoprotein inhibitors, platinum complex derivatives, other immunotherapeutic drugs, and other anticancer agents. Further, they can be used together with hypoleukocytosis (neutrophil) medicines that are cancer treatment adjuvant, thrombopenia medicines, antiemetic drugs, and cancer pain medicines for patient's QOL recovery or be made as a mixture with them.

In various embodiments, this invention provides a method of modulating c-Myc mRNA translation in a cell, comprising contacting a compound represented by the structure of formula I, I(a), I(a(i)), I(a(ii)), I(a(iii)), I(b), I(b(i)), I(b(ii)), I(b(iii)), II and/or by the structures listed in Table 1, as defined herein above, with a cell, thereby modulating c-Myc mRNA translation in said cell. In some embodiments, the method is carried out by regulating c-Myc mRNA splicing. In some embodiments, the method is carried out by inclusion or exclusion of untranslated region or alternative usage of exons. In some embodiments, the method is carried out by regulation of c-Myc mRNA modifications. In some embodiments, the method is carried out by regulation of the interaction of RNA binding protein with c-Myc mRNA thereby changing mRNA localization. In some embodiments, the method is carried out by regulating c-Myc mRNA localization in the cytoplasm. In some embodiments, the method is carried out by regulating ribosomes or ribosome accessory factor to c-Myc mRNA. In some embodiments, the method is carried out by reducing the amount of c-Myc protein in the cell.

This invention further provides a method of regulating c-Myc mRNA transcription in a cell, comprising contacting a compound represented by the structure of formula I, I(a), I(a(i)), I(a(ii)), I(a(iii)), I(b), I(b(i)), I(b(ii)), I(b(iii)), II and/or by the structures listed in Table 1, as defined herein above, with a cell, thereby regulating c-Myc mRNA transcription in said cell. In some embodiments, the method is carried out by regulating c-Myc mRNA splicing. In some embodiments, the method is carried out by inclusion or exclusion of untranslated region or alternative usage of exons. In some embodiments, the method is carried out by regulation of c-Myc mRNA modifications. In some embodiments, the method is carried out by regulation of the interaction of RNA binding protein with c-Myc mRNA thereby changing mRNA localization. In some embodiments, the method is carried out by regulating c-Myc mRNA localization in the cytoplasm. In some embodiments, the method is carried out by regulating ribosomes or ribosome accessory factor to c-Myc mRNA. In some embodiments, the method is carried out by reducing the amount of c-Myc protein in the cell.

In various embodiments, this invention is directed to a method of destroying a cancerous cell comprising providing a compound of this invention and contacting the cancerous cell with the compound under conditions effective to destroy the contacted cancerous cell. According to various embodiments of destroying the cancerous cells, the cells to be destroyed can be located either in vivo or ex vivo (i.e., in culture).

A still further aspect of the present invention relates to a method of treating or preventing a cancerous condition that includes providing a compound of the present invention and then administering an effective amount of the compound to a patient in a manner effective to treat or prevent a cancerous condition.

According to one embodiment, the patient to be treated is characterized by the presence of a precancerous condition, and the administering of the compound is effective to prevent development of the precancerous condition into the cancerous condition. This can occur by destroying the precancerous cell prior to or concurrent with its further development into a cancerous state.

According to other embodiments, the patient to be treated is characterized by the presence of a cancerous condition, and the administering of the compound is effective either to cause regression of the cancerous condition or to inhibit growth of the cancerous condition, i.e., stopping its growth altogether or reducing its rate of growth. This preferably occurs by destroying cancer cells, regardless of their location in the patient body. That is, whether the cancer cells are located at a primary tumor site or whether the cancer cells have metastasized and created secondary tumors within the patient body.

As used herein, subject or patient refers to any mammalian patient, including without limitation, humans and other primates, dogs, cats, horses, cows, sheep, pigs, rats, mice, and other rodents. In various embodiments, the subject is male. In some embodiments, the subject is female. In some embodiments, while the methods as described herein may be useful for treating either males or females.

When administering the compounds of the present invention, they can be administered systemically or, alternatively, they can be administered directly to a specific site where cancer cells or precancerous cells are present. Thus, administering can be accomplished in any manner effective for delivering the compounds or the pharmaceutical compositions to the cancer cells or precancerous cells.

Exemplary modes of administration include, without limitation, administering the compounds or compositions orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

The following examples are presented in order to more fully illustrate the preferred embodiments of the invention. They should in no way, however, be construed as limiting the broad scope of the invention.

EXAMPLES

Example 1

Synthetic Details for Compounds of the Invention (Schemes 1-2)

General Methods

All reagents were commercial grade and were used as received without further purification, unless otherwise specified. Reagent grade solvents were used in all cases, unless otherwise specified. Thin layer chromatography was carried out using pre-coated silica gel F-254 plates (thickness 0.25 mm). $^1$H-NMR and $^{19}$F-NMR spectra were recorded on a Bruker Avance 400 MHz or Bruker Avance III 400 MHz spectrometer. The chemical shifts are expressed in ppm using the residual solvent as internal standard. Splitting patterns are designated as s (singlet), d (doublet), dd (doublet of doublets), t (triplet), dt (doublet of triplets), q (quartet), m (multiplet) and br s (broad singlet).

Abbreviations

AcOH Acetic acid
amphos Bis(di-tert-butyl(4-dimethylaminophenyl)phosphine
Boc tert-Butyloxycarbonyl
BuLi n-butyl lithium
t-BuLi tert-butyl lithium
BOP (Benzotriazol-1-yloxy)tris(dimethylamino)phosphonium hexafluorophosphate
CDI 1,1'-Carbonyldiimidazole
DBU 1,8-Diazabicyclo[5.4.0]undec-7-ene
dppb 1,4-Bis(diphenylphosphino)butane
dppf 1,1'-Bis(diphenylphosphino)ferrocene DCM Dichloromethane
DCE 1,2-Dichloroethane
DIBAL-H Diisobutylaluminum hydride
DIPEA N,N-Diisopropylethylamine
DMF N,N-Dimethylformamide
DMA Dimethylacetamide
DMAP 4-Dimethylaminopyridine
DME 1,2-Dimethoxyethane
DMSO Dimethyl sulfoxide
EDC·HCl N-(3-Dimethylaminopropyl)-N'-ethylcarbodiimide hydrochloride
HATU N-[(Dimethylamino)-1H-1,2,3-triazolo-[4,5-b]pyridin-1-ylmethylene]-N-methylmethanaminium hexafluorophosphate N-oxide
HBTU N,N,N',N'-Tetramethyl-O-(1H-benzotriazol-1-yl) uronium hexafluorophosphate
HPLC High performance liquid chromatography
KI Potassium iodide
$K_2CO_3$ Potassium carbonate
MsCl Methanesulfonyl chloride
$Na_2SO_4$ Sodium sulfate
NBS N-Bromosuccinimide
rt Room temperature
SEM 2-(Trimethylsilyl)ethoxymethyl
T3P Propylphosphonic anhydride
TBAF Tetrabutylammonium fluoride
TCFH N,N,N,N-tetramethylchloroformamidinium hexafluorophosphate
THF Tetrahydrofuran
TMS-OTf Trimethylsilyl trifluoromethanesulfonate General Synthesis of Compounds of the Invention

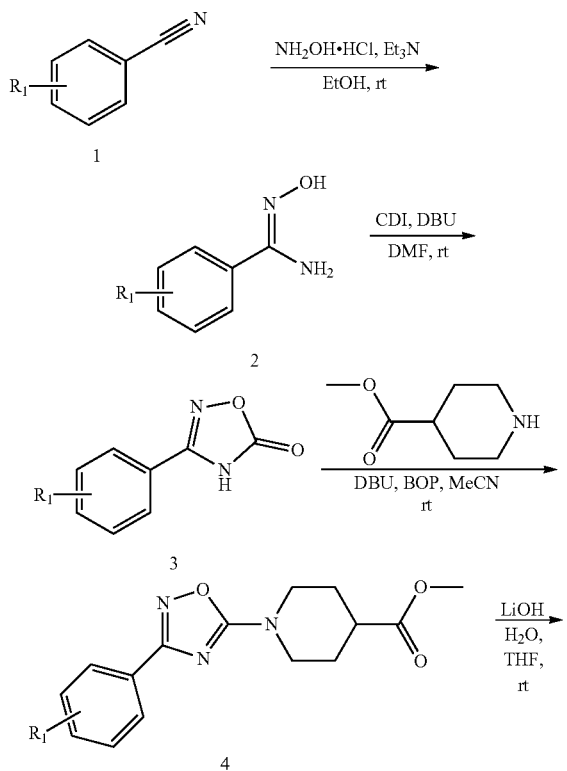

Scheme 1.

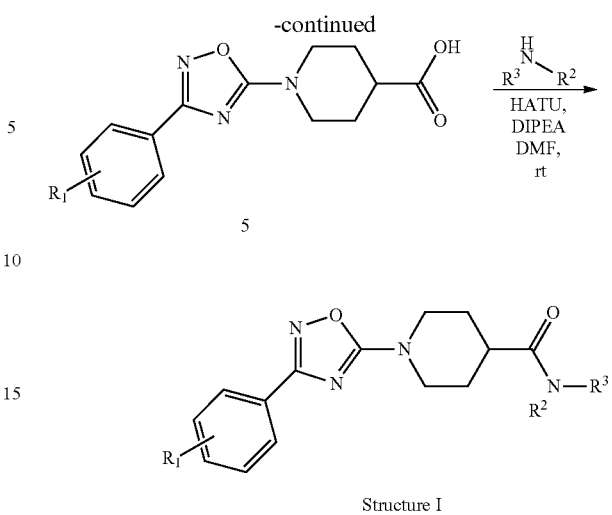

Synthesis of Modified 1,2,4-oxadiazol-5-yl-piperidine amides, Structure I

The first step of the synthesis involves base-mediated reaction of hydroxylamine hydrochloride with substituted benzonitrile 1 to afford substituted benzamidoxime intermediate 2. Intermediate 2 then undergoes cyclization with CDI in the presence of DBU in DMF to afford substituted 1,2,4-oxadiazol-5(2H)-one intermediate 3. In the third step, methyl 4-piperidinecarboxylate reacts with intermediate 3 via a direct amination reaction mediated by BOP and DBU in acetonitrile to provide intermediate 4. The ester moiety of intermediate 4 is hydrolyzed to the corresponding carboxylic acid 5, using lithium hydroxide in a mixture of water/THF at room temperature. The final step involves amide coupling reaction of carboxylic acid intermediate 5 using HATU as the coupling reagent, with a variety of primary and secondary amines, to provide substituted 1,2,4-oxadiazol-5-yl-piperidine amides, Structure I.

Scheme 2.

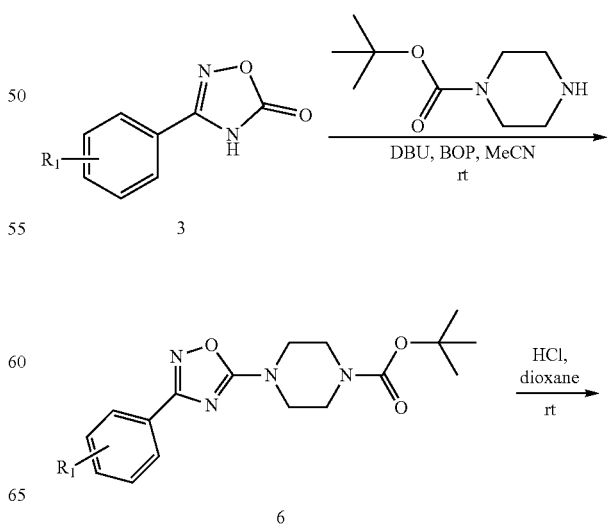

-continued

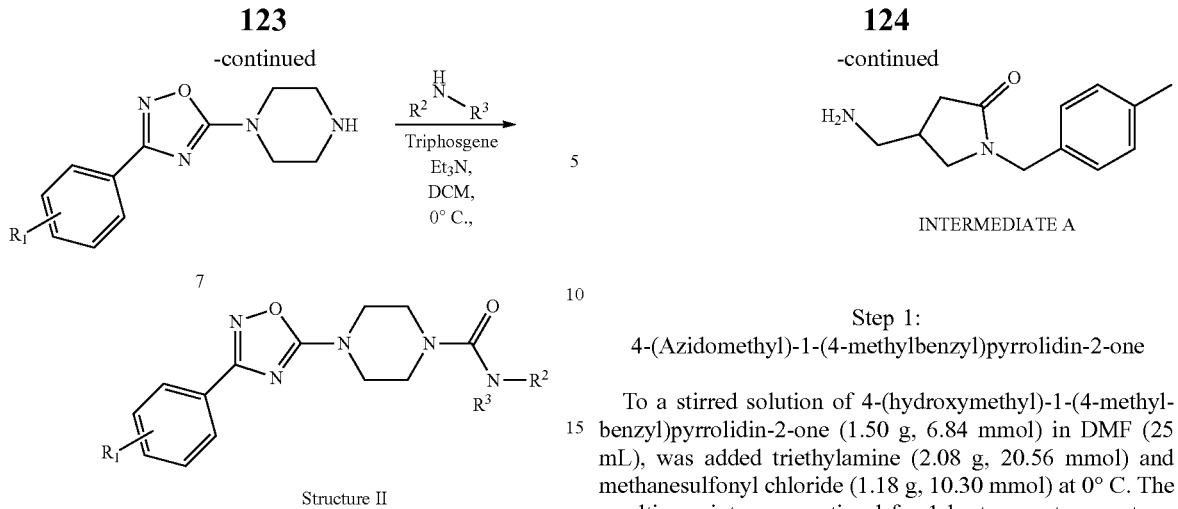

Structure II

Synthesis of Modified 1,2,4-oxadiazol-5-yl-piperazine ureas, Structure II

The first step involves a direct amination reaction between 1,2,4-oxadiazol-5(2H)-one intermediate 3 (previously described in Scheme 1) and N-Boc-piperazine, using BOP and DBU in acetonitrile to deliver intermediate 6. The N-Boc protecting group is removed under acidic conditions, using hydrogen chloride in dioxane to generate substituted 1,2,4-oxadiazol-5-yl-piperazine intermediate 7. The final urea formation step uses triphosgene to activate carboxylic acid intermediate 5. The activated piperazinecarbonyl chloride reacts with a number of primary and secondary amines, to provide the final substituted 1,2,4-oxadiazol-5-yl-piperazine ureas, Structure II.

Example 2

Synthetic Details for Intermediates and Compounds of the Invention (Schemes 3-25)

Intermediate Preparation 4-(Aminomethyl)-1-(4-methylbenzyl)pyrrolidin-2-one (Intermediate A)

INTERMEDIATE A

Step 1:
4-(Azidomethyl)-1-(4-methylbenzyl)pyrrolidin-2-one

To a stirred solution of 4-(hydroxymethyl)-1-(4-methylbenzyl)pyrrolidin-2-one (1.50 g, 6.84 mmol) in DMF (25 mL), was added triethylamine (2.08 g, 20.56 mmol) and methanesulfonyl chloride (1.18 g, 10.30 mmol) at 0° C. The resulting mixture was stirred for 1 h at room temperature. Sodium azide (0.89 g, 13.69 mmol), was then added to the stirred reaction mixture at room temperature. The resulting solution was stirred for an additional 3 h at room temperature. The reaction was quenched with water (100 mL) and extracted with ethyl acetate (3×20 mL). The combined organic layers were washed with water (3×20 mL) and dried over anhydrous $Na_2SO_4$. After filtration, the filtrate was concentrated under reduced pressure. The residue was purified by reverse phase flash chromatography with the following conditions: Column: Spherical C18, 20-40 um, 330 g; Mobile Phase A: water (plus 10 mM $NH_4HCO_3$); Mobile Phase B: acetonitrile; Flow rate: 80 mL/min; Gradient: 50% B-75% B in 20 min; Detector: UV 220/254 nm. The fractions containing the desired product were collected and concentrated under reduced pressure to afford 4-(azidomethyl)-1-(4-methylbenzyl)pyrrolidin-2-one as a light yellow oil.

Yield: 1.20 g (72%). $^1$HNMR (400 MHz, $CDCl_3$) δ 7.17-7.08 (m, 4H), 4.38 (s, 2H), 3.40-3.32 (m, 2H), 3.30-3.23 (m, 1H), 3.03-2.97 (m, 1H), 2.63-2.46 (m, 2H), 2.32 (s, 3H), 2.25-2.18 (m, 1H). m/z: [ESI$^+$] 245 (M+H)$^+$.

Step 2:
4-(Aminomethyl)-1-(4-methylbenzyl)pyrrolidin-2-one

To a stirred solution of 4-(azidomethyl)-1-(4-methylbenzyl)pyrrolidin-2-one (1.30 g, 5.32 mmol) in methanol (15 mL) and water (9 mL), was added tributyl phosphine (3.23 g, 15.96 mmol) dropwise at room temperature. The resulting mixture was stirred for 3 h at room temperature. The resulting mixture was filtered and the residue was washed with methanol (3×10 mL). The filtrate was then concentrated under reduced pressure. The resulting residue was purified by reverse phase flash chromatography with the following conditions: Column: Spherical C18, 20-40 um, 330 g; Mobile Phase A: water (plus 10 mM $NH_4HCO_3$); Mobile Phase B: acetonitrile; Flow rate: 80 mL/min; Gradient: 50% B-75% B in 20 min; Detector: UV 220/254 nm. The fractions containing the desired product were collected and concentrated under reduced pressure to afford 4-(aminomethyl)-1-(4-methylbenzyl)pyrrolidin-2-one as a light yellow oil.

Yield: 0.70 g (60%). $^1$H NMR (400 MHz, $CDCl_3$) δ 7.13 (s, 4H), 4.40 (s, 2H), 3.37 (dd, J=8.0, 10.0 Hz, 1H), 3.00 (dd, J=5.6, 10.0 Hz, 1H), 2.79-2.55 (m, 3H), 2.36-2.34 (m, 1H), 2.34 (s, 3H), 2.20 (dd, J=6.4, 16.8 Hz, 1H). $NH_2$ protons not observed. m/z: [ESI$^+$] 219 (M+H)$^+$.

Tert-butyl (3-(4-phenoxypiperidin-1-yl)propyl)carbamate (Intermediate B)

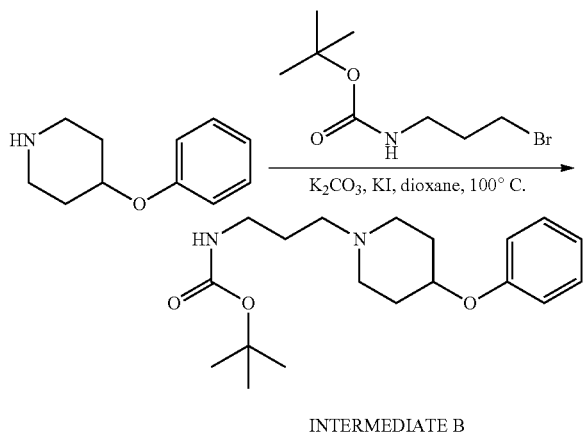

INTERMEDIATE B

To a stirred solution of 4-phenoxypiperidine (0.60 g, 3.39 mmol) and tert-butyl (3-bromopropyl)carbamate (3.22 g, 13.52 mmol), in 1,4-dioxane (15 mL), were added KI (0.28 g, 1.69 mmol) and $K_2CO_3$ (1.87 g, 13.53 mmol) portionwise at room temperature. The resulting mixture was stirred for overnight at 100° C. Upon completion, the resulting mixture was cooled to room temperature and filtered. The filtered residue was washed with acetonitrile (3×10 mL). The combined filtrate was then concentrated under reduced pressure. The residue was purified by reverse phase flash chromatography with the following conditions: Column: Spherical C18, 20-40 um, 330 g; Mobile Phase A: water (plus 10 mM $NH_4HCO_3$); Mobile Phase B: acetonitrile; Flow rate: 80 mL/min; Gradient: 50% B-75% B in 20 min; Detector: 220/254 nm. The fractions containing the desired product were collected and concentrated under reduced pressure to afford tert-butyl (3-(4-phenoxypiperidin-1-yl) propyl)carbamate as a light yellow oil.

Yield: 0.60 g (53%). $^1$H NMR (400 MHz, $CDCl_3$) δ 7.35-7.25 (m, 2H), 7.00-6.89 (m, 3H), 5.52 (br s, 1H), 4.39-4.33 (m, 1H), 3.25-3.20 (m, 2H), 2.75 (d, J=11.2 Hz, 2H), 2.51-2.42 (m, 2H), 2.32 (s, 2H), 2.05-2.00 (m, 2H), 1.90-1.85 (m, 2H), 1.74-1.66 (m, 2H), 1.47 (s, 9H). m/z: [ESI$^+$] 335 (M+H)$^+$.

The intermediates below were prepared according to the procedure described for Intermediate B.

Tert-butyl (3-(4-(pyridin-2-ylmethyl)piperidin-1-yl) propyl)carbamate

The compound was synthesized according to the procedure described for Intermediate B, using 2-(piperidin-4-ylmethyl)pyridine (0.40 g, 2.27 mmol) and tert-butyl (3-bromopropyl)carbamate (2.16 g, 9.08 mmol) as the starting material.

Yield 0.25 g (33%), as a light yellow oil. $^1$H NMR (400 MHz, $CDCl_3$) δ 8.57 (dd, J=2.0, 4.8 Hz, 1H), 7.63 (dd, J=2.0, 7.6 Hz, 1H), 7.20-7.10 (m, 2H), 5.32 (br s, 1H), 3.52-3.47 (m, 2H), 3.25-3.16 (m, 2H), 2.97-2.90 (m, 2H), 2.81-2.75 (m, 2H), 2.60-2.45 (m, 2H), 2.09-2.00 (m, 1H), 1.94 (td, J=6.4, 13.2 Hz, 2H), 1.82-1.73 (m, 4H), 1.45 (s, 9H). m/z: [ESI$^+$] 334 (M+H)$^+$.

Tert-butyl 2-(1-(pyridin-2-ylmethyl)piperidin-4-yloxy)ethylcarbamate

The compound was synthesized according to the procedure described for Intermediate B, using tert-butyl 2-(piperidin-4-yloxy)ethylcarbamate (0.30 g, 1.23 mmol) and 2-(bromomethyl)pyridine (0.25 g, 1.45 mmol) as the starting material.

Yield 0.35 g (85%), as an off-white solid. $^1$H NMR (400 MHz, $CDCl_3$) δ 8.59-8.57 (m, 1H), 7.68 (dd, J=2.0, 7.6 Hz, 1H), 7.44 (d, J=7.6 Hz, 1H), 7.22-7.15 (m, 1H), 4.90 (br s, 1H), 3.67 (s, 2H), 3.53-3.51 (m, 2H), 3.37-3.31 (m, 2H), 2.85-2.77 (m, 2H), 2.55-2.48 (m, 1H), 2.30-2.20 (m, 2H), 1.98-1.85 (m, 2H), 1.66-1.58 (m, 2H), 1.47 (s, 9H). m/z: [ESI$^+$] 336 (M+H)$^+$.

Tert-butyl 3-[3-(4-methoxyphenyl)-1,2,4-oxadiazol-5-yl]azetidine-1-carboxylate (Intermediate C)

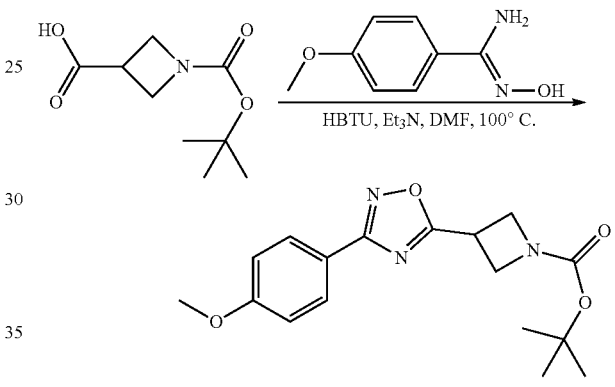

INTERMEDIATE C

To a stirred solution of 1-(tert-butoxycarbonyl)azetidine-3-carboxylic acid (3.00 g, 14.91 mmol) and N'-hydroxy-4-methoxybenzimidamide (3.00 g, 18.05 mmol) in DMF (50 mL), was added HBTU (8.50 g, 22.41 mmol) and triethylamine (3.00 g, 29.65 mmol), at room temperature. The mixture was stirred for 16 h at 100° C. After cooling to room temperature, the resulting mixture was purified by reverse phase flash chromatography with the following conditions: Column: Spherical C18, 20-40 um, 330 g; Mobile Phase A: water (plus 10 mM $NH_4HCO_3$); Mobile Phase B: acetonitrile; Flow rate: 80 mL/min; Gradient: 60% B-80% B in 20 min; Detector: UV 254/215 nm. The fractions containing desired product were collected and concentrated under reduced pressure to afford tert-butyl 3-[3-(4-methoxyphenyl)-1,2,4-oxadiazol-5-yl]azetidine-1-carboxylate as a brown oil.

Yield: 3.20 g (65%). $^1$H NMR (400 MHz, $CDCl_3$) δ 7.97 (d, J=8.8 Hz, 2H), 7.12 (d, J=8.8 Hz, 2H), 4.35-4.26 (m, 2H), 4.25-4.16 (m, 1H), 4.15-4.08 (m, 2H), 3.85 (s, 3H), 1.41 (s, 9H). m/z: [ESI$^+$]276 (M+H−56)$^+$.

The intermediates below were prepared according the procedure described for Intermediate C.

Methyl (1r,4r)-4-(3-(4-methoxyphenyl)-1,2,4-oxadiazol-5-yl)cyclohexane-1-carboxylate The compound was synthesized according to the procedure described for Intermediate C, using N-hydroxy-4- methoxybenzimidamide (4.02 g, 24.19 mmol) and (1r,4r)-4-(methoxycarbonyl)cyclohexane-1-carboxylic acid (4.51 g, 24.22 mmol) as the starting material.

Yield 4.00 g (52%), as an off-white solid. $^1$H NMR (400 MHz, DMSO) δ 7.93 (d, J=9.0 Hz, 2H), 7.09 (d, J=9.0 Hz, 2H), 3.83 (s, 3H), 3.61 (s, 3H), 3.07 (dt, J=3.2, 11.6 Hz, 1H), 2.42 (dt, J=6.6, 11.2 Hz, 1H), 2.16 (dd, J=3.6, 12.8 Hz, 2H), 2.01 (dd, J=3.6, 13.6 Hz, 2H), 1.70-1.57 (m, 2H), 1.55-1.47 (m, 2H). m/z: [ESI$^+$] 317 (M+H)$^+$.

Methyl (1s,4s)-4-(3-(4-methoxyphenyl)-1,2,4-oxadiazol-5-yl)cyclohexane-1-carboxylate The compound was synthesized according to the procedure described for Intermediate C, using N-hydroxy-4-methoxybenzimidamide (2.00 g, 12.04 mmol) and (1s,4s)-4-(methoxycarbonyl)cyclohexane-1-carboxylic acid (2.25 g, 12.08 mmol) as the starting material.

Yield 3.00 g (79%), as a yellow solid. $^1$H NMR (400 MHz, DMSO) δ 7.93 (d, J=9.0 Hz, 2H), 7.09 (d, J=9.0 Hz, 2H), 3.83 (s, 3H), 3.60 (s, 3H), 3.27 (q, J=5.6 Hz, 1H), 2.62 (td, J=4.4, 8.2 Hz, 1H), 1.92 (t, J=5.6 Hz, 4H), 1.85-1.65 (m, 4H). m/z: [ESI$^+$] 317 (M+H)$^+$.

Tert-butyl 1-[4-methoxy-[1,1-biphenyl]-3-yl]piperidine-4-carboxylate (Intermediate D)

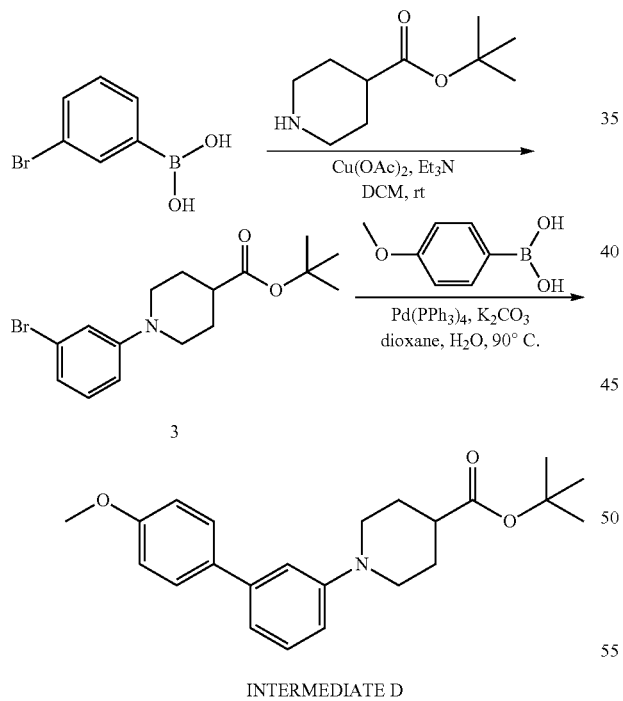

INTERMEDIATE D

Step 1: Tert-butyl 1-(3-bromophenyl)piperidine-4-carboxylate

To a stirred solution of (3-bromophenyl)boronic acid (5.00 g, 24.90 mmol) and tert-butyl piperidine-4-carboxylate (4.61 g, 24.90 mmol) in DCM (120 mL), were added copper(II) acetate(6.78 g, 37.33 mmol) and triethylamine (7.56 g, 74.71 mmol) at room temperature under an oxygen atmosphere (1.5 atm.). The resulting mixture was stirred at room temperature under an oxygen atmosphere for 16 h. The resulting mixture was diluted with water (100 mL) and extracted with DCM (3×100 mL). The combined organic layers were washed with brine (100 mL) and dried over anhydrous Na$_2$SO$_4$. After filtration, the filtrate was concentrated under reduced pressure. The residue was purified by silica gel column chromatography, eluting with 5% ethyl acetate in petroleum ether to afford tert-butyl 1-(3-bromophenyl)piperidine-4-carboxylate as a light brown oil.

Yield: 0.96 g (11%). $^1$H NMR (400 MHz, DMSO) δ 7.16-7.10 (m, 1H), 7.06 (t, J=2.0 Hz, 1H), 6.95-6.86 (m, 2H), 3.64 (td, J=3.6, 12.4 Hz, 2H), 2.86-2.73 (m, 2H), 2.45-2.35 (m, 1H), 1.89-1.80 (m, 2H), 1.64-1.51 (m, 2H), 1.41 (s, 9H). m/z: [ESI$^+$] 340, 342 (M+H)$^+$.

Step 2: Tert-butyl 1-[4'-methoxy-[1,1'-biphenyl]-3-yl]piperidine-4-carboxylate

To a stirred solution of tert-butyl 1-(3-bromophenyl)piperidine-4-carboxylate (0.95 g, 2.79 mmol) and (4-methoxyphenyl)boronic acid (0.85 g, 5.59 mmol) in 1,4-dioxane (8 mL) and water (2 mL), were added K$_2$CO$_3$ (1.12 g, 8.10 mmol) and tetrakis(triphenylphosphine)palladium(0) (0.32 g, 0.28 mmol). The resulting mixture was then purged with nitrogen gas. The reaction mixture was then stirred for 2 h at 90° C. The resulting mixture was cooled to room temperature, diluted with water (50 mL) and extracted with ethyl acetate (3×50 mL). The combined organic phases were washed with brine (50 mL), dried with anhydrous Na$_2$SO$_4$ and filtered. The filtrate was then concentrated under reduced pressure. The residue was purified by reverse phase flash chromatography with the following conditions: Column, Spherical C18, 20-40 um, 330 g; Mobile Phase A: water (plus 10 mM formic acid); Mobile Phase B; acetonitrile; Flow rate: 80 mL/min; Gradient: 45% B-65% B in 20 min; Detector: UV 220/254 nm. The fractions containing the desired product were collected and concentrated under reduced pressure to afford tert-butyl 1-[4-methoxy-[1,1-biphenyl]-3-yl]piperidine-4-carboxylate as a dark yellow solid.

Yield: 1.00 g (97%). $^1$H NMR (400 MHz, DMSO) δ 7.57 (d, J=8.8 Hz, 2H), 7.25 (t, J=8.0 Hz, 1H), 7.11-7.07 (m, 1H), 7.03-6.95 (m, 3H), 6.91-6.86 (m, 1H), 3.79 (s, 3H), 3.73-3.66 (m, 2H), 2.86-2.73 (m, 2H), 2.43-2.34 (m, 1H), 1.92-1.82 (m, 2H), 1.71-1.55 (m, 2H), 1.41 (s, 9H). m/z: [ESI$^+$] 368 (M+H)$^+$.

Methyl 1-(4-(4-methoxyphenyl)thiazol-2-yl)piperidine-4-carboxylate (Intermediate E)

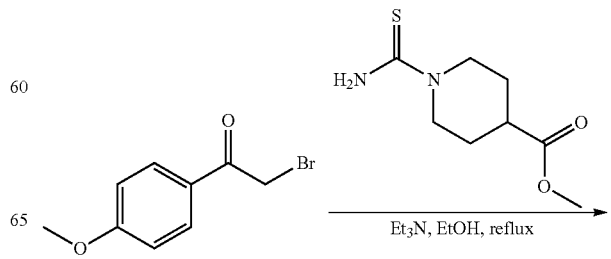

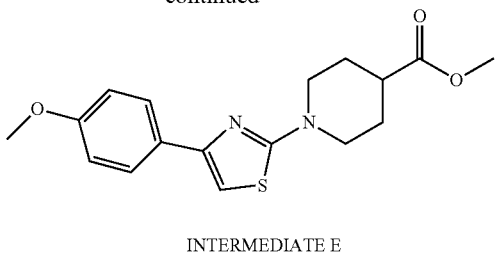

INTERMEDIATE E

To a stirred solution of methyl 1-carbamothioylpiperidine-4-carboxylate (1.00 g, 4.94 mmol) and 2-bromo-1-(4-methoxyphenyl)ethan-1-one (1.25 g, 5.46 mmol) in ethanol (20 mL) was added triethylamine (1.50 g, 14.82 mmol) at room temperature under a nitrogen atmosphere. The resulting solution was stirred for 16 h at reflux. The resulting mixture was cooled to room temperature and concentrated under reduced pressure. The residue was purified by silica gel column chromatography, eluting with 25% ethyl acetate in petroleum ether to afford methyl 1-(4-(4-methoxyphenyl)thiazol-2-yl)piperidine-4-carboxylate as an off-white solid.

Yield: 1.20 g (73%). $^1$H NMR (400 MHz, DMSO) δ 7.81-7.75 (m, 2H), 7.09 (s, 1H), 6.97-6.91 (m, 2H), 3.94-3.86 (m, 2H), 3.78 (s, 3H), 3.64 (s, 3H), 3.18-3.08 (m, 2H), 2.70-2.60 (m, 1H), 2.00-1.90 (m, 2H), 1.72-1.58 (m, 2H). m/z: [ESI$^+$] 333 (M+H)$^+$.

1-[3-(4-Methoxyphenyl)-1,2,4-oxadiazol-5-yl]piperidine-4-carboxylic acid (Intermediate F) and 1-[3-(4-Methoxyphenyl)-1,2,4-oxadiazol-5-yl]-N-(pyrrolidin-3-ylmethyl)piperidine-4-carboxamide hydrochloride (Intermediate G)

Scheme 8

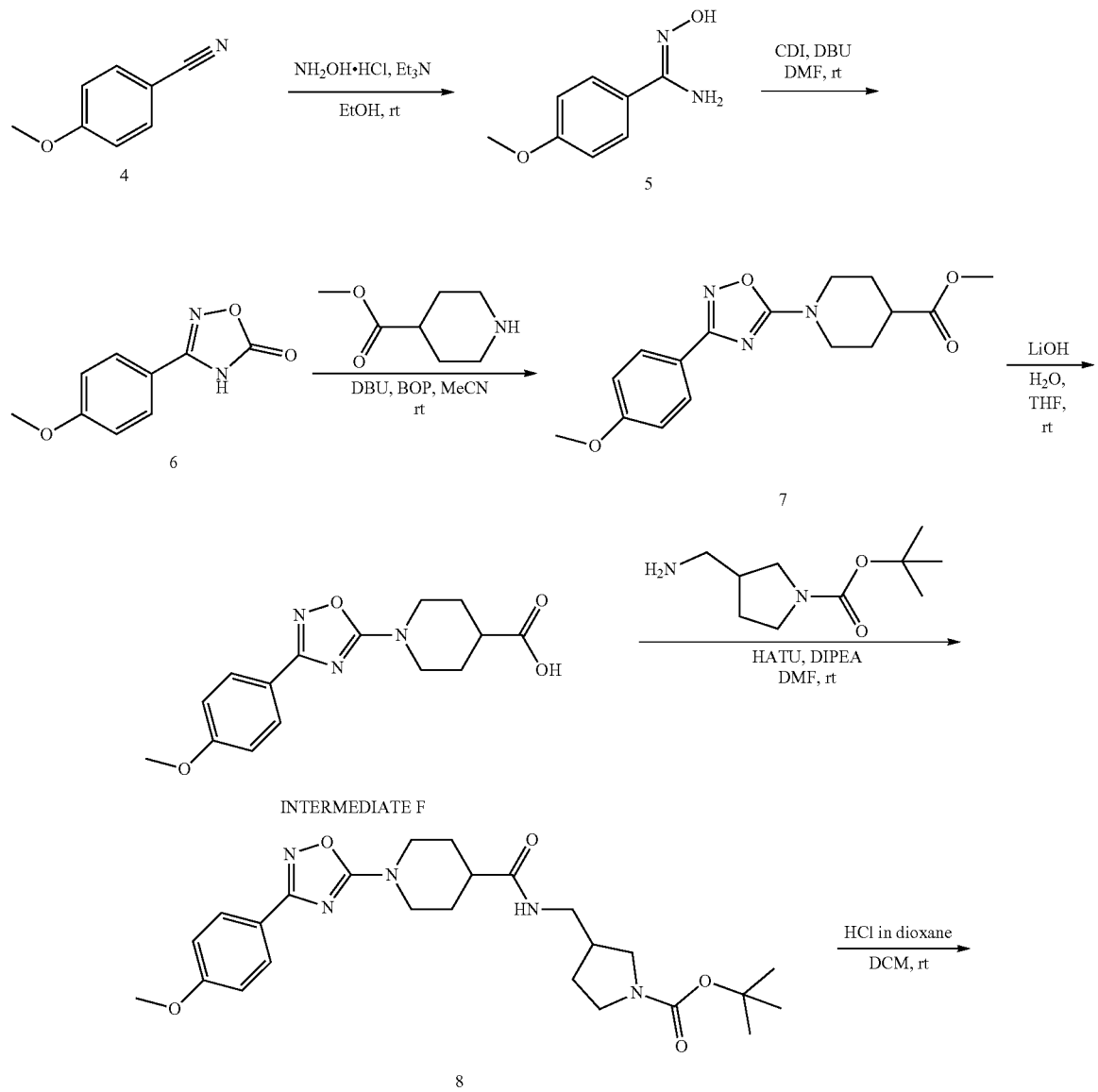

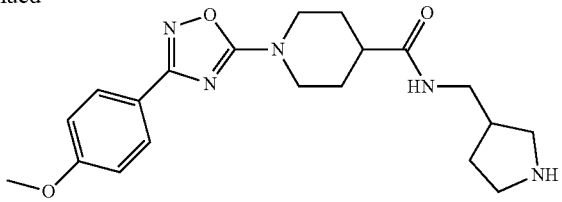

INTERMEDIATE G

Step 1: N-hydroxy-4-methoxybenzimidamide

To a stirred solution of 4-methoxybenzonitrile (100.00 g, 0.751 mol) in ethanol (1.50 L) were added hydroxylamine hydrochloride (78.29 g, 1.127 mol) and triethylamine (91.20 g, 0.901 mol) at room temperature. The reaction mixture was stirred for 16 h at room temperature. The resulting mixture was then concentrated under reduced pressure. The residue was dissolved in water (1.5 L) and extracted with ethyl acetate (3×1.5 L). The combined organic layers were washed with brine (2 L), dried over anhydrous $Na_2SO_4$ and filtered. The filtrate was concentrated under reduced pressure to afford N'-hydroxy-4-methoxybenzimidamide as a light blue solid.

Yield 120.00 g (96%). $^1$H NMR (400 MHz, DMSO) δ 9.45 (br s, 1H), 7.62 (d, J=8.8 Hz, 2H), 6.93 (d, J=8.8 Hz, 2H), 5.72 (br s, 2H), 3.78 (s, 3H). m/z: [ESI$^+$] 167 (M+H)$^+$.

The intermediates were prepared according to the procedure described above.

N'-hydroxy-5-methoxypyrazine-2-carboximidamide. The compound was synthesized according to the procedure described above, using 5-methoxypyrazine-2-carbonitrile (0.20 g, 1.48 mmol) as the starting material.

Yield 0.20 g (80%), as an off-white solid. $^1$H NMR (400 MHz, CD$_3$OD) δ 8.64 (d, J=1.4 Hz, 1H), 8.21 (d, J=1.4 Hz, 1H), 4.02 (s, 3H). NH$_2$ and OH protons not observed. m/z: [ESI$^+$] 169 (M+H)$^+$.

N'-hydroxy-5-methoxypyrimidine-2-carboximidamide. The compound was synthesized according to the procedure described above, using 5-methoxypyrimidine-2-carbonitrile (3.60 g, 26.64 mmol) as the starting material.

Yield 3.50 g (78%), as an off-white solid. $^1$H NMR (400 MHz, DMSO) δ 9.99 (br s, 1H), 8.56 (s, 2H), 5.75 (br s, 2H), 3.95 (s, 3H). m/z: [ESI$^+$] 169 (M+H)$^+$.

4-(Difluoromethyl)-N'-hydroxybenzimidamide. The compound was synthesized according to the procedure described above, using 4-(difluoromethyl)benzonitrile (5.00 g, 32.65 mmol) as the starting material.

Yield 6.00 g (99%), as a light blue solid. $^1$H NMR (400 MHz, DMSO) δ 9.82 (br s, 1H), 7.81 (d, J=8.0 Hz, 2H), 7.58 (d, J=8.0 Hz, 2H), 7.05 (t, J=56.0 Hz, 1H), 5.93 (br s, 2H). m/z: [ESI$^+$] 187 (M+H)$^+$.

Step 2: 3-(4-Methoxyphenyl)-1,2,4-oxadiazol-5(4H)-one

To a stirred solution of N-hydroxy-4-methoxybenzimidamide (80.00 g, 0.481 mol) in 1,4-dioxane (1.20 L) were added DBU (80.62 g, 0.530 mol) and CDI (117.09 g, 0.722 mol), portion-wise at room temperature. The reaction mixture was stirred for 16 h at 100° C. The mixture was cooled to room temperature and diluted with water (1 L). The resulting mixture was acidified to pH 2 with 3M HCl and extracted with ethyl acetate (3×1 L). The combined organic layers were washed with brine (1 L) and dried over anhydrous $Na_2SO_4$. After filtration, the filtrate was concentrated under reduced pressure. The residue was triturated with cold chloroform (800 mL) for 1 h. After filtration, the filter cake was washed with cold chloroform (3×100 mL) and air dried to afford 3-(4-methoxyphenyl)-1,2,4-oxadiazol-5(4H)-one as a light yellow solid.

Yield 80.00 g (86%). $^1$H NMR (400 MHz, DMSO) δ 12.81 (s, 1H), 7.77 (d, J=8.8 Hz, 2H), 7.14 (d, J=8.8 Hz, 2H), 3.84 (s, 3H). m/z: [ESI$^+$] 193 (M+H)$^+$.

The intermediates below were prepared according to the procedure described above.

3-(6-Methoxypyridin-3-yl)-1,2,4-oxadiazol-5(4H)-one. The compound was synthesized according to the procedure described above, using N-hydroxy-6-methoxynicotinimidamide (12.00 g, 71.78 mmol) as the starting material.

Yield 12.00 g (87%), as a light yellow solid. $^1$H NMR (400 MHz, DMSO) δ 13.00 (s, 1H), 8.65-8.55 (m, 1H), 8.12-8.02 (m, 1H), 7.03 (dd, J=1.2, 8.8 Hz, 1H), 3.94 (s, 3H). m/z: [ESI$^+$] 194 (M+H)$^+$.

N-(4-(5-oxo-4,5-dihydro-1,2,4-oxadiazol-3-yl)phenyl) acetamide. The compound was synthesized according to the procedure described above, using N-(4-(N-hydroxycarbamimidoyl)phenyl)acetamide (4.50 g, 23.29 mmol) as the starting material.

Yield 4.00 g (78%), as a grey solid. $^1$H NMR (400 MHz, DMSO) δ 13.03 (br s, 1H), 10.52 (s, 1H), 7.85-7.73 (m, 4H), 1.99 (s, 3H). m/z: [ESI$^+$] 220 (M+H)$^+$.

3-(5-Methoxypyridin-2-yl)-1,2,4-oxadiazol-5(4H)-one. The compound was synthesized according to the procedure described above, using N-hydroxy-5-methoxypicolinimidamide (10.00 g, 59.82 mmol) as the starting material.

Yield 9.00 g (78%), as a light yellow solid. $^1$H NMR (400 MHz, DMSO) δ 13.00 (br s, 1H), 8.44 (d, J=2.8 Hz, 1H), 7.95 (dd, J=0.8, 8.8 Hz, 1H), 7.61 (dd, J=2.8, 8.8 Hz, 1H), 3.93 (s, 3H). m/z: [ESI$^+$] 194 (M+H)$^+$.

3-(5-Oxo-4,5-dihydro-1,2,4-oxadiazol-3-yl)benzonitrile. The compound was synthesized according to the procedure described above, using 3-cyano-N-hydroxybenzimidamide (15.00 g, 93.08 mmol) as the starting material.

Yield 14.80 g (85%), as a yellow solid. $^1$H NMR (400 MHz, DMSO) δ 13.14 (br s, 1H), 8.21 (t, J=1.6 Hz, 1H), 8.15-8.08 (m, 2H), 7.81 (d, J=8.0 Hz, 1H). m/z: [ESI$^+$] 188 (M+H)$^+$.

N-(3-(5-oxo-4,5-dihydro-1,2,4-oxadiazol-3-yl)phenyl) acetamide. The compound was synthesized according to the procedure described above, using N-(3-(N-hydroxycarbamimidoyl)phenyl)acetamide (8.00 g, 41.41 mmol) as the starting material.

Yield 6.50 g (72%), as a yellow solid. $^1$H NMR (400 MHz, DMSO) δ 13.02 (br s, 1H), 10.23 (br s, 1H), 8.17 (s, 1H), 7.78-7.70 (m, 1H), 7.55-7.46 (m, 1H), 7.46-7.40 (m, 1H), 2.08 (s, 3H). m/z: [ESI$^+$] 220 (M+H)$^+$.

3-(4-(Trifluoromethoxy)phenyl)-1,2,4-oxadiazol-5(4H)-one. The compound was synthesized according to the procedure described above, using N-hydroxy-4-(trifluoromethoxy)benzimidamide (15.00 g, 68.14 mmol) as the starting material.

Yield 10.50 g (63%), as an off-white solid. ¹H NMR (400 MHz, DMSO) δ 13.12 (br s, 1H), 7.95 (d, J=8.8 Hz, 2H), 7.61 (dd, J=1.2, 8.8 Hz, 2H). m/z: [ESI⁺] 247 (M+H)⁺.

3-(4-(Difluoromethoxy)phenyl)-1,2,4-oxadiazol-5(4H)-one. The compound was synthesized according to the procedure described above, using 4-(difluoromethoxy)-N-hydroxybenzimidamide (10.00 g, 49.47 mmol) as the starting material.

Yield 8.00 g (71%), as a light yellow solid. ¹H NMR (400 MHz, DMSO) δ 13.00 (br s, 1H), 7.90-7.83 (m, 2H), 7.42-7.36 (m, 2H), 7.40 (t, J=74.0 Hz, 1H). m/z: [ESI⁺] 229 (M+H)⁺.

3-(2-Chloro-4-methoxyphenyl)-1,2,4-oxadiazol-5(4H)-one. The compound was synthesized according to the procedure described above, using 2-chloro-N-hydroxy-4-methoxybenzimidamide (15.00 g, 74.77 mmol) as the starting material.

Yield 10.00 g (59%), as a light yellow solid. ¹H NMR (400 MHz, CDCl₃) δ 9.26 (br s, 1H), 7.86 (d, J=8.8 Hz, 1H), 7.05 (d, J=2.6 Hz, 1H), 6.98 (dd, J=2.6, 8.8 Hz, 1H), 3.91 (s, 3H). m/z: [ESI⁺] 227, 229 (M+H)⁺.

3-(2-Methoxypyrimidin-5-yl)-1,2,4-oxadiazol-5(4H)-one. The compound was synthesized according to the procedure described above, using N-hydroxy-2-methoxypyrimidine-5-carboximidamide (4.40 g, 26.17 mmol) as the starting material.

Yield 4.00 g (79%), as a light yellow solid. ¹H NMR (400 MHz, CD₃OD) δ 8.96 (s, 2H), 4.11 (s, 3H). NH proton not observed. m/z: [ESI⁺] 195 (M+H)⁺.

3-(5-Methoxypyrazin-2-yl)-1,2,4-oxadiazol-5(4H)-one. The compound was synthesized according to the procedure described above, using N-hydroxy-5-methoxypyrazine-2-carboximidamide (9.00 g, 53.52 mmol) as the starting material.

Yield 7.60 g (73%), as a light yellow solid. ¹HNMR (400 MHz, CD₃OD) δ 8.79 (d, J=1.4 Hz, 1H), 8.33 (d, J=1.4 Hz, 1H), 4.08 (s, 3H). NH proton not observed. m/z: [ESI⁺] 195 (M+H)⁺.

3-(5-Methoxypyrimidin-2-yl)-1,2,4-oxadiazol-5(4H)-one. The compound was synthesized according to the procedure described above, using N-hydroxy-5-methoxypyrimidine-2-carboximidamide (3.50 g, 20.81 mmol) as the starting material.

Yield 2.50 g (62%), as a light yellow solid. ¹H NMR (400 MHz, DMSO) δ 13.15 (br s, 1H), 8.75 (s, 2H), 4.03 (s, 3H). m/z: [ESI⁺] 195 (M+H)⁺.

3-(4-(Difluoromethyl)phenyl)-1,2,4-oxadiazol-5(4H)-one. The compound was synthesized according to the procedure described above, using 4-(difluoromethyl)-N'-hydroxybenzimidamide (6.00 g, 32.23 mmol) as the starting material.

Yield 6.10 g (89%), as a light yellow solid. ¹H NMR (400 MHz, DMSO) δ 13.11 (br s, 1H), 7.95 (d, J=8.0 Hz, 2H), 7.79 (d, J=8.0 Hz, 2H), 7.13 (t, J=55.6 Hz, 1H). m/z: [ESI⁺] 211 (M−H)⁻.

3-(4-(Allyloxy)phenyl)-1,2,4-oxadiazol-5(4H)-one. The compound was synthesized according to the procedure described above, using 4-(allyloxy)-N-hydroxybenzimidamide (38.00 g, 197.69 mmol) as the starting material.

Yield 38 g (88%), as an off-white solid. ¹H NMR (400 MHz, DMSO) δ 12.83 (br s, 1H), 7.78-7.72 (m, 2H), 7.18-7.12 (m, 2H), 6.13-5.99 (m, 1H), 5.47-5.37 (m, 1H), 5.33-5.26 (m, 1H), 4.70-4.63 (m, 2H). m/z: [ESI⁺] 219 (M+H)⁺.

Step 3: Methyl 1-[3-(4-methoxyphenyl)-1,2,4-oxadiazol-5-yl]piperidine-4-carboxylate To a stirred solution of 3-(4-methoxyphenyl)-1,2,4-oxadiazol-5(4H)-one (15.00 g, 78.05 mmol) in acetonitrile (225 mL) were added methyl piperidine-4-carboxylate (16.76 g, 117.05 mmol), DBU (17.82 g, 117.05) mmol) and BOP (44.88 g, 101.47 mmol) portion-wise at room temperature. The reaction mixture was then stirred for 16 h at 60° C. The resulting mixture was cooled to room temperature and concentrated under reduced pressure. The residue was purified by silica gel column chromatography, eluting with 45%-60% ethyl acetate in petroleum ether to afford methyl 1-[3-(4-methoxyphenyl)-1,2,4-oxadiazol-5-yl]piperidine-4-carboxylate as a light yellow solid.

Yield 14.00 g (57%). ¹H NMR (400 MHz, CDCl₃) δ 7.94 (d, J=8.8 Hz, 2H), 6.96 (d, J=8.8 Hz, 2H), 4.20-4.12 (m, 2H), 3.86 (s, 3H), 3.73 (s, 3H), 3.30-3.25 (m, 2H), 2.63-2.56 (m, 1H), 2.09-1.99 (m, 2H), 1.93-1.76 (m, 2H). m/z: [ESI⁺] 318 (M+H)⁺.

The intermediates below were prepared according to the procedure described above.

Tert-butyl 4-(3-(4-methoxyphenyl)-1,2,4-oxadiazol-5-yl)piperazine-1-carboxylate. The compound was synthesized according to the procedure described above, using 3-(4-methoxyphenyl)-1,2,4-oxadiazol-5(4H)-one (10.00 g, 52.04 mmol) and tert-butyl piperazine-1-carboxylate (19.39 g, 104.08 mmol) as the starting material.

Yield 8.00 g (43%), as a light yellow solid. ¹H NMR (400 MHz, DMSO) δ 7.85 (d, J=8.4 Hz, 2H), 7.07 (d, J=8.4 Hz, 2H), 3.83 (s, 3H), 3.69-3.56 (m, 4H), 3.53-3.46 (m, 4H), 1.44 (s, 9H). m/z: [ESI⁺] 361 (M+H)⁺.

Tert-butyl 4-(3-(4-cyanophenyl)-1,2,4-oxadiazol-5-yl)piperazine-1-carboxylate. The compound was synthesized according to the procedure described above, using 4-(5-oxo-4,5-dihydro-1,2,4-oxadiazol-3-yl)benzonitrile (5.00 g, 26.72 mmol) and tert-butyl piperazine-1-carboxylate(7.46 g, 40.05 mmol) as the starting material.

Yield 2.50 g (26%), as a light yellow solid. ¹H NMR (400 MHz, CDCl₃) δ 8.12 (d, J=8.4 Hz, 2H), 7.75 (d, J=8.4 Hz, 2H), 3.70 (dd, J=3.8, 6.6 Hz, 4H), 3.60 (dd, J=3.8, 6.6 Hz, 4H), 1.51 (s, 9H). m/z: [ESI⁺] 356 (M+H)⁺.

Tert-butyl 4-(3-(4-(trifluoromethoxy)phenyl)-1,2,4-oxadiazol-5-yl)piperazine-1-carboxylate.

The compound was synthesized according to the procedure described above, using 3-(4-(trifluoromethoxy)phenyl)-1,2,4-oxadiazol-5(4H)-one (10.00 g, 40.63 mmol) and tert-butyl piperazine-1-carboxylate (11.35 g, 60.95 mmol) as the starting material.

Yield 4.25 g (25%), as an off-white solid. ¹H NMR (400 MHz, CDCl₃) δ 8.05 (d, J=8.8 Hz, 2H), 7.29 (d, J=8.8 Hz, 2H), 3.69 (dd, J=4.0, 6.8 Hz, 4H), 3.60 (dd, J=4.0, 6.8 Hz, 4H), 1.51 (s, 9H). m/z: [ESI⁺] 415 (M+H)⁺.

Tert-butyl 4-(3-(4-(difluoromethoxy)phenyl)-1,2,4-oxadiazol-5-yl)piperazine-1-carboxylate.

The compound was synthesized according to the procedure described above, using 3-(4-(difluoromethoxy)phenyl)-1,2,4-oxadiazol-5(4H)-one (12.00 g, 52.60 mmol) and tert-butyl piperazine-1-carboxylate (29.39 g, 157.80 mmol) as the starting material.

Yield 3.10 g (15%), as a light yellow solid. ¹H NMR (400 MHz, DMSO) δ 7.99-7.92 (m, 2H), 7.36 (t, J=72.0 Hz, 1H), 7.34-7.28 (m, 2H), 3.64-3.56 (m, 4H), 3.53-3.45 (m, 4H), 1.43 (s, 9H). m/z: [ESI$^+$] 397 (M+H)$^+$.

Tert-butyl 4-(3-(4-(difluoromethyl)phenyl)-1,2,4-oxadiazol-5-yl)piperazine-1-carboxylate. The compound was synthesized according to the procedure described above, using 3-(4-(difluoromethyl)phenyl)-1,2,4-oxadiazol-5(4H)-one (12.00 g, 56.56 mmol) and tert-butyl piperazine-1-carboxylate (29.13 g, 156.42 mmol) as the starting material.

Yield 6.00 g (28%), as an off-white solid. m/z: [ESI$^+$] 381 (M+H)$^+$. The crude material was used in the next step without further purification.

Tert-butyl 4-(3-(4-(allyloxy)phenyl)-1,2,4-oxadiazol-5-yl)piperazine-1-carboxylate. The compound was synthesized according to the procedure described above, using 3-(4-(allyloxy)phenyl)-1,2,4-oxadiazol-5(4H)-one (5.00 g, 22.91 mmol) and tert-butyl piperazine-1-carboxylate (8.54 g, 45.82 mmol) as the starting material.

Yield 6.00 g (68%), as a yellow oil. $^1$H NMR (400 MHz, DMSO) δ 7.86-7.80 (m, 2H), 7.10-7.04 (m, 2H), 6.13-5.99 (m, 1H), 5.47-5.37 (m, 1H), 5.32-5.25 (m, 1H), 4.66-4.61 (m, 2H), 3.62-3.54 (m, 4H), 3.52-3.44 (m, 4H), 1.43 (s, 9H). m/z: [ESI$^+$] 387 (M+H)$^+$.

Methyl 1-(3-(4-(allyloxy)phenyl)-1,2,4-oxadiazol-5-yl)piperidine-4-carboxylate. The compound was synthesized according to the procedure described above, using 3-(4-(allyloxy)phenyl)-1,2,4-oxadiazol-5(4H)-one (5.00 g, 22.91 mmol) and methyl piperidine-4-carboxylate (4.27 g, 29.82 mmol) as the starting material.

Yield 4.00 g (51%), as an off-white solid. $^1$H NMR (400 MHz, CDCl$_3$) δ 7.99-7.92 (m, 2H), 7.01-6.95 (m, 2H), 6.16-6.01 (m, 1H), 5.50-5.41 (m, 1H), 5.37-5.29 (m, 1H), 4.64-4.57 (m, 2H), 4.24-4.15 (m, 2H), 3.74 (s, 3H), 3.35-3.24 (m, 2H), 2.65-2.55 (m, 1H), 2.12-2.01 (m, 2H), 1.94-1.79 (m, 2H). m/z: [ESI$^+$] 344 (M+H)$^+$.

Methyl 1-(3-(4-chlorophenyl)-1,2,4-oxadiazol-5-yl)piperidine-4-carboxylate. The compound was synthesized according to the procedure described above, using 3-(4-chlorophenyl)-1,2,4-oxadiazol-5(4H)-one (8.00 g, 40.69 mmol) and methyl piperidine-4-carboxylate (11.65 g, 81.38 mmol) as the starting material.

Yield 2.50 g (19%), as a yellow solid. $^1$H NMR (400 MHz, CDCl$_3$) δ 7.99-7.92 (m, 2H), 7.45-7.41 (m, 2H), 4.22-4.12 (m, 2H), 3.74 (s, 3H), 3.35-3.24 (m, 2H), 2.68-2.55 (m, 1H), 2.12-2.00 (m, 2H), 1.92-1.82 (m, 2H). m/z: [ESI$^+$] 322, 324 (M+H)$^+$.

Methyl 1-(3-(3-chlorophenyl)-1,2,4-oxadiazol-5-yl)piperidine-4-carboxylate. The compound was synthesized according to the procedure described above, using 3-(3-chlorophenyl)-1,2,4-oxadiazol-5(4H)-one (8.00 g, 40.69 mmol) and methyl piperidine-4-carboxylate (11.65 g, 81.38 mmol) as the starting material.

Yield 1.00 g (8%), as a yellow solid. $^1$H NMR (400 MHz, CDCl$_3$) δ 8.02-7.99 (m, 1H), 7.92-7.87 (m, 1H), 7.47-7.42 (m, 1H), 7.41-7.35 (m, 1H), 4.25-4.13 (m, 2H), 3.74 (s, 3H), 3.36-3.24 (m, 2H), 2.68-2.55 (m, 1H), 2.13-2.01 (m, 2H), 1.92-1.80 (m, 2H). m/z: [ESI$^+$] 322, 324 (M+H)$^+$.

Methyl 1-(3-(2-chlorophenyl)-1,2,4-oxadiazol-5-yl)piperidine-4-carboxylate. The compound was synthesized according to the procedure described above, using 3-(2-chlorophenyl)-1,2,4-oxadiazol-5(4H)-one (8.00 g, 40.69 mmol) and methyl piperidine-4-carboxylate (11.65 g, 81.38 mmol) as the starting material.

Yield 0.65 g (5%), as a yellow solid. $^1$H NMR (400 MHz, CDCl$_3$) δ 7.88-7.82 (m, 1H), 7.55-7.48 (m, 1H), 7.43-7.33 (m, 2H), 4.24-4.10 (m, 2H), 3.74 (s, 3H), 3.36-3.23 (m, 2H), 2.67-2.55 (m, 1H), 2.11-2.03 (m, 2H), 1.94-1.80 (m, 2H). m/z: [ESI$^+$] 322, 324 (M+H)$^+$.

Methyl 1-(3-(4-cyanophenyl)-1,2,4-oxadiazol-5-yl)piperidine-4-carboxylate. The compound was synthesized according to the procedure described above, using 4-(5-oxo-4,5-dihydro-1,2,4-oxadiazol-3-yl)benzonitrile (10.00 g, 53.43 mmol) and methyl piperidine-4-carboxylate (15.30 g, 106.86 mmol) as the starting material.

Yield 1.87 g (11%), as a yellow solid. $^1$H NMR (400 MHz, CDCl$_3$) δ 8.17-8.10 (m, 2H), 7.78-7.73 (m, 2H), 4.23-4.13 (m, 2H), 3.75 (s, 3H), 3.37-3.27 (m, 2H), 2.68-2.58 (m, 1H), 2.13-2.03 (m, 2H), 1.93-1.80 (m, 2H). m/z: [ESI$^+$] 313 (M+H)$^+$.

Methyl 1-(3-(6-methoxypyridin-3-yl)-1,2,4-oxadiazol-5-yl)piperidine-4-carboxylate. The compound was synthesized according to the procedure described above, using 3-(6-methoxypyridin-3-yl)-1,2,4-oxadiazol-5(4H)-one (12.00 g, 62.12 mmol) and methyl piperidine-4-carboxylate (17.79 g, 124.24 mmol) as the starting material.

Yield 3.80 g (19%), as a light yellow solid. $^1$H NMR (400 MHz, CDCl$_3$) δ 8.80 (dd, J=0.8, 2.4 Hz, 1H), 8.14 (dd, J=2.4, 8.6 Hz, 1H), 6.81 (dd, J=0.8, 8.6 Hz, 1H), 4.17 (td, J=4.4, 13.8 Hz, 2H), 4.01 (s, 3H), 3.74 (s, 3H), 3.34-3.24 (m, 2H), 2.67-2.56 (m, 1H), 2.11-2.02 (m, 2H), 1.92-1.79 (m, 2H). m/z: [ESI$^+$] 319 (M+H)$^+$.

Tert-butyl 1-(3-(4-methoxyphenyl) isoxazol-5-yl)piperidine-4-carboxylate. The compound was synthesized according to the procedure described above, using 3-(4-methoxyphenyl) isoxazol-5(4H)-one (4.60 g, 24.06 mmol) and tert-butyl piperidine-4-carboxylate (6.69 g, 36.09 mmol) as the starting material.

Yield 3.30 g (38%), as a brown solid. $^1$H NMR (400 MHz, DMSO) δ 7.71-7.65 (m, 2H), 7.05-6.99 (m, 2H), 5.79 (s, 1H), 3.80 (s, 3H), 3.72-3.63 (m, 2H), 3.09-2.99 (m, 2H), 2.49-2.40 (m, 1H), 1.92-1.84 (m, 2H), 1.65-1.53 (m, 2H), 1.41 (s, 9H). m/z: [ESI$^+$] 359 (M+H)$^+$.

Tert-butyl 1-(3-(2-methoxyphenyl)-1,2,4-oxadiazol-5-yl)piperidine-4-carboxylate. The compound was synthesized according to the procedure described above, using 3-(2-methoxyphenyl)-1,2,4-oxadiazol-5(4H)-one (10.00 g, 52.04 mmol) and tert-butyl piperidine-4-carboxylate (14.46 g, 78.06 mmol) as the starting material.

Yield 3.20 g (17%), as a light yellow solid. $^1$H NMR (400 MHz, DMSO) δ 7.72 (dd, J=1.8, 7.6 Hz, 1H), 7.53-7.46 (m, 1H), 7.16 (dd, J=1.0, 8.4 Hz, 1H), 7.05 (dd, J=1.0, 7.6 Hz, 1H), 4.00-3.92 (m, 2H), 3.83 (s, 3H), 3.30-3.20 (m, 2H), 2.59-2.51 (m, 1H), 1.96-1.87 (m, 2H), 1.64-1.52 (m, 2H), 1.42 (s, 9H). m/z: [ESI$^+$] 360 (M+H)$^+$.

Tert-butyl 1-(3-(4-acetamidophenyl)-1,2,4-oxadiazol-5-yl)piperidine-4-carboxylate. The compound was synthesized according to the procedure described above, using N-(4-(5-oxo-4,5-dihydro-1,2,4-oxadiazol-3-yl)phenyl)acetamide (4.00 g, 18.25 mmol) and tert-butyl piperidine-4-carboxylate (5.07 g, 27.37 mmol) as the starting material.

Yield 2.79 g (40%), as a light yellow solid. $^1$H NMR (400 MHz, DMSO) δ 10.19 (br s, 1H), 7.85-7.80 (m, 2H), 7.73-7.68 (m, 2H), 4.01-3.93 (m, 2H), 3.30-3.20 (m, 2H), 2.60-2.52 (m, 1H), 2.08 (s, 3H), 1.97-1.88 (m, 2H), 1.64-1.53 (m, 2H), 1.41 (s, 9H). m/z: [ESI$^+$] 387 (M+H)$^+$.

Tert-butyl 1-(3-(5-methoxypyridin-2-yl)-1,2,4-oxadiazol-5-yl)piperidine-4-carboxylate. The compound was synthesized according to the procedure described above, using 3-(5-methoxypyridin-2-yl)-1,2,4-oxadiazol-5(4H)-one (8.00 g, 41.42 mmol) and tert-butyl piperidine-4-carboxylate (11.51 g, 62.13 mmol) as the starting material.

Yield 3.00 g (20%), as a light yellow solid. $^1$H NMR (400 MHz, CD$_3$OD) δ 8.35 (dd, J=0.6, 2.8 Hz, 1H), 8.02 (dd, J=0.6, 8.8 Hz, 1H), 7.52 (dd, J=2.8, 8.8 Hz, 1H), 4.19-4.14

(m, 2H), 3.96 (s, 3H), 3.33-3.27 (m, 2H), 2.63-2.52 (m, 1H), 2.07-1.98 (m, 2H), 1.80-1.67 (m, 2H), 1.49 (s, 9H). m/z: [ESI$^+$] 361 (M+H)$^+$.

Tert-butyl 1-(3-(3-methylphenyl)-1,2,4-oxadiazol-5-yl)piperidine-4-carboxylate. The compound was synthesized according to the procedure described above, using 3-(3-methylphenyl)-1,2,4-oxadiazol-5(4H)-one (4.70 g, 26.68 mmol) and tert-butyl piperidine-4-carboxylate (6.94 g, 37.46 mmol) as the starting material.

Yield 2.10 g (23%), as a light yellow solid. $^1$H NMR (400 MHz, DMSO) δ 7.75-7.72 (m, 1H), 7.72-7.68 (m, 1H), 7.42-7.36 (m, 1H), 7.36-7.32 (m, 1H), 4.02-3.94 (m, 2H), 3.31-3.21 (m, 2H), 2.58-2.52 (m, 1H), 2.37 (s, 3H), 1.96-1.87 (m, 2H), 1.65-1.52 (m, 2H), 1.41 (s, 9H). m/z: [ESI$^+$] 344 (M+H)$^+$.

Tert-butyl 1-(3-(3-methoxyphenyl)-1,2,4-oxadiazol-5-yl)piperidine-4-carboxylate. The compound was synthesized according to the procedure described above, using 3-(3-methoxyphenyl)-1,2,4-oxadiazol-5(4H)-one (8.00 g, 41.63 mmol) and tert-butyl piperidine-4-carboxylate (11.57 g, 62.44 mmol) as the starting material.

Yield 6.00 g (40%), as a yellow solid. $^1$H NMR (400 MHz, DMSO) δ 7.52-7.46 (m, 1H), 7.45-7.37 (m, 2H), 7.13-7.08 (m, 1H), 4.03-3.94 (m, 2H), 3.81 (s, 3H), 3.32-3.22 (m, 2H), 2.59-2.51 (m, 1H), 1.97-1.87 (m, 2H), 1.66-1.51 (m, 2H), 1.41 (s, 9H). m/z: [ESI$^+$] 360 (M+H)$^+$.

Tert-butyl 1-(3-(2-methylphenyl)-1,2,4-oxadiazol-5-yl)piperidine-4-carboxylate. The compound was synthesized according to the procedure described above, using 3-(2-methylphenyl)-1,2,4-oxadiazol-5(4H)-one (6.40 g, 36.33 mmol) and tert-butyl piperidine-4-carboxylate (10.10 g, 54.49 mmol) as the starting material.

Yield 2.50 g (20%), as a yellow solid. $^1$H NMR (400 MHz, DMSO) δ 7.82 (dd, J=1.6, 7.6 Hz, 1H), 7.41 (dd, J=1.6, 7.6 Hz, 1H), 7.37-7.29 (m, 2H), 4.05-3.92 (m, 2H), 3.32-3.23 (m, 2H), 2.59-2.51 (m, 1H), 2.51 (s, 3H), 1.97-1.86 (m, 2H), 1.66-1.52 (m, 2H), 1.42 (s, 9H). m/z: [ESI$^+$] 344 (M+H)$^+$.

Tert-butyl 1-(4-(4-methoxyphenyl)oxazol-2-yl)piperidine-4-carboxylate. The compound was synthesized according to the procedure described above, using 4-(4-methoxyphenyl)oxazol-2(3H)-one (3.50 g, 18.31 mmol) and tert-butyl piperidine-4-carboxylate (5.09 g, 27.46 mmol) as the starting material.

Yield 0.44 g (7%), as a yellow solid. $^1$H NMR (400 MHz, DMSO) δ 7.95 (s, 1H), 7.60 (d, J=8.8 Hz, 2H), 6.94 (d, J=8.8 Hz, 2H), 3.90 (td, J=4.0, 12.8 Hz, 2H), 3.76 (s, 3H), 3.06 (dt, J=2.8, 13.2 Hz, 2H), 2.49-2.40 (m, 1H), 1.87 (dd, J=4.0, 13.2 Hz, 2H), 1.61-1.48 (m, 2H), 1.41 (s, 9H). m/z: [ESI$^+$] 359 (M+H)$^+$.

Methyl 1-(3-(3-cyanophenyl)-1,2,4-oxadiazol-5-yl)piperidine-4-carboxylate. The compound was synthesized according to the procedure described above, using 3-(5-oxo-4,5-dihydro-1,2,4-oxadiazol-3-yl)benzonitrile (14.00 g, 74.80 mmol) and methyl piperidine-4-carboxylate (16.07 g, 112.21 mmol) as the starting material.

Yield 5.50 g (24%), as a yellow solid. $^1$H NMR (400 MHz, DMSO) δ 8.25-8.22 (m, 1H), 8.22-8.18 (m, 1H), 8.05-8.01 (m, 1H), 7.77-7.71 (m, 1H), 4.09-3.95 (m, 2H), 3.64 (s, 3H), 3.37-3.27 (m, 2H), 2.74-2.64 (m, 1H), 2.04-1.93 (m, 2H), 1.72-1.57 (m, 2H). m/z: [ESI$^+$] 313 (M+H)$^+$.

Tert-butyl 1-(3-(pyridin-4-yl)-1,2,4-oxadiazol-5-yl)piperidine-4-carboxylate. The compound was synthesized according to the procedure described above, using 3-(pyridin-4-yl)-1,2,4-oxadiazol-5(4H)-one (3.20 g, 19.62 mmol) and tert-butyl piperidine-4-carboxylate (5.45 g, 29.42 mmol) as the starting material.

Yield 2.40 g (37%), as a yellow solid. $^1$H NMR (400 MHz, DMSO) δ 8.74 (d, J=6.2 Hz, 2H), 7.81 (d, J=6.2 Hz, 2H), 4.01-3.95 (m, 2H), 3.34-3.22 (m, 2H), 2.57-2.50 (m, 1H), 1.95-1.86 (m, 2H), 1.66-1.51 (m, 2H), 1.39 (s, 9H). m/z: [ESI$^+$] 331 (M+H)$^+$.

Tert-butyl 1-(3-(3-acetamidophenyl)-1,2,4-oxadiazol-5-yl)piperidine-4-carboxylate. The compound was synthesized according to the procedure described above, using N-(3-(5-oxo-4,5-dihydro-1,2,4-oxadiazol-3-yl)phenyl)acetamide (3.00 g, 13.69 mmol) and tert-butyl piperidine-4-carboxylate(3.80 g, 20.53 mmol) as the starting material.

Yield 1.68 g (32%), as a yellow solid. $^1$H NMR (400 MHz, DMSO) δ 10.13 (br s, 1H), 8.18-8.08 (m, 1H), 7.80-7.74 (m, 1H), 7.59-7.46 (m, 1H), 7.45-7.37 (m, 1H), 4.02-3.95 (m, 2H), 3.33-3.21 (m, 2H), 2.58-2.51 (m, 1H), 2.08 (s, 3H), 1.97-1.88 (m 2H), 1.64-1.56 (m, 2H), 1.41 (s, 9H). m/z: [ESI$^+$] 387 (M+H)$^+$.

Tert-butyl 1-(3-(4-(trifluoromethoxy)phenyl)-1,2,4-oxadiazol-5-yl)piperidine-4-carboxylate. The compound was synthesized according to the procedure described above, using 3-(4-(trifluoromethoxy)phenyl)-1,2,4-oxadiazol-5(4H)-one (5.00 g, 20.31 mmol) and tert-butyl piperidine-4-carboxylate (5.65 g, 30.47 mmol) as the starting material.

Yield 0.29 g (3%), as a yellow solid. $^1$H NMR (400 MHz, DMSO) δ 7.95 (d, J=8.8 Hz, 2H), 7.30 (d, J=8.8 Hz, 2H), 4.04-3.94 (m, 2H), 3.32-3.24 (m, 2H), 2.60-2.50 (m, 1H), 1.98-1.88 (m, 2H), 1.67-1.53 (m, 2H), 1.41 (s, 9H). m/z: [ESI$^+$] 414 (M+H)$^+$.

Tert-butyl 1-(3-(4-(difluoromethoxy)phenyl)-1,2,4-oxadiazol-5-yl)piperidine-4-carboxylate. The compound was synthesized according to the procedure described above, using 3-(4-(difluoromethoxy)phenyl)-1,2,4-oxadiazol-5(4H)-one (8.00 g, 35.06 mmol) and tert-butyl piperidine-4-carboxylate (9.74 g, 52.60 mmol) as the starting material.

Yield 5.00 g (36%), as a yellow solid. $^1$H NMR (400 MHz, DMSO) δ 7.95 (d, J=8.8 Hz, 2H), 7.53 (t, J=73.4 Hz, 1H), 7.30 (d, J=8.8 Hz, 2H), 4.03-3.93 (m, 2H), 3.33-3.22 (m, 2H), 2.58-2.51 (m, 1H), 1.97-1.85 (m, 2H), 1.66-1.52 (m, 2H), 1.41 (s, 9H). m/z: [ESI$^+$] 396 (M+H)$^+$.

Tert-butyl 1-(3-(2-chloro-4-methoxyphenyl)-1,2,4-oxadiazol-5-yl)piperidine-4-carboxylate. The compound was synthesized according to the procedure described above, using 3-(2-chloro-4-methoxyphenyl)-1,2,4-oxadiazol-5(4H)-one (8.00 g, 35.30 mmol) and tert-butyl piperidine-4-carboxylate (9.81 g, 52.95 mmol) as the starting material.

Yield 2.00 g (14%), as a yellow solid. $^1$H NMR (400 MHz, CDCl$_3$) δ 7.82 (d, J=8.8 Hz, 1H), 7.04 (d, J=2.4 Hz, 1H), 6.89 (dd, J=3.6, 8.8 Hz, 1H), 4.33-4.17 (m, 2H), 3.82 (s, 3H), 3.33-3.22 (m, 2H), 2.55-2.43 (m, 1H), 2.07-1.97 (m, 2H), 1.88-1.76 (m, 2H), 1.50 (s, 9H). m/z: [ESI$^+$]394, 396 (M+H)$^+$.

Tert-butyl 1-(3-(2-methoxypyrimidin-5-yl)-1,2,4-oxadiazol-5-yl)piperidine-4-carboxylate. The compound was synthesized according to the procedure described above, using 3-(2-methoxypyrimidin-5-yl)-1,2,4-oxadiazol-5(4H)-one (4.00 g, 20.60 mmol) and tert-butyl piperidine-4-carboxylate (4.96 g, 26.78 mmol) as the starting material.

Yield 1.50 g (20%), as a yellow solid. $^1$H NMR (400 MHz, CD$_3$OD) δ 9.06 (s, 2H), 4.20-4.10 (m, 2H), 4.10 (s, 3H), 3.37-3.30 (m, 2H), 2.64-2.53 (m, 1H), 2.08-1.97 (m, 2H), 1.80-1.67 (m, 2H), 1.49 (s, 9H). m/z: [ESI$^+$] 362 (M+H)$^+$.

Tert-butyl 1-(3-(5-methoxypyrazin-2-yl)-1,2,4-oxadiazol-5-yl)piperidine-4-carboxylate. The compound was synthesized according to the procedure described above, using 3-(5-methoxypyrazin-2-yl)-1,2,4-oxadiazol-5(4H)-one (0.20 g, 1.03 mmol) and tert-butyl piperidine-4-carboxylate (0.25 g, 1.34 mmol) as the starting material.

Yield 0.15 g (40%), as a light yellow solid. $^1$H NMR (400 MHz, CD$_3$OD) δ 8.78 (d, J=1.4 Hz, 1H), 8.31 (d, J=1.4 Hz, 1H), 4.19-4.11 (m, 2H), 4.06 (s, 3H), 3.40-3.28 (m, 2H), 2.64-2.52 (m, 1H), 2.08-1.97 (m, 2H), 1.80-1.67 (m, 2H), 1.49 (s, 9H). m/z: [ESI$^+$] 362 (M+H)$^+$.

Tert-butyl 1-(3-(5-methoxypyrimidin-2-yl)-1,2,4-oxadiazol-5-yl)piperidine-4-carboxylate. The compound was synthesized according to the procedure described above, using 3-(5-methoxypyrimidin-2-yl)-1,2,4-oxadiazol-5(4H)-one (1.30 g, 6.70 mmol) and tert-butyl piperidine-4-carboxylate (1.61 g, 8.71 mmol) as the starting material.

Yield 0.70 g (29%), as a yellow solid. $^1$H NMR (400 MHz, CD$_3$OD) δ 8.65 (s, 2H), 4.06 (s, 3H), 3.43-3.30 (m, 2H), 3.12-3.03 (m, 2H), 2.70-2.60 (m, 1H), 2.18-2.08 (m, 2H), 1.90-1.75 (m, 2H), 1.48 (s, 9H). m/z: [ESI$^+$] 362 (M+H)$^+$.

3-(4-Methoxyphenyl)-5-(4-phenoxypiperidin-1-yl)-1,2,4-oxadiazole (Compound 135). Using 3-(4-methoxyphenyl)-1,2,4-oxadiazol-5(4H)-one (0.20 g, 1.04 mmol) and 4-phenoxypiperidine (0.37 g, 2.09 mmol) as the starting material.

Yield 0.20 g (55%), as a light yellow solid. $^1$H NMR (400 MHz, DMSO) δ 7.85 (d, J=8.8 Hz, 2H), 7.31 (dd, J=7.2, 8.8 Hz, 2H), 7.06 (d, J=8.8 Hz, 2H), 7.04-7.00 (m, 2H), 6.98-6.93 (m, 1H), 4.74-4.62 (m, 1H), 3.93-3.82 (m, 2H), 3.82 (s, 3H), 3.63-3.53 (m, 2H), 2.12-2.01 (m, 2H), 1.81-1.68 (m, 2H). m/z: [ESI$^+$] 352 (M+H)$^+$, (C$_{20}$H$_{21}$N$_3$O$_3$)

3-(4-Methoxyphenyl)-5-(4-phenylpiperidin-1-yl)-1,2,4-oxadiazole (Compound 136). Using 3-(4-methoxyphenyl)-1,2,4-oxadiazol-5(4H)-one (0.20 g, 1.04 mmol) and 4-phenylpiperidine (0.34 g, 2.11 mmol) as the starting material.

Yield 0.24 g (69%), as a light yellow solid. $^1$H NMR (400 MHz, DMSO) δ 7.86 (d, J=8.8 Hz, 2H), 7.35-7.26 (m, 4H), 7.22-7.20 (m, 1H), 7.06 (d, J=8.8 Hz, 2H), 4.26-4.13 (m, 2H), 3.82 (s, 3H), 3.41-3.27 (m, 2H), 2.89-2.75 (m, 1H), 1.95-1.84 (m, 2H), 1.80-1.65 (m, 2H). m/z: [ESI$^+$] 336 (M+H)$^+$, (C$_{20}$H$_{21}$N$_3$O$_2$).

5-(4-(1H-Benzo[d]imidazol-2-yl)piperidin-1-yl)-3-(4-methoxyphenyl)-1,2,4-oxadiazole (Compound 214): Using 3-(4-methoxyphenyl)-1,2,4-oxadiazol-5(4H)-one (0.20 g, 1.04 mmol) and 2-(piperidin-4-yl)-1H-1,3-benzodiazole (0.31 g, 1.54 mmol) as the starting material.

Yield 0.14 g (36%), as a light yellow solid. $^1$H NMR (400 MHz, DMSO-d$_6$) δ 12.26 (br s, 1H), 7.86 (d, J=8.8 Hz, 2H), 7.49 (br s, 2H), 7.13 (dd, J=3.0, 6.0 Hz, 2H), 7.06 (d, J=8.8 Hz, 2H), 4.28-4.14 (m, 2H), 3.83 (s, 3H), 3.48-3.30 (m, 2H), 3.27-3.16 (m, 1H), 2.19-2.07 (m, 2H), 1.99-1.82 (m, 2H). m/z: [ESI$^+$] 376 (M+H)$^+$, (C$_{21}$H$_{21}$N$_5$O$_2$).

5-(4-(1H-benzo[d]imidazol-2-yl)piperazin-1-yl)-3-(4-methoxyphenyl)-1,2,4-oxadiazole hemiformate (Compound 235). Using 3-(4-methoxyphenyl)-1,2,4-oxadiazol-5(4H)-one (0.20 g, 1.04 mmol) and 2-(piperazin-1-yl)-1H-1,3-benzodiazole (0.25 g, 1.24 mmol) as the starting material.

Yield 60 mg (15%), as a light yellow solid. $^1$H NMR (400 MHz, DMSO) δ 11.54 (br s, 1H), 8.14 (s, 0.57H, HCOOH), 7.87 (d, J=8.8 Hz, 2H), 7.22 (d, J=5.4 Hz, 2H), 7.07 (d, J=8.8 Hz, 2H), 6.95 (d, J=6.4 Hz, 2H), 3.83 (s, 3H), 3.80-3.72 (m, 4H), 3.72-3.63 (m, 4H). m/z: [ESI$^+$] 377 (M+H)$^+$, (C$_{20}$H$_{20}$N$_6$O$_2$).

Step 4: 1-[3-(4-Methoxyphenyl)-1,2,4-oxadiazol-5-yl]piperidine-4-carboxylic acid To a stirred solution of methyl 1-[3-(4-methoxyphenyl)-1,2,4-oxadiazol-5-yl]piperidine-4-carboxylate (10.00 g, 31.51 mmol) in THF (150 mL) were added water (50 mL) and lithium hydroxide (3.77 g, 0.157 mol) at room temperature. The reaction solution was stirred for 2 h at room temperature. The solvents were then removed under reduced pressure. The resulting residue was dissolved in water (100 mL) and acidified to pH 4-5 with a 1M solution of aqueous hydrochloric acid. The resulting mixture was filtered. The filtered solid was washed with water (150 mL) and air dried to afford 1-[3-(4-methoxyphenyl)-1,2,4-oxadiazol-5-yl]piperidine-4-carboxylic acid, as a light brown solid.

Yield: 8.00 g (84%). $^1$H NMR (400 MHz, DMSO) δ 12.37 (br s, 1H), 7.84 (d, J=8.8 Hz, 2H), 7.06 (d, J=8.8 Hz, 2H), 4.10-3.97 (m, 2H), 3.83 (s, 3H), 3.31-3.24 (m, 2H), 2.64-2.52 (m, 1H), 1.99-1.93 (m, 2H), 1.69-1.54 (m, 2H). m/z: [ESI$^+$] 304 (M+H)$^+$.

The intermediates below were prepared according to the procedure described above.

1-(3-(4-Chlorophenyl)-1,2,4-oxadiazol-5-yl)piperidine-4-carboxylic acid. The compound was synthesized according to the procedure described above, using methyl 1-(3-(4-chlorophenyl)-1,2,4-oxadiazol-5-yl)piperidine-4-carboxylate (0.50 g, 1.55 mmol) as the starting material.

Yield 0.45 g (94%), as a light yellow solid. $^1$H NMR (400 MHz, DMSO) δ 12.36 (br s, 1H), 7.91 (d, J=8.6 Hz, 2H), 7.59 (d, J=8.6 Hz, 2H), 4.06-3.97 (m, 2H), 3.31-3.25 (m, 2H), 2.64-2.56 (m, 1H), 1.99-1.93 (m, 2H), 1.65-1.57 (m, 2H). m/z: [ESI$^+$] 308, 310 (M+H)$^+$.

1-(3-(3-Chlorophenyl)-1,2,4-oxadiazol-5-yl)piperidine-4-carboxylic acid. The compound was synthesized according to the procedure described above, using methyl 1-(3-(3-chlorophenyl)-1,2,4-oxadiazol-5-yl)piperidine-4-carboxylate (0.50 g, 1.55 mmol) as the starting material.

Yield 0.34 g (71%), as a light yellow solid. $^1$H NMR (400 MHz, DMSO) δ 12.34 (br s, 1H), 7.90-7.84 (m, 2H), 7.66-7.61 (m, 1H), 7.59-7.54 (m, 1H), 4.06-3.97 (m, 2H), 3.31-3.26 (m, 2H), 2.64-2.56 (m, 1H), 2.02-1.89 (m, 2H), 1.70-1.55 (m, 2H). m/z: [ESI$^+$] 308, 310 (M+H)$^+$.

1-(3-(2-Chlorophenyl)-1,2,4-oxadiazol-5-yl)piperidine-4-carboxylic acid. The compound was synthesized according to the procedure described above, using methyl 1-(3-(2-chlorophenyl)-1,2,4-oxadiazol-5-yl)piperidine-4-carboxylate (0.50 g, 1.55 mmol) as the starting material.

Yield 0.27 g (57%), as a light yellow solid. $^1$H NMR (400 MHz, DMSO) δ 12.38 (br s, 1H), 7.82 (dd, J=1.8, 7.6 Hz, 1H), 7.62 (dd, J=1.4, 8.0 Hz, 1H), 7.57-7.54 (m, 1H), 7.52-7.45 (m, 1H), 4.01-3.94 (m, 2H), 3.30-3.20 (m, 2H), 2.62-2.52 (m, 1H), 2.02-1.89 (m, 2H), 1.70-1.54 (m, 2H). m/z: [ESI$^+$] 308, 310 (M+H)$^+$.

1-(3-(4-Cyanophenyl)-1,2,4-oxadiazol-5-yl)piperidine-4-carboxylic acid. The compound was synthesized according to the procedure described above, using methyl 1-(3-(4-cyanophenyl)-1,2,4-oxadiazol-5-yl)piperidine-4-carboxylate (1.00 g, 3.20 mmol) as the starting material.

Yield 0.85 g (89%), as a light yellow solid. $^1$H NMR (400 MHz, CDCl$_3$) δ 8.13 (d, J=8.6 Hz, 2H), 7.76 (d, J=8.6 Hz, 2H), 4.22-4.16 (m, 2H), 3.41-3.29 (m, 2H), 2.74-2.63 (m, 1H), 2.18-2.08 (m, 2H), 1.97-1.82 (m, 2H). Carboxylic acid proton not observed. m/z: [ESI$^+$] 299 (M+H)$^+$.

1-(3-(3-Cyanophenyl)-1,2,4-oxadiazol-5-yl)piperidine-4-carboxylic acid. The compound was synthesized according to the procedure described above, using methyl 1-(3-(3-cyanophenyl)-1,2,4-oxadiazol-5-yl)piperidine-4-carboxylate (1.00 g, 3.20 mmol) as the starting material.

Yield 0.70 g (73%), as a yellow solid. $^1$H NMR (400 MHz, DMSO) δ 12.37 (br s, 1H), 8.24 (dd, J=1.7, 2.0 Hz, 1H), 8.23-8.18 (m, 1H), 8.06-8.00 (m, 1H), 7.78-7.71 (m, 1H), 4.06-3.95 (m, 2H), 3.35-3.23 (m, 2H), 2.62-2.52 (m, 1H), 2.02-1.90 (m, 2H), 1.70-1.55 (m, 2H). m/z: [ESI+] 299 (M+H)+.

1-(3-(6-Methoxypyridin-3-yl)-1,2,4-oxadiazol-5-yl)piperidine-4-carboxylic acid. The compound was synthesized according to the procedure described above, using methyl 1-(3-(6-methoxypyridin-3-yl)-1,2,4-oxadiazol-5-yl)piperidine-4-carboxylate (1.00 g, 3.14 mmol) as the starting material.

Yield 0.80 g (84%), as a light yellow solid. $^{1}$H NMR (400 MHz, CDCl$_3$) δ 8.81 (dd, J=0.8, 2.4 Hz, 1H), 8.15 (dd, J=2.4, 8.8 Hz, 1H), 6.83 (dd, J=0.8, 8.8 Hz, 1H), 4.24-4.16 (m, 2H), 4.02 (s, 3H), 3.38-3.26 (m, 2H), 2.73-2.61 (m, 1H), 2.17-2.06 (m, 2H), 1.97-1.83 (m, 2H). Carboxylic acid proton not observed. m/z: [ESI+] 305 (M+H)+.

1-(4-(4-Methoxyphenyl)thiazol-2-yl)piperidine-4-carboxylic acid. The compound was synthesized according to the procedure described above, using methyl 1-(4-(4-methoxyphenyl)thiazol-2-yl)piperidine-4-carboxylate (1.20 g, 3.61 mmol) as the starting material.

Yield 1.00 g (87%), as an off-white solid. $^{1}$H NMR (400 MHz, DMSO) δ 7.78 (d, J=8.8 Hz, 2H), 7.07 (s, 1H), 6.94 (d, J=8.8 Hz, 2H), 3.93-3.85 (m, 2H), 3.78 (s, 3H), 3.16-3.04 (m, 2H), 2.50-2.42 (m, 1H), 1.98-1.87 (m, 2H), 1.70-1.53 (m, 2H). Carboxylic acid proton not observed. m/z: [ESI+] 319 (M+H)+.

(1r,4r)-4-(3-(4-Methoxyphenyl)-1,2,4-oxadiazol-5-yl)cyclohexane-1-carboxylic acid (Compound 175). The compound was synthesized according to the procedure described above, using methyl (1r,4r)-4-(3-(4-methoxyphenyl)-1,2,4-oxadiazol-5-yl)cyclohexane-1-carboxylate (3.00 g, 9.48 mmol) as the starting material.

Yield 1.60 g (56%), as an off-white solid. $^{1}$H NMR (400 MHz, DMSO) δ 12.15 (br s, 1H), 7.94 (d, J=8.8 Hz, 2H), 7.10 (d, J=8.8 Hz, 2H), 3.84 (s, 3H), 3.13-3.00 (m, 1H), 2.37-2.24 (m 1H), 2.16 (dd, J=3.6, 13.4 Hz, 2H), 2.02 (dd, J=3.6, 13.4 Hz, 2H), 1.69-1.56 (m, 2H), 1.56-1.41 (m, 2H). m/z: [ESI+] 303 (M+H)+.

(1s,4s)-4-(3-(4-Methoxyphenyl)-1,2,4-oxadiazol-5-yl)cyclohexane-1-carboxylic acid (Compound 173). The compound was synthesized according to the procedure described above, using methyl (1s,4s)-4-(3-(4-methoxyphenyl)-1,2,4-oxadiazol-5-yl)cyclohexane-1-carboxylate (3.00 g, 9.48 mmol) as the starting material.

Yield 2.20 g (77%), as an off-white solid. $^{1}$H NMR (400 MHz, DMSO) δ 7.94 (d, J=8.8 Hz, 2H), 7.10 (d, J=8.8 Hz, 2H), 3.84 (s, 3H), 3.12-3.00 (m, 1H), 2.34-2.23 (m, 1H), 2.16 (dd, J=3.6, 13.4 Hz, 2H), 2.02 (dd, J=3.6, 13.4 Hz, 2H), 1.69-1.55 (m, 2H), 1.56-1.41 (m, 2H). Carboxylic acid proton not observed. m/z: [ESI+] 303 (M+H)+.

1-(3-(4-(Allyloxy)phenyl)-1,2,4-oxadiazol-5-yl)piperidine-4-carboxylic acid. The compound was synthesized according to the procedure described above, using methyl 1-(3-(4-(allyloxy)phenyl)-1,2,4-oxadiazol-5-yl)piperidine-4-carboxylate (2.30 g, 6.70 mmol) as the starting material.

Yield 2.00 g (91%), as an off-white solid. $^{1}$H NMR (400 MHz, DMSO) δ 12.36 (br s, 1H), 7.83 (d, J=8.8 Hz, 2H), 7.07 (d, J=8.8 Hz, 2H), 6.13-6.00 (m, 1H), 5.46-5.36 (m, 1H), 5.34-5.26 (m, 1H), 4.68-4.61 (m, 2H), 4.03-3.95 (m, 2H), 3.29-3.23 (m, 2H), 2.60-2.52 (m, 1H), 1.99-1.92 (m, 2H), 1.71-1.49 (m, 2H). m/z: [ESI+] 330 (M+H)+.

Step 5: Tert-butyl 3-((1-(3-(4-methoxyphenyl)-1,2,4-oxadiazol-5-yl)piperidine-4-carboxamido)methyl)pyrrolidine-1-carboxylate To a stirred solution of 1-[3-(4-methoxyphenyl)-1,2,4-oxadiazol-5-yl]piperidine-4-carboxylic acid (1.00 g, 3.30 mmol) in DMF (5 mL) were added HATU (1.50 g, 3.94 mmol), DIPEA (0.85 g, 6.58 mmol) and tert-butyl 3-(aminomethyl)pyrrolidine-1-carboxylate (0.79 g, 3.94 mmol). The resulting solution was stirred for 2 h at room temperature. The resulting mixture was concentrated under reduced pressure. The resulting residue was purified by reverse phase flash chromatography with the following conditions: Column: Spherical C18, 20-40 um, 330 g; Mobile Phase A: water (plus 10 mM NH$_4$HCO$_3$); Mobile Phase B: acetonitrile; Flow rate: 80 mL/min; Gradient: 50% B-75% B in 20 min; Detector: UV 220/254 nm. The fractions containing the desired product were collected and concentrated under reduced pressure to afford tert-butyl 3-((1-(3-(4-methoxyphenyl)-1,2,4-oxadiazol-5-yl)piperidine-4-carboxamido)methyl)pyrrolidine-1-carboxylate as a light yellow oil.

Yield: 1.40 g (87%). $^{1}$H NMR (400 MHz, DMSO) δ 7.99 (t, J=5.4 Hz, 1H), 7.84 (d, J=8.8 Hz, 2H), 7.05 (d, J=8.8 Hz, 2H), 4.06 (d, J=12.6 Hz, 2H), 3.82 (s, 3H), 3.33-3.25 (m, 2H), 3.25-2.99 (m, 5H), 2.94-2.85 (m, 1H), 2.47-2.38 (m, 1H), 2.32-2.21 (m, 1H), 1.91-1.77 (m, 3H), 1.69-1.47 (m, 3H), 1.39 (s, 9H). m/z: [ESI+] 486 (M+H)+.

The intermediates below were prepared according to the procedure described above.

Tert-butyl 4-(((1-(4-methylbenzyl)pyrrolidin-3-yl)methyl)carbamoyl)piperidine-1-carboxylate. The compound was synthesized according to the procedure described above, using 1-(tert-butoxycarbonyl)piperidine-4-carboxylic acid (1.44 g, 6.28 mmol) and (1-(4-methylbenzyl)pyrrolidin-3-yl)methanamine (1.41 g, 6.91 mmol) as the starting material.

Yield 1.08 g (41%), as a yellow oil. $^{1}$H NMR (400 MHz, CDCl$_3$) δ 7.22 (d, J=8.0 Hz, 2H), 7.16 (d, J=8.0 Hz, 2H), 6.79 (br s, 1H), 4.28-4.02 (m, 2H), 3.69-3.53 (m, 2H), 3.34-3.16 (m, 2H), 3.01-2.88 (m, 1H), 2.83-2.70 (m, 2H), 2.68-2.61 (m, 1H), 2.53-2.45 (m, 2H), 2.37 (s, 3H), 2.28-2.17 (m, 1H), 2.10-2.00 (m, 1H), 1.79 (d, J=13.6 Hz, 2H), 1.73-1.54 (m, 4H), 1.49 (s, 9H). m/z: [ESI+] 416 (M+H)+.

Tert-butyl 3-(((1s,4s)-4-(3-(4-methoxyphenyl)-1,2,4-oxadiazol-5-yl)cyclohexane-1-carboxamido)methyl)pyrrolidine-1-carboxylate. The compound was synthesized according to the procedure described above, using (1s,4s)-4-(3-(4-methoxyphenyl)-1,2,4-oxadiazol-5-yl)cyclohexane-1-carboxylic acid (0.40 g, 1.32 mmol) and tert-butyl 3-(aminomethyl)pyrrolidine-1-carboxylate (0.32 g, 1.59 mmol) as the starting material.

Yield 0.40 g (63%), as an off-white solid. $^{1}$H NMR (400 MHz, DMSO) δ 7.94 (d, J=8.8 Hz, 2H), 7.93 (br s, 1H), 7.10 (d, J=8.8 Hz, 2H), 3.84 (s, 3H), 3.32-3.25 (m, 1H), 3.23-3.14 (m, 1H), 3.12-2.99 (m, 3H), 2.97-2.85 (m, 1H), 2.31-2.10 (m, 3H), 1.89-1.79 (m, 4H), 1.66-1.48 (m, 6H), 1.40 (s, 9H). m/z: [ESI+] 485 (M+H)+.

Tert-butyl 3-(((1r,4r)-4-(3-(4-methoxyphenyl)-1,2,4-oxadiazol-5-yl)cyclohexane-1-carboxamido)methyl)pyrrolidine-1-carboxylate. The compound was synthesized according to the procedure described above, using (1r,4r)-4-(3-(4-methoxyphenyl)-1,2,4-oxadiazol-5-yl)cyclohexane-1-carboxylic acid (0.50 g, 1.65 mmol) and tert-butyl 3-(aminomethyl)pyrrolidine-1-carboxylate (0.40 g, 2.00 mmol) as the starting material.

Yield 0.70 g (87%), as an off-white solid. $^{1}$H NMR (400 MHz, DMSO) δ 7.94 (d, J=8.8 Hz, 2H), 7.93 (br s, 1H), 7.11 (d, J=8.8 Hz, 2H), 3.84 (s, 3H), 3.34-3.24 (m, 1H), 3.22-3.11 (m, 1H), 3.10-2.96 (m, 3H), 2.97-2.85 (m, 1H), 2.34-2.13 (m, 3H), 1.88-1.80 (m, 4H), 1.66-1.48 (m, 6H), 1.40 (s, 9H). m/z: [ESI+] 485 (M+H)+.

Tert-butyl 3-(4-(3-(4-methoxyphenyl)-1,2,4-oxadiazol-5-yl)piperazine-1-carbonyl)piperidine-1-carboxylate. The compound was synthesized according to the procedure described above, using 1-(tert-butoxycarbonyl)piperidine-3-carboxylic acid (0.50 g, 2.18 mmol) and 3-(4-methoxyphenyl)-5-(piperazin-1-yl)-1,2,4-oxadiazole (0.68 g, 2.61 mmol) as the starting material.

Yield 0.60 g (58%), as a light yellow oil. ¹H NMR (400 MHz, DMSO) δ 7.85 (d, J=8.8 Hz, 2H), 7.06 (d, J=8.8 Hz, 2H), 3.95-3.85 (m, 2H), 3.82 (s, 3H), 3.72-3.53 (m, 8H), 2.81 (m, 1H), 2.76-2.65 (m, 2H), 1.87-1.79 (m, 1H), 1.71-1.60 (m, 1H), 1.58-1.41 (m, 2H), 1.41 (s, 9H). m/z: [ESI⁺] 472 (M+H)⁺.

Tert-butyl 4-(3-(1-(3-(4-methoxyphenyl)-1,2,4-oxadiazol-5-yl)piperidine-4-carboxamido)propyl)piperazine-1-carboxylate. The compound was synthesized according to the procedure described above, using 1-(3-(4-methoxyphenyl)-1,2,4-oxadiazol-5-yl)piperidine-4-carboxylic acid (0.20 g, 0.66 mmol) and tert-butyl 4-(3-aminopropyl)piperazine-1-carboxylate (0.19 g, 0.78 mmol) as the starting material.

Yield 0.27 g (77%), as a light yellow solid. ¹H NMR (400 MHz, CDCl₃) δ 7.95 (d, J=8.8 Hz, 2H), 6.97 (d, J=8.8 Hz, 2H), 6.82 (br s, 1H), 4.28 (td, J=3.6, 12.8 Hz, 2H), 3.87 (s, 3H), 3.49-3.43 (m, 4H), 3.42-3.34 (m, 2H), 3.28-3.16 (m, 2H), 2.49 (t, J=6.3 Hz, 2H), 2.46-2.41 (m, 4H), 2.36-2.25 (m, 1H), 1.97 (dd, J=3.6, 13.6 Hz, 2H), 1.92-1.82 (m, 2H), 1.78-1.63 (m, 2H), 1.49 (s, 9H). m/z: [ESI⁺] 529 (M+H)⁺.

Tert-butyl 3-((1-(3-(4-chlorophenyl)-1,2,4-oxadiazol-5-yl)piperidine-4-carboxamido)methyl)pyrrolidine-1-carboxylate. The compound was synthesized according to the procedure described above, using 1-(3-(4-chlorophenyl)-1,2,4-oxadiazol-5-yl)piperidine-4-carboxylic acid (0.30 g, 0.97 mmol) and tert-butyl 3-(aminomethyl)pyrrolidine-1-carboxylate (0.23 g, 1.15 mmol) as the starting material.

Yield 0.40 g (85%), as a light yellow solid. ¹H NMR (400 MHz, CDCl₃) δ 8.11 (d, J=8.4 Hz, 2H), 7.74 (d, J=8.4 Hz, 2H), 5.97 (br s, 1H), 4.38-4.16 (m, 2H), 3.55-3.39 (m, 3H), 3.35-3.28 (m, 2H), 3.27-3.17 (m, 2H), 3.15-3.04 (m, 1H), 2.48-2.35 (m, 2H), 2.01-1.93 (m, 3H), 1.94-1.86 (m, 2H), 1.66-1.55 (m, 1H), 1.47 (s, 9H). m/z: [ESI⁺] 490, 492 (M+H)⁺.

Tert-butyl 3-((1-(3-(4-cyanophenyl)-1,2,4-oxadiazol-5-yl)piperidine-4-carboxamido)methyl)pyrrolidine-1-carboxylate. The compound was synthesized according to the procedure described above, using 1-(3-(4-cyanophenyl)-1,2,4-oxadiazol-5-yl)piperidine-4-carboxylic acid (0.30 g, 1.01 mmol) and tert-butyl 3-(aminomethyl)pyrrolidine-1-carboxylate (0.24 g, 1.20 mmol) as the starting material.

Yield 0.40 g (82%), as a light yellow solid. ¹H NMR (400 MHz, CDCl₃) δ 7.94 (d, J=8.6 Hz, 2H), 7.43 (d, J=8.6 Hz, 2H), 5.77 (br s, 1H), 4.37-4.20 (m, 2H), 3.53-3.40 (m, 2H), 3.35-3.28 (m, 2H), 3.26-3.14 (m, 3H), 3.04 (s, 1H), 2.50-2.28 (m, 2H), 2.00-1.94 (m, 3H), 1.93-1.81 (m, 2H), 1.66-1.57 (m, 1H), 1.47 (s, 9H). m/z: [ESI⁺] 481 (M+H)⁺.

Tert-butyl (1R,5S,6s)-6-(1-(3-(4-methoxyphenyl)-1,2,4-oxadiazol-5-yl)piperidine-4-carboxamido)-3-azabicyclo[3.1.0]hexane-3-carboxylate. The compound was synthesized according to the procedure described above, using 1-(3-(4-methoxyphenyl)-1,2,4-oxadiazol-5-yl)piperidine-4-carboxylic acid (0.30 g, 0.99 mmol) and tert-butyl (1R,5S,6s)-6-amino-3-azabicyclo[3.1.0]hexane-3-carboxylate (0.24 g, 1.21 mmol) as the starting material.

Yield 0.29 g (61%), as a light yellow solid. ¹H NMR (400 MHz, CDCl₃) δ 7.94 (d, J=8.8 Hz, 2H), 6.96 (d, J=8.8 Hz, 2H), 5.72 (d, J=2.4 Hz, 1H), 4.34-4.22 (m, 2H), 3.87 (s, 3H), 3.77-3.65 (m, 2H), 3.44-3.32 (m, 2H), 3.25-3.11 (m, 2H), 2.50-2.44 (m, 1H), 2.37-2.26 (m, 1H), 1.99-1.89 (m, 2H), 1.89-1.73 (m, 2H), 1.69-1.64 (m, 2H), 1.44 (s, 9H). m/z: [ESI⁺] 484 (M+H)⁺.

Tert-butyl (R)-2-((1-(3-(4-methoxyphenyl)-1,2,4-oxadiazol-5-yl)piperidine-4-carboxamido)methyl)pyrrolidine-1-carboxylate. The compound was synthesized according to the procedure described above, using 1-(3-(4-methoxyphenyl)-1,2,4-oxadiazol-5-yl)piperidine-4-carboxylic acid (0.10 g, 0.33 mmol) and tert-butyl (2R)-2-(aminomethyl)pyrrolidine-1-carboxylate (79 mg, 0.394 mmol) as the starting material.

Yield 0.10 g (64%), as a light yellow solid. ¹H NMR (400 MHz, CDCl₃) δ 7.95 (d, J=8.8 Hz, 2H), 7.78 (br s, 1H), 6.97 (d, J=8.8 Hz, 2H), 4.33-4.21 (m, 2H), 4.12-4.01 (m, 1H), 3.87 (s, 3H), 3.42-3.33 (m, 3H), 3.27-3.15 (m, 3H), 2.42-2.30 (m, 1H), 2.09-1.97 (m, 3H), 1.96-1.76 (m, 4H), 1.73-1.6 (m, 1H), 1.49 (s, 9H). m/z: [ESI⁺] 486 (M+H)⁺.

Tert-butyl (R)-3-((1-(3-(4-methoxyphenyl)-1,2,4-oxadiazol-5-yl)piperidine-4-carboxamido)methyl)pyrrolidine-1-carboxylate. The compound was synthesized according to the procedure described above, using 1-(3-(4-methoxyphenyl)-1,2,4-oxadiazol-5-yl)piperidine-4-carboxylic acid (0.40 g, 1.32 mmol) and tert-butyl (3R)-3-(aminomethyl)pyrrolidine-1-carboxylate (0.32 g, 1.60 mmol) as the starting material.

Yield 0.50 g (78%), as a light yellow solid. ¹H NMR (400 MHz, CDCl₃) δ 7.94 (d, J=8.8 Hz, 2H), 6.96 (d, J=8.8 Hz, 2H), 5.73 (br s, 1H), 4.37-4.20 (m, 2H), 3.87 (s, 3H), 3.55-3.39 (m, 3H), 3.32 (d, J=9.0 Hz, 2H), 3.26-3.12 (m, 2H), 3.12-2.93 (m, 1H), 2.52-2.28 (m, 1H), 2.04-1.92 (m, 3H), 1.92-1.80 (m, 3H), 1.68-1.56 (m, 1H), 1.48 (s, 9H). m/z: [ESI⁺] 486 (M+H)⁺.

Tert-butyl (S)-3-((1-(3-(4-methoxyphenyl)-1,2,4-oxadiazol-5-yl)piperidine-4-carboxamido)methyl)pyrrolidine-1-carboxylate. The compound was synthesized according to the procedure described above, using 1-(3-(4-methoxyphenyl)-1,2,4-oxadiazol-5-yl)piperidine-4-carboxylic acid (0.50 g, 1.65 mmol) and tert-butyl (3S)-3-(aminomethyl)pyrrolidine-1-carboxylate (0.40 g, 2.00 mmol).

Yield 0.34 g (42%), as an off-white solid. ¹H NMR (400 MHz, CDCl₃) δ 7.97 (d, J=8.8 Hz, 2H), 6.97 (d, J=8.8 Hz, 2H), 5.70 (t, J=5.6 Hz, 1H), 4.33 (d, J=13.2 Hz, 2H), 3.88 (s, 3H), 3.55-3.28 (m, 3H), 3.28-3.14 (m, 3H), 3.10-3.00 (m, 1H), 2.50-2.30 (m, 2H), 2.04-1.96 (m, 4H), 1.94-1.80 (m, 2H), 1.66-1.56 (m, 1H), 1.48 (s, 9H). m/z: [ESI⁺] 486 (M+H)⁺.

1-(3-(4-(Allyloxy)phenyl)-1,2,4-oxadiazol-5-yl)-N-((1-(4-methylbenzyl)pyrrolidin-3-yl)methyl)piperidine-4-carboxamide. The compound was synthesized according to the procedure described above, using 1-(3-(4-(allyloxy)phenyl)-1,2,4-oxadiazol-5-yl)piperidine-4-carboxylic acid (0.50 g, 1.52 mmol) and (1-(4-methylbenzyl)pyrrolidin-3-yl)methanamine (0.42 g, 2.06 mmol).

Yield 0.54 g (69%), as an off-white solid. ¹H NMR (400 MHz, CDCl₃) δ 7.95 (d, J=8.8 Hz, 2H), 7.20 (d, J=8.0 Hz, 2H), 7.16 (d, J=8.0 Hz, 2H), 7.00 (d, J=8.8 Hz, 2H), 6.94 (br s, 1H), 6.18-6.01 (m, 1H), 5.51-5.39 (m, 1H), 5.38-5.27 (m, 1H), 4.61 (td, J=1.6, 5.4 Hz, 2H), 4.36-4.16 (m, 2H), 3.59 (s, 2H), 3.39-3.27 (m, 1H), 3.27-3.13 (m, 3H), 3.00-2.88 (m, 1H), 2.73-2.63 (m, 1H), 2.54-2.43 (m, 2H), 2.37 (s, 3H), 2.32-2.28 (m, 1H), 2.14-2.01 (m, 1H), 2.00-1.88 (m, 2H), 1.85-1.75 (m, 2H), 1.67-1.49 (m, 2H). m/z: [ESI⁺] 516 (M+H)⁺.

Step 6: 1-[3-(4-Methoxyphenyl)-1,2,4-oxadiazol-5-yl]-N-(pyrrolidin-3-ylmethyl)piperidine-4-carboxamide hydrochloride To a solution of tert-butyl 3-((1-(3-(4-methoxyphenyl)-1,2,4-oxadiazol-5-yl)piperidine-4-carboxamido)methyl)pyrrolidine-1-carboxylate (7.00 g, 14.42 mmol) in DCM (150 mL) was added a 4M solution of HCl in dioxane (70 mL) at room temperature. The resulting solution was stirred for 3 h at room temperature. The mixture was then concentrated under reduced pressure, triturated with diethyl ether (3×10 mL) and air dried, to afford 1-[3-(4-methoxyphenyl)-1,2,4-oxadiazol-5-yl]-N-(pyrrolidin-3-ylmethyl)piperidine-4-carboxamide hydrochloride as a brown solid.

Yield: 5.00 g (82%). $^1$H NMR (400 MHz, CD$_3$OD) δ 7.90 (d, J=8.4 Hz, 2H), 7.06 (d, J=8.4 Hz, 2H), 4.36-4.22 (m, 2H), 3.88 (s, 3H), 3.47-3.38 (m, 2H), 3.35-3.26 (m, 5H), 3.04-2.95 (m, 1H), 2.65-2.54 (m, 2H), 2.25-2.15 (m, 1H), 2.01-1.94 (m, 2H), 1.90-1.71 (m, 3H). m/z: [ESI$^+$] 386 (M+H)$^+$.

The following compounds were synthesized according to the procedure described above. A selection of compounds were treated with trifluoroacetic acid (5 eq.) producing the corresponding trifluoroacetate salt. Purification by reverse phase chromatography with the addition of ammonium bicarbonate produced the parent compound, while the addition of formic acid, produced corresponding formate salt.

3-(4-Methoxyphenyl)-5-(piperazin-1-yl)-1,2,4-oxadiazole. The compound was synthesized according to the procedure described above, using tert-butyl 4-(3-(4-methoxyphenyl)-1,2,4-oxadiazol-5-yl)piperazine-1-carboxylate (1.00 g, 2.77 mmol) as the starting material.

Yield 0.58 g (81%), as an off-white solid. $^1$H NMR (400 MHz, DMSO) δ 7.84 (d, J=8.8 Hz, 2H), 7.05 (d, J=8.8 Hz, 2H), 3.82 (s, 3H), 3.56-3.42 (m, 4H), 2.88-2.71 (m, 4H). m/z: [ESI$^+$] 261 (M+H)$^+$.

4-(5-(Piperazin-1-yl)-1,2,4-oxadiazol-3-yl)benzonitrile hydrochloride. The compound was synthesized according to the procedure described above, using tert-butyl 4-(3-(4-cyanophenyl)-1,2,4-oxadiazol-5-yl)piperazine-1-carboxylate (2.50 g, 7.03 mmol) as the starting material.

Yield 1.70 g (83%), as an off-white solid. $^1$H NMR (400 MHz, CD$_3$OD) δ 8.15 (d, J=8.0 Hz, 2H), 7.87 (d, J=8.0 Hz, 2H), 4.01 (t, J=5.4 Hz, 4H), 3.44 (t, J=5.4 Hz, 4H). Aliphatic NH proton not observed. m/z: [ESI$^+$] 256 (M+H)$^+$.

5-(Piperazin-1-yl)-3-(4-(trifluoromethoxy)phenyl)-1,2,4-oxadiazole. The compound was synthesized according to the procedure described above, using tert-butyl 4-(3-(4-(trifluoromethoxy)phenyl)-1,2,4-oxadiazol-5-yl)piperazine-1-carboxylate (4.25 g, 10.26 mmol) as the starting material.

Yield 2.50 g (78%), as an off-white solid. m/z: [ESI$^+$] 315 (M+H)$^+$. Crude material was used in the next step without further purification.

3-(4-(Difluoromethoxy)phenyl)-5-(piperazin-1-yl)-1,2,4-oxadiazole. The compound was synthesized according to the procedure described above, using tert-butyl 4-(3-(4-(difluoromethoxy)phenyl)-1,2,4-oxadiazol-5-yl)piperazine-1-carboxylate (3.10 g, 7.82 mmol) as the starting material.

Yield 2.00 g (86%), as an off-white solid. $^1$H NMR (400 MHz, DMSO) δ 7.96 (d, J=8.8 Hz, 2H), 7.37 (t, J=73.6 Hz, 1H), 7.33 (d, J=8.8 Hz, 2H), 3.89-3.82 (m, 4H), 3.30-3.23 (m, 4H). Aliphatic NH proton not observed. m/z: [ESI$^+$] 297 (M+H)$^+$.

3-(4-(Difluoromethyl)phenyl)-5-(piperazin-1-yl)-1,2,4-oxadiazole. The compound was synthesized according to the procedure described above, using tert-butyl 4-(3-(4-(difluoromethyl)phenyl)-1,2,4-oxadiazol-5-yl)piperazine-1-carboxylate (6.00 g, 15.77 mmol) as the starting material.

Yield 4.00 g (90%), as an off-white solid. $^1$H NMR (400 MHz, DMSO-d) δ 8.05 (d, J=8.0 Hz, 2H), 7.73 (d, J=8.0 Hz, 2H), 7.13 (t, J=55.6 Hz, 1H), 3.89 (t, J=5.2 Hz, 4H), 3.77 (br s, 1H), 3.26 (t, J=5.2 Hz, 4H). m/z: [ESI$^+$] 281 (M+H)$^+$.

3-(4-(Allyloxy)phenyl)-5-(piperazin-1-yl)-1,2,4-oxadiazol hydrochloride. The compound was synthesized according to the procedure described above, using tert-butyl 4-(3-(4-(allyloxy)phenyl)-1,2,4-oxadiazol-5-yl)piperazine-1-carboxylate (4.00 g, 10.35 mmol) as the starting material.

Yield 2.80 g (84%), as an off-white solid. $^1$H NMR (400 MHz, DMSO) δ 9.67 (br s, 2H), 7.84 (d, J=8.8 Hz, 2H), 7.09 (d, J=8.8 Hz, 2H), 6.06 (tdd, J=5.4, 10.6, 17.2 Hz, 1H), 5.42 (td, J=1.6, 17.2 Hz, 1H), 5.28 (td, J=1.6, 10.6 Hz, 1H), 4.64 (td, J=1.6, 5.4 Hz, 2H), 3.86 (t, J=5.4 Hz, 4H), 3.24 (t, J=5.4 Hz, 4H). m/z: [ESI$^+$] 287 (M+H)$^+$.

4-(3-(4-Methoxyphenyl)-1,2,4-oxadiazol-5-yl)-N-(pyrrolidin-3-ylmethyl)piperazine-1-carboxamide hydrochloride. The compound was synthesized according to the procedure described above, using tert-butyl 3-((4-(3-(4-methoxyphenyl)-1,2,4-oxadiazol-5-yl)piperazine-1-carboxamido)methyl)pyrrolidine-1-carboxylate (0.80 g, 1.64 mmol) as the starting material.

Yield 0.50 g (72%), as a light brown solid. $^1$H NMR (400 MHz, DMSO) δ 9.55 (br s, 2H), 7.82 (d, J=8.8 Hz, 2H), 7.45 (br s, 1H), 7.03 (d, J=8.8 Hz, 2H), 3.79 (s, 3H), 3.66-3.60 (m, 2H), 3.56-3.52 (m, 4H), 3.51-3.45 (m, 4H), 3.44-3.40 (m, 2H), 3.10-2.98 (m, 2H), 2.48-2.38 (m, 1H), 2.01-1.82 (m, 1H), 1.66-1.55 (m, 1H). m/z: [ESI$^+$] 387 (M+H)$^+$.

N-((1-(4-methylbenzyl)pyrrolidin-3-yl)methyl)piperidine-4-carboxamide. The compound was synthesized according to the procedure described above, using tert-butyl 4-(((1-(4-methylbenzyl)pyrrolidin-3-yl)methyl)carbamoyl)piperidine-1-carboxylate (2.58 g, 6.21 mmol) as the starting material.

Yield 0.86 g (44%), as a light yellow solid. $^1$H NMR (400 MHz, CDCl$_3$) δ 7.66 (br s, 1H), 7.29 (d, J=8.0 Hz, 2H), 7.21 (d, J=8.0 Hz, 2H), 3.41 (d, J=13.8 Hz, 2H), 3.37-3.31 (m, 1H), 3.31-3.21 (m, 2H), 3.12-3.01 (m, 2H), 3.00-2.83 (m, 3H), 2.76-2.65 (m, 1H), 2.56-2.44 (m, 1H), 2.38 (s, 3H), 2.23-2.09 (m, 2H), 2.06-1.96 (m, 5H), 1.82-1.72 (m, 1H). Aliphatic NH proton not observed. m/z: [ESI$^+$] 316 (M+H)$^+$.

3-(4-Phenoxypiperidin-1-yl)propan-1-amine hydrochloride. The compound was synthesized according to the procedure described above, using tert-butyl (3-(4-phenoxypiperidin-1-yl)propyl)carbamate (0.20 g, 0.60 mmol) as the starting material.

Yield 0.12 g (73%), as a light yellow solid. m/z: [ESI$^+$] 235 (M+H)$^+$.

3-(4-(Pyridin-2-ylmethyl)piperidin-1-yl)propan-1-amine hydrochloride. The compound was synthesized according to the procedure described above, using tert-butyl (3-(4-(pyridin-2-ylmethyl)piperidin-1-yl)propyl)carbamate (100 mg, 0.300 mmol) as the starting material.

Yield 50 mg (62%), as a light yellow solid. m/z: [ESI$^+$] 234 (M+H)$^+$.

2-(1-(Pyridin-2-ylmethyl)piperidin-4-yloxy)ethanamine dihydrochloride. The compound was synthesized according to the procedure described above, using tert-butyl 2-(1-(pyridin-2-ylmethyl)piperidin-4-yloxy)ethylcarbamate (0.35 g, 1.04 mmol) as the starting material.

Yield 0.25 g (78%), as an off-white solid. $^1$H NMR (400 MHz, DMSO) δ 10.60 (br s, 1H), 8.69 (dd, J=1.6, 4.8 Hz, 1H), 8.18 (br s, 3H, NH$_3$*), 7.96 (dd, J=6.8, 8.4 Hz, 1H), 7.75-7.68 (m, 1H), 7.50 (dd, J=4.8, 7.6 Hz, 1H), 4.50 (s, 2H), 3.70-3.64 (m, 1H), 3.61 (t, J=5.2 Hz, 2H), 3.47-3.41 (m, 2H), 3.16-3.01 (m, 2H), 3.03-2.93 (m, 2H), 2.07-1.97 (m, 2H), 1.96-1.86 (m, 2H). m/z: [ESI$^+$] 236 (M+H)$^+$.

3-(4-Fluoro-4-(pyridin-2-ylmethyl)piperidin-1-yl)propan-1-amine. The compound was synthesized according to the procedure described above, using tert-butyl (3-(4-fluoro-4-(pyridin-2-ylmethyl)piperidin-1-yl)propyl)carbamate (0.30 g, 0.85 mmol) as the starting material.

Yield 0.20 g (93%), as a yellow solid. ¹H NMR (400 MHz, CD₃OD) δ 8.91-8.79 (m, 1H), 8.65 (dd, J=6.8, 8.4 Hz, 1H), 8.15-7.98 (m, 2H), 3.96 (d, J=5.4 Hz, 2H), 3.84-3.59 (m, 2H), 3.41-3.34 (m, 4H), 3.22-3.02 (m, 4H), 2.46-2.40 (m, 1H), 2.28-2.18 (m, 2H), 2.17-2.08 (m, 1H). Aliphatic NH₂ not observed. m/z: [ESI⁺] 252 (M+H)⁺.

3-(4-(2-Fluorobenzyl)piperidin-1-yl)propan-1-amine. The compound was synthesized according to the procedure described above, using tert-butyl (3-(4-(2-fluorobenzyl)piperidin-1-yl)propyl)carbamate (0.15 g, 0.43 mmol) as the starting material.

Yield 0.10 g (93%), as a yellow solid. ¹H NMR (400 MHz, DMSO) δ 7.36-7.22 (m, 2H), 7.22-7.08 (m, 2H), 3.46-3.36 (m, 2H), 3.11-3.04 (m, 2H), 2.96-2.77 (m, 4H), 2.61-2.56 (m, 2H), 2.08-1.98 (m, 2H), 1.89-1.53 (m, 5H). Aliphatic NH₂ not observed. m/z: [ESI⁺] 251 (M+H)⁺.

3-(4-Fluoro-4-(pyridin-2-yl)piperidin-1-yl)propan-1-amine. The compound was synthesized according to the procedure described above, using tert-butyl (3-(4-fluoro-4-(pyridin-2-yl)piperidin-1-yl)propyl)carbamate (1.20 g, 3.56 mmol) as the starting material.

Yield 0.80 g (95%), as a yellow solid. ¹H NMR (400 MHz, DMSO) δ 8.66-8.59 (m, 1H), 7.94 (dd, J=1.6, 7.8 Hz, 1H), 7.63 (dd, J=1.2, 7.8 Hz, 1H), 7.58-40 (m, 1H), 3.61-3.52 (m, 2H), 3.33-3.12 (m, 4H), 2.98-2.93 (m, 2H), 2.84-2.59 (m, 2H), 2.27-2.17 (m, 2H), 2.17-2.06 (m, 2H). Aliphatic NH₂ not observed. m/z: [ESI⁺] 238 (M+H)⁺.

5-(Azetidin-3-yl)-3-(4-methoxyphenyl)-1,2,4-oxadiazole. The compound was synthesized according to the procedure described above, using tert-butyl 3-(3-(4-methoxyphenyl)-1,2,4-oxadiazol-5-yl)azetidine-1-carboxylate (1.00 g, 3.02 mmol) as the starting material.

Yield 0.55 g (79%), as a brown oil. ¹H NMR (400 MHz, CDCl₃) δ 8.05 (d, J=8.8 Hz, 2H), 7.01 (d, J=8.8 Hz, 2H), 4.32-4.22 (m, 1H), 4.18 (t, J=8.1 Hz, 2H), 4.03 (t, J=8.1 Hz, 2H), 3.90 (s, 3H). Aliphatic NH not observed. m/z: [ESI⁺] 232 (M+H)⁺.

(1s,4s)-4-(3-(4-Methoxyphenyl)-1,2,4-oxadiazol-5-yl)-N-(pyrrolidin-3-ylmethyl)cyclohexane-1-carboxamide hydrochloride. The compound was synthesized according to the procedure described above, using tert-butyl 3-(((1s,4s)-4-(3-(4-methoxyphenyl)-1,2,4-oxadiazol-5-yl)cyclohexane-1-carboxamido) methyl)pyrrolidine-1-carboxylate (0.40 g, 0.83 mmol) as the starting material.

Yield 0.30 g (86%), as an off-white solid. ¹H NMR (400 MHz, DMSO) δ 9.24 (br s, 2H), 8.09 (t, J=5.6 Hz, 1H), 7.93 (d, J=8.8 Hz, 1H), 7.10 (d, J=8.8 Hz, 2H), 3.83 (s, 3H), 3.25-3.03 (m, 6H), 2.80-2.70 (m, 1H), 2.45-2.33 (m, 1H), 2.27-2.15 (m, 3H), 2.02-1.90 (m, 1H), 1.89-1.81 (m, 2H), 1.66-1.46 (m, 5H). [ESI⁺] 385 (M+H)⁺.

(1r,4r)-4-(3-(4-methoxyphenyl)-1,2,4-oxadiazol-5-yl)-N-(pyrrolidin-3-ylmethyl)cyclohexane-1-carboxamide hydrochloride. The compound was synthesized according to the procedure described above, using tert-butyl 3-(((1r,4r)-4-(3-(4-methoxyphenyl)-1,2,4-oxadiazol-5-yl)cyclohexane-1-carboxamido)methyl)pyrrolidine-1-carboxylate (0.70 g, 1.44 mmol) as the starting material.

Yield 0.40 g (66%), as an off-white solid. ¹H NMR (400 MHz, DMSO) δ 9.08 (br s, 2H), 8.06 (t, J=5.8 Hz, 1H), 7.94 (d, J=8.8 Hz, 2H), 7.11 (d, J=8.8 Hz, 2H), 3.84 (s, 3H), 3.26-3.01 (m, 6H), 2.80-2.70 (m, 1H), 2.45-2.33 (m, 1H), 2.27-2.16 (m, 3H), 2.02-1.90 (m, 1H), 1.91-1.84 (m, 2H), 1.69-1.46 (m, 5H). m/z: [ESI⁺] 385 (M+H)⁺.

(4-(3-(4-Methoxyphenyl)-1,2,4-oxadiazol-5-yl)piperazin-1-yl)(piperidin-3-yl)methanone hydrochloride. The compound was synthesized according to the procedure described above, using tert-butyl 3-(4-(3-(4-methoxyphenyl)-1,2,4-oxadiazol-5-yl)piperazine-1-carbonyl)piperidine-1-carboxylate (0.80 g, 1.70 mmol) as the starting material.

Yield 0.60 g (86%), as a light yellow solid. ¹H NMR (400 MHz, DMSO) δ 9.26 (br s, 1H), 9.07 (br s, 1H), 7.85 (d, J=8.8 Hz, 2H), 7.06 (d, J=8.8 Hz, 2H), 3.82 (s, 3H), 3.76-3.58 (m, 8H), 3.28-3.13 (m, 3H), 3.04-2.78 (m, 2H), 1.92-1.83 (m, 1H), 1.83-1.70 (m, 2H), 1.68-1.43 (m, 1H). m/z: [ESI⁺] 372 (M+H)⁺.

1-(3-(4-Methoxyphenyl)-1,2,4-oxadiazol-5-yl)-N-(3-(piperazin-1-yl)propyl)piperidine-4-carboxamide hydrochloride. The compound was synthesized according to the procedure described above, using tert-butyl 4-(3-(1-(3-(4-methoxyphenyl)-1,2,4-oxadiazol-5-yl)piperidine-4-carboxamido)propyl)piperazine-1-carboxylate (0.20 g, 0.38 mmol) as the starting material.

Yield 0.15 g (84%), as a light brown solid. m/z: [ESI⁺] 429 (M+H)⁺.

1-(3-(4-Chlorophenyl)-1,2,4-oxadiazol-5-yl)-N-(pyrrolidin-3-ylmethyl)piperidine-4-carboxamide trifluoroacetate. The compound was synthesized according to the procedure described above, using tert-butyl 3-((1-(3-(4-chlorophenyl)-1,2,4-oxadiazol-5-yl)piperidine-4-carboxamido) methyl)pyrrolidine-1-carboxylate (0.20 g, 0.41 mmol) as the starting material.

Yield 0.12 g (61%), as a light yellow solid. ¹H NMR (400 MHz, CD₃OD) δ 7.95 (d, J=8.4 Hz, 2H), 7.51 (d, J=8.4 Hz, 2H), 4.29-4.22 (m, 2H), 3.88-3.82 (m, 1H), 3.64-3.53 (m, 2H), 3.46-3.36 (m, 2H), 3.31-3.22 (m, 2H), 3.05-2.95 (m, 1H), 2.62-2.54 (m, 2H), 2.22-2.12 (m, 1H), 2.01-1.90 (m, 2H), 1.89-1.64 (m, 3H). m/z: [ESI⁺] 390, 392 (M+H)⁺.

1-(3-(4-Cyanophenyl)-1,2,4-oxadiazol-5-yl)-N-(pyrrolidin-3-ylmethyl)piperidine-4-carboxamide trifluoroacetate. The compound was synthesized according to the procedure described above, using tert-butyl 3-((1-(3-(4-cyanophenyl)-1,2,4-oxadiazol-5-yl)piperidine-4-carboxamido)methyl)pyrrolidine-1-carboxylate (0.20 g, 0.42 mmol) as the starting material.

Yield 0.20 g (crude), as a light yellow solid. ¹H NMR (400 MHz, CD₃OD) δ 8.13 (d, J=8.0 Hz, 2H), 7.86 (d, J=8.0 Hz, 2H), 4.27 (dd, J=4.0, 12.8 Hz, 2H), 3.65-3.51 (m, 1H), 3.47-3.36 (m, 2H), 3.321-3.25 (m, 4H), 3.02-2.96 (m, 1H), 2.64-2.53 (m, 2H), 2.23-2.12 (m, 1H), 1.99-1.89 (m, 2H), 1.87-1.73 (m, 3H). m/z: [ESI⁺] 381 (M+H)⁺.

N-((1R,5S,6s)-3-azabicyclo[3.1.0]hexan-6-yl)-1-(3-(4-methoxyphenyl)-1,2,4-oxadiazol-5-yl)piperidine-4-carboxamide hydrochloride. The compound was synthesized according to the procedure described above, using tert-butyl (1R,5S,6s)-6-(1-(3-(4-methoxyphenyl)-1,2,4-oxadiazol-5-yl)piperidine-4-carboxamido)-3-azabicyclo[3.1.0]hexane-3-carboxylate (0.29 g, 0.60 mmol) as the starting material.

Yield 0.22 g (87%), as a light yellow solid. ¹H NMR (400 MHz, CD₃OD) δ 7.89 (d, J=8.8 Hz, 2H), 7.03 (d, J=8.8 Hz, 2H), 4.24 (d, J=13.2 Hz, 2H), 3.87 (s, 3H), 3.53 (s, 4H), 3.25 (ddd, J=2.8, 10.8, 15.2 Hz, 2H), 2.65 (t, J=2.8 Hz, 1H), 2.58-2.42 (m, 1H), 2.04-1.99 (m, 2H), 1.95-1.86 (m, 2H), 1.85-1.72 (m, 2H). m/z: [ESI⁺] 384 (M+H)⁺.

(R)-1-(3-(4-methoxyphenyl)-1,2,4-oxadiazol-5-yl)-N-(pyrrolidin-2-ylmethyl)piperidine-4-carboxamide hydrochloride. The compound was synthesized according to the procedure described above, using tert-butyl (R)-2-((1-(3-(4-methoxyphenyl)-1,2,4-oxadiazol-5-yl)piperidine-4-carboxamido)methyl)pyrrolidine-1-carboxylate (0.34 g, 0.70 mmol) as the starting material.

Yield 0.24 g (81%), as a light yellow solid. ¹H NMR (400 MHz, CDCl₃) δ 10.00 (br s, 1H), 9.20 (br s, 1H), 7.95 (d, J=8.0 Hz, 2H), 6.96 (d, J=8.0 Hz, 2H), 4.38-4.22 (m, 2H), 3.87 (s, 3H), 3.46-3.16 (m, 3H), 2.71-2.51 (m, 1H), 2.30-

2.00 (m, 8H), 1.98-1.76 (m, 2H), 1.28 (s, 1H), 1.17 (d, J=6.4 Hz, 1H). Amide NH proton not observed. m/z: [ESI+] 386 (M+H)+.

(S)-1-(3-(4-methoxyphenyl)-1,2,4-oxadiazol-5-yl)-N-(pyrrolidin-3-ylmethyl)piperidine-4-carboxamide hydrochloride. The compound was synthesized according to the procedure described above, using tert-butyl (R)-3-((1-(3-(4-methoxyphenyl)-1,2,4-oxadiazol-5-yl)piperidine-4-carboxamido)methyl)pyrrolidine-1-carboxylate (0.50 g, 1.03 mmol) as the starting material.

Yield 0.34 g (79%), as a light yellow solid. m/z: [ESI+] 386 (M+H)+.

(R)-1-(3-(4-methoxyphenyl)-1,2,4-oxadiazol-5-yl)-N-(pyrrolidin-3-ylmethyl)piperidine-4-carboxamide. The compound was synthesized according to the procedure described above, using tert-butyl (S)-3-((1-(3-(4-methoxyphenyl)-1,2,4-oxadiazol-5-yl)piperidine-4-carboxamido)methyl)pyrrolidine-1-carboxylate (0.27 g, 0.56 mmol) as the starting material.

Yield 0.20 g (93%), as an off-white solid. m/z: [ESI+] 386 (M+H)+. Crude material was used in the next step without further purification.

1-(3-(4-Methoxyphenyl)-1,2,4-oxadiazol-5-yl)-N-((1-(((S)-piperidin-3-yl)methyl)pyrrolidin-3-yl)methyl)piperidine-4-carboxamide. The compound was synthesized according to the procedure described above, using tert-butyl (3R)-3-((3-((1-(3-(4-methoxyphenyl)-1,2,4-oxadiazol-5-yl)piperidine-4-carboxamido)methyl)pyrrolidin-1-yl)methyl)piperidine-1-carboxylate (0.24 g, 0.41 mmol) as the starting material.

Yield 0.18 g (91%), as a yellow solid. $^1$H NMR (400 MHz, CDCl$_3$) δ 7.94 (d, J=8.8 Hz, 2H), 6.97 (d, J=8.8 Hz, 2H), 6.91-6.86 (m, 1H), 4.33-4.25 (m, 2H), 3.87 (s, 3H), 3.37-3.26 (m, 1H), 3.26-3.09 (m, 5H), 3.08-2.98 (m, 1H), 2.95-2.82 (m, 1H), 2.71-2.49 (m, 2H), 2.49-2.14 (m, 6H), 2.10-1.92 (m, 2H), 1.92-1.39 (m, 9H), 1.13-1.01 (m, 1H). m/z: [ESI+] 483 (M+H)+.

1-(3-(4-Methoxyphenyl)-1,2,4-oxadiazol-5-yl)-N—(((R)-1-(((S)-piperidin-3-yl)methyl)pyrrolidin-3-yl)methyl)piperidine-4-carboxamide. The compound was synthesized according to the procedure described above, using tert-butyl (R)-3-(((R)-3-((1-(3-(4-methoxyphenyl)-1,2,4-oxadiazol-5-yl)piperidine-4-carboxamido)methyl)pyrrolidin-1-yl)methyl)piperidine-1-carboxylate (0.30 g, 0.51 mmol) as the starting material.

Yield 0.15 g (60%), as an off-white solid. m/z: [ESI+] 483 (M+H)+. Crude material was used in the next step without further purification.

1-(3-(4-Methoxyphenyl)-1,2,4-oxadiazol-5-yl)-N—(((S)-1-(((S)-piperidin-3-yl)methyl)pyrrolidin-3-yl)methyl)piperidine-4-carboxamide. The compound was synthesized according to the procedure described above, using tert-butyl (R)-3-(((S)-3-((1-(3-(4-methoxyphenyl)-1,2,4-oxadiazol-5-yl)piperidine-4-carboxamido)methyl)pyrrolidin-1-yl)methyl)piperidine-1-carboxylate (0.30 g, 0.51 mmol) as the starting material.

Yield 0.15 g (60%), as an off-white solid. $^1$H NMR (400 MHz, CD$_3$OD) δ 7.89 (d, J=8.8 Hz, 2H), 7.03 (d, J=8.8 Hz, 2H), 4.30-4.23 (m, 2H), 3.87 (s, 3H), 3.84-3.73 (m, 1H), 3.70-3.46 (m, 1H), 3.44-3.12 (m, 7H), 3.01-2.66 (m, 5H), 2.63-2.53 (m, 1H), 2.39-2.20 (m, 2H), 2.11-1.72 (m, 9H), 1.48-1.33 (m, 1H). Amide NH and aliphatic NH not observed. m/z: [ESI+] 483 (M+H)+.

1-(3-(4-Cyanophenyl)-1,2,4-oxadiazol-5-yl)-N-((1-(((S)-piperidin-3-yl)methyl)pyrrolidin-3-yl)methyl)piperidine-4-carboxamide dihydrochloride. The compound was synthesized according to the procedure described above, using tert-butyl (3R)-3-((3-((1-(3-(4-cyanophenyl)-1,2,4-oxadiazol-5-yl)piperidine-4-carboxamido)methyl)pyrrolidin-1-yl)methyl)piperidine-1-carboxylate (0.25 g, 0.43 mmol) as the starting material.

Yield 0.18 g (76%), as an off-white solid. $^1$H NMR (400 MHz, DMSO) δ 11.09 (br s, 1H, HCl), 9.32 (br s, 1H), 9.10 (br s, 1H), 8.23 (br s, 1H), 8.07 (d, J=8.8 Hz, 2H), 7.99 (d, J=8.8 Hz, 2H), 4.13-4.06 (m, 2H), 3.66-3.50 (m, 2H), 3.37-2.94 (m, 9H), 2.84-2.58 (m, 2H), 2.53-2.45 (m, 4H), 2.31-2.19 (m, 0.5H), 2.15-1.99 (m, 0.5H), 1.95-1.54 (m, 8H), 1.29-1.20 (m, 1H). m/z: [ESI+] 478 (M+H)+.

1-(3-(4-Chlorophenyl)-1,2,4-oxadiazol-5-yl)-N-((1-(((S)-piperidin-3-yl)methyl)pyrrolidin-3-yl)methyl)piperidine-4-carboxamide. The compound was synthesized according to the procedure described above, using tert-butyl (3R)-3-((3-((1-(3-(4-chlorophenyl)-1,2,4-oxadiazol-5-yl)piperidine-4-carboxamido)methyl)pyrrolidin-1-yl)methyl)piperidine-1-carboxylate (0.35 g, 0.60 mmol) as the starting material.

Yield 0.26 g (90%), as an off-white solid. m/z: [ESI+] 487, 489 (M+H)+. Crude material was used in the next step without further purification.

1-(3-(4-Methoxyphenyl)-1,2,4-oxadiazol-5-yl)-N-((1-(((R)-piperidin-3-yl)methyl)pyrrolidin-3-yl)methyl)piperidine-4-carboxamide: Using tert-butyl (3S)-3-((3-((1-(3-(4-methoxyphenyl)-1,2,4-oxadiazol-5-yl)piperidine-4-carboxamido)methyl)pyrrolidin-1-yl)methyl)piperidine-1-carboxylate (100 mg, 0.172 mmol) as the starting material.

Yield 30 mg (36%), as a yellow solid. $^1$H NMR (400 MHz, DMSO) δ 7.89 (t, J=5.6 Hz, 1H), 7.84 (d, J=8.8 Hz, 2H), 7.06 (d, J=8.8 Hz, 2H), 4.06 (td, J=3.6, 13.2 Hz, 2H), 3.82 (s, 3H), 3.20 (dt, J=3.2, 12.8 Hz, 2H), 3.09-2.93 (m, 2.5H), 2.85 (d, J=11.2 Hz, 0.5H), 2.52-2.30 (m, 7H), 2.28-2.16 (m, 2H), 2.16-2.08 (m, 2H), 1.89-1.69 (m, 4H), 1.67-1.50 (m, 4H), 1.33 (d, J=13.6 Hz, 2H), 1.04-0.89 (m, 1H). Aliphatic NH not observed. m/z: [ESI+] 483 (M+H)+, (C$_{26}$H$_{38}$N$_6$O$_3$).

N-((1-(azepan-4-ylmethyl)pyrrolidin-3-yl)methyl)-1-(3-(4-methoxyphenyl)-1,2,4-oxadiazol-5-yl)piperidine-4-carboxamide (Compound 391): Using tert-butyl 4-((3-((1-(3-(4-methoxyphenyl)-1,2,4-oxadiazol-5-yl)piperidine-4-carboxamido)methyl)pyrrolidin-1-yl)methyl)azepane-1-carboxylate (100 mg, 0.168 mmol) as the starting material.

Yield 19 mg (23%), as an off-white solid. $^1$H NMR (400 MHz, DMSO) δ 7.89 (t, J=5.6 Hz, 1H), 7.84 (d, J=8.8 Hz, 2H), 7.05 (d, J=8.8 Hz, 2H), 4.06 (td, J=3.6, 13.2 Hz, 2H), 3.82 (s, 3H), 3.24-3.14 (m, 2H), 3.08-2.95 (m, 2H), 2.91-2.76 (m, 1H), 2.76-2.62 (m, 1H), 2.50-2.32 (m, 5H), 2.27-2.09 (m, 5H), 1.89-1.71 (m, 7H), 1.62 (dt, J=4.4, 12.4 Hz, 2H), 1.53-1.28 (m, 2H), 1.21-0.96 (m, 2H). Aliphatic NH not observed. m/z: [ESI+] 497 (M+H)+, (C$_{27}$H$_{40}$N$_6$O$_3$).

1-(3-(4-Methoxyphenyl)-1,2,4-oxadiazol-5-yl)-N-((1-(((S)-pyrrolidin-2-yl)methyl)pyrrolidin-3-yl)methyl)piperidine-4-carboxamide (Compound 392): Using tert-butyl (2S)-2-((3-((1-(3-(4-methoxyphenyl)-1,2,4-oxadiazol-5-yl)piperidine-4-carboxamido)methyl)pyrrolidin-1-yl)methyl)pyrrolidine-1-carboxylate (200 mg, 0.352 mmol) as the starting material.

Yield 87 mg (53%), as an off-white solid. $^1$H NMR (400 MHz, DMSO) δ 7.93 (t, J=5.6 Hz, 1H), 7.84 (d, J=8.8 Hz, 2H), 7.05 (d, J=8.8 Hz, 2H), 4.06 (d, J=13.2 Hz, 2H), 3.82 (s, 3H), 3.24-3.14 (m, 2H), 3.02 (d, J=5.8 Hz, 2H), 2.90-2.75 (m, 1H), 2.61-2.50 (m, 4H), 2.48-2.36 (m, 4H), 2.30-2.18 (m, 2H), 1.90-1.68 (m, 5H), 1.62 (m, 3H), 1.30 (m, 2H). Aliphatic NH not observed. m/z: [ESI+] 469 (M+H)+, (C$_{25}$H$_{36}$N$_6$O$_3$).

N-((1-(((R)-azetidin-2-yl)methyl)pyrrolidin-3-yl)methyl)-1-(3-(4-methoxyphenyl)-1,2,4-oxadiazol-5-yl)piperidine-4-carboxamide (Compound 413): Using tert-butyl (2R)-2-((3-((1-(3-(4-methoxyphenyl)-1,2,4-oxadiazol-5-yl)piperidine-4-carboxamido)methyl)pyrrolidin-1-yl)methyl)azetidine-1-carboxylate (80 mg, 0.144 mmol) as the starting material.

Yield 14 mg (21%), as an off-white solid. $^1$H NMR (400 MHz, DMSO) δ 7.92 (br s, 1H), 7.84 (d, J=8.8 Hz, 2H), 7.06 (d, J=8.8 Hz, 2H), 4.06 (d, J=13.2 Hz, 2H), 3.82 (s, 3H), 3.48-3.30 (m, 2H), 3.25-3.14 (m, 2H), 3.08-2.93 (m, 2H), 2.85-2.55 (m, 1H), 2.50-2.35 (m, 6H), 2.28-2.08 (m, 3H), 1.92-1.75 (m, 4H), 1.68-1.56 (m, 2H), 1.45-1.28 (m, 1H). Aliphatic NH not observed. m/z: [ESI$^+$] 455 (M+H)$^+$, ($C_{24}H_{34}N_6O_3$).

N-((1-(((1s,3s)-3-aminocyclobutyl)methyl)pyrrolidin-3-yl)methyl)-1-(3-(4-methoxyphenyl)-1,2,4-oxadiazol-5-yl)piperidine-4-carboxamide (Compound 394): Using tert-butyl ((1s,3s)-3-((3-((1-(3-(4-methoxyphenyl)-1,2,4-oxadiazol-5-yl)piperidine-4-carboxamido)methyl)pyrrolidin-1-yl)methyl)cyclobutyl)carbamate (100 mg, 0.176 mmol) as the starting material.

Yield 40 mg (49%), as an off-white solid. $^1$H NMR (400 MHz, DMSO) δ 7.83 (d, J=8.8 Hz, 2H), 7.05 (d, J=8.8 Hz, 2H), 4.05 (td, J=3.6, 13.2 Hz, 2H), 3.81 (s, 3H), 3.19 (dt, J=3.2, 12.8 Hz, 2H), 3.12-3.03 (m, 1H), 2.99 (t, J=7.2 Hz, 2H), 2.50-2.42 (m, 1H), 2.41-2.28 (m, 5H), 2.28-2.14 (m, 3H), 2.14-2.07 (m, 1H), 1.95-1.84 (m, 1H), 1.83-1.71 (m, 3H), 1.68-1.54 (m, 2H), 1.39-1.19 (m, 3H). Amide NH and aliphatic NH$_2$ not observed. m/z: [ESI$^+$] 469 (M+H)$^+$, ($C_{25}H_{36}N_6O_3$).

N-((1-(((1s,4s)-4-aminocyclohexyl)methyl)pyrrolidin-3-yl)methyl)-1-(3-(4-methoxyphenyl)-1,2,4-oxadiazol-5-yl)piperidine-4-carboxamide (Compound 423): Using tert-butyl ((1s,4s)-4-((3-((1-(3-(4-methoxyphenyl)-1,2,4-oxadiazol-5-yl)piperidine-4-carboxamido)methyl)pyrrolidin-1-yl)methyl)cyclohexyl)carbamate (100 mg, 0.168 mmol) as the starting material.

Yield 11 mg (13%), as an off-white solid. $^1$H NMR (400 MHz, DMSO) δ 7.82 (d, J=8.8 Hz, 2H), 7.06 (d, J=8.8 Hz, 2H), 4.05 (td, J=3.6, 13.2 Hz, 2H), 3.80 (s, 3H), 3.18 (dt, J=3.2, 12.8 Hz, 2H), 3.07-2.93 (m, 2H), 2.90-2.80 (m, 1H), 2.50-2.43 (m, 1H), 2.43-2.34 (m, 3H), 2.30-2.08 (m, 4H), 1.89-1.73 (m, 3H), 1.68-1.54 (m, 2H), 1.52-1.27 (m, 10H). Amide NH and aliphatic NH$_2$ not observed. m/z: [ESI$^+$] 497 (M+H)$^+$, ($C_{27}H_{40}N_6O_3$).

1-(3-(4-Methoxyphenyl)-1,2,4-oxadiazol-5-yl)-N-((1-(((R)-piperidin-2-yl)methyl)pyrrolidin-3-yl)methyl)piperidine-4-carboxamide (Compound 415): Using tert-butyl (2R)-2-((3-((1-(3-(4-methoxyphenyl)-1,2,4-oxadiazol-5-yl)piperidine-4-carboxamido)methyl)pyrrolidin-1-yl)methyl)piperidine-1-carboxylate (100 mg, 0.172 mmol) as the starting material.

Yield 31 mg (37%), as an off-white solid. $^1$H NMR (400 MHz, DMSO) δ 7.91 (t, J=5.6 Hz, 1H), 7.84 (d, J=8.8 Hz, 2H), 7.06 (d, J=8.8 Hz, 2H), 4.06 (td, J=3.6, 13.2 Hz, 2H), 3.82 (s, 3H), 3.25-3.14 (m, 2H), 3.10-2.98 (m, 2H), 2.96-2.89 (m, 1H), 2.53-2.31 (m, 8H), 2.30-2.17 (m, 1H), 2.16-2.02 (m, 2H), 1.86-1.72 (m, 3H), 1.72-1.45 (m, 5H), 1.40-1.16 (m, 3H), 1.01-0.86 (m, 1H). m/z: [ESI$^+$] 483 (M+H)$^+$, ($C_{26}H_{38}N_6O_3$).

1-(3-(4-Methoxyphenyl)-1H-1,2,4-triazol-5-yl)piperidine-4-carboxylic acid (Intermediate H)

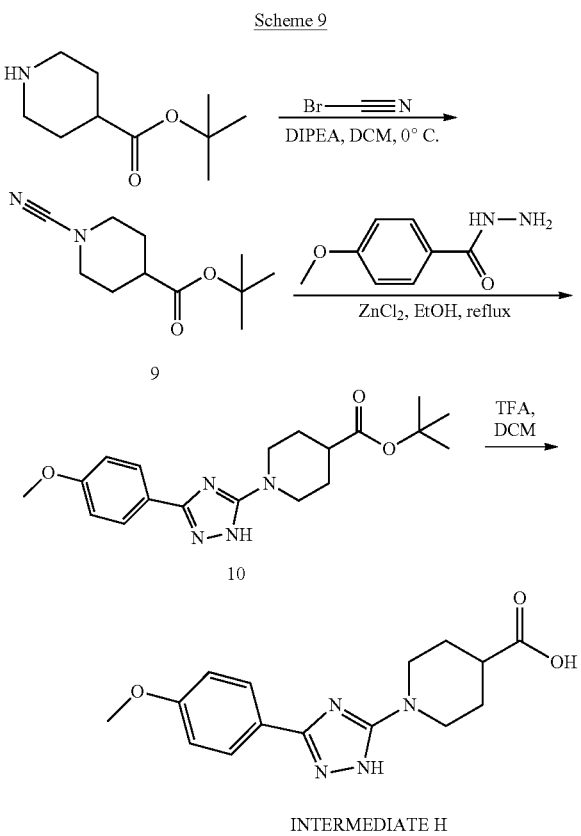

Scheme 9

INTERMEDIATE H

Step 1: Tert-butyl 1-cyanopiperidine-4-carboxylate

To a stirred solution of tert-butyl piperidine-4-carboxylate (2.00 g, 10.80 mmol) in DCM (20 mL) were added cyanogen bromide (1.26 g, 11.90 mmol) and DIPEA (3.07 g, 23.75 mmol) at 0° C. The resulting solution was stirred for 2 h at 0° C. The resulting mixture was diluted with water (10 mL) and extracted with DCM (2×10 mL). The combined organic layers were washed with brine (3×10 mL) and dried over anhydrous Na$_2$SO$_4$. After filtration, the filtrate was concentrated under reduced pressure to afford tert-butyl 1-cyanopiperidine-4-carboxylate as a yellow oil.

Yield: 1.60 g (70%). $^1$H NMR (400 MHz, DMSO) δ 3.38-3.30 (m, 2H), 3.06 (ddd, J=2.8, 11.4, 12.6 Hz, 2H), 2.44-2.37 (m, 1H), 1.81 (dd, J=3.6, 13.8 Hz, 2H), 1.62-1.49 (m, 2H), 1.40 (s, 9H). m/z: [ESI$^+$] 211 (M+H)$^+$.

Step 2: Tert-butyl 1-(3-(4-methoxyphenyl)-1H-1,2,4-triazol-5-yl)piperidine-4-carboxylate To a stirred solution of 4-methoxybenzohydrazide (1.00 g, 6.02 mmol) and tert-butyl 1-cyanopiperidine-4-carboxylate (1.52 g, 7.23 mmol) in ethanol (20 mL) were added a 0.7M solution of zinc chloride in THF (1.70 mL, 1.19 mmol) at room temperature under a nitrogen atmosphere. The resulting mixture was stirred for 16 h at 80° C. under a nitrogen atmosphere. The resulting mixture was cooled to room temperature and concentrated under reduced pressure. The residue was purified by reverse phase flash chromatography with the following conditions: column, C18, 20-40 um, 330 g; Mobile Phase A: water (plus 10 mM formic acid); Mobile Phase B: acetonitrile; Flow rate: 80 mL/min; Gradient: 45% B-70% B in 25 min; Detector, UV: 220/254 nm. The fractions containing desired product were collected and concentrated under reduced pressure to afford tert-butyl 1-(3-(4-methoxyphenyl)-1H-1,2,4-triazol-5-yl)piperidine-4-carboxylate as an off-white solid.

Yield: 2.00 g (93%). $^1$H NMR (400 MHz, DMSO) δ 12.49 (br, s, 1H), 7.83 (d, J=8.8 Hz, 2H), 6.99 (d, J=8.8 Hz, 2H), 3.85 (d, J=12.0 Hz, 2H), 3.79 (s, 3H), 2.99-2.86 (s, 2H), 2.40 (t, J=11.0 Hz, 1H), 1.84 (dd, J=3.8, 13.4 Hz, 2H), 1.63-1.46 (m, 2H), 1.40 (s, 9H). m/z: [ESI$^+$] 359 (M+H)$^+$.

Step 3: 1-(3-(4-methoxyphenyl)-JH-1,2,4-triazol-5-yl)piperidine-4-carboxylic acid A solution of tert-butyl 1-(3-(4-methoxyphenyl)-1H-1,2,4-triazol-5-yl)piperidine-4-carboxylate (2.00 g, 5.58 mmol) in DCM (20 mL) was treated with trifluoroacetic acid (8 mL) for 16 h at room temperature. The resulting solution was concentrated under reduced pressure. The residue was triturated with diethyl ether (30 mL). The precipitated solids were collected by filtration, washed with diethyl ether (2×5 mL) and dried in the air to afford 1-(3-(4-methoxyphenyl)-1H-1,2,4-triazol-5-yl)piperidine-4-carboxylic acid as an off-white solid.

Yield: 1.60 g (95%). $^1$H NMR (400 MHz, DMSO) δ 7.85 (d, J=8.8 Hz, 2H), 7.04 (d, J=8.8 Hz, 2H), 3.88 (dd, J=3.6, 12.4 Hz, 2H), 3.81 (s, 3H), 3.03 (t, J=12.0 Hz, 2H), 2.48 (t, J=11.0 Hz, 1H), 1.96-1.85 (m, 2H), 1.72-1.52 (m, 2H). Triazole NH and carboxylic acid protons not observed. m/z: [ESI$^+$] 303 (M+H)$^+$.

The intermediates below were prepared according to the procedure described above.

1-(3-(4-Methoxyphenyl) isoxazol-5-yl)piperidine-4-carboxylic acid. The compound was synthesized according to the procedure described above, using tert-butyl 1-(3-(4-methoxyphenyl) isoxazol-5-yl)piperidine-4-carboxylate (2.40 g, 6.70 mmol) as the starting material.

Yield 1.83 g (90%), as a brown solid. $^1$H NMR (400 MHz, DMSO) δ 12.20 (br s, 1H), 7.68 (d, J=8.8 Hz, 2H), 7.02 (d, J=8.8 Hz, 2H), 5.78 (s, 1H), 3.81 (s, 3H), 3.69 (td, J=4.0, 12.8 Hz, 2H), 3.13-2.99 (m, 2H), 2.55-2.46 (m, 1H), 1.97-1.87 (m, 2H), 1.69-1.57 (m, 2H). m/z: [ESI$^+$] 303 (M+H)$^+$.

1-(4'-Methoxy-[1,1'-biphenyl]-3-yl)piperidine-4-carboxylic acid. The compound was synthesized according to the procedure described above, using tert-butyl 1-(3-(5-methoxypyridin-2-yl)-1,2,4-oxadiazol-5-yl)piperidine-4-carboxylate (1.00 g, 2.77 mmol) as the starting material.

Crude yield 0.82 g, as an off-white solid. m/z: [ESI$^+$] 312 (M+H)$^+$.

1-(3-(2-Methoxyphenyl)-1,2,4-oxadiazol-5-yl)piperidine-4-carboxylic acid. The compound was synthesized according to the procedure described above, using tert-butyl 1-(3-(2-methoxyphenyl)-1,2,4-oxadiazol-5-yl)piperidine-4-carboxylate (1.00 g, 2.78 mmol) as the starting material.

Yield 0.50 g (59%), as a light yellow solid. $^1$H NMR (400 MHz, CD$_3$OD) δ 7.90 (d, J=8.8 Hz, 2H), 7.69 (d, J=8.8 Hz, 2H), 4.15 (td, J=4.0, 13.6 Hz, 2H), 3.36-3.30 (m, 2H), 2.69-2.55 (m, 1H), 2.17 (s, 3H), 2.07 (td, J=3.6, 11.6 Hz, 2H), 1.85-1.71 (m, 2H). Carboxylic acid proton not observed. m/z: [ESI$^+$] 304 (M+H)$^+$.

1-(3-(4-Acetamidophenyl)-1,2,4-oxadiazol-5-yl)piperidine-4-carboxylic acid. The compound was synthesized according to the procedure described above, using tert-butyl 1-(3-(4-acetamidophenyl)-1,2,4-oxadiazol-5-yl)piperidine-4-carboxylate (1.00 g, 2.59 mmol) as the starting material.

Yield 0.45 g (53%), as a light yellow solid. $^1$H NMR (400 MHz, CD$_3$OD) δ 7.90 (d, J=8.8 Hz, 2H), 7.69 (d, J=8.8 Hz, 2H), 4.15 (td, J=4.0, 13.6 Hz, 2H), 3.36-3.30 (m, 2H), 2.69-2.55 (m, 1H), 2.17 (s, 3H), 2.07 (td, J=3.6, 11.6 Hz, 2H), 1.85-1.71 (m, 2H). Amide NH and carboxylic acid protons not observed. m/z: [ESI$^+$] 331 (M+H)$^+$.

1-(3-(5-Methoxypyridin-2-yl)-1,2,4-oxadiazol-5-yl)piperidine-4-carboxylic acid. The compound was synthesized according to the procedure described above, using tert-butyl 1-(3-(5-methoxypyridin-2-yl)-1,2,4-oxadiazol-5-yl)piperidine-4-carboxylate (2.00 g, 5.55 mmol) as the starting material.

Crude yield 1.50 g, as a light yellow solid. m/z: [ESI$^+$] 305 (M+H)$^+$ 1-(3-(3-methylphenyl)-1,2,4-oxadiazol-5-yl)piperidine-4-carboxylic acid. The compound was synthesized according to the procedure described above, using tert-butyl 1-(3-(3-methylphenyl)-1,2,4-oxadiazol-5-yl)piperidine-4-carboxylate (1.00 g, 2.91 mmol) as the starting material.

Yield 0.60 g (72%), as a light yellow solid. $^1$H NMR (400 MHz, CD$_3$OD) δ 7.79 (dd, J=0.8, 1.6 Hz, 1H), 7.77-7.72 (m, 1H), 7.42-7.29 (m, 2H), 4.16 (td, J=4.0, 13.6 Hz, 2H), 3.40-3.29 (m, 2H), 2.69-2.55 (m, 1H), 2.42 (s, 3H), 2.07 (td, J=3.6, 11.8 Hz, 2H), 1.85-1.73 (m, 2H). Carboxylic acid proton not observed. m/z: [ESI$^+$] 288 (M+H)$^+$.

1-(3-(3-Methoxyphenyl)-1,2,4-oxadiazol-5-yl)piperidine-4-carboxylic acid. The compound was synthesized according to the procedure described above, using tert-butyl 1-(3-(3-methoxyphenyl)-1,2,4-oxadiazol-5-yl)piperidine-4-carboxylate (1.00 g, 2.78 mmol) as the starting material.

Yield 0.52 g (62%), as a light yellow solid. $^1$H NMR (400 MHz, CD$_3$OD) δ 7.54 (dd, J=1.2, 7.6 Hz, 1H), 7.50 (dd, J=1.4, 2.8 Hz, 1H), 7.39 (dd, J=2.0, 8.0 Hz, 1H), 7.08 (ddd, J=1.0, 2.8, 8.4 Hz, 1H), 4.15 (td, J=3.6, 13.2 Hz, 2H), 3.86 (s, 3H), 3.40-3.28 (m, 2H), 2.69-2.55 (m, 1H), 2.07 (dd, J=3.8, 13.8 Hz, 2H), 1.85-1.73 (m, 2H). Carboxylic acid proton not observed. m/z: [ESI$^+$] 304 (M+H)$^+$.

1-(3-(2-Methylphenyl)-1,2,4-oxadiazol-5-yl)piperidine-4-carboxylic acid. The compound was synthesized according to the procedure described above, using tert-butyl 1-(3-(2-methylphenyl)-1,2,4-oxadiazol-5-yl)piperidine-4-carboxylate (2.00 g, 5.82 mmol) as the starting material.

Yield 0.90 g (54%), as a light yellow solid. $^1$H NMR (400 MHz, CD$_3$OD) δ 7.79 (dd, J=1.6, 7.6 Hz, 1H), 7.39 (dd, J=1.6, 7.6 Hz, 1H), 7.35-7.27 (m, 2H), 4.14 (td, J=3.6, 13.2 Hz, 2H), 3.42-3.30 (m, 2H), 2.69-2.55 (m, 1H), 2.54 (s, 3H), 2.08 (dd, J=3.6, 13.8 Hz, 2H), 1.85-1.74 (m, 2H). Carboxylic acid proton not observed. m/z: [ESI$^+$] 288 (M+H)$^+$.

1-(4-(4-Methoxyphenyl)oxazol-2-yl)piperidine-4-carboxylic acid. The compound was synthesized according to the procedure described above, using tert-butyl 1-(4-(4-methoxyphenyl)oxazol-2-yl)piperidine-4-carboxylate (0.44 g, 1.23 mmol) as the starting material.

Yield 0.37 g (99%), as an off-white solid. $^1$H NMR (400 MHz, DMSO) δ 7.97 (s, 1H), 7.60 (d, J=8.8 Hz, 2H), 6.95 (d, J=8.8 Hz, 2H), 3.92 (d, J=12.8 Hz, 2H), 3.77 (s, 3H), 3.15-3.01 (m, 2H), 2.54-2.44 (m, 1H), 1.96-1.85 (m, 2H), 1.65-1.49 (m, 2H). Carboxylic acid proton not observed. m/z: [ESI$^+$] 303 (M+H)$^+$.

1-(3-(Pyridin-4-yl)-1,2,4-oxadiazol-5-yl)piperidine-4-carboxylic acid. The compound was synthesized according to the procedure described above, using tert-butyl 1-(3-(pyridin-4-yl)-1,2,4-oxadiazol-5-yl)piperidine-4-carboxylate (1.20 g, 3.63 mmol) as the starting material.

Yield 0.90 g (90%), as a yellow solid. ¹H NMR (400 MHz, CD₃OD) δ 8.96 (d, J=6.8 Hz, 2H), 8.49 (d, J=6.8 Hz, 2H), 4.18 (td, J=4.0, 13.6 Hz, 2H), 3.39 (ddd, J=3.2, 11.2, 13.8 Hz, 2H), 2.08 (ddd, J=4.6, 9.2, 13.0 Hz, 2H), 2.72-2.63 (m, 1H), 2.08 (ddd, J=4.6, 9.2, 13.0 Hz, 2H), 1.93-1.82 (m, 2H). Carboxylic acid proton not observed. m/z: [ESI⁺] 275 (M+H)⁺.

1-(3-(3-Acetamidophenyl)-1,2,4-oxadiazol-5-yl)piperidine-4-carboxylic acid. The compound was synthesized according to the procedure described above, using tert-butyl 1-(3-(3-acetamidophenyl)-1,2,4-oxadiazol-5-yl)piperidine-4-carboxylate (1.00 g, 2.59 mmol) as the starting material.

Yield 0.15 g (17%), as a yellow solid. ¹H NMR (400 MHz, DMSO) δ 10.14 (br s, 1H), 8.15 (d, J=2.0 Hz, 1H), 7.77 (dd, J=2.0, 7.6 Hz, 1H), 7.59-7.53 (m, 1H), 7.41 (d, J=7.8 Hz, 1H), 3.99 (td, J=4.2, 13.2 Hz, 2H), 3.35-3.24 (m, 2H), 2.61-2.52 (m, 1H), 2.06 (s, 3H), 1.96 (dd, J=3.6, 13.6 Hz, 2H), 1.69-1.53 (m, 2H). Carboxylic acid proton not observed. m/z: [ESI⁺] 331 (M+H)⁺.

1-(3-(4-(Trifluoromethoxy)phenyl)-1,2,4-oxadiazol-5-yl)piperidine-4-carboxylic acid. The compound was synthesized according to the procedure described above, using tert-butyl 1-(3-(4-(trifluoromethoxy)phenyl)-1,2,4-oxadiazol-5-yl)piperidine-4-carboxylate (0.28 g, 0.68 mmol) as the starting material.

Yield 0.20 g (82%), as a light yellow solid. ¹H NMR (400 MHz, DMSO) δ 12.37 (br s, 1H), 8.02 (d, J=8.8 Hz, 2H), 7.51 (d, J=8.8 Hz, 2H), 4.00 (td, J=4.0, 13.2 Hz, 2H), 3.32-3.22 (m, 2H), 2.68-2.58 (m, 1H), 2.03-1.91 (m, 2H), 1.70-1.58 (m, 2H). m/z: [ESI⁺] 358 (M+H)⁺.

1-(3-(4-(Difluoromethoxy)phenyl)-1,2,4-oxadiazol-5-yl)piperidine-4-carboxylic acid. The compound was synthesized according to the procedure described above, using tert-butyl 1-(3-(4-(difluoromethoxy)phenyl)-1,2,4-oxadiazol-5-yl)piperidine-4-carboxylate (2.00 g, 5.06 mmol) as the starting material.

Yield 1.00 g (58%), as a light yellow solid. ¹H NMR (400 MHz, CDCl₃) δ 8.02 (d, J=8.8 Hz, 2H), 7.20 (d, J=8.8 Hz, 2H), 6.59 (t, J=73.4 Hz, 1H), 4.19 (td, J=4.2, 13.6 Hz, 2H), 3.33 (ddd, J=3.2, 10.8, 13.8 Hz, 2H), 2.72-2.58 (m, 1H), 2.11 (dd, J=3.8, 13.8 Hz, 2H), 1.90-1.76 (m, 2H). Carboxylic acid proton not observed. m/z: [ESI⁺] 340 (M+H)⁺.

1-(3-(2-Chloro-4-methoxyphenyl)-1,2,4-oxadiazol-5-yl)piperidine-4-carboxylic acid. The compound was synthesized according to the procedure described above, using tert-butyl 1-(3-(2-chloro-4-methoxyphenyl)-1,2,4-oxadiazol-5-yl)piperidine-4-carboxylate (2.00 g, 5.08 mmol) as the starting material.

Yield 0.80 g (47%), as a light yellow solid. ¹H NMR (400 MHz, CDCl₃) δ 7.81 (d, J=8.8 Hz, 1H), 7.04 (d, J=2.6 Hz, 1H), 6.89 (dd, J=8.8, 2.6 Hz, 1H), 4.17 (td, J=4.2, 13.4 Hz, 2H), 3.86 (s, 3H), 3.31 (ddd, J=3.2, 10.8, 13.8 Hz, 2H), 2.72-2.58 (m, 1H), 2.10 (dd, J=4.0, 13.8 Hz, 2H), 1.90-1.76 (m, 2H). Carboxylic acid proton not observed. m/z: [ESI⁺] 338, 340 (M+H)⁺.

1-(3-(2-Methoxypyrimidin-5-yl)-1,2,4-oxadiazol-5-yl)piperidine-4-carboxylic acid. The compound was synthesized according to the procedure described above, using tert-butyl 1-(3-(2-methoxypyrimidin-5-yl)-1,2,4-oxadiazol-5-yl)piperidine-4-carboxylate (0.20 g, 0.55 mmol) as the starting material.

Yield 0.11 g (65%), as an off-white solid. ¹H NMR (400 MHz, CD₃OD) δ 9.07 (s, 2H), 4.17 (td, J=4.2, 13.6 Hz, 2H), 4.10 (s, 3H), 3.40-3.34 (m, 2H), 2.72-2.58 (m, 1H), 2.08 (dd, J=3.8, 13.8 Hz, 2H), 1.87-1.71 (m, 2H). Carboxylic acid proton not observed. m/z: [ESI⁺] 306 (M+H)⁺.

1-(3-(5-Methoxypyrazin-2-yl)-1,2,4-oxadiazol-5-yl)piperidine-4-carboxylic acid. The compound was synthesized according to the procedure described above, using tert-butyl 1-(3-(5-methoxypyrazin-2-yl)-1,2,4-oxadiazol-5-yl)piperidine-4-carboxylate (140 mg, 0.387 mmol) as the starting material.

Yield 90 mg (76%), as a light yellow solid. ¹H NMR (400 MHz, DMSO) δ 12.38 (br s, 1H), 8.71 (d, J=1.4 Hz, 1H), 8.43 (d, J=1.4 Hz, 1H), 4.00 (td, J=4.2, 13.6 Hz, 2H), 3.99 (s, 3H), 3.31-3.25 (m, 2H), 2.61-2.54 (m, 1H), 2.02-1.92 (m, 2H), 1.68-1.57 (m, 2H). m/z: [ESI⁺] 306 (M+H)⁺.

1-(3-(5-Methoxypyrimidin-2-yl)-1,2,4-oxadiazol-5-yl)piperidine-4-carboxylic acid. The compound was synthesized according to the procedure described above, using tert-butyl 1-(3-(5-methoxypyrimidin-2-yl)-1,2,4-oxadiazol-5-yl)piperidine-4-carboxylate (0.70 g, 1.94 mmol) as the starting material.

Yield 0.50 g (85%) as a yellow solid. ¹H NMR (400 MHz, CD₃OD) δ 8.63 (s, 2H), 4.21 (td, J=3.6, 13.4 Hz, 2H), 4.05 (s, 3H), 3.32-3.23 (m, 2H), 2.48-2.38 (m, 1H), 2.03 (dd, J=3.6, 13.8 Hz, 2H), 1.88-1.70 (m, 2H). Carboxylic acid proton not observed. m/z: [ESI⁺] 306 (M+H)⁺.

Tert-butyl 3-((4-(3-(4-methoxyphenyl)-1,2,4-oxadiazol-5-yl)piperazine-1 carboxamido)methyl)pyrrolidine-1-carboxylate (Intermediate I)

Scheme 10

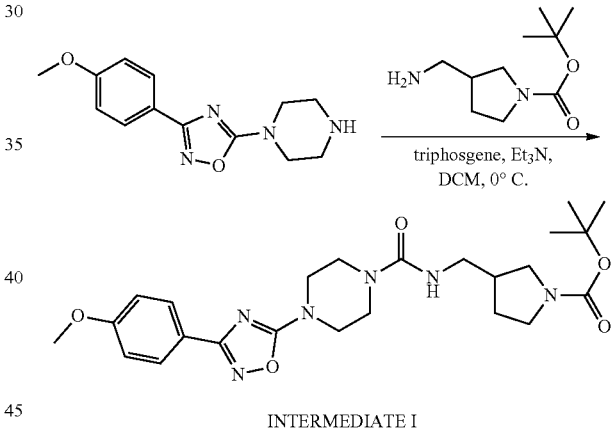

INTERMEDIATE I

To a stirred solution of 3-(4-methoxyphenyl)-5-(piperazin-1-yl)-1,2,4-oxadiazole (0.50 g, 1.92 mmol) in DCM (8 mL) were added bis(trichloromethyl)carbonate (0.29 g, 0.98 mmol) and triethylamine (0.39 g, 3.85 mmol) at 0° C. under a nitrogen atmosphere. The resulting solution was stirred for 0.5 h at 0° C. To the resulting mixture, was added tert-butyl 3-(aminomethyl)pyrrolidine-1-carboxylate (0.39 g, 1.92 mmol) at 0° C. under a nitrogen atmosphere and stirring was continued for an additional 0.5 h. The resulting mixture was diluted with water (30 mL) and extracted with ethyl acetate (3×30 mL). The combined organic layers were washed with brine (30 mL) and dried over anhydrous sodium sulfate. After filtration, the filtrate was concentrated under reduced pressure. The residue was purified by reverse phase flash chromatography with the following conditions: Column: Spherical C18, 20-40 m, 330 g; Mobile Phase A: water (plus 10 mM NH₄HCO₃); Mobile Phase B: acetonitrile; Flow rate: 80 mL/min; Gradient: 50% B-75% B in 20 min; Detector: UV 254/215 nm. The fractions containing desired product were collected at 64% B and concentrated under reduced pressure to afford tert-butyl 3-((4-(3-(4-methoxyphenyl)-1,2,4-oxadiazol-5-yl)piperazine-1-carboxamido)methyl)pyrrolidine-1-carboxylate as a light yellow oil.

Yield: 0.73 g (78%). $^1$H NMR (400 MHz, DMSO) δ 7.85 (d, J=8.8 Hz, 2H), 7.06 (d, J=8.8 Hz, 2H), 6.79 (t, J=5.6 Hz, 1H), 3.82 (s, 3H), 3.64-3.53 (m, 4H), 3.47 (m, 4H), 3.37-3.25 (m, 2H), 3.25-3.15 (m, 1H), 3.04 (dd, J=7.6, 16.8 Hz, 2H), 2.94 (q, J=7.2 Hz, 1H), 2.38-2.23 (m, 1H), 1.91-1.80 (m, 1H), 1.63-1.49 (m, 1H), 1.39 (s, 9H). m/z: [ESI$^+$] 487 (M+H)$^+$.

The compounds below were prepared according to the procedure described above.

4-(3-(4-(Allyloxy)phenyl)-1,2,4-oxadiazol-5-yl)-N-((1-(4-methylbenzyl)pyrrolidin-3-yl)methyl)piperazine-1-carboxamide. The compound was synthesized according to the procedure described above, using 3-(4-(allyloxy)phenyl)-5-(piperazin-1-yl)-1,2,4-oxadiazole hydrochloride (1.00 g, 3.10 mmol) and (1-(4-methylbenzyl)pyrrolidin-3-yl)methanamine hydrochloride (1.68 g, 6.70 mmol) as the starting material.

Yield 1.50 g (94%), as a yellow oil. $^1$H NMR (400 MHz, DMSO) δ 7.84 (d, J=8.4 Hz, 2H), 7.21 (d, J=7.8 Hz, 2H), 7.12 (d, J=7.8 Hz, 2H), 7.08 (d, J=8.4 Hz, 2H), 6.74 (t, J=5.6 Hz, 1H), 6.06 (tdd, J=5.2, 10.6, 17.2 Hz, 1H), 5.48-5.36 (m, 1H), 5.29 (td, J=1.6, 10.6 Hz, 1H), 4.64 (td, J=1.6, 5.2 Hz, 2H), 3.57 (s, 2H), 3.54 (dd, J=4.0, 6.8 Hz, 4H), 3.44 (dd, J=4.0, 6.8 Hz, 4H), 3.09-2.98 (m, 3H), 2.64-2.54 (m, 2H), 2.37-2.30 (m, 2H), 2.28 (s, 3H), 1.90-1.76 (m, 1H), 1.50-1.40 (m, 1H). m/z: [ESI$^+$] 517 (M+H)$^+$.

(4-(3-(4-Methoxyphenyl)-1,2,4-oxadiazol-5-yl)piperazin-1-yl)(4-methylpiperidin-1-yl)methanone (Compound 145): Using 3-(4-methoxyphenyl)-5-(piperazin-1-yl)-1,2,4-oxadiazole (200 mg, 0.768 mmol) and 4-methylpiperidine (76 mg, 0.766 mmol) as the starting material.

Yield 66 mg (22%), as an off-white solid. $^1$H NMR (400 MHz, DMSO) δ 7.84 (d, J=8.8 Hz, 2H), 7.06 (d, J=8.8 Hz, 2H), 3.82 (s, 3H), 3.65-3.58 (m, 6H), 3.32-3.23 (m, 4H), 2.74 (dd, J=1.6, 13.6 Hz, 2H), 1.60 (d, J=13.2 Hz, 2H), 1.53-1.48 (m, 1H), 1.13-1.02 (m, 2H), 0.92 (d, J=6.4 Hz, 3H). m/z: [ESI$^+$] 386 (M+H)$^+$, (C$_{20}$H$_{27}$N$_5$O$_3$).

(4-(3-(4-Methoxyphenyl)-1,2,4-oxadiazol-5-yl)piperazin-1-yl)(4-methoxypiperidin-1-yl)methanone (Compound 190): Using 3-(4-methoxyphenyl)-5-(piperazin-1-yl)-1,2,4-oxadiazole (0.20 g, 0.77 mmol) and 4-methoxypiperidine (0.11 g, 0.92 mmol) as the starting material.

Yield 0.22 g (71%), as a light yellow solid. $^1$H NMR (400 MHz, DMSO) δ 7.83 (d, J=8.8 Hz, 2H), 7.05 (d, J=8.8 Hz, 2H), 3.81 (s, 3H), 3.60 (dd, J=3.6, 6.4 Hz, 4H), 3.43 (td, J=4.4, 13.2 Hz, 2H), 3.33 (s, 2H), 3.27-3.24 (m, 6H), 2.95 (ddd, J=3.2, 9.2, 13.2 Hz, 2H), 1.88-1.78 (m, 2H), 1.47-1.32 (m, 2H). m/z: [ESI$^+$] 402 (M+H)$^+$, (C$_{20}$H$_{27}$N$_5$O$_4$).

1-(4-(4-(3-(4-Methoxyphenyl)-1,2,4-oxadiazol-5-yl)piperazine-1-carbonyl)piperazin-1-yl)ethan-1-one (Compound 225): Using 3-(4-methoxyphenyl)-5-(piperazin-1-yl)-1,2,4-oxadiazole (0.20 g, 0.77 mmol) and 1-(piperazin-1-yl)ethan-1-one (0.10 g, 0.77 mmol) as the starting material.

Yield 0.20 g (62%), as a light yellow solid. $^1$H NMR (400 MHz, DMSO) δ 7.84 (d, J=8.8 Hz, 2H), 7.06 (d, J=8.8 Hz, 2H), 3.82 (s, 3H), 3.66-3.58 (m, 4H), 3.51-3.39 (m, 4H), 3.32 (s, 2H), 3.31 (s, 2H), 3.22 (t, J=5.2 Hz, 2H), 3.16 (t, J=5.2 Hz, 2H), 2.02 (s, 3H). m/z: [ESI$^+$] 415 (M+H)$^+$, (C$_{20}$H$_{26}$N$_6$O$_4$).

(3-Isobutylpiperidin-1-yl)(4-(3-(4-methoxyphenyl)-1,2,4-oxadiazol-5-yl)piperazin-1-yl)methanone (Compound 226): Using 3-(4-methoxyphenyl)-5-(piperazin-1-yl)-1,2,4-oxadiazole (0.15 g, 0.58 mmol) and 3-isobutylpiperidine (81 mg, 0.573 mmol) as the starting material.

Yield 0.20 g (82%), as a light yellow solid. $^1$H NMR (400 MHz, DMSO) δ 7.84 (d, J=8.8 Hz, 2H), 7.06 (d, J=8.8 Hz, 2H), 3.82 (s, 3H), 3.68-3.49 (m, 6H), 3.26 (dd, J=4.0, 6.4 Hz, 4H), 2.81-2.70 (m, 1H), 2.45-2.30 (m, 1H), 1.76 (d, J=12.8 Hz, 1H), 1.64 (dt, J=3.6, 13.2 Hz, 2H), 1.57-1.33 (m, 2H), 1.13-0.95 (m, 3H), 0.88 (d, J=6.4 Hz, 3H), 0.86 (d, J=6.4 Hz, 3H). m/z: [ESI$^+$] 428 (M+H)$^+$, (C$_{23}$H$_{33}$N$_5$O$_3$).

(4-(3-(4-Methoxyphenyl)-1,2,4-oxadiazol-5-yl)piperazin-1-yl)(4-phenoxypiperidin-1-yl)methanone (Compound 216): Using 3-(4-methoxyphenyl)-5-(piperazin-1-yl)-1,2,4-oxadiazole (0.15 g, 0.58 mmol) and 4-phenoxypiperidine (0.10 g, 0.58 mmol) as the starting material.

Yield 0.15 g (55%), as a light yellow solid. $^1$H NMR (400 MHz, DMSO) δ 7.84 (d, J=8.8 Hz, 2H), 7.32-7.26 (m, 2H), 7.05 (d, J=8.8 Hz, 2H), 6.98 (d, J=8.0 Hz, 2H), 6.93 (t, J=7.2 Hz, 1H), 4.62-4.54 (m, 1H), 3.81 (s, 3H), 3.61 (dd, J=3.6, 6.4 Hz, 4H), 3.49 (d, J=13.2 Hz, 2H), 3.30 (dd, J=3.6, 6.4 Hz, 4H), 3.10 (ddd, J=3.2, 9.2, 12.8 Hz, 2H), 1.95 (d, J=12.8 Hz, 2H), 1.67-1.53 (m, 2H). m/z: [ESI$^+$] 464 (M+H)$^+$, (C$_{25}$H$_{29}$N$_5$O$_4$).

4-(3-(4-Methoxyphenyl)-1,2,4-oxadiazol-5-yl)-N-methylpiperazine-1-carboxamide (Compound 191): Using 3-(4-methoxyphenyl)-5-(piperazin-1-yl)-1,2,4-oxadiazole (0.20 g, 0.77 mmol) and methanamine hydrochloride (63 mg, 0.933 mmol) as the starting material.

Yield 0.15 g (62%), as a light yellow solid. $^1$H NMR (400 MHz, DMSO) δ 7.84 (d, J=8.8 Hz, 2H), 7.05 (d, J=8.8 Hz, 2H), 6.59 (q, J=4.2 Hz, 1H), 3.81 (s, 3H), 3.56 (dd, J=3.6, 6.8 Hz, 4H), 3.44 (dd, J=3.6, 6.8 Hz, 4H), 2.59 (d, J=4.2 Hz, 3H). m/z: [ESI$^+$] 318 (M+H)$^+$, (C$_{15}$H$_{19}$N$_5$O$_3$).

(3-(3-(4-Methoxyphenyl)-1,2,4-oxadiazol-5-yl)azetidin-1-yl)(4-methylpiperidin-1-yl)methanone (Compound 153): Using 5-(azetidin-3-yl)-3-(4-methoxyphenyl)-1,2,4-oxadiazole (0.20 g, 0.87 mmol) and 4-methylpiperidine (0.17 g, 1.73 mmol) as the starting material.

Yield 0.16 g (52%), as a light yellow oil. $^1$H NMR (400 MHz, DMSO) δ 8.96 (d, J=8.8 Hz, 2H), 7.12 (d, J=8.8 Hz, 2H), 4.32 (m, 2H), 4.28-4.18 (m, 1H), 4.16 (m, 2H), 3.85 (s, 3H), 3.78-3.69 (d, J=13.2 Hz, 2H), 2.77-2.66 (m, 2H), 1.63-1.55 (m, 2H), 1.56-1.46 (m, 1H), 1.06-0.93 (m, 2H), 0.90 (d, J=6.4 Hz, 3H). m/z: [ESI$^+$] 357 (M+H)$^+$, (C$_{19}$H$_{24}$N$_4$O$_3$).

4-(3-(4-Methoxyphenyl)-1,2,4-oxadiazol-5-yl)-N-((1-methylpyrrolidin-3-yl)methyl)piperazine-1-carboxamide formate (Compound 206): Using 3-(4-methoxyphenyl)-5-(piperazin-1-yl)-1,2,4-oxadiazole (150 mg, 0.576 mmol) and (1-methylpyrrolidin-3-yl)methanamine (66 mg, 0.578 mmol) as the starting material.

Yield 150 mg (58%), as a light yellow solid. $^1$H NMR (400 MHz, DMSO) δ 8.23 (s, 1H, HCOOH), 7.84 (d, J=8.8 Hz, 2H), 7.06 (d, J=8.8 Hz, 2H), 6.77 (t, J=5.6 Hz, 1H), 3.82 (s, 3H), 3.57 (dd, J=3.6, 6.8 Hz, 4H), 3.46 (dd, J=3.6, 6.8 Hz, 4H), 3.07-3.00 (m, 2H), 2.64 (t, J=8.8 Hz, 2H), 2.56 (t, J=7.8 Hz, 1H), 2.43 (dd, J=5.6, 9.6 Hz, 1H), 2.35 (s, 4H), 1.95-1.80 (m, 1H), 1.52-1.40 (m, 1H). m/z: [ESI$^+$] 401 (M+H)$^+$, (C$_{20}$H$_{28}$N$_6$O$_3$).

4-(3-(4-Methoxyphenyl)-1,2,4-oxadiazol-5-yl)-N-((1-phenylpyrrolidin-3-yl)methyl)piperazine-1-carboxamide (Compound 345): Using 3-(4-methoxyphenyl)-5-(piperazin-1-yl)-1,2,4-oxadiazole (100 mg, 0.384 mmol) and (1-phenylpyrrolidin-3-yl)methanamine (81 mg, 0.460 mmol) as the starting material.

Yield 10 mg (6%), as an off-white solid. $^1$H NMR (400 MHz, DMSO) δ 7.84 (d, J=8.8 Hz, 2H), 7.15 (dd, J=7.2, 8.4 Hz, 2H), 7.05 (d, J=8.8 Hz, 2H), 6.83 (t, J=5.6 Hz, 1H), 6.57 (dd, J=1.6, 7.2 Hz, 1H), 6.51 (dd, J=1.2, 8.4 Hz, 2H), 3.82 (s, 3H), 3.57 (dd, J=3.6, 6.8 Hz, 4H), 3.51-3.44 (m, 4H), 3.32-3.25 (m, 2H), 3.20 (dd, J=1.6, 7.2 Hz, 1H), 3.15-3.05 (m, 2H), 3.00 (dd, J=6.0, 9.6 Hz, 1H), 2.50-2.46 (m, 1H), 2.10-1.97 (m, 1H), 1.80-1.67 (m, 1H). m/z: [ESI$^+$] 463 (M+H)$^+$, (C$_{25}$H$_{30}$N$_6$O$_3$).

N-(3-(4-Benzylpiperidin-1-yl)propyl)-4-(3-(4-methoxyphenyl)-1,2,4-oxadiazol-5-yl)piperazine-1-carboxamide (Compound 207): Using 3-(4-methoxyphenyl)-5-(piperazin-1-yl)-1,2,4-oxadiazole (150 mg, 0.576 mmol) and 3-(4-benzylpiperidin-1-yl)propan-1-amine (134 mg, 0.577 mmol) as the starting material.

Yield 0.15 g (50%), as a light yellow solid. $^1$H NMR (400 MHz, DMSO) δ 7.84 (d, J=8.8 Hz, 2H), 7.27 (d, J=7.4 Hz, 2H), 7.21-7.11 (m, 3H), 7.05 (d, J=8.8 Hz, 2H), 6.69 (t, J=5.6 Hz, 1H), 3.81 (s, 3H), 3.55 (dd, J=3.6, 6.8 Hz, 4H), 3.43 (dd, J=3.6, 6.8 Hz, 4H), 3.09-3.02 (m, 2H), 2.82 (d, J=11.0 Hz, 2H), 2.50-2.48 (m, 2H), 2.24 (t, J=7.2 Hz, 2H), 1.76 (t, J=11.6 Hz, 2H), 1.60-1.49 (m, 4H), 1.48-1.37 (m, 1H), 1.23-1.08 (m, 2H). m/z: [ESI$^+$] 519 (M+H)$^+$, (C$_{29}$H$_{38}$N$_6$O$_3$).

4-(3-(4-Methoxyphenyl)-1,2,4-oxadiazol-5-yl)-N-(3-(4-methylpiperidin-1-yl)propyl)piperazine-1-carboxamide formate (Compound 208): Using 3-(4-methoxyphenyl)-5-(piperazin-1-yl)-1,2,4-oxadiazole (150 mg, 0.576 mmol) and 3-(4-methylpiperidin-1-yl)propan-1-amine (90 mg, 0.576 mmol) as the starting material.

Yield 0.15 g (53%), as a light yellow solid. $^1$H NMR (400 MHz, DMSO) δ 8.22 (s, 1H, HCOOH), 7.84 (d, J=8.8 Hz, 2H), 7.05 (d, J=8.8 Hz, 2H), 6.73 (t, J=5.6 Hz, 1H), 3.82 (s, 3H), 3.56 (dd, J=3.6, 6.8 Hz, 4H), 3.45 (dd, J=3.6, 6.8 Hz, 4H), 3.13-3.02 (m, 2H), 2.91 (d, J=10.6 Hz, 2H), 2.39 (t, J=7.2 Hz, 2H), 2.00 (t, J=11.6 Hz, 2H), 1.68-1.55 (m, 4H), 1.36 (td, J=5.6, 11.4 Hz, 1H), 1.20-1.08 (m, 2H), 0.89 (d, J=6.4 Hz, 3H). m/z: [ESI$^+$] 443 (M+H)$^+$, (C$_{23}$H$_{34}$N$_6$O$_3$).

4-(3-(4-Methoxyphenyl)-1,2,4-oxadiazol-5-yl)-N-(3-(4-phenoxypiperidin-1-yl)propyl)piperazine-1-carboxamide formate (Compound 245): Using 3-(4-methoxyphenyl)-5-(piperazin-1-yl)-1,2,4-oxadiazole (0.20 g, 0.77 mmol) and 3-(4-phenoxypiperidin-1-yl)propan-1-amine (0.22 g, 0.92 mmol) as the starting material.

Yield 0.12 g (28%), as a light yellow solid. $^1$H NMR (400 MHz, DMSO) δ 8.17 (s, 1H, HCOOH), 7.85 (d, J=8.8 Hz, 2H), 7.32-7.23 (m, 2H), 7.05 (d, J=8.8 Hz, 2H), 6.96 (s, 1H), 6.97-6.87 (m, 2H), 6.70 (t, J=5.2 Hz, 1H), 4.43-4.34 (m, 1H), 3.83 (s, 3H), 3.57 (dd, J=3.6, 6.8 Hz, 4H), 3.46 (dd, J=3.6, 6.8 Hz, 4H), 3.12-3.05 (m, 2H), 2.74 (t, J=7.6 Hz, 2H), 2.36 (t, J=7.2 Hz, 2H), 2.26 (t, J=9.6 Hz, 2H), 1.94 (t, J=8.0 Hz, 2H), 1.70-1.55 (m, 4H). m/z: [ESI$^+$] 521 (M+H)$^+$, (C$_{28}$H$_{36}$N$_6$O$_4$).

4-(3-(4-Methoxyphenyl)-1,2,4-oxadiazol-5-yl)-N-(3-(4-(pyridin-2-ylmethyl)piperidin-1-yl)propyl)piperazine-1-carboxamide formate (Compound 248): Using 3-(4-methoxyphenyl)-5-(piperazin-1-yl)-1,2,4-oxadiazole (60 mg, 0.231 mmol) and 3-(4-(pyridin-2-ylmethyl)piperidin-1-yl)propan-1-amine (65 mg, 0.279 mmol) as the starting material.

Yield 20 mg (15%), as a light yellow solid. $^1$H NMR (400 MHz, DMSO) δ 8.51-8.45 (m, 1H), 8.19 (s, 1H, HCOOH), 7.85 (d, J=8.8 Hz, 2H), 7.68 (dd, J=2.0, 7.6 Hz, 1H), 7.22 (dd, J=1.2, 7.8 Hz, 1H), 7.20-7.15 (m, 1H), 7.06 (d, J=8.8 Hz, 2H), 6.71 (t, J=5.2 Hz, 1H), 3.82 (s, 3H), 3.56 (dd, J=3.6, 6.8 Hz, 4H), 3.45 (dd, J=3.6, 6.4 Hz, 4H), 3.12-3.05 (m, 2H), 2.89 (d, J=11.2 Hz, 2H), 2.65 (d, J=7.2 Hz, 2H), 2.34 (t, J=7.2 Hz, 2H), 1.97-1.87 (m, 2H), 1.75 (ddd, J=4.0, 7.2, 11.2 Hz, 1H), 1.62-1.50 (m, 4H), 1.31-1.13 (m, 2H). m/z: [ESI$^+$] 520 (M+H)$^+$, (C$_{28}$H$_{37}$N$_7$O$_3$).

4-(3-(4-Cyanophenyl)-1,2,4-oxadiazol-5-yl)-N-((1-(4-methylbenzyl)-5-oxopyrrolidin-3-yl)methyl)piperazine-1-carboxamide (Compound 268): Using 4-(5-(piperazin-1-yl)-1,2,4-oxadiazol-3-yl)benzonitrile (0.20 g, 0.77 mmol) and 4-(aminomethyl)-1-(4-methylbenzyl)pyrrolidin-2-one (0.21 g, 0.94 mmol) as the starting material.

Yield 0.10 g (26%), as a light yellow solid. $^1$H NMR (400 MHz, DMSO) δ 8.07 (d, J=8.4 Hz, 2H), 8.00 (d, J=8.4 Hz, 2H), 7.15 (d, J=8.0 Hz, 2H), 7.09 (d, J=8.0 Hz, 2H), 6.81 (t, J=5.6 Hz, 1H), 4.35-4.25 (m, 2H), 3.57 (dd, J=3.6, 6.8 Hz, 4H), 3.45 (dd, J=3.6, 6.8 Hz, 4H), 3.26 (dd, J=7.6, 10.0 Hz, 1H), 3.06 (t, J=5.6 Hz, 2H), 2.96 (dd, J=5.2, 10.0 Hz, 1H), 2.47-2.32 (m, 2H), 2.27 (s, 3H), 2.14 (dd, J=6.0, 16.4 Hz, 1H). m/z: [ESI$^+$] 500 (M+H)$^+$, (C$_{27}$H$_{29}$N$_7$O$_3$).

N-(3-(4-(pyridin-2-ylmethyl)piperidin-1-yl)propyl)-4-(3-(4-(trifluoromethoxy)phenyl)-1,2,4-oxadiazol-5-yl)piperazine-1-carboxamide (Compound 436): Using 5-(piperazin-1-yl)-3-(4-(trifluoromethoxy)phenyl)-1,2,4-oxadiazole (80 mg, 0.255 mmol) and 3-(4-(pyridin-2-ylmethyl)piperidin-1-yl)propan-1-amine (60 mg, 0.257 mmol) as the starting material.

Yield 40 mg (27%), as a light yellow solid. $^1$H NMR (400 MHz, DMSO) δ 8.48 (ddd, J=0.8, 2.0, 4.8 Hz, 1H), 8.03 (d, J=8.8 Hz, 2H), 7.68 (dd, J=2.0, 7.6 Hz, 1H), 7.52 (dd, J=1.0, 8.8 Hz, 2H), 7.21 (dd, J=1.0, 8.0 Hz, 1H), 7.18 (ddd, J=1.0, 2.4, 8.0 Hz, 1H), 6.69 (t, J=5.6 Hz, 1H), 3.58 (dd, J=3.6, 6.8 Hz, 4H), 3.45 (dd, J=3.6, 6.8 Hz, 4H), 3.08-3.01 (m, 2H), 2.82 (d, J=11.2 Hz, 2H), 2.63 (d, J=7.2 Hz, 2H), 2.24 (t, J=7.2 Hz, 2H), 1.84-1.62 (m, 3H), 1.62-1.45 (m, 4H), 1.28-1.12 (m, 2H); $^{19}$F NMR (376 MHz, DMSO) δ −56.67. m/z: [ESI$^+$] 574 (M+H)$^+$, (C$_{28}$H$_{34}$F$_3$N$_7$O$_3$).

4-(3-(4-(Difluoromethoxy)phenyl)-1,2,4-oxadiazol-5-yl)-N-(3-(4-(pyridin-2-ylmethyl)piperidin-1-yl)propyl)piperazine-1-carboxamide (Compound 437): Using 3-(4-(difluoromethoxy)phenyl)-5-(piperazin-1-yl)-1,2,4-oxadiazole (100 mg, 0.337 mmol) and 3-(4-(pyridin-2-ylmethyl)piperidin-1-yl)propan-1-amine (79 mg, 0.339 mmol) as the starting material.

Yield 38 mg (20%), as a light orange solid. $^1$H NMR (400 MHz, DMSO) δ 8.51-8.43 (m, 1H), 7.96 (d, J=8.8 Hz, 2H), 7.68 (dd, J=2.0, 7.6 Hz, 1H), 7.35 (t, J=73.6 Hz, 1H), 7.31 (d, J=8.8 Hz, 2H), 7.23-7.18 (m, 2H), 6.68 (t, J=5.6 Hz, 1H), 3.58 (t, J=5.2 Hz, 4H), 3.45 (t, J=5.2 Hz, 4H), 3.05 (q, J=6.4 Hz, 2H), 2.82 (d, J=11.2 Hz, 2H), 2.64 (d, J=7.2 Hz, 2H), 2.24 (t, J=7.2 Hz, 2H), 1.86-1.63 (m, 3H), 1.63-1.48 (m, 4H), 1.20 (q, J=10.8 Hz, 2H); $^{19}$F NMR (376 MHz, DMSO) δ −82.61. m/z: [ESI$^+$] 556 (M+H)$^+$, (C$_{28}$H$_{35}$F$_2$N$_7$O$_3$).

4-(3-(4-Methoxyphenyl)-1,2,4-oxadiazol-5-yl)-N-(2-((1-(pyridin-2-ylmethyl)piperidin-4-yl)oxy)ethyl)piperazine-1-carboxamide (Compound 457): Using 3-(4-methoxyphenyl)-5-(piperazin-1-yl)-1,2,4-oxadiazole (100 mg, 0.384 mmol) and 2-((1-(pyridin-2-ylmethyl)piperidin-4-yl)oxy)ethan-1-amine (110 mg, 0.467 mmol) as the starting material.

Yield 26 mg (13%), as a light yellow solid. $^1$H NMR (400 MHz, DMSO) δ 8.50-8.43 (m, 1H), 7.84 (d, J=8.8 Hz, 2H), 7.75 (dd, J=2.0, 7.6 Hz, 1H), 7.42 (d, J=7.6 Hz, 1H), 7.24 (dd, J=4.8, 7.2 Hz, 1H), 7.06 (d, J=8.8 Hz, 2H), 6.70 (t, J=5.6 Hz, 1H), 3.82 (s, 3H), 3.61-3.52 (m, 6H), 3.48-3.42 (m, 4H), 3.40-3.31 (m, 3H), 3.22-2.16 (m, 2H), 2.69 (d, J=10.4 Hz, 2H), 2.12 (t, J=10.8 Hz, 2H), 1.83 (d, J=12.3 Hz, 2H), 1.48-1.38 (m, 2H). m/z: [ESI$^+$] 522 (M+H)$^+$, (C$_{27}$H$_{35}$N$_7$O$_4$).

N-(3-(4-phenoxypiperidin-1-yl)propyl)-4-(3-(4-(trifluoromethoxy)phenyl)-1,2,4-oxadiazol-5-yl)piperazine-1-carboxamide (Compound 428): Using 5-(piperazin-1-yl)-3-(4-(trifluoromethoxy)phenyl)-1,2,4-oxadiazole (100 mg, 0.318 mmol) and 3-(4-phenoxypiperidin-1-yl)propan-1-amine (75 mg, 0.320 mmol) as the starting material.

Yield 48 mg (26%), as an off-white solid. $^1$H NMR (400 MHz, DMSO) δ 8.04 (d, J=8.8 Hz, 2H), 7.59-7.48 (m, 2H), 7.30-7.23 (m, 2H), 6.98-6.86 (m, 3H), 6.70 (t, J=5.6 Hz, 1H), 4.41-4.33 (m, 1H), 3.59 (t, J=5.2 Hz, 4H), 3.46 (t, J=5.2 Hz, 4H), 3.13-3.02 (m, 2H), 2.74-2.63 (m, 2H), 2.30 (t, J=7.2 Hz, 2H), 2.18 (t, J=10.4 Hz, 2H), 1.98-1.89 (m, 2H), 1.66-1.55 (m, 4H); $^{19}$F NMR (376 MHz, DMSO) δ −56.67. m/z: [ESI$^+$] 575 (M+H)$^+$, ($C_{28}H_{33}F_3N_6O_4$).

N-((1-((4-(pyridin-2-ylmethyl)piperidin-1-yl)methyl)cyclopropyl)methyl)-4-(3-(4-(trifluoromethoxy)phenyl)-1,2,4-oxadiazol-5-yl)piperazine-1-carboxamide (Compound 450): Using 5-(piperazin-1-yl)-3-(4-(trifluoromethoxy)phenyl)-1,2,4-oxadiazole (90 mg, 0.286 mmol) and (1-((4-(pyridin-2-ylmethyl)piperidin-1-yl)methyl)cyclopropyl)methanamine (80 mg, 0.308 mmol) as the starting material.

Yield 35 mg (20%), as an off-white solid. $^1$H NMR (400 MHz, DMSO) δ 8.52-8.42 (m, 1H), 8.04 (d, J=8.8 Hz, 2H), 7.68 (dd, J=2.0, 7.6 Hz, 1H), 7.53 (d, J=8.8 Hz, 2H), 7.29-7.12 (m, 2H), 6.69 (t, J=5.6 Hz, 1H), 3.59 (t, J=5.2 Hz, 4H), 3.46 (t, J=5.2 Hz, 4H), 3.14 (d, J=5.2 Hz, 2H), 2.96 (d, J=11.2 Hz, 2H), 2.66 (d, J=7.2 Hz, 2H), 2.21 (s, 2H), 1.82-1.66 (m, 3H), 1.54 (d, J=12.8 Hz, 2H), 1.28-1.17 (m, 2H), 0.48-0.40 (m, 2H), 0.21-0.18 (m, 2H); $^{19}$F NMR (376 MHz, DMSO) δ −56.67. m/z: [ESI$^+$] 600 (M+H)$^+$, ($C_{30}H_{36}F_3N_7O_3$).

N-(3-(4-fluoro-4-(pyridin-2-ylmethyl)piperidin-1-yl)propyl)-4-(3-(4-methoxyphenyl)-1,2,4-oxadiazol-5-yl)piperazine-1-carboxamide formate (Compound 461): Using 3-(4-methoxyphenyl)-5-(piperazin-1-yl)-1,2,4-oxadiazole (100 mg, 0.384 mmol) and 3-(4-fluoro-4-(pyridin-2-ylmethyl)piperidin-1-yl)propan-1-amine (120 mg, 0.477 mmol) as the starting material.

Yield 14 mg (6%), as an off-white solid. $^1$H NMR (400 MHz, DMSO) δ 8.53-8.46 (m, 1H), 8.17 (s, 1H, HCOOH), 7.84 (d, J=8.8 Hz, 2H), 7.73 (dd, J=2.0, 7.6 Hz, 1H), 7.33-7.23 (m, 2H), 7.06 (d, J=8.8 Hz, 2H), 6.66 (t, J=5.6 Hz, 1H), 3.82 (s, 3H), 3.55 (m, 4H), 3.44-3.41 (m, 4H), 3.30-3.20 (m, 2H), 3.04 (d, J=4.4 Hz, 2H), 2.66 (d, J=11.2 Hz, 2H), 2.30 (t, J=7.2 Hz, 2H), 2.16 (d, J=11.6 Hz, 2H), 1.78-1.63 (m, 4H), 1.57 (t, J=7.2 Hz, 2H). $^{19}$F NMR (376 MHz, DMSO): signal not observed. m/z: [ESI$^+$] 538 (M+H)$^+$, ($C_{28}H_{36}FN_7O_3$).

N-(3-(4-(2-fluorobenzyl)piperidin-1-yl)propyl)-4-(3-(4-(trifluoromethoxy)phenyl)-1,2,4-oxadiazol-5-yl)piperazine-1-carboxamide (Compound 429): Using 5-(piperazin-1-yl)-3-(4-(trifluoromethoxy)phenyl)-1,2,4-oxadiazole (100 mg, 0.318 mmol) and 3-(4-(2-fluorobenzyl)piperidin-1-yl)propan-1-amine (80 mg, 0.320 mmol) as the starting material.

Yield 20 mg (11%), as a yellow solid. $^1$H NMR (400 MHz, DMSO) δ 8.04 (d, J=8.8 Hz, 2H), 7.52 (d, J=8.8 Hz, 2H), 7.30-7.21 (m, 2H), 7.18-7.08 (m, 2H), 6.69 (t, J=5.6 Hz, 1H), 3.59 (t, J=5.2 Hz, 4H), 3.45 (t, J=5.2 Hz, 4H), 3.08-3.02 (m, 2H), 2.90-2.80 (m, 2H), 2.55-2.50 (m, 2H), 2.32-2.20 (m, 2H), 1.85-1.70 (m, 2H), 1.60-1.47 (m, 5H), 1.32-1.09 (m, 2H). $^{19}$F NMR (376 MHz, DMSO) δ −56.66, −118.30. m/z: [ESI$^+$] 591 (M+H)$^+$, ($C_{29}H_{34}F_4N_6O_3$).

4-(3-(4-(Difluoromethoxy)phenyl)-1,2,4-oxadiazol-5-yl)-N-(3-(4-(2-fluorobenzyl)piperidin-1-yl)propyl)piperazine-1-carboxamide (Compound 438): Using 3-(4-(difluoromethoxy)phenyl)-5-(piperazin-1-yl)-1,2,4-oxadiazole (100 mg, 0.338 mmol) and 3-(4-(2-fluorobenzyl)piperidin-1-yl)propan-1-amine (85 mg, 0.340 mmol) as the starting material.

Yield 20 mg (10%), as a light orange solid. $^1$H NMR (400 MHz, DMSO) δ 7.96 (d, J=8.8 Hz, 2H), 7.35 (t, J=73.6 Hz, 1H), 7.31 (d, J=8.8 Hz, 2H), 7.28-7.20 (m, 2H), 7.15-7.10 (m, 2H), 6.68 (t, J=5.6 Hz, 1H), 3.57 (dd, J=4.0, 6.8 Hz, 4H), 3.45 (dd, J=4.0, 6.8 Hz, 4H), 3.08-3.02 (m, 2H), 2.82 (d, J=11.2 Hz, 2H), 2.54-2.50 (m, 2H), 2.24 (t, J=7.2 Hz, 2H), 1.77 (t, J=11.2 Hz, 2H), 1.60-1.43 (m, 5H), 1.32-1.09 (m, 2H). $^{19}$F NMR (376 MHz, DMSO) δ −82.61, −118.31. m/z: [ESI$^+$] 573 (M+H)$^+$, ($C_{29}H_{35}F_3N_6O_3$).

N-((1H-indol-2-yl)methyl)-4-(3-(4-methoxyphenyl)-1,2,4-oxadiazol-5-yl)piperazine-1-carboxamide (Compound 417): Using 3-(4-methoxyphenyl)-5-(piperazin-1-yl)-1,2,4-oxadiazole (100 mg, 0.384 mmol) and (1H-indol-2-yl)methanamine (84 mg, 0.575 mmol) as the starting material.

Yield 50 mg (30%), as an off-white solid. $^1$H NMR (400 MHz, DMSO) δ 10.80 (br s, 1H), 7.86 (d, J=8.8 Hz, 2H), 7.44 (d, J=8.0 Hz, 1H), 7.34 (d, J=8.0 Hz, 1H), 7.22 (t, J=5.6 Hz, 1H), 7.06 (d, J=8.8 Hz, 2H), 7.04-6.99 (m, 1H), 6.97-6.91 (m, 1H), 6.24 (s, 1H), 4.41 (d, J=5.6 Hz, 2H), 3.82 (s, 3H), 3.61 (dd, J=4.0, 6.8 Hz, 4H), 3.57-3.50 (m, 4H). m/z: [ESI$^+$] 433 (M+H)$^+$, ($C_{23}H_{24}N_6O_3$).

4-(3-(4-Cyanophenyl)-1,2,4-oxadiazol-5-yl)-N-(3-(4-(pyridin-2-ylmethyl)piperidin-1-yl)propyl)piperazine-1-carboxamide (Compound 431): Using 4-(5-(piperazin-1-yl)-1,2,4-oxadiazol-3-yl)benzonitrile (100 mg, 0.392 mmol) and 3-(4-(pyridin-2-ylmethyl)piperidin-1-yl)propan-1-amine (100 mg, 0.429 mmol) as the starting material.

Yield 15 mg (7%), as a brown solid. $^1$H NMR (400 MHz, DMSO) δ 8.47 (dd, J=1.6, 4.4 Hz, 1H), 8.08 (d, J=8.4 Hz, 2H), 8.00 (d, J=8.4 Hz, 2H), 7.68 (dd, J=2.0, 7.6 Hz, 1H), 7.26-7.14 (m, 2H), 6.70 (t, J=5.6 Hz, 1H), 3.59 (dd, J=4.0, 6.8 Hz, 4H), 3.46 (dd, J=4.0, 6.8 Hz, 4H), 3.10-3.01 (m, 2H), 2.85 (d, J=11.2 Hz, 2H), 2.64 (d, J=7.2 Hz, 2H), 2.32-2.24 (m, 2H), 1.91-1.80 (m, 2H), 1.77-1.67 (m, 1H), 1.65-1.47 (m, 4H), 1.28-1.16 (m, 2H). m/z: [ESI$^+$] 515 (M+H)$^+$, ($C_{28}H_{34}N_8O_2$).

4-(3-(4-Methoxyphenyl)-1,2,4-oxadiazol-5-yl)-N-(3-(4-(trifluoromethyl)piperidin-1-yl)propyl)piperazine-1-carboxamide (Compound 426): Using 3-(4-methoxyphenyl)-5-(piperazin-1-yl)-1,2,4-oxadiazole (100 mg, 0.384 mmol) and 3-(4-(trifluoromethyl)piperidin-1-yl)propan-1-amine (121 mg, 0.576 mmol) as the starting material.

Yield 20 mg (10%), as an off-white solid. $^1$H NMR (400 MHz, DMSO) δ 7.84 (d, J=8.8 Hz, 2H), 7.06 (d, J=8.8 Hz, 2H), 6.67 (d, J=5.6 Hz, 1H), 3.82 (s, 3H), 3.57 (dd, J=4.0, 6.8 Hz, 4H), 3.45 (dd, J=4.0, 6.8 Hz, 4H), 3.10-3.01 (m, 2H), 2.94 (d, J=11.2 Hz, 2H), 2.36-2.20 (m, 3H), 1.93-1.83 (m, 2H), 1.78 (d, J=12.8 Hz, 2H), 1.64-1.52 (m, 2H), 1.52-1.36 (m, 2H); $^{19}$F NMR (376 MHz, DMSO) δ −72.41. m/z: [ESI$^+$] 497 (M+H)$^+$, ($C_{23}H_{31}F_3N_6O_3$).

N-(3-(4-(difluoromethyl)piperidin-1-yl)propyl)-4-(3-(4-methoxyphenyl)-1,2,4-oxadiazol-5-yl)piperazine-1-carboxamide (Compound 439): Using 3-(4-methoxyphenyl)-5-(piperazin-1-yl)-1,2,4-oxadiazole (100 mg, 0.384 mmol) and 3-(4-(difluoromethyl)piperidin-1-yl)propan-1-amine (111 mg, 0.577 mmol) as the starting material.

Yield 47 mg (26%), as an off-white solid. $^1$H NMR (400 MHz, DMSO) δ 7.85 (d, J=8.8 Hz, 2H), 7.06 (d, J=8.8 Hz, 2H), 6.68 (t, J=5.6 Hz, 1H), 5.89 (dt, J=4.4, 56.8 Hz, 1H), 3.82 (s, 3H), 3.57 (dd, J=4.0, 6.8 Hz, 4H), 3.45 (dd, J=4.0, 6.8 Hz, 4H), 3.09-3.01 (m, 2H), 2.91 (d, J=11.2 Hz, 2H), 2.28 (t, J=7.2 Hz, 2H), 1.89-1.79 (m, 2H), 1.79-1.69 (m, 1H), 1.65 (d, J=13.2 Hz, 2H), 1.58 (t, J=7.2 Hz, 2H), 1.38-1.25 (m, 2H). $^{19}$F NMR (376 MHz, DMSO) δ −123.21. m/z: [ESI$^+$] 479 (M+H)$^+$, ($C_{23}H_{32}F_2N_6O_3$).

N-(3-(4-fluoro-4-(pyridin-2-yl)piperidin-1-yl)propyl)-4-(3-(4-methoxyphenyl)-1,2,4-oxadiazol-5-yl)piperazine-1-carboxamide (Compound 440): Using 3-(4-methoxyphenyl)-5-(piperazin-1-yl)-1,2,4-oxadiazole (100 mg, 0.384 mmol) and 3-(4-fluoro-4-(pyridin-2-yl)piperidin-1-yl)propan-1-amine (109 mg, 0.459 mmol) as the starting material.

Yield 40 mg (20%), as an off-white solid. $^1$H NMR (400 MHz, DMSO) δ 8.68-8.57 (m, 1H), 7.91-7.80 (m, 3H), 7.57

(dd, J=1.2, 8.0 Hz, 1H), 7.37 (ddd, J=1.2, 4.8, 7.6 Hz, 1H), 7.06 (d, J=8.8 Hz, 2H), 6.87 (t, J=5.6 Hz, 1H), 3.83 (s, 3H), 3.61 (dd, J=4.0, 6.8 Hz, 4H), 3.47 (dd, J=4.0, 6.8 Hz, 4H), 3.19-3.11 (m, 2H), 2.87 (d, J=8.4 Hz, 2H), 2.40 (t, J=6.8 Hz, 2H), 2.36-2.15 (m, 4H), 1.86 (t, J=12.0 Hz, 2H), 1.68-1.58 (m, 2H); $^{19}$F NMR (376 MHz, DMSO) δ −162.06. m/z: [ESI$^+$] 524 (M+H)$^+$, ($C_{27}H_{34}FN_7O_3$).

4-(3-(4-Methoxyphenyl)-1,2,4-oxadiazol-5-yl)-N-(3-(4-(pyridin-2-ylmethyl)piperazin-1-yl)propyl)piperazine-1-carboxamide formate (Compound 441): Using 3-(4-methoxyphenyl)-5-(piperazin-1-yl)-1,2,4-oxadiazole (112 mg, 0.430 mmol) and 3-(4-(pyridin-2-ylmethyl)piperazin-1-yl)propan-1-amine (100 mg, 0.427 mmol) as the starting material.

Yield 64 mg (25%), as a dark yellow solid. $^1$H NMR (400 MHz, DMSO) δ 8.52-8.42 (m, 1H), 8.16 (s, 1.58H, HCOOH), 7.85 (d, J=8.8 Hz, 2H), 7.76 (dd, J=2.0, 7.8 Hz, 1H), 7.47-7.39 (m, 1H), 7.26 (ddd, J=1.2, 4.8, 7.6 Hz, 1H), 7.06 (d, J=8.8 Hz, 2H), 6.70 (t, J=5.6 Hz, 1H), 3.82 (s, 3H), 3.59 (s, 2H), 3.56 (dd, J=4.0, 6.8 Hz, 4H), 3.44 (dd, J=4.0, 6.8 Hz, 4H), 3.12-3.04 (m, 2H), 2.44 (s, 8H), 2.33 (t, J=7.2 Hz, 2H), 1.68-1.53 (m, 2H). m/z: [ESI$^+$] 521 (M+H)$^+$, ($C_{27}H_{36}N_8O_3$).

4-(3-(4-Chlorophenyl)-1,2,4-oxadiazol-5-yl)-N-(3-(4-(pyridin-2-ylmethyl)piperidin-1-yl)propyl)piperazine-1-carboxamide (Compound 458): Using 3-(4-chlorophenyl)-5-(piperazin-1-yl)-1,2,4-oxadiazole (330 mg, 1.247 mmol) and 3-(4-(pyridin-2-ylmethyl)piperidin-1-yl)propan-1-amine (300 mg, 1.286 mmol) as the starting material.

Yield 43 mg (7%), as an off-white solid. $^1$H NMR (400 MHz, DMSO) δ 8.47 (ddd, J=0.8, 2.0, 4.8 Hz, 1H), 7.92 (d, J=8.4 Hz, 2H), 7.67 (dd, J=2.0, 7.8 Hz, 1H), 7.59 (d, J=8.4 Hz, 2H), 7.24-7.13 (m, 2H), 6.69 (t, J=5.6 Hz, 1H), 3.57 (dd, J=4.0, 6.8 Hz, 4H), 3.48-3.41 (m, 4H), 3.09-3.03 (m, 2H), 2.81 (d, J=11.2 Hz, 2H), 2.63 (d, J=7.2 Hz, 2H), 2.23 (t, J=7.2 Hz, 2H), 1.83-1.64 (m, 3H), 1.60-1.45 (m, 4H), 1.28-1.12 (m, 2H). m/z: [ESI$^+$] 524, 526 (M+H)$^+$, ($C_{27}H_{34}ClN_7O_2$).

4-(3-(4-Fluorophenyl)-1,2,4-oxadiazol-5-yl)-N-(3-(4-(pyridin-2-ylmethyl)piperidin-1-yl)propyl)piperazine-1-carboxamide (Compound 430): Using 3-(4-fluorophenyl)-5-(piperazin-1-yl)-1,2,4-oxadiazole (100 mg, 0.403 mmol) and 3-(4-(pyridin-2-ylmethyl)piperidin-1-yl)propan-1-amine (94 mg, 0.403 mmol) as the starting material.

Yield 30 mg (15%), as a yellow solid. $^1$H NMR (400 MHz, DMSO) δ 8.51-8.45 (m, 1H), 7.96 (dd, J=5.6, 8.8 Hz, 2H), 7.68 (dd, J=2.0, 7.6 Hz, 1H), 7.36 (d, J=8.8 Hz, 2H), 7.26-7.15 (m, 2H), 6.72 (br s, 1H), 3.58 (dd, J=4.0, 6.8 Hz, 4H), 3.45 (dd, J=4.0, 6.8 Hz, 4H), 3.10-3.02 (m, 2H), 2.96-2.78 (m, 2H), 2.65 (d, J=7.2 Hz, 2H), 2.54-2.50 (m, 2H), 2.39-2.19 (m, 1H), 1.91-1.70 (m, 2H), 1.66-1.50 (m, 4H), 1.33-1.15 (m, 2H); $^{19}$F NMR (376 MHz, DMSO) δ −109.27. m/z: [ESI$^+$] 508 (M+H)$^+$, ($C_{27}H_{34}N_7O_2$).

N-(3-(4-(pyridin-2-ylmethyl)piperidin-1-yl)propyl)-4-(3-(4-(trifluoromethyl)phenyl)-1,2,4-oxadiazol-5-yl)piperazine-1-carboxamide (Compound 459): Using 5-(piperazin-1-yl)-3-(4-(trifluoromethyl)phenyl)-1,2,4-oxadiazole (100 mg, 0.335) and 3-(4-(pyridin-2-ylmethyl)piperidin-1-yl)propan-1-amine (100 mg, 0.429 mmol) as the starting material.

Yield 60 mg (32%), as an off-white solid. $^1$H NMR (400 MHz, DMSO) δ 8.48 (ddd, J=0.8, 2.0, 4.8 Hz, 1H), 8.13 (d, J=8.4 Hz, 2H), 7.90 (d, J=8.4 Hz, 2H), 7.68 (dd, J=2.0, 7.6 Hz, 1H), 7.25-7.13 (m, 2H), 6.70 (t, J=5.6 Hz, 1H), 3.60 (dd, J=4.0, 6.8 Hz, 4H), 3.49-3.42 (m, 4H), 3.10-3.02 (m, 2H), 2.82 (d, J=11.2 Hz, 2H), 2.64 (d, J=7.2 Hz, 2H), 2.24 (t, J=7.2 Hz, 2H), 1.78 (t, J=11.2 Hz, 2H), 1.74-1.64 (m, 1H), 1.61-1.46 (m, 4H), 1.27-1.13 (m, 2H); $^{19}$F NMR (376 MHz, DMSO) δ −61.42. m/z: [ESI$^+$] 558 (M+H)$^+$, ($C_{28}H_{34}F_3N_7O_2$).

4-(3-(4-(Difluoromethyl)phenyl)-1,2,4-oxadiazol-5-yl)-N-(3-(4-(pyridin-2-ylmethyl)piperidin-1-yl)propyl)piperazine-1-carboxamide (Compound 460): Using 3-(4-(difluoromethyl)phenyl)-5-(piperazin-1-yl)-1,2,4-oxadiazole (100 mg, 0.357 mmol) and 3-(4-(pyridin-2-ylmethyl)piperidin-1-yl)propan-1-amine (100 mg, 0.429 mmol) as the starting material.

Yield 50 mg (26%), as a yellow solid. $^1$H NMR (400 MHz, DMSO) δ 8.47 (dd, J=1.6, 4.8 Hz, 1H), 8.05 (d, J=8.0 Hz, 2H), 7.72 (d, J=8.0 Hz, 2H), 7.67 (dd, J=2.0, 7.6 Hz, 1H), 7.23-7.15 (m, 2H), 7.12 (t, J=55.6 Hz, 1H), 6.69 (t, J=5.4 Hz, 1H), 3.59 (dd, J=4.0, 6.8 Hz, 4H), 3.45 (dd, J=4.0, 6.8 Hz, 4H), 3.10-3.00 (m, 2H), 2.81 (d, J=11.2 Hz, 2H), 2.63 (d, J=7.2 Hz, 2H), 2.24 (t, J=7.2 Hz, 2H), 1.78 (t, J=11.2 Hz, 2H), 1.73-1.61 (m, 1H), 1.60-1.45 (m, 4H), 1.27-1.13 (m, 2H); $^{19}$F NMR (376 MHz, DMSO) δ −110.66. m/z: [ESI$^+$] 540 (M+H)$^+$, ($C_{28}H_{35}F_2N_7O_2$).

(1,1-Dioxidothiomorpholino)(4-(3-(4-methoxyphenyl)-1,2,4-oxadiazol-5-yl)piperazin-1-yl)methanone (Compound 146): Using 3-(4-methoxyphenyl)-5-(piperazin-1-yl)-1,2,4-oxadiazole (200 mg, 0.768 mmol) and thiomorpholine 1,1-dioxide (104 mg, 0.769 mmol) as the starting material.

$^1$H NMR (400 MHz, DMSO) δ 7.84 (d, J=8.8 Hz, 2H), 7.06 (d, J=8.8 Hz, 2H), 3.83 (s, 3H), 3.62 (m, 8H), 3.37 (m, 4H), 3.20 (m, 4H). m/z: [ESI$^+$] 422 (M+H)$^+$, ($C_{18}H_{23}N_5O_5S$).

4-(3-(4-Methoxyphenyl)-1,2,4-oxadiazol-5-yl)-N-phenylpiperazine-1-carboxamide (Compound 209)

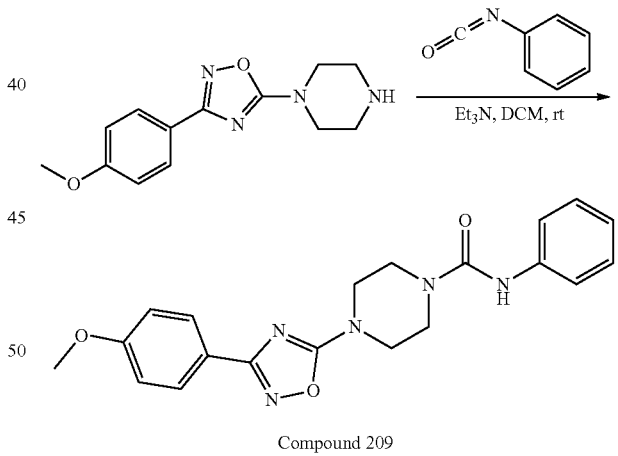

Scheme 11

Compound 209

To a stirred solution of 3-(4-methoxyphenyl)-5-(piperazin-1-yl)-1,2,4-oxadiazole (0.20 g, 0.77 mmol) in DCM (5 mL) were added phenyl isocyanate (92 mg, 0.768 mmol) and triethylamine (93 mg, 0.92 mmol) at room temperature under a nitrogen atmosphere. The resulting solution was stirred for 0.5 h at room temperature. The resulting solution was diluted with water (20 mL) and extracted with ethyl acetate (3×20 mL). The combined organic layers were washed with brine (20 mL) and dried over anhydrous Na$_2$SO$_4$. After filtration, the filtrate was concentrated under reduced pressure. The residue was purified by reverse phase flash chromatography with the following conditions: Column: Spherical C18, 20-40 m, 330 g; Mobile Phase A: water (plus 10 mM $NH_4HCO_3$); Mobile Phase B: acetonitrile; Flow rate: 80 mL/min; Gradient: 50% B-75% B in 20 min; Detector: UV 254/215 nm. The fractions containing desired product were collected and concentrated under reduced pressure to afford 4-(3-(4-methoxyphenyl)-1,2,4-oxadiazol-5-yl)-N-phenylpiperazine-1-carboxamide as a light yellow solid.

Yield: 0.22 g (75%). $^1$H NMR (400 MHz, DMSO) δ 8.68 (s, 1H), 7.86 (d, J=8.8 Hz, 2H), 7.47 (d, J=8.0 Hz, 2H), 7.25 (t, J=8.0 Hz, 2H), 7.06 (d, J=8.8 Hz, 2H), 6.95 (t, J=7.2 Hz, 1H), 3.82 (s, 3H), 3.70-3.58 (m, 8H). m/z: [ESI$^+$] 380 (M+H)$^+$, ($C_{20}H_{21}N_5O_3$).

The compounds below were prepared according to the procedure described above.

N-(4-chlorophenyl)-4-(3-(4-methoxyphenyl)-1,2,4-oxadiazol-5-yl)piperazine-1-carboxamide (Compound 193): Using 3-(4-methoxyphenyl)-5-(piperazin-1-yl)-1,2,4-oxadiazole (200 mg, 0.768 mmol) and 1-chloro-4-isocyanatobenzene (118 mg, 0.768 mmol) as the starting material.

Yield 220 mg (69%), as a light yellow solid. $^1$H NMR (400 MHz, DMSO) δ 8.82 (br s, 1H), 7.86 (d, J=8.8 Hz, 2H), 7.51 (d, J=6.8 Hz, 2H), 7.30 (d, J=6.8 Hz, 2H), 7.11-7.02 (d, J=8.8 Hz, 2H), 3.83 (s, 3H), 3.70-3.60 (m, 8H). m/z: [ESI$^+$] 414, 416 (M+H)$^+$, ($C_{20}H_{20}ClN_5O_3$).

N-(3-Chlorophenyl)-4-(3-(4-methoxyphenyl)-1,2,4-oxadiazol-5-yl)piperazine-1-carboxamide (Compound 194): Using 3-(4-methoxyphenyl)-5-(piperazin-1-yl)-1,2,4-oxadiazole (150 mg, 0.576 mmol) and 1-chloro-3-isocyanatobenzene (89 mg, 0.580 mmol) as the starting material.

Yield 130 mg (55%), as a light yellow solid. $^1$H NMR (400 MHz, DMSO) δ 8.87 (br s, 1H), 7.85 (d, J=8.8 Hz, 2H), 7.67 (d, J=2.0 Hz, 1H), 7.41 (dd, J=2.0, 8.0 Hz, 1H), 7.27 (d, J=8.0 Hz, 1H), 7.06 (d, J=8.8 Hz, 2H), 6.99 (dd, J=2.0, 8.0 Hz, 1H), 3.83 (s, 3H), 3.69-3.60 (m, 8H). m/z: [ESI$^+$] 414, 416 (M+H)$^+$, ($C_{20}H_{20}ClN_5O_3$).

N-(2-Chlorophenyl)-4-(3-(4-methoxyphenyl)-1,2,4-oxadiazol-5-yl)piperazine-1-carboxamide (Compound 195): Using 3-(4-methoxyphenyl)-5-(piperazin-1-yl)-1,2,4-oxadiazole (200 mg, 0.768 mmol) and 1-chloro-2-isocyanatobenzene (118 mg, 0.768 mmol) as the starting material.

Yield 150 mg (47%), as a light yellow solid. $^1$H NMR (400 MHz, DMSO) δ 8.42 (br s, 1H), 7.85 (d, J=8.8 Hz, 2H), 7.51-7.42 (m, 2H), 7.30 (dd, J=1.6, 7.6 Hz, 1H), 7.16 (dd, J=1.6, 7.6 Hz, 1H), 7.06 (d, J=8.8 Hz, 2H), 3.82 (s, 3H), 3.70-3.60 (m, 8H). m/z: [ESI$^+$] 414, 416 (M+H)$^+$, ($C_{20}H_{20}ClN_5O_3$).

Tert-butyl ((1-(4-methylbenzyl)pyrrolidin-3-yl)methyl)carbamate (Intermediate J)

Scheme 12

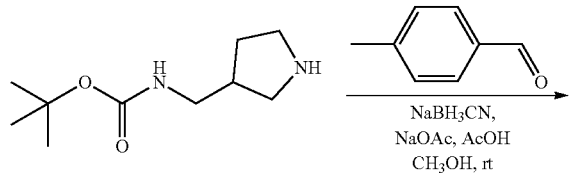

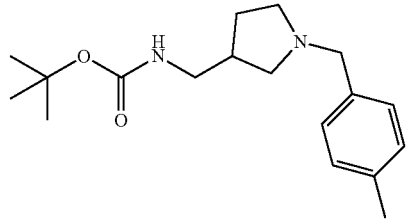

INTERMEDIATE J

To a stirred solution of tert-butyl (pyrrolidin-3-ylmethyl)carbamate hydrochloride (10.00 g, 42.24 mmol) and p-tolualdehyde (10.15 g, 84.48 mmol) in methanol (300 mL) were added sodium cyanoborohyride (5.65 g, 84.50 mmol), sodium acetate (10.40 g, 0.127 mol) and acetic acid (0.25 g, 4.16 mmol) at room temperature under a nitrogen atmosphere. The solution was stirred for 2 h at room temperature. The resulting mixture was filtered and the filter cake was washed with DCM (2×100 mL). The filtrate was then concentrated under reduced pressure. The residue was purified by silica gel column chromatography, eluting with 10% methanol in DCM to afford tert-butyl ((1-(4-methylbenzyl)pyrrolidin-3-yl)methyl)carbamate as a yellow oil.

Yield: 11.00 g (86%). $^1$H NMR (400 MHz, CDCl$_3$) δ 7.34 (d, J=7.6 Hz, 2H), 7.24 (d, J=7.6 Hz, 2H), 5.15 (br s, 1H), 4.16 (s, 2H), 3.37-3.27 (m, 3H), 3.28-3.15 (m, 2H), 3.06 (t, J=9.6 Hz, 1H), 2.79-2.67 (m, 1H), 2.37 (s, 3H), 2.24 (dd J=7.6, 14.4 Hz, 1H), 1.89-1.75 (m, 1H), 1.44 (s, 9H). m/z: [ESI$^+$] 305 (M+H)$^+$, ($C_{18}H_{28}N_2O_2$).

The following compounds were synthesized according to the procedure described above. Purification by reverse phase chromatography with the addition of ammonium bicarbonate as a modifier produced the parent compound, whilst the addition of formic acid as a modifier produced the desired compound as the formate salt.

N-((1-(cyclopropylmethyl)pyrrolidin-3-yl)methyl)-4-(3-(4-methoxyphenyl)-1,2,4-oxadiazol-5-yl)piperazine-1-carboxamide (Compound 221): Using 4-(3-(4-methoxyphenyl)-1,2,4-oxadiazol-5-yl)-N-(pyrrolidin-3-ylmethyl)piperazine-1-carboxamide (200 mg, 0.518 mmol) and cyclopropanecarbaldehyde (40 mg, 0.571 mmol) as the starting material.

Yield 150 mg (66%), as a light yellow solid. $^1$H NMR (400 MHz, DMSO) δ 7.84 (d, J=8.8 Hz, 2H), 7.06 (d, J=8.8 Hz, 2H), 6.75 (t, J=5.2 Hz, 1H), 3.82 (s, 3H), 3.57 (dd, J=3.6, 6.4 Hz, 4H), 3.46 (dd, J=3.6, 6.4 Hz, 4H), 3.08-2.96 (m, 2H), 2.57-2.51 (m, 2H), 2.49-2.45 (m, 1H), 2.39-2.17 (m, 4H), 1.87-1.78 (m, 1H), 1.45-1.36 (m, 1H), 0.88-0.80 (m, 1H), 0.44 (q, J=4.8 Hz, 2H), 0.08 (q, J=4.8 Hz, 2H). m/z: [ESI$^+$] 441 (M+H)$^+$, ($C_{23}H_{32}N_6O_3$).

Tert-butyl 4-((3-((1-(3-(4-methoxyphenyl)-1,2,4-oxadiazol-5-yl)piperidine-4-carboxamido)methyl)pyrrolidin-1-yl)methyl)azepane-1-carboxylate. The compound was synthesized according to the procedure described above, using 1-(3-(4-methoxyphenyl)-1,2,4-oxadiazol-5-yl)-N-(pyrrolidin-3-ylmethyl)piperidine-4-carboxamide (100 mg, 0.259 mmol) and tert-butyl 4-formylazepane-1-carboxylate (80 mg, 0.350 mmol) as the starting material.

Yield 100 mg (65%), as an off-white solid. m/z: [ESI$^+$] 597 (M+H)$^+$. The crude material was used in the next step without further purification.

Tert-butyl (2S)-2-((3-((1-(3-(4-methoxyphenyl)-1,2,4-oxadiazol-5-yl)piperidine-4-carboxamido)methyl)pyrrolidin-1-yl)methyl)pyrrolidine-1-carboxylate. The compound was synthesized according to the described procedure above, using 1-(3-(4-methoxyphenyl)-1,2,4-oxadiazol-5-yl)-N-(pyrrolidin-3-ylmethyl)piperidine-4-carboxamide (0.30 g, 0.78 mmol) as the starting material.

Yield 0.40 g (90%), as an off-white solid. $^1$H NMR (400 MHz, CDCl$_3$) δ 7.94 (d, J=8.8 Hz, 2H), 6.96 (d, J=8.8 Hz, 2H), 4.50 (t, J=5.6 Hz, 1H), 4.27 (d, J=13.2 Hz, 2H), 4.06 (m, 1H), 3.87 (s, 3H), 3.76-3.26 (m, 8H), 3.21 (t, J=12.4 Hz, 2H), 2.95-2.81 (m, 1H), 2.52 (t, J=11.6 Hz, 1H), 2.23 (t, J=8.8 Hz, 2H), 2.06-1.76 (m, 10H), 1.49 (s, 9H). m/z: [ESI$^+$] 569 (M+H)$^+$.

Tert-butyl (2R)-2-((3-((1-(3-(4-methoxyphenyl)-1,2,4-oxadiazol-5-yl)piperidine-4-carboxamido)methyl)pyrrolidin-1-yl)methyl)azetidine-1-carboxylate. The compound was synthesized according to the procedure described above, using 1-(3-(4-methoxyphenyl)-1,2,4-oxadiazol-5-yl)-N-(pyrrolidin-3-ylmethyl)piperidine-4-carboxamide (100 mg, 0.259 mmol) and tert-butyl (R)-2-formylazetidine-1-carboxylate (53 mg, 0.286 mmol) as the starting material.

Yield 86 mg (60%), as an off-white solid. $^1$H NMR (400 MHz, CDCl$_3$) δ 7.96 (d, J=8.8 Hz, 2H), 6.96 (d, J=8.8 Hz, 2H), 4.36 (br s, 1H), 4.28 (d, J=13.2 Hz, 2H), 3.93-3.79 (m, 2H), 3.88 (s, 3H), 3.38-3.15 (m, 5H), 3.13-2.93 (m, 2H), 2.84-2.58 (m, 1H), 2.55-2.30 (m, 4H), 2.13-1.92 (m, 4H), 1.92-1.77 (m, 2H), 1.75-1.52 (m, 3H), 1.46 (s, 9H). m/z: [ESI$^+$] 555 (M+H)$^+$. The crude material was used in the next step without further purification.

Tert-butyl ((1s,3s)-3-((3-((1-(3-(4-methoxyphenyl)-1,2,4-oxadiazol-5-yl)piperidine-4-carboxamido)methyl)pyrrolidin-1-yl)methyl)cyclobutyl)carbamate. The compound was synthesized according to the procedure described above, using 1-(3-(4-methoxyphenyl)-1,2,4-oxadiazol-5-yl)-N-(pyrrolidin-3-ylmethyl)piperidine-4-carboxamide (100 mg, 0.259 mmol) and tert-butyl ((1s,3s)-3-formylcyclobutyl)carbamate (60 mg, 0.301 mmol) as the starting material.

Yield 100 mg (68%), as an off-white solid. m/z: [ESI$^+$] 569 (M+H)$^+$. The crude material was used in the next step without further purification.

Tert-butyl ((1s,4s)-4-((3-((1-(3-(4-methoxyphenyl)-1,2,4-oxadiazol-5-yl)piperidine-4-carboxamido)methyl)pyrrolidin-1-yl)methyl)cyclohexyl)carbamate. The compound was synthesized according to the procedure described above, using 1-(3-(4-methoxyphenyl)-1,2,4-oxadiazol-5-yl)-N-(pyrrolidin-3-ylmethyl)piperidine-4-carboxamide (100 mg, 0.259 mmol) and tert-butyl ((1s,4s)-4-formylcyclohexyl)carbamate (71 mg, 0.313 mmol) as the starting material.

Yield 100 mg (65%), as an off-white solid. m/z: [ESI$^+$] 597 (M+H)$^+$. The crude material was used in the next step without further purification.

Tert-butyl (2R)-2-((3-((1-(3-(4-methoxyphenyl)-1,2,4-oxadiazol-5-yl)piperidine-4-carboxamido)methyl)pyrrolidin-1-yl)methyl)piperidine-1-carboxylate. The compound was synthesized according to the procedure described above, using 1-(3-(4-methoxyphenyl)-1,2,4-oxadiazol-5-yl)-N-(pyrrolidin-3-ylmethyl)piperidine-4-carboxamide (100 mg, 0.259 mmol) and tert-butyl (R)-2-formylpiperidine-1-carboxylate (66 mg, 0.310 mmol) as the starting material.

Yield 100 mg (66%), as an off-white solid. m/z: [ESI$^+$] 583 (M+H)$^+$. The crude material was used in the next step without further purification.

(1-Isobutylpiperidin-3-yl)(4-(3-(4-methoxyphenyl)-1,2,4-oxadiazol-5-yl)piperazin-1-yl)methanone formate (Compound 227). Using (4-(3-(4-methoxyphenyl)-1,2,4-oxadiazol-5-yl)piperazin-1-yl)(piperidin-3-yl)methanone (150 mg, 0.404 mmol) and isobutyraldehyde (58 mg, 0.804 mmol) as the starting material.

Yield 120 mg (63%), as a light yellow solid. $^1$H NMR (400 MHz, DMSO) δ 8.17 (s, 1HHCOOH), 7.85 (d, J=8.8 Hz, 2H), 7.06 (d, J=8.8 Hz, 2H), 3.82 (s, 3H), 3.64 (s, 4H), 3.58 (s, 4H), 2.90-2.78 (m, 3H), 2.18-2.00 (m, 3H), 2.00-1.88 (m, 1H), 1.76 (t, J=12.8 Hz, 2H), 1.69-1.52 (m, 2H), 1.38-1.22 (m, 1H), 0.86 (d, J=6.4 Hz, 6H). m/z: [ESI$^+$] 428 (M+H)$^+$, (C$_{23}$H$_{33}$N$_5$O$_3$).

1-(3-(4-Methoxyphenyl)-1,2,4-oxadiazol-5-yl)-N-((1-((5-methylpyridin-2-yl)methyl)pyrrolidin-3-yl)methyl)piperidine-4-carboxamide formate (Compound 223): Using 1-(3-(4-methoxyphenyl)-1,2,4-oxadiazol-5-yl)-N-(pyrrolidin-3-ylmethyl)piperidine-4-carboxamide (150 mg, 0.389 mmol) and 5-methylpicolinaldehyde (57 mg, 0.471 mmol) as the starting material.

Yield 100 mg (48%), as a light yellow solid. $^1$H NMR (400 MHz, DMSO) δ 8.32 (d, J=2.0 Hz, 1H), 8.19 (s, 1H, HCOOH), 7.92 (t, J=5.6 Hz, 1H), 7.84 (d, J=8.8 Hz, 2H), 7.57 (dd, J=2.4, 8.0 Hz, 1H), 7.31 (d, J=8.0 Hz, 1H), 7.06 (d, J=8.8 Hz, 2H), 4.05 (d, J=13.2 Hz, 2H), 3.82 (s, 3H), 3.69 (s, 2H), 3.19 (dt, J=2.8, 12.4 Hz, 2H), 3.13-2.98 (m, 2H), 2.70-2.51 (m, 3H), 2.44-2.35 (m, 1H), 2.35-2.25 (m, 2H), 2.27 (s, 3H), 1.92-1.82 (m, 1H), 1.78 (d, J=14.8 Hz, 2H), 1.68-1.53 (m, 2H), 1.42 (dt, J=6.2, 12.3 Hz, 1H). m/z: [ESI$^+$] 491 (M+H)$^+$, (C$_{27}$H$_{34}$N$_6$O$_3$).

N-((1-(Cyclopropylmethyl)pyrrolidin-3-yl)methyl)-1-(3-(4-methoxyphenyl)-1,2,4-oxadiazol-5-yl)piperidine-4-carboxamide (Compound 220): Using 1-(3-(4-methoxyphenyl)-1,2,4-oxadiazol-5-yl)-N-(pyrrolidin-3-ylmethyl)piperidine-4-carboxamide (150 mg, 0.389 mmol) and cyclopropanecarbaldehyde (30 mg, 0.428 mmol) as the starting material.

Yield 150 mg (88%), as a light yellow solid. $^1$H NMR (400 MHz, DMSO) δ 7.92 (t, J=5.6 Hz, 1H), 7.84 (d, J=8.8 Hz, 2H), 7.06 (d, J=8.8 Hz, 2H), 4.06 (d, J=13.2 Hz, 2H), 3.82 (s, 3H), 3.20 (dt, J=3.2, 12.8 Hz, 2H), 3.10-2.95 (m, 2H), 2.60-2.53 (m, 2H), 2.49-2.35 (m, 2H), 2.22 (dd, J=3.2, 6.8 Hz, 4H), 1.84-1.76 (m, 3H), 1.69-1.56s (m, 2H), 1.37 (dt, J=6.4, 12.8 Hz, 1H), 0.87-0.77 (m, 1H), 0.43 (td, J=2.8, 4.8 Hz, 2H), 0.07 (td, J=2.8, 4.8 Hz, 2H). m/z: [ESI$^+$] 440 (M+H)$^+$, (C$_{24}$H$_{33}$N$_5$O$_3$).

1-(3-(4-Chlorophenyl)-1,2,4-oxadiazol-5-yl)-N-((1-((5-methylpyridin-2-yl)methyl)pyrrolidin-3-yl)methyl)piperidine-4-carboxamide (Compound 243): Using 1-(3-(4-chlorophenyl)-1,2,4-oxadiazol-5-yl)-N-(pyrrolidin-3-ylmethyl) piperidine-4-carboxamide (200 mg, 0.513 mmol) and 5-methylpicolinaldehyde (75 mg, 0.619 mmol) as the starting material.

Yield 180 mg (71%), as a light yellow solid. $^1$H NMR (400 MHz, DMSO) δ 8.31 (d, J=2.3 Hz, 1H), 7.95-1.88 (m, 3H), 7.62-7.53 (m, 3H), 7.30 (d, J=8.0 Hz, 1H), 4.05 (d, J=12.8 Hz, 2H), 3.64 (s, 2H), 3.21 (dt, J=2.8, 12.8 Hz, 2H), 3.12-2.96 (m, 2H), 2.62-2.52 (m, 2H), 2.48-2.33 (m, 2H), 2.27 (s, 3H), 2.26 (s, 2H), 1.90-1.75 (m, 3H), 1.67-1.54 (m, 2H), 1.47-1.30 (m, 1H). m/z: [ESI$^+$] 495, 497 (M+H)$^+$, (C$_{26}$H$_{31}$ClN$_6$O$_2$).

1-(3-(4-Cyanophenyl)-1,2,4-oxadiazol-5-yl)-N-((1-((5-methylpyridin-2-yl)methyl)pyrrolidin-3-yl)methyl)piperidine-4-carboxamide (Compound 244): Using 1-(3-(4-cyanophenyl)-1,2,4-oxadiazol-5-yl)-N-(pyrrolidin-3-ylmethyl) piperidine-4-carboxamide (200 mg, 0.526 mmol) and 5-methylpicolinaldehyde (76 mg, 0.627 mmol) as the starting material.

Yield 150 mg (59%), as a light yellow solid. $^1$H NMR (400 MHz, DMSO) δ 8.30 (d, J=2.0 Hz, 1H), 8.07 (d, J=8.4 Hz, 2H), 7.99 (d, J=8.4 Hz, 2H), 7.92 (t, J=5.6 Hz, 1H), 7.57 (dd, J=2.0, 8.0 Hz, 1H), 7.31 (d, J=8.0 Hz, 1H), 4.15-4.00 (m, 2H), 3.63 (s, 2H), 3.23 (dt, J=2.8, 12.8 Hz, 2H), 3.14-2.98 (m, 2H), 2.66-2.50 (m, 3H), 2.44-2.35 (m, 1H), 2.27 (s, 5H), 1.92-1.82 (m, 1H), 1.82-1.76 (m, 2H), 1.66-1.56 (m, 2H), 1.48-1.33 (m, 1H). m/z: [ESI$^+$] 486 (M+H)$^+$, (C$_{27}$H$_{31}$N$_7$O$_2$).

1-(3-(4-Methoxyphenyl)-1,2,4-oxadiazol-5-yl)-N-((1R,5S,6s)-3-methyl-3-azabicyclo[3.1.0]hexan-6-yl)piperidine-4-carboxamide (Compound 295): Using N-((1R,5S,6s)-3-azabicyclo[3.1.0]hexan-6-yl)-1-(3-(4-methoxyphenyl)-1,2,4-oxadiazol-5-yl)piperidine-4-carboxamide (0.26 g, 0.68 mmol) and paraformaldehyde (0.37 g, 4.11 mmol) as the starting material.

Yield 0.10 g (37%), as a light yellow solid. $^1$H NMR (400 MHz, DMSO) δ 7.83 (d, J=8.8 Hz, 2H), 7.82 (br s, 1H), 7.05 (d, J=8.8 Hz, 2H), 4.04 (td, J=3.6, 13.2 Hz, 2H), 3.82 (s, 3H), 3.17 (dt, J=2.8, 12.8 Hz, 2H), 2.94 (d, J=8.8 Hz, 2H), 2.83 (td, J=2.0, 4.4 Hz, 1H), 2.32-2.29 (m, 1H), 2.25 (d, J=8.8 Hz, 2H), 2.19 (s, 3H), 1.82-1.71 (m, 2H), 1.68-1.53 (m, 2H), 1.47-1.39 (m, 2H). m/z: [ESI$^+$] 398 (M+H)$^+$, (C$_{21}$H$_{27}$N$_5$O$_3$).

(R)-1-(3-(4-Methoxyphenyl)-1,2,4-oxadiazol-5-yl)-N-((1-methylpyrrolidin-2-yl)methyl)piperidine-4-carboxamide (Compound 252): Using (R)-1-(3-(4-methoxyphenyl)-1,2,4-oxadiazol-5-yl)-N-(pyrrolidin-2-ylmethyl)piperidine-4-carboxamide (150 mg, 0.389 mmol) and paraformaldehyde (47 mg, 0.522 mmol) as the starting material.

Yield 80 mg (51%), as a light yellow solid. $^1$H NMR (400 MHz, DMSO) δ 7.84 (d, J=8.8 Hz, 2H), 7.75 (t, J=5.6 Hz, 1H), 7.07 (d, J=8.8 Hz, 2H), 4.06 (td, J=3.6, 13.0 Hz, 2H), 3.82 (s, 3H), 3.29 (d, J=3.8 Hz, 1H), 3.26-3.12 (m, 2H), 2.99-2.84 (m, 2H), 2.38-2.49 (m, 1H), 2.25 (s, 3H), 2.24-2.16 (m, 1H), 2.15-2.05 (m, 1H), 1.83-1.72 (m, 3H), 1.68-1.53 (m, 4H), 1.51-1.38 (m, 1H). m/z: [ESI$^+$] 400 (M+H)$^+$, (C$_{21}$H$_{29}$N$_5$O$_3$).

(R)-1-(3-(4-Methoxyphenyl)-1,2,4-oxadiazol-5-yl)-N-((1-methylpyrrolidin-3-yl)methyl)piperidine-4-carboxamide (Compound 253): Using (S)-1-(3-(4-methoxyphenyl)-1,2,4-oxadiazol-5-yl)-N-(pyrrolidin-3-ylmethyl)piperidine-4-carboxamide (150 mg, 0.389 mmol) and paraformaldehyde (47 mg, 0.522 mmol) as the starting material.

Yield 120 mg (77%), as a light yellow solid. $^1$H NMR (400 MHz, DMSO) δ 7.91 (t, J=5.6 Hz, 1H), 7.84 (d, J=8.8 Hz, 2H), 7.06 (d, J=8.8 Hz, 2H), 4.06 (dt, J=3.6, 13.2 Hz, 2H), 3.82 (s, 3H), 3.20 (dt, J=2.8, 12.8 Hz, 2H), 3.09-2.93 (m, 2H), 2.48-2.30 (m, 4H), 2.29-2.12 (m, 2H), 2.20 (s, 3H), 1.88-1.75 (m, 3H), 1.69-1.54 (m, 2H), 1.42-1.30 (m, 1H). m/z: [ESI$^+$] 400 (M+H)$^+$, (C$_{21}$H$_{29}$N$_5$O$_3$).

1-(3-(4-Methoxyphenyl)-1,2,4-oxadiazol-5-yl)-N-((1-((3-methyloxetan-3-yl)methyl)pyrrolidin-3-yl)methyl)piperidine-4-carboxamide (Compound 371): Using 1-(3-(4-methoxyphenyl)-1,2,4-oxadiazol-5-yl)-N-(pyrrolidin-3-ylmethyl)piperidine-4-carboxamide (100 mg, 0.259 mmol) and 3-methyloxetane-3-carbaldehyde (65 mg, 0.649 mmol) as the starting material.

Yield 27 mg (22%), as an off-white solid. $^1$H NMR (400 MHz, DMSO) δ 7.90 (t, J=5.6 Hz, 1H), 7.84 (d, J=8.8 Hz, 2H), 7.06 (d, J=8.8 Hz, 2H), 4.34 (t, J=5.2 Hz, 2H), 4.18 (dd, J=1.2, 5.6 Hz, 2H), 4.06 (td, J=3.6, 13.2 Hz, 2H), 3.82 (s, 3H), 3.20 (dt, J=2.8, 12.8 Hz, 2H), 3.01 (t, J=5.6 Hz, 2H), 2.64-2.52 (m, 2H), 2.50-2.33 (m, 4H), 2.24-2.11 (m, 2H), 1.86-1.73 (m, 3H), 1.68-1.56 (m, 2H), 1.41-1.31 (m, 1H), 1.29 (s, 3H). m/z: [ESI$^+$] 470 (M+H)$^+$, (C$_{25}$H$_{35}$N$_5$O$_4$).

N-((1-(Furan-2-ylmethyl)pyrrolidin-3-yl)methyl)-1-(3-(4-methoxyphenyl)-1,2,4-oxadiazol-5-yl)piperidine-4-carboxamide (Compound 320): Using 1-(3-(4-methoxyphenyl)-1,2,4-oxadiazol-5-yl)-N-(pyrrolidin-3-ylmethyl) piperidine-4-carboxamide (50 mg, 0.130 mmol) and furan-2-carbaldehyde (14 mg, 0.146 mmol) as the starting material.

Yield 30 mg (50%), as an off-white solid. $^1$H NMR (400 MHz, DMSO) δ 7.91 (t, J=5.6 Hz, 1H), 7.84 (d, J=8.8 Hz, 2H), 7.56 (d, J=1.6 Hz, 1H), 7.05 (d, J=8.8 Hz, 2H), 6.38 (d, J=3.2 Hz, 1H), 6.25 (d, J=3.2 Hz, 1H), 4.05 (td, J=3.6, 13.2 Hz, 2H), 3.82 (s, 3H), 3.55 (s, 2H), 3.19 (dt, J=2.8, 12.8 Hz, 2H), 3.10-2.93 (m, 2H), 2.54-2.40 (m, 4H), 2.23 (d, J=6.4 Hz, 2H), 1.86-1.73 (m, 3H), 1.66-1.53 (m, 2H), 1.42-1.29 (m, 1H). m/z: [ESI$^+$] 466 (M+H)$^+$, (C$_{25}$H$_{31}$N$_5$O$_4$).

N-((1-(2-Hydroxybenzyl)pyrrolidin-3-yl)methyl)-1-(3-(4-methoxyphenyl)-1,2,4-oxadiazol-5-yl)piperidine-4-carboxamide (Compound 321): Using 1-(3-(4-methoxyphenyl)-1,2,4-oxadiazol-5-yl)-N-(pyrrolidin-3-ylmethyl) piperidine-4-carboxamide (100 mg, 0.259 mmol) and 2-hydroxybenzaldehyde (35 mg, 0.287 mmol) as the starting material.

Yield 25 mg (20%), as an off-white solid. $^1$H NMR (400 MHz, DMSO) δ 7.95 (t, J=5.6 Hz, 1H), 7.83 (d, J=8.8 Hz, 2H), 7.12-7.06 (m, 2H), 7.05 (d, J=8.8 Hz, 2H), 6.78-6.68 (m, 2H), 4.05 (d, J=12.8 Hz, 2H), 3.82 (s, 3H), 3.71 (s, 2H), 3.19 (dt, J=2.8, 12.4 Hz, 2H), 3.10-2.99 (m, 2H), 2.64-2.51 (m, 3H), 2.45-2.35 (m, 1H), 2.35-2.24 (m, 2H), 1.95-1.84 (m, 1H), 1.87-1.74 (m, 2H), 1.64-1.54 (m, 2H), 1.51-1.38 (m, 1H). Phenol OH proton not observed. m/z: [ESI$^+$] 492 (M+H)$^+$, (C$_{27}$H$_{33}$N$_5$O$_4$).

1-(3-(4-Methoxyphenyl)-1,2,4-oxadiazol-5-yl)-N-((1-(pyridin-4-ylmethyl)pyrrolidin-3-yl)methyl)piperidine-4-carboxamide (Compound 322): Using 1-(3-(4-methoxyphenyl)-1,2,4-oxadiazol-5-yl)-N-(pyrrolidin-3-ylmethyl) piperidine-4-carboxamide hydrochloride (100 mg, 0.237 mmol) and isonicotinaldehyde (30 mg, 0.280 mmol) as the starting material.

Yield 55 mg (49%), as an off-white solid. $^1$H NMR (400 MHz, DMSO) δ 8.50 (d, J=6.0 Hz, 2H), 7.91 (t, J=5.6 Hz, 1H), 7.84 (d, J=8.8 Hz, 2H), 7.32 (d, J=6.0 Hz, 2H), 7.05 (d, J=8.4 Hz, 2H), 4.05 (d, J=13.2 Hz, 2H), 3.82 (s, 3H), 3.68-3.50 (m, 2H), 3.19 (dt, J=2.8, 12.4 Hz, 2H), 3.10-2.93 (m, 2H), 2.50-2.36 (m, 4H), 2.30-2.18 (m, 2H), 1.93-1.82 (m, 1H), 1.78 (td, J=3.2, 13.2 Hz, 2H), 1.67-1.52 (m, 2H), 1.49-1.32 (m, 1H). m/z: [ESI$^+$] 477 (M+H)$^+$, (C$_{26}$H$_{32}$N$_6$O$_3$).

N-((1-(cyclopentylmethyl)pyrrolidin-3-yl)methyl)-1-(3-(4-methoxyphenyl)-1,2,4-oxadiazol-5-yl)piperidine-4-carboxamide (Compound 323): Using 1-(3-(4-methoxyphenyl)-1,2,4-oxadiazol-5-yl)-N-(pyrrolidin-3-ylmethyl) piperidine-4-carboxamide hydrochloride (70 mg, 0.166 mmol) and cyclopentanecarbaldehyde (20 mg, 0.204 mmol) as the starting material.

Yield 40 mg (52%) as an off-white solid. $^1$H NMR (400 MHz, DMSO) δ 7.90 (t, J=5.6 Hz, 1H), 7.83 (d, J=8.8 Hz, 2H), 7.05 (d, J=8.8 Hz, 2H), 4.06 (td, J=3.6, 13.2 Hz, 2H), 3.82 (s, 3H), 3.19 (dt, J=2.8, 12.8 Hz, 2H), 3.09-2.94 (m, 2H), 2.50-2.40 (m, 4H), 2.27-2.15 (m, 4H), 1.96 (m, J=7.6 Hz, 1H), 1.85-1.75 (m, 3H), 1.73-1.42 (m, 8H), 1.40-1.28 (m, 1H), 1.21-1.08 (m, 2H). m/z: [ESI$^+$] 468 (M+H)$^+$, (C$_{26}$H$_{37}$N$_5$O$_3$).

N-((1-(Isothiazol-4-ylmethyl)pyrrolidin-3-yl)methyl)-1-(3-(4-methoxyphenyl)-1,2,4-oxadiazol-5-yl)piperidine-4-carboxamide (Compound 373): Using 1-(3-(4-methoxyphenyl)-1,2,4-oxadiazol-5-yl)-N-(pyrrolidin-3-ylmethyl) piperidine-4-carboxamide (100 mg, 0.259 mmol) and isothiazole-4-carbaldehyde (32 mg, 0.283 mmol) as the starting material.

Yield 40 mg (32%), as an off-white solid. $^1$H NMR (400 MHz, DMSO) δ 8.83 (s, 1H), 8.50 (s, 1H), 7.91 (t, J=5.6 Hz, 1H), 7.84 (d, J=8.8 Hz, 2H), 7.06 (d, J=8.8 Hz, 2H), 4.05 (d, J=12.8 Hz, 2H), 3.82 (s, 3H), 3.68 (s, 2H), 3.19 (dt, J=2.8, 12.8 Hz, 2H), 3.10-2.98 (m, 2H), 2.54-2.45 (m, 3H), 2.44-

2.33 (m, 1H), 2.26-2.21 (m, 2H), 1.88-1.72 (m, 3H), 1.68-1.52 (m, 2H), 1.38 (dd, J=6.4, 12.6 Hz, 1H). m/z: [ESI$^+$] 483 (M+H)$^+$, ($C_{24}H_{30}N_6O_3S$).

1-(3-(4-Methoxyphenyl)-1,2,4-oxadiazol-5-yl)-N-((1-((tetrahydrofuran-3-yl)methyl)pyrrolidin-3-yl)methyl)piperidine-4-carboxamide (Compound 347): Using 1-(3-(4-methoxyphenyl)-1,2,4-oxadiazol-5-yl)-N-(pyrrolidin-3-ylmethyl)piperidine-4-carboxamide (100 mg, 0.259 mmol) and tetrahydrofuran-3-carbaldehyde (70 mg, 0.699 mmol) as the starting material.

Yield 10 mg (8%), as an off-white solid. $^1$H NMR (400 MHz, DMSO) δ 7.92 (t, J=5.6 Hz, 1H), 7.84 (d, J=8.8 Hz, 2H), 7.06 (d, J=8.8 Hz, 2H), 4.06 (d, J=12.8 Hz, 2H), 3.82 (s, 3H), 3.79-3.71 (m, 1H), 3.70 (dt, J=5.2, 8.0 Hz, 1H), 3.66-3.56 (m, 1H), 3.31-3.30 (m, 1H), 3.20 (dt, J=3.2, 12.8 Hz, 2H), 3.02 (s, 2H), 2.51-2.28 (m, 7H), 2.23 (s, 2H), 1.94 (s, 1H), 1.83-1.75 (m, 3H), 1.66-1.54 (m, 2H), 1.51 (s, 1H), 1.37 (s, 1H). m/z: [ESI$^+$] 470 (M+H)$^+$, ($C_{25}H_{35}N_5O_4$).

N-((1-(3-ethynylbenzyl)pyrrolidin-3-yl)methyl)-1-(3-(4-methoxyphenyl)-1,2,4-oxadiazol-5-yl)piperidine-4-carboxamide (Compound 324): Using 1-(3-(4-methoxyphenyl)-1,2,4-oxadiazol-5-yl)-N-(pyrrolidin-3-ylmethyl)piperidine-4-carboxamide (100 mg, 0.259 mmol) and 3-ethynylbenzaldehyde (37 mg, 0.284 mmol) as the starting material.

Yield 40 mg (31%), as an off-white solid. $^1$H NMR (400 MHz, DMSO) δ 7.89 (t, J=5.6 Hz, 1H), 7.83 (d, J=8.8 Hz, 2H), 7.39 (s, 1H), 7.34 (s, 3H), 7.05 (d, J=8.8 Hz, 2H), 4.16 (s, 1H), 4.05 (d, J=13.2 Hz, 2H), 3.82 (s, 3H), 3.55 (s, 2H), 3.19 (dt, J=3.2, 12.4 Hz, 2H), 3.10-2.92 (m, 2H), 2.59-2.33 (m, 4H), 2.30-2.12 (m, 2H), 1.91-1.70 (m, 3H), 1.67-1.54 (m, 2H), 1.43-1.32 (m, 1H). m/z: [ESI$^+$] 500 (M+H)$^+$, ($C_{29}H_{33}N_5O_3$).

1-(3-(4-Methoxyphenyl)-1,2,4-oxadiazol-5-yl)-N-((1-((3-methylpyridin-4-yl)methyl)pyrrolidin-3-yl)methyl)piperidine-4-carboxamide (Compound 348): Using 1-(3-(4-methoxyphenyl)-1,2,4-oxadiazol-5-yl)-N-(pyrrolidin-3-ylmethyl)piperidine-4-carboxamide (70 mg, 0.182 mmol) and 3-methylisonicotinaldehyde (24 mg, 0.198 mmol) as the starting material.

Yield 20 mg (22%), as an off-white solid. $^1$H NMR (400 MHz, DMSO) δ 8.34 (d, J=4.8 Hz, 1H), 8.32 (s, 1H), 7.91 (t, J=5.6 Hz, 1H), 7.83 (d, J=8.8 Hz, 2H), 7.29 (d, J=4.8 Hz, 1H), 7.06 (d, J=8.8 Hz, 2H), 4.05 (d, J=13.2 Hz, 2H), 3.82 (s, 3H), 3.55 (s, 2H), 3.19 (td, J=12.4, 3.2 Hz, 2H), 3.06-3.02 (m, 2H), 2.54 (m, 2H), 2.51 (m, J=1.6 Hz, 2H), 2.26 (m, 5H), 1.87 (ddd, J=5.6, 8.4, 12.8 Hz, 1H), 1.78 (dt, J=13.6, 3.2 Hz, 2H), 1.68-1.52 (m, 2H), 1.41 (m, 1H). m/z: [ESI$^+$] 491 (M+H)$^+$, ($C_{27}H_{34}N_6O_3$).

N-((1-((1H-pyrrol-3-yl)methyl)pyrrolidin-3-yl)methyl)-1-(3-(4-methoxyphenyl)-1,2,4-oxadiazol-5-yl)piperidine-4-carboxamide (Compound 325): Using 1-(3-(4-methoxyphenyl)-1,2,4-oxadiazol-5-yl)-N-(pyrrolidin-3-ylmethyl)piperidine-4-carboxamide (100 mg, 0.259 mmol) and 1H-pyrrole-3-carbaldehyde (27 mg, 0.284 mmol) as the starting material.

Yield 35 mg (29%), as an off-white solid. $^1$H NMR (400 MHz, DMSO) δ 10.51 (br, 1H), 7.89 (t, J=5.6 Hz, 1H), 7.84 (d, J=8.8 Hz, 2H), 7.05 (d, J=8.8 Hz, 2H), 6.64-6.62 (m, 1H), 6.63 (m, 1H), 5.93 (m, 1H), 4.05 (d, J=13.2, 3.9 Hz, 2H), 3.82 (s, 3H), 3.35 (m, 2H), 3.18 (td, J=12.8, 3.2 Hz, 2H), 3.09-2.99 (m, 1H), 3.01-2.91 (m, 1H), 2.54 (m, 4H), 2.26-2.11 (m, 2H), 1.86-1.72 (m, 3H), 1.66-1.53 (m, 2H), 1.39-1.27 (m, 1H). m/z: [ESI$^+$] 465 (M+H)$^+$, ($C_{25}H_{32}N_6O_3$).

1-(3-(4-Methoxyphenyl)-1,2,4-oxadiazol-5-yl)-N-((1-neopentylpyrrolidin-3-yl)methyl)piperidine-4-carboxamide (Compound 327): Using 1-(3-(4-methoxyphenyl)-1,2,4-oxadiazol-5-yl)-N-(pyrrolidin-3-ylmethyl)piperidine-4-carboxamide (100 mg, 0.259 mmol) and pivalaldehyde (30 mg, 0.348 mmol) as the starting material.

Yield 41 mg (35%), as an off-white solid. $^1$H NMR (400 MHz, DMSO) δ 7.90 (t, J=5.6 Hz, 1H), 7.83 (d, J=8.8 Hz, 2H), 7.05 (d, J=8.8 Hz, 2H), 4.06 (dt, J=13.2, 3.6 Hz, 2H), 3.82 (s, 3H), 3.19 (td, J=12.8, 2.8 Hz, 2H), 3.03 (t, J=6.2 Hz, 2H), 2.58-2.53 (m, 3H), 2.39-2.29 (m, 2H), 2.25-2.11 (m, 3H), 1.84-1.76 (m, 3H), 1.68-1.53 (m, 2H), 1.41-1.32 (m, 1H), 0.86 (s, 9H). m/z: [ESI$^+$] 456 (M+H)$^+$, ($C_{25}H_{37}N_5O_3$).

1-(3-(4-Methoxyphenyl)-1,2,4-oxadiazol-5-yl)-N-((1-(3-methylbenzyl)pyrrolidin-3-yl)methyl)piperidine-4-carboxamide (Compound 349): Using 1-(3-(4-methoxyphenyl)-1,2,4-oxadiazol-5-yl)-N-(pyrrolidin-3-ylmethyl)piperidine-4-carboxamide (100 mg, 0.259 mmol) and 3-methylbenzaldehyde (34 mg, 0.283 mmol) as the starting material.

Yield 15 mg (12%), as an off-white solid. $^1$H NMR (400 MHz, DMSO) δ 7.90-7.85 (m, 3H), 7.20 (t, J=7.6 Hz, 1H), 7.11 (s, 1H), 7.07 (m, 4H), 4.06 (d, J=12.8 Hz, 2H), 3.83 (s, 3H), 3.51 (s, 2H), 3.20 (t, J=12.4 Hz, 2H), 3.13-2.97 (m, 2H), 2.50-2.35 (m, 4H), 2.30 (s, 3H), 2.23 (d, J=8.3 Hz, 2H), 1.91-1.77 (m, 3H), 1.72-1.52 (m, 2H), 1.44-1.28 (m, 1H). m/z: [ESI$^+$] 490 (M+H)$^+$, ($C_{28}H_{35}N_5O_3$).

1-(3-(4-Methoxyphenyl)-1,2,4-oxadiazol-5-yl)-N-((1-((3-methylpyridin-2-yl)methyl)pyrrolidin-3-yl)methyl)piperidine-4-carboxamide (Compound 350): Using 1-(3-(4-methoxyphenyl)-1,2,4-oxadiazol-5-yl)-N-(pyrrolidin-3-ylmethyl)piperidine-4-carboxamide (70 mg, 0.182 mmol) and 3-methylpicolinaldehyde (24 mg, 0.198 mmol) as the starting material.

Yield 45 mg (51%), as an off-white solid. $^1$H NMR (400 MHz, DMSO) δ 8.29 (dd, J=1.6, 4.8 Hz, 1H), 7.88 (t, J=5.6 Hz, 1H), 7.84 (d, J=8.8 Hz, 2H), 7.53 (dd, J=1.6, 7.6 Hz, 1H), 7.18 (dd, J=4.8, 7.6 Hz, 1H), 7.05 (d, J=8.8 Hz, 2H), 4.08-4.00 (m, 2H), 3.82 (s, 3H), 3.73-3.60 (m, 2H), 3.24-3.13 (m, 2H), 3.09-2.92 (m, 2H), 2.58-2.32 (m, 4H), 2.36 (s, 3H), 2.28-2.16 (m, 2H), 1.87-1.76 (m, 1H), 1.80-1.72 (m, 2H), 1.66-1.51 (m, 2H), 1.41-1.29 (m, 1H). m/z: [ESI$^+$] 491 (M+H)$^+$, ($C_{27}H_{34}N_6O_3$).

1-(3-(4-Methoxyphenyl)-1,2,4-oxadiazol-5-yl)-N-((1-((4-methylpyridin-2-yl)methyl)pyrrolidin-3-yl)methyl)piperidine-4-carboxamide (Compound 326): Using 1-(3-(4-methoxyphenyl)-1,2,4-oxadiazol-5-yl)-N-(pyrrolidin-3-ylmethyl)piperidine-4-carboxamide (70 mg, 0.182 mmol) and 4-methylpicolinaldehyde (24 mg, 0.200 mmol) as the starting material.

Yield 30 mg (34%), as an off-white solid. $^1$H NMR (400 MHz, DMSO) δ 8.32 (d, J=4.8 Hz, 1H), 7.91 (t, J=5.6 Hz, 1H), 7.84 (d, J=8.8 Hz, 2H), 7.24 (d, J=1.6 Hz, 1H), 7.10-7.01 (m, 3H), 4.10-3.98 (m, 2H), 3.82 (s, 3H), 3.65 (s, 2H), 3.25-3.13 (m, 2H), 3.05 (t, J=6.0 Hz, 2H), 2.68 (m, 2H), 2.53 (m, 2H), 2.44-2.32 (m, 3H), 2.31 (m, 2H), 1.94-1.73 (m, 3H), 1.68-1.53 (m, 2H), 1.47-1.34 (m, 1H). m/z: [ESI$^+$] 491 (M+H)$^+$, ($C_{27}H_{34}N_6O_3$).

1-(3-(4-Methoxyphenyl)-1,2,4-oxadiazol-5-yl)-N-((1-((6-methylpyridin-3-yl)methyl)pyrrolidin-3-yl)methyl)piperidine-4-carboxamide formate (Compound 351): Using 1-(3-(4-methoxyphenyl)-1,2,4-oxadiazol-5-yl)-N-(pyrrolidin-3-ylmethyl)piperidine-4-carboxamide (100 mg, 0.259 mmol) and 6-methylnicotinaldehyde (35 mg, 0.289 mmol) as the starting material.

Yield 15 mg (11%), as a yellow solid. $^1$H NMR (400 MHz, DMSO) δ 8.35 (d, J=2.2 Hz, 1H), 8.16 (s, 1H, HCOOH), 7.89 (t, J=5.6 Hz, 1H), 7.84 (d, J=8.8 Hz, 2H), 7.58 (dd, J=2.4, 8.0 Hz, 1H), 7.20 (d, J=8.0 Hz, 1H), 7.05 (d, J=8.8 Hz, 2H), 4.04 (dd, J=3.6, 12.8 Hz, 2H), 3.82 (s, 3H), 3.54 (d, J=4.4 Hz, 2H), 3.19 (td, J=2.8, 12.4 Hz, 2H), 3.07 (dd, J=12.8, 6.0 Hz, 1H), 2.98 (ddd, J=5.6, 7.2, 12.8 Hz, 1H), 2.44 (m, 7H), 2.25-2.17 (m, 2H), 1.88-1.74 (m, 3H), 1.69-1.52 (m, 2H), 1.43-1.33 (m, 1H). m/z: [ESI$^+$] 491 (M+H)$^+$, ($C_{27}H_{34}N_6O_3$).

1-(3-(4-Methoxyphenyl)-1,2,4-oxadiazol-5-yl)-N-((1-(2-methylbenzyl)pyrrolidin-3-yl)methyl)piperidine-4-carboxamide (Compound 328): Using 1-(3-(4-methoxyphenyl)-1,2,4-oxadiazol-5-yl)-N-(pyrrolidin-3-ylmethyl)piperidine-4-carboxamide (100 mg, 0.259 mmol) and 2-methylbenzaldehyde (40 mg, 0.333 mmol) as the starting material.

Yield 43 mg (34%), as an off-white solid. $^1$H NMR (400 MHz, DMSO) δ 7.89 (t, J=5.6 Hz, 1H), 7.84 (d, J=8.8 Hz, 2H), 7.23 (dd, J=2.0, 2.4 Hz, 1H), 7.13-7.12 (m, 3H), 7.05 (d, J=8.8 Hz, 2H), 4.05 (dd, J=3.6, 13.2 Hz, 2H), 3.82 (s, 3H), 3.51 (d, J=2.4 Hz, 2H), 3.18 (td, J=3.2, 12.8 Hz, 2H), 3.02 (ddt, J=6.0, 12.8, 19.2 Hz, 2H), 2.62-2.52 (m, 4H), 2.32-2.28 (m, 3H), 2.28-2.17 (m, 2H), 1.95-1.71 (m, 3H), 1.67-1.51 (m, 2H), 1.47-1.31 (m, 1H). m/z: [ESI$^+$] 490 (M+H)$^+$, ($C_{28}H_{35}N_5O_3$).

N-((1-(isothiazol-5-ylmethyl)pyrrolidin-3-yl)methyl)-1-(3-(4-methoxyphenyl)-1,2,4-oxadiazol-5-yl)piperidine-4-carboxamide (Compound 352): Using 1-(3-(4-methoxyphenyl)-1,2,4-oxadiazol-5-yl)-N-(pyrrolidin-3-ylmethyl)piperidine-4-carboxamide (100 mg, 0.259 mmol) and isothiazole-5-carbaldehyde (32 mg, 0.283 mmol) as the starting material.

Yield 25 mg (20%), as an off-white solid. $^1$H NMR (400 MHz, DMSO) δ 8.46 (d, J=1.6 Hz, 1H), 7.92 (t, J=5.6 Hz, 1H), 7.84 (d, J=8.8 Hz, 2H), 7.26 (d, J=1.6 Hz, 1H), 7.05 (d, J=8.8 Hz, 2H), 4.05 (d, J=12.8 Hz, 2H), 3.95 (s, 2H), 3.82 (s, 3H), 3.19 (td, J=12.8, 2.8 Hz, 2H), 3.06-3.02 (m, 2H), 2.60 (dt, J=24.8, 8.0 Hz, 2H), 2.50 (s, 1H), 2.44-2.23 (m, 3H), 1.93-1.82 (m, 1H), 1.82-1.74 (m, 2H), 1.66-1.52 (m, 2H), 1.47-1.37 (m, 1H). m/z: [ESI$^+$] 483 (M+H)$^+$, ($C_{24}H_{30}N_6O_3S$).

1-(3-(4-Methoxyphenyl)-1,2,4-oxadiazol-5-yl)-N-((1-((4-methylpyridin-3-yl)methyl)pyrrolidin-3-yl)methyl)piperidine-4-carboxamide (Compound 329): Using 1-(3-(4-methoxyphenyl)-1,2,4-oxadiazol-5-yl)-N-(pyrrolidin-3-ylmethyl)piperidine-4-carboxamide (70 mg, 0.182 mmol) and 4-methylnicotinaldehyde (24 mg, 0.198 mmol) as the starting material.

Yield 26 mg (29%), as an off-white solid. $^1$H NMR (400 MHz, DMSO) δ 8.34 (s, 1H), 8.31 (d, J=4.8 Hz, 1H), 7.89 (t, J=5.6 Hz, 1H), 7.84 (d, J=8.8 Hz, 2H), 7.17 (d, J=4.8 Hz, 1H), 7.05 (d, J=8.8 Hz, 2H), 4.04 (dd, J=3.6, 12.8 Hz, 2H), 3.82 (s, 3H), 3.55 (s, 2H), 3.18 (td, J=3.2, 12.8 Hz, 2H), 3.11-2.92 (m, 2H), 2.52-2.40 (m, 4H), 2.33 (s, 3H), 2.30-2.17 (m, 2H), 1.89-1.77 (m, 1H), 1.80-1.72 (m, 2H), 1.66-1.51 (m, 2H), 1.43-1.31 (m, 1H). m/z: [ESI$^+$] 491 (M+H)$^+$, ($C_{27}H_{34}N_6O_3$).

1-(3-(4-Methoxyphenyl)-1,2,4-oxadiazol-5-yl)-N-((1-((1-methylpiperidin-4-yl)methyl)pyrrolidin-3-yl)methyl)piperidine-4-carboxamide (Compound 353): Using 1-(3-(4-methoxyphenyl)-1,2,4-oxadiazol-5-yl)-N-(pyrrolidin-3-ylmethyl)piperidine-4-carboxamide (100 mg, 0.259 mmol) and 1-methylpiperidine-4-carbaldehyde (70 mg, 0.550 mmol) as the starting material.

Yield 6 mg (5%), as an off-white solid. $^1$H NMR (400 MHz, DMSO) δ 7.90 (t, J=5.6 Hz, 1H), 7.84 (d, J=8.8 Hz, 2H), 7.06 (d, J=8.8 Hz, 2H), 4.06 (d, J=13.2 Hz, 2H), 3.82 (s, 3H), 3.20 (td, J=12.8, 3.2 Hz, 2H), 3.08-2.94 (m, 2H), 2.75 (d, J=11.2 Hz, 2H), 2.48-2.34 (m, 4H), 2.17 (m, 7H), 1.87-1.76 (m, 5H), 1.68-1.53 (m, 4H), 1.35 (dd, J=5.6, 12.0 Hz, 2H), 1.18-1.03 (m, 2H). m/z: [ESI$^+$] 497 (M+H)$^+$, ($C_{27}H_{40}N_6O_3$).

1-(3-(4-Methoxyphenyl)-1,2,4-oxadiazol-5-yl)-N-((1-((tetrahydro-2H-thiopyran-4-yl)methyl)pyrrolidin-3-yl)methyl)piperidine-4-carboxamide diformate (Compound 354): Using 1-(3-(4-methoxyphenyl)-1,2,4-oxadiazol-5-yl)-N-(pyrrolidin-3-ylmethyl)piperidine-4-carboxamide (100 mg, 0.259 mmol) and tetrahydro-2H-thiopyran-4-carbaldehyde (80 mg, 0.614 mmol) as the starting material.

Yield 47 mg (31%), as a off-white solid. $^1$H NMR (400 MHz, DMSO) δ 8.16 (s, 2H, HCOOH), 7.90 (t, J=5.6 Hz, 1H), 7.84 (d, J=8.8 Hz, 2H), 7.05 (d, J=8.8 Hz, 2H), 4.10-4.02 (m, 2H), 3.82 (s, 3H), 3.27-3.15 (m, 4H), 3.07-2.97 (m, 2H), 2.70-2.35 (m, 6H) 2.22 (m, 4H), 2.03 (d, J=13.6 Hz, 2H), 1.80 (d, J=12.8 Hz, 3H), 1.68-1.57 (m, 2H), 1.47 (s, 1H), 1.37 (d, J=6.4 Hz, 1H), 1.28-1.13 (m, 2H). m/z: [ESI$^+$] 500 (M+H)$^+$, ($C_{26}H_{37}N_5O_3S$).

1-(3-(4-Methoxyphenyl)-1,2,4-oxadiazol-5-yl)-N-((1-((tetrahydro-2H-pyran-4-yl)methyl)pyrrolidin-3-yl)methyl)piperidine-4-carboxamide (Compound 355): Using 1-(3-(4-methoxyphenyl)-1,2,4-oxadiazol-5-yl)-N-(pyrrolidin-3-ylmethyl)piperidine-4-carboxamide (100 mg, 0.259 mmol) and tetrahydro-2H-pyran-4-carbaldehyde (70 mg, 0.613 mmol) as the starting material.

Yield 10 mg (8%), as an off-white solid. $^1$H NMR (400 MHz, DMSO) δ 7.90 (t, J=5.6 Hz, 1H), 7.84 (d, J=8.8 Hz, 2H), 7.06 (d, J=8.8 Hz, 2H), 4.06 (d, J=13.2 Hz, 2H), 3.82 (s, 3H), 3.86-3.77 (m, 2H), 3.31-3.14 (m, 4H), 3.09-2.94 (m, 2H), 2.50-2.32 (m, 4H), 2.27-2.14 (m, 4H), 1.79 (d, J=12.8 Hz, 3H), 1.66-1.54 (m, 5H), 1.39-1.27 (m, 1H), 1.20-1.01 (m, 2H). m/z: [ESI$^+$] 484 (M+H)$^+$, ($C_{26}H_{37}N_5O_4$).

1-(3-(4-Methoxyphenyl)-1,2,4-oxadiazol-5-yl)-N-((1-(pyridin-3-ylmethyl)pyrrolidin-3-yl)methyl)piperidine-4-carboxamide (Compound 356): Using 1-(3-(4-methoxyphenyl)-1,2,4-oxadiazol-5-yl)-N-(pyrrolidin-3-ylmethyl)piperidine-4-carboxamide (100 mg, 0.259 mmol) and nicotinaldehyde (80 mg, 0.747 mmol) as the starting material.

Yield 19 mg (15%), as a off-white solid. $^1$H NMR (400 MHz, DMSO) δ 8.49 (d, J=2.4 Hz, 1H), 8.46 (dd, J=1.6, 4.8 Hz, 1H), 7.89 (t, J=5.6 Hz, 1H), 7.83 (d, J=8.8 Hz, 2H), 7.70 (d, J=7.6 Hz, 1H), 7.39-7.31 (m, 1H), 7.05 (d, J=8.8 Hz, 2H), 4.05 (d, J=12.8 Hz, 2H), 3.82 (s, 3H), 3.59 (s, 2H), 3.24-3.13 (m, 2H), 3.12-2.96 (m, 2H), 2.50-2.49 (m, 1H), 2.43-2.33 (m, 3H), 2.23-1.85 (m, 2H), 1.77 (d, J=13.2 Hz, 3H), 1.60-1.57 (m, 2H), 1.39 (dd, J=6.4, 12.8 Hz, 1H). m/z: [ESI$^+$] 477 (M+H)$^+$, ($C_{26}H_{32}N_6O_3$).

1-(3-(4-Methoxyphenyl)-1,2,4-oxadiazol-5-yl)-N-((1-(thiophen-3-ylmethyl)pyrrolidin-3-yl)methyl)piperidine-4-carboxamide (Compound 357): Using 1-(3-(4-methoxyphenyl)-1,2,4-oxadiazol-5-yl)-N-(pyrrolidin-3-ylmethyl)piperidine-4-carboxamide (100 mg, 0.259 mmol) and thiophene-3-carbaldehyde (30 mg, 0.267 mmol) as the starting material.

Yield 26 mg (21%), as an off-white solid. $^1$H NMR (400 MHz, DMSO) δ 7.90 (t, J=5.6 Hz, 1H), 7.84 (d, J=8.8 Hz, 2H), 7.46 (dd, J=2.8, 5.2 Hz, 1H), 7.28 (dd, J=1.2, 2.8 Hz, 1H), 7.06 (d, J=2.0 Hz, 1H), 7.04 (d, J=4.8 Hz, 2H), 4.05 (d, J=12.8 Hz, 2H), 3.82 (s, 3H), 3.53 (s, 2H), 3.19 (dd, J=2.8, 12.8 Hz, 2H), 3.11-2.94 (m, 2H), 2.56-2.33 (m, 4H), 2.30-2.15 (m, 2H), 1.89-1.73 (m, 3H), 1.68-1.51 (m, 2H), 1.43-1.31 (m, 1H). m/z: [ESI$^+$] 482 (M+H)$^+$, ($C_{25}H_{31}N_5O_3S$).

N-((1-(Furan-3-ylmethyl)pyrrolidin-3-yl)methyl)-1-(3-(4-methoxyphenyl)-1,2,4-oxadiazol-5-yl)piperidine-4-carboxamide (Compound 330): Using 1-(3-(4-methoxyphenyl)-1,2,4-oxadiazol-5-yl)-N-(pyrrolidin-3-ylmethyl)piperidine-4-caarboxamide (70 mg, 0.182 mmol) and furan-3-carbaldehyde (20 mg, 0.208 mmol) as the starting material.

Yield 35 mg (41%), as an off-white solid. $^1$H NMR (400 MHz, DMSO) δ 7.90 (t, J=5.6 Hz, 1H), 7.84 (d, J=8.8 Hz, 2H), 7.58 (dd, J=1.6, 2.0 Hz, 1H), 7.54-7.52 (m, 1H), 7.05 (d, J=8.8 Hz, 2H), 6.41 (d, J=1.6 Hz, 1H), 4.05 (dd, J=3.6, 13.2 Hz, 2H), 3.82 (s, 3H), 3.39-3.34 (m, 2H), 3.18 (dd, J=2.8, 12.8 Hz, 2H), 3.03-3.00 (m, 2H), 2.52-2.33 (m, 4H), 2.27-2.14 (m, 2H), 1.88-1.78 (m, 3H), 1.62-1.58 (m, 2H), 1.42-1.29 (m, 1H). m/z: [ESI$^+$] 466 (M+H)$^+$, ($C_{25}H_{31}N_5O_4$)

N-((1-(4-fluorobenzyl)pyrrolidin-3-yl)methyl)-1-(3-(4-methoxyphenyl)-1,2,4-oxadiazol-5-yl)piperidine-4-carboxamide (Compound 331): Using 1-(3-(4-methoxyphenyl)-1,2,4-oxadiazol-5-yl)-N-(pyrrolidin-3-ylmethyl)piperidine-4-carboxamide (100 mg, 0.259 mmol), and 4-fluorobenzaldehyde (65 mg, 0.524 mmol) as the starting material.

Yield 61 mg (48%), as an off-white solid. $^1$H NMR (400 MHz, DMSO) δ 7.89 (t, J=5.6 Hz, 1H), 7.83 (d, J=8.8 Hz, 2H), 7.32 (m, 2H), 7.17-7.09 (m, 2H), 7.05 (d, J=8.8 Hz, 2H), 4.04 (d, J=13.2 Hz, 2H), 3.82 (s, 3H), 3.51 (s, 2H), 3.20-3.17 (m, 2H), 3.11-2.93 (m, 2H), 2.54-2.36 (m, 4H), 2.24 (s, 1H), 2.17 (dd, J=5.6, 8.8 Hz, 1H), 1.89-1.75 (m, 3H), 1.60-1.57 (m, 2H), 1.43-1.31 (m, 1H). $^{19}$F NMR (376 MHz, DMSO) δ −116.29. m/z: [ESI$^+$] 494 (M+H)$^+$, ($C_{27}H_{32}FN_5O_3$).

N-((1-(3-fluorobenzyl)pyrrolidin-3-yl)methyl)-1-(3-(4-methoxyphenyl)-1,2,4-oxadiazol-5-yl)piperidine-4-carboxamide (Compound 332): Using 1-(3-(4-methoxyphenyl)-1,2,4-oxadiazol-5-yl)-N-(pyrrolidin-3-ylmethyl)piperidine-4-carboxamide (100 mg, 0.259 mmol) and 3-fluorobenzaldehyde (80 mg, 0.645 mmol) as the starting material.

Yield 30 mg (23%), as an off-white solid. $^1$H NMR (400 MHz, DMSO) δ 7.90 (t, J=5.6 Hz, 1H), 7.84 (d, J=8.8 Hz, 2H), 7.35 (dd, J=6.4, 8.0 Hz, 1H), 7.17-7.07 (m, 2H), 7.10-7.01 (m, 3H), 4.10-4.00 (m, 2H), 3.82 (s, 3H), 3.56 (s, 2H), 3.20-3.18 (m, 2H), 3.13-2.94 (m, 2H), 2.57-2.52 (m, 4H), 2.25-2.16 (m, 2H), 1.91-1.74 (m, 3H), 1.67-1.52 (m, 2H), 1.45-1.33 (m, 1H). $^{19}$F NMR (376 MHz, DMSO) δ −113.85. m/z: [ESI$^+$] 494 (M+H)$^+$, ($C_{27}H_{32}FN_5O_3$).

N-((1-(2-fluorobenzyl)pyrrolidin-3-yl)methyl)-1-(3-(4-methoxyphenyl)-1,2,4-oxadiazol-5-yl)piperidine-4-carboxamide (Compound 358): Using 1-(3-(4-methoxyphenyl)-1,2,4-oxadiazol-5-yl)-N-(pyrrolidin-3-ylmethyl)piperidine-4-carboxamide (100 mg, 0.259 mmol) and 2-fluorobenzaldehyde (40 mg, 0.322 mmol) as the starting material.

Yield 25 mg (20%), as an off-white solid. $^1$H NMR (400 MHz, DMSO) δ 7.89 (t, J=5.6 Hz, 1H), 7.84 (d, J=8.8 Hz, 2H), 7.42-7.40 (m, 1H), 7.33-7.29 (m, 1H), 7.17 (m, 2H), 7.06 (d, J=8.8 Hz, 2H), 4.05 (d, J=12.8 Hz, 2H), 3.82 (s, 3H), 3.60 (s, 2H), 3.20-3.18 (m, 2H), 3.02 (m, 2H), 2.56-2.32 (m, 4H), 2.25 (m, 2H), 1.90-1.73 (m, 3H), 1.61-1.58 (m, 2H), 1.44-1.33 (m, 1H); $^{19}$F NMR (376 MHz, DMSO) δ −113.85. m/z: [ESI$^+$] 494 (M+H)$^+$, ($C_{27}H_{32}FN_5O_3$).

N-((1-((3-Fluoropyridin-4-yl)methyl)pyrrolidin-3-yl)methyl)-1-(3-(4-methoxyphenyl)-1,2,4-oxadiazol-5-yl)piperidine-4-carboxamide (Compound 359): Using 1-(3-(4-methoxyphenyl)-1,2,4-oxadiazol-5-yl)-N-(pyrrolidin-3-ylmethyl)piperidine-4-carboxamide (100 mg, 0.259 mmol) and 3-fluoroisonicotinaldehyde (36 mg, 0.288 mmol) as the starting material.

Yield 25 mg (19%), as an off-white solid. $^1$H NMR (400 MHz, DMSO) δ 8.50 (d, J=1.6 Hz, 1H), 8.39 (dd, J=1.2, 4.8 Hz, 1H), 7.91 (t, J=5.6 Hz, 1H), 7.83 (d, J=8.8 Hz, 2H), 7.48 (dd, J=4.8, 6.4 Hz, 1H), 7.05 (d, J=8.8 Hz, 2H), 4.09-4.01 (m, 2H), 3.82 (s, 3H), 3.72-3.59 (m, 2H), 3.20-3.16 (m, 2H), 3.05-3.00 (m, 2H), 2.60-2.40 (m, 4H), 2.31-2.22 (m, 2H), 1.91-1.78 (m, 1H), 1.78-1.76 (m, 2H), 1.60-1.58 (m, 2H), 1.46-1.34 (m, 1H). $^{19}$F NMR (376 MHz, DMSO) δ −133.26. m/z: [ESI$^+$] 495 (M+H)$^+$, ($C_{26}H_{31}FN_6O_3$).

N-((1-((5-Fluoropyridin-3-yl)methyl)pyrrolidin-3-yl)methyl)-1-(3-(4-methoxyphenyl)-1,2,4-oxadiazol-5-yl)piperidine-4-carboxamide (Compound 333): Using 1-(3-(4-methoxyphenyl)-1,2,4-oxadiazol-5-yl)-N-(pyrrolidin-3-ylmethyl)piperidine-4-carboxamide hydrochloride (100 mg, 0.237 mmol) and 5-fluoronicotinaldehyde (36 mg, 0.288 mmol) as the starting material.

Yield 65 mg (55%), as an off-white solid. $^1$H NMR (400 MHz, DMSO) δ 8.46 (d, J=2.8 Hz, 1H), 8.39 (s, 1H), 7.91 (t, J=5.6 Hz, 1H), 7.85 (d, J=8.8 Hz, 2H), 7.67-7.59 (m, 1H), 7.05 (d, J=8.8 Hz, 2H), 4.04 (dd, J=3.6, 13.2 Hz, 2H), 3.82 (s, 3H), 3.64 (t, J=11.2 Hz, 2H), 3.20-3.17 (m, 2H), 3.11-2.96 (m, 2H), 2.60-2.53 (m, 4H), 2.24 (m, 2H), 1.88-1.85 (m, 1H), 1.79-1.75 (m, 2H), 1.60-1.58 (m, 2H), 1.40 (dd, J=6.4, 12.4 Hz, 1H). $^{19}$F NMR (376 MHz, DMSO) δ −128.03. m/z: [ESI$^+$] 495 (M+H)$^+$, ($C_{26}H_{31}FN_6O_3$).

1-(3-(4-Methoxyphenyl)-1,2,4-oxadiazol-5-yl)-N-((1-(thiazol-4-ylmethyl)pyrrolidin-3-yl)methyl)piperidine-4-carboxamide (Compound 360): Using 1-(3-(4-methoxyphenyl)-1,2,4-oxadiazol-5-yl)-N-(pyrrolidin-3-ylmethyl)piperidine-4-carboxamide (100 mg, 0.259 mmol) and thiazole-4-carbaldehyde (60 mg, 0.530 mmol) as the starting material.

Yield 12 mg (10%), as an off-white solid. $^1$H NMR (400 MHz, DMSO) δ 9.02 (d, J=2.0 Hz, 1H), 7.91 (t, J=5.6 Hz, 1H), 7.83 (d, J=8.8 Hz, 2H), 7.48 (d, J=2.0 Hz, 1H), 7.05 (d, J=8.8 Hz, 2H), 4.05 (d, J=12.8 Hz, 2H), 3.82 (s, 3H), 3.73 (s, 2H), 3.20-3.18 (m, 2H), 3.09-2.96 (m, 2H), 2.57-2.50 (m, 3H), 2.46-2.34 (m, 1H), 2.29-2.26 (m, 2H), 1.89-1.75 (m, 3H), 1.62-1.59 (m, 2H), 1.44-1.33 (m, 1H). m/z: [ESI$^+$] 483 (M+H)$^+$, ($C_{24}H_{30}N_6O_3S$).

N-((1-((3-Fluoropyridin-2-yl)methyl)pyrrolidin-3-yl)methyl)-1-(3-(4-methoxyphenyl)-1,2,4-oxadiazol-5-yl)piperidine-4-carboxamide (Compound 334): Using 1-(3-(4-methoxyphenyl)-1,2,4-oxadiazol-5-yl)-N-(pyrrolidin-3-ylmethyl)piperidine-4-caarboxamide hydrochloride (100 mg, 0.237 mmol) and 3-fluoropicolinaldehyde (36 mg, 0.288 mmol) as the starting material.

Yield 58 mg (49%), as an off-white solid. $^1$H NMR (400 MHz, DMSO) δ 8.39-8.37 (m, 1H), 7.90 (t, J=5.6 Hz, 1H), 7.87-7.79 (m, 2H), 7.69-7.67 (m, 1H), 7.42-7.40 (m, 1H), 7.10-7.01 (m, 2H), 4.07-4.05 (m, 2H), 3.82 (s, 3H), 3.75 (t, J=2.8 Hz, 2H), 3.20-3.17 (m, 2H), 3.06-3.04 (m, 1H), 2.97-2.95 (m, 1H), 2.54-2.20 (m, 4H), 2.42-2.16 (m, 2H), 1.87-1.73 (m, 3H), 1.59-1.57 (m, 2H), 1.37-1.35 (m, 1H). $^{19}$F NMR (376 MHz, DMSO) δ −124.78. m/z: [ESI$^+$] 495 (M+H)$^+$, ($C_{26}H_{31}FN_6O_3$).

N-((1-((5-Fluoropyridin-2-yl)methyl)pyrrolidin-3-yl)methyl)-1-(3-(4-methoxyphenyl)-1,2,4-oxadiazol-5-yl)piperidine-4-carboxamide (Compound 335): Using 1-(3-(4-methoxyphenyl)-1,2,4-oxadiazol-5-yl)-N-(pyrrolidin-3-ylmethyl)piperidine-4-carboxamide hydrochloride (70 mg, 0.166 mmol) and 5-fluoropicolinaldehyde (25 mg, 0.200 mmol) as the starting material.

Yield 25 mg (30%), as an off-white solid. $^1$H NMR (400 MHz, DMSO) δ 8.46 (d, J=2.8 Hz, 1H), 7.91 (t, J=5.6 Hz, 1H), 7.87-7.79 (m, 2H), 7.69-7.67 (m, 1H), 7.48 (dd, J=4.8, 8.8 Hz, 1H), 7.09-7.01 (m, 2H), 4.05 (d, J=12.8 Hz, 2H), 3.82 (s, 3H), 3.66 (s, 2H), 3.20-3.17 (m, 2H), 3.06-3.04 (m, 2H), 2.56-2.52 (m, 4H), 2.25 (d, J=5.6 Hz, 2H), 1.85-1.83 (m, 1H), 1.77 (d, J=12.8 Hz, 2H), 1.60-1.58 (m, 2H), 1.45-1.33 (m, 1H). $^{19}$F NMR (376 MHz, DMSO) δ −130.54. m/z: [ESI$^+$] 495 (M+H)$^+$, ($C_{26}H_{31}FN_6O_3$).

N-((1-(Cyclobutylmethyl)pyrrolidin-3-yl)methyl)-1-(3-(4-methoxyphenyl)-1,2,4-oxadiazol-5-yl)piperidine-4-carboxamide (Compound 336): Using 1-(3-(4-methoxyphenyl)-1,2,4-oxadiazol-5-yl)-N-(pyrrolidin-3-ylmethyl)piperidine-4-carboxamide hydrochloride (100 mg, 0.237 mmol) and cyclobutanecarbaldehyde (24 mg, 0.285 mmol) as the starting material.

Yield 66 mg (61%), as an off-white solid. $^1$H NMR (400 MHz, DMSO) δ 7.91 (t, J=5.6 Hz, 1H), 7.83 (d, J=8.8 Hz, 2H), 7.05 (d, J=8.8 Hz, 2H), 4.10-3.99 (m, 2H), 3.82 (s, 3H), 3.20-3.18 (m, 2H), 3.09-2.92 (m, 2H), 2.49-2.35 (m, 7H), 2.21 (s, 2H), 2.06-1.95 (m, 2H), 1.87-1.69 (m, 5H), 1.68-1.52 (m, 4H), 1.43-1.22 (m, 1H). m/z: (ESI$^+$): 454 (M+H)$^+$, ($C_{25}H_{35}N_5O_3$).

N-((1-((2,2-Dimethylcyclopropyl)methyl)pyrrolidin-3-yl)methyl)-1-(3-(4-methoxyphenyl)-1,2,4-oxadiazol-5-yl)piperidine-4-carboxamide (Compound 337): Using 1-(3-(4-methoxyphenyl)-1,2,4-oxadiazol-5-yl)-N-(pyrrolidin-3-ylmethyl)piperidine-4-carboxamide (100 mg, 0.259 mmol) and 2,2-dimethylcyclopropane-1-carbaldehyde (30 mg, 0.306 mmol) as the starting material.

Yield 38 mg (31%), as an off-white solid. $^1$H NMR (400 MHz, DMSO) δ 7.91 (t, J=5.6 Hz, 1H), 7.84 (d, J=8.8 Hz, 2H), 7.05 (d, J=8.8 Hz, 2H), 4.08-4.05 (m, 2H), 3.82 (s, 3H), 3.21-3.19 (m, 2H), 3.07-2.97 (m, 2H), 2.50-2.26 (m, 6H), 2.26-2.12 (m, 2H), 1.83-1.75 (m, 3H), 1.62-1.60 (m, 2H), 1.42-1.30 (m, 1H), 1.01 (s, 6H), 0.71-0.55 (m, 1H), 0.43-0.35 (m, 1H), 0.00-−0.04 (m, 1H). m/z: (ESI$^+$): 468 (M+H)$^+$, ($C_{26}H_{37}N_5O_3$).

N-((1-(Cyclohexylmethyl)pyrrolidin-3-yl)methyl)-1-(3-(4-methoxyphenyl)-1,2,4-oxadiazol-5-yl)piperidine-4-carboxamide formate (Compound 338): Using 1-(3-(4-methoxyphenyl)-1,2,4-oxadiazol-5-yl)-N-(pyrrolidin-3-ylmethyl)piperidine-4-carboxamide (100 mg, 0.259 mmol) and cyclohexane carbaldehyde (32 mg, 0.285 mmol) as the starting material.

Yield 56 mg, (41%), as an orange solid. $^1$H NMR (400 MHz, DMSO) δ 8.20 (s, 1H, HCOOH), 7.92 (t, J=5.6 Hz, 1H), 7.84 (d, J=8.8 Hz, 2H), 7.05 (d, J=8.8 Hz, 2H), 4.08-4.05 (m, 2H), 3.82 (s, 3H), 3.21-3.19 (m, 2H), 3.12-2.96 (m, 2H), 2.63-2.45 (m, 3H), 2.39 (t, J=11.2 Hz, 1H), 2.31-2.19 (m, 3H), 1.89-1.69 (m, 5H), 1.68-1.53 (m, 5H), 1.48-1.32 (m, 3H), 1.28-1.05 (m, 3H), 0.92-0.73 (m, 2H). m/z: (ESI$^+$): 482 (M+H)$^+$, ($C_{27}H_{39}N_5O_3$).

1-(3-(4-Methoxyphenyl)-1,2,4-oxadiazol-5-yl)-N-((1-((tetrahydro-2H-pyran-2-yl)methyl)pyrrolidin-3-yl)methyl)piperidine-4-carboxamide formate (Compound 361): Using 1-(3-(4-methoxyphenyl)-1,2,4-oxadiazol-5-yl)-N-(pyrrolidin-3-ylmethyl)piperidine-4-carboxamide (100 mg, 0.259 mmol) and tetrahydro-2H-pyran-2-carbaldehyde (100 mg, 0.876 mmol) as the starting material.

Yield 15 mg (11%), as a colorless solid. $^1$H NMR (400 MHz, DMSO) δ 8.18 (s, 1H, HCOOH), 7.92 (t, J=5.6 Hz, 1H), 7.84 (d, J=8.8 Hz, 2H), 7.05 (d, J=8.8 Hz, 2H), 4.06 (d, J=13.2 Hz, 2H), 3.86-3.83 (m, 2H), 3.82 (s, 3H), 3.45-3.30 (m, 4H), 3.21-3.19 (m, 2H), 3.02-3.00 (m, 2H), 2.76-2.54 (m, 3H), 2.49-2.21 (m, 3H), 1.89-1.73 (m, 4H), 1.63-1.54 (m, 3H), 1.49-1.34 (m, 4H), 1.21-1.08 (m, 1H). m/z: (ESI$^+$): 484 (M+H)$^+$, ($C_{26}H_{37}N_5O_4$).

N-((1-(4-Hydroxybenzyl)pyrrolidin-3-yl)methyl)-1-(3-(4-methoxyphenyl)-1,2,4-oxadiazol-5-yl)piperidine-4-carboxamide (Compound 339): Using 1-(3-(4-methoxyphenyl)-1,2,4-oxadiazol-5-yl)-N-(pyrrolidin-3-ylmethyl)piperidine-4-carboxamide (70 mg, 0.182 mmol) and 4-hydroxybenzaldehyde (30 mg, 0.246 mmol) as the starting material.

Yield 24 mg (27%) as an off-white solid. $^1$H NMR (400 MHz, DMSO) δ 9.23 (br s, 1H), 7.89 (t, J=5.6 Hz, 1H), 7.84 (d, J=8.8 Hz, 2H), 7.07 (d, J=8.4 Hz, 2H), 7.05 (d, J=8.8 Hz, 2H), 6.69 (d, J=8.4 Hz, 2H), 4.05 (d, J=13.2 Hz, 2H), 3.82 (s, 3H), 3.40 (s, 2H), 3.20-3.18 (m, 2H), 3.09-2.91 (m, 2H), 2.50-2.46 (m, 1H), 2.44-2.33 (m, 3H), 2.25-2.22 (m, 1H), 2.14 (dd, J=5.6, 9.0 Hz, 1H), 1.90-1.72 (m, 3H), 1.61-1.59 (m, 2H), 1.36-1.34 (m, 1H). m/z: (ESI$^+$): 492 (M+H)$^+$, ($C_{27}H_{33}N_5O_4$).

1-(3-(4-Methoxyphenyl)-1,2,4-oxadiazol-5-yl)-N-((1-((1-methyl-1H-pyrrol-2-yl)methyl)pyrrolidin-3-yl)methyl)piperidine-4-carboxamide (Compound 363): Using 1-(3-(4-methoxyphenyl)-1,2,4-oxadiazol-5-yl)-N-(pyrrolidin-3-ylmethyl)piperidine-4-carboxamide (100 mg, 0.259 mmol) and 1-methyl-1H-pyrrole-2-carbaldehyde (31 mg, 0.284 mmol) as the starting material.

Yield 30 mg (24%), as an off-white solid. $^1$H NMR (400 MHz, DMSO) δ 7.89 (t, J=5.6 Hz, 1H), 7.85 (d, J=8.8 Hz, 2H), 7.15 (d, J=8.8 Hz, 2H), 6.62 (t, J=2.4 Hz, 1H), 5.85 (d, J=2.4 Hz, 2H), 4.05 (d, J=12.8 Hz, 2H), 3.82 (s, 3H), 3.57 (s, 3H), 3.46 (s, 2H), 3.20-3.18 (m, 2H), 3.10-2.96 (m, 2H), 2.50-2.33 (m, 4H), 2.30-2.10 (m, 2H), 1.90-1.73 (m, 3H), 1.67-1.52 (m, 2H), 1.42-1.29 (m, 1H). m/z: (ESI$^+$): 479 (M+H)$^+$, ($C_{26}H_{34}N_6O_3$).

1-(3-(4-Methoxyphenyl)-1,2,4-oxadiazol-5-yl)-N-((1-(pyridin-2-ylmethyl)pyrrolidin-3-yl)methyl)piperidine-4-carboxamide formate (Compound 340): Using 1-(3-(4-methoxyphenyl)-1,2,4-oxadiazol-5-yl)-N-(pyrrolidin-3-ylmethyl)piperidine-4-carboxamide (100 mg, 0.259 mmol) and picolinaldehyde (30 mg, 0.280 mmol) as the starting material.

Yield 45 mg (34%), as an off-white solid. $^1$H NMR (400 MHz, DMSO) δ 8.49-8.47 (m, 1H), 8.16 (s, 1H, HCOOH), 7.91 (t, J=5.6 Hz, 1H), 7.84 (d, J=8.8 Hz, 2H), 7.77-7.75 (m, 1H), 7.42 (d, J=7.8 Hz, 1H), 7.26-7.24 (m, 1H), 7.05 (d, J=8.8 Hz, 2H), 4.05 (d, J=13.2 Hz, 2H), 3.82 (s, 3H), 3.70 (s, 2H), 3.19 (dd, J=10.0, 13.2 Hz, 2H), 3.10-3.00 (m, 2H), 2.60-2.51 (m, 3H), 2.45-2.34 (m, 1H), 2.34-2.21 (m, 2H), 1.92-1.82 (m, 1H), 1.78 (d, J=13.2 Hz, 2H), 1.68-1.53 (m, 2H), 1.47-1.34 (m, 1H). m/z: (ESI$^+$): 477 (M+H)$^+$, ($C_{26}H_{32}N_6O_3$).

1-(3-(4-Methoxyphenyl)-1,2,4-oxadiazol-5-yl)-N-((1-(thiazol-2-ylmethyl)pyrrolidin-3-yl)methyl)piperidine-4-carboxamide (Compound 364): Using 1-(3-(4-methoxyphenyl)-1,2,4-oxadiazol-5-yl)-N-(pyrrolidin-3-ylmethyl)piperidine-4-carboxamide (100 mg, 0.259 mmol), and thiazole-2-carbaldehyde (70 mg, 0.619 mmol) as the starting material.

Yield 14 mg (11%), as an off-white solid. $^1$H NMR (400 MHz, DMSO) δ 7.92 (t, J=5.6 Hz, 1H), 7.84 (d, J=8.8 Hz, 2H), 7.70 (d, J=3.3 Hz, 1H), 7.65 (d, J=3.3 Hz, 1H), 7.05 (d, J=8.8 Hz, 2H), 4.06 (d, J=13.2 Hz, 2H), 3.91 (d, J=1.2 Hz, 2H), 3.82 (s, 3H), 3.26-3.14 (m, 2H), 3.06-3.04 (m, 2H), 2.70-2.56 (m, 3H), 2.45-2.23 (m, 3H), 1.93-1.82 (m, 1H), 1.79 (d, J=13.2 Hz, 2H), 1.62-1.60 (m, 2H), 1.45-1.42 (m, 1H). m/z: (ESI$^+$): 483 (M+H)$^+$, ($C_{24}H_{30}N_6O_3S$).

1-(3-(4-Methoxyphenyl)-1,2,4-oxadiazol-5-yl)-N-((1-((5-methylpyridin-3-yl)methyl)pyrrolidin-3-yl)methyl)piperidine-4-carboxamide (Compound 365): Using 1-(3-(4-methoxyphenyl)-1,2,4-oxadiazol-5-yl)-N-(pyrrolidin-3-ylmethyl)piperidine-4-carboxamide (100 mg, 0.259 mmol) and 5-methylnicotinaldehyde (35 mg, 0.289 mmol) as the starting material.

Yield 45 mg (35%), as an off-white solid. $^1$H NMR (400 MHz, DMSO) δ 8.29 (d, J=2.4 Hz, 2H), 7.89 (t, J=5.6 Hz, 1H), 7.84 (d, J=8.8 Hz, 2H), 7.51 (s, 1H), 7.06 (d, J=8.8 Hz, 2H), 4.05 (dd, J=3.6, 13.4 Hz, 2H), 3.82 (s, 3H), 3.54 (s, 2H), 3.25-3.12 (m, 2H), 3.11-2.94 (m, 2H), 2.57-2.35 (m, 4H), 2.29 (s, 3H), 2.28-2.16 (m, 2H), 1.90-1.73 (m, 3H), 1.69-1.50 (m, 2H), 1.44-1.32 (m, 1H). m/z: (ESI$^+$): 491 (M+H)$^+$, (C$_{27}$H$_{34}$N$_6$O$_3$).

1-(3-(4-Methoxyphenyl)-1,2,4-oxadiazol-5-yl)-N-((1-(thiazol-5-ylmethyl)pyrrolidin-3-yl)methyl)piperidine-4-carboxamide (Compound 341): Using 1-(3-(4-methoxyphenyl)-1,2,4-oxadiazol-5-yl)-N-(pyrrolidin-3-ylmethyl)piperidine-4-carboxamide (100 mg, 0.259 mmol) and thiazole-5-carbaldehyde (30 mg, 0.265 mmol) as the starting material.

Yield 40 mg (32%), as an off-white solid. $^1$H NMR (400 MHz, DMSO) δ 9.01 (s, 1H), 7.90 (t, J=5.6 Hz, 1H), 7.84 (d, J=8.8 Hz, 2H), 7.76 (s, 1H), 7.05 (d, J=8.8 Hz, 2H), 4.05 (d, J=13.4 Hz, 2H), 3.82 (s, 3H), 3.81 (s, 2H), 3.20-3.18 (m, 2H), 3.04-3.01 (m, 2H), 2.61-2.53 (m, 2H), 2.50-2.48 (m, 1H), 2.40-2.37 (m, 1H), 2.31-2.17 (m, 2H), 1.91-1.71 (m, 3H), 1.61-1.58 (m, 2H), 1.40-1.37 (m, 1H). m/z: (ESI$^+$): 483 (M+H)$^+$, (C$_{24}$H$_{30}$N$_6$O$_3$S).

N-((1-benzylpyrrolidin-3-yl)methyl)-1-(3-(4-methoxyphenyl)-1,2,4-oxadiazol-5-yl)piperidine-4-carboxamide (Compound 342): Using 1-(3-(4-methoxyphenyl)-1,2,4-oxadiazol-5-yl)-N-(pyrrolidin-3-ylmethyl)piperidine-4-carboxamide (70 mg, 0.182 mmol) and benzaldehyde (30 mg, 0.283 mmol) as the starting material.

Yield 11 mg (13%), as an off-white solid. $^1$H NMR (400 MHz, DMSO) δ 7.89 (t, J=5.6 Hz, 1H), 7.87-7.80 (d, J=8.8 Hz, 2H), 7.33-7.8 (m, 4H), 7.23 (dd, J=2.4, 8.4 Hz, 1H), 7.05 (d, J=8.8 Hz, 2H), 4.10-3.99 (m, 2H), 3.82 (s, 3H), 3.53 (s, 2H), 3.20-3.18 (m, 2H), 3.12-2.94 (m, 2H), 2.50-2.34 (m, 4H), 2.30-2.24 (m, 1H), 2.22-2.14 (m, 1H), 1.88-1.73 (m, 3H), 1.67-1.51 (m, 2H), 1.44-1.31 (m, 1H). m/z: (ESI$^+$): 476 (M+H)$^+$, (C$_{27}$H$_{33}$N$_5$O$_3$).

1-(3-(4-methoxyphenyl)-1,2,4-oxadiazol-5-yl)-N-((1-((2-methylcyclopropyl)methyl)pyrrolidin-3-yl)methyl)piperidine-4-carboxamide formate (Compound 368): Using 1-(3-(4-methoxyphenyl)-1,2,4-oxadiazol-5-yl)-N-(pyrrolidin-3-ylmethyl)piperidine-4-carboxamide (100 mg, 0.259 mmol) and 2-methylcyclopropane-1-carbaldehyde (80 mg, 0.951 mmol) as the starting material.

Yield 81 mg (62%), as a colorless solid. $^1$H NMR (400 MHz, DMSO) δ 8.21 (s, 1H, HCOOH), 7.96 (t, J=5.6 Hz, 1H), 7.84 (d, J=8.8 Hz, 2H), 7.06 (d, J=8.8 Hz, 2H), 4.07 (d, J=12.8 Hz, 2H), 3.83 (s, 3H), 3.26-3.16 (m, 2H), 3.06 (t, J=6.4 Hz, 2H), 2.78 (t, J=8.4 Hz, 1.3H), 2.69 (t, J=7.8 Hz, 2H), 2.63-2.54 (m, 0.7H), 2.47-2.36 (m, 2H), 2.36-2.20 (m, 2H), 1.95-1.78 (m, 3H), 1.63-1.60 (m, 2H), 1.45 (m, 1H), 1.04-0.98 (m, 3H), 0.91-0.81 (d, J=7.2 Hz, 0.7H), 0.72-0.65 (m, 0.3H), 0.63-0.50 (m, 1.3H), 0.33-0.27 (m, 0.7H), 0.26-0.21 (m, 0.7H), −0.12 (q, J=5.0 Hz, 0.3H). (3:7 mixture of cis/trans isomers). m/z: (ESI$^+$): 454 (M+H)$^+$, (C$_{25}$H$_{35}$N$_5$O$_3$).

1-(3-(4-Methoxyphenyl)-1,2,4-oxadiazol-5-yl)-N-((1-(((S)-1-methylpyrrolidin-2-yl)methyl)pyrrolidin-3-yl)methyl)piperidine-4-carboxamide (Compound 369): Using 1-(3-(4-methoxyphenyl)-1,2,4-oxadiazol-5-yl)-N-((1-(((S)-pyrrolidin-2-yl)methyl)pyrrolidin-3-yl)methyl) piperidine-4-carboxamide (100 mg, 0.213 mmol) and polyoxymethylene (30 mg, 0.666 mmol) as the starting material.

Yield 50 mg (49%), as an off-white solid. $^1$H NMR (400 MHz, DMSO) δ 7.91 (t, J=5.6 Hz, 1H), 7.84 (d, J=8.8 Hz, 2H), 7.06 (d, J=8.8 Hz, 2H), 4.18-3.99 (m, 2H), 3.83 (s, 3H), 3.22-3.19 (m, 2H), 3.09-2.95 (m, 2H), 2.90 (d, J=8.0 Hz, 1H), 2.50-2.34 (m, 5H), 2.28 (s, 3H), 2.25-2.12 (m, 4H), 2.07 (d, J=9.2 Hz, 1H), 1.96-1.72 (m, 4H), 1.62 (m, 4H), 1.53-1.42 (m, 1H), 1.40-1.30 (m, 1H). m/z: (ESI$^+$): 483 (M+H)$^+$, (C$_{26}$H$_{38}$N$_6$O$_3$).

1-(3-(4-Methoxyphenyl)-1,2,4-oxadiazol-5-yl)-N-((1-(tetrahydrofuran-3-yl)pyrrolidin-3-yl)methyl)piperidine-4-carboxamide (Compound 370): Using 1-(3-(4-methoxyphenyl)-1,2,4-oxadiazol-5-yl)-N-(pyrrolidin-3-ylmethyl)piperidine-4-carboxamide (100 mg, 0.259 mmol) and dihydrofuran-3(2H)-one (25 mg, 0.290 mmol) as the starting material.

Yield 30 mg (25%), as an off-white solid. $^1$H NMR (400 MHz, DMSO) δ 7.92 (t, J=5.6 Hz, 1H), 7.84 (d, J=8.8 Hz, 2H), 7.04 (d, J=8.8 Hz, 2H), 4.08-4.05 (m, 2H), 3.82 (s, 3H), 3.80-3.60 (m, 3H), 3.47 (t, J=5.6 Hz, 1H), 3.22-3.19 (m, 2H), 3.11-2.92 (m, 2H), 2.78 (s, 1H), 2.60-2.34 (m, 4H), 2.22 (s, 2H), 2.00-1.88 (m, 1H), 1.87-1.72 (m, 4H), 1.68-1.53 (m, 2H), 1.38-1.35 (m, 1H). m/z: (ESI$^+$): 456 (M+H)$^+$, (C$_{24}$H$_{33}$N$_5$O$_4$).

1-(3-(4-Methoxyphenyl)-1,2,4-oxadiazol-5-yl)-N-((1-(thiophen-2-ylmethyl)pyrrolidin-3-yl)methyl)piperidine-4-carboxamide (Compound 372): Using 1-(3-(4-methoxyphenyl)-1,2,4-oxadiazol-5-yl)-N-(pyrrolidin-3-ylmethyl)piperidine-4-carboxamide (100 mg, 0.259 mmol) and thiophene-2-carbaldehyde (32 mg, 0.285 mmol) as the starting material.

Yield 80 mg (64%), as an off-white solid. $^1$H NMR (400 MHz, DMSO) δ 7.90 (t, J=5.6 Hz, 1H), 7.84 (d, J=8.8 Hz, 2H), 7.40 (dd, J=2.0, 4.4 Hz, 1H), 7.05 (d, J=8.8 Hz, 2H), 6.98-6.90 (m, 2H), 4.06 (dd, J=4.0, 13.6 Hz, 2H), 3.82 (s, 3H), 3.74 (s, 2H), 3.19 (dt, J=2.8, 12.8 Hz, 2H), 3.12-2.93 (m, 2H), 2.62-2.54 (m, 1H), 2.50-2.45 (m, 2H), 2.46-2.35 (m, 1H), 2.29-2.20 (m, 2H), 1.92-1.73 (m, 3H), 1.68-1.52 (m, 2H), 1.43-1.32 (m, 1H). m/z: [ESI$^+$] 482 (M+H)$^+$, (C$_{25}$H$_{31}$N$_5$O$_3$S).

1-(3-(4-methoxyphenyl)-1,2,4-oxadiazol-5-yl)-N-((1-((4-methylthiazol-5-yl)methyl)pyrrolidin-3-yl)methyl)piperidine-4-carboxamide (Compound 404): Using 1-(3-(4-methoxyphenyl)-1,2,4-oxadiazol-5-yl)-N-(pyrrolidin-3-ylmethyl)piperidine-4-carboxamide (100 mg, 0.259 mmol) and 4-methylthiazole-5-carbaldehyde (36 mg, 0.283 mmol) as the starting material.

Yield 65 mg (50%), as an off-white solid. $^1$H NMR (400 MHz, DMSO) δ 8.88 (s, 1H), 7.90 (t, J=5.6 Hz, 1H), 7.84 (d, J=8.8 Hz, 2H), 7.06 (d, J=8.8 Hz, 2H), 4.06 (d, J=12.8 Hz, 2H), 3.82 (s, 3H), 3.71 (s, 2H), 3.25-3.13 (m, 2H), 3.12-2.92 (m, 2H), 2.58-2.50 (m, 3H), 2.44-2.35 (m, 1H), 2.34 (s, 3H), 2.28-2.20 (m, 2H), 1.88-1.75 (m, 3H), 1.67-1.52 (m, 2H), 1.44-1.35 (m, 1H). m/z: [ESI$^+$] 497 (M+H)$^+$, (C$_{25}$H$_{32}$N$_6$O$_3$S).

N-((1-isobutylpyrrolidin-3-yl)methyl)-1-(3-(4-methoxyphenyl)-1,2,4-oxadiazol-5-yl)piperidine-4-carboxamide (Compound 374): Using 1-(3-(4-methoxyphenyl)-1,2,4-oxadiazol-5-yl)-N-(pyrrolidin-3-ylmethyl)piperidine-4-carboxamide (100 mg, 0.259 mmol) and isobutyraldehyde (40 mg, 0.555 mmol) as the starting material.

Yield 31 mg (27%), as an off-white solid. $^1$H NMR (400 MHz, DMSO) δ 7.90 (t, J=5.6 Hz, 1H), 7.84 (d, J=8.8 Hz, 2H), 7.05 (d, J=8.8 Hz, 2H), 4.06 (td, J=3.6, 12.8 Hz, 2H), 3.82 (s, 3H), 3.20 (dt, J=3.2, 12.8 Hz, 2H), 3.08-2.95 (m, 2H), 2.55-2.30 (m, 4H), 2.26-2.08 (m, 4H), 1.88-1.73 (m, 3H), 1.72-1.50 (m, 3H), 1.45-1.29 (m, 1H), 0.86 (d, J=6.4 Hz, 6H). m/z: [ESI⁺] 442 (M+H)⁺, ($C_{24}H_{35}N_5O_3$).

1-(3-(4-Methoxyphenyl)-1,2,4-oxadiazol-5-yl)-N-((1-((tetrahydro-2H-pyran-3-yl)methyl)pyrrolidin-3-yl)methyl)piperidine-4-carboxamide (Compound 375): Using 1-(3-(4-methoxyphenyl)-1,2,4-oxadiazol-5-yl)-N-(pyrrolidin-3-ylmethyl)piperidine-4-carboxamide (100 mg, 0.259 mmol) and tetrahydro-2H-pyran-3-carbaldehyde (60 mg, 0.526 mmol) as the starting material.

Yield 42 mg (33%), as an off-white solid. ¹H NMR (400 MHz, DMSO) δ 7.91 (t, J=5.6 Hz, 1H), 7.84 (d, J=8.8 Hz, 2H), 7.05 (d, J=8.8 Hz, 2H), 4.12-4.01 (m, 2H), 3.82 (s, 3H), 3.85-3.69 (m, 2H), 3.25-3.14 (m, 3H), 3.10-2.92 (m, 3H), 2.47-2.31 (m, 4H), 2.30-2.02 (m, 4H), 1.88-1.71 (m, 4H), 1.70-1.58 (m, 3H), 1.58-1.41 (m, 2H), 1.40-1.27 (m, 1H), 1.20-1.04 (m, 1H). m/z: [ESI⁺] 484 (M+H)⁺, ($C_{26}H_{37}N_5O_4$).

1-(3-(4-Methoxyphenyl)-1,2,4-oxadiazol-5-yl)-N-((1-((tetrahydrofuran-2-yl)methyl)pyrrolidin-3-yl)methyl)piperidine-4-carboxamide (Compound 405): Using 1-(3-(4-methoxyphenyl)-1,2,4-oxadiazol-5-yl)-N-(pyrrolidin-3-ylmethyl)piperidine-4-carboxamide (100 mg, 0.259 mmol) and tetrahydrofuran-2-carbaldehyde (29 mg, 0.290 mmol) as the starting material.

Yield 48 mg (39%), as an off-white solid. ¹H NMR (400 MHz, DMSO) δ 7.91 (t, J=5.6 Hz, 1H), 7.84 (d, J=8.8 Hz, 2H), 7.05 (d, J=8.8 Hz, 2H), 4.06 (d, J=13.2 Hz, 2H), 3.85 (t, J=7.2 Hz, 1H), 3.82 (s, 3H), 3.77-3.66 (m, 1H), 3.59 (dt, J=6.2, 7.6 Hz, 1H), 3.20 (dt, J=3.2, 12.8 Hz, 2H), 3.09-2.92 (m, 2H), 2.65-2.35 (m, 6H), 2.30-2.15 (m, 2H), 1.95-1.87 (m, 1H), 1.83-1.74 (m, 5H), 1.70-1.52 (m, 2H), 1.54-1.41 (m, 1H), 1.41-1.29 (m, 1H). m/z: [ESI⁺] 470 (M+H)⁺, ($C_{25}H_{35}N_5O_4$).

N-((1-ethylpyrrolidin-3-yl)methyl)-1-(3-(4-methoxyphenyl)-1,2,4-oxadiazol-5-yl)piperidine-4-carboxamide formate (Compound 376): Using 1-(3-(4-methoxyphenyl)-1,2,4-oxadiazol-5-yl)-N-(pyrrolidin-3-ylmethyl)piperidine-4-carboxamide (100 mg, 0.259 mmol) and acetaldehyde (40 mg, 0.908 mmol) as the starting material.

Yield 40 mg (34%), as an off-white solid. ¹H NMR (400 MHz, DMSO) δ 8.27 (s, 1H, HCOOH), 7.98 (t, J=5.6 Hz, 1H), 7.84 (d, J=8.8 Hz, 2H), 7.05 (d, J=8.8 Hz, 2H), 4.06 (td, J=3.6, 12.8 Hz, 2H), 3.82 (s, 3H), 3.20 (dt, J=2.8, 12.8 Hz, 2H), 3.13-2.97 (m, 2H), 2.82-2.54 (m, 5H), 2.48-2.35 (m, 2H), 2.33-2.27 (m, 1H), 1.95-1.78 (m, 3H), 1.70-1.52 (m, 2H), 1.45 (td, J=6.8, 13.6 Hz, 1H), 1.07 (t, J=7.2 Hz, 3H). m/z: [ESI⁺] 414 (M+H)⁺, ($C_{22}H_{31}N_5O_3$).

1-(3-(4-methoxyphenyl)-1,2,4-oxadiazol-5-yl)-N-((1-((4-methyltetrahydro-2H-pyran-4-yl)methyl)pyrrolidin-3-yl)methyl)piperidine-4-carboxamide (Compound 377): Using 1-(3-(4-methoxyphenyl)-1,2,4-oxadiazol-5-yl)-N-(pyrrolidin-3-ylmethyl)piperidine-4-carboxamide (100 mg, 0.259 mmol) and 4-methyltetrahydro-2H-pyran-4-carbaldehyde (37 mg, 0.289 mmol) as the starting material.

Yield 50 mg (39%), as an off-white solid. ¹H NMR (400 MHz, DMSO) δ 7.90 (t, J=5.6 Hz, 1H), 7.84 (d, J=8.8 Hz, 2H), 7.05 (d, J=8.8 Hz, 2H), 4.06 (d, J=13.2 Hz, 2H), 3.82 (s, 3H), 3.59 (td, J=4.4, 11.6 Hz, 2H), 3.49 (ddd, J=3.2, 9.6, 12.0 Hz, 2H), 3.20 (dt, J=3.2, 12.8 Hz, 2H), 3.06-2.96 (m, 2H), 2.68-2.50 (m, 3H), 2.47-2.32 (m, 2H), 2.32-2.12 (m, 3H), 1.84-1.76 (m, 3H), 1.71-1.52 (m, 2H), 1.50-1.30 (m, 3H), 1.25-1.12 (m, 2H), 0.96 (s, 3H). m/z: [ESI⁺] 498 (M+H)⁺, ($C_{27}H_{39}N_5O_4$).

N-((1-(4-ethynylbenzyl)pyrrolidin-3-yl)methyl)-1-(3-(4-methoxyphenyl)-1,2,4-oxadiazol-5-yl)piperidine-4-carboxamide (Compound 378): Using 1-(3-(4-methoxyphenyl)-1,2,4-oxadiazol-5-yl)-N-(pyrrolidin-3-ylmethyl)piperidine-4-carboxamide (100 mg, 0.259 mmol) and 4-ethynylbenzaldehyde (70 mg, 0.538 mmol) as the starting material.

Yield 23 mg (18%), as an off-white solid. ¹H NMR (400 MHz, DMSO) δ 7.88 (t, J=5.6 Hz, 1H), 7.83 (d, J=8.8 Hz, 2H), 7.42 (d, J=8.2 Hz, 2H), 7.31 (d, J=8.2 Hz, 2H), 7.05 (d, J=8.8 Hz, 2H), 4.13 (s, 1H), 4.05 (d, J=13.2 Hz, 2H), 3.82 (s, 3H), 3.55 (s, 2H), 3.19 (dt, J=3.2, 12.8 Hz, 2H), 3.11-2.95 (m, 2H), 2.51-2.31 (m, 4H), 2.30-2.14 (m, 2H), 1.89-1.75 (m, 3H), 1.68-1.50 (m, 2H), 1.43-1.31 (m, 1H). m/z: [ESI⁺] 500 (M+H)⁺, ($C_{29}H_{33}N_5O_3$).

1-(3-(4-Methoxyphenyl)-1,2,4-oxadiazol-5-yl)-N-((1-((2-methylpyridin-3-yl)methyl)pyrrolidin-3-yl)methyl)piperidine-4-carboxamide (Compound 380): Using 1-(3-(4-methoxyphenyl)-1,2,4-oxadiazol-5-yl)-N-(pyrrolidin-3-ylmethyl)piperidine-4-carboxamide (100 mg, 0.259 mmol) and 2-methylnicotinaldehyde (65 mg, 0.537 mmol) as the starting material Yield 19 mg (15%), as an off-white solid. ¹H NMR (400 MHz, DMSO) δ 8.30 (dd, J=1.6, 4.8 Hz, 1H), 7.89 (t, J=5.6 Hz, 1H), 7.83 (d, J=8.8 Hz, 2H), 7.60 (dd, J=1.6, 7.6 Hz, 1H), 7.16 (dd, J=4.8, 7.6 Hz, 1H), 7.05 (d, J=8.8 Hz, 2H), 4.04 (d, J=13.2 Hz, 2H), 3.82 (s, 3H), 3.53 (s, 2H), 3.18 (t, J=12.4 Hz, 2H), 3.10-2.96 (m, 2H), 2.52-2.50 (m, 2H), 2.48 (s, 3H), 2.47-2.31 (m, 2H), 2.31-2.18 (m, 2H), 1.92-1.70 (m, 3H), 1.67-1.51 (m, 2H), 1.40 (td, J=6.4, 12.8 Hz, 1H). m/z: [ESI⁺] 491 (M+H)⁺, ($C_{27}H_{34}N_6O_3$).

1-(3-(4-Methoxyphenyl)-1,2,4-oxadiazol-5-yl)-N-((1-((5-methylfuran-2-yl)methyl)pyrrolidin-3-yl)methyl)piperidine-4-carboxamide (Compound 379): Using 1-(3-(4-methoxyphenyl)-1,2,4-oxadiazol-5-yl)-N-(pyrrolidin-3-ylmethyl)piperidine-4-carboxamide (100 mg, 0.259 mmol) and 5-methylfuran-2-carbaldehyde (31 mg, 0.282 mmol) as the starting material.

Yield 54 mg (43%), as an off-white solid. ¹H NMR (400 MHz, DMSO) δ 7.91 (t, J=5.6 Hz, 1H), 7.84 (d, J=8.8 Hz, 2H), 7.06 (d, J=8.8 Hz, 2H), 6.10 (d, J=2.8 Hz, 1H), 5.97 (dd, J=1.2, 2.8 Hz, 1H), 4.06 (td, J=3.6, 13.2 Hz, 2H), 3.83 (s, 3H), 3.47 (d, J=3.6 Hz, 2H), 3.20 (dt, J=3.2, 12.8 Hz, 2H), 3.11-2.92 (m, 2H), 2.51-2.32 (m, 4H), 2.28-2.16 (m, 5H), 1.88-1.75 (m, 3H), 1.70-1.52 (m, 2H), 1.44-1.29 (m, 1H). m/z: [ESI⁺] 480 (M+H)⁺, ($C_{26}H_{33}N_5O_4$).

1-(3-(4-Methoxyphenyl)-1,2,4-oxadiazol-5-yl)-N-((1-((3-methylthiophen-2-yl)methyl)pyrrolidin-3-yl)methyl)piperidine-4-carboxamide (Compound 381): Using 1-(3-(4-methoxyphenyl)-1,2,4-oxadiazol-5-yl)-N-(pyrrolidin-3-ylmethyl)piperidine-4-carboxamide (100 mg, 0.259 mmol) and 3-methylthiophene-2-carbaldehyde (67 mg, 0.531 mmol) as the starting material.

Yield 39 mg (30%), as an off-white solid. ¹H NMR (400 MHz, DMSO) δ 7.89 (t, J=5.6 Hz, 1H), 7.83 (d, J=8.8 Hz, 2H), 7.28 (s, 1H), 7.05 (d, J=8.8 Hz, 2H), 6.81 (s, 1H), 4.05 (d, J=13.2 Hz, 2H), 3.82 (s, 3H), 3.65 (s, 2H), 3.19 (dt, J=4.4, 12.8 Hz, 2H), 3.11-2.95 (m, 2H), 2.62-2.52 (m, 3H), 2.44-2.34 (m, 1H), 2.24 (s, 2H), 2.15 (s, 3H), 1.89-1.75 (m, 3H), 1.68-1.52 (m, 2H), 1.45-1.33 (m, 1H). m/z: [ESI⁺] 496 (M+H)⁺, ($C_{26}H_{33}N_5O_3S$).

1-(3-(4-Methoxyphenyl)-1,2,4-oxadiazol-5-yl)-N-((1-((4-methylfuran-2-yl)methyl)pyrrolidin-3-yl)methyl)piperidine-4-carboxamide (Compound 382): Using 1-(3-(4-methoxyphenyl)-1,2,4-oxadiazol-5-yl)-N-(pyrrolidin-3-ylmethyl)piperidine-4-carboxamide (100 mg, 0.259 mmol) and 4-methylfuran-2-carbaldehyde (31 mg, 0.282 mmol) as the starting material.

Yield 58 mg (47%), as an off-white solid. ¹H NMR (400 MHz, DMSO) δ 7.92 (t, J=5.6 Hz, 1H), 7.84 (d, J=8.8 Hz, 2H), 7.30 (d, J=1.2 Hz, 1H), 7.06 (d, J=8.8 Hz, 2H), 6.12 (s, 1H), 4.06 (td, J=3.6, 13.2 Hz, 2H), 3.83 (s, 3H), 3.49 (s, 2H), 3.20 (dt, J=3.2, 12.8 Hz, 2H), 3.12-2.91 (m, 2H), 2.60-2.34 (m, 4H), 2.28-2.18 (m, 2H), 1.95 (s, 3H), 1.87-1.75 (m, 3H), 1.68-1.52 (m, 2H), 1.43-1.28 (m, 1H). m/z: [ESI$^+$] 480 (M+H)$^+$, (C$_{26}$H$_{33}$N$_5$O$_4$).

1-(3-(4-Methoxyphenyl)-1,2,4-oxadiazol-5-yl)-N-((1-((3-methylfuran-2-yl)methyl)pyrrolidin-3-yl)methyl)piperidine-4-carboxamide (Compound 406): Using 1-(3-(4-methoxyphenyl)-1,2,4-oxadiazol-5-yl)-N-(pyrrolidin-3-ylmethyl)piperidine-4-carboxamide (100 mg, 0.259 mmol) and 3-methylfuran-2-carbaldehyde (31 mg, 0.282 mmol) as the starting material.

Yield 45 mg (36%), as an off-white solid. $^1$H NMR (400 MHz, DMSO) δ 7.91 (t, J=5.6 Hz, 1H), 7.84 (d, J=8.8 Hz, 2H), 7.45 (d, J=1.8 Hz, 1H), 7.06 (d, J=8.8 Hz, 2H), 6.27 (d, J=1.8 Hz, 1H), 4.05 (td, J=3.6, 13.2 Hz, 2H), 3.82 (s, 3H), 3.49 (d, J=4.0 Hz, 2H), 3.19 (dt, J=3.2, 12.8 Hz, 2H), 3.11-2.90 (m, 2H), 2.57-2.52 (m, 1H), 2.47-2.33 (m, 3H), 2.26-2.16 (m, 2H), 1.96 (s, 3H), 1.86-1.71 (m, 3H), 1.67-1.51 (m, 2H), 1.41-1.27 (m, 1H). m/z: [ESI$^+$] 480 (M+H)$^+$, (C$_{26}$H$_{33}$N$_5$O$_4$).

1-(3-(4-methoxyphenyl)-1,2,4-oxadiazol-5-yl)-N-((1-((2-methylthiazol-4-yl)methyl)pyrrolidin-3-yl)methyl)piperidine-4-carboxamide (Compound 383): Using 1-(3-(4-methoxyphenyl)-1,2,4-oxadiazol-5-yl)-N-(pyrrolidin-3-ylmethyl)piperidine-4-carboxamide (100 mg, 0.259 mmol) and 2-methylthiazole-4-carbaldehyde (36 mg, 0.283 mmol) as the starting material.

Yield 66 mg (51%), as an off-white solid. $^1$H NMR (400 MHz, DMSO) δ 7.91 (t, J=5.6 Hz, 1H), 7.84 (d, J=8.8 Hz, 2H), 7.22 (s, 1H), 7.05 (d, J=8.8 Hz, 2H), 4.05 (d, J=13.2 Hz, 2H), 3.82 (s, 3H), 3.61 (s, 2H), 3.20 (dt, J=3.2, 12.8 Hz, 2H), 3.09-2.95 (m, 2H), 2.62 (s, 3H), 2.60-2.53 (m, 2H), 2.50-2.45 (m, 1H), 2.43-2.33 (m, 1H), 2.33-2.18 (m, 2H), 1.89-1.74 (m, 3H), 1.69-1.52 (m, 2H), 1.46-1.29 (m, 1H). m/z: [ESI$^+$] 497 (M+H)$^+$, (C$_{25}$H$_{32}$N$_6$O$_3$S).

1-(3-(4-methoxyphenyl)-1,2,4-oxadiazol-5-yl)-N-((1-((5-methylthiazol-2-yl)methyl)pyrrolidin-3-yl)methyl)piperidine-4-carboxamide (Compound 407): Using 1-(3-(4-methoxyphenyl)-1,2,4-oxadiazol-5-yl)-N-(pyrrolidin-3-ylmethyl)piperidine-4-carboxamide (100 mg, 0.259 mmol) and 5-methylthiazole-2-carbaldehyde (80 mg, 0.629 mmol) as the starting material.

Yield 15 mg (12%), as an off-white solid. $^1$H NMR (400 MHz, DMSO) δ 7.91 (t, J=5.6 Hz, 1H), 7.84 (d, J=8.8 Hz, 2H), 7.35 (d, J=1.6 Hz, 1H), 7.05 (d, J=8.8 Hz, 2H), 4.05 (d, J=13.6 Hz, 2H), 3.82 (s, 5H), 3.20 (dt, J=3.2, 12.8 Hz, 2H), 3.14-2.94 (m, 2H), 2.69-2.54 (m, 3H), 2.40 (s, 3H), 2.43-2.21 (m, 3H), 1.91-1.75 (m, 3H), 1.71-1.52 (m, 2H), 1.47-1.37 (m, 1H). m/z: [ESI$^+$] 497 (M+H)$^+$, (C$_{25}$H$_{32}$N$_6$O$_3$S).

1-(3-(4-methoxyphenyl)-1,2,4-oxadiazol-5-yl)-N-((1-((4-methylthiazol-2-yl)methyl)pyrrolidin-3-yl)methyl)piperidine-4-carboxamide (Compound 384): Using 1-(3-(4-methoxyphenyl)-1,2,4-oxadiazol-5-yl)-N-(pyrrolidin-3-ylmethyl)piperidine-4-carboxamide (100 mg, 0.259 mmol) and 4-methylthiazole-2-carbaldehyde (60 mg, 0.472 mmol) as the starting material.

Yield 15 mg (12%), as an off-white solid. $^1$H NMR (400 MHz, DMSO) δ 7.91 (t, J=5.6 Hz, 1H), 7.84 (d, J=8.8 Hz, 2H), 7.16 (s, 1H), 7.05 (d, J=8.8 Hz, 2H), 4.05 (d, J=13.2 Hz, 2H), 3.84 (s, 2H), 3.82 (s, 3H), 3.19 (t, J=12.4 Hz, 2H), 3.12-2.96 (m, 2H), 2.69-2.51 (m, 3H), 2.46-2.24 (m, 3H), 2.32 (s, 3H), 1.92-1.84 (m, 1H), 1.79 (d, J=13.2 Hz, 2H), 1.70-1.53 (m, 2H), 1.50-1.36 (m, 1H). m/z: [ESI$^+$] 497 (M+H)$^+$, (C$_{25}$H$_{32}$N$_6$O$_3$S).

1-(3-(4-Methoxyphenyl)-1,2,4-oxadiazol-5-yl)-N-((1-((5-methylthiophen-2-yl)methyl)pyrrolidin-3-yl)methyl)piperidine-4-carboxamide (Compound 385): Using 1-(3-(4-methoxyphenyl)-1,2,4-oxadiazol-5-yl)-N-(pyrrolidin-3-ylmethyl)piperidine-4-carboxamide (100 mg, 0.259 mmol) and 5-methylthiophene-2-carbaldehyde (36 mg, 0.285 mmol) as the starting material.

Yield 16 mg (12%), as an off-white solid. $^1$H NMR (400 MHz, DMSO) δ 7.90 (t, J=5.6 Hz, 1H), 7.84 (d, J=8.8 Hz, 2H), 7.05 (d, J=8.8 Hz, 2H), 6.71 (s, 1H), 6.61 (d, J=3.2 Hz, 1H), 4.05 (d, J=12.8 Hz, 2H), 3.82 (s, 3H), 3.65 (s, 2H), 3.19 (dt, J=3.2, 12.8 Hz, 2H), 3.11-2.93 (m, 2H), 2.60-2.45 (m, 3H), 2.45-2.33 (m, 1H), 2.39 (s, 3H), 2.23 (s, 2H), 1.90-1.73 (m, 3H), 1.70-1.52 (m, 2H), 1.38 (s, 1H). m/z: [ESI$^+$] 496 (M+H)$^+$, (C$_{26}$H$_{33}$N$_5$O$_3$S).

1-(3-(4-Methoxyphenyl)-1,2,4-oxadiazol-5-yl)-N-((1-(oxetan-3-ylmethyl)pyrrolidin-3-yl)methyl)piperidine-4-carboxamide (Compound 408): Using 1-(3-(4-methoxyphenyl)-1,2,4-oxadiazol-5-yl)-N-(pyrrolidin-3-ylmethyl)piperidine-4-carboxamide (200 mg, 0.519 mmol) and oxetane-3-carbaldehyde(120 mg, 1.394 mmol) as the starting material.

Yield 140 mg (59%), as an off-white solid. $^1$H NMR (400 MHz, DMSO) δ 7.89 (t, J=5.6 Hz, 1H), 7.84 (d, J=8.8 Hz, 2H), 7.06 (d, J=8.8 Hz, 2H), 4.63 (dd, J=5.6, 7.6 Hz, 2H), 4.25 (t, J=6.0 Hz, 2H), 4.06 (d, J=13.2 Hz, 2H), 3.82 (s, 3H), 3.20 (dt, J=3.2, 12.8 Hz, 2H), 3.09 (td, J=6.8, 14.0 Hz, 1H), 3.05-2.93 (m, 2H), 2.66 (d, J=7.6 Hz, 2H), 2.51-2.47 (m, 1H), 2.45-2.33 (m, 3H), 2.27-2.08 (m, 2H), 1.86-1.74 (m, 3H), 1.70-1.53 (m, 2H), 1.42-1.27 (m, 1H). m/z: [ESI$^+$] 456 (M+H)$^+$, (C$_{24}$H$_{33}$N$_5$O$_4$).

1-(3-(4-Methoxyphenyl)-1,2,4-oxadiazol-5-yl)-N-((1-propylpyrrolidin-3-yl)methyl)piperidine-4-carboxamide (Compound 386): Using 1-(3-(4-methoxyphenyl)-1,2,4-oxadiazol-5-yl)-N-(pyrrolidin-3-ylmethyl)piperidine-4-carboxamide (100 mg, 0.259 mmol) and propionaldehyde (40 mg, 0.689 mmol) as the starting material.

Yield 48 mg (43%), as an off-white solid. $^1$H NMR (400 MHz, DMSO) δ 7.92 (t, J=5.6 Hz, 1H), 7.84 (d, J=8.8 Hz, 2H), 7.06 (d, J=8.8 Hz, 2H), 4.07 (td, J=3.6, 13.2 Hz, 2H), 3.83 (s, 3H), 3.20 (dt, J=3.2, 12.8 Hz, 2H), 3.09-2.96 (m, 2H), 2.52-2.37 (m, 4H), 2.36-2.28 (m, 2H), 2.21 (d, J=6.8 Hz, 2H), 1.90-1.73 (m, 3H), 1.69-1.53 (m, 2H), 1.48-1.34 (m, 3H), 0.87 (t, J=7.2 Hz, 3H). m/z: [ESI$^+$] 428 (M+H)$^+$, (C$_{23}$H$_{33}$N$_5$O$_3$).

N-((1-(cyclohex-1-en-1-ylmethyl)pyrrolidin-3-yl)methyl)-1-(3-(4-methoxyphenyl)-1,2,4-oxadiazol-5-yl)piperidine-4-carboxamide (Compound 409): Using 1-(3-(4-methoxyphenyl)-1,2,4-oxadiazol-5-yl)-N-(pyrrolidin-3-ylmethyl)piperidine-4-carboxamide (100 mg, 0.259 mmol) and cyclohex-1-ene-1-carbaldehyde (31 mg, 0.281 mmol) as the starting material.

Yield 30 mg (24%), as an off-white solid. $^1$H NMR (400 MHz, DMSO) δ 7.90 (t, J=5.6 Hz, 1H), 7.84 (d, J=8.8 Hz, 2H), 7.06 (d, J=8.8 Hz, 2H), 5.54 (d, J=3.2 Hz, 1H), 4.06 (td, J=3.6, 13.2 Hz, 2H), 3.82 (s, 3H), 3.20 (dt, J=3.2, 12.8 Hz, 2H), 3.10-2.93 (m, 2H), 2.90-2.76 (m, 2H), 2.48-2.30 (m, 4H), 2.28-2.14 (m, 1H), 2.11 (dd, J=5.6, 9.2 Hz, 1H), 2.00-1.90 (m, 4H), 1.88-1.75 (m, 3H), 1.70-1.45 (m, 6H), 1.41-1.29 (m, 1H). m/z: [ESI$^+$] 480 (M+H)$^+$, (C$_{27}$H$_{37}$N$_5$O$_3$).

1-(3-(4-Methoxyphenyl)-1,2,4-oxadiazol-5-yl)-N-((1-((6-methylpyridin-2-yl)methyl)pyrrolidin-3-yl)methyl)piperidine-4-carboxamide (Compound 387): Using 1-(3-(4-methoxyphenyl)-1,2,4-oxadiazol-5-yl)-N-(pyrrolidin-3-ylmethyl)piperidine-4-carboxamide (100 mg, 0.259 mmol) and 6-methylpicolinaldehyde (80 mg, 0.660 mmol) as the starting material.

Yield 16 mg (13%), as an off-white solid. $^1$H NMR (400 MHz, DMSO) δ 7.91 (t, J=5.6 Hz, 1H), 7.84 (d, J=8.8 Hz, 2H), 7.63 (d, J=7.6 Hz, 1H), 7.21 (d, J=7.6 Hz, 1H), 7.10 (d, J=7.6 Hz, 1H), 7.06 (d, J=8.8 Hz, 2H), 4.05 (d, J=12.8 Hz, 2H), 3.82 (s, 3H), 3.63 (s, 2H), 3.19 (t, J=12.6 Hz, 2H), 3.11-2.98 (m, 2H), 2.65-2.50 (m, 3H), 2.43 (s, 3H), 2.41-2.32 (m, 1H), 2.27 (s, 2H), 1.92-1.72 (m, 3H), 1.68-1.52 (m, 2H), 1.47-1.36 (m, 1H). m/z: [ESI$^+$] 491 (M+H)$^+$, ($C_{27}H_{34}N_6O_3$).

1-(3-(4-methoxyphenyl)-1,2,4-oxadiazol-5-yl)-N-((1-(3-methylbut-2-en-1-yl)pyrrolidin-3-yl)methyl)piperidine-4-carboxamide (Compound 410): Using 1-(3-(4-methoxyphenyl)-1,2,4-oxadiazol-5-yl)-N-(pyrrolidin-3-ylmethyl)piperidine-4-carboxamide (100 mg, 0.259 mmol) and 3-methylbut-2-enal (24 mg, 0.285 mmol) as the starting material.

Yield 24 mg (20%), as an off-white solid. $^1$H NMR (400 MHz, DMSO) δ 7.91 (t, J=5.6 Hz, 1H), 7.84 (d, J=8.8 Hz, 2H), 7.05 (d, J=8.8 Hz, 2H), 5.27-5.16 (m, 1H), 4.06 (d, J=13.2 Hz, 2H), 3.82 (s, 3H), 3.25-3.13 (m, 2H), 3.05 (td, J=6.2, 12.8 Hz, 1H), 3.00-2.92 (m, 3H), 2.50-2.35 (m, 4H), 2.27-2.10 (m, 2H), 1.86-1.72 (m, 3H), 1.68 (s, 3H), 1.67-1.53 (m, 5H), 1.41-1.28 (m, 1H). m/z: [ESI$^+$] 454 (M+H)$^+$, ($C_{25}H_{35}N_5O_3$).

N-((1-isopentylpyrrolidin-3-yl)methyl)-1-(3-(4-methoxyphenyl)-1,2,4-oxadiazol-5-yl)piperidine-4-carboxamide (Compound 411): Using 1-(3-(4-methoxyphenyl)-1,2,4-oxadiazol-5-yl)-N-(pyrrolidin-3-ylmethyl)piperidine-4-carboxamide (100 mg, 0.259 mmol) and 3-methylbut-2-enal (24 mg, 0.285 mmol) as the starting material.

Yield 21 mg (18%), as an off-white solid. $^1$H NMR (400 MHz, DMSO) δ 7.91 (t, J=5.6 Hz, 1H), 7.84 (d, J=8.8 Hz, 2H), 7.06 (d, J=8.8 Hz, 2H), 4.06 (d, J=12.8 Hz, 2H), 3.82 (s, 3H), 3.27-3.14 (m, 2H), 3.11-2.93 (m, 2H), 2.50-2.29 (m, 6H), 2.25-2.16 (s, 2H), 1.88-1.73 (m, 3H), 1.68-1.53 (m, 3H), 1.40-1.27 (m, 3H), 0.87 (d, J=6.4 Hz, 6H). m/z: [ESI$^+$] 456 (M+H)$^+$, ($C_{25}H_{37}N_5O_3$).

1-(3-(4-Methoxyphenyl)-1,2,4-oxadiazol-5-yl)-N-((1-((2-methylthiazol-5-yl)methyl)pyrrolidin-3-yl)methyl)piperidine-4-carboxamide (Compound 388): Using 1-(3-(4-methoxyphenyl)-1,2,4-oxadiazol-5-yl)-N-(pyrrolidin-3-ylmethyl)piperidine-4-carboxamide (100 mg, 0.259 mmol) and 2-methylthiazole-5-carbaldehyde (80 mg, 0.629 mmol) as the starting material.

Yield 8 mg (6%), as an off-white solid. $^1$H NMR (400 MHz, DMSO) δ 7.90 (t, J=5.6 Hz, 1H), 7.84 (d, J=8.8 Hz, 2H), 7.44 (s, 1H), 7.06 (d, J=8.8 Hz, 2H), 4.05 (d, J=13.2 Hz, 2H), 3.82 (s, 3H), 3.72 (s, 2H), 3.19 (dt, J=3.2, 12.8 Hz, 2H), 3.13-2.92 (m, 2H), 2.60 (s, 3H), 2.56-2.45 (m, 3H), 2.40 (dt, J=5.6, 11.2 Hz, 1H), 2.29-2.19 (s, 2H), 1.90-1.73 (m, 3H), 1.68-1.52 (m Hz, 2H), 1.43-1.33 (m, 1H). m/z: [ESI$^+$] 497 (M+H)$^+$, ($C_{25}H_{32}N_6O_3S$).

N-((1-((1H-pyrrol-2-yl)methyl)pyrrolidin-3-yl)methyl)-1-(3-(4-methoxyphenyl)-1,2,4-oxadiazol-5-yl)piperidine-4-carboxamide (Compound 389): Using 1-(3-(4-methoxyphenyl)-1,2,4-oxadiazol-5-yl)-N-(pyrrolidin-3-ylmethyl)piperidine-4-carboxamide (100 mg, 0.259 mmol) and 1H-pyrrole-2-carbaldehyde (27 mg, 0.284 mmol) as the starting material.

Yield 30 mg (25%), as an off-white solid. $^1$H NMR (400 MHz, DMSO) δ 10.61 (br s, 1H), 7.90 (t, J=5.6 Hz, 1H), 7.84 (d, J=8.8 Hz, 2H), 7.05 (d, J=8.8 Hz, 2H), 6.60 (dt, J=1.6, 2.8 Hz, 1H), 5.90 (d, J=2.8 Hz, 1H), 5.84 (dt, J=1.6, 2.8 Hz, 1H), 4.05 (td, J=3.6, 13.2 Hz, 2H), 3.82 (s, 3H), 3.46 (s, 2H), 3.19 (dt, J=3.2, 12.8 Hz, 2H), 3.09-2.91 (m, 2H), 2.54-2.50 (m, 1H), 2.46-2.34 (m, 3H), 2.29-2.18 (m, 1H), 2.15 (dd, J=5.6, 8.8 Hz, 1H), 1.87-1.74 (m, 3H), 1.68-1.52 (m, 2H), 1.42-1.28 (m, 1H). m/z: [ESI$^+$] 465 (M+H)$^+$, ($C_{25}H_{32}N_6O_3$).

N-((1-(3-hydroxybenzyl)pyrrolidin-3-yl)methyl)-1-(3-(4-methoxyphenyl)-1,2,4-oxadiazol-5-yl)piperidine-4-carboxamide (Compound 390): Using 1-(3-(4-methoxyphenyl)-1,2,4-oxadiazol-5-yl)-N-(pyrrolidin-3-ylmethyl)piperidine-4-carboxamide (100 mg, 0.259 mmol) and 3-hydroxybenzaldehyde (65 mg, 0.532 mmol) as the starting material.

Yield 52 mg (41%), as an off-white solid. $^1$H NMR (400 MHz, DMSO) δ 9.28 (br s, 1H), 7.91 (t, J=5.6 Hz, 1H), 7.84 (d, J=8.8 Hz, 2H), 7.14-7.01 (m, 3H), 6.73 (s, 1H), 6.71 (d, J=8.0 Hz, 1H), 6.63 (d, J=8.0 Hz, 1H), 4.05 (d, J=13.2 Hz, 2H), 3.82 (s, 3H), 3.55-3.40 (m, 2H), 3.19 (t, J=12.4 Hz, 2H), 3.13-2.92 (m, 2H), 2.58-2.35 (m, 4H), 2.30-2.14 (m, 2H), 1.89-1.75 (m, 3H), 1.68-1.52 (m, 2H), 1.45-1.35 (m, 1H). m/z: [ESI$^+$] 492 (M+H)$^+$, ($C_{27}H_{33}N_5O_4$).

N-((1-((3,3-difluorocyclobutyl)methyl)pyrrolidin-3-yl)methyl)-1-(3-(4-methoxyphenyl)-1,2,4-oxadiazol-5-yl)piperidine-4-carboxamide (Compound 393): Using 1-(3-(4-methoxyphenyl)-1,2,4-oxadiazol-5-yl)-N-(pyrrolidin-3-ylmethyl)piperidine-4-carboxamide (100 mg, 0.259 mmol) and 3,3-difluorocyclobutane-1-carbaldehyde (80 mg, 0.666 mmol) as the starting material.

Yield 27 mg (21%), as an off-white solid. $^1$H NMR (400 MHz, DMSO) δ 7.90 (t, J=5.6 Hz, 1H), 7.84 (d, J=8.8 Hz, 2H), 7.05 (d, J=8.8 Hz, 2H), 4.06 (td, J=3.6, 13.2 Hz, 2H), 3.82 (s, 3H), 3.20 (dt, J=3.2, 12.8 Hz, 2H), 3.10-2.93 (m, 2H), 2.72-2.58 (m, 2H), 2.56-2.34 (m, 6H), 2.29-2.13 (m, 5H), 1.85-1.74 (m, 3H), 1.69-1.52 (m, 2H), 1.41-1.29 (m, 1H). $^{19}$F NMR (376 MHz, DMSO) δ −80.19, −80.69, −92.16, −92.66. m/z: [ESI$^+$] 490 (M+H)$^+$, ($C_{25}H_{33}F_2N_5O_3$).

1-(3-(4-Methoxyphenyl)-1,2,4-oxadiazol-5-yl)-N-((1-(tetrahydro-2H-pyran-3-yl)pyrrolidin-3-yl)methyl)piperidine-4-carboxamide (Compound 396): Using 1-(3-(4-methoxyphenyl)-1,2,4-oxadiazol-5-yl)-N-(pyrrolidin-3-ylmethyl)piperidine-4-carboxamide (100 mg, 0.259 mmol) and dihydro-2H-pyran-3(4H)-one (29 mg, 0.290 mmol) as the starting material.

Yield 56 mg (46%), as an off-white solid. $^1$H NMR (400 MHz, DMSO) δ 7.91 (t, J=5.6 Hz, 1H), 7.84 (d, J=8.8 Hz, 2H), 7.06 (d, J=8.8 Hz, 2H), 4.07 (td, J=3.6, 13.2 Hz, 2H), 3.92-3.84 (m, 1H), 3.83 (s, 3H), 3.72 (dd, J=3.2, 10.8 Hz, 1H), 3.28-3.15 (m, 3H), 3.15-2.90 (m, 3H), 2.65-2.50 (m, 3H), 2.48-2.32 (m, 1H), 2.30-2.14 (m, 2H), 2.09 (d, J=4.8 Hz, 1H), 1.99-1.89 (m, 1H), 1.84-1.76 (m, 3H), 1.69-1.55 (m, 3H), 1.55-1.41 (m, 1H), 1.39-1.29 (m, 2H). m/z: [ESI$^+$] 470 (M+H)$^+$, ($C_{25}H_{35}N_5O_4$).

N-((1-(1-hydroxypropan-2-yl)pyrrolidin-3-yl)methyl)-1-(3-(4-methoxyphenyl)-1,2,4-oxadiazol-5-yl)piperidine-4-carboxamide (Compound 397): Using 1-(3-(4-methoxyphenyl)-1,2,4-oxadiazol-5-yl)-N-(pyrrolidin-3-ylmethyl)piperidine-4-carboxamide (100 mg, 0.259 mmol) and 1-hydroxypropan-2-one (50 mg, 0.675 mmol) as the starting material.

Yield 19 mg (17%), as an off-white solid. $^1$H NMR (400 MHz, DMSO) δ 7.93 (t, J=5.6 Hz, 1H), 7.84 (d, J=8.8 Hz, 2H), 7.06 (d, J=8.8 Hz, 2H), 4.37 (br s, 1H), 4.07 (td, J=3.6, 13.2 Hz, 2H), 3.83 (s, 3H), 3.48 (t, J=6.4 Hz, 1H), 3.20 (dt, J=2.8, 12.8 Hz, 2H), 3.10-2.92 (m, 2H), 2.67-2.56 (m, 1H), 2.54-2.50 (m, 3H), 2.45-2.35 (m, 1H), 2.35-2.10 (m, 3H), 1.86-1.73 (m, 3H), 1.70-1.53 (m, 2H), 1.42-1.27 (m, 1H), 1.00 (d, J=6.4 Hz, 3H). m/z: [ESI$^+$] 444 (M+H)$^+$, ($C_{23}H_{33}N_5O_4$).

1-(3-(4-Methoxyphenyl)-1,2,4-oxadiazol-5-yl)-N-((1-(tetrahydro-2H-pyran-4-yl)pyrrolidin-3-yl)methyl)piperidine-4-carboxamide (Compound 398): Using 1-(3-(4-methoxyphenyl)-1,2,4-oxadiazol-5-yl)-N-(pyrrolidin-3- ylmethyl)piperidine-4-carboxamide (100 mg, 0.259 mmol) and tetrahydro-4H-pyran-4-one (70 mg, 0.699 mmol) as the starting material.

Yield 58 mg (48%), as an off-white solid. $^1$H NMR (400 MHz, DMSO) δ 7.90 (t, J=5.6 Hz, 1H), 7.84 (d, J=8.8 Hz, 2H), 7.05 (d, J=8.8 Hz, 2H), 4.06 (td, J=3.6, 13.2 Hz, 2H), 3.86-3.83 (m, 2H), 3.82 (s, 3H), 3.28 (dt, J=2.0, 11.6 Hz, 2H), 3.20 (dt, J=3.2, 12.8 Hz, 2H), 3.07-2.96 (m, 2H), 2.64-2.54 (m, 1H), 2.49-2.44 (m, 2H), 2.42-2.35 (m, 1H), 2.25-2.17 (m, 2H), 2.16-2.09 (m, 1H), 1.84-1.76 (m, 3H), 1.76-1.67 (m, 2H), 1.66-1.52 (m, 2H), 1.42-1.24 (m, 3H). m/z: [ESI$^+$] 470 (M+H)$^+$, ($C_{25}H_{35}N_5O_4$).

N-((1-(2-oxaspiro[3.3]heptan-6-yl)pyrrolidin-3-yl) methyl)-1-(3-(4-methoxyphenyl)-1,2,4-oxadiazol-5-yl)piperidine-4-carboxamide (Compound 399): Using 1-(3-(4-methoxyphenyl)-1,2,4-oxadiazol-5-yl)-N-(pyrrolidin-3-ylmethyl)piperidine-4-carboxamide (100 mg, 0.259 mmol) and 2-oxaspiro[3.3]heptan-6-one (32 mg, 0.285 mmol) as the starting material.

Yield 63 mg (50%), as an off-white solid. $^1$H NMR (400 MHz, DMSO) δ 7.91 (t, J=5.6 Hz, 1H), 7.84 (d, J=8.8 Hz, 2H), 7.06 (d, J=8.8 Hz, 2H), 4.55 (s, 2H), 4.46 (s, 2H), 4.06 (td, J=3.6, 13.2 Hz, 2H), 3.82 (s, 3H), 3.20 (dt, J=3.2, 12.8 Hz, 2H), 3.10-2.90 (m, 2H), 2.70-2.58 (m, 1H), 2.48-2.31 (m, 4H), 2.31-2.23 (m, 2H), 2.23-2.15 (m, 2H), 2.09 (d, J=8.0 Hz, 1H), 1.99 (t, J=9.6 Hz, 2H), 1.86-1.71 (m, 3H), 1.68-1.52 (m, 2H), 1.42-1.28 (m, 1H). m/z: [ESI$^+$] 482 (M+H)$^+$, ($C_{26}H_{35}N_5O_4$).

1-(3-(4-Methoxyphenyl)-1,2,4-oxadiazol-5-yl)-N-((1-(1-(tetrahydro-2H-pyran-4-yl)ethyl)pyrrolidin-3-yl)methyl)piperidine-4-carboxamide (Compound 416): Using 1-(3-(4-methoxyphenyl)-1,2,4-oxadiazol-5-yl)-N-(pyrrolidin-3-ylmethyl)piperidine-4-carboxamide (100 mg, 0.259 mmol) and 1-(tetrahydro-2H-pyran-4-yl)ethan-1-one (60 mg, 0.468 mmol) as the starting material.

Yield 14 mg (11%), as an off-white solid. $^1$H NMR (400 MHz, DMSO) δ 7.93 (t, J=5.6 Hz, 1H), 7.84 (d, J=8.8 Hz, 2H), 7.05 (d, J=8.8 Hz, 2H), 4.06 (d, J=13.2 Hz, 2H), 3.86 (d, J=11.6 Hz, 2H), 3.82 (s, 3H), 3.38-3.17 (m, 4H), 3.10-3.00 (m, 2H), 2.70-2.50 (m, 3H), 2.46-2.35 (m, 1H), 2.33-2.10 (m, 2H), 1.90-1.75 (m, 3H), 1.70-1.36 (m, 6H), 1.35-1.17 (m, 3H), 1.04-0.85 (m, 3H). m/z: [ESI$^+$] 498 (M+H)$^+$, ($C_{27}H_{39}N_5O_4$).

1-(3-(4-Methoxyphenyl)-1,2,4-oxadiazol-5-yl)-N-((1-(oxepan-4-yl)pyrrolidin-3-yl)methyl)piperidine-4-carboxamide (Compound 400): Using 1-(3-(4-methoxyphenyl)-1,2,4-oxadiazol-5-yl)-N-(pyrrolidin-3-ylmethyl)piperidine-4-carboxamide (100 mg, 0.259 mmol) and oxepan-4-one (33 mg, 0.289 mmol) as the starting material.

Yield 38 mg (30%), as an off-white solid. $^1$H NMR (400 MHz, DMSO) δ 7.90 (t, J=5.6 Hz, 1H), 7.84 (d, J=8.8 Hz, 2H), 7.05 (d, J=8.8 Hz, 2H), 4.06 (td, J=3.6, 13.2 Hz, 2H), 3.82 (s, 3H), 3.70-3.47 (m, 4H), 3.20 (dt, J=3.2, 12.8 Hz, 2H), 3.10-2.95 (m, 2H), 2.60-2.52 (m, 2H), 2.49-2.31 (m, 3H), 2.30-2.13 (m, 2H), 1.83-1.72 (m, 6H), 1.71-1.50 (m, 5H), 1.42-1.29 (m, 1H). m/z: [ESI$^+$] 484 (M+H)$^+$, ($C_{26}H_{37}N_5O_4$).

1-(3-(4-Methoxyphenyl)-1,2,4-oxadiazol-5-yl)-N-((1-(oxetan-3-yl)pyrrolidin-3-yl)methyl)piperidine-4-carboxamide (Compound 401): Using 1-(3-(4-methoxyphenyl)-1,2,4-oxadiazol-5-yl)-N-(pyrrolidin-3-ylmethyl)piperidine-4-carboxamide (100 mg, 0.259 mmol) and oxetan-3-one (50 mg, 0.694 mmol) as the starting material.

Yield 73 mg (64%), as an off-white solid. $^1$H NMR (400 MHz, DMSO) δ 7.94 (t, J=5.6 Hz, 1H), 7.84 (d, J=8.8 Hz, 2H), 7.05 (d, J=8.8 Hz, 2H), 4.55 (t, J=6.4 Hz, 2H), 4.43 (dt, J=3.2, 6.0 Hz, 2H), 4.06 (d, J=13.2 Hz, 2H), 3.82 (s, 3H), 3.56-3.46 (m, 1H), 3.20 (dt, J=3.2, 12.8 Hz, 2H), 3.13-2.92 (m, 2H), 2.49-2.32 (m, 4H), 2.30-2.20 (m, 1H), 2.15 (dd, J=5.6, 8.8 Hz, 1H), 1.94-1.73 (m, 3H), 1.70-1.53 (m, 2H), 1.45-1.30 (m, 1H). m/z: [ESI$^+$] 442 (M+H)$^+$, ($C_{23}H_{31}N_5O_4$).

1-(3-(4-methoxyphenyl)-1,2,4-oxadiazol-5-yl)-N-((1-(2-methyltetrahydro-2H-pyran-4-yl)pyrrolidin-3-yl)methyl)piperidine-4-carboxamide (Compound 402): Using 1-(3-(4-methoxyphenyl)-1,2,4-oxadiazol-5-yl)-N-(pyrrolidin-3-ylmethyl)piperidine-4-carboxamide (100 mg, 0.259 mmol) and 2-methyltetrahydro-4H-pyran-4-one (33 mg, 0.289 mmol) as the starting material.

Yield 50 mg (40%), as an off-white solid. $^1$H NMR (400 MHz, DMSO) δ 7.91 (t, J=5.6 Hz, 1H), 7.84 (d, J=8.8 Hz, 2H), 7.06 (d, J=8.8 Hz, 2H), 4.06 (td, J=3.6, 13.2 Hz, 2H), 3.89-3.83 (m, 1H), 3.82 (s, 3H), 3.40-3.25 (m, 2H), 3.20 (dt, J=3.2, 12.8 Hz, 2H), 3.13-2.91 (m, 2H), 2.55-2.50 (m, 3H), 2.45-2.34 (m, 1H), 2.30-2.07 (m, 3H), 1.87-1.75 (m, 4H), 1.72 (d, J=12.4 Hz, 1H), 1.68-1.56 (m, 2H), 1.43-1.18 (m, 2H), 1.09 (d, J=6.4 Hz, 3H), 1.06-0.95 (m, 1H). m/z: [ESI$^+$] 484 (M+H)$^+$, ($C_{26}H_{37}N_5O_4$).

1-(3-(4-Methoxyphenyl)-1,2,4-oxadiazol-5-yl)-N-((1-(((R)-1-methylpiperidin-3-yl)methyl)pyrrolidin-3-yl) methyl)piperidine-4-carboxamide (Compound 464): Using 1-(3-(4-Methoxyphenyl)-1,2,4-oxadiazol-5-yl)-N-((1-(((R)-piperidin-3-yl)methyl)pyrrolidin-3-yl)methyl)piperidine-4-carboxamide (150 mg, 0.311 mmol) and polyoxymethylene (40 mg, 0.888 mmol) as the starting material.

Yield 22 mg (14%), as an off-white solid. $^1$H NMR (400 MHz, DMSO) δ 7.96-7.87 (m, 1H), 7.84 (d, J=8.8 Hz, 2H), 7.05 (d, J=8.8 Hz, 2H), 4.11-4.01 (m, 2H), 3.82 (s, 3H), 3.20 (dt, J=3.2, 12.8 Hz, 2H), 3.09-2.94 (m, 2H), 2.82-2.70 (m, 1H), 2.63 (d, J=11.2 Hz, 1H), 2.48-2.30 (m, 4H), 2.27-2.17 (m, 3H), 2.15-2.10 (m, 1H), 2.12 (s, 3H), 1.87-1.74 (m, 4H), 1.71-1.27 (m, 8H), 0.86-0.75 (m, 1H). m/z: [ESI$^+$] 497 (M+H)$^+$, ($C_{27}H_{40}N_6O_3$).

1-(3-(4-Methoxyphenyl)-1,2,4-oxadiazol-5-yl)-N—(((R)-1-(((S)-1-methylpiperidin-3-yl)methyl)pyrrolidin-3-yl)methyl)piperidine-4-carboxamide formate (Compound 465): Using 1-(3-(4-methoxyphenyl)-1,2,4-oxadiazol-5-yl)-N—(((R)-1-((S)-piperidin-3-ylmethyl)pyrrolidin-3-yl) methyl)piperidine-4-carboxamide (150 mg, 0.311 mmol) and polyoxymethylene (40 mg, 0.888 mmol) as the starting material.

Yield 47 mg (27%), as an off-white solid. $^1$H NMR (400 MHz, DMSO) δ 8.17 (s, 1H, HCOOH), 7.94 (t, J=5.6 Hz, 1H), 7.82 (d, J=8.8 Hz, 2H), 7.05 (d, J=8.8 Hz, 2H), 4.06 (d, J=13.2 Hz, 2H), 3.82 (s, 3H), 3.26-3.14 (m, 2H), 3.14-2.96 (m, 3H), 2.59-2.50 (m, 3H), 2.46 (s, 3H), 2.42-2.31 (m, 3H), 2.31-2.19 (m, 3H), 2.10 (t, J=11.2 Hz, 1H), 1.88-1.75 (m, 5H), 1.73-1.46 (m, 5H), 1.45-1.35 (m, 1H), 0.96 (t, J=11.2 Hz, 1H). m/z: [ESI$^+$] 497 (M+H)$^+$, ($C_{27}H_{40}N_6O_3$).

(R)-1-(3-(4-methoxyphenyl)-1,2,4-oxadiazol-5-yl)-N-((1-((1-methylpiperidin-4-yl)methyl)pyrrolidin-3-yl) methyl)piperidine-4-carboxamide (Compound 433): Using (S)-1-(3-(4-methoxyphenyl)-1,2,4-oxadiazol-5-yl)-N-(pyrrolidin-3-ylmethyl)piperidine-4-carboxamide (200 mg, 0.519 mmol) and 1-methylpiperidine-4-carbaldehyde (80 mg, 0.629 mmol) as the starting material.

Yield 66 mg (26%), as an off-white solid. $^1$H NMR (400 MHz, DMSO) δ 7.88 (t, J=5.6 Hz, 1H), 7.84 (d, J=8.8 Hz, 2H), 7.06 (d, J=8.8 Hz, 2H), 4.12-4.00 (m, 2H), 3.82 (s, 3H), 3.20 (dt, J=3.2, 12.8 Hz, 2H), 3.08-2.95 (m, 2H), 2.71 (d, J=10.8 Hz, 2H), 2.48-2.30 (m, 4H), 2.25-2.16 (m, 4H), 2.12 (s, 3H), 1.86-1.72 (m, 5H), 1.69-1.55 (m, 4H), 1.40-1.29 (m, 2H), 1.14-1.02 (m, 2H). m/z: [ESI$^+$] 497 (M+H)$^+$, ($C_{27}H_{40}N_6O_3$).

(S)-1-(3-(4-methoxyphenyl)-1,2,4-oxadiazol-5-yl)-N-((1-((1-methylpiperidin-4-yl)methyl)pyrrolidin-3-yl)methyl)piperidine-4-carboxamide (Compound 434): Using (R)-1-(3-(4-methoxyphenyl)-1,2,4-oxadiazol-5-yl)-N-(pyrrolidin-3-ylmethyl)piperidine-4-carboxamide (200 mg, 0.519 mmol) and 1-methylpiperidine-4-carbaldehyde (73 mg, 0.574 mmol) as the starting material.

Yield 78 mg (30%), as an off-white solid. $^1$H NMR (400 MHz, DMSO) δ 7.90 (t, J=5.6 Hz, 1H), 7.84 (d, J=8.8 Hz, 2H), 7.05 (d, J=8.8 Hz, 2H), 4.06 (td, J=3.6, 13.2 Hz, 2H), 3.82 (s, 3H), 3.20 (dt, J=3.2, 12.8 Hz, 2H), 3.08-2.94 (m, 2H), 2.75-2.65 (m, 2H), 2.48-2.29 (m, 4H), 2.26-2.15 (m, 4H), 2.12 (s, 3H), 1.88-1.74 (m, 5H), 1.71-1.54 (m, 4H), 1.41-1.26 (m, 2H), 1.16-0.99 (m, 2H). m/z: [ESI$^+$] 497 (M+H)$^+$, ($C_{27}H_{40}N_6O_3$).

1-(3-(4-Methoxyphenyl)-1,2,4-oxadiazol-5-yl)-N-((1-(((R)-1-methylpiperidin-2-yl)methyl)pyrrolidin-3-yl)methyl)piperidine-4-carboxamide (Compound 414): Using 1-(3-(4-methoxyphenyl)-1,2,4-oxadiazol-5-yl)-N-((1-(((R)-piperidin-2-yl)methyl)pyrrolidin-3-yl)methyl)piperidine-4-carboxamide (100 mg, 0.207 mmol) and polyoxymethylene (11 mg, 0.244 mmol) as the starting material.

Yield 30 mg (29%), as an off-white solid. $^1$H NMR (400 MHz, DMSO) δ 7.91 (t, J=5.6 Hz, 1H), 7.84 (d, J=8.8 Hz, 2H), 7.06 (d, J=8.8 Hz, 2H), 4.06 (d, J=12.8 Hz, 2H), 3.82 (s, 3H), 3.27-3.14 (m, 2H), 3.06-2.97 (m, 2H), 2.81-2.65 (m, 1H), 2.50 (s, 3H), 2.47-2.36 (m, 4H), 2.32-2.17 (m, 5H), 2.10-1.90 (m, 1H), 1.84-1.70 (m, 4H), 1.69-1.55 (m, 3H), 1.55-1.29 (m, 3H), 1.28-1.12 (m, 2H). m/z: [ESI$^+$] 497 (M+H)$^+$, ($C_{27}H_{40}N_6O_3$).

N-((1-(cyclohexylmethyl)pyrrolidin-3-yl)methyl)-4-(3-(4-methoxyphenyl)-1,2,4-oxadiazol-5-yl)piperazine-1-carboxamide (Compound 421): Using 4-(3-(4-methoxyphenyl)-1,2,4-oxadiazol-5-yl)-N-(pyrrolidin-3-ylmethyl)piperazine-1-carboxamide (50 mg, 0.129 mmol) and cyclohexanecarbaldehyde (16 mg, 0.143 mmol) as the starting material.

Yield 20 mg (32%), as a yellow solid. $^1$H NMR (400 MHz, DMSO) δ 7.84 (d, J=8.8 Hz, 2H), 7.06 (d, J=8.8 Hz, 2H), 6.69 (d, J=5.6 Hz, 1H), 3.82 (s, 3H), 3.58-3.54 (m, 4H), 3.47-3.43 (m, 4H), 3.06-2.95 (m, 2H), 2.50-2.41 (m, 2H), 2.35 (d, J=8.8 Hz, 1H), 2.30-2.11 (m, 4H), 1.86-1.72 (m, 3H), 1.69-1.58 (m, 3H), 1.47-1.32 (m, 2H), 1.27-1.09 (m, 3H), 0.89-0.76 (m, 2H). m/z: [ESI$^+$] 483 (M+H)$^+$, ($C_{26}H_{38}N_6O_3$).

4-(3-(4-Methoxyphenyl)-1,2,4-oxadiazol-5-yl)-N-((1-((tetrahydro-2H-pyran-4-yl)methyl)pyrrolidin-3-yl)methyl)piperazine-1-carboxamide (Compound 432): Using 4-(3-(4-methoxyphenyl)-1,2,4-oxadiazol-5-yl)-N-(pyrrolidin-3-ylmethyl)piperazine-1-carboxamide (100 mg, 0.259 mmol) and tetrahydro-2H-pyran-4-carbaldehyde (65 mg, 0.569 mmol) as the starting material.

Yield 25 mg (20%), as an off-white solid. $^1$H NMR (400 MHz, DMSO) δ 7.85 (d, J=8.8 Hz, 2H), 7.06 (d, J=8.8 Hz, 2H), 6.71 (t, J=5.6 Hz, 1H), 3.86-3.78 (m, 2H), 3.82 (s, 3H), 3.59-3.53 (m, 4H), 3.51-3.40 (m, 4H), 3.32-3.22 (m, 2H), 3.11-2.93 (m, 2H), 2.49-2.40 (m, 2H), 2.39-2.32 (m, 1H), 2.31-2.16 (m, 4H), 1.86-1.72 (m, 1H), 1.71-1.55 (m, 3H), 1.38 (dd, J=6.0, 12.4 Hz, 1H), 1.17-1.05 (m, 2H). m/z: [ESI$^+$] 485 (M+H)$^+$, ($C_{25}H_{36}N_6O_4$).

N-((1-((1,1-dioxidotetrahydro-2H-thiopyran-4-yl)methyl)pyrrolidin-3-yl)methyl)-4-(3-(4-methoxyphenyl)-1,2,4-oxadiazol-5-yl)piperazine-1-carboxamide (Compound 425): Using 4-(3-(4-methoxyphenyl)-1,2,4-oxadiazol-5-yl)-N-(pyrrolidin-3-ylmethyl)piperazine-1-carboxamide (50 mg, 0.129 mmol) and tetrahydro-2H-thiopyran-4-carbaldehyde 1,1-dioxide (30 mg, 0.185 mmol) as the starting material.

Yield 36 mg (52%), as an off-white solid. $^1$H NMR (400 MHz, DMSO) δ 7.84 (d, J=8.8 Hz, 2H), 7.06 (d, J=8.8 Hz, 2H), 6.70 (t, J=5.6 Hz, 1H), 3.82 (s, 3H), 3.60-3.54 (m, 4H), 3.49-3.43 (m, 4H), 3.15-3.06 (m, 2H), 3.05-2.93 (m, 4H), 2.51-2.42 (m, 2H), 2.42-2.34 (m, 1H), 2.31-2.19 (m, 4H), 2.08 (d, J=13.6 Hz, 2H), 1.86-1.67 (m, 2H), 1.57-1.46 (m, 2H), 1.39 (dd, J=6.8, 12.8 Hz, 1H). m/z: [ESI$^+$] 533 (M+H)$^+$, ($C_{25}H_{36}N_6O_5S$).

1-(3-(4-methoxyphenyl)-1,2,4-oxadiazol-5-yl)-N-((1-(((S)-1-methylpiperidin-3-yl)methyl)pyrrolidin-3-yl)methyl)piperidine-4-carboxamide diformate (Compound 422): Using 1-(3-(4-methoxyphenyl)-1,2,4-oxadiazol-5-yl)-N-((1-(((S)-piperidin-3-yl)methyl)pyrrolidin-3-yl)methyl)piperidine-4-carboxamide (150 mg, 0.311 mmol) and polyoxymethylene (40 mg, 0.888 mmol) as the starting material.

Yield 64 mg (38%), as a dark yellow solid. $^1$H NMR (400 MHz, DMSO) δ 8.23 (s, 1.74H, HCOOH), 7.99 (d, J=5.6 Hz, 0.5H), 7.91 (t, J=5.6 Hz, 0.5H), 7.84 (d, J=8.8 Hz, 2H), 7.05 (d, J=8.8 Hz, 2H), 4.06 (d, J=12.8 Hz, 2H), 3.82 (s, 3H), 3.20 (dt, J=3.2, 12.8 Hz, 2H), 3.08-3.00 (m, 3H), 2.98-2.78 (m, 1H), 2.62-2.51 (m, 4H), 2.41 (t, J=8.0 Hz, 2H), 2.35-2.28 (m, 5H), 2.27-2.02 (m, 2H), 1.90-1.74 (m, 5H), 1.72-1.58 (m, 3H), 1.57-1.45 (m, 1H), 1.43-1.32 (m, 1H), 0.90 (t, J=11.6 Hz, 1H). m/z: [ESI$^+$] 497 (M+H)$^+$, ($C_{27}H_{40}N_6O_3$).

1-(3-(4-Methoxyphenyl)-1,2,4-oxadiazol-5-yl)-N—(((S)-1-(((S)-1-methylpiperidin-3-yl)methyl)pyrrolidin-3-yl)methyl)piperidine-4-carboxamide hemiformate (Compound 466): Using 1-(3-(4-methoxyphenyl)-1,2,4-oxadiazol-5-yl)-N—(((S)-1-(((S)-piperidin-3-yl)methyl)pyrrolidin-3-yl)methyl)piperidine-4-carboxamide (150 mg, 0.311 mmol) and polyoxymethylene (40 mg, 0.888 mmol) as the starting material.

Yield 14 mg (9%), as an off-white solid. $^1$H NMR (400 MHz, DMSO) δ 8.21 (s, 0.54H, HCOOH), 7.92 (t, J=5.6 Hz, 1H), 7.84 (d, J=8.8 Hz, 2H), 7.05 (d, J=8.8 Hz, 2H), 4.06 (d, J=13.2 Hz, 2H), 3.82 (s, 3H), 3.20 (dt, J=2.8, 12.8 Hz, 2H), 3.04-2.98 (m, 2H), 2.82 (d, J=10.8 Hz, 1H), 2.71-2.64 (m, 1H), 2.49-2.36 (m, 4H), 2.31-2.19 (m, 3H), 2.17 (s, 3H), 2.16-2.11 (m, 1H), 1.89-1.75 (m, 4H), 1.71-1.51 (m, 6H), 1.51-1.29 (m, 2H), 0.86-0.75 (m, 1H). m/z: [ESI$^+$] 497 (M+H)$^+$, ($C_{27}H_{40}N_6O_3$).

1-(3-(4-Cyanophenyl)-1,2,4-oxadiazol-5-yl)-N-((1-(((S)-1-methylpiperidin-3-yl)methyl)pyrrolidin-3-yl)methyl)piperidine-4-carboxamide diformate (Compound 467): Using 1-(3-(4-cyanophenyl)-1,2,4-oxadiazol-5-yl)-N-((1-(((S)-piperidin-3-yl)methyl)pyrrolidin-3-yl)methyl)piperidine-4-carboxamide hydrochloride (360 mg, 0.700 mmol) and polyoxymethylene (60 mg, 1.332 mmol) as the starting material.

Yield 80 mg (17%), as an off-white solid. $^1$H NMR (400 MHz, DMSO) δ 8.24 (s, 2.28H, HCOOH), 8.07 (d, J=8.4 Hz, 2H), 7.98 (d, J=8.4 Hz, 2H), 7.93 (t, J=5.6 Hz, 1H), 4.08 (d, J=13.2 Hz, 2H), 3.24 (t, J=12.8 Hz, 2H), 3.10-2.82 (m, 4H), 2.60-2.50 (m, 3H), 2.46-2.30 (m, 6H), 2.29-2.15 (m, 3H), 2.04-1.75 (m, 5H), 1.73-1.49 (m, 5H), 1.44-1.32 (m, 1H), 0.98-0.85 (m, 1H). m/z: [ESI$^+$] 492 (M+H)$^+$, ($C_{27}H_{37}N_7O_2$).

1-(3-(4-Chlorophenyl)-1,2,4-oxadiazol-5-yl)-N-((1-(((S)-1-methylpiperidin-3-yl)methyl)pyrrolidin-3-yl)methyl)piperidine-4-carboxamide (Compound 468): Using 1-(3-(4-chlorophenyl)-1,2,4-oxadiazol-5-yl)-N-((1-(((S)-piperidin-3-yl)methyl)pyrrolidin-3-yl)methyl)piperidine-4- carboxamide (260 mg, 0.534 mmol) and polyoxymethylene (26 mg, 0.577 mmol) as the starting material.

Yield 93 mg (35%), as an off-white solid. $^1$H NMR (400 MHz, DMSO) δ 7.93-7.87 (m, 3H), 7.58 (d, J=8.4 Hz, 2H), 4.06 (td, J=3.6, 13.2 Hz, 2H), 3.21 (dt, J=3.2, 12.8 Hz, 2H), 3.07-2.94 (m, 2H), 2.77 (t, J=11.2 Hz, 1H), 2.64 (d, J=11.2 Hz, 1H), 2.50-2.28 (m, 4H), 2.27-2.18 (m, 2H), 2.17-2.06 (m, 5H), 1.86-1.75 (m, 4H), 1.70-1.27 (m, 8H), 0.88-0.71 (m, 1H). m/z: [ESI$^+$] 501, 503 (M+H)$^+$, ($C_{26}H_{37}ClN_6O_2$).

1-(3-(4-Hydroxyphenyl)-1,2,4-oxadiazol-5-yl)-N-((1-(4-methylbenzyl)pyrrolidin-3-yl)methyl)piperidine-4-carboxamide (Compound 170)

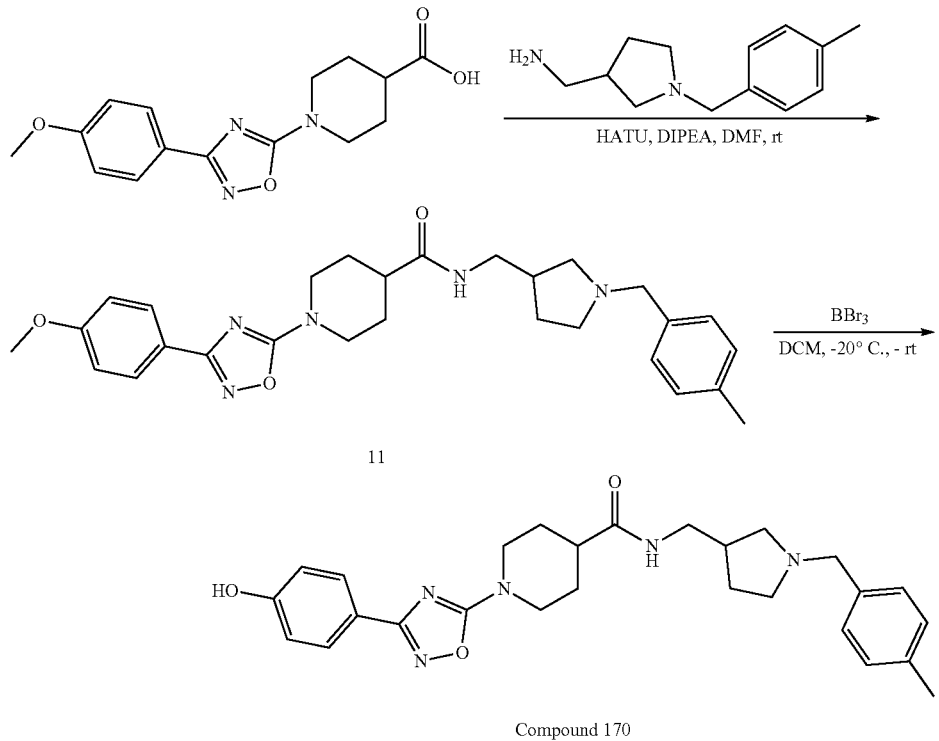

Scheme 13

Compound 170

Step 1: 1-[3-(4-Methoxyphenyl)-1,2,4-oxadiazol-5-yl]-N-([1-[(4-methylphenyl)methyl]pyrrolidin-3-yl]methyl)piperidine-4-carboxamide To a stirred solution of 1-[3-(4-methoxyphenyl)-1,2,4-oxadiazol-5-yl]piperidine-4-carboxylic acid (0.50 g, 1.65 mmol) in DMF (5 mL), were added HATU (0.94 g, 2.47 mmol), DIPEA (0.43 g, 3.33 mmol) and 1-[1-[(4-methylphenyl)methyl]pyrrolidin-3-yl]methanamine (0.44 g, 2.15 mmol). The resulting solution was stirred for 2 h at room temperature. The mixture was directly purified by reverse phase flash chromatography with the following conditions: Column: Spherical C18, 20-40 um, 330 g; Mobile Phase A: water (plus 10 mM NH$_4$HCO$_3$); Mobile Phase B: acetonitrile; Flow rate: 80 mL/min; Gradient: 50% B-75% B in 20 min; Detector: UV 220/254 nm. The fractions containing desired product were collected and concentrated under reduced pressure to afford 1-[3-(4-methoxyphenyl)-1,2,4-oxadiazol-5-yl]-N-([1-[(4-methylphenyl)methyl]pyrrolidin-3-yl]methyl)piperidine-4-carboxamide as a light yellow solid.

Yield 0.45 g (56%). $^1$H NMR (400 MHz, DMSO) δ 7.87 (t, J=5.6 Hz, 1H), 7.84 (d, J=8.8 Hz, 2H), 7.17 (d, J=8.0 Hz, 2H), 7.11 (d, J=8.0 Hz, 2H), 7.05 (d, J=8.8 Hz, 2H), 4.05 (dd, J=3.6, 13.0 Hz, 2H), 3.82 (s, 3H), 3.49 (s, 2H), 3.20-3.18 (m, 2H), 3.11-2.93 (m, 2H), 2.50-2.35 (m, 4H), 2.27 (s, 3H), 2.25-2.12 (m, 2H), 1.88-1.71 (m, 3H), 1.60-1.57 (m, 2H), 1.44-1.29 (m, 1H). m/z: (ESI$^+$): 490 (M+H)$^+$, ($C_{28}H_{35}N_5O_3$).

The compounds below were prepared according to the procedure described above.

(1-(3-(4-Methoxyphenyl)-1,2,4-oxadiazol-5-yl)piperidin-4-yl)(4-methoxypiperidin-1-yl)methanone (Compound 134): Using 1-(3-(4-methoxyphenyl)-1,2,4-oxadiazol-5-yl)piperidine-4-carboxylic acid (150 mg, 0.495 mmol) and 4-methoxypiperidine (68 mg, 0.590 mmol) as the starting material.

Yield 165 mg (83%), as an off-white solid. $^1$H NMR (400 MHz, DMSO) δ 7.84 (d, J=8.8 Hz, 2H), 7.06 (d, J=8.8 Hz, 2H), 4.06 (d, J=13.2 Hz, 2H), 3.82 (s, 3H), 3.78-3.80 (m, 2H) 3.42 (m, 1H), 3.27 (s, 3H), 3.25-3.33 (m, 3H), 3.09 (t, J=11.2 Hz, 1H), 2.97 (t, J=11.2 Hz, 1H), 1.85-1.89 (m, 1H), 1.80-1.71 (m, 3H), 1.70-1.50 (m, 2H), 1.43 (d, J=10.0 Hz, 1H), 1.31 (d, J=10.8 Hz, 1H). m/z: [ESI$^+$] 401 (M+H)$^+$, ($C_{21}H_{28}N_4O_4$).

1-(3-(4-Methoxyphenyl)-1,2,4-oxadiazol-5-yl)-N-((1-methylpiperidin-4-yl)methyl)piperidine-4-carboxamide formate (Compound 217): Using 1-(3-(4-methoxyphenyl)-1,2,4-oxadiazol-5-yl)piperidine-4-carboxylic acid (150 mg, 0.495 mmol) and (1-methylpiperidin-4-yl)methanamine (76 mg, 0.593 mmol) as the starting material.

Yield 120 mg (53%), as a light yellow solid. ¹H NMR (400 MHz, DMSO) δ 8.27 (s, 1H, HCOOH), 7.90 (t, J=6.0 Hz, 1H), 7.84 (d, J=8.8 Hz, 2H), 7.05 (d, J=8.8 Hz, 2H), 4.12-4.02 (m, 2H), 3.82 (s, 3H), 3.19 (dt, J=2.8, 12.8 Hz, 2H), 3.00-2.91 (m, 4H), 2.47-2.37 (m, 1H), 2.32 (s, 3H), 2.23-2.11 (m, 2H), 1.80 (dd, J=3.6, 13.6 Hz, 2H), 1.68-1.58 (m, 4H), 1.52-1.38 (m, 1H), 1.27-1.14 (m, 2H). m/z: [ESI⁺] 414 (M+H)⁺, ($C_{22}H_{31}N_5O_3$).

1-(3-(4-Methoxyphenyl)-1,2,4-oxadiazol-5-yl)-N-((1-methylpyrrolidin-3-yl)methyl)piperidine-4-carboxamide (Compound 219): Using 1-(3-(4-methoxyphenyl)-1,2,4-oxadiazol-5-yl)piperidine-4-carboxylic acid (150 mg, 0.495 mmol) and (1-methylpyrrolidin-3-yl)methanamine (68 mg, 0.595 mmol) as the starting material.

Yield 85 mg (43%), as a light yellow solid. ¹H NMR (400 MHz, DMSO) δ 7.92 (t, J=5.6 Hz, 1H), 7.84 (d, J=8.8 Hz, 2H), 7.05 (d, J=8.8 Hz, 2H), 4.06 (d, J=13.2 Hz, 2H), 3.82 (s, 3H), 3.20 (dt, J=2.8, 12.8 Hz, 2H), 3.01 (td, J=5.2, 7.2 Hz, 2H), 2.49-2.31 (m, 4H), 2.29-2.13 (m, 5H), 1.88-1.74 (m, 3H), 1.71-1.54 (m, 2H), 1.43-1.30 (m, 1H). m/z: [ESI⁺] 400 (M+H)⁺, ($C_{21}H_{29}N_5O_3$).

N-((1-(tert-butyl)pyrrolidin-3-yl)methyl)-1-(3-(4-methoxyphenyl)-1,2,4-oxadiazol-5-yl)piperidine-4-carboxamide (Compound 250): Using 1-(3-(4-methoxyphenyl)-1,2,4-oxadiazol-5-yl)piperidine-4-carboxylic acid (150 mg, 0.495 mmol) and (1-(tert-butyl)pyrrolidin-3-yl)methanamine (93 mg, 0.595 mmol) as the starting material.

Yield 100 mg (46%), as a light yellow solid. ¹H NMR (400 MHz, DMSO) δ 7.90 (t, J=5.6 Hz, 1H), 7.84 (d, J=8.8 Hz, 2H), 7.05 (d, J=8.8 Hz, 2H), 4.06 (d, J=13.2 Hz, 2H), 3.82 (s, 3H), 3.20 (dt, J=2.8, 12.8 Hz, 2H), 3.11-2.91 (m, 2H), 2.67 (t, J=8.0 Hz, 1H), 2.62-2.51 (m, 2H), 2.46-2.35 (m, 1H), 2.26 (dd, J=5.8, 8.8 Hz, 1H), 2.19-2.12 (m, 1H), 1.87-1.71 (m, 3H), 1.69-1.55 (m, 2H), 1.38-1.28 (m, 1H), 1.00 (s, 9H). m/z: [ESI⁺] 442 (M+H)⁺, ($C_{24}H_{35}N_5O_3$).

1-(3-(4-Methoxyphenyl)-1,2,4-oxadiazol-5-yl)-N-(1-methylpiperidin-4-yl)piperidine-4-carboxamide (Compound 218): Using 1-(3-(4-methoxyphenyl)-1,2,4-oxadiazol-5-yl)piperidine-4-carboxylic acid (150 mg, 0.495 mmol) and 1-methylpiperidin-4-amine (68 mg, 0.595 mmol) as the starting material.

Yield 100 mg (51%), as a light yellow solid. ¹H NMR (400 MHz, DMSO) δ 7.84 (d, J=8.8 Hz, 2H), 7.76 (d, J=7.6 Hz, 1H), 7.05 (d, J=8.8 Hz, 2H), 4.06 (td, J=3.6, 13.2 Hz, 2H), 3.82 (s, 3H), 3.54-3.42 (m, 1H), 3.18 (dt, J=2.8, 12.8 Hz, 2H), 2.68 (d, J=11.6 Hz, 2H), 2.38 (ddd, J=3.6, 7.6, 11.2 Hz, 1H), 2.13 (s, 3H), 1.90 (dt, J=2.8, 11.6 Hz, 2H), 1.78 (dd, J=3.6, 13.6 Hz, 2H), 1.72-1.54 (m, 4H), 1.46-1.28 (m, 2H). m/z: [ESI⁺] 400 (M+H)⁺, ($C_{21}H_{29}N_5O_3$).

N-(3-(4-Benzylpiperidin-1-yl)propyl)-1-(3-(4-methoxyphenyl)-1,2,4-oxadiazol-5-yl)piperidine-4-carboxamide formate (Compound 152): Using 1-(3-(4-methoxyphenyl)-1,2,4-oxadiazol-5-yl)piperidine-4-carboxylic acid (300 mg 0.989 mmol) and 3-(4-benzylpiperidin-1-yl)propan-1-amine (276 mg, 1.188 mmol) as the starting material.

Yield 450 mg (81%), as a light yellow solid. ¹H NMR (400 MHz, DMSO) δ 8.17 (s, 1H, HCOOH), 7.90 (t, J=5.6 Hz, 1H), 7.84 (d, J=8.8 Hz, 2H), 7.30 (t, J=8.0 Hz, 2H), 7.18-7.14 (m, 3H), 7.04 (d, J=8.8 Hz, 2H), 4.06 (d, J=13.2 Hz, 2H), 3.82 (s, 3H), 3.22-3.19 (m, 4H), 3.09-3.02 (m, 2H), 2.93 (d, J=11.2 Hz, 2H), 2.35 (s, 3H), 2.01 (t, J=11.6 Hz, 2H), 1.85-1.75 (m, 2H), 1.66-1.44 (m, 7H), 1.30-1.15 (m, 2H). m/z: [ESI⁺] 518 (M+H)⁺, ($C_{30}H_{39}N_5O_3$).

1-(3-(3-Chlorophenyl)-1,2,4-oxadiazol-5-yl)-N-((1-(4-methylbenzyl)pyrrolidin-3-yl)methyl)piperidine-4-carboxamide formate (Compound 155): Using 1-(3-(3-chlorophenyl)-1,2,4-oxadiazol-5-yl)piperidine-4-carboxylic acid (200 mg, 0.650 mmol) and (1-(4-methylbenzyl)pyrrolidin-3-yl)methanamine (173 mg, 0.847 mmol) as the starting material.

Yield 270 mg (77%), as a light brown solid. ¹H NMR (400 MHz, DMSO) δ 8.17 (s, 1H, HCOOH), 7.88 (d, J=1.6 Hz, 2H), 7.86 (t, J=1.6 Hz, 1H), 7.67-7.59 (m, 1H), 7.57-7.55 (m, 1H), 7.19 (d, J=8.0 Hz, 2H), 7.12 (d, J=7.6 Hz, 2H), 4.06 (d, J=10.4 Hz, 2H), 3.55 (s, 2H), 3.27-3.16 (m, 3H), 3.09-3.06 (m, 1H), 3.04-2.95 (m, 1H), 2.59-2.54 (m, 1H), 2.48-2.33 (m, 2H), 2.28 (s, 3H), 2.26-2.19 (m, 2H), 1.92-1.65 (m, 3H), 1.61-1.59 (m, 2H), 1.40-1.38 (m, 1H). m/z: [ESI⁺] 494, 496 (M+H)⁺, ($C_{27}H_{32}ClN_5O_2$).

1-(3-(2-Chlorophenyl)-1,2,4-oxadiazol-5-yl)-N-((1-(4-methylbenzyl)pyrrolidin-3-yl)methyl)piperidine-4-carboxamide (Compound 156): Using 1-(3-(2-chlorophenyl)-1,2,4-oxadiazol-5-yl)piperidine-4-carboxylic acid (200 mg, 0.650 mmol) and (1-(4-methylbenzyl)pyrrolidin-3-yl)methanamine (173 mg, 0.847 mmol) as the starting material.

Yield 210 mg (65%), as an off-white solid. ¹H NMR (400 MHz, DMSO) δ 7.88 (t, J=5.6 Hz, 1H), 7.82-7.80 (m, 1H), 7.63-7.61 (m, 1H), 7.57-7.55 (m, 1H), 7.48-7.46 (m, 1H), 7.17 (d, J=8.0 Hz, 2H), 7.11 (d, J=7.6 Hz, 2H), 4.10-4.00 (m, 2H), 3.50 (s, 2H), 3.25-3.15 (m, 2H), 3.12-2.96 (m, 2H), 2.48-2.33 (m, 4H), 2.26 (s, 3H), 2.26-2.12 (m, 2H), 1.90-1.70 (m, 3H), 1.65-1.55 (m, 2H), 1.44-1.35 (m, 1H). m/z: [ESI⁺] 494,496 (M+H)⁺, ($C_{27}H_{32}ClN_5O_2$).

1-(3-(4-Methoxyphenyl)-1,2,4-oxadiazol-5-yl)-N-(pyridin-4-ylmethyl)piperidine-4-carboxamide (Compound 161): Using 1-(3-(4-Methoxyphenyl)-1,2,4-oxadiazol-5-yl) piperidine-4-carboxylic acid (150 mg, 0.495 mmol) and pyridin-4-ylmethanamine (64 mg, 0.592 mmol) as the starting material.

Yield 120 mg, (62%), as an off-white solid. ¹H NMR (400 MHz, DMSO) δ 8.52 (t, J=6.0 Hz, 1H), 8.49 (d, J=6.0 Hz, 2H), 7.82 (d, J=8.8 Hz, 2H), 7.22 (d, J=6.0 Hz, 2H), 7.04 (d, J=8.8 Hz, 2H), 4.30 (d, J=6.0 Hz, 2H), 4.08 (d, J=13.2 Hz, 2H), 3.81 (s, 3H), 3.23-3.21 (m, 2H), 2.56-2.52 (m, 1H), 1.89 (d, J=14.0 Hz, 2H), 1.67-1.55 (m, 2H). m/z: [ESI⁺] 394 (M+H)⁺, ($C_{21}H_{23}N_5O_3$).

1-(3-(4-Methoxyphenyl)-1,2,4-oxadiazol-5-yl)-N-(pyrimidin-5-ylmethyl)piperidine-4-carboxamide (Compound 162): Using 1-(3-(4-methoxyphenyl)-1,2,4-oxadiazol-5-yl) piperidine-4-carboxylic acid (150 mg, 0.495 mmol) and pyrimidin-5-ylmethanamine (65 mg, 0.596 mmol) as the starting material.

Yield 100 mg (51%), as an off-white solid. ¹H NMR (400 MHz, DMSO) δ 9.08 (s, 1H), 8.68 (s, 2H), 8.53 (t, J=6.0 Hz, 1H), 7.82 (d, J=8.8 Hz, 2H), 7.04 (d, J=8.8 Hz, 2H), 4.31 (d, J=5.6 Hz, 2H), 4.06 (d, J=13.2 Hz, 2H), 3.81 (s, 3H), 3.25-3.14 (m, 2H), 2.49-2.43 (m, 1H), 1.85 (dd, J=3.6, 13.6 Hz, 2H), 1.70-1.55 (m, 2H). m/z: [ESI⁺] 395 (M+H)⁺, ($C_{20}H_{22}N_6O_3$).

1-(3-(3-Methoxyphenyl)-1,2,4-oxadiazol-5-yl)-N-(pyridin-3-ylmethyl)piperidine-4-carboxamide (Compound 180): Using 1-(3-(3-Methoxyphenyl)-1,2,4-oxadiazol-5-yl) piperidine-4-carboxylic acid (150 mg, 0.495 mmol) and pyridin-3-ylmethanamine (86 mg, 0.795 mmol) as the starting material.

Yield 100 mg (51%), as an off-white solid. ¹H NMR (400 MHz, DMSO) δ 8.53 (t, J=6.0 Hz, 1H), 7.82 (d, J=8.8 Hz, 2H), 7.64 (d, J=2.4 Hz, 1H), 7.50-7.48 (m, 1H), 7.44 (d, J=8.0 Hz, 1H), 7.41-7.39 (m, 1H), 7.36 (dd, J=0.8, 7.6 Hz, 1H), 7.11 (dd, J=2.8, 8.0 Hz, 1H), 4.30 (d, J=6.0 Hz, 2H), 4.08 (d, J=13.2 Hz, 2H), 3.82 (s, 3H), 3.25-3.15 (m, 2H), 2.49-2.44 (m, 1H), 1.92-1.82 (m, 2H), 1.67-1.55 (m, 2H). m/z: [ESI⁺] 394 (M+H)⁺, ($C_{21}H_{23}N_5O_3$).

1-(3-(4-methoxyphenyl)-1H-1,2,4-triazol-5-yl)-N-((1-(4-methylbenzyl)pyrrolidin-3-yl)methyl)piperidine-4-carboxamide formate (Compound 169): Using 1-(3-(4-methoxyphenyl)-1H-1,2,4-triazol-5-yl)piperidine-4-carboxylic acid (300 mg, 0.992 mmol) and (1-(4-methylbenzyl)pyrrolidin-3-yl)methanamine (243 mg, 1.191 mmol) as the starting material.

Yield 81 mg (16%), as an off-white solid. $^1$H NMR (400 MHz, DMSO) δ 8.17 (s, 1H, HCOOH), 7.90 (t, J=6.0 Hz, 1H), 7.82 (d, J=8.8 Hz, 2H), 7.18 (d, J=7.6 Hz, 2H), 7.12 (d, J=7.8 Hz, 2H), 7.00 (d, J=8.4 Hz, 2H), 3.95 (d, J=12.8 Hz, 2H), 3.80 (s, 3H), 3.53 (s, 2H), 3.07 (dd, J=6.4, 13.2 Hz, 1H), 3.02-2.95 (m, 1H), 2.84 (s, 2H), 2.56 (d, J=8.0 Hz, 2H), 2.46 (t, J=8.0 Hz, 2H), 2.28 (s, 3H), 2.22 (d, J=8.0 Hz, 2H), 1.84-1.82 (m, 1H), 1.69 (d, J=12.8 Hz, 2H), 1.64-1.51 (m, 2H), 1.45-1.37 (m, 1H). m/z: [ESI$^+$] 489 (M+H)$^+$, ($C_{28}H_{36}N_6O_2$).

1-(3-(4-Cyanophenyl)-1,2,4-oxadiazol-5-yl)-N-((1-(4-methylbenzyl)pyrrolidin-3-yl)methyl)piperidine-4-carboxamide (Compound 158): Using 1-(3-(4-cyanophenyl)-1,2,4-oxadiazol-5-yl)piperidine-4-carboxylic acid (200 mg, 0.670 mmol) and (1-(4-methylbenzyl)pyrrolidin-3-yl)methanamine (164 mg, 0.803 mmol) as the starting material.

Yield 220 mg (68%), as an off-white solid. $^1$H NMR (400 MHz, DMSO) δ 8.07 (d, J=8.8 Hz, 2H), 7.99 (d, J=8.8 Hz, 2H), 7.90 (t, J=5.6 Hz, 1H), 7.17 (d, J=8.0 Hz, 2H), 7.10 (d, J=8.0 Hz, 2H), 4.06 (d, J=13.2 Hz, 2H), 3.48 (s, 2H), 3.22 (t, J=12.0 Hz, 2H), 3.10-2.29 (m, 2H), 2.50-2.33 (m, 4H), 2.27 (s, 3H), 2.20-2.16 (m, 2H), 1.83-1.76 (m, 3H), 1.67-1.53 (m, 2H), 1.34-1.38 (m, 1H). m/z: [ESI$^+$] 485 (M+H)$^+$, ($C_{28}H_{32}N_6O_2$).

1-(3-(6-Methoxypyridin-3-yl)-1,2,4-oxadiazol-5-yl)-N-((1-(4-methylbenzyl)pyrrolidin-3-yl)methyl)piperidine-4-carboxamide (Compound 159): Using 1-(3-(6-methoxypyridin-3-yl)-1,2,4-oxadiazol-5-yl)piperidine-4-carboxylic acid (200 mg, 0.657 mmol) and (1-(4-methylbenzyl)pyrrolidin-3-yl)methanamine (175 mg, 0.857 mmol) as the starting material.

Yield 210 mg (65%), as an off-white solid. $^1$H NMR (400 MHz, DMSO) δ 8.67 (dd, J=0.8, 2.4 Hz, 1H), 8.12 (dd, J=2.4, 8.8 Hz, 1H), 7.89 (t, J=5.6 Hz, 1H), 7.16 (d, J=8.0 Hz, 2H), 7.10 (d, J=8.0 Hz, 2H), 6.96 (dd, J=0.8, 8.8 Hz, 1H), 4.05 (d, J=12.8 Hz, 2H), 3.92 (s, 3H), 3.48 (s, 2H), 3.20 (t, J=12.0 Hz, 2H), 3.07-3.05 (m, 1H), 2.98-2.96 (m, 1H), 2.48-2.31 (m, 4H), 2.27 (s, 3H), 2.23-2.13 (m, 2H), 1.88-1.70 (m, 3H), 1.65-1.55 (m, 2H), 1.38-1.30 (m, 1H). m/z: [ESI$^+$] 491 (M+H)$^+$, ($C_{27}H_{34}N_6O_3$).

1-(4-(4-Methoxyphenyl)thiazol-2-yl)-N-((1-(4-methylbenzyl)pyrrolidin-3-yl)methyl)piperidine-4-carboxamide formate (Compound 160): Using 1-(4-(4-Methoxyphenyl)thiazol-2-yl)piperidine-4-carboxylic acid (200 mg, 0.628 mmol) and (1-(4-methylbenzyl)pyrrolidin-3-yl)methanamine (257 mg, 1.258 mmol) as the starting material.

Yield 85 mg (25%), as an off-white solid. $^1$H NMR (400 MHz, DMSO) δ 8.18 (s, 1H, HCOOH), 7.88 (t, J=5.6 Hz, 1H), 7.78 (d, J=8.8 Hz, 2H), 7.19 (d, J=8.8 Hz, 2H), 7.12 (d, J=7.6 Hz, 2H), 7.07 (d, J=2.0 Hz, 1H), 6.95 (d, J=5.6 Hz, 2H), 3.97-3.94 (m, 2H), 3.78 (s, 3H), 3.56 (s, 2H), 3.14-2.98 (m, 4H), 2.58 (s, 1H), 2.40-2.22 (m, 6H), 1.87-1.84 (m, 1H), 1.80-1.72 (m, 2H), 1.69-1.56 (m, 2H), 1.46-1.34 (m, 1H). m/z: [ESI$^+$] 505 (M+H)$^+$, ($C_{29}H_{36}N_4O_2S$).

1-(3-(4-Chlorophenyl)-1,2,4-oxadiazol-5-yl)-N-(pyridin-3-ylmethyl)piperidine-4-carboxamide (Compound 163): Using 1-(3-(4-chlorophenyl)-1,2,4-oxadiazol-5-yl)piperidine-4-carboxylic acid (200 mg, 0.650 mmol) and pyridin-3-ylmethanamine (84 mg, 0.777 mmol) as the starting material.

Yield 220 mg (85%), as an off-white solid. $^1$H NMR (400 MHz, DMSO) δ 8.51-8.43 (m, 3H), 7.92 (d, J=8.8 Hz, 2H), 7.64 (t, J=7.2 Hz, 1H), 7.58 (d, J=8.8 Hz, 2H), 7.35 (d, J=7.6 Hz, 1H), 4.30 (d, J=6.0 Hz, 2H), 4.08 (d, J=13.2 Hz, 2H), 3.30-3.18 (m, 2H), 2.53-2.44 (m, 1H), 1.90-1.81 (m, 2H), 1.71-1.58 (m, 2H). m/z: [ESI$^+$] 398, 400 (M+H)$^+$, ($C_{20}H_{20}ClN_5O_2$).

(1-(3-(2-Chlorophenyl)-1,2,4-oxadiazol-5-yl)piperidin-4-yl)(morpholino)methanone (Compound 164): Using 1-(3-(2-chlorophenyl)-1,2,4-oxadiazol-5-yl)piperidine-4-carboxylic acid (70 mg, 0.227 mmol) and morpholine (30 mg, 0.344 mmol) as the starting material.

Yield 40 mg (47%), as an off-white solid. $^1$H NMR (400 MHz, DMSO) δ 7.82 (dd, J=1.6, 7.8 Hz, 1H), 7.63 (dd, J=1.6, 8.0 Hz, 1H), 7.56 (dt, J=1.6, 7.6 Hz, 1H), 7.49 (dt, J=1.6, 7.6 Hz, 1H), 4.10-4.05 (m, 2H), 3.65-3.55 (m, 6H), 3.47-3.45 (m, 2H), 3.29-3.23 (m, 2H), 3.00-2.91 (m, 1H), 1.85-1.76 (m, 2H), 1.69-1.56 (m, 2H). m/z: [ESI$^+$] 377, 379 (M+H)$^+$, ($C_{18}H_{21}ClN_4O_3$).

(1-(3-(3-Chlorophenyl)-1,2,4-oxadiazol-5-yl)piperidin-4-yl)(morpholino)methanone (Compound 165): Using 1-(3-(3-chlorophenyl)-1,2,4-oxadiazol-5-yl)piperidine-4-carboxylic acid (140 mg, 0.455 mmol) and morpholine (60 mg, 0.689 mmol) as the starting material.

Yield 140 mg (82%), as a yellow solid, $^1$H NMR (400 MHz, DMSO) δ 7.88 (d, J=1.6 Hz, 1H), 7.86 (d, J=1.6 Hz, 1H), 7.63 (d, J=7.6 Hz, 1H), 7.55 (dd, J=1.2, 7.2 Hz 1H), 4.12-4.05 (m, 2H), 3.70-3.58 (m, 6H), 3.46 (s, 2H), 3.28-3.26 (m, 2H), 3.01-2.92 (m, 1H), 1.85-1.76 (m, 2H), 1.70-1.53 (m, 2H). m/z: [ESI$^+$] 377, 379 (M+H)$^+$, ($C_{18}H_{21}ClN_4O_3$).

1-(3-(4-Methoxyphenyl) isoxazol-5-yl)-N-(pyridin-3-ylmethyl)piperidine-4-carboxamide (Compound 181): Using 1-(3-(4-methoxyphenyl) isoxazol-5-yl)piperidine-4-carboxylic acid (200 mg, 0.662 mmol) and pyridin-3-ylmethanamine (86 mg, 0.795 mmol) as the starting material.

Yield 160 mg (62%), as an off-white solid. $^1$H NMR (400 MHz, DMSO) δ 8.47-8.45 (m, 3H), 7.68 (d, J=8.8 Hz, 2H), 7.64 (t, J=5.6 Hz, 1H), 7.37-7.35 (m, 1H), 7.03 (d, J=8.8 Hz, 2H), 5.79 (s, 1H), 4.30 (d, J=5.6 Hz, 2H), 3.80 (s, 3H), 3.77-3.75 (m, 2H), 3.05-2.95 (m, 2H), 2.48-2.38 (m, 1H), 1.82-1.80 (m, 2H), 1.66-1.55 (m, 2H). m/z: [ESI$^+$] 393 (M+H)$^+$, ($C_{22}H_{24}N_4O_3$).

(1-(3-(4-Methoxyphenyl) isoxazol-5-yl)piperidin-4-yl)(morpholino)methanone (Compound 183): Using 1-(3-(4-methoxyphenyl) isoxazol-5-yl)piperidine-4-carboxylic acid (200 mg, 0.662 mmol) and morpholine (69 mg, 0.792 mmol) as the starting material.

Yield 130 mg (53%), as an off-white solid. $^1$H NMR (400 MHz, DMSO) δ 7.68 (d, J=8.8 Hz, 2H), 7.03 (d, J=8.8 Hz, 2H), 5.79 (s, 1H), 3.80 (s, 3H), 3.76-3.74 (m, 2H), 3.62-3.50 (m, 6H), 3.44 (t, J=4.8 Hz, 2H), 3.10-3.03 (m, 2H), 2.95-2.87 (m, 1H), 1.80-1.50 (m, 4H). m/z: [ESI$^+$] 372 (M+H)$^+$, ($C_{20}H_{25}N_3O_4$).

1-(4'-Methoxy-[1,1'-biphenyl]-3-yl)-N-((1-(4-methylbenzyl)pyrrolidin-3-yl)methyl)piperidine-4-carboxamide (Compound 171): Using 1-(4'-methoxy-[1,1'-biphenyl]-3-yl)piperidine-4-carboxylic acid (300 mg, 0.963 mmol) and (1-(4-methylbenzyl)pyrrolidin-3-yl)methanamine (300 mg, 1.468 mmol) as the starting material.

Yield 54 mg (11%), as an off-white solid. $^1$H NMR (400 MHz, DMSO) δ 7.85 (t, J=5.6 Hz, 1H), 7.58 (d, J=8.8 Hz, 2H), 7.26-7.24 (m, 1H), 7.17 (d, J=7.6 Hz, 2H), 7.14-7.07 (m, 3H), 7.03-6.98 (m, 3H), 6.89 (d, J=2.0 Hz, 1H), 3.82-3.77 (m, 5H), 3.49 (s, 2H), 3.08-3.03 (m, 1H), 3.02-2.96 (m, 1H), 2.75-2.68 (m, 2H), 2.44-2.42 (m, 2H), 2.28-2.15 (m, 7H), 1.84-1.82 (m, 1H), 1.77-1.61 (m, 4H), 1.43-1.33 (m, 1H). m/z: [ESI$^+$] 498 (M+H)$^+$, ($C_{32}H_{39}N_3O_2$).

1-(3-(2-Methoxyphenyl)-1,2,4-oxadiazol-5-yl)-N-(pyridin-3-ylmethyl)piperidine-4-carboxamide (Compound 179): Using 1-(3-(2-methoxyphenyl)-1,2,4-oxadiazol-5-yl)piperidine-4-carboxylic acid (200 mg, 0.662 mmol) and pyridin-3-ylmethanamine (86 mg, 0.795 mmol) as the starting material.

Yield 220 mg (85%), as a light yellow solid. $^1$H NMR (400 MHz, DMSO) δ 8.52-8.44 (m, 3H), 7.72 (dd, J=1.6, 7.6 Hz, 1H), 7.65-7.63 (m, 1H), 7.52-7.49 (m, 1H), 7.37-7.35 (m, 1H), 7.16 (dd, J=1.2, 8.4 Hz, 1H), 7.06-7.04 (m, 1H), 4.30 (d, J=6.0 Hz, 2H), 4.05 (d, J=13.2 Hz, 2H), 3.83 (s, 3H), 3.25-3.15 (m, 2H), 2.49-2.44 (m, 1H), 1.87-1.85 (m, 2H), 1.66-1.55 (m, 2H). m/z: [ESI$^+$] 394 (M+H)$^+$, (C$_{21}$H$_{23}$N$_5$O$_3$).

(1s,4s)-N-((1-benzylpyrrolidin-3-yl)methyl)-4-(3-(4-methoxyphenyl)-1,2,4-oxadiazol-5-yl)cyclohexane-1-carboxamide (Compound 172): Using (1s,4s)-4-(3-(4-methoxyphenyl)-1,2,4-oxadiazol-5-yl)cyclohexane-1-carboxylic acid (200 mg, 0.662 mmol) and (1-benzylpyrrolidin-3-yl)methanamine (151 mg, 0.794 mmol) as the starting material.

Yield 45 mg (14%), as an off-white solid. $^1$H NMR (400 MHz, DMSO) δ 7.94 (d, J=8.8 Hz, 2H), 7.82 (t, J=5.6 Hz, 1H), 7.34-7.26 (m, 4H), 7.24-7.22 (m, 1H), 7.09 (d, J=8.8 Hz, 2H), 3.83 (s, 3H), 3.53 (s, 2H), 3.12-2.92 (m, 3H), 2.55-2.52 (m, 1H), 2.47-2.39 (m, 2H), 2.27-2.11 (m, 5H), 1.89-1.76 (m, 3H), 1.62-1.53 (m, 4H), 1.43-1.33 (m, 1H). m/z: [ESI$^+$] 475 (M+H)$^+$, (C$_{28}$H$_{34}$N$_4$O$_3$).

(1r,4r)-N-((1-benzylpyrrolidin-3-yl)methyl)-4-(3-(4-methoxyphenyl)-1,2,4-oxadiazol-5-yl)cyclohexane-1-carboxamide (Compound 174): Using (1r,4r)-4-(3-(4-methoxyphenyl)-1,2,4-oxadiazol-5-yl)cyclohexane-1-carboxylic acid (200 mg, 0.662 mmol) and (1-benzylpyrrolidin-3-yl)methanamine (151 mg, 0.794 mmol) as the starting material.

Yield 17 mg (5%), as an off-white solid. $^1$H NMR (400 MHz, DMSO) δ 7.94 (d, J=8.8 Hz, 2H), 7.82 (t, J=5.6 Hz, 1H), 7.34-7.26 (m, 4H), 7.24-7.22 (m, 1H), 7.09 (d, J=8.8 Hz, 2H), 3.84 (s, 3H), 3.54 (s, 2H), 3.11-2.94 (m, 3H), 2.55-2.53 (m, 1H), 2.46-2.44 (m, 2H), 2.31-2.10 (m, 5H), 1.89-1.77 (m, 3H), 1.65-1.52 (m, 4H), 1.43-1.34 (m, 1H). m/z: [ESI$^+$] 475 (M+H)$^+$, (C$_{28}$H$_{34}$N$_4$O$_3$).

(1s,4s)-N-((1-Benzyl-5-oxopyrrolidin-3-yl)methyl)-4-(3-(4-methoxyphenyl)-1,2,4-oxadiazol-5-yl)cyclohexane-1-carboxamide (Compound 176): Using (1s,4s)-4-(3-(4-methoxyphenyl)-1,2,4-oxadiazol-5-yl)cyclohexane-1-carboxylic acid (200 mg, 0.662 mmol) and 4-(aminomethyl)-1-benzylpyrrolidin-2-one (162 mg, 0.793 mmol) as the starting material.

Yield 100 mg (31%), as an off-white solid. $^1$H NMR (400 MHz, DMSO) δ 7.96-7.89 (m, 3H), 7.35 (dd, J=6.4, 8.0 Hz, 2H), 7.28 (d, J=5.2 Hz, 1H), 7.21 (d, J=8.0 Hz, 2H), 7.09 (d, J=8.8 Hz, 2H), 4.35 (s, 2H), 3.83 (s, 3H), 3.29-3.27 (m, 1H), 3.17-2.99 (m, 3H), 2.95-2.93 (m, 1H), 2.48-2.36 (m, 2H), 2.21-2.08 (m, 4H), 1.82-1.75 (m, 2H), 1.65-1.45 (m, 4H). m/z: [ESI$^+$] 489 (M+H)$^+$, (C$_{28}$H$_{32}$N$_4$O$_4$).

(1r,4r)-N-((1-Benzyl-5-oxopyrrolidin-3-yl)methyl)-4-(3-(4-methoxyphenyl)-1,2,4-oxadiazol-5-yl)cyclohexane-1-carboxamide (Compound 177): Using (1r,4r)-4-(3-(4-methoxyphenyl)-1,2,4-oxadiazol-5-yl)cyclohexane-1-carboxylic acid (200 mg, 0.662 mmol) and 4-(aminomethyl)-1-benzylpyrrolidin-2-one (162 mg, 0.793 mmol) as the starting material.

Yield 220 mg (68%), as an off-white solid. $^1$H NMR (400 MHz, DMSO) δ 7.97-7.90 (m, 3H), 7.36-7.34 (m, 2H), 7.28 (t, J=7.2 Hz, 1H), 7.20 (d, J=7.4 Hz, 2H), 7.10 (d, J=8.4 Hz, 2H), 4.35 (s, 2H), 3.83 (s, 3H), 3.31-3.23 (m, 2H), 3.15-3.00 (m, 3H), 2.95-2.93 (m, 1H), 2.46-2.36 (m, 2H), 2.21-2.06 (m, 4H), 1.81-1.79 (m, 2H), 1.63-1.42 (m, 4H). m/z: [ESI$^+$] 489 (M+H)$^+$, (C$_{28}$H$_{32}$N$_4$O$_4$).

(1r,4r)-4-(3-(4-Methoxyphenyl)-1,2,4-oxadiazol-5-yl)-N-((1-methyl-5-oxopyrrolidin-3-yl)methyl)cyclohexane-1-carboxamide (Compound 229): Using (1r,4r)-4-(3-(4-methoxyphenyl)-1,2,4-oxadiazol-5-yl)cyclohexane-1-carboxylic acid (100 mg, 0.331 mmol) and 4-(aminomethyl)-1-methylpyrrolidin-2-one (51 mg, 0.398 mmol) as the starting material.

Yield 120 mg (88%), as a light yellow solid. $^1$H NMR (400 MHz, DMSO) δ 7.93 (t, J=5.6 Hz, 1H), 7.90 (d, J=8.8 Hz, 2H), 7.10 (d, J=8.4 Hz, 2H), 3.84 (s, 3H), 3.45-3.37 (m, 1H), 3.14-3.01 (m, 4H), 2.69 (s, 3H), 2.44-2.42 (m, 1H), 2.32-2.30 (m, 1H), 2.19-2.17 (m, 3H), 2.01-1.99 (m, 1H), 1.86-1.84 (m, 2H), 1.65-1.45 (m, 4H). m/z: [ESI$^+$] 413 (M+H)$^+$, (C$_{22}$H$_{28}$N$_4$O$_4$).

1-(3-(4-Acetamidophenyl)-1,2,4-oxadiazol-5-yl)-N-((1-(4-methylbenzyl)pyrrolidin-3-yl)methyl)piperidine-4-carboxamide (Compound 184): Using 1-(3-(4-acetamidophenyl)-1,2,4-oxadiazol-5-yl)piperidine-4-carboxylic acid (200 mg, 0.605 mmol) and (1-(4-methylbenzyl)pyrrolidin-3-yl)methanamine (148 mg, 0.724 mmol) as the starting material.

Yield 240 mg (77%), as a light yellow solid. $^1$H NMR (400 MHz, DMSO) δ 10.18 (s, 1H), 7.89 (t, J=5.6 Hz, 1H), 7.82 (d, J=5.2 Hz, 2H), 7.72 (d, J=8.8 Hz, 2H), 7.17 (d, J=8.8 Hz, 2H), 7.11 (d, J=8.0 Hz, 2H), 4.09-4.04 (m, 2H), 3.50 (s, 2H), 3.24-3.14 (m, 2H), 3.10-3.05 (m, 1H), 2.99-2.97 (m, 1H), 2.48-2.52 (m, 1H), 2.46-2.33 (m, 3H), 2.27 (s, 3H), 2.25-2.15 (m, 2H), 2.08 (s, 3H), 1.90-1.75 (m, 3H), 1.65-1.53 (m, 2H), 1.42-1.36 (m, 1H). m/z: [ESI$^+$] 517 (M+H)$^+$, (C$_{29}$H$_{36}$N$_6$O$_3$).

1-(3-(5-Methoxypyridin-2-yl)-1,2,4-oxadiazol-5-yl)-N-((1-(4-methylbenzyl)pyrrolidin-3-yl)methyl)piperidine-4-carboxamide (Compound 185): Using 1-(3-(5-methoxypyridin-2-yl)-1,2,4-oxadiazol-5-yl)piperidine-4-carboxylic acid (200 mg, 0.657 mmol) and (1-(4-methylbenzyl)pyrrolidin-3-yl)methanamine (161 mg, 0.788 mmol) as the starting material.

Yield 200 mg (62%), as a yellow solid. $^1$H NMR (400 MHz, DMSO) δ 8.39 (d, J=2.8 Hz, 1H), 7.92 (dd, J=0.8, 8.8 Hz, 1H), 7.89 (t, J=5.6 Hz, 1H), 7.52 (dd, J=3.2, 8.8 Hz, 1H), 7.17 (d, J=8.0 Hz, 2H), 7.11 (d, J=8.0 Hz, 2H), 4.09-4.04 (m, 2H), 3.90 (s, 3H), 3.48 (s, 2H), 3.25-3.15 (m, 2H), 3.07-3.05 (m, 1H), 2.99-2.97 (m, 1H), 2.52-2.47 (m, 1H), 2.45-2.35 (m, 3H), 2.27 (s, 3H), 2.24-2.22 (m, 1H), 2.18-2.16 (m, 1H), 1.88-1.73 (m, 3H), 1.65-1.57 (m, 2H), 1.38-1.36 (m, 1H). m/z: [ESI$^+$] 491 (M+H)$^+$, (C$_{27}$H$_{34}$N$_6$O$_3$).

N-((1-(4-methylbenzyl)pyrrolidin-3-yl)methyl)-1-(3-(m-tolyl)-1,2,4-oxadiazol-5-yl)piperidine-4-carboxamide (Compound 186): Using 1-(3-(3-methylphenyl)-1,2,4-oxadiazol-5-yl)piperidine-4-carboxylic acid (200 mg, 0.696 mmol) and (1-(4-methylbenzyl)pyrrolidin-3-yl)methanamine (170 mg, 0.832 mmol) as the starting material.

Yield 200 mg (61%), as a light yellow solid. $^1$H NMR (400 MHz, DMSO) δ 7.89 (t, J=5.6 Hz, 1H), 7.73 (s, 1H), 7.70 (d, J=3.6 Hz, 1H), 7.39-7.37 (m, 2H), 7.17 (d, J=8.0 Hz, 2H), 7.11 (d, J=8.0 Hz, 2H), 4.09-4.03 (m, 2H), 3.50 (s, 2H), 3.21-3.19 (m, 2H), 3.08-3.06 (m, 1H), 2.99-2.97 (m, 1H), 2.50-2.42 (m, 4H), 2.38 (s, 3H), 2.28 (s, 3H), 2.26-2.14 (m, 2H), 1.90-1.65 (m, 3H), 1.69-1.50 (m, 2H), 1.43-1.33 (m, 1H). m/z: [ESI$^+$] 491 (M+H)$^+$, (C$_{28}$H$_{35}$N$_5$O$_2$).

1-(3-(3-Methoxyphenyl)-1,2,4-oxadiazol-5-yl)-N-((1-(4-methylbenzyl)pyrrolidin-3-yl)methyl)piperidine-4-carboxamide formate (Compound 187): Using 1-(3-(3-methoxyphenyl)-1,2,4-oxadiazol-5-yl)piperidine-4-carboxylic acid (200 mg, 0.659 mmol) and (1-(4-methylbenzyl)pyrrolidin-3-yl)methanamine (162 mg, 0.793 mmol) as the starting material.

Yield 200 mg (57%), as a light yellow solid. $^1$H NMR (400 MHz, DMSO) δ 8.17 (s, 1H, HCOOH), 7.91 (t, J=5.6 Hz, 1H), 7.50-7.48 (m, 1H), 7.43 (d, J=8.0 Hz, 1H), 7.40 (d, J=4.0 Hz, 1H), 7.18 (d, J=8.0 Hz, 2H), 7.15 (d, J=3.6 Hz, 1H), 7.09 (d, J=8.8 Hz, 2H), 4.06-4.04 (m, 2H), 3.81 (s, 3H), 3.55 (s, 2H), 3.23-3.16 (m, 2H), 3.08-3.01 (m, 1H), 2.99-2.97 (m, 1H), 2.61-2.52 (m, 2H), 2.47-2.45 (m, 1H), 2.39-2.37 (m, 1H), 2.27 (s, 3H), 2.26-2.19 (m, 2H), 1.90-1.73 (m, 3H), 1.65-1.54 (m, 2H), 1.35-1.37 (m, 1H). m/z: [ESI$^+$] 490 (M+H)$^+$, ($C_{28}H_{35}N_5O_3$).

N-((1-(4-methylbenzyl)pyrrolidin-3-yl)methyl)-1-(3-(o-tolyl)-1,2,4-oxadiazol-5-yl)piperidine-4-carboxamide (Compound 188): Using 1-(3-(2-methylphenyl)-1,2,4-oxadiazol-5-yl)piperidine-4-carboxylic acid (200 mg, 0.696 mmol) and (1-(4-methylbenzyl)pyrrolidin-3-yl)methanamine (171 mg, 0.837 mmol) as the starting material.

Yield 220 mg (67%), as a light yellow solid. $^1$H NMR (400 MHz, DMSO) δ 7.89 (t, J=5.6 Hz, 1H), 7.83 (dd, J=1.6, 7.6 Hz, 1H), 7.43-7.41 (m, 1H), 7.35 (d, J=7.2 Hz, 2H), 7.17 (d, J=8.0 Hz, 2H), 7.11 (d, J=8.0 Hz, 2H), 4.09-4.04 (m, 2H), 3.49 (s, 2H), 3.25-3.15 (m, 2H), 3.08-3.01 (m, 1H), 2.99-2.95 (m, 1H), 2.60-2.52 (m, 4H), 2.50-2.35 (m, 3H), 2.27 (s, 3H), 2.25-2.14 (m, 2H), 1.88-1.74 (m, 3H), 1.67-1.54 (m, 2H), 1.43-1.32 (m, 1H). m/z: [ESI$^+$] 474 (M+H)$^+$, ($C_{28}H_{35}N_5O_2$).

1-(4-(4-Methoxyphenyl)oxazol-2-yl)-N-((1-(4-methylbenzyl)pyrrolidin-3-yl)methyl)piperidine-4-carboxamide (Compound 196): Using 1-(4-(4-methoxyphenyl)oxazol-2-yl)piperidine-4-carboxylic acid (136 mg, 0.450 mmol) and (1-(4-methylbenzyl)pyrrolidin-3-yl)methanamine (184 mg, 0.901 mmol) as the starting material.

Yield 17 mg (8%), as an off-white solid. $^1$H NMR (400 MHz, DMSO) δ 7.95 (s, 1H), 7.87 (t, J=5.6 Hz, 1H), 7.63 (d, J=8.0 Hz, 2H), 7.18 (d, J=8.0 Hz, 2H), 7.11 (d, J=7.6 Hz, 2H), 6.94 (d, J=7.6 Hz, 2H), 4.05-3.95 (m, 2H), 3.77 (s, 3H), 3.50 (s, 2H), 3.07-3.05 (m, 1H), 3.02-2.92 (m, 3H), 2.52-2.48 (m, 1H), 2.49-2.38 (m, 2H), 2.35-2.33 (m, 1H), 2.28 (s, 3H), 2.22-2.20 (m, 2H), 1.84-1.82 (m, 1H), 1.76-1.71 (m, 2H), 1.65-1.56 (m, 2H), 1.45-1.37 (m, 1H). m/z: [ESI$^+$] 489 (M+H)$^+$, ($C_{29}H_{36}N_4O_3$).

1-(4-(4-Methoxyphenyl)oxazol-2-yl)-N-(pyridin-3-ylmethyl)piperidine-4-carboxamide (Compound 201): Using 1-(4-(4-methoxyphenyl)oxazol-2-yl)piperidine-4-carboxylic acid (118 mg, 0.390 mmol) and pyridin-3-ylmethanamine (51 mg, 0.472 mmol) as the starting material.

Yield 43 mg (28%), as an off-white solid. $^1$H NMR (400 MHz, DMSO) δ 8.52-8.42 (m, 3H), 7.96 (s, 1H), 7.66 (t, J=5.6 Hz, 1H), 7.59 (d, J=8.8 Hz, 2H), 7.35 (d, J=7.6 Hz, 1H), 6.94 (d, J=8.8 Hz, 2H), 4.30 (d, J=5.6 Hz, 2H), 4.06-3.97 (m, 2H), 3.77 (s, 3H), 3.06-2.95 (m, 2H), 2.47-2.38 (m, 1H), 1.85-1.77 (m, 2H), 1.69-1.55 (m, 2H). m/z: [ESI$^+$] 393 (M+H)$^+$, ($C_{22}H_{24}N_4O_3$).

(1-(4-(4-Methoxyphenyl)oxazol-2-yl)piperidin-4-yl)(morpholino)methanone (Compound 203): Using 1-(4-(4-methoxyphenyl)oxazol-2-yl)piperidine-4-carboxylic acid (125 mg, 0.413 mmol) and morpholine (54 mg, 0.620 mmol) as the starting material.

Yield 44 mg (29%), as an off-white solid. $^1$H NMR (400 MHz, DMSO) δ 7.95 (s, 1H), 7.62 (d, J=8.8 Hz, 2H), 6.91 (d, J=8.8 Hz, 2H), 4.04-3.96 (m, 2H), 3.77 (s, 3H), 3.64-3.51 (m, 6H), 3.45 (t, J=4.8 Hz, 2H), 3.10-3.00 (m, 2H), 2.93-2.83 (m, 1H), 1.75-1.67 (m, 2H), 1.65-1.52 (m, 2H). m/z: [ESI$^+$] 372 (M+H)$^+$, ($C_{20}H_{25}N_3O_4$).

1-(3-(2-Methoxyphenyl)-1,2,4-oxadiazol-5-yl)-N-((1-(4-methylbenzyl)pyrrolidin-3-yl)methyl)piperidine-4-carboxamide (Compound 189): Using 1-(3-(2-methoxyphenyl)-1,2,4-oxadiazol-5-yl)piperidine-4-carboxylic acid (200 mg, 0.659 mmol) and (1-(4-methylbenzyl)pyrrolidin-3-yl)methanamine (162 mg, 0.793 mmol) as the starting material.

Yield 220 mg (68%), as a light yellow solid. $^1$H NMR (400 MHz, DMSO) δ 7.89 (t, J=5.6 Hz, 1H), 7.72 (d, J=7.6 Hz, 1H), 7.51-7.49 (m, 1H), 7.20-7.14 (m, 3H), 7.11 (d, J=7.6 Hz, 2H), 7.08-7.02 (m, 1H), 4.07-3.98 (m, 2H), 3.83 (s, 3H), 3.50-3.48 (m, 2H), 3.22-3.13 (m, 2H), 3.11-3.02 (m, 1H), 3.02-2.94 (m, 1H), 2.52-2.48 (m, 3H), 2.48-2.33 (m, 1H), 2.27 (s, 3H), 2.21-2.12 (m, 2H), 1.88-1.73 (m, 3H), 1.65-1.53 (m, 2H), 1.42-1.32 (m, 1H). m/z: [ESI$^+$] 490 (M+H)$^+$, ($C_{28}H_{35}N_5O_3$).

1-(3-(3-Cyanophenyl)-1,2,4-oxadiazol-5-yl)-N-((1-(4-methylbenzyl)pyrrolidin-3-yl)methyl)piperidine-4-carboxamide (Compound 198): Using 1-(3-(3-cyanophenyl)-1,2,4-oxadiazol-5-yl)piperidine-4-carboxylic acid (200 mg, 0.670 mmol) and (1-(4-methylbenzyl)pyrrolidin-3-yl)methanamine (164 mg, 0.803 mmol) as the starting material.

Yield 10 mg (3%), as a yellow solid. $^1$H NMR (400 MHz, DMSO) δ 8.25 (d, J=1.6 Hz, 1H), 8.23-8.18 (m, 1H), 8.03 (d, J=8.8 Hz, 1H), 7.91 (t, J=5.6 Hz, 1H), 7.75 (d, J=7.6 Hz, 1H), 7.18 (d, J=6.4 Hz, 2H), 7.12 (d, J=7.6 Hz, 2H), 4.13-4.02 (m, 2H), 3.52 (s, 2H), 3.28-3.18 (m, 2H), 3.12-2.94 (m, 2H), 2.52-2.50 (m, 1H), 2.49-2.35 (m, 3H), 2.28 (s, 5H), 1.90-1.74 (m, 3H), 1.68-1.53 (m, 2H), 1.40 (s, 1H). m/z: [ESI$^+$] 485 (M+H)$^+$, ($C_{28}H_{32}N_6O_2$).

Morpholino(1-(3-(pyridin-4-yl)-1,2,4-oxadiazol-5-yl)piperidin-4-yl)methanone (Compound 202): Using 1-(3-(pyridin-4-yl)-1,2,4-oxadiazol-5-yl)piperidine-4-carboxylic acid (200 mg, 0.729 mmol) and morpholine (76 mg, 0.872 mmol) as the starting material.

Yield 75 mg (30%), as a yellow solid. $^1$H NMR (400 MHz, DMSO) δ 8.74 (dd, J=1.6, 4.4 Hz, 2H), 7.83 (dd, J=1.6, 4.4 Hz, 2H), 4.13-4.05 (m, 2H), 3.64-3.52 (m, 6H), 3.49-3.42 (m, 2H), 3.31-3.23 (m, 2H), 3.01-2.92 (m, 1H), 1.82-1.74 (m, 2H), 1.69-1.57 (m, 2H). m/z: [ESI$^+$] 344 (M+H)$^+$, ($C_{17}H_{21}N_5O_3$).

N-(pyridin-3-ylmethyl)-1-(3-(pyridin-4-yl)-1,2,4-oxadiazol-5-yl)piperidine-4-carboxamide (Compound 200): Using 1-(3-(pyridin-4-yl)-1,2,4-oxadiazol-5-yl)piperidine-4-carboxylic acid (200 mg, 0.729 mmol) and pyridin-3-ylmethanamine (95 mg, 0.878 mmol) as the starting material.

Yield 14 mg (5%), as a yellow solid. $^1$H NMR (400 MHz, DMSO) δ 8.74 (dd, J=1.6, 4.4 Hz, 2H), 8.54-8.43 (m, 3H), 7.83 (dd, J=1.6, 4.4 Hz, 2H), 7.65 (t, J=5.6 Hz, 1H), 7.36 (dd, J=4.8, 8.0 Hz, 1H), 4.34-4.27 (m, 2H), 4.14-4.04 (m, 2H), 3.31-3.20 (m, 2H), 2.51-2.47 (m, 1H), 1.93-1.83 (m, 2H), 1.73-1.60 (m, 2H). m/z: [ESI$^+$] 365 (M+H)$^+$, ($C_{19}H_{20}N_6O_3$).

1-(3-(3-Acetamidophenyl)-1,2,4-oxadiazol-5-yl)-N-((1-(4-methylbenzyl)pyrrolidin-3-yl)methyl)piperidine-4-carboxamideformate (Compound 230): Using 1-(3-(3-acetamidophenyl)-1,2,4-oxadiazol-5-yl)piperidine-4-carboxylic acid (200 mg, 0.605 mmol) and (1-(4-methylbenzyl)pyrrolidin-3-yl)methanamine (148 mg, 0.724 mmol) as the starting material.

Yield 120 mg (35%), as a light yellow solid. $^1$H NMR (400 MHz, DMSO) δ 10.14 (s, 1H), 8.20 (s, 1H, HCOOH), 8.16 (d, J=2.0 Hz, 1H), 7.92 (t, J=5.6 Hz, 1H), 7.76 (d, J=4.4 Hz, 1H), 7.59-7.54 (m, 1H), 7.46-7.39 (m, 1H), 7.21 (d, J=7.6 Hz, 2H), 7.13 (d, J=7.6 Hz, 2H), 4.10-4.01 (m, 2H), 3.61 (s, 2H), 3.26-3.17 (m, 2H), 3.14-2.96 (m, 2H), 2.69-2.54 (m, 3H), 2.46-2.35 (m, 1H), 2.33-2.28 (m, 5H), 2.06 (s, 3H), 1.91-1.74 (m, 3H), 1.67-1.53 (m, 2H), 1.48-1.36 (m, 1H). m/z: [ESI$^+$] 517 (M+H)$^+$, ($C_{29}H_{36}N_6O_3$).

N-((1-(4-methylbenzyl)pyrrolidin-3-yl)methyl)-1-(3-(4-(trifluoromethoxy)phenyl)-1,2,4-oxadiazol-5-yl)piperidine-4-carboxamide formate (Compound 237): Using 1-(3-(4-(trifluoromethoxy)phenyl)-1,2,4-oxadiazol-5-yl)piperidine-4-carboxylic acid (200 mg, 0.560 mmol) and (1-(4-methylbenzyl)pyrrolidin-3-yl)methanamine (137 mg, 0.671 mmol) as the starting material.

Yield 150 mg (45%), as a light yellow solid. $^1$H NMR (400 MHz, DMSO) δ 8.17 (s, 1H, HCOOH), 8.03 (d, J=8.8 Hz, 2H), 7.90 (t, J=5.6 Hz, 1H), 7.51 (d, J=8.8 Hz, 2H), 7.19 (d, J=8.0 Hz, 2H), 7.12 (d, J=8.0 Hz, 2H), 4.07-4.05 (m, 2H), 3.56 (s, 2H), 3.25-3.19 (m, 2H), 3.09-3.06 (m, 1H), 3.05-2.99 (m, 1H), 2.57-2.50 (m, 2H), 2.47-2.37 (m, 2H), 2.28 (s, 3H), 2.24 (d, J=7.2 Hz, 2H), 1.83-1.77 (m, 3H), 1.62-1.58 (m, 2H), 1.40-1.38 (m, 1H). $^{19}$F NMR (376 MHz, DMSO) δ −56.67. m/z: [ESI$^+$] 544 (M+H)$^+$, ($C_{28}H_{32}F_3N_5O_3$).

1-(3-(4-(Difluoromethoxy)phenyl)-1,2,4-oxadiazol-5-yl)-N-((1-(4-methylbenzyl)pyrrolidin-3-yl)methyl)piperidine-4-carboxamide formate (Compound 238): Using 1-(3-(4-(difluoromethoxy)phenyl)-1,2,4-oxadiazol-5-yl)piperidine-4-carboxylic acid (200 mg, 0.589 mmol) and (1-(4-methylbenzyl)pyrrolidin-3-yl)methanamine (145 mg, 0.710 mmol) as the starting material.

Yield 150 mg (45%), as a light yellow solid. $^1$H NMR (400 MHz, DMSO) δ 8.21 (s, 1H, HCOOH), 7.95 (d, J=8.8 Hz, 2H), 7.92 (t, J=5.6 Hz, 1H), 7.35 (t, J=76.0 Hz, 1H), 7.31 (d, J=8.8 Hz, 2H), 7.20 (d, J=8.0 Hz, 2H), 7.13 (d, J=8.0 Hz, 2H), 4.06 (dd, J=3.2, 13.2 Hz, 2H), 3.60 (s, 2H), 3.21 (dt, J=3.2, 12.4 Hz, 2H), 3.08-3.00 (m, 2H), 2.61-2.51 (m, 3H), 2.49-2.36 (m, 1H), 2.29-2.25 (m, 5H), 1.84-1.77 (m, 3H), 1.64-1.59 (m, 2H), 1.48-1.37 (m, 1H). $^{19}$F NMR (376 MHz, DMSO) δ −82.60. m/z: [ESI$^+$] 526 (M+H)$^+$, ($C_{28}H_{33}F_2N_5O_3$).

1-(3-(2-Chloro-4-methoxyphenyl)-1,2,4-oxadiazol-5-yl)-N-((1-(4-methylbenzyl)pyrrolidin-3-yl)methyl)piperidine-4-carboxamide formate (Compound 231): Using 1-(3-(2-chloro-4-methoxyphenyl)-1,2,4-oxadiazol-5-yl)piperidine-4-carboxylic acid (200 mg, 0.592 mmol) and (1-(4-methylbenzyl)pyrrolidin-3-yl)methanamine (145 mg, 0.710 mmol) as the starting material.

Yield 150 mg (44%), as a light yellow solid. $^1$H NMR (400 MHz, DMSO) δ 8.18 (s, 1H, HCOOH), 7.89 (t, J=5.6 Hz, 1H), 7.78 (d, J=8.8 Hz, 1H), 7.20-7.18 (m, 3H), 7.12 (d, J=7.6 Hz, 2H), 7.05 (dd, J=2.8, 8.8 Hz, 1H), 4.05-4.02 (m, 2H), 3.85 (s, 3H), 3.55 (s, 2H), 3.22-3.17 (m, 2H), 3.09-3.05 (m, 1H), 3.04-2.98 (m, 1H), 2.57-2.50 (m, 3H), 2.49-2.38 (m, 1H), 2.28-2.20 (m, 5H), 1.83-1.76 (m, 3H), 1.62-1.58 (m, 2H), 1.40-1.39 (m, 1H). m/z: [ESI$^+$] 524, 526 (M+H)$^+$, ($C_{28}H_{34}ClN_5O_4$).

N-(3-(4-benzylpiperidin-1-yl)propyl)-1-(3-(4-(trifluoromethoxy)phenyl)-1,2,4-oxadiazol-5-yl)piperidine-4-carboxamide formate (Compound 239): Using 1-(3-(4-(trifluoromethoxy)phenyl)-1,2,4-oxadiazol-5-yl)piperidine-4-carboxylic acid (200 mg, 0.560 mmol) and 3-(4-benzylpiperidin-1-yl)propan-1-amine (156 mg, 0.671 mmol) as the starting material.

Yield 160 mg (46%), as a light yellow solid. $^1$H NMR (400 MHz, DMSO) δ 8.21 (s, 1H, HCOOH), 8.03 (d, J=8.8 Hz, 2H), 7.90 (t, J=5.6 Hz, 1H), 7.52-7.50 (m, 2H), 7.30-7.24 (d, J=8.8 Hz, 2H), 7.19-7.14 (m, 3H), 4.09-4.06 (m, 2H), 3.26-3.19 (m, 2H), 3.08-3.03 (m, 2H), 2.91-2.89 (m, 2H), 2.52-2.49 (m, 2H), 2.39-2.33 (m, 2H), 1.98-1.92 (m, 2H), 1.83-1.79 (m, 2H), 1.64-1.54 (m, 7H), 1.22-1.19 (m, 2H). $^{19}$F NMR (376 MHz, DMSO) δ −56.68. m/z: [ESI$^+$] 572 (M+H)$^+$, ($C_{30}H_{36}F_3N_5O_3$).

N-(3-(4-benzylpiperidin-1-yl)propyl)-1-(3-(4-(difluoromethoxy)phenyl)-1,2,4-oxadiazol-5-yl)piperidine-4-carboxamide (Compound 240): Using 1-(3-(4-(difluoromethoxy)phenyl)-1,2,4-oxadiazol-5-yl)piperidine-4-carboxylic acid (200 mg, 0.589 mmol) and 3-(4-benzylpiperidin-1-yl)propan-1-amine (164 mg, 0.706 mmol) as the starting material.

Yield 120 mg (37%), as a light yellow solid. $^1$H NMR (400 MHz, DMSO) δ 7.91 (d, J=8.8 Hz, 2H), 7.90 (t, J=5.6 Hz, 1H), 7.35 (t, J=76.0 Hz, 1H), 7.30 (dd, J=2.8, 9.6 Hz, 2H), 7.26 (d, J=7.6 Hz, 2H), 7.19-7.14 (m, 3H), 4.08-4.05 (m, 2H), 3.24-3.17 (m, 2H), 3.06-3.01 (m, 2H), 2.81-2.78 (m, 2H), 2.52-2.48 (m, 2H), 2.38-2.33 (m, 1H), 2.24-2.20 (m, 2H), 1.81-1.73 (m, 4H), 1.63-1.50 (m, 7H), 1.17-1.14 (m, 2H). $^{19}$F NMR (376 MHz, DMSO) δ −82.60. m/z: [ESI$^+$] 554 (M+H)$^+$, ($C_{30}H_{37}F_2N_5O_3$).

N-(3-(4-benzylpiperidin-1-yl)propyl)-1-(3-(4-cyanophenyl)-1,2,4-oxadiazol-5-yl)piperidine-4-carboxamide formate (Compound 241): Using 1-(3-(4-cyanophenyl)-1,2,4-oxadiazol-5-yl)piperidine-4-carboxylic acid (150 mg, 0.503 mmol) and 3-(4-benzylpiperidin-1-yl)propan-1-amine (140 mg, 0.602 mmol) as the starting material.

Yield 150 mg (53%), as a light yellow solid. $^1$H NMR (400 MHz, DMSO) δ 8.21 (s, 1H, HCOOH), 8.03 (d, J=8.8 Hz, 2H), 7.98-7.90 (m, 2H), 7.90 (t, J=5.6 Hz, 1H), 7.30-7.26 (m, 2H), 7.19-7.14 (m, 3H), 4.09-4.06 (m, 2H), 3.27-3.19 (m, 2H), 3.06-3.03 (m, 2H), 2.91-2.88 (m, 2H), 2.52-2.48 (m, 2H), 2.39-2.33 (m, 3H), 1.96-1.94 (m, 2H), 1.83-1.79 (m, 2H), 1.64-1.54 (m, 7H), 1.22-1.19 (m, 2H). m/z: [ESI$^+$] 513 (M+H)$^+$, ($C_{30}H_{36}N_6O_2$).

1-(3-(2-Methoxypyrimidin-5-yl)-1,2,4-oxadiazol-5-yl)-N-((1-(4-methylbenzyl)pyrrolidin-3-yl)methyl)piperidine-4-carboxamide (Compound 232): Using 1-(3-(2-methoxypyrimidin-5-yl)-1,2,4-oxadiazol-5-yl)piperidine-4-carboxylic acid (150 mg, 0.491 mmol) and (1-(4-methylbenzyl)pyrrolidin-3-yl)methanamine (120 mg, 0.587 mmol) as the starting material.

Yield 80 mg (33%), as an off-white solid. $^1$H NMR (400 MHz, DMSO) δ 9.03 (s, 2H), 7.90 (t, J=5.6 Hz, 1H), 7.18 (d, J=7.6 Hz, 2H), 7.12 (d, J=7.6 Hz, 2H), 4.07-4.05 (m, 2H), 4.00 (s, 3H), 3.50 (s, 2H), 3.30-3.22 (m, 2H), 3.08-3.01 (m, 1H), 2.99-2.97 (m, 1H), 2.39 (s, 3H), 2.38-2.35 (m, 1H), 2.28 (s, 3H), 2.26-2.11 (m, 2H), 1.80-1.78 (m, 3H), 1.69-1.57 (m, 2H), 1.41-1.37 (m, 1H). m/z: [ESI$^+$] 492 (M+H)$^+$, ($C_{26}H_{33}N_7O_3$).

1-(3-(5-Methoxypyrazin-2-yl)-1,2,4-oxadiazol-5-yl)-N-((1-(4-methylbenzyl)pyrrolidin-3-yl)methyl)piperidine-4-carboxamide (Compound 233): Using 1-(3-(5-methoxypyrazin-2-yl)-1,2,4-oxadiazol-5-yl)piperidine-4-carboxylic acid (90 mg, 0.295 mmol) and (1-(4-methylbenzyl)pyrrolidin-3-yl)methanamine (72 mg, 0.352 mmol) as the starting material.

Yield 50 mg (35%), as an off-white solid. $^1$H NMR (400 MHz, DMSO) δ 8.71 (d, J=1.2 Hz, 1H), 8.43 (d, J=1.2 Hz, 1H), 7.89 (t, J=5.6 Hz, 1H), 7.17 (d, J=8.0 Hz, 2H), 7.11 (d, J=8.0 Hz, 2H), 4.08-4.05 (m, 2H), 3.99 (s, 3H), 3.48 (s, 2H), 3.28-3.20 (m, 2H), 3.11-2.94 (m, 2H), 2.45-2.37 (m, 4H), 2.27 (s, 3H), 2.26-2.14 (m, 2H), 1.89-1.76 (m, 3H), 1.68-1.54 (m, 2H), 1.44-1.32 (m, 1H). m/z: [ESI$^+$] 492 (M+H)$^+$, ($C_{26}H_{33}N_7O_3$).

1-(3-(4-Cyanophenyl)-1,2,4-oxadiazol-5-yl)-N-((1-(4-methylbenzyl)-5-oxopyrrolidin-3-yl)methyl)piperidine-4-carboxamide (Compound 267): Using 1-(3-(4-cyanophenyl)-1,2,4-oxadiazol-5-yl)piperidine-4-carboxylic acid (200 mg, 0.670 mmol) and 4-(aminomethyl)-1-(4-methylbenzyl)pyrrolidin-2-one (176 mg, 0.806 mmol) as the starting material.

Yield 100 mg (30%), as a light yellow solid. $^1$H NMR (400 MHz, DMSO) δ 8.07 (dd, J=2.0, 6.8 Hz, 2H), 7.97 (dd, J=2.0, 6.8 Hz, 2H), 7.90 (t, J=5.6 Hz, 1H) 7.15 (d, J=8.0 Hz, 2H), 7.09 (d, J=8.0 Hz, 2H), 4.30 (d, J=1.6 Hz, 2H), 4.10-4.02 (m, 2H), 3.30-3.18 (m, 3H), 3.17-3.02 (m, 2H), 2.94-2.89 (m, 1H), 2.50-2.33 (m, 3H), 2.28 (s, 3H), 2.14-2.05 (m, 1H), 1.82-1.73 (m, 2H), 1.67-1.51 (m, 2H). m/z: [ESI$^+$] 499 (M+H)$^+$, (C$_{28}$H$_{30}$N$_6$O$_3$).

1-(3-(5-Methoxypyrimidin-2-yl)-1,2,4-oxadiazol-5-yl)-N-((1-(4-methylbenzyl)pyrrolidin-3-yl)methyl)piperidine-4-carboxamide (Compound 247): Using 1-(3-(5-methoxypyrimidin-2-yl)-1,2,4-oxadiazol-5-yl)piperidine-4-carboxylic acid (200 mg, 0.655 mmol) and (1-(4-methylbenzyl)pyrrolidin-3-yl)methanamine (174 mg, 0.852 mmol) as the starting material.

Yield 50 mg (16%), as an off-white solid. $^1$H NMR (400 MHz, DMSO) δ 8.68 (s, 2H), 7.90 (t, J=5.6 Hz, 1H), 7.18 (d, J=7.6 Hz, 2H), 7.12 (d, J=7.6 Hz, 2H), 4.07-4.05 (m, 2H), 4.00 (s, 3H), 3.50 (s, 2H), 3.27-3.18 (m, 2H), 3.11-3.04 (m, 1H), 3.03-2.95 (m, 1H), 2.50-2.35 (m, 4H), 2.28 (s, 3H), 2.26-2.15 (m, 2H), 1.90-1.77 (m, 3H), 1.70-1.54 (m, 2H), 1.42-1.36 (m, 1H). m/z: [ESI$^+$] 492 (M+H)$^+$, (C$_{26}$H$_{33}$N$_7$O$_3$).

1-(3-(4-Methoxyphenyl)-1,2,4-oxadiazol-5-yl)-N-(1-oxaspiro[5.5]undecan-4-yl)piperidine-4-carboxamide (Compound 289): Using 1-(3-(4-methoxyphenyl)-1,2,4-oxadiazol-5-yl)piperidine-4-carboxylic acid (100 mg, 0.330 mmol) and 1-oxaspiro[5.5]undecan-4-amine (67 mg, 0.396 mmol) as the starting material.

Yield 48 mg (32%), as an off-white solid. $^1$H NMR (400 MHz, DMSO) δ 7.84 (d, J=8.8 Hz, 2H), 7.72 (d, J=7.6 Hz, 1H), 7.05 (d, J=8.8 Hz, 2H), 4.06 (d J=13.2 Hz, 2H), 3.98-3.87 (m, 1H), 3.82 (s, 3H), 3.67-3.59 (m, 1H), 3.52 (dt, J=2.4, 12.4 Hz, 1H), 3.18 (dt, J=3.4, 12.8 Hz, 2H), 2.38 (d, J=3.6 Hz, 1H), 1.96 (d, J=13.2 Hz, 1H), 1.78 (dd, J=3.6, 13.6 Hz, 2H), 1.73-1.51 (m, 5H), 1.50-1.31 (m, 6H), 1.30-1.17 (m, 3H), 1.07-1.05 (m, 1H). m/z: [ESI$^+$] 455 (M+H)$^+$, (C$_{25}$H$_{34}$N$_4$O$_4$).

1-(3-(4-Methoxyphenyl)-1,2,4-oxadiazol-5-yl)-N-(3-oxaspiro[5.5]undecan-9-yl)piperidine-4-carboxamide (Compound 312): Using 1-(3-(4-methoxyphenyl)-1,2,4-oxadiazol-5-yl)piperidine-4-carboxylic acid (100 mg, 0.330 mmol) and 3-oxaspiro[5.5]undecan-9-amine (67 mg, 0.396 mmol) as the starting material.

Yield 50 mg (33%), as an off-white solid. $^1$H NMR (400 MHz, DMSO) δ 7.84 (d, J=8.8 Hz, 2H), 7.72 (d, J=7.6 Hz, 1H), 7.05 (d, J=8.8 Hz, 2H), 4.06 (d, J=13.2 Hz, 2H), 3.82 (s, 3H), 3.54-3.50 (m, 5H), 3.18 (dt, J=3.2, 12.8 Hz, 2H), 2.41-2.37 (m, 1H), 1.77 (dd, J=3.6, 13.6 Hz, 2H), 1.73-1.51 (m, 6H), 1.44 (t, J=5.6 Hz, 2H), 1.38-1.25 (m, 4H), 1.15 (dt, J=3.6, 13.2 Hz, 2H). m/z: [ESI$^+$] 455 (M+H)$^+$, (C$_{25}$H$_{34}$N$_4$O$_4$).

1-(3-(4-Methoxyphenyl)-1,2,4-oxadiazol-5-yl)-N-(1-oxaspiro[4.5]decan-3-yl)piperidine-4-carboxamide (Compound 290): Using 1-(3-(4-methoxyphenyl)-1,2,4-oxadiazol-5-yl)piperidine-4-carboxylic acid (100 mg, 0.330 mmol) and 1-oxaspiro[4.5]decan-3-amine (77 mg, 0.496 mmol) as the starting material.

Yield 60 mg (41%), as an off-white solid. $^1$H NMR (400 MHz, DMSO) δ 8.03 (d, J=6.4 Hz, 1H), 7.83 (d, J=8.8 Hz, 2H), 7.05 (d, J=8.8 Hz, 2H), 4.28-4.18 (m, 1H), 4.06 (td, J=3.6, 13.2 Hz, 2H), 3.86 (dd, J=6.4, 8.8 Hz, 1H), 3.82 (s, 3H), 3.44 (dd, J=5.6, 8.8 Hz, 1H), 3.18 (dt, J=2.8, 12.8 Hz, 2H), 2.45-2.39 (m, 1H), 1.99 (dd, J=8.4, 12.8 Hz, 1H), 1.78 (td, J=3.2, 13.4 Hz, 2H), 1.69-1.49 (m, 7H), 1.47-1.38 (m, 2H), 1.38-1.28 (m, 4H). m/z: [ESI$^+$] 441 (M+H)$^+$, (C$_{24}$H$_{32}$N$_4$O$_4$).

N-((1-(dimethylamino)cyclohexyl)methyl)-1-(3-(4-methoxyphenyl)-1,2,4-oxadiazol-5-yl)piperidine-4-carboxamide (Compound 249): Using 1-(3-(4-methoxyphenyl)-1,2,4-oxadiazol-5-yl)piperidine-4-carboxylic acid (100 mg, 0.330 mmol) and 1-(aminomethyl)-N,N-dimethylcyclohexanamine (67 mg, 0.429 mmol) as the starting material.

Yield 80 mg (55%), as an off-white solid. $^1$H NMR (400 MHz, DMSO) δ 7.84 (d, J=8.8 Hz, 2H), 7.53 (t, J=5.6 Hz, 1H), 7.06 (d, J=8.8 Hz, 2H), 4.12-4.04 (m, 2H), 3.82 (s, 3H), 3.19 (dt, J=3.2, 12.4 Hz, 2H), 3.13 (d, J=6.0 Hz, 2H), 2.50 (s, 1H), 2.23 (s, 6H), 1.85-1.75 (m, 2H), 1.68-1.54 (m, 4H), 1.54-1.38 (m, 3H), 1.38-1.18 (m, 5H). m/z: [ESI$^+$] 442 (M+H)$^+$, (C$_{24}$H$_{35}$N$_5$O$_3$).

N-(4-cyclopropyltetrahydro-2H-pyran-4-yl)-1-(3-(4-methoxyphenyl)-1,2,4-oxadiazol-5-yl)piperidine-4-carboxamide (Compound 291): Using 1-(3-(4-methoxyphenyl)-1,2,4-oxadiazol-5-yl)piperidine-4-carboxylic acid (100 mg, 0.330 mmol) and 4-cyclopropyl-tetrahydro-2H-pyran-4-amine (46 mg, 0.326 mmol) as the starting material.

Yield 56 mg (40%), as an off-white solid. $^1$H NMR (400 MHz, DMSO) δ 7.84 (d, J=8.8 Hz, 2H), 7.15 (s, 1H), 7.05 (d, J=8.8 Hz, 2H), 4.08 (td, J=3.6, 13.2 Hz, 2H), 3.82 (s, 3H), 3.64 (ddd, J=2.0, 4.6, 11.6 Hz, 2H), 3.41 (dt, J=1.6, 11.8 Hz, 2H), 3.18 (dt, J=2.8, 12.8 Hz, 2H), 2.45 (d, J=3.6 Hz, 1H), 2.13 (dd, J=2.0, 13.6 Hz, 2H), 1.81 (dd, J=3.6, 13.6 Hz, 2H), 1.69-1.55 (m, 2H), 1.40 (dt, J=4.4, 12.8 Hz, 2H), 1.19-1.08 (m, 1H), 0.33-0.20 (m, 4H). m/z: [ESI$^+$] 427 (M+H)$^+$, (C$_{23}$H$_{30}$N$_4$O$_4$).

N-(1-cyclohexylcyclopropyl)-1-(3-(4-methoxyphenyl)-1,2,4-oxadiazol-5-yl)piperidine-4-carboxamide (Compound 292): Using 1-(3-(4-methoxyphenyl)-1,2,4-oxadiazol-5-yl)piperidine-4-carboxylic acid (100 mg, 0.330 mmol) and 1-cyclohexylcyclopropanamine (67 mg, 0.481 mmol) as the starting material.

Yield 70 mg (50%), as an off-white solid. $^1$H NMR (400 MHz, DMSO) δ 7.94 (s, 1H), 7.84 (d, J=8.8 Hz, 2H), 7.05 (d, J=8.8 Hz, 2H), 4.10-4.00 (m, 2H), 3.82 (s, 3H), 3.16 (dt, J=2.8, 12.8 Hz, 2H), 2.45 (d, J=11.2 Hz, 1H), 1.75 (dd, J=3.4, 13.2 Hz, 2H), 1.67 (d, J=11.2 Hz, 4H), 1.64-1.50 (m, 3H), 1.18-1.00 (m, 4H), 0.99-0.87 (m, 2H), 0.54 (td, J=2.4, 10.2 Hz, 4H). m/z: [ESI$^+$] 425 (M+H)$^+$, (C$_{24}$H$_{32}$N$_4$O$_3$).

N-(2-(2,2-dimethylpyrrolidin-1-yl)ethyl)-1-(3-(4-methoxyphenyl)-1,2,4-oxadiazol-5-yl)piperidine-4-carboxamide (Compound 269): Using 1-(3-(4-methoxyphenyl)-1,2,4-oxadiazol-5-yl)piperidine-4-carboxylic acid (100 mg, 0.330 mmol) and 2-(2,2-dimethylpyrrolidin-1-yl)ethanamine (56 mg, 0.394 mmol) as the starting material.

Yield 40 mg (28%), as an off-white solid. $^1$H NMR (400 MHz, DMSO) δ 7.84 (d, J=8.8 Hz, 2H), 7.76 (t, J=5.6 Hz, 1H), 7.06 (d, J=8.8 Hz, 2H), 4.05 (td, J=3.6, 13.2 Hz, 2H), 3.82 (s, 3H), 3.19 (dt, J=2.8, 12.8 Hz, 2H), 3.09 (dt, J=4.8, 6.8 Hz, 2H), 2.74-2.65 (m, 2H), 2.41 (d, J=3.6 Hz, 1H), 2.37 (d, J=6.8 Hz, 2H), 1.85-1.75 (m, 2H), 1.72-1.57 (m, 4H), 1.57-1.50 (m, 2H), 0.90 (s, 6H). m/z: [ESI$^+$] 428 (M+H)$^+$, (C$_{23}$H$_{33}$N$_5$O$_3$).

1-(3-(4-Methoxyphenyl)-1,2,4-oxadiazol-5-yl)-N-(1-propylpiperidin-4-yl)piperidine-4-carboxamide (Compound 251): Using 1-(3-(4-methoxyphenyl)-1,2,4-oxadiazol-5-yl)piperidine-4-carboxylic acid (100 mg, 0.330 mmol) and 1-propylpiperidin-4-amine (61 mg, 0.429 mmol) as the starting material.

Yield 50 mg (35%), as an off-white solid. $^1$H NMR (400 MHz, DMSO) δ 7.84 (d, J=8.8 Hz, 2H), 7.75 (d, J=7.8 Hz, 1H), 7.06 (d, J=8.8 Hz, 2H), 4.06 (d, J=13.2 Hz, 2H), 3.82

(s, 3H), 3.57-3.44 (m, 1H), 3.24-3.14 (m, 2H), 2.77 (d, J=11.2 Hz, 2H), 2.43-2.32 (m, 1H), 2.21 (t, J=7.2 Hz, 2H), 1.92 (t, J=11.2 Hz, 2H), 1.78 (d, J=13.2 Hz, 2H), 1.73-1.55 (m, 4H), 1.45-1.35 (m, 4H), 0.84 (t, J=7.2 Hz, 3H). m/z: [ESI$^+$] 428 (M+H)$^+$, ($C_{23}H_{33}N_5O_3$).

1-(3-(4-Methoxyphenyl)-1,2,4-oxadiazol-5-yl)-N-(1-(tetrahydro-2H-pyran-2-yl)ethyl)piperidine-4-carboxamide (Compound 313): Using 1-(3-(4-methoxyphenyl)-1,2,4-oxadiazol-5-yl)piperidine-4-carboxylic acid (100 mg, 0.330 mmol) and 1-(tetrahydro-2H-pyran-2-yl)ethanamine (51 mg, 0.395 mmol) as the starting material.

Yield 30 mg (22%), as an off-white solid. $^1$H NMR (400 MHz, DMSO) δ 7.84 (d, J=8.8, 2H), 7.72 (d, J=8.8 Hz, 0.8H), 7.63 (d, J=8.8 Hz, 0.2H), 7.05 (d, J=8.8, 2H), 4.06 (td, J=3.6, 13.2 Hz, 2H), 3.90 (dd, J=3.2, 11.2 Hz, 1H), 3.82 (s, 3H), 3.75-3.62 (m, 1H), 3.36-3.33 (m, 1H), 3.24-3.12 (m, 2H), 3.11-3.05 (m, 1H), 2.44-2.37 (m, 1H), 1.82-1.73 (m, 3H), 1.66-1.51 (m, 3H), 1.48-1.35 (m, 3H), 1.25-1.08 (m, 1H), 1.01 (dd, J=2.4, 6.8 Hz, 3H). m/z: [ESI$^+$] 415 (M+H)$^+$, ($C_{22}H_{30}N_4O_4$). (1:4 ratio of diastereoisomers).

N-(((1S,2R)-2-hydroxycyclohexyl)methyl)-1-(3-(4-methoxyphenyl)-1,2,4-oxadiazol-5-yl)piperidine-4-carboxamide (Compound 293): Using 1-(3-(4-methoxyphenyl)-1,2,4-oxadiazol-5-yl)piperidine-4-carboxylic acid (79 mg, 0.260 mmol) and (1R,2S)-2-(aminomethyl)cyclohexanol (50 mg, 0.387 mmol) as the starting material.

Yield 60 mg (56%), as an off-white solid. $^1$H NMR (400 MHz, DMSO) δ 7.84 (d, J=8.8 Hz, 2H), 7.78 (t, J=6.0 Hz, 1H), 7.05 (d, J=8.8 Hz, 2H), 4.62 (d, J=4.8 Hz, 1H), 4.06 (td, J=3.6, 13.2 Hz, 2H), 3.82 (s, 3H), 3.30-3.15 (m, 3H), 3.12-2.98 (m, 2H), 2.44 (t, J=3.6 Hz, 1H), 1.80 (td, J=3.6, 12.4 Hz, 3H), 1.72-1.53 (m, 5H), 1.35-1.21 (m, 1H), 1.20-1.00 (m, 3H), 0.97-0.83 (m, 1H). m/z: [ESI$^+$] 415 (M+H)$^+$, ($C_{22}H_{30}N_4O_4$).

N-((1-hydroxycyclohexyl)methyl)-1-(3-(4-methoxyphenyl)-1,2,4-oxadiazol-5-yl)piperidine-4-carboxamide (Compound 270): Using 1-(3-(4-methoxyphenyl)-1,2,4-oxadiazol-5-yl)piperidine-4-carboxylic acid (100 mg, 0.330 mmol) and 1-(aminomethyl)cyclohexanol (55 mg, 0.426 mmol) as the starting material.

Yield 75 mg (55%), as an off-white solid. $^1$H NMR (400 MHz, DMSO) δ 7.84 (d, J=8.8 Hz, 2H), 7.67 (t, J=6.0 Hz, 1H), 7.06 (d, J=8.8 Hz, 2H), 4.22 (s, 1H), 4.07 (td, J=3.6, 13.2 Hz, 2H), 3.82 (s, 3H), 3.19 (dt, J=2.8, 12.8 Hz, 2H), 3.05 (d, J=6.0 Hz, 2H), 2.50-2.38 (m, 1H), 1.81 (dd, J=3.6, 13.6 Hz, 2H), 1.64 (dt, J=4.4, 12.4 Hz, 2H), 1.59-1.49 (m, 2H), 1.49-1.35 (m, 5H), 1.32-1.13 (m, 3H). m/z: [ESI$^+$] 415 (M+H)$^+$, ($C_{22}H_{30}N_4O_3$).

1-(3-(4-Methoxyphenyl)-1,2,4-oxadiazol-5-yl)-N-(2-methyl-2-azaspiro[3.3]heptan-6-yl)piperidine-4-carboxamide (Compound 271): Using 1-(3-(4-methoxyphenyl)-1,2,4-oxadiazol-5-yl)piperidine-4-carboxylic acid (100 mg, 0.330 mmol) and 2-methyl-2-azaspiro[3.3]heptan-6-amine (50 mg, 0.396 mmol) as the starting material.

Yield 20 mg (15%), as an off-white solid. $^1$H NMR (400 MHz, DMSO) δ 8.04 (d, J=7.2 Hz, 1H), 7.84 (d, J=8.8 Hz, 2H), 7.05 (d, J=8.8 Hz, 2H), 4.10-3.98 (m, 3H), 3.82 (s, 3H), 3.23-3.15 (m, 2H), 3.13 (s, 2H), 3.03 (s, 2H), 2.54 (s, 1H), 2.30 (td, J=2.0, 7.6 Hz, 2H), 2.15 (s, 3H), 2.00-1.91 (m, 2H), 1.82-1.74 (m, 2H), 1.65-1.50 (m, 2H). m/z: [ESI$^+$] 412 (M+H)$^+$, ($C_{22}H_{29}N_5O_3$).

N-(2-(cyclopropyl(methyl)amino)ethyl)-1-(3-(4-methoxyphenyl)-1,2,4-oxadiazol-5-yl)piperidine-4-carboxamide (Compound 314): Using 1-(3-(4-methoxyphenyl)-1,2,4-oxadiazol-5-yl)piperidine-4-carboxylic acid (60 mg, 0.198 mmol) and N$^1$-cyclopropyl-N$^1$-methylethane-1,2-diamine (27 mg, 0.236 mmol) as the starting material.

Yield 20 mg (25%), as an off-white solid. $^1$H NMR (400 MHz, DMSO) δ 7.84 (d, J=8.8 Hz, 2H), 7.74 (t, J=5.6 Hz, 1H), 7.05 (d, J=8.8 Hz, 2H), 4.11-4.02 (m, 2H), 3.82 (s, 3H), 3.23-3.12 (m, 4H), 2.52-2.37 (m, 3H), 2.25 (s, 3H), 1.78 (dd, J=3.2, 13.6 Hz, 2H), 1.68-1.54 (m, 3H), 0.41 (td, J=2.8, 6.4 Hz, 2H), 0.30-0.24 (m, 2H). m/z: [ESI$^+$] 400 (M+H)$^+$, ($C_{21}H_{29}N_5O_3$).

(R)—N-((4,4-dimethyloxetan-2-yl)methyl)-1-(3-(4-methoxyphenyl)-1,2,4-oxadiazol-5-yl)piperidine-4-carboxamide (Compound 272): Using 1-(3-(4-methoxyphenyl)-1,2,4-oxadiazol-5-yl)piperidine-4-carboxylic acid (100 mg, 0.330 mmol) and (R)-(4,4-dimethyloxetan-2-yl)methanamine (46 mg, 0.399 mmol) as the starting material.

Yield 58 mg (44%), as an off-white solid. $^1$H NMR (400 MHz, DMSO) δ 8.06 (t, J=5.6 Hz, 1H), 7.84 (d, J=8.8 Hz, 2H), 7.06 (d, J=8.8 Hz, 2H), 4.52-4.43 (m, 1H), 4.06 (td, J=3.6, 13.2 Hz, 2H), 3.82 (s, 3H), 3.29-3.15 (m, 4H), 2.50-2.44 (m, 1H), 2.28 (dd, J=7.6, 10.8 Hz, 1H), 2.09 (dd, J=7.2, 10.8 Hz, 1H), 1.86-1.76 (m, 2H), 1.70-1.50 (m, 2H), 1.36 (s, 3H), 1.31 (s, 3H). m/z: [ESI$^+$] 401 (M+H)$^+$, ($C_{21}H_{28}N_4O_4$).

(S)—N-(1-hydroxy-4-methylpentan-3-yl)-1-(3-(4-methoxyphenyl)-1,2,4-oxadiazol-5-yl)piperidine-4-carboxamide (Compound 315): Using 1-(3-(4-methoxyphenyl)-1,2,4-oxadiazol-5-yl)piperidine-4-carboxylic acid (100 mg, 0.330 mmol) and (S)-3-amino-4-methylpentan-1-ol (50 mg, 0.427 mmol) as the starting material.

Yield 13 mg (10%), as an off-white solid. $^1$H NMR (400 MHz, DMSO) δ 7.84 (d, J=8.8, 2H), 7.54 (d, J=7.2 Hz, 1H), 7.06 (d, J=8.8 Hz, 2H), 4.34 (t, J=5.2 Hz, 1H), 4.13-4.02 (m, 2H), 3.82 (s, 3H), 3.70-3.60 (m, 1H), 3.44-3.38 (m, 1H), 3.31-3.27 (m, 1H), 3.25-3.14 (m, 2H), 2.42 (d, J=3.6 Hz, 1H), 1.79 (d, J=12.4 Hz, 2H), 1.72-1.54 (m, 4H), 1.49-1.36 (m, 1H), 0.82 (d, J=6.8 Hz, 6H). m/z: [ESI$^+$] 403 (M+H)$^+$, ($C_{21}H_{30}N_4O_4$).

N-(3-hydroxy-2,2-dimethylcyclobutyl)-1-(3-(4-methoxyphenyl)-1,2,4-oxadiazol-5-yl)piperidine-4-carboxamide (Compound 294): Using 1-(3-(4-methoxyphenyl)-1,2,4-oxadiazol-5-yl)piperidine-4-carboxylic acid (100 mg, 0.330 mmol) and 3-amino-2,2-dimethylcyclobutanol (50 mg, 0.434 mmol) as the starting material.

Yield 43 mg (33%), as an off-white solid. $^1$H NMR (400 MHz, DMSO) δ 7.87 (s, 0.5H), 7.85-7.81 (m, 2H), 7.72 (d, J=7.4 Hz, 0.5H), 7.08-7.02 (m, 2H), 4.82 (t, J=5.2 Hz, 1H), 4.06 (td, J=3.6, 12.8 Hz, 2H), 3.82 (s, 4H), 3.54-3.42 (m, 1H), 3.25-3.13 (m, 2H), 2.42 (td, J=3.6, 11.2 Hz, 1H), 2.36-2.26 (m, 0.5H), 2.12-1.96 (m, 1H), 1.87-1.70 (m, 2.5H), 1.68-1.53 (m, 2H), 1.02 (s, 1.5H), 0.97 (s, 1.5H), 0.82 (s, 1.5H), 0.78 (s, 1.5H). m/z: [ESI$^+$] 401 (M+H)$^+$, ($C_{21}H_{28}N_4O_4$). (1:1 ratio of cis/trans isomers).

N-((2-(dimethylamino)-2,3-dihydro-1H-inden-2-yl)methyl)-1-(3-(4-methoxyphenyl)-1,2,4-oxadiazol-5-yl)piperidine-4-carboxamide formate (Compound 296): Using 1-(3-(4-methoxyphenyl)-1,2,4-oxadiazol-5-yl)piperidine-4-carboxylic acid (100 mg, 0.330 mmol) and 2-(aminomethyl)-N,N-dimethyl-2,3-dihydro-1H-inden-2-amine (75 mg, 0.394 mmol) as the starting material.

Yield 40 mg (23%), as an off-white solid. $^1$H NMR (400 MHz, DMSO) δ 8.16 (s, 1H, HCOOH), 7.84 (d, J=8.8 Hz, 2H), 7.64 (t, J=5.6 Hz, 1H), 7.08 (d, J=8.8 Hz, 2H), 7.07 (d, J=7.6 Hz, 2H), 7.05 (d, J=8.8 Hz, 2H) 4.00 (td, J=3.6, 13.2 Hz, 2H), 3.82 (s, 3H), 3.31 (s, 2H), 3.17-3.10 (m, 2H), 3.00 (d, J=16.4 Hz, 2H), 2.86 (d, J=16.4 Hz, 2H), 2.50-2.41 (m, 1H), 2.25 (s, 6H), 1.65 (dd, J=3.6, 13.6 Hz, 1H), 1.54-1.40 (m, 2H). m/z: [ESI$^+$] 476 (M+H)$^+$, ($C_{27}H_{33}N_5O_3$).

1-(3-(4-Methoxyphenyl)-1,2,4-oxadiazol-5-yl)-N-((4-phenyltetrahydro-2H-pyran-4-yl)methyl)piperidine-4-carboxamide (Compound 273): Using 1-(3-(4-methoxyphenyl)-1,2,4-oxadiazol-5-yl)piperidine-4-carboxylic acid (100 mg, 0.330 mmol) and (4-phenyltetrahydro-2H-pyran-4-yl)methanamine (76 mg, 0.397 mmol) as the starting material.

Yield 80 mg (51%), as an off-white solid. $^1$H NMR (400 MHz, DMSO) δ 7.83 (d, J=8.8 Hz, 2H), 7.55 (t, J=6.4 Hz, 1H), 7.35 (m, 4H), 7.25-7.18 (m, 1H), 7.05 (d, J=8.8 Hz, 2H), 4.00 (td, J=3.6, 13.6 Hz, 2H), 3.82 (s, 3H), 3.80-3.65 (m, 2H), 3.39-3.34 (m, 2H), 3.25 (d, J=6.4 Hz, 2H), 3.14 (dt, J=2.8, 12.8 Hz, 2H), 2.40-2.30 (m, 1H), 1.99 (td, J=3.6, 14.4 Hz, 2H), 1.90-1.70 (m, 2H), 1.72-1.64 (m, 2H), 1.57-1.44 (m, 2H). m/z: [ESI$^+$] 477 (M+H)$^+$, (C$_{27}$H$_{32}$N$_4$O$_4$).

N-(3-hydroxy-3-methylbutan-2-yl)-1-(3-(4-methoxyphenyl)-1,2,4-oxadiazol-5-yl)piperidine-4-carboxamide (Compound 297): Using 1-(3-(4-methoxyphenyl)-1,2,4-oxadiazol-5-yl)piperidine-4-carboxylic acid (100 mg, 0.330 mmol) and 3-amino-2-methylbutan-2-ol (41 mg, 0.397 mmol) as the starting material.

Yield 25 mg (20%), as an off-white solid. $^1$H NMR (400 MHz, DMSO) δ 7.85 (d, J=8.8 Hz, 2H), 7.47 (d, J=7.2 Hz, 1H), 7.05 (d, J=8.8 Hz, 2H), 4.32 (s, 1H), 4.07 (td, J=3.6, 13.6 Hz, 2H), 3.82 (s, 3H), 3.73 (qd, J=6.8, 9.2 Hz, 1H), 3.23-3.10 (m, 2H), 2.40-2.35 (m, 1H), 1.78 (td, J=3.6, 14.4 Hz, 2H), 1.70-1.50 (m, 2H), 1.06-0.99 (m, 9H). m/z: [ESI$^+$] 389 (M+H)$^+$, (C$_{20}$H$_{28}$N$_4$O$_4$).

1-(3-(4-Methoxyphenyl)-1,2,4-oxadiazol-5-yl)-N-(tetrahydro-2H-pyran-4-yl)piperidine-4-carboxamide (Compound 254): Using 1-(3-(4-methoxyphenyl)-1,2,4-oxadiazol-5-yl)piperidine-4-carboxylic acid (200 mg, 0.659 mmol) and tetrahydro-2H-pyran-4-amine (80 mg, 0.791 mmol) as the starting material.

Yield 50 mg (20%), as an off-white solid. $^1$H NMR (400 MHz, DMSO) δ 7.87-7.81 (m, 3H), 7.05 (d, J=8.8 Hz, 2H), 4.07 (td, J=3.6, 13.2 Hz, 2H), 3.82-3.80 (m, 5H), 3.80-3.70 (m, 1H), 3.37-3.28 (m, 2H), 3.19 (dt, J=2.8, 12.8 Hz, 2H), 2.45-2.33 (m, 1H), 1.84-1.76 (m, 2H), 1.72-1.55 (m, 4H), 1.45-1.30 (m, 2H). m/z: [ESI$^+$] 387 (M+H)$^+$, (C$_{20}$H$_{26}$N$_4$O$_4$).

1-(3-(4-Methoxyphenyl)-1,2,4-oxadiazol-5-yl)-N-((tetrahydrofuran-3-yl)methyl)piperidine-4-carboxamide (Compound 255): Using 1-(3-(4-methoxyphenyl)-1,2,4-oxadiazol-5-yl)piperidine-4-carboxylic acid (150 mg, 0.495 mmol) and (tetrahydrofuran-3-yl)methanamine (60 mg, 0.593 mmol) as the starting material.

Yield 120 mg (63%), as a light yellow solid. $^1$H NMR (400 MHz, DMSO) δ 7.98 (t, J=5.6 Hz, 1H), 7.84 (d, J=8.8 Hz, 2H), 7.05 (d, J=8.8 Hz, 2H), 4.06 (td, J=3.6, 13.2 Hz, 2H), 3.82 (s, 3H), 3.75-3.56 (m, 3H), 3.37 (dd, J=5.6, 8.4 Hz, 1H), 3.20 (dt, J=2.8, 12.8 Hz, 2H), 3.12-2.99 (m, 2H), 2.46-2.26 (m, 2H), 1.99-1.86 (m, 1H), 1.84-1.76 (m, 2H), 1.69-1.46 (m, 3H). m/z: [ESI$^+$] 387 (M+H)$^+$, (C$_{20}$H$_{26}$N$_4$O$_4$).

N-((1s,3s)-3-methoxycyclobutyl)-1-(3-(4-methoxyphenyl)-1,2,4-oxadiazol-5-yl)piperidine-4-carboxamide (Compound 256): Using 1-(3-(4-methoxyphenyl)-1,2,4-oxadiazol-5-yl)piperidine-4-carboxylic acid (150 mg, 0.495 mmol) and (1s,3s)-3-methoxycyclobutan-1-amine (65 mg, 0.643 mmol) as the starting material.

Yield 80 mg (42%), as a light yellow solid. $^1$H NMR (400 MHz, DMSO) δ 8.07 (d, J=7.6 Hz, 1H), 7.84 (d, J=8.8 Hz, 2H), 7.05 (d, J=8.8 Hz, 2H), 4.06 (td, J=3.6, 13.2 Hz, 2H), 3.90-3.70 (m, 4H), 3.60-3.50 (m, 1H), 3.19 (dt, J=2.8, 12.8 Hz, 2H), 3.12 (s, 3H), 2.54-2.49 (m, 2H), 2.43-2.30 (m, 1H), 1.84-1.69 (m, 4H), 1.65-1.52 (m, 2H). m/z: [ESI$^+$] 387 (M+H)$^+$, (C$_{20}$H$_{26}$N$_4$O$_4$).

N-((1R,3S)-3-hydroxycyclopentyl)-1-(3-(4-methoxyphenyl)-1,2,4-oxadiazol-5-yl)piperidine-4-carboxamide (Compound 274): Using 1-(3-(4-methoxyphenyl)-1,2,4-oxadiazol-5-yl)piperidine-4-carboxylic acid (150 mg, 0.495 mmol) and (1S,3R)-3-aminocyclopentan-1-ol (75 mg, 0.741 mmol) as the starting material.

Yield 80 mg (42%), as a light yellow solid. $^1$H NMR (400 MHz, DMSO) δ 7.91-7.83 (m, 3H), 7.06 (d, J=8.8 Hz, 2H), 4.64 (d, J=4.0 Hz, 1H), 4.06 (dd, J=4.4, 12.4 Hz, 3H), 4.03-3.89 (m, 1H), 3.82 (s, 3H), 3.18 (dt, J=2.8, 12.8 Hz, 2H), 2.45-2.38 (m, 1H), 2.08 (ddd, J=6.4, 8.0, 13.6 Hz, 1H), 1.89-1.78 (m, 3H), 1.71-1.46 (m, 5H), 1.31 (ddd, J=5.2, 6.8, 12.8 Hz, 1H). m/z: [ESI$^+$] 387 (M+H)$^+$, (C$_{20}$H$_{26}$N$_4$O$_4$).

1-(3-(4-Methoxyphenyl)-1,2,4-oxadiazol-5-yl)-N-(2-(pyrrolidin-1-yl)benzyl)piperidine-4-carboxamide (Compound 257): Using 1-(3-(4-methoxyphenyl)-1,2,4-oxadiazol-5-yl)piperidine-4-carboxylic acid (100 mg, 0.330 mmol) and (2-(pyrrolidin-1-yl)phenyl)methanamine (70 mg, 0.397 mmol) as the starting material.

Yield 55 mg (36%), as an off-white solid. $^1$H NMR (400 MHz, DMSO) δ 8.25 (t, J=5.6 Hz, 1H), 7.84 (d, J=8.8 Hz, 2H), 7.16-7.14 (m, 2H), 7.05 (d, J=8.8 Hz, 2H), 6.94 (dd, J=1.2, 8.8 Hz, 1H), 6.89 (dd, J=1.2, 7.6 Hz, 1H), 4.29 (d, J=5.6 Hz, 2H), 4.09 (td, J=3.6, 13.2 Hz, 2H), 3.82 (s, 3H), 3.22 (dt, J=2.8, 12.8 Hz, 2H), 3.13-3.02 (m, 4H), 2.58-2.52 (m, 1H), 1.95-1.80 (m, 6H), 1.74-1.58 (m, 2H). m/z: [ESI$^+$] 462 (M+H)$^+$, (C$_{26}$H$_{31}$N$_5$O$_3$).

(S)—N-(1-benzylpyrrolidin-3-yl)-1-(3-(4-methoxyphenyl)-1,2,4-oxadiazol-5-yl)piperidine-4-carboxamide (Compound 316): Using 1-(3-(4-methoxyphenyl)-1,2,4-oxadiazol-5-yl)piperidine-4-carboxylic acid (100 mg, 0.330 mmol) and (S)-1-benzylpyrrolidin-3-amine (88 mg, 0.499 mmol) as the starting material.

Yield 65 mg (43%), as an off-white solid. $^1$H NMR (400 MHz, DMSO) δ 8.02 (d, J=6.8 Hz, 1H), 7.84 (d, J=8.8 Hz, 2H), 7.40-7.30 (m, 4H), 7.26-7.20 (m, 1H), 7.05 (d, J=8.8 Hz, 2H), 4.20-4.10 (m, 1H), 4.05 (td, J=3.6, 1.32 Hz, 2H), 3.82 (s, 3H), 3.56 (d, J=3.6 Hz, 2H), 3.18 (dt, J=3.2, 12.8 Hz, 2H), 2.64-2.57 (m, 2H), 2.40 (m, 2H), 2.27 (dd, J=4.8, 9.2 Hz, 1H), 2.08 (m, 1H), 1.82-1.73 (m, 2H), 1.66-1.51 (m, 3H). m/z: [ESI$^+$] 462 (M+H)$^+$, (C$_{26}$H$_{31}$N$_5$O$_3$).

N-(3,3-difluorocyclopentyl)-1-(3-(4-methoxyphenyl)-1,2,4-oxadiazol-5-yl)piperidine-4-carboxamide (Compound 275): Using 1-(3-(4-methoxyphenyl)-1,2,4-oxadiazol-5-yl)piperidine-4-carboxylic acid (100 mg, 0.330 mmol) and 3,3-difluorocyclopentan-1-amine (48 mg, 0.396 mmol) as the starting material.

Yield 50 mg (37%), as an off-white solid. $^1$H NMR (400 MHz, DMSO) δ 8.10 (d, J=7.2 Hz, 1H), 7.84 (d, J=8.8 Hz, 2H), 7.05 (d, J=8.8 Hz, 2H), 4.22-4.12 (m, 1H), 4.06 (td, J=3.6, 13.2 Hz, 2H), 3.82 (s, 3H), 3.20 (dt, J=2.8, 12.8 Hz, 2H), 2.44-2.35 (m, 2H), 2.28-2.14 (m, 1H), 2.12-1.88 (m, 3H), 1.85-1.76 (m, 2H), 1.71-1.54 (m, 3H). $^{19}$F NMR (376 MHz, DMSO) δ −88.09, −88.10, −88.12. m/z: [ESI$^+$] 407 (M+H)$^+$, (C$_{20}$H$_{24}$F$_2$N$_4$O$_3$).

(S)-1-(3-(4-methoxyphenyl)-1,2,4-oxadiazol-5-yl)-N-(2-methoxypropyl)piperidine-4-carboxamide (Compound 276): Using 1-(3-(4-methoxyphenyl)-1,2,4-oxadiazol-5-yl)piperidine-4-carboxylic acid (150 mg, 0.495 mmol) and (S)-2-methoxypropan-1-amine (53 mg, 0.595 mmol) as the starting material.

Yield 120 mg (65%), as a light yellow solid. $^1$H NMR (400 MHz, DMSO) δ 7.90 (t, J=5.6 Hz, 1H), 7.84 (d, J=8.8 Hz, 2H), 7.05 (d, J=8.8 Hz, 2H), 4.06 (td, J=3.6, 13.2 Hz, 2H), 3.82 (s, 3H), 3.35 (s, 1H), 3.24 (s, 3H), 3.18 (dd, J=2.8, 12.8 Hz, 2H), 3.10 (dt, J=3.6, 5.6 Hz, 2H), 2.48-2.44 (m, 1H), 1.80 (dd, J=3.6, 13.6 Hz, 2H), 1.68-1.52 (m, 2H), 1.03 (d, J=6.4 Hz, 3H). m/z: [ESI$^+$] 375 (M+H)$^+$, (C$_{19}$H$_{26}$N$_4$O$_4$).

1-(3-(4-Methoxyphenyl)-1,2,4-oxadiazol-5-yl)-N-(1-(4-methylthiazol-2-yl)cyclobutyl)piperidine-4-carboxamide (Compound 298): Using 1-(3-(4-methoxyphenyl)-1,2,4- oxadiazol-5-yl)piperidine-4-carboxylic acid (100 mg, 0.330 mmol) and 1-(4-methylthiazol-2-yl)cyclobutan-1-amine (67 mg, 0.398 mmol) as the starting material.

Yield 40 mg (27%), as an off-white solid. $^1$H NMR (400 MHz, DMSO) δ 8.87 (s, 1H), 7.84 (d, J=8.8 Hz, 2H), 7.05-7.01 (m, 3H), 4.07 (dt, J=3.6, 13.2 Hz, 2H), 3.82 (s, 3H), 3.24 (dt, J=2.8, 12.8 Hz, 2H), 2.63-2.55 (m, 3H), 2.43-2.37 (m, 2H), 2.34 (s, 3H), 2.05-1.90 (m, 2H), 1.87 (dd, J=3.6, 13.6 Hz, 2H), 1.69-1.52 (m, 2H). m/z: [ESI$^+$] 454 (M+H)$^+$, ($C_{23}H_{27}N_5O_3S$).

1-(3-(4-Methoxyphenyl)-1,2,4-oxadiazol-5-yl)-N-(4,4,4-trifluoro-1-hydroxybutan-2-yl)piperidine-4-carboxamide (Compound 299): Using 1-(3-(4-methoxyphenyl)-1,2,4-oxadiazol-5-yl)piperidine-4-carboxylic acid (100 mg, 0.330 mmol) and 2-amino-4,4,4-trifluorobutan-1-ol (52 mg, 0.363 mmol) as the starting material.

Yield 33 mg (23%), as an off-white solid. $^1$H NMR (400 MHz, DMSO) δ 7.88 (d, J=8.8 Hz, 1H), 7.84 (d, J=8.8 Hz, 2H), 7.04 (d, J=8.8 Hz, 2H), 5.00 (t, J=5.6 Hz, 1H), 4.05 (dd, J=3.6, 12.4 Hz, 3H), 3.82 (s, 3H), 3.41-3.35 (m, 1H), 3.27-3.14 (m, 3H), 2.43-2.36 (m, 3H), 1.79 (dd, J=3.6, 13.6 Hz, 2H), 1.70-1.50 (m, 2H). $^{19}$F NMR (376 MHz, DMSO) δ −62.56. m/z: [ESI$^+$] 429 (M+H)$^+$, ($C_{19}H_{23}F_3N_4O_4$).

N-(3-isopropoxybenzyl)-1-(3-(4-methoxyphenyl)-1,2,4-oxadiazol-5-yl)piperidine-4-carboxamide (Compound 300): Using 1-(3-(4-methoxyphenyl)-1,2,4-oxadiazol-5-yl)piperidine-4-carboxylic acid (100 mg, 0.330 mmol) and (3-isopropoxyphenyl)methanamine (65 mg, 0.393 mmol) as the starting material.

Yield 55 mg (37%), as an off-white solid. $^1$H NMR (400 MHz, DMSO) δ 8.38 (t, J=6.0 Hz, 1H), 7.84 (d, J=8.8 Hz, 2H), 7.24-7.16 (m, 1H), 7.05 (d, J=8.8 Hz, 2H), 6.81-6.74 (m, 3H), 4.61-4.52 (m, 1H), 4.24 (d, J=4.4 Hz, 2H), 4.08 (td, J=3.6, 13.2 Hz, 2H), 3.82 (s, 3H), 3.21 (dt, J=2.8, 12.8 Hz, 2H), 2.54 (m, 1H), 1.85 (dd, J=3.6, 13.6 Hz, 2H), 1.72-1.57 (m, 2H), 1.25 (d, J=6.0 Hz, 6H). m/z: [ESI$^+$] 451 (M+H)$^+$, ($C_{25}H_{30}N_4O_4$).

N-(3-benzyloxetan-3-yl)-1-(3-(4-methoxyphenyl)-1,2,4-oxadiazol-5-yl)piperidine-4-carboxamide (Compound 277): Using 1-(3-(4-methoxyphenyl)-1,2,4-oxadiazol-5-yl)piperidine-4-carboxylic acid (40 mg, 0.132 mmol) and 3-benzyloxetan-3-amine (26 mg, 0.159 mmol) as the starting material.

Yield 35 mg (59%), as an off-white solid. $^1$H NMR (400 MHz, DMSO) δ 8.35 (s, 1H), 7.84 (d, J=8.8 Hz, 2H), 7.31 (dd, J=6.4, 8.0 Hz, 2H), 7.27-7.19 (m, 1H), 7.17-7.12 (m, 2H), 7.05 (d, J=8.8 Hz, 2H), 4.55 (d, J=6.4 Hz, 2H), 4.43 (d, J=6.4 Hz, 2H), 4.07 (td, J=3.6, 13.2 Hz, 2H), 3.82 (s, 3H), 3.26 (s, 2H), 3.19 (dt, J=2.8, 12.8 Hz, 2H), 2.45-2.40 (m, 1H), 1.87-1.74 (m, 2H), 1.71-1.57 (m, 2H). m/z: [ESI$^+$] 449 (M+H)$^+$, ($C_{25}H_{28}N_4O_4$).

N-(1-(hydroxy(phenyl)methyl)cyclopropyl)-1-(3-(4-methoxyphenyl)-1,2,4-oxadiazol-5-yl)piperidine-4-carboxamide (Compound 258): Using 1-(3-(4-methoxyphenyl)-1,2,4-oxadiazol-5-yl)piperidine-4-carboxylic acid (100 mg, 0.330 mmol) and (1-aminocyclopropyl)(phenyl)methanol (70 mg, 0.429 mmol) as the starting material.

Yield 85 mg (57%), as an off-white solid. $^1$H NMR (400 MHz, DMSO) δ 8.09 (s, 1H), 7.84 (d, J=8.8 Hz, 2H), 7.37-7.23 (m, 5H), 7.05 (d, J=8.8 Hz, 2H), 5.78 (d, J=5.6 Hz, 1H), 4.58 (d, J=5.6 Hz, 1H), 4.02 (td, J=3.6, 13.2 Hz, 2H), 3.82 (s, 3H), 3.20-3.05 (m, 2H), 2.34-2.22 (m, 1H), 1.72-1.63 (m, 2H), 1.59-1.48 (m, 2H), 1.09-1.00 (m, 1H), 1.00-0.85 (m, 1H), 0.66-0.51 (m, 2H). m/z: [ESI$^+$] 449 (M+H)$^+$, ($C_{25}H_{28}N_4O_4$).

1-(3-(4-methoxyphenyl)-1,2,4-oxadiazol-5-yl)-N-((5,6,7,8-tetrahydroquinolin-8-yl)methyl)piperidine-4-carboxamide (Compound 301): Using 1-(3-(4-methoxyphenyl)-1,2,4-oxadiazol-5-yl)piperidine-4-carboxylic acid (100 mg, 0.330 mmol) and (5,6,7,8-tetrahydroquinolin-8-yl)methanamine (64 mg, 0.394 mmol) as the starting material.

Yield 40 mg (27%), as an off-white solid. $^1$H NMR (400 MHz, DMSO) δ 8.35 (dd, J=1.6, 4.8 Hz, 1H), 8.00-7.92 (m, 1H), 7.84 (d, J=8.8 Hz, 2H), 7.46 (dd, J=1.6, 7.6 Hz, 1H), 7.13 (dd, J=4.8, 7.6 Hz, 1H), 7.05 (d, J=8.8 Hz, 2H), 4.07 (td, J=3.6, 13.2 Hz, 2H), 3.82 (s, 3H), 3.64 (td, J=4.8, 13.2 Hz, 1H), 3.23 (m, 3H), 2.96-2.85 (m, 1H), 2.76-2.66 (m, 2H), 2.51-2.44 (m, 1H), 1.91-1.76 (m, 4H), 1.72-1.55 (m, 4H). m/z: [ESI$^+$] 448 (M+H)$^+$, ($C_{25}H_{29}N_5O_3$).

1-(3-(4-Methoxyphenyl)-1,2,4-oxadiazol-5-yl)-N-(1-methyl-1,2,3,4-tetrahydroquinolin-4-yl)piperidine-4-carboxamide (Compound 302): Using 1-(3-(4-methoxyphenyl)-1,2,4-oxadiazol-5-yl)piperidine-4-carboxylic acid (60 mg, 0.198 mmol) and 1-methyl-1,2,3,4-tetrahydroquinolin-4-amine (49 mg, 0.302 mmol) as the starting material.

Yield 60 mg (68%), as an off-white solid. $^1$H NMR (400 MHz, DMSO) δ 8.21 (d, J=8.4 Hz, 1H), 7.84 (d, J=8.8 Hz, 2H), 7.13-7.02 (m, 3H), 6.96 (dd, J=1.6, 7.6 Hz, 1H), 6.66-6.54 (m, 2H), 4.90 (td, J=5.6, 8.0 Hz, 1H), 4.07 (td, J=3.6, 12.6 Hz, 2H), 3.82 (s, 3H), 3.20-3.16 (m, 4H), 2.85 (s, 3H), 2.50-2.43 (m, 1H), 1.97-1.88 (m, 1H), 1.90-1.70 (m, 1H), 1.76-1.60 (m, 2H). m/z: [ESI$^+$] 448 (M+H)$^+$, ($C_{25}H_{29}N_5O_3$).

N-(chroman-2-ylmethyl)-1-(3-(4-methoxyphenyl)-1,2,4-oxadiazol-5-yl)piperidine-4-carboxamide (Compound 278): Using 1-(3-(4-methoxyphenyl)-1,2,4-oxadiazol-5-yl)piperidine-4-carboxylic acid (100 mg, 0.330 mmol) and chroman-2-ylmethanamine (65 mg, 0.398 mmol) as the starting material.

Yield 45 mg (30%), as an off-white solid. $^1$H NMR (400 MHz, DMSO) δ 8.13 (t, J=5.6 Hz, 1H), 7.85 (d, J=8.8 Hz, 2H), 7.10-7.01 (m, 4H), 6.81 (dd, J=1.2, 7.2 Hz, 1H), 6.75 (d, J=8.0 Hz, 1H), 4.02-4.10 (m, 3H), 3.82 (s, 3H), 3.39 (dd, J=6.0, 13.6 Hz, 1H), 3.30 (d, J=5.6 Hz, 1H), 3.21 (dt, J=3.2, 12.8 Hz, 2H), 2.85-2.72 (m, 2H), 2.47 (d, J=3.6 Hz, 1H), 1.95-1.99 (m, 1H), 1.87-1.79 (m, 2H), 1.70-1.55 (m, 3H). m/z: [ESI$^+$] 449 (M+H)$^+$, ($C_{25}H_{28}N_4O_4$).

N-(isochroman-1-ylmethyl)-1-(3-(4-methoxyphenyl)-1,2,4-oxadiazol-5-yl)piperidine-4-carboxamide (Compound 303): Using 1-(3-(4-Methoxyphenyl)-1,2,4-oxadiazol-5-yl)piperidine-4-carboxylic acid (100 mg, 0.330 mmol) and isochroman-1-ylmethanamine (65 mg, 0.398 mmol) as the starting material.

Yield 55 mg (37%), as an off-white solid. $^1$H NMR (400 MHz, DMSO) δ 8.04 (t, J=5.6 Hz, 1H), 7.83 (d, J=8.8 Hz, 2H), 7.21-7.10 (m, 4H), 7.05 (d, J=8.8 Hz 2H), 4.73 (dd, J=3.0, 8.2 Hz, 1H), 4.10-3.95 (m, 3H), 3.82 (s, 3H), 3.70 (ddd, J=4.2, 8.4, 11.2 Hz, 1H), 3.58 (ddd, J=3.2, 5.6, 14.0 Hz, 1H), 3.42-3.37 (m, 1H), 3.16-3.19 (m, 2H), 2.86 (ddd, J=5.2, 8.4, 16.4 Hz, 1H), 2.72 (t, J=4.8 Hz, 1H), 2.45 (d, J=3.6 Hz, 1H), 1.79 (dd, J=3.6, 13.6 Hz, 1H), 1.74-1.65 (m, 1H), 1.65-1.57 (m, 1H), 1.56-1.48 (m, 1H). m/z: [ESI$^+$] 449 (M+H)$^+$, ($C_{25}H_{28}N_4O_4$).

N-(2-(dimethylamino)-2-phenylethyl)-1-(3-(4-methoxyphenyl)-1,2,4-oxadiazol-5-yl)piperidine-4-carboxamide hemiformate (Compound 304): Using 1-(3-(4-methoxyphenyl)-1,2,4-oxadiazol-5-yl)piperidine-4-carboxylic acid (100 mg, 0.330 mmol) and $N^1,N^1$-dimethyl-1-phenylethane-1,2-diamine (65 mg, 0.396 mmol) as the starting material.

Yield 47 mg (30%), as an off-white solid. $^1$H NMR (400 MHz, DMSO) δ 8.15 (s, 0.7H, HCOOH), 7.83 (d, J=8.8 Hz, 2H), 7.67 (t, J=5.6 Hz, 1H), 7.33 (dd, J=6.4, 8.0 Hz, 2H), 7.28 (d, J=4.0 Hz, 1H), 7.22 (dd, J=6.4, 8.0 Hz, 2H), 7.06 (d, J=8.8 Hz, 2H), 3.97-3.82 (m, 2H), 3.82 (s, 3H), 3.57-3.52

(m, 1H), 3.45 (t, J=6.8 Hz, 2H), 3.17-3.10 (m, 2H), 2.38 (dd, J=3.6, 7.8 Hz, 1H), 2.09 (s, 6H), 1.65 (dt, J=3.6, 13.6 Hz, 2H), 1.48-1.56 (m, 2H). m/z: [ESI$^+$] 450 (M+H)$^+$, ($C_{25}H_{31}N_5O_3$).

(S)—N-(sec-butyl)-1-(3-(4-methoxyphenyl)-1,2,4-oxadiazol-5-yl)piperidine-4-carboxamide (Compound 279): Using 1-(3-(4-methoxyphenyl)-1,2,4-oxadiazol-5-yl)piperidine-4-carboxylic acid (100 mg, 0.330 mmol) and (S)-butan-2-amine (29 mg, 0.397 mmol) as the starting material.

Yield 20 mg (17%), as an off-white solid. $^1$H NMR (400 MHz, DMSO) δ 7.85 (d, J=8.8 Hz, 2H), 7.64 (d, J=8.2 Hz, 1H), 7.05 (d, J=8.8 Hz, 2H), 4.07 (td, J=3.6, 13.2 Hz, 2H), 3.82 (s, 3H), 3.73-3.60 (m, 1H), 3.19-3.16 (m, 2H), 2.40 (td, J=3.6, 11.6 Hz, 1H), 1.85-1.74 (m, 2H), 1.69-1.56 (m, 2H), 1.44-1.33 (m, 2H), 1.01 (d, J=6.8 Hz, 3H), 0.82 (t, J=7.6 Hz, 3H). m/z: [ESI$^+$] 359 (M+H)$^+$, ($C_{19}H_{26}N_4O_3$).

1-(3-(4-Methoxyphenyl)-1,2,4-oxadiazol-5-yl)-N-(1-phenylpyrrolidin-3-yl)piperidine-4-carboxamide (Compound 346): Using 1-(3-(4-methoxyphenyl)-1,2,4-oxadiazol-5-yl)piperidine-4-carboxylic acid (70 mg, 0.231 mmol) and 1-phenylpyrrolidin-3-amine (45 mg, 0.277 mmol) as the starting material.

Yield 40 mg (39%), as an off-white solid. $^1$H NMR (400 MHz, DMSO) δ 8.21 (d, J=6.8 Hz, 1H), 7.85 (d, J=8.8 Hz, 2H), 7.17 (t, J=8.0 Hz, 2H), 7.06 (d, J=8.8 Hz, 2H), 6.60 (t, J=3.8 Hz, 1H), 6.54 (td, J=1.2, 8.8 Hz, 2H), 4.44-4.34 (m, 1H), 4.07 (td, J=3.6, 13.2 Hz, 2H), 3.83 (s, 3H), 3.48 (dd, J=6.4, 9.8 Hz, 1H), 3.28-3.15 (m, 4H), 3.05 (dd, J=4.4, 9.8 Hz, 1H), 2.47-2.37 (m, 1H), 2.24-2.13 (m, 1H), 1.95-1.75 (m, 3H), 1.65-1.61 (m, 2H). m/z: [ESI$^+$] 448 (M+H)$^+$, ($C_{25}H_{29}N_5O_3$).

N-(2-hydroxy-3-phenylpropyl)-1-(3-(4-methoxyphenyl)-1,2,4-oxadiazol-5-yl)piperidine-4-carboxamide (Compound 305): Using 1-(3-(4-methoxyphenyl)-1,2,4-oxadiazol-5-yl)piperidine-4-carboxylic acid (100 mg, 0.330 mmol) and 1-amino-3-phenylpropan-2-ol (60 mg, 0.397 mmol) as the starting material.

Yield 52 mg (36%), as an off-white solid. $^1$H NMR (400 MHz, DMSO) δ 7.86 (d, J=4.0 Hz, 1H), 7.83 (d, J=8.8 Hz, 2H), 7.27 (t, J=8.0 Hz, 2H), 7.23-7.15 (m, 3H), 7.05 (d, J=8.8 Hz, 2H), 4.83 (d, J=5.2 Hz, 1H), 4.06 (td, J=3.6, 13.2 Hz, 2H), 3.82 (s, 3H), 3.74-3.63 (m, 1H), 3.25-3.07 (m, 3H), 3.00 (td, J=6.0, 12.8 Hz, 1H), 2.74-2.68 (m, 1H), 2.63-2.55 (m, 2H), 1.81 (td, J=3.6, 13.2 Hz, 2H), 1.67-1.53 (m, 2H). m/z: [ESI$^+$] 437 (M+H)$^+$, ($C_{24}H_{28}N_4O_4$).

N-(cyclopropyl(pyridin-2-yl)methyl)-1-(3-(4-methoxyphenyl)-1,2,4-oxadiazol-5-yl)piperidine-4-carboxamide (Compound 280): Using 1-(3-(4-methoxyphenyl)-1,2,4-oxadiazol-5-yl)piperidine-4-carboxylic acid (100 mg, 0.330 mmol) and cyclopropyl(pyridin-2-yl)methanamine (59 mg, 0.398 mmol) as the starting material.

Yield 30 mg (21%), as an off-white solid. $^1$H NMR (400 MHz, DMSO) δ 8.52 (dd, J=1.6, 4.8 Hz, 1H), 8.42 (d, J=8.4 Hz, 1H), 7.84 (d, J=8.8 Hz, 2H), 7.76 (dd, J=1.6, 7.8 Hz, 1H), 7.38 (dd, J=1.2, 7.8 Hz, 1H), 7.26 (ddd, J=1.2, 4.8, 7.6 Hz, 1H), 7.05 (d, J=8.8 Hz, 2H), 4.37 (t, J=8.4 Hz, 1H), 4.11-4.01 (m, 2H), 3.82 (s, 3H), 3.27-3.13 (m, 2H), 2.61-2.55 (m, 1H), 1.93-1.74 (m, 2H), 1.75-1.55 (m, 2H), 1.30-1.10 (m, 1H), 0.50-0.41 (m, 2H), 0.35 (dd, J=2.4, 5.2 Hz, 2H). m/z: [ESI$^+$] 434 (M+H)$^+$, ($C_{24}H_{27}N_5O_3$).

N-((1S,2R)-2-hydroxy-2,3-dihydro-1H-inden-1-yl)-1-(3-(4-methoxyphenyl)-1,2,4-oxadiazol-5-yl)piperidine-4-carboxamide (Compound 259): Using 1-(3-(4-Methoxyphenyl)-1,2,4-oxadiazol-5-yl)piperidine-4-carboxylic acid (200 mg, 0.659 mmol) and (1S,2R)-1-amino-2,3-dihydro-1H-inden-2-ol (118 mg, 0.791 mmol) as the starting material.

Yield 200 mg (70%), as a light yellow solid. $^1$H NMR (400 MHz, DMSO) δ 7.90 (d, J=5.6 Hz, 1H), 7.84 (d, J=8.8 Hz, 2H), 7.24 (d, J=5.6 Hz, 1H), 7.21-7.17 (m, 2H), 7.15-7.11 (m, 1H), 7.05 (d, J=8.8 Hz, 2H), 5.20 (dd, J=4.8, 8.8 Hz, 1H), 5.02 (br s, 1H), 4.42 (dd, J=4.2, 5.6 Hz, 1H), 4.11 (d, J=13.2 Hz, 2H), 3.83 (s, 3H), 3.25-3.18 (m, 2H), 3.05 (dd, J=4.8, 16.0 Hz, 1H), 2.81 (dd, J=1.6, 16.2 Hz, 1H), 2.74-2.62 (m, 1H), 2.01-1.85 (m, 2H), 1.77-1.62 (m, 2H). m/z: [ESI$^+$] 435 (M+H)$^+$, ($C_{24}H_{26}N_4O_4$).

1-(3-(4-Methoxyphenyl)-1,2,4-oxadiazol-5-yl)-N-(4-(oxetan-3-yl)phenyl)piperidine-4-carboxamide (Compound 306): Using 1-(3-(4-methoxyphenyl)-1,2,4-oxadiazol-5-yl)piperidine-4-carboxylic acid (150 mg, 0.495 mmol) and 4-(oxetan-3-yl)aniline (89 mg, 0.597 mmol) as the starting material.

Yield 120 mg (56%), as a light yellow solid. $^1$H NMR (400 MHz, DMSO) δ 9.97 (s, 1H), 7.85 (d, J=8.8 Hz, 2H), 7.60 (dd, J=1.6, 8.6 Hz, 2H), 7.33 (d, J=8.4 Hz, 2H), 7.06 (d, J=8.8 Hz, 2H), 4.92 (dd, J=5.6, 8.4 Hz, 2H), 4.58 (t, J=6.4 Hz, 2H), 4.25-4.17 (m, 1H), 4.12 (td, J=3.6, 13.2 Hz, 2H), 3.82 (s, 3H), 3.24 (dd, J=3.2, 12.8 Hz, 2H), 2.63 (d, J=3.8 Hz, 1H), 1.94 (dd, J=3.6, 13.6 Hz, 2H), 1.78-1.62 (m, 2H). m/z: [ESI$^+$] 435 (M+H)$^+$, ($C_{24}H_{26}N_4O_4$)

N-(2-hydroxy-2-phenylpropyl)-1-(3-(4-methoxyphenyl)-1,2,4-oxadiazol-5-yl)piperidine-4-carboxamide (Compound 260): Using 1-(3-(4-methoxyphenyl)-1,2,4-oxadiazol-5-yl)piperidine-4-carboxylic acid (100 mg, 0.330 mmol) and 1-amino-2-phenylpropan-2-ol (65 mg, 0.430 mmol) as the starting material.

Yield 78 mg (54%), as an off-white solid. $^1$H NMR (400 MHz, DMSO) δ 7.84 (d, J=8.8 Hz 2H), 7.71 (t, J=5.6 Hz, 1H), 7.44 (dd, J=1.6, 7.6, Hz, 2H), 7.31 (dd, J=6.8, 8.4 Hz, 2H), 7.23-7.18 (m, 1H), 7.05 (d, J=8.8 Hz, 2H), 5.27 (s, 1H), 3.99 (dd, J=3.6, 13.6 Hz, 2H), 3.82 (s, 3H), 3.39 (d, J=5.8 Hz, 1H), 3.28 (d, J=5.8 Hz, 1H), 3.25-3.10 (m, 2H), 2.43 (s, 1H), 1.77-1.69 (m, 1H), 1.63 (d, J=14.0 Hz, 1H), 1.58-1.44 (m, 2H), 1.38 (s, 3H). m/z: [ESI$^+$] 437 (M+H)$^+$, ($C_{24}H_{28}N_4O_4$)

N-((1-(2,4-difluorophenyl)cyclopropyl)methyl)-1-(3-(4-methoxyphenyl)-1,2,4-oxadiazol-5-yl)piperidine-4-carboxamide (Compound 307): Using 1-(3-(4-methoxyphenyl)-1,2,4-oxadiazol-5-yl)piperidine-4-carboxylic acid (100 mg, 0.330 mmol) and (1-(2,4-difluorophenyl)cyclopropyl)methanamine (72 mg, 0.393 mmol) as the starting material.

Yield 60 mg (39%), as an off-white solid. $^1$H NMR (400 MHz, DMSO) δ 7.89 (t, J=5.6 Hz, 1H), 7.83 (d, J=8.8 Hz, 2H), 7.32 (dd, J=6.8, 8.8 Hz, 1H), 7.13 (ddd, J=2.8, 9.6, 10.8 Hz, 1H), 7.05 (d, J=8.8 Hz, 2H), 6.98 (dd, J=2.8, 8.4 Hz, 1H), 4.00 (td, J=3.6, 13.2 Hz, 2H), 3.82 (s, 3H), 3.25-3.11 (m, 4H), 2.46 (s, 1H), 1.69 (dd, J=3.6, 13.6 Hz, 2H), 1.57-1.43 (m, 2H), 0.90-0.83 (m, 2H), 0.72-0.65 (m, 2H). $^{19}$F NMR (376 MHz, DMSO) δ −111.16, −111.18, −112.51, −112.53. m/z: [ESI$^+$] 469 (M+H)$^+$, ($C_{25}H_{26}F_2N_4O_3$)

N-((2,3-dihydrobenzofuran-5-yl)methyl)-1-(3-(4-methoxyphenyl)-1,2,4-oxadiazol-5-yl)piperidine-4-carboxamide (Compound 281): Using 1-(3-(4-methoxyphenyl)-1,2,4-oxadiazol-5-yl)piperidine-4-carboxylic acid (100 mg, 0.330 mmol) and (2,3-dihydrobenzofuran-5-yl)methanamine (64 mg, 0.429 mmol) as the starting material.

Yield 40 mg (28%), as an off-white solid. $^1$H NMR (400 MHz, DMSO) δ 8.29 (t, J=5.6 Hz, 1H), 7.84 (d, J=8.8 Hz, 2H), 7.10 (d, J=1.6 Hz, 1H), 7.05 (d, J=8.8 Hz, 2H), 6.95 (dd, J=2.0, 8.0 Hz, 1H), 6.68 (d, J=8.0 Hz, 1H), 4.49 (t, J=8.8 Hz, 2H), 4.17 (d, J=6.0 Hz, 2H), 4.07 (td, J=3.6, 13.2 Hz, 2H), 3.82 (s, 3H), 3.23-3.10 (m, 4H), 2.43 (t, J=3.6 Hz, 1H), 1.88-1.78 (m, 2H), 1.71-1.55 (m, 2H). m/z: [ESI$^+$] 435 (M+H)$^+$, ($C_{24}H_{26}N_4O_4$)

N-(4-methoxy-3-(trifluoromethyl)benzyl)-1-(3-(4-methoxyphenyl)-1,2,4-oxadiazol-5-yl)piperidine-4-carboxamide (Compound 308): Using 1-(3-(4-methoxyphenyl)-1,2,4-oxadiazol-5-yl)piperidine-4-carboxylic acid (100 mg, 0.330 mmol) and (4-methoxy-3-(trifluoromethyl)phenyl)methanamine (81 mg, 0.395 mmol) as the starting material.

Yield 21 mg (13%), as an off-white solid. $^1$H NMR (400 MHz, DMSO) δ 8.43 (t, J=6.0 Hz, 1H), 7.83 (d, J=8.8 Hz, 2H), 7.52-7.47 (m, 2H), 7.22 (d, J=8.4 Hz, 1H), 7.06 (d, J=8.8 Hz, 2H), 4.26 (d, J=6.0 Hz, 2H), 4.07 (td, J=3.6, 13.2 Hz, 2H), 3.87 (s, 3H), 3.82 (s, 3H), 3.21 (dt, J=3.2, 12.8 Hz, 2H), 2.44 (d, J=4.0 Hz, 1H), 1.84 (dd, J=3.6, 13.6 Hz, 2H), 1.69-1.58 (m, 2H). $^{19}$F NMR (376 MHz, CDCl$_3$) δ −62.52. m/z: [ESI$^+$] 491 (M+H)$^+$, (C$_{24}$H$_{25}$F$_3$N$_4$O$_4$)

1-(3-(4-Methoxyphenyl)-1,2,4-oxadiazol-5-yl)-N-(2-(6-(trifluoromethyl)pyridin-2-yl)ethyl)piperidine-4-carboxamide (Compound 309): Using 1-(3-(4-methoxyphenyl)-1,2,4-oxadiazol-5-yl)piperidine-4-carboxylic acid (70 mg, 0.231 mmol) and 2-(6-(trifluoromethyl)pyridin-2-yl)ethan-1-amine (53 mg, 0.279 mmol) as the starting material.

Yield 40 mg (36%), as an off-white solid. $^1$H NMR (400 MHz, DMSO) δ 8.01 (d, J=7.8 Hz, 1H), 7.95 (t, J=5.6 Hz, 1H), 7.83 (d, J=8.8 Hz, 2H), 7.73 (d, J=7.6 Hz, 1H), 7.58 (d, J=7.6 Hz, 1H), 7.05 (d, J=8.8 Hz, 2H), 4.02 (td, J=3.6, 13.2 Hz, 2H), 3.82 (s, 3H), 3.46-3.39 (m, 2H), 3.18 (dt, J=3.2, 12.8 Hz, 2H), 2.96 (t, J=7.2 Hz, 2H), 2.38 (t, J=3.8 Hz, 1H), 1.75 (dd, J=3.6, 13.6 Hz, 2H), 1.63-1.49 (m, 2H). $^{19}$F NMR (376 MHz, CDCl$_3$) δ −68.10. m/z: [ESI$^+$] 476 (M+H)$^+$, (C$_{23}$H$_{24}$F$_3$N$_5$O$_3$)

N-(4,5-dihydrothiazol-2-yl)-1-(3-(4-methoxyphenyl)-1,2,4-oxadiazol-5-yl)piperidine-4-carboxamide (Compound 261): Using 1-(3-(4-methoxyphenyl)-1,2,4-oxadiazol-5-yl)piperidine-4-carboxylic acid (150 mg, 0.495 mmol) and 4,5-dihydrothiazol-2-amine (61 mg, 0.597 mmol) as the starting material.

Yield 46 mg (24%), as an off-white solid. $^1$H NMR (400 MHz, DMSO) δ 10.46 (br s, 1H), 7.86 (d, J=8.8 Hz, 2H), 7.11 (d, J=8.8 Hz, 2H), 4.05 (td, J=3.6, 13.2 Hz, 2H), 3.82 (s, 3H), 3.73 (t, J=8.2 Hz, 2H), 3.28-3.13 (m, 4H), 2.66-2.55 (m, 1H), 1.95-1.86 (m, 2H), 1.69-1.54 (m, 2H). m/z: [ESI$^+$] 388 (M+H)$^+$, (C$_{18}$H$_{21}$N$_5$O$_3$S)

N-(2-hydroxy-1-(thiophen-2-yl)ethyl)-1-(3-(4-methoxyphenyl)-1,2,4-oxadiazol-5-yl)piperidine-4-carboxamide (Compound 262): Using 1-(3-(4-methoxyphenyl)-1,2,4-oxadiazol-5-yl)piperidine-4-carboxylic acid (100 mg, 0.330 mmol) and 2-amino-2-(thiophen-2-yl)ethan-1-ol (61 mg, 0.426 mmol) as the starting material.

Yield 76 mg (54%), as an off-white solid. $^1$H NMR (400 MHz, DMSO) δ 8.34 (d, J=8.4 Hz, 1H), 7.85 (d, J=8.8 Hz, 2H), 7.37 (dd, J=2.4, 4.2, Hz, 1H), 7.06 (d, J=8.8 Hz, 2H), 6.97 (d, J=4.2 Hz, 2H), 5.13-5.05 (m, 1H), 5.02 (t, J=5.6 Hz, 1H), 4.08 (d, J=12.8 Hz, 2H), 3.82 (s, 3H), 3.68-3.55 (m, 2H), 3.21 (dd, J=10.8, 13.6 Hz, 2H), 2.36 (d, J=1.8 Hz, 1H), 1.85 (d, J=12.0 Hz, 2H), 1.72-1.55 (m, 2H). m/z: [ESI$^+$] 429 (M+H)$^+$, (C$_{21}$H$_{24}$N$_4$O$_4$S)

1-(3-(4-Methoxyphenyl)-1,2,4-oxadiazol-5-yl)-N-(2-phenoxyethyl)piperidine-4-carboxamide (Compound 282): Using 1-(3-(4-methoxyphenyl)-1,2,4-oxadiazol-5-yl)piperidine-4-carboxylic acid (150 mg, 0.495 mmol) and 2-phenoxyethan-1-amine (81 mg, 0.590 mmol) as the starting material.

Yield 100 mg (48%), as an off-white solid. $^1$H NMR (400 MHz, DMSO) δ 8.13 (t, J=5.6 Hz, 1H), 7.84 (d, J=8.8 Hz, 2H), 7.33-7.26 (m, 2H), 7.06 (d, J=8.8 Hz, 2H), 6.94 (d, J=7.2 Hz, 3H), 4.06 (td, J=3.6, 13.2 Hz, 2H), 3.99 (t, J=5.6 Hz, 2H), 3.82 (s, 3H), 3.46-3.39 (m, 2H), 3.20 (dt, J=2.8, 12.8 Hz, 2H), 2.47-2.44 (m, 1H), 1.85-1.78 (m, 2H), 1.70-1.55 (m, 2H). m/z: [ESI$^+$] 423 (M+H)$^+$, (C$_{23}$H$_{26}$N$_4$O$_4$)

1-(3-(4-Methoxyphenyl)-1,2,4-oxadiazol-5-yl)-N-(1-(pyridin-2-yl)propan-2-yl)piperidine-4-carboxamide (Compound 263): Using 1-(3-(4-methoxyphenyl)-1,2,4-oxadiazol-5-yl)piperidine-4-carboxylic acid (100 mg, 0.330 mmol) and 1-(pyridin-2-yl)propan-2-amine (54 mg, 0.396 mmol) as the starting material.

Yield 30 mg (22%), as an off-white solid. $^1$H NMR (400 MHz, DMSO) δ 8.48 (ddd, J=1.0, 1.6, 4.8 Hz, 1H), 7.87-7.79 (m, 3H), 7.69 (dd, J=1.6, 7.6 Hz, 1H), 7.26-7.17 (m, 2H), 7.06 (d, J=8.8 Hz, 2H), 4.23-4.10 (m, 1H), 4.01 (dd, J=12.0, 16.4 Hz, 2H), 3.82 (s, 3H), 3.22-3.10 (m, 2H), 2.88 (dd, J=7.5, 13.2 Hz, 1H), 2.79 (dd, J=6.6, 13.2 Hz, 1H), 2.37-2.26 (m, 1H), 1.77-1.64 (m, 2H), 1.63-1.43 (m, 2H), 1.05 (d, J=6.6 Hz, 3H). m/z: [ESI$^+$] 422 (M+H)$^+$, (C$_{23}$H$_{27}$N$_5$O$_3$)

1-(3-(4-Methoxyphenyl)-1,2,4-oxadiazol-5-yl)-N-(1-phenylcyclopropyl)piperidine-4-carboxamide (Compound 264): Using 1-(3-(4-methoxyphenyl)-1,2,4-oxadiazol-5-yl)piperidine-4-carboxylic acid (100 mg, 0.330 mmol) and 1-phenylcyclopropan-1-amine (57 mg, 0.428 mmol) as the starting material.

Yield 66 mg (48%), as an off-white solid. $^1$H NMR (400 MHz, DMSO) δ 8.61 (s, 1H), 7.85 (d, J=8.8 Hz, 2H), 7.30-7.23 (m, 2H), 7.18-7.09 (m, 3H), 7.05 (d, J=8.8 Hz, 2H), 4.13-4.03 (m, 2H), 3.82 (s, 3H), 3.22 (dt, J=2.8, 12.8 Hz, 2H), 2.44 (td, J=3.6, 11.2 Hz, 1H), 1.87 (dd, J=3.6, 13.6 Hz, 2H), 1.69-1.56 (m, 2H), 1.21-1.08 (m, 4H). m/z: [ESI$^+$] 419 (M+H)$^+$, (C$_{24}$H$_{26}$N$_4$O$_3$)

N-(2,3-dihydrobenzofuran-3-yl)-1-(3-(4-methoxyphenyl)-1,2,4-oxadiazol-5-yl)piperidine-4-carboxamide (Compound 283): Using 1-(3-(4-methoxyphenyl)-1,2,4-oxadiazol-5-yl)piperidine-4-carboxylic acid (100 mg, 0.330 mmol) and 2,3-dihydrobenzofuran-3-amine (58 mg, 0.429 mmol) as the starting material.

Yield 50 mg (36%), as an off-white solid. $^1$H NMR (400 MHz, DMSO) δ 8.54 (d, J=7.2 Hz, 1H), 7.83 (d, J=8.8 Hz, 2H), 7.29 (d, J=7.2 Hz, 1H), 7.22 (dd, J=1.6, 7.8 Hz, 1H), 7.06 (d, J=8.8 Hz, 2H), 6.95-6.89 (m, 1H), 6.85 (d, J=8.0 Hz, 1H), 5.50 (dt, J=4.8, 8.0 Hz, 1H), 4.67 (dd, J=8.6, 9.6 Hz, 1H), 4.19 (dd, J=4.8, 9.6 Hz, 1H), 4.07 (d, J=13.2 Hz, 2H), 3.82 (s, 3H), 3.19 (t, J=12.0 Hz, 2H), 2.44 (d, J=3.8 Hz, 1H), 1.83 (d, J=13.2 Hz, 2H), 1.73-1.59 (m, 2H). m/z: [ESI$^+$] 421 (M+H)$^+$, (C$_{23}$H$_{24}$N$_4$O$_4$)

(R)—N-(2-hydroxy-1-phenylethyl)-1-(3-(4-methoxyphenyl)-1,2,4-oxadiazol-5-yl)piperidine-4-carboxamide (Compound 265): Using 1-(3-(4-methoxyphenyl)-1,2,4-oxadiazol-5-yl)piperidine-4-carboxylic acid (100 mg, 0.330 mmol) and (R)-2-amino-2-phenylethan-1-ol (59 mg, 0.430 mmol) as the starting material.

Yield 115 mg (83%), as an off-white solid. $^1$H NMR (400 MHz, DMSO) δ 8.26 (d, J=8.0 Hz, 1H), 7.83 (d, J=8.8 Hz, 2H), 7.31 (d, J=5.6 Hz, 4H), 7.23 (dd, J=2.8, 8.6 Hz, 1H), 7.05 (d, J=8.8 Hz, 2H), 4.95-4.78 (m, 2H), 4.07 (t, J=11.8 Hz, 2H), 3.82 (s, 3H), 3.58-3.52 (m, 2H), 3.30-3.15 (m, 2H), 2.59-2.54 (m, 1H), 1.84 (t, J=14.2 Hz, 2H), 1.72-1.52 (m, 2H). m/z: [ESI$^+$] 423 (M+H)$^+$, (C$_{23}$H$_{26}$N$_4$O$_4$)

N-(1-(1H-indol-3-yl)propan-2-yl)-1-(3-(4-methoxyphenyl)-1,2,4-oxadiazol-5-yl)piperidine-4-carboxamide (Compound 310): Using 1-(3-(4-methoxyphenyl)-1,2,4-oxadiazol-5-yl)piperidine-4-carboxylic acid (100 mg, 0.330 mmol) and 1-(1H-indol-3-yl)propan-2-amine (69 mg, 0.396 mmol) as the starting material.

Yield 30 mg (20%), as an off-white solid. $^1$H NMR (400 MHz, DMSO) δ 10.78 (d, J=2.4 Hz, 1H), 7.84 (d, J=8.8 Hz, 2H), 7.78 (d, J=7.6 Hz, 1H), 7.58 (d, J=7.6 Hz, 1H), 7.32 (d, J=8.0 Hz, 1H), 7.10 (d, J=1.8 Hz, 1H), 7.08-7.02 (m, 3H), 7.00-6.90 (m, 1H), 4.12-3.98 (m, 3H), 3.82 (s, 3H), 3.18-3.16 (m, 2H), 2.87 (dd, J=6.0, 14.2 Hz, 1H), 2.73-2.69 (m, 1H), 2.38 (td, J=3.6, 11.2 Hz, 1H), 1.83-1.70 (m, 2H), 1.67-1.49 (m, 2H), 1.04 (d, J=6.4 Hz, 3H). m/z: [ESI⁺] 460 (M+H)⁺, (C$_{26}$H$_{29}$N$_5$O$_3$)

1-(3-(4-Methoxyphenyl)-1,2,4-oxadiazol-5-yl)-N-(2-(6-methyl-1H-indol-3-yl)ethyl)piperidine-4-carboxamide (Compound 317): Using 1-(3-(4-methoxyphenyl)-1,2,4-oxadiazol-5-yl)piperidine-4-carboxylic acid (100 mg, 0.330 mmol) and 2-(6-methyl-1H-indol-3-yl)ethan-1-amine (63 mg, 0.362 mmol) as the starting material.

Yield 50 mg (33%), as an off-white solid. $^1$H NMR (400 MHz, DMSO) δ 10.62 (d, J=2.4 Hz, 1H), 7.96 (t, J=5.6 Hz, 1H), 7.84 (d, J=8.8 Hz, 2H), 7.40 (d, J=8.0 Hz, 1H), 7.12 (s, 1H), 7.08-7.01 (m, 3H), 6.81 (dd, J=1.4, 8.2 Hz, 1H), 4.05 (td, J=3.6, 13.2 Hz, 2H), 3.82 (s, 3H), 3.30 (d, J=6.8 Hz, 2H), 3.19 (dt, J=2.8, 12.8 Hz, 2H), 2.79 (t, J=7.6 Hz, 2H), 2.44-2.39 (m, 1H), 2.37 (s, 3H), 1.85-1.74 (m, 2H), 1.69-1.56 (m, 2H). m/z: [ESI⁺] 460 (M+H)⁺, (C$_{26}$H$_{29}$N$_5$O$_3$)

N-(2-(difluoromethoxy)benzyl)-1-(3-(4-methoxyphenyl)-1,2,4-oxadiazol-5-yl)piperidine-4-carboxamide (Compound 284): Using 1-(3-(4-methoxyphenyl)-1,2,4-oxadiazol-5-yl)piperidine-4-carboxylic acid (100 mg, 0.330 mmol) and (2-(difluoromethoxy)phenyl)methanamine (74 mg, 0.427 mmol) as the starting material.

Yield 65 mg (43%), as an off-white solid. $^1$H NMR (400 MHz, DMSO) δ 8.36 (t, J=5.6 Hz, 1H), 7.85 (d, J=8.8 Hz, 2H), 7.33 (dd, J=1.8, 7.6 Hz, 2H), 7.27-7.16 (m, 2H), 7.21 (t, J=74.4 Hz, 1H), 7.06 (d, J=8.8 Hz, 2H), 4.30 (d, J=5.8 Hz, 2H), 4.08 (td, J=3.6, 13.2 Hz, 2H), 3.82 (s, 3H), 3.22 (dt, J=2.8, 12.8 Hz, 2H), 2.49-2.47 (m, 1H), 1.87 (dd, J=3.6, 13.6 Hz, 2H), 1.72-1.58 (m, 2H). $^{19}$F NMR (376 MHz, CDCl$_3$) δ −80.14. m/z: [ESI⁺] 459 (M+H)⁺, (C$_{23}$H$_{24}$F$_2$N$_4$O$_4$)

(S)—N-(1-(2-fluorophenyl)ethyl)-1-(3-(4-methoxyphenyl)-1,2,4-oxadiazol-5-yl)piperidine-4-carboxamide (Compound 266): Using 1-(3-(4-methoxyphenyl)-1,2,4-oxadiazol-5-yl)piperidine-4-carboxylic acid (150 mg, 0.495 mmol) and (S)-1-(2-fluorophenyl)ethan-1-amine (74 mg, 0.532 mmol) as the starting material.

Yield 50 mg (24%), as an off-white solid. $^1$H NMR (400 MHz, DMSO) δ 8.41 (d, J=7.8 Hz, 1H), 7.83 (d, J=8.8 Hz, 2H), 7.37 (dd, J=1.6, 7.6 Hz, 1H), 7.28 (ddd, J=1.6, 5.2, 7.6 Hz, 1H), 7.21-7.11 (m, 2H), 7.05 (d, J=8.8 Hz, 2H), 5.19-5.08 (m, 1H), 4.07 (dt, J=4.0, 8.8 Hz, 2H), 3.82 (s, 3H), 3.21 (td, J=3.2, 12.8 Hz, 2H), 2.46 (d, J=3.6 Hz, 1H), 1.89-1.79 (m, 2H), 1.68-1.50 (m, 2H), 1.35 (d, J=7.2 Hz, 3H). $^{19}$F NMR (376 MHz, DMSO) δ −119.87. m/z: [ESI⁺] 425 (M+H)⁺, (C$_{23}$H$_{25}$FN$_4$O$_3$)

N-(2-fluoro-5-methylbenzyl)-1-(3-(4-methoxyphenyl)-1,2,4-oxadiazol-5-yl)piperidine-4-carboxamide (Compound 311): Using 1-(3-(4-methoxyphenyl)-1,2,4-oxadiazol-5-yl)piperidine-4-carboxylic acid (100 mg, 0.330 mmol) and (2-fluoro-5-methylphenyl)methanamine (55 mg, 0.395 mmol) as the starting material.

Yield 20 mg (14%), as an off-white solid. $^1$H NMR (400 MHz, DMSO) δ 8.36 (t, J=5.6 Hz, 1H), 7.83 (d, J=8.8 Hz, 2H), 7.12-7.00 (m, 3H), 7.04 (d, J=8.8 Hz, 2H), 4.27 (d, J=5.6 Hz, 2H), 4.07 (td, J=3.6, 13.2 Hz, 2H), 3.82 (s, 3H), 3.21 (dt, J=2.8, 12.8 Hz, 2H), 2.46-2.37 (m, 1H), 2.27 (s, 3H), 1.90-1.81 (m, 2H), 1.72-1.59 (m, 2H). $^{19}$F NMR (376 MHz, DMSO) δ −124.21. m/z: [ESI⁺] 425 (M+H)⁺, (C$_{23}$H$_{25}$FN$_4$O$_3$)

1-(3-(4-Methoxyphenyl)-1,2,4-oxadiazol-5-yl)-N-((2-(trifluoromethyl)thiazol-5-yl)methyl)piperidine-4-carboxamide (Compound 318): Using 1-(3-(4-methoxyphenyl)-1,2,4-oxadiazol-5-yl)piperidine-4-carboxylic acid (100 mg, 0.330 mmol) and (2-(trifluoromethyl)thiazol-5-yl)methanamine (72 mg, 0.395 mmol) as the starting material.

Yield 15 mg (10%), as an off-white solid. $^1$H NMR (400 MHz, DMSO) δ 8.74 (t, J=5.6 Hz, 1H), 8.00 (q, J=1.0 Hz, 1H), 7.84 (d, J=8.8 Hz, 2H), 7.05 (d, J=8.8 Hz, 2H), 4.56 (d, J=5.6 Hz, 2H), 4.11-4.02 (m, 2H), 3.82 (s, 3H), 3.27-3.16 (m, 2H), 2.45 (td, J=3.6, 11.2 Hz, 1H), 1.90-1.80 (m, 2H), 1.70-1.56 (m, 2H). m/z: [ESI⁺] 468 (M+H)⁺, (C$_{20}$H$_{20}$F$_3$N$_5$O$_3$S)

N-((1H-indol-2-yl)methyl)-1-(3-(4-methoxyphenyl)-1,2,4-oxadiazol-5-yl)piperidine-4-carboxamide (Compound 285): Using 1-(3-(4-methoxyphenyl)-1,2,4-oxadiazol-5-yl)piperidine-4-carboxylic acid (150 mg, 0.495 mmol) and (1H-indol-2-yl)methanamine (87 mg, 0.595 mmol) as the starting material.

Yield 100 mg (47%), as a yellow solid. $^1$H NMR (400 MHz, DMSO) δ 10.90 (br s, 1H), 8.40 (t, J=5.6 Hz, 1H), 7.85 (d, J=8.8 Hz, 2H), 7.45 (dd, J=1.2, 7.8 Hz, 1H), 7.33 (dd, J=1.2, 8.0 Hz, 1H), 7.06 (d, J=8.8 Hz, 2H), 7.02 (dd, J=1.2, 8.0 Hz, 1H), 6.95 (ddd, J=1.2, 6.8, 8.0 Hz, 1H), 6.30-6.22 (m, 1H), 4.42 (d, J=5.6 Hz, 2H), 4.09 (td, J=3.6, 13.2 Hz, 2H), 3.82 (s, 3H), 3.22 (dt, J=2.8, 12.8 Hz, 2H), 2.55 (d, J=3.4 Hz, 1H), 1.94-1.82 (m, 2H), 1.74-1.60 (m, 2H). m/z: [ESI⁺] 432 (M+H)⁺, (C$_{24}$H$_{25}$N$_5$O$_3$)

1-(3-(4-Methoxyphenyl)-1,2,4-oxadiazol-5-yl)-N-((1-(4-methylbenzoyl)pyrrolidin-3-yl)methyl)piperidine-4-carboxamide (Compound 222): Using 1-(3-(4-methoxyphenyl)-1,2,4-oxadiazol-5-yl)-N-(pyrrolidin-3-ylmethyl)piperidine-4-carboxamide (204 mg, 0.529 mmol) and 4-methylbenzoic acid (60 mg, 0.441 mmol) as the starting material.

Yield 180 mg (81%), as a light yellow solid. $^1$H NMR (400 MHz, DMSO) δ 8.04 (t, J=5.6 Hz, 0.5H), 7.92 (t, J=5.6 Hz, 0.5H), 7.84 (d, J=8.8 Hz, 2H), 7.41 (d, J=7.8 Hz, 1H), 7.39 (d, J=7.8 Hz, 1H), 7.23 (d, J=7.8 Hz, 2H), 7.05 (d, J=8.8 Hz, 2H), 4.13-3.94 (m, 2H), 3.82 (s, 3H), 3.58 (dd, J=7.4, 12.0 Hz, 1H), 3.47-3.42 (m, 2H), 3.27-2.95 (m, 5H), 2.50-2.40 (m, 1H), 2.34 (s, 3H), 2.32-2.20 (m, 1H), 2.01-1.68 (m, 3H), 1.68-1.44 (m, 3H). m/z: [ESI⁺] 504 (M+H)⁺, (C$_{28}$H$_{33}$N$_5$O$_4$).

N-(3-(4-benzoylpiperazin-1-yl)propyl)-1-(3-(4-methoxyphenyl)-1,2,4-oxadiazol-5-yl)piperidine-4-carboxamide (Compound 228): Using 1-(3-(4-methoxyphenyl)-1,2,4-oxadiazol-5-yl)-N-(3-(piperazin-1-yl)propyl)piperidine-4-carboxamide (211 mg, 0.492 mmol) and benzoic acid (50 mg, 0.409 mmol) as the starting material.

Yield 120 mg (55%), as a light yellow solid. $^1$H NMR (400 MHz, DMSO) δ 7.86 (t, J=5.6 Hz, 1H), 7.84 (d, J=8.8 Hz, 2H), 7.47-7.42 (m, 3H), 7.38 (dd, J=2.8, 6.4 Hz, 2H), 7.05 (d, J=8.8 Hz, 2H), 4.06 (d, J=13.2 Hz, 2H), 3.82 (s, 3H), 3.61 (s, 2H), 3.30-3.26 (m, 2H), 3.19 (dt, J=2.8, 12.8 Hz, 2H), 3.11-3.03 (m, 2H), 2.47-2.26 (m, 7H), 1.80 (d, J=13.2 Hz, 2H), 1.68-1.50 (m, 4H). m/z: [ESI⁺] 533 (M+H)⁺, (C$_{29}$H$_{36}$N$_6$O$_4$).

(4-(3-(4-Methoxyphenyl)-1,2,4-oxadiazol-5-yl)piperazin-1-yl)(3-(piperidin-1-ylmethyl)phenyl)methanone (Compound 236): Using 3-(piperidin-1-ylmethyl)benzoic acid (150 mg, 0.684 mmol) and 3-(4-methoxyphenyl)-5-(piperazin-1-yl)-1,2,4-oxadiazole (214 mg, 0.822 mmol) as the starting material.

Yield 0.26 g (82%), as a light yellow solid. $^1$H NMR (400 MHz, DMSO) δ 7.84 (d, J=8.8 Hz, 2H), 7.46-7.30 (m, 4H), 7.06 (d, J=8.8 Hz, 2H), 3.82 (s, 3H), 3.80-3.58 (m, 6H), 3.50-3.40 (m, 4H), 2.44-2.24 (m, 4H), 1.58-1.48 (m, 4H), 1.44-1.37 (s, 2H). m/z: [ESI⁺] 462 (M+H)⁺, (C$_{26}$H$_{31}$N$_5$O$_3$).

1-(3-(4-Methoxyphenyl)-1,2,4-oxadiazol-5-yl)-N-((1-(5-methylpicolinoyl)pyrrolidin-3-yl)methyl)piperidine-4-carboxamide (Compound 242): Using 5-methylpicolinic acid (100 mg, 0.729 mmol) and 1-(3-(4-methoxyphenyl)-1,2,4-oxadiazol-5-yl)-N-(pyrrolidin-3-ylmethyl)piperidine-4-carboxamide (337 mg, 0.874 mmol) as the starting material.

Yield 240 mg (65%), as a light yellow solid. $^1$H NMR (400 MHz, DMSO) δ 8.43 (d, J=2.0 Hz, 1H), 8.06 (t, J=5.6 Hz, 0.5H), 7.96 (t, J=5.6 Hz, 0.5H), 7.84 (d, J=8.8 Hz, 2H), 7.73 (d, J=8.0 Hz, 1H), 7.63 (dd, J=4.4, 8.0 Hz, 1H), 7.05 (d, J=8.8 Hz, 2H), 4.12-3.98 (m, 2H), 3.82 (s, 3H), 3.77-3.69 (m, 1H), 3.67-3.57 (m, 1.5H), 3.51-3.42 (m, 0.5H), 3.27-3.15 (m, 3H), 3.15-3.02 (m, 1H), 2.46-2.29 (m, 6H), 2.00-1.89 (m, 1H), 1.87-1.70 (m, 2H), 1.69-1.50 (m, 3H). m/z: [ESI$^+$] 505 (M+H)$^+$, (C$_{27}$H$_{32}$N$_6$O$_4$).

(R)-3-(3-(4-Methoxyphenyl)-1,2,4-oxadiazol-5-yl)-N-((1-(4-methylbenzyl)pyrrolidin-3-yl)methyl)propanamide (Compound 149): Using 3-(3-(4-methoxyphenyl)-1,2,4-oxadiazol-5-yl)propanoic acid (200 mg, 0.806 mmol) and (1-(4-methylbenzyl)pyrrolidin-3-yl)methanamine (197 mg, 0.964 mmol) as the starting material then followed by Prep-Chiral-HPLC.

Yield 25 mg (7%), as a light yellow solid. $^1$H NMR (400 MHz, DMSO) δ 8.03 (t, J=5.6 Hz, 1H), 7.92 (d, J=8.8 Hz, 2H), 7.22-7.04 (m, 6H), 3.83 (s, 3H), 3.43 (s, 2H), 3.15 (t, J=7.2 Hz, 2H), 3.11-2.91 (m, 2H), 2.65 (t, J=7.2 Hz, 2H), 2.50-2.47 (m, 2H), 2.42-2.35 (m, 2H), 2.27 (s, 3H), 2.24-2.16 (m, 1H), 2.13 (dd, J=5.6, 8.8 Hz, 1H), 1.87-1.71 (m, 1H), 1.40-1.27 (m, 1H). m/z: [ESI$^+$] 435 (M+H)$^+$, (C$_{25}$H$_{30}$N$_4$O$_3$).

(S)-3-(3-(4-Methoxyphenyl)-1,2,4-oxadiazol-5-yl)-N-((1-(4-methylbenzyl)pyrrolidin-3-yl)methyl)propanamide (Compound 150): Using 3-(3-(4-methoxyphenyl)-1,2,4-oxadiazol-5-yl)propanoic acid (200 mg, 0.806 mmol) and (1-(4-methylbenzyl)pyrrolidin-3-yl)methanamine (197 mg, 0.964 mmol) as the starting material then followed by Prep-Chiral-HPLC.

Yield 30 mg (9%), as a light yellow solid. $^1$H NMR (400 MHz, DMSO) δ 8.04 (t, J=5.6 Hz, 1H), 7.92 (d, J=8.8 Hz, 2H), 7.21-7.04 (m, 6H), 3.83 (s, 3H), 3.46 (s, 2H), 3.35-3.30 (m, 1H), 3.15 (t, J=7.2 Hz, 2H), 3.10-2.90 (m, 2H), 2.65 (t, J=7.2 Hz, 2H), 2.41 (s, 1H), 2.27 (s, 3H), 2.24-2.08 (m, 3H), 1.85-1.76 (m, 1H), 1.39-1.30 (m, 1H). m/z: [ESI$^+$] 435 (M+H)$^+$, (C$_{25}$H$_{30}$N$_4$O$_3$).

1-(3-(4-Methoxyphenyl)-1,2,4-oxadiazol-5-yl)-N-(1-methylindolin-5-yl)piperidine-4-carboxamide (Compound 403): Using 1-(3-(4-methoxyphenyl)-1,2,4-oxadiazol-5-yl)piperidine-4-carboxylic acid (110 mg, 0.363 mmol) and 1-methylindolin-5-amine (81 mg, 0.547 mmol) as the starting material.

Yield 11 mg (7%), as an off-white solid. $^1$H NMR (400 MHz, DMSO) δ 9.63 (s, 1H), 7.85 (d, J=8.8 Hz, 2H), 7.34 (d, J=2.0 Hz, 1H), 7.19 (dd, J=2.0, 8.4 Hz, 1H), 7.07 (d, J=8.8 Hz, 2H), 6.44 (d, J=8.4 Hz, 1H), 4.12 (d, J=13.0 Hz, 2H), 3.83 (s, 3H), 3.26 (dt, J=2.8, 12.8 Hz, 2H), 3.19 (t, J=8.0 Hz, 2H), 2.83 (t, J=8.0 Hz, 2H), 2.65 (s, 3H), 2.62-2.54 (m, 1H), 1.90 (d, J=12.4 Hz, 2H), 1.76-1.61 (m, 2H). m/z: [ESI$^+$] 434 (M+H)$^+$, (C$_{24}$H$_{27}$N$_5$O$_3$).

1-(3-(4-Methoxyphenyl)-1,2,4-oxadiazol-5-yl)-N-(1-methyl-1H-indol-5-yl)piperidine-4-carboxamide (Compound 427): Using 1-(3-(4-methoxyphenyl)-1,2,4-oxadiazol-5-yl)piperidine-4-carboxylic acid (100 mg, 0.330 mmol) and 1-methyl-1H-indol-5-amine (60 mg, 0.410 mmol) as the starting material.

Yield 37 mg (26%) as an off-white solid. $^1$H NMR (400 MHz, DMSO) δ 9.79 (s, 1H), 7.89 (d, J=2.0 Hz, 1H), 7.86 (d, J=8.8 Hz, 2H), 7.35 (d, J=8.8 Hz, 1H), 7.30-7.26 (m, 2H), 7.06 (d, J=8.8 Hz, 2H), 6.36 (dd, J=0.8, 3.2 Hz, 1H), 4.14 (td, J=3.6, 13.2 Hz, 2H), 3.83 (s, 3H), 3.76 (s, 3H), 3.27 (dt, J=2.8, 12.8 Hz, 2H), 2.69-2.58 (m, 1H), 1.95 (dd, J=3.6, 13.6 Hz, 2H), 1.80-1.66 (m, 2H). m/z: [ESI$^+$] 432 (M+H)$^+$, (C$_{24}$H$_{25}$N$_5$O$_3$).

N-(3-(4-(pyridin-2-ylmethyl)piperidin-1-yl)propyl)-1-(3-(4-(trifluoromethoxy)phenyl)-1,2,4-oxadiazol-5-yl)piperidine-4-carboxamide (Compound 435): Using 1-(3-(4-(trifluoromethoxy)phenyl)-1,2,4-oxadiazol-5-yl)piperidine-4-carboxylic acid (100 mg, 0.280 mmol) and 3-(4-(pyridin-2-ylmethyl)piperidin-1-yl)propan-1-amine (78 mg, 0.334 mmol) as the starting material.

Yield 39 mg (24%), as an off-white solid. $^1$H NMR (400 MHz, DMSO) δ 8.47 (ddd, J=1.0, 2.0, 4.8 Hz, 1H), 8.02 (d, J=8.8 Hz, 2H), 7.87 (t, J=5.6 Hz, 1H), 7.67 (dd, J=2.0, 7.6 Hz, 1H), 7.50 (d, J=8.8 Hz, 2H), 7.23-7.14 (m, 2H), 4.07 (d, J=12.8 Hz, 2H), 3.22 (dt, J=2.8, 12.8 Hz, 2H), 3.08-3.03 (m, 2H), 2.79 (d, J=11.2 Hz, 2H), 2.63 (d, J=7.2 Hz, 2H), 2.41-2.32 (m, 1H), 2.22 (t, J=7.2 Hz, 2H), 1.84-1.74 (m, 4H), 1.73-1.57 (m, 3H), 1.57-1.47 (m, 4H), 1.25-1.12 (m, 2H); $^{19}$F NMR (376 MHz, DMSO) δ −56.68. m/z: [ESI$^+$] 573 (M+H)$^+$, (C$_{29}$H$_{35}$F$_3$N$_6$O$_3$).

1-(3-(4-(Difluoromethoxy)phenyl)-1,2,4-oxadiazol-5-yl)-N-(3-(4-(pyridin-2-ylmethyl)piperidin-1-yl)propyl)piperidine-4-carboxamide (Compound 453): Using 1-(3-(4-(difluoromethoxy)phenyl)-1,2,4-oxadiazol-5-yl)piperidine-4-carboxylic acid (100 mg, 0.295 mmol) and 3-(4-(pyridin-2-ylmethyl)piperidin-1-yl)propan-1-amine (83 mg, 0.356 mmol) as the starting material.

Yield 70 mg (43%), as an off-white solid. $^1$H NMR (400 MHz, DMSO) δ 8.48 (dd, J=1.6, 4.8 Hz, 1H), 7.96 (d, J=8.8 Hz, 2H), 7.89 (t, J=5.6 Hz, 1H), 7.68 (dd, J=2.0, 7.6 Hz, 1H), 7.36 (t, J=73.6 Hz, 1H), 7.31 (d, J=8.8 Hz, 2H), 7.23-7.17 (m, 2H), 4.07 (td, J=3.6, 13.2 Hz, 2H), 3.21 (dt, J=3.2, 12.8 Hz, 2H), 3.08-3.01 (m, 2H), 2.85 (s, 2H), 2.63 (d, J=7.2 Hz, 2H), 2.43-2.35 (m, 1H), 2.29 (s, 2H), 1.97-1.70 (m, 4H), 1.67-1.50 (m, 7H), 1.29-1.12 (m, 2H); $^{19}$F NMR (376 MHz, DMSO) δ −82.60. m/z: [ESI$^+$] 555 (M+H)$^+$, (C$_{29}$H$_{36}$F$_2$N$_6$O$_3$).

N-((1H-pyrrolo[2,3-b]pyridin-2-yl)methyl)-1-(3-(4-methoxyphenyl)-1,2,4-oxadiazol-5-yl)piperidine-4-carboxamide (Compound 418): Using 1-(3-(4-methoxyphenyl)-1,2,4-oxadiazol-5-yl)piperidine-4-carboxylic acid (100 mg, 0.330 mmol) and (1H-pyrrolo[2,3-b]pyridin-2-yl)methanamine (58 mg, 0.394 mmol) as the starting material.

Yield 45 mg (32%), as an off-white solid. $^1$H NMR (400 MHz, DMSO) δ 11.50 (br s, 1H), 8.42 (t, J=5.6 Hz, 1H), 8.14 (dd, J=1.6, 4.8 Hz, 1H), 7.88-7.83 (m, 3H), 7.06 (d, J=8.8 Hz, 2H), 7.01 (dd, J=4.8, 7.6 Hz, 1H), 6.25 (s, 1H), 4.44 (d, J=5.6 Hz, 2H), 4.09 (td, J=3.6, 13.6 Hz, 2H), 3.82 (s, 3H), 3.23 (dt, J=2.8, 12.8 Hz, 2H), 2.58-2.51 (m, 1H), 1.90 (dd, J=3.6, 13.6 Hz, 2H), 1.74-1.60 (m, 2H). m/z: [ESI$^+$] 433 (M+H)$^+$, (C$_{23}$H$_{24}$N$_6$O$_3$).

N-((1H-benzo[d]imidazol-2-yl)methyl)-1-(3-(4-methoxyphenyl)-1,2,4-oxadiazol-5-yl)piperidine-4-carboxamide (Compound 419): Using 1-(3-(4-methoxyphenyl)-1,2,4-oxadiazol-5-yl)piperidine-4-carboxylic acid (100 mg, 0.330 mmol) and (1H-benzo[d]imidazol-2-yl)methanamine (60 mg, 0.408 mmol) as the starting material.

Yield 50 mg (35%), as an off-white solid. $^1$H NMR (400 MHz, DMSO) δ 12.18 (br s, 1H), 8.56 (t, J=5.6 Hz, 1H), 7.84 (d, J=8.8 Hz, 2H), 7.51 (s, 2H), 7.15 (m, 2H), 7.06 (d, J=8.8 Hz, 2H), 4.50 (d, J=5.6 Hz, 2H), 4.09 (dd, J=3.6, 13.2 Hz, 2H), 3.82 (s, 3H), 3.23 (dt, J=3.2, 12.8 Hz, 2H), 2.59-2.52 (m, 1H), 1.90 (dd, J=3.6, 13.6 Hz, 2H), 1.73-1.60 (m, 2H). m/z: [ESI$^+$] 433 (M+H)$^+$, (C$_{23}$H$_{24}$N$_6$O$_3$).

N-(benzo[d]oxazol-2-ylmethyl)-1-(3-(4-methoxyphenyl)-1,2,4-oxadiazol-5-yl)piperidine-4-carboxamide (Compound 420): Using 1-(3-(4-methoxyphenyl)-1,2,4-oxadiazol-5-yl)piperidine-4-carboxylic acid (100 mg, 0.330 mmol) and benzo[d]oxazol-2-ylmethanamine (60 mg, 0.405 mmol) as the starting material.

Yield 70 mg (49%), as an off-white solid. $^1$H NMR (400 MHz, DMSO) δ 8.73 (t, J=5.6 Hz, 1H), 7.84 (d, J=8.8 Hz, 2H), 7.76-7.67 (m, 2H), 7.46-7.31 (m, 2H), 7.05 (d, J=8.8 Hz, 2H), 4.59 (d, J=5.6 Hz, 2H), 4.08 (d, J=13.2 Hz, 2H), 3.82 (s, 3H), 3.24 (t, J=11.8 Hz, 2H), 2.59-2.52 (m, 1H), 1.90 (dd, J=3.6, 13.6 Hz, 2H), 1.72-1.59 (m, 2H). m/z: [ESI$^+$] 434 (M+H)$^+$, (C$_{23}$H$_{23}$N$_5$O$_4$).

1-(3-(4-Methoxyphenyl)-1,2,4-oxadiazol-5-yl)-N-(2-((1-(pyridin-2-ylmethyl)piperidin-4-yl)oxy)ethyl)piperidine-4-carboxamide (Compound 456): Using 1-(3-(4-methoxyphenyl)-1,2,4-oxadiazol-5-yl)piperidine-4-carboxylic acid (60 mg, 0.198 mmol) and 2-((1-(pyridin-2-ylmethyl)piperidin-4-yl)oxy)ethan-1-amine (60 mg, 0.255 mmol) as the starting material.

Yield 20 mg (19%), as an off-white solid. $^1$H NMR (400 MHz, CDCl$_3$) δ 8.47 (ddd, J=0.8, 2.0, 4.8 Hz, 1H), 7.92 (t, J=5.6 Hz, 1H), 7.83 (d, J=8.8 Hz, 2H), 7.75 (dd, J=2.0, 7.6 Hz, 1H), 7.42 (d, J=8.0 Hz, 1H), 7.25 (ddd, J=1.2, 4.8, 7.6 Hz, 1H), 7.05 (d, J=8.8 Hz, 2H), 4.05 (d, J=13.2 Hz, 2H), 3.81 (s, 3H), 3.55 (s, 2H), 3.42-3.35 (m, 2H), 3.31-3.25 (m, 1H), 3.24-3.14 (m, 4H), 2.74-2.63 (m, 2H), 2.47-2.36 (m, 1H), 2.12 (t, J=10.6 Hz, 2H), 1.85-1.76 (m, 4H), 1.66-1.52 (m, 2H), 1.50-1.36 (m, 2H). m/z: [ESI$^+$] 521 (M+H)$^+$, (C$_{28}$H$_{36}$N$_6$O$_4$).

Step 2: 1-(3-(4-Hydroxyphenyl)-1,2,4-oxadiazol-5-yl)-N-((1-(4-methylbenzyl)pyrrolidin-3-yl)methyl)piperidine-4-carboxamide To a stirred solution of 1-[3-(4-methoxyphenyl)-1,2,4-oxadiazol-5-yl]-N-([1-[(4-methylphenyl)methyl]pyrrolidin-3-yl]methyl)piperidine-4-carboxamide (100 mg, 0.204 mmol) in DCM (5 mL) was added boron tribromide (259 mg, 1.034 mmol) at −20° C. under a nitrogen atmosphere. The resulting solution was stirred for 2 h at room temperature under a nitrogen atmosphere. The reaction was quenched by the addition of methanol (10 mL) at 0° C. The resulting mixture was concentrated under reduced pressure. The residue was purified by reverse phase flash chromatography with the following conditions: Column: Spherical C18, 20-40 m, 330 g; Mobile Phase A: water (plus 10 mM NH$_4$HCO$_3$); Mobile Phase B: acetonitrile; Flow rate: 80 mL/min; Gradient: 50% B-75% B in 20 min; Detector: UV 220/254 nm. The fractions containing desired product were collected and concentrated under reduced pressure to afford 1-[3-(4-hydroxyphenyl)-1,2,4-oxadiazol-5-yl]-N-([1-[(4-methylphenyl)methyl]pyrrolidin-3-yl]methyl)piperidine-4-carboxamide as a light yellow solid.

Yield 80 mg (82%). $^1$H NMR (400 MHz, DMSO) δ 9.99 (br s, 1H), 7.88 (t, J=5.6 Hz, 1H), 7.72 (d, J=8.8 Hz, 2H), 7.17 (d, J=7.8 Hz, 2H), 7.11 (d, J=7.8 Hz, 2H), 6.86 (d, J=8.8 Hz, 2H), 4.03 (d, J=13.0 Hz, 2H), 3.49 (s, 2H), 3.24-3.11 (m, 2H), 3.09-2.92 (m, 2H), 2.49-2.31 (m, 4H), 2.27 (s, 3H), 2.25-2.14 (m, 2H), 1.91-1.70 (m, 3H), 1.66-1.51 (m, 2H), 1.42-1.30 (m, 1H). m/z: [ESI$^+$] 476 (M+H)$^+$, (C$_{27}$H$_{33}$N$_5$O$_3$).

The following compounds were prepared according to the procedure described above.

(1-(3-(4-Hydroxyphenyl)-1,2,4-oxadiazol-5-yl)piperidin-4-yl)(morpholino)methanone (Compound 182): Using (1-(3-(4-methoxyphenyl)-1,2,4-oxadiazol-5-yl)piperidin-4-yl)(morpholino)methanone (150 mg, 0.403 mmol) as the starting material.

Yield 80 mg (55%), as an off-white solid. $^1$H NMR (400 MHz, DMSO) δ 10.01 (br s, 1H), 7.72 (d, J=8.8 Hz, 2H), 6.85 (d, J=8.8 Hz, 2H), 4.05 (dd, J=3.6, 13.2 Hz, 2H), 3.63-3.50 (m, 6H), 3.44 (t, J=4.8 Hz, 2H), 3.23 (dt, J=2.8, 12.8 Hz, 2H), 3.00-2.81 (m, 1H), 1.80-1.71 (m, 2H), 1.67-1.51 (m, 2H). m/z: [ESI$^+$] 359 (M+H)$^+$, (C$_{18}$H$_{22}$N$_4$O$_4$).

1-(3-(4-Hydroxyphenyl)-1,2,4-oxadiazol-5-yl)-N-(pyridin-3-ylmethyl)piperidine-4-carboxamide (Compound 178): Using 1-(3-(4-methoxyphenyl)-1,2,4-oxadiazol-5-yl)-N-(pyridin-3-ylmethyl)piperidine-4-carboxamide (250 mg, 0.635 mmol) as the starting material.

Yield 150 mg (62%), as an off-white solid. $^1$H NMR (400 MHz, DMSO) δ 10.01 (br s, 1H), 8.55-8.39 (m, 3H), 7.73 (d, J=8.8 Hz, 2H), 7.64 (dd, J=2.0, 7.8 Hz, 1H), 7.35 (ddd, J=0.8, 4.8, 7.8 Hz, 1H), 6.86 (d, J=8.8 Hz, 2H), 4.30 (d, J=5.6 Hz, 2H), 4.06 (d, J=13.2 Hz, 2H), 3.20 (dt, J=2.8, 12.8 Hz, 2H), 2.50-2.45 (m, 1H), 1.85 (dd, J=3.6, 13.6 Hz, 2H), 1.69-1.56 (m, 2H). m/z: [ESI$^+$] 380 (M+H)$^+$, (C$_{20}$H$_{21}$N$_5$O$_3$).

1-(3-(3-Hydroxyphenyl)-1,2,4-oxadiazol-5-yl)-N-((1-(4-methylbenzyl)pyrrolidin-3-yl)methyl)piperidine-4-carboxamide (Compound 199): Using 1-(3-(3-methoxyphenyl)-1,2,4-oxadiazol-5-yl)-N-((1-(4-methylbenzyl)pyrrolidin-3-yl)methyl)piperidine-4-carboxamide (200 mg, 0.408 mmol) as the starting material.

Yield 150 mg (77%), as a light yellow solid. $^1$H NMR (400 MHz, DMSO) δ 9.72 (br s, 1H), 7.89 (t, J=5.6 Hz, 1H), 7.36-7.26 (m, 3H), 7.17 (d, J=8.0 Hz, 2H), 7.11 (d, J=8.0 Hz, 2H), 6.96-6.86 (m, 1H), 4.04 (dd, J=3.2, 12.8 Hz, 2H), 3.48 (s, 2H), 3.26-3.13 (m, 2H), 3.13-2.91 (m, 2H), 2.49-2.34 (m, 4H), 2.27 (s, 3H), 2.26-2.13 (m, 2H), 1.90-1.72 (m, 3H), 1.67-1.52 (m, 2H), 1.42-1.29 (m, 1H). m/z: [ESI$^+$] 476 (M+H)$^+$, (C$_{27}$H$_{33}$N$_5$O$_3$).

N-(4,5-dichloropyridin-2-yl)-1-(3-(4-methoxyphenyl)-1,2,4-oxadiazol-5-yl)piperidine-4-carboxamide (Compound 319)

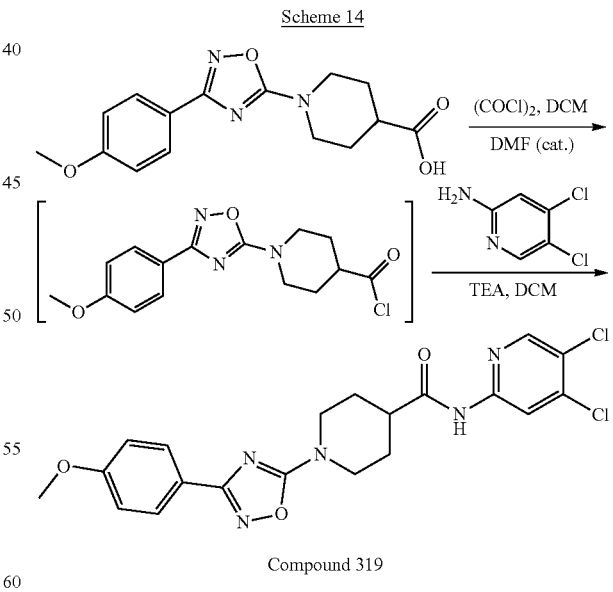

Compound 319

To a stirred solution of 1-[3-(4-methoxyphenyl)-1,2,4-oxadiazol-5-yl]piperidine-4-carboxylic acid (150 mg, 0.495 mmol) and oxalyl chloride (130 mg, 1.025 mmol) in DCM (5 mL) was added DMF (5 mg, 0.068 mmol) at 0° C. under a nitrogen atmosphere. The resulting solution was stirred for 2 h at 0° C. under a nitrogen atmosphere. After this time, triethylamine (100 mg, 0.988 mmol) and 4,5-dichloropyridin-2-amine (160 mg, 0.982 mmol) were added. The reaction mixture was stirred for additional 16 h. The reaction was quenched by the addition of water/ice (20 mL) at room temperature. The resulting mixture was extracted with ethyl acetate (3×20 mL). The combined organic layers were washed with brine (50 mL) and dried over anhydrous $Na_2SO_4$. After filtration, the filtrate was concentrated under reduced pressure. The residue was purified by reverse phase flash chromatography with the following conditions: Column: Spherical C18, 20-40 um, 330 g; Mobile Phase A: water (plus 10 mM $NH_4HCO_3$); Mobile Phase B: acetonitrile; Flow rate: 80 mL/min; Gradient: 50% B-75% B in 20 min; Detector: UV 220/254 nm. The fractions containing desired product were collected and concentrated under reduced pressure to afford N-(4,5-dichloropyridin-2-yl)-1-(3-(4-methoxyphenyl)-1,2,4-oxadiazol-5-yl)piperidine-4-carboxamide as a light yellow solid.

Yield 6 mg (3%). $^1H$ NMR (400 MHz, DMSO) δ 10.99 (br s, 1H), 8.55 (s, 1H), 8.36 (s, 1H), 7.84 (d, J=8.8 Hz, 2H), 7.05 (d, J=8.8 Hz, 2H), 4.11 (d, J=13.2 Hz, 2H), 3.82 (s, 3H), 3.23 (dt, J=3.2, 12.8 Hz, 2H), 2.81 (t, J=11.6 Hz, 1H), 2.01-1.85 (m, 2H), 1.75-1.61 (m, 2H). m/z: [ESI+] 448, 450 (M+H)+, ($C_{20}H_{19}Cl_2N_5O_3$).

The following targets were prepared according to the procedure described above.

(4-(3-(4-Methoxyphenyl)-1,2,4-oxadiazol-5-yl)piperazin-1-yl)(morpholino)methanone (Compound 144): Using 3-(4-methoxyphenyl)-5-(piperazin-1-yl)-1,2,4-oxadiazole (150 mg, 0.576 mmol) and morpholine-4-carbonyl chloride (130 mg, 0.869 mmol) as the starting material.

Yield 200 mg (93%), as a light yellow solid. $^1H$ NMR (400 MHz, DMSO) δ 7.84 (d, J=8.8 Hz, 2H), 7.05 (d, J=8.8 Hz, 2H), 3.82 (s, 3H), 3.65-3.55 (m, 8H), 3.38-3.30 (m, 4H), 3.19 (t, J=4.8 Hz, 4H). m/z: [ESI+] 374 (M+H)+, ($C_{18}H_{23}N_5O_4$).

1-(6-(4-methoxyphenyl)pyridin-2-yl)-N-((1-(4-methylbenzyl)pyrrolidin-3-yl)methyl)piperidine-4-carboxamide (Compound 157)

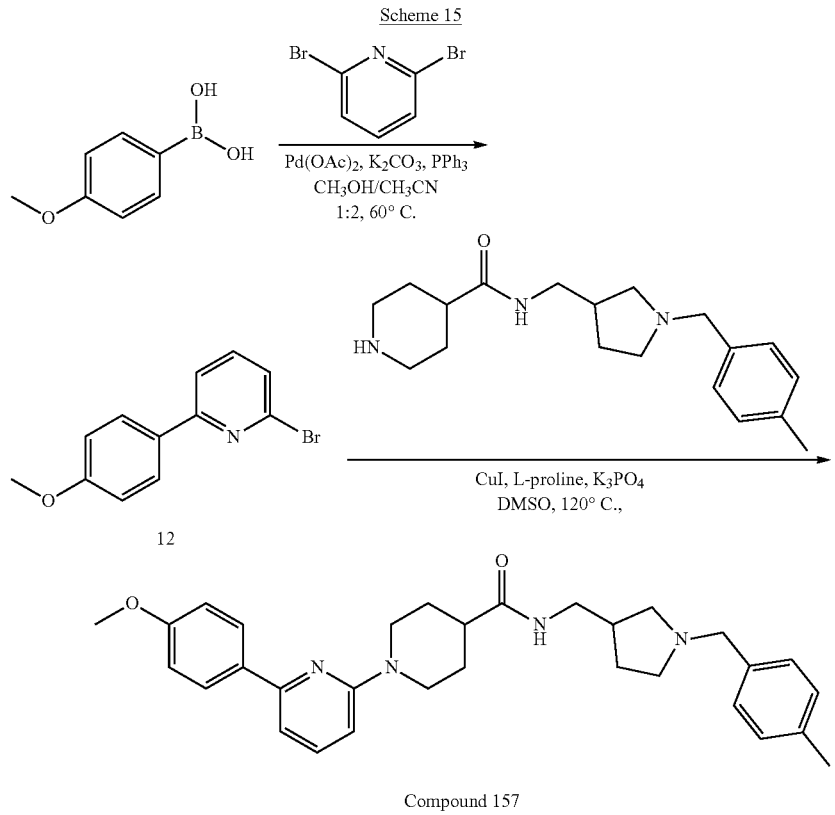

Compound 157

Step 1: 2-Bromo-6-(4-methoxyphenyl)pyridine

To a stirred solution of 4-methoxyphenylboronic acid (5.00 g, 32.90 mmol) in acetonitrile (20 mL) were added methanol (80 mL), 2,6-dibromopyridine (3.90 g, 16.46 mmol), potassium carbonate (9.09 g, 65.77 mmol), triphenylphosphine (1.75 g, 6.67 mmol) and palladium(II)acetate (0.75 g, 3.34 mmol) at room temperature. The reaction mixture was purged with nitrogen three times and then stirred at 60° C. for 4 h under a nitrogen atmosphere. The resulting mixture was cooled to room temperature, diluted with water (100 mL) and extracted with ethyl acetate (3×100 mL). The combined organic layer was washed with brine (200 mL) and dried with anhydrous $Na_2SO_4$. After filtration, the filtrate was concentrated under reduced pressure. The residue was purified by silica gel column chromatography, eluting with 10% ethyl acetate in petroleum ether to afford 2-bromo-6-(4-methoxyphenyl)pyridine as a as an off-white solid.

Yield: 1.80 g (23%) $^1H$ NMR (400 MHz, DMSO) δ 8.06 (d, J=8.8 Hz, 2H), 7.95 (dd, J=0.8, 8.0 Hz, 1H), 7.79 (d, J=7.6 Hz, 1H), 7.52 (dd, J=0.8, 7.6 Hz, 1H), 7.05 (d, J=8.8 Hz, 2H), 3.83 (s, 3H), m/z: [ESI+] 264, 266 (M+H)+.

Step 2: 1-(6-(4-methoxyphenyl)pyridin-2-yl)-N-((1-(4-methylbenzyl)pyrrolidin-3-yl)methyl)piperidine-4-carboxamide To a stirred solution of 2-bromo-6-(4-methoxyphenyl) pyridine (200 mg, 0.757 mmol) in DMSO (5 mL) were added potassium phosphate tribasic (482 mg, 2.272 mmol), N-([1-[(4-methylphenyl)methyl]pyrrolidin-3-yl]methyl)piperidine-4-carboxamide (717 mg, 2.273 mmol), L-proline (17 mg, 0.148 mmol) and copper(I) iodide (14 mg, 0.0734 mmol) portion-wise at room temperature, under a nitrogen atmosphere. The mixture was stirred at 120° C. for 16 h under a nitrogen atmosphere. The mixture was cooled to room temperature and filtered. The filtrate was purified by reverse phase flash chromatography with the following conditions: column, C18, 20-40 um, 330 g; Mobile Phase A: water (plus 10 mM $NH_4HCO_3$); Mobile Phase B: acetonitrile; Flow rate: 80 mL/min; Gradient: 50% B-70% B in 25 min; Detector, UV 220/254 nm. The fractions containing desired product were collected and concentrated under reduced pressure to afford 1-(6-(4-methoxyphenyl)pyridin-2-yl)-N-((1-(4-methylbenzyl)pyrrolidin-3-yl)methyl)piperidine-4-carboxamide as an off-white solid.

Yield: 57 mg (15%). $^1$H NMR (400 MHz, DMSO) δ 7.98 (d, J=8.8 Hz, 2H), 7.85 (t, J=5.6 Hz, 1H), 7.56 (dd, J=7.2, 8.4 Hz, 1H), 7.16 (d, J=8.0 Hz, 2H), 7.14-7.08 (m, 3H), 7.00 (d, J=8.8 Hz, 2H), 6.73 (d, J=8.4 Hz, 1H), 4.41 (d, J=12.8 Hz, 2H), 3.80 (s, 3H), 3.47 (s, 2H), 3.12-2.91 (m, 2H), 2.84 (dd, J=11.2, 13.8 Hz, 2H), 2.50-2.39 (m, 4H), 2.27 (s, 3H), 2.25-2.13 (m, 2H), 1.86-1.75 (m, 1H), 1.71 (d, J=12.8 Hz, 2H), 1.62-1.49 (m, 2H), 1.41-1.30 (m, 1H). m/z: (ESI$^+$): 499 (M+H)$^+$, ($C_{31}H_{38}N_4O_2$).

(1s,4s)-N-((1-(2-hydroxyethyl)pyrrolidin-3-yl)methyl)-4-(3-(4-methoxyphenyl)-1,2,4-oxadiazol-5-yl)cyclohexane-1-carboxamide (Compound 215)

cooling to room temperature, the resulting mixture was purified by reverse phase flash chromatography with the following conditions: Column: Spherical C18, 20-40 um, 330 g; Mobile Phase A: water (plus 10 mM $NH_4HCO_3$); Mobile Phase B: acetonitrile; Flow rate: 80 mL/min; Gradient: 40% B-60% B in 20 min; Detector: UV 220/254 nm. The fractions containing desired product were collected and concentrated under reduced pressure to afford (1s,4s)-N-((1-(2-hydroxyethyl)pyrrolidin-3-yl)methyl)-4-(3-(4-methoxyphenyl)-1,2,4-oxadiazol-5-yl)cyclohexane-1-carboxamide as an off-white solid.

Yield: 43 mg (10%). $^1$H NMR (400 MHz, DMSO) δ 7.94 (d, J=8.8 Hz, 2H), 7.84 (t, J=5.6 Hz, 1H), 7.11 (d, J=8.8 Hz, 2H), 4.42 (t, J=5.6 Hz, 1H), 3.84 (s, 3H), 3.51-3.42 (m, 2H), 3.12-2.91 (m, 3H), 2.55-2.46 (m, 5H), 2.28-2.12 (m, 5H), 1.90-1.74 (m, 3H), 1.64-1.46 (m, 4H), 1.39-1.32 (m, 1H). m/z: (ESI$^+$): 429 (M+H)$^+$, ($C_{23}H_{32}N_4O_4$).

The following intermediates and targets were synthesized according to the procedure described above.

2-(3-(4-(Pyridin-2-ylmethyl)piperazin-1-yl)propyl) isoindoline-1,3-dione. The compound was synthesized according to the procedure described above, using 1-(pyridin-2-ylmethyl)piperazine (0.50 g, 2.82 mmol) and 2-(3-bromopropyl) isoindoline-1,3-dione (0.76 g, 2.83 mmol) as the starting material.

Yield 0.80 g (78%), as a dark yellow solid. $^1$H NMR (400 MHz, CDCl$_3$) δ 8.60 (ddd, J=0.8, 1.6, 4.8 Hz, 1H), 7.70-7.65 (m, 2H), 7.58-7.54 (m, 1H), 7.41-7.37 (m, 2H), 7.31 (dd, J=1.2, 8.0 Hz, 1H), 7.21 (ddd, J=1.2, 4.8, 7.6 Hz, 1H), 3.67 (s, 2H), 3.44 (t, J=6.0 Hz, 2H), 3.00 (s, 4H), 2.91 (t, J=7.2 Hz, 2H), 2.70 (s, 4H), 2.01-1.90 (m, 2H). m/z: [ESI$^+$] 365 (M+H)$^+$.

Tert-butyl (3R)-3-((3-((1-(3-(4-methoxyphenyl)-1,2,4-oxadiazol-5-yl)piperidine-4-carboxamido)methyl)pyrrolidin-1-yl)methyl)piperidine-1-carboxylate. The compound was synthesized according to the procedure described

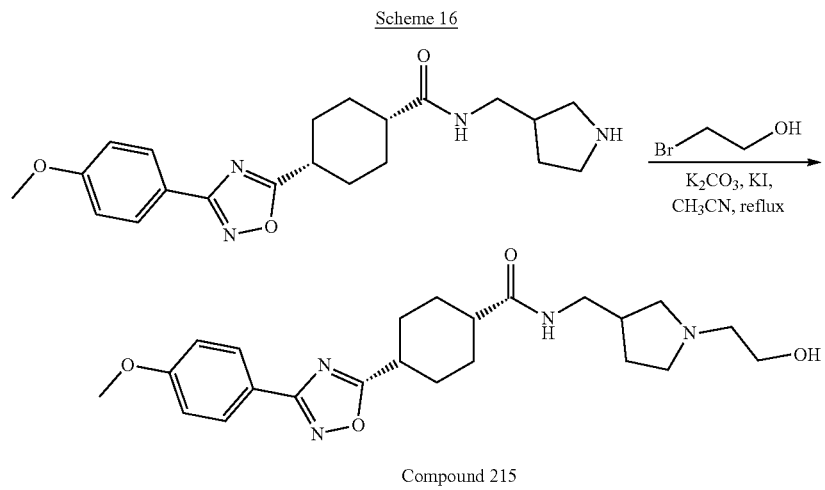

Scheme 16

Compound 215

To a stirred solution of (1s,4s)-4-[3-(4-methoxyphenyl)-1,2,4-oxadiazol-5-yl]-N-(pyrrolidin-3-ylmethyl)cyclohexane-1-carboxamide (400 mg, 1.040 mmol) in acetonitrile (5 mL) were added potassium carbonate (288 mg, 2.084 mmol), potassium iodide (17 mg, 0.102 mmol) and 2-bromoethanol (130 mg, 1.040 mmol) at room temperature under a nitrogen atmosphere. The resulting mixture was stirred overnight at reflux under a nitrogen atmosphere. After above, using 1-(3-(4-methoxyphenyl)-1,2,4-oxadiazol-5-yl)-N-(pyrrolidin-3-ylmethyl)piperidine-4-carboxamide (0.30 g, 0.78 mmol) and tert-butyl (S)-3-(bromomethyl) piperidine-1-carboxylate (0.22 g, 0.79 mmol) as the starting material.

Yield 0.24 g (53%), as a dark yellow solid. $^1$H NMR (400 MHz, CDCl$_3$) δ 8.00 (d, J=8.8 Hz, 2H), 7.10 (br s, 1H), 6.97 (d, J=8.8 Hz, 2H), 4.27 (d, J=12.8 Hz, 2H), 4.20-4.02 (m, 2H), 3.94 (d, J=13.6 Hz, 1H), 3.87 (s, 3H), 3.42-3.12 (m, 3H), 2.88-2.75 (m, 2H), 2.70-2.31 (m, 5H), 2.26-2.15 (m, 1H), 2.10-1.78 (m, 6H), 1.75-1.54 (m, 6H), 1.47 (d, J=7.6 Hz, 9H), 1.21-1.09 (m, 1H). m/z: [ESI$^+$] 583 (M+H)$^+$.

Tert-butyl (3S)-3-((3-((1-(3-(4-methoxyphenyl)-1,2,4-oxadiazol-5-yl)piperidine-4-carboxamido)methyl)pyrrolidin-1-yl)methyl)piperidine-1-carboxylate. The compound was synthesized according to the procedure described above, using 1-(3-(4-methoxyphenyl)-1,2,4-oxadiazol-5-yl)-N-(pyrrolidin-3-ylmethyl)piperidine-4-carboxamide (0.15 g, 0.39 mmol) and tert-butyl (R)-3-(bromomethyl)piperidine-1-carboxylate (0.11 g, 0.40 mmol) as the starting material.

Yield 0.10 g (44%), as an off-white solid. $^1$H NMR (400 MHz, CDCl$_3$) δ 7.94 (d, J=8.8 Hz, 2H), 7.37 (br s, 1H), 6.96 (d, J=8.8 Hz, 2H), 4.27 (d, J=13.2 Hz, 2H), 3.97 (d, J=13.2 Hz, 1H), 3.87 (s, 3H), 3.85-3.72 (m, 1H), 3.61-3.38 (m, 2H), 3.37-3.27 (m, 1H), 3.20 (t, J=12.4 Hz, 1H), 3.13-2.69 (m, 13H), 2.50 (m, 1H), 2.16 (m, 1H), 2.04-1.72 (m, 4H), 1.67 (d, J=13.4 Hz, 1H), 1.48 (s, 9H), 1.39-1.27 (m, 1H). m/z: [ESI$^+$] 583 (M+H)$^+$.

Tert-butyl (R)-3-(((R)-3-((1-(3-(4-methoxyphenyl)-1,2,4-oxadiazol-5-yl)piperidine-4-carboxamido)methyl)pyrrolidin-1-yl)methyl)piperidine-1-carboxylate. The compound was synthesized according to the procedure described above, using (S)-1-(3-(4-methoxyphenyl)-1,2,4-oxadiazol-5-yl)-N-(pyrrolidin-3-ylmethyl)piperidine-4-carboxamide (0.25 g, 0.65 mmol) and tert-butyl (S)-3-(bromomethyl)piperidine-1-carboxylate (0.22 g, 0.79 mmol) as the starting material.

Yield 0.30 g (79%), as an off-white solid. $^1$H NMR (400 MHz, CDCl$_3$) δ 7.95 (d, J=8.8 Hz, 2H), 7.16 (br s, 1H), 6.97 (d, J=8.8 Hz, 2H), 4.26 (d, J=12.8 Hz, 2H), 4.16-4.05 (m, 1H), 3.87 (s, 3H), 3.51 (d, J=5.6 Hz, 2H), 3.42-3.16 (m, 4H), 2.86 (t, J=11.2 Hz, 1H), 2.72-2.30 (m, 4H), 2.13-1.77 (m, 6H), 1.73-1.58 (m, 8H), 1.47 (s, 9H), 1.21-1.06 (m, 1H). m/z: [ESI$^+$] 583 (M+H)$^+$.

Tert-butyl (R)-3-(((S)-3-((1-(3-(4-methoxyphenyl)-1,2,4-oxadiazol-5-yl)piperidine-4-carboxamido)methyl)pyrrolidin-1-yl)methyl)piperidine-1-carboxylate. The compound was synthesized according to the procedure described above, using (R)-1-(3-(4-methoxyphenyl)-1,2,4-oxadiazol-5-yl)-N-(pyrrolidin-3-ylmethyl)piperidine-4-carboxamide (0.25 g, 0.65 mmol) and tert-butyl (S)-3-(bromomethyl)piperidine-1-carboxylate (0.22 g, 0.79 mmol) as the starting material.

Yield 0.30 g (79%), as an off-white solid. $^1$H NMR (400 MHz, CDCl$_3$) δ 7.95 (d, J=8.8 Hz, 2H), 6.97 (d, J=8.8 Hz, 2H), 4.28 (d, J=13.2 Hz, 2H), 4.17-4.01 (m, 1H), 3.96-3.82 (m, 1H), 3.87 (s, 3H), 3.41-3.27 (m, 1H), 3.20 (t, J=12.4 Hz, 2H), 3.11 (d, J=6.6 Hz, 2H), 2.90-2.79 (m, 2H), 2.60-2.35 (m, 5H), 2.09-1.95 (m, 3H), 1.88 (d, J=12.0 Hz, 2H), 1.71-1.62 (m, 7H), 1.49 (s, 9H), 1.37-1.14 (m, 1H). Amide NH not observed. m/z: [ESI$^+$] 583 (M+H)$^+$.

Tert-butyl (3R)-3-((3-((1-(3-(4-cyanophenyl)-1,2,4-oxadiazol-5-yl)piperidine-4-carboxamido)methyl)pyrrolidin-1-yl)methyl)piperidine-1-carboxylate. The compound was synthesized according to the procedure described above, using 1-(3-(4-cyanophenyl)-1,2,4-oxadiazol-5-yl)-N-(pyrrolidin-3-ylmethyl)piperidine-4-carboxamide hydrochloride (0.40 g, 0.96 mmol) and tert-butyl (S)-3-(bromomethyl)piperidine-1-carboxylate (0.32 g, 1.15 mmol) as the starting material.

Yield 0.25 g (45%), as an off-white solid. m/z: [ESI$^+$] 578 (M+H)$^+$.

Tert-butyl (3R)-3-((3-((1-(3-(4-chlorophenyl)-1,2,4-oxadiazol-5-yl)piperidine-4-carboxamido)methyl)pyrrolidin-1-yl)methyl)piperidine-1-carboxylate. The compound was synthesized according to the procedure described above, using 1-(3-(4-chlorophenyl)-1,2,4-oxadiazol-5-yl)-N-(pyrrolidin-3-ylmethyl)piperidine-4-carboxamide (0.25 g, 0.64 mmol) and tert-butyl (S)-3-(bromomethyl)piperidine-1-carboxylate (0.18 g, 0.65 mmol) as the starting material.

Yield 0.15 g (40%), as an off-white solid. $^1$H NMR (400 MHz, DMSO) δ 7.97-7.84 (m, 3H), 7.59 (d, J=8.4 Hz, 2H), 4.14-4.03 (m, 3H), 4.00-3.87 (m, 1H), 3.77 (d, J=12.8 Hz, 1H), 3.26-3.14 (m, 5H), 3.10-2.94 (m, 2H), 2.74 (t, J=11.6 Hz, 1H), 2.51-2.35 (m, 2H), 2.30-2.05 (m, 4H), 1.87-1.77 (m, 3H), 1.76-1.69 (m, 1H), 1.68-1.44 (m, 3H), 1.39 (s, 9H), 1.38-1.25 (m, 2H), 1.17-0.98 (m, 1H). m/z: [ESI$^+$] 587, 589 (M+H)$^+$.

Methyl 2-(3-((1-(3-(4-methoxyphenyl)-1,2,4-oxadiazol-5-yl)piperidine-4-carboxamido)methyl)pyrrolidin-1-yl)-2-methylpropanoate. The compound was synthesized according to the procedure described above, using 1-(3-(4-methoxyphenyl)-1,2,4-oxadiazol-5-yl)-N-(pyrrolidin-3-ylmethyl)piperidine-4-carboxamide (100 mg, 0.259 mmol) and methyl 2-bromo-2-methylpropanoate (47 mg, 0.260 mmol) as the starting material.

Yield 70 mg (56%), as a light yellow solid. $^1$H NMR (400 MHz, DMSO) δ 7.89 (t, J=5.6 Hz, 1H), 7.84 (d, J=8.8 Hz, 2H), 7.05 (d, J=8.8 Hz, 2H), 4.06 (d, J=13.2 Hz, 2H), 3.82 (s, 3H), 3.61 (s, 3H), 3.20 (dt, J=3.2, 12.8 Hz, 2H), 3.11-2.91 (m, 2H), 2.80-2.60 (m, 3H), 2.46-2.32 (m, 2H), 2.21-2.13 (m, 1H), 1.84-1.75 (m, 3H), 1.67-1.54 (m, 2H), 1.40-1.32 (m, 1H), 1.26 (s, 6H). m/z: [ESI$^+$] 486 (M+H)$^+$.

(1r,4r)-N-((1-(2-Hydroxyethyl)pyrrolidin-3-yl)methyl)-4-(3-(4-methoxyphenyl)-1,2,4-oxadiazol-5-yl)cyclohexane-1-carboxamide (Compound 197): Using (1r,4r)-4-[3-(4-methoxyphenyl)-1,2,4-oxadiazol-5-yl]-N-(pyrrolidin-3-ylmethyl)cyclohexane-1-carboxamide (200 mg, 0.520 mmol) and 2-bromoethan-1-ol (65 mg, 0.520 mmol) as the starting material.

Yield 30 mg (14%), as an off-white solid. $^1$H NMR (400 MHz, DMSO) δ 7.93 (d, J=8.8 Hz, 2H), 7.83 (t, J=5.6 Hz, 1H), 7.10 (d, J=8.8 Hz, 2H), 4.39 (t, J=5.6 Hz, 1H), 3.83 (s, 3H), 3.49-3.40 (m, 2H), 3.13-2.89 (m, 3H), 2.53-2.45 (m, 3H), 2.43 (t, J=6.4 Hz, 2H), 2.22-2.10 (m, 5H), 1.86-1.69 (m, 3H), 1.65-1.46 (m, 4H), 1.38-1.26 (m, 1H). m/z: (ESI$^+$): 429 (M+H)$^+$, (C$_{23}$H$_{32}$N$_4$O$_4$).

N-((1-(2-hydroxyethyl)pyrrolidin-3-yl)methyl)-1-(3-(4-methoxyphenyl)-1,2,4-oxadiazol-5-yl)piperidine-4-carboxamide formate (Compound 362): Using 1-(3-(4-methoxyphenyl)-1,2,4-oxadiazol-5-yl)-N-(pyrrolidin-3-ylmethyl)piperidine-4-carboxamide (100 mg, 0.259 mmol) and 2-bromoethan-1-ol (50 mg, 0.400 mmol) as the starting material.

Yield 24 mg (19%), as an off-white solid. $^1$H NMR (400 MHz, DMSO) δ 8.23 (s, 1H, HCOOH), 7.94 (t, J=5.6 Hz, 1H), 7.84 (d, J=8.8 Hz, 2H), 7.05 (d, J=8.8 Hz, 2H), 4.06 (td, J=3.6, 13.2 Hz, 2H), 3.82 (s, 3H), 3.49 (t, J=6.2 Hz, 2H), 3.20 (dt, J=3.2, 12.8 Hz, 2H), 3.12-2.95 (m, 2H), 2.69 (dd, J=7.6, 9.4 Hz, 1H), 2.64-2.51 (m, 4H), 2.45-2.20 (m, 3H), 1.90-1.75 (m, 3H), 1.67-1.53 (m, 2H), 1.46-1.32 (m, 1H). OH proton not observed. m/z: (ESI$^+$): 430 (M+H)$^+$, (C$_{22}$H$_{31}$N$_5$O$_4$).

N-((1-(2-fluoroethyl)pyrrolidin-3-yl)methyl)-1-(3-(4-methoxyphenyl)-1,2,4-oxadiazol-5-yl)piperidine-4-carboxamide (Compound 366): Using 1-(3-(4-methoxyphenyl)-1,2,4-oxadiazol-5-yl)-N-(pyrrolidin-3-ylmethyl)piperidine-4-carboxamide (100 mg, 0.259 mmol) and 1-fluoro-2-iodoethane (50 mg, 0.287 mmol) as the starting material.

Yield 7 mg (6%), as an off-white solid. $^1$H NMR (400 MHz, DMSO) δ 7.93 (t, J=5.6 Hz, 1H), 7.84 (d, J=8.8 Hz, 2H), 7.05 (d, J=8.8 Hz, 2H), 4.50 (td, J=4.8, 47.8 Hz, 2H), 4.11-4.00 (m, 2H), 3.82 (s, 3H), 3.20 (dt, J=2.8, 12.8 Hz, 2H), 3.10-2.95 (m, 2H), 2.76-2.67 (m, 1H), 2.67-2.51 (m, 4H), 2.43-2.35 (m, 1H), 2.25 (d, J=6.8 Hz, 2H), 1.87-1.75 (m, 3H), 1.68-1.55 (m, 2H), 1.44-1.31 (m, 1H). $^{19}$F NMR (376 MHz, DMSO) δ −217.94. m/z: (ESI$^+$): 430 (M+H)$^+$, ($C_{22}H_{30}FN_5O_3$).

1-(3-(4-Methoxyphenyl)-1,2,4-oxadiazol-5-yl)-N-((1-(2,2,2-trifluoroethyl)pyrrolidin-3-yl)methyl)piperidine-4-carboxamide (Compound 343): Using 1-(3-(4-methoxyphenyl)-1,2,4-oxadiazol-5-yl)-N-(pyrrolidin-3-ylmethyl)piperidine-4-carboxamide (100 mg, 0.259 mmol) and 1,1,1-trifluoro-2-iodoethane (60 mg, 0.286 mmol) as the starting material.

Yield 16 mg (13%), as an off-white solid. $^1$H NMR (400 MHz, DMSO) δ 7.94 (t, J=5.6 Hz, 1H), 7.84 (d, J=8.8 Hz, 2H), 7.05 (d, J=8.8 Hz, 2H), 4.14-3.97 (m, 2H), 3.82 (s, 3H), 3.28-3.13 (m, 4H), 3.09-2.96 (m, 2H), 2.76 (t, J=8.4 Hz, 1H), 2.70-2.64 (m, 2H), 2.43-2.35 (m, 2H), 2.31-2.20 (m, 1H), 1.92-1.78 (m, 3H), 1.67-1.55 (m, 2H), 1.46-1.35 (m, 1H). $^{19}$F NMR (376 MHz, DMSO) δ −68.57. m/z: (ESI$^+$): 468 (M+H)$^+$, ($C_{22}H_{28}F_3N_5O_3$).

N-((1-(2,2-difluoroethyl)pyrrolidin-3-yl)methyl)-1-(3-(4-methoxyphenyl)-1,2,4-oxadiazol-5-yl)piperidine-4-carboxamide (Compound 367): Using 1-(3-(4-methoxyphenyl)-1,2,4-oxadiazol-5-yl)-N-(pyrrolidin-3-ylmethyl)piperidine-4-carboxamide (100 mg, 0.259 mmol) and 1,1-difluoro-2-iodoethane (50 mg, 0.260 mmol) as the starting material.

Yield 40 mg (34%), as an off-white solid. $^1$H NMR (400 MHz, DMSO) δ 7.93 (t, J=5.6 Hz, 1H), 7.84 (d, J=8.8 Hz, 2H), 7.05 (d, J=8.8 Hz, 2H), 6.10-6.05 (m, 1H), 4.06 (td, J=3.6, 13.2 Hz, 2H), 3.82 (s, 3H), 3.20 (dt, J=3.2, 12.8 Hz, 2H), 3.10-2.94 (m, 2H), 2.80 (dt, J=4.4, 16.0 Hz, 2H), 2.66 (t, J=8.0 Hz, 1H), 2.62-2.54 (m, 2H), 2.45-2.35 (m, 1H), 2.34-2.17 (m, 2H), 1.87-1.75 (m, 3H), 1.69-1.54 (m, 2H), 1.42-1.33 (m, 1H); $^{19}$F NMR (376 MHz, DMSO) δ −118.80. m/z: [ESI$^+$] 450 (M+H)$^+$, ($C_{22}H_{29}F_2N_5O_3$).

1-(3-(4-Methoxyphenyl)-1,2,4-oxadiazol-5-yl)-N-((1-(oxetan-2-ylmethyl)pyrrolidin-3-yl)methyl)piperidine-4-carboxamide (Compound 395): Using 1-(3-(4-methoxyphenyl)-1,2,4-oxadiazol-5-yl)-N-(pyrrolidin-3-ylmethyl)piperidine-4-carboxamide (100 mg, 0.259 mmol) and 2-(iodomethyl)oxetane (50 mg, 0.253 nnol) as the starting material.

Yield 30 mg (26%), as an off-white solid. $^1$H NMR (400 MHz, DMSO) δ 7.90 (t, J=5.6 Hz, 1H), 7.84 (d, J=8.8 Hz, 2H), 7.05 (d, J=8.8 Hz, 2H), 4.85-4.73 (m, 1H), 4.49 (dt, J=5.6, 8.0 Hz, 1H), 4.35 (td, J=5.6, 9.2 Hz, 1H), 4.06 (td, J=3.6, 13.2 Hz, 2H), 3.82 (s, 3H), 3.19 (dt, J=3.2, 12.8 Hz, 2H), 3.07-2.94 (m, 2H), 2.71-2.63 (m, 1H), 2.62-2.51 (m, 3H), 2.49-2.28 (m, 4H), 2.27-2.12 (m, 2H), 1.85-1.73 (m, 3H), 1.67-1.52 (m, 2H), 1.38-1.28 (m, 1H). m/z: [ESI$^+$] 456 (M+H)$^+$, ($C_{24}H_{33}N_5O_4$).

1-(3-(4-methoxyphenyl)-1,2,4-oxadiazol-5-yl)-N-((1-phenylpyrrolidin-3-yl)methyl)piperidine-4-carboxamide (Compound 234)

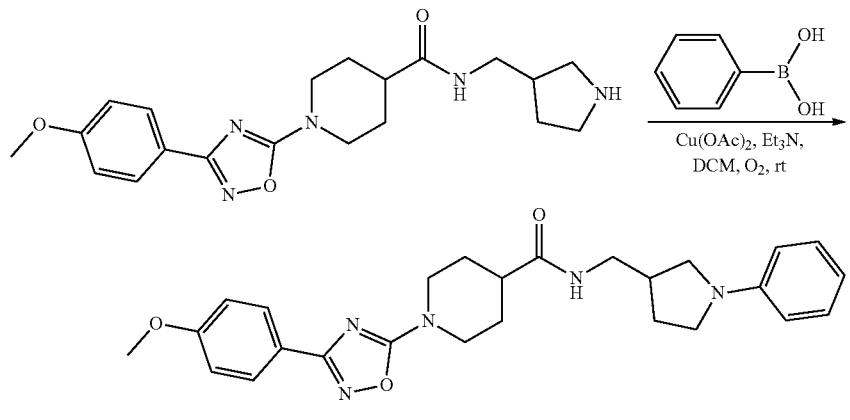

Compound 234

To a stirred solution of 1-[3-(4-methoxyphenyl)-1,2,4-oxadiazol-5-yl]-N-(pyrrolidin-3-ylmethyl)piperidine-4-carboxamide (200 mg, 0.519 mmol) and phenyl boronic acid (95 mg, 0.779 mmol) in DCM (5 mL), were added copper (II) acetate (0.188 g, 1.035 mmol) and triethylamine (105 mg, 1.039 mmol) at room temperature under air atmosphere. The resulting mixture was stirred overnight at room temperature under an oxygen atmosphere (balloon). The resulting mixture was filtered, and the filter cake was washed with acetonitrile (3×10 mL). The filtrate was then concentrated under reduced pressure. The residue was purified by reverse phase flash chromatography with the following conditions: Column, C18 silica gel; Mobile phase: 10% to 50% methanol in water in 10 min; Detector: UV 220/254 nm. The fractions containing the desired product were collected and concentrated under reduced pressure to afford 1-[3-(4-methoxyphenyl)-1,2,4-oxadiazol-5-yl]-N-[(1-phenylpyrrolidin-3-yl)methyl]piperidine-4-carboxamide as a light yellow solid.

Yield: 60 mg (25%). $^1$H NMR (400 MHz, DMSO) δ 8.04 (t, J=5.6 Hz, 1H), 7.84 (d, J=8.8 Hz, 2H), 7.15 (d, J=7.6 Hz, 2H), 7.05 (d, J=8.8 Hz, 2H), 6.58 (t, J=7.2 Hz, 1H), 6.50 (d, J=8.0 Hz, 2H), 4.07 (d, J=13.0 Hz, 2H), 3.82 (s, 3H), 3.30-3.28 (m, 2H), 3.25-3.08 (m, 4H), 2.95 (dd, J=6.2, 9.4 Hz, 1H), 2.48-2.37 (m, 3H), 2.11-1.98 (m, 1H), 1.83 (d, J=12.8 Hz, 2H), 1.75-1.58 (m, 3H). m/z: (ESI$^+$): 462 (M+H)$^+$, ($C_{26}H_{31}N_5O_3$).

229

(1-((4-(Pyridin-2-ylmethyl)piperidin-1-yl)methyl)cyclopropyl)methanamine

Scheme 18

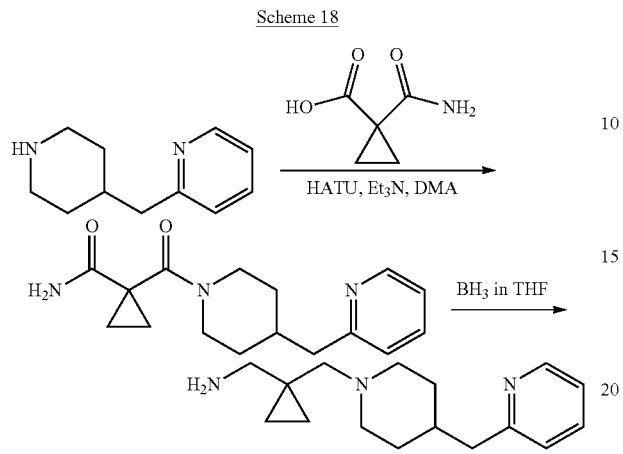

Step 1: 1-(4-(pyridin-2-ylmethyl)piperidine-1-carbonyl)cyclopropane-1-carboxamide To a stirred solution of 2-(piperidin-4-ylmethyl)pyridine (0.60 g, 3.40 mmol) in DMA (10 mL) were added HATU (1.55 g, 4.08 mmol), triethylamine (0.69 g, 6.82 mmol) and 1-carbamoylcyclopropane-1-carboxylic acid (0.53 g, 4.10 mmol) at room temperature. The resulting solution was stirred for 2 h at room temperature under a nitrogen atmosphere. The resulting mixture was purified by reverse phase flash chromatography with the following conditions: Column: Spherical C18, 20-40 um, 330 g; Mobile Phase A: water (plus 10 mM NH$_4$HCO$_3$); Mobile Phase B: acetonitrile; Flow rate: 80 mL/min; Gradient: 20 B-35% B in 15 min; Detector: UV 220/254 nm. The fractions containing desired product were collected and concentrated under reduced pressure to afford 1-(4-(pyridin-2-ylmethyl)piperidine-1-carbonyl)cyclopropane-1-carboxamide as a yellow solid.

Yield: 0.28 g (29%). m/z: [ESI$^+$] 288 (M+H)$^+$. Crude material was used in the next step without further purification.

Step 2: (1-((4-(pyridin-2-ylmethyl)piperidin-1-yl)methyl)cyclopropyl)methanamine To a stirred solution of 1-(4-(pyridin-2-ylmethyl)piperidine-1-carbonyl)cyclopropane-1-carboxamide (0.28 g, 0.97 mmol) in THF (5 mL) was added borane-tetrahydrofuran complex (1 M in THF, 6 mL) dropwise at 0° C. under a nitrogen atmosphere. The resulting solution was stirred overnight at 60° C. under a nitrogen atmosphere. The reaction was quenched by the addition of methanol (5 mL) at 0° C. After being stirred for 10 min at room temperature, the solution was concentrated under reduced pressure. The residue was purified by reverse phase flash chromatography with the following conditions: Column: Spherical C18, 20-40 um, 330 g; Mobile Phase A: water (plus 10 mM NH$_4$HCO$_3$); Mobile Phase B: acetonitrile; Flow rate: 80 mL/min; Gradient: 30% B-60% B in 20 min; Detector: UV 220/254 nm. The fractions containing desired product were collected and concentrated under reduced pressure to afford

230

(1-((4-(pyridin-2-ylmethyl)piperidin-1-yl)methyl)cyclopropyl)methanamine as a light yellow oil.

Yield: 0.20 g (79%). m/z: [ESI$^+$] 260 (M+H)$^+$. Crude material was used in the next step without further purification.

3-(4-(Pyridin-2-ylmethyl)piperazin-1-yl)propan-1-amine

Scheme 19

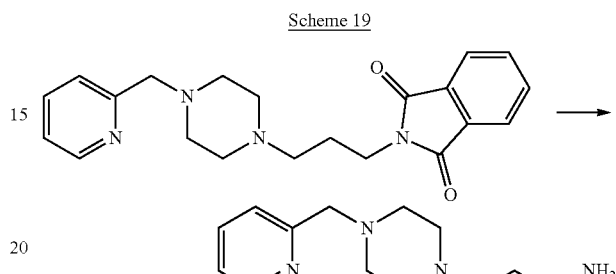

To a solution of 2-(3-(4-(pyridin-2-ylmethyl)piperazin-1-yl)propyl) isoindoline-1,3-dione (0.40 g, 1.10 mmol) in ethanol (20 mL) was added hydrazine hydrate (85%, 0.20 g, 3.40 mmol) dropwise at room temperature under a nitrogen atmosphere. The resulting solution was stirred for 16 h at 70° C. under a nitrogen atmosphere. The resulting solution was cooled to room temperature and filtered. The filter cake was washed with ethanol (3×5 mL) and the filtrate was concentrated under reduced pressure. The residue was purified by reverse phase flash chromatography with the following conditions: Column, Spherical C18, 20-40 um, 330; Mobile Phase A: water (plus 10 mM NH$_4$HCO$_3$); Mobile Phase B: acetonitrile; Flow rate: 80 mL/min; Gradient: 15% B-35% B in 20 min; Detector, UV 220/254 nm. The fractions containing desired product were collected and concentrated under reduced pressure to afford 3-(4-(pyridin-2-ylmethyl)piperazin-1-yl)propan-1-amine as an off-white solid.

Yield: 0.14 g (54%). $^1$H NMR (400 MHz, CDCl$_3$) δ 8.58 (d, J=1.6 Hz, 1H), 7.66 (dd, J=1.6, 7.6 Hz, 1H), 7.41 (d, J=7.6 Hz, 1H), 7.18 (dd, J=5.2, 7.6 Hz, 1H), 3.68 (s, 2H), 2.77 (t, J=6.8 Hz, 2H), 2.56 (s, 8H), 2.43 (t, J=7.4 Hz, 2H), 1.66-1.54 (m, 2H). Aliphatic NH$_2$ not observed. m/z: [ESI$^+$] 235 (M+H)$^+$.

Tert-butyl (3-(4-fluoro-4-(pyridin-2-ylmethyl)piperidin-1-yl)propyl)carbamate

Scheme 20

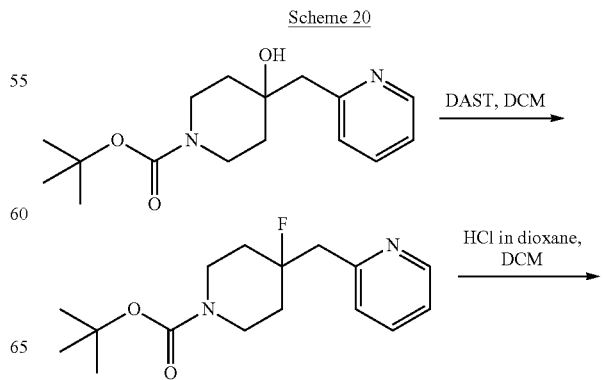

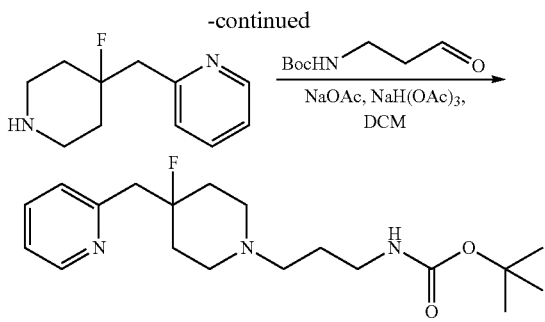

Step 1: tert-butyl 4-fluoro-4-(pyridin-2-ylmethyl)piperidine-1-carboxylate

To a stirred solution of tert-butyl 4-hydroxy-4-(pyridin-2-ylmethyl)piperidine-1-carboxylate (3.00 g, 10.26 mmol) in DCM (50 mL) was added diethylaminosulfur trifluoride (4.96 g, 30.77 mmol) dropwise at −78° C. under a nitrogen atmosphere over 5 min. The resulting solution was stirred for 2 h at −78° C. under a nitrogen atmosphere. The reaction was quenched with sat. aqueous sodium bicarbonate (30 mL) and the resulting mixture was concentrated under reduced pressure. The residue was purified by reverse phase flash chromatography with the following conditions: Column: Spherical C18, 20-40 um, 330 g; Mobile Phase A: water (plus 10 mM $NH_4HCO_3$); Mobile Phase B: acetonitrile; Flow rate: 80 mL/min; Gradient: 20% B-40% B in 20 min; Detector: UV 220/254 nm. The fractions containing desired product were collected and concentrated under reduced pressure to afford tert-butyl 4-fluoro-4-(pyridin-2-ylmethyl)piperidine-1-carboxylate as a light yellow oil.

Yield: 1.00 g (33%). $^1$H NMR (400 MHz, $CDCl_3$) δ 8.58 (ddd, J=1.2, 3.6, 6.2 Hz, 1H), 7.73 (d, J=8.0 Hz, 1H), 7.27-7.23 (m, 2H), 3.92 (s, 2H), 3.61 (s, 2H), 3.49 (t, J=5.6 Hz, 2H), 2.07 (d, J=6.4 Hz, 2H), 1.81-1.70 (m, 2H), 1.47 (s, 9H); $^{19}$F NMR (376 MHz, $CDCl_3$) δ −160.01. m/z: [ESI$^+$] 295 (M+H)$^+$.

Step 2: 2-((4-fluoropiperidin-4-yl)methyl)pyridine hydrochloride

To a stirred solution of tert-butyl 4-fluoro-4-(pyridin-2-ylmethyl)piperidine-1-carboxylate (1.00 g, 3.40 mmol) in DCM (10 mL) was added 4.0 M hydrogen chloride solution in dioxane (10 mL) dropwise at room temperature under a nitrogen atmosphere. The mixture was stirred for 2 h at room temperature under a nitrogen atmosphere. The resulting mixture was concentrated under reduced pressure. to afford ((4-fluoropiperidin-4-yl)methyl)pyridine hydrochloride as a light blue solid.

Yield: 0.70 g (89%). $^1$H NMR (400 MHz, $CD_3OD$) δ 8.83 (dd, J=1.6, 6.0 Hz, 1H), 8.64 (dd, J=1.6, 8.0 Hz, 1H), 8.13-7.99 (m, 2H), 3.95 (d, J=4.8 Hz, 2H), 3.80-3.70 (m, 2H), 3.38 (t, J=6.4 Hz, 2H), 2.41 (ddd, J=2.4, 4.4, 6.4 Hz, 2H), 2.35-1.99 (m, 2H). $NH_2^+$ of the HCl salt not observed. $^{19}$F NMR (376 MHz, $CDCl_3$) δ −159.89. m/z: [ESI$^+$] 195 (M+H)$^+$.

Step 3: tert-butyl (3-(4-fluoro-4-(pyridin-2-ylmethyl)piperidin-1-yl)propyl)carbamate To a stirred solution of 2-((4-fluoropiperidin-4-yl)methyl)pyridine hydrochloride (0.30 g, 1.30 mmol) in methanol (10 mL) were added acetic acid (0.50 mL), sodium acetate (0.24 g, 2.93 mmol) and tert-butyl N-(3-oxopropyl)carbamate (0.42 g, 2.42 mmol). Sodium cyanoborohydride (0.15 g, 2.39 mmol) was then added portion-wise at room temperature under a nitrogen atmosphere. The mixture was then stirred for 1 h at room temperature under a nitrogen atmosphere. The resulting solution was purified by reverse phase flash chromatography with the following conditions: Column: Spherical C18, 20-40 um, 330 g; Mobile Phase A: water (plus 10 mM $NH_4HCO_3$); Mobile Phase B: acetonitrile; Flow rate: 80 mL/min; Gradient: 40% B-60% B in 20 min; Detector: UV 220/254 nm. The fractions containing desired product were collected and concentrated under reduced pressure to afford tert-butyl (3-(4-fluoro-4-(pyridin-2-ylmethyl)piperidin-1-yl)propyl)carbamate as an off-white solid.

Yield: 0.30 g (66%). m/z: [ESI$^+$] 352 (M+H)$^+$. Crude material was used in the next step without further purification.

The following intermediates below were prepared according to the procedure described above.

Tert-butyl (3-(4-(2-fluorobenzyl)piperidin-1-yl)propyl)carbamate. The compound was synthesized according to the procedure described above, using 4-(2-fluorobenzyl)piperidine (0.20 g, 1.03 mmol) as the starting material.

Yield 0.15 g (41%), as a pale oil. m/z: [ESI$^+$] 351 (M+H)$^+$. Crude material was used in the next step without further purification.

Tert-butyl (3-(4-fluoro-4-(pyridin-2-yl)piperidin-1-yl)propyl)carbamate. The compound was synthesized according to the procedure described above, using 2-(4-fluoropiperidin-4-yl)pyridine hydrochloride (1.00 g, 4.62 mmol) as the starting material.

Yield 1.20 g (77%), as a pale oil. m/z: [ESI$^+$] 338 (M+H)$^+$. Crude material was used in the next step without further purification.

1-(3-(4-Chlorophenyl)-1,2,4-oxadiazol-5-yl)-N—(((S)-1-(((S)-1-methylpiperidin-3-yl)methyl)pyrrolidin-3-yl)methyl)piperidine-4-carboxamide (Compound 470)

1-(3-(4-Chlorophenyl)-1,2,4-oxadiazol-5-yl)-N—(((R)-1-(((S)-1-methylpiperidin-3-yl)methyl)pyrrolidin-3-yl)methyl)piperidine-4-carboxamide (Compound 471)

Scheme 21

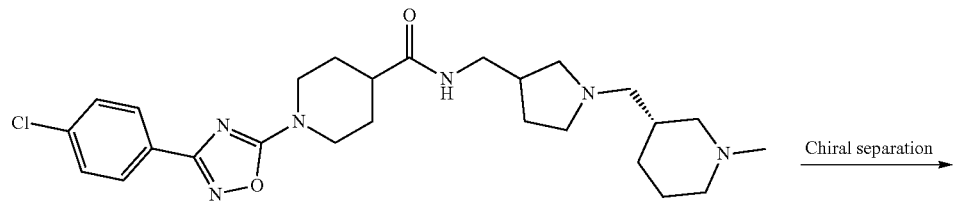

Compound 468

-continued

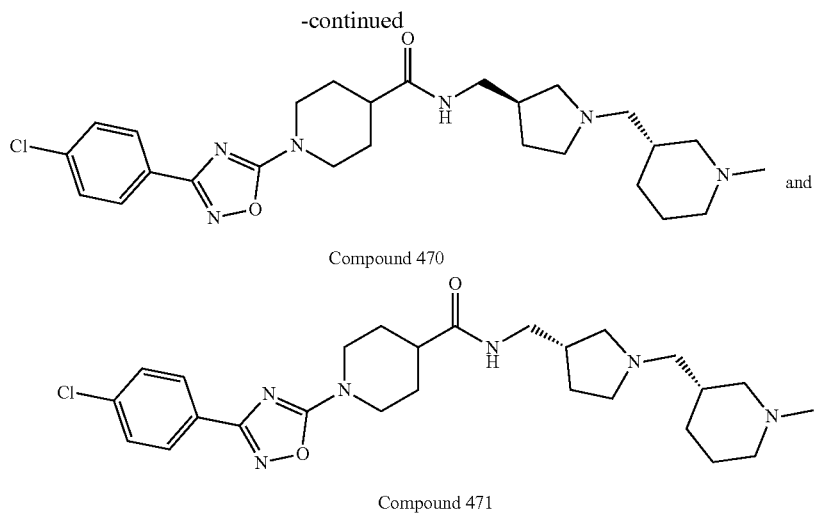

Compound 470

Compound 471

1-[3-(4-Chlorophenyl)-1,2,4-oxadiazol-5-yl]-N-[(1-[[(3S)-1-methylpiperidin-3-yl]methyl]pyrrolidin-3-yl)methyl]piperidine-4-carboxamide (80 mg, 0.160 mmol) was purified by CHIRAL-HPLC with the following conditions (Column: CHIRALPAK IG, 2×25 cm, 5 m; Mobile Phase A: Hexane (0.5% 2M $NH_3$-MeOH), Mobile Phase B: EtOH; Flow rate: 16 mL/min; Gradient: 50% B to 50% B in 25 min; Wave Length: 220/254 nm; RT1: 11.8 min; RT2: 19.2 min). The faster eluting peak was concentrated under reduced pressure to afford 1-(3-(4-chlorophenyl)-1,2,4-oxadiazol-5-yl)-N—(((S)-1-(((S)-1-methylpiperidin-3-yl)methyl)pyrrolidin-3-yl)methyl)piperidine-4-carboxamide as a pale solid.

Yield 28 mg (35%). $^1$H NMR (400 MHz, DMSO) δ 7.91 (d, J=8.4 Hz, 2H), 7.88 (t, J=5.6 Hz, 1H), 7.58 (d, J=8.4 Hz, 2H), 4.07 (td, J=3.6, 13.2 Hz, 2H), 3.22 (dt, J=3.2, 12.8 Hz, 2H), 3.11-2.93 (m, 2H), 2.74 (d, J=10.8 Hz, 1H), 2.62 (d, J=10.8 Hz, 1H), 2.49-2.28 (m, 4H), 2.27-2.12 (m, 4H), 2.11 (s, 3H), 1.86-1.73 (m, 4H), 1.70-1.29 (m, 8H), 0.87-0.71 (m, 1H). m/z: [ESI$^+$] 501, 503 (M+H)$^+$, ($C_{26}H_{37}ClN_6O_2$).

The slower eluting peak was concentrated under reduced pressure to afford 1-(3-(4-chlorophenyl)-1,2,4-oxadiazol-5-yl)-N—(((R)-1-(((S)-1-methylpiperidin-3-yl)methyl)pyrrolidin-3-yl)methyl)piperidine-4-carboxamide as a pale solid.

Yield 30 mg (38%). $^1$H NMR (400 MHz, DMSO) δ 7.91 (d, J=8.4 Hz, 2H), 7.89 (t, J=5.6 Hz, 1H), 7.59 (d, J=8.4 Hz, 2H), 4.07 (td, J=3.6, 13.2 Hz, 2H), 3.22 (dt, J=3.2, 12.8 Hz, 2H), 3.11-2.93 (m, 2H), 2.77 (d, J=10.8 Hz, 1H), 2.62 (d, J=10.8 Hz, 1H), 2.49-2.35 (m, 4H), 2.27-2.15 (m, 3H), 2.14-2.09 (m, 4H), 1.86-1.73 (m, 4H), 1.71-1.28 (m, 8H), 0.87-0.73 (m, 1H). m/z: [ESI$^+$] 501, 503 (M+H)$^+$, ($C_{26}H_{37}ClN_6O_2$).

N-((1-(1-hydroxy-2-methylpropan-2-yl)pyrrolidin-3-yl)methyl)-1-(3-(4-methoxyphenyl)-1,2,4-oxadiazol-5-yl)piperidine-4-carboxamide (Compound 424)

Scheme 22

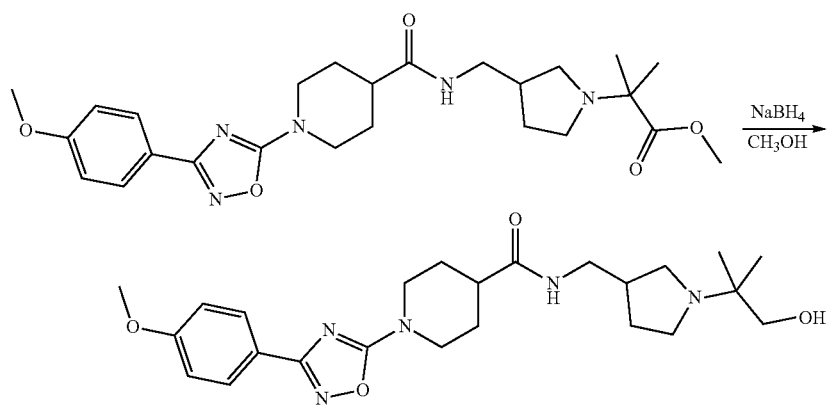

Compound 424

To a stirred solution of methyl 2-(3-((1-(3-(4-methoxyphenyl)-1,2,4-oxadiazol-5-yl)piperidine-4-carboxamido)methyl)pyrrolidin-1-yl)-2-methylpropanoate (100 mg, 0.206 mmol) in methanol (5 mL) was added portion-wise sodium borohydride (24 mg, 0.634 mmol) at 0° C. under a nitrogen atmosphere. The mixture was then stirred at 45° C. overnight, under a nitrogen atmosphere. The resulting mixture was concentrated under reduced pressure. The residue was purified by Prep-TLC (DCM:Methanol=5:1, v:v) to afford N-((1-(1-hydroxy-2-methylpropan-2-yl)pyrrolidin-3-yl)methyl)-1-(3-(4-methoxyphenyl)-1,2,4-oxadiazol-5-yl)piperidine-4-carboxamide as an off-white solid.

Yield: 25 mg (27%). $^1$H NMR (400 MHz, DMSO) δ 7.94 (t, J=5.6 Hz, 1H), 7.84 (d, J=8.8 Hz, 2H), 7.06 (d, J=8.8 Hz, 2H), 4.37 (br s, 1H), 4.06 (d, J=13.2 Hz, 2H), 3.82 (s, 3H), 3.31 (s, 2H), 3.27-3.15 (m, 3H), 3.08-3.00 (m, 2H), 2.82-2.57 (m, 2H), 2.46-2.31 (m, 2H), 2.24-2.12 (m, 1H), 1.86-1.71 (m, 3H), 1.67-1.56 (m, 2H), 1.40-1.29 (m, 1H), 0.95 (s, 6H). m/z: [ESI$^+$] 458 (M+H)$^+$, ($C_{24}H_{35}N_5O_4$).

1-(3-(4-(2,3-Dihydroxypropoxy)phenyl)-1,2,4-oxadiazol-5-yl)-N-((1-(4-methylbenzyl)pyrrolidin-3-yl)methyl)piperidine-4-carboxamide (Compound 472)

1-(3-(4-(2-Hydroxyethoxy)phenyl)-1,2,4-oxadiazol-5-yl)-N-((1-(4-methylbenzyl)pyrrolidin-3-yl)methyl)piperidine-4-carboxamide (Compound 463)

Step 1: 1-(3-(4-(2,3-dihydroxypropoxy)phenyl)-1,2,4-oxadiazol-5-yl)-N-((1-(4-methylbenzyl)pyrrolidin-3-yl)methyl)piperidine-4-carboxamide (Compound 472)

To a stirred solution of 1-(3-(4-(allyloxy)phenyl)-1,2,4-oxadiazol-5-yl)-N-((1-(4-methylbenzyl)pyrrolidin-3-yl)methyl)piperidine-4-carboxamide (0.80 g, 1.55 mmol) in DCM (50 mL) and water (5 mL) were added 4-methylmorpholin 4-oxide (0.30 g, 2.56 mmol), potassium(VI) osmate dihydrate (60 mg, 0.163 mmol) was added portion-wise at room temperature under a nitrogen atmosphere. The reaction mixture was then stirred for 16 h at room temperature under a nitrogen atmosphere. The resulting mixture was concentrated under reduced pressure. The residue was purified by reverse phase flash chromatography with the following conditions: Column: Spherical C18, 20-40 μm, 330 g; Mobile Phase A: water (plus 10 mM NH$_4$HCO$_3$); Mobile Phase B: acetonitrile; Flow rate: 80 mL/min; Gradient: 40% B-60% B in 20 min; Detector: UV 220/254 nm. The fractions containing desired product were collected and concentrated under reduced pressure to afford 1-(3-(4-(2,3-dihydroxypropoxy)phenyl)-1,2,4-oxadiazol-5-yl)-N-((1-(4-methylbenzyl)pyrrolidin-3-yl)methyl)piperidine-4-carboxamide as an off-white solid.

Yield: 0.30 g (35%). $^1$H NMR (400 MHz, DMSO) δ 7.88 (t, J=5.6 Hz, 1H), 7.83 (d, J=8.8 Hz, 2H), 7.17 (d, J=8.0 Hz,

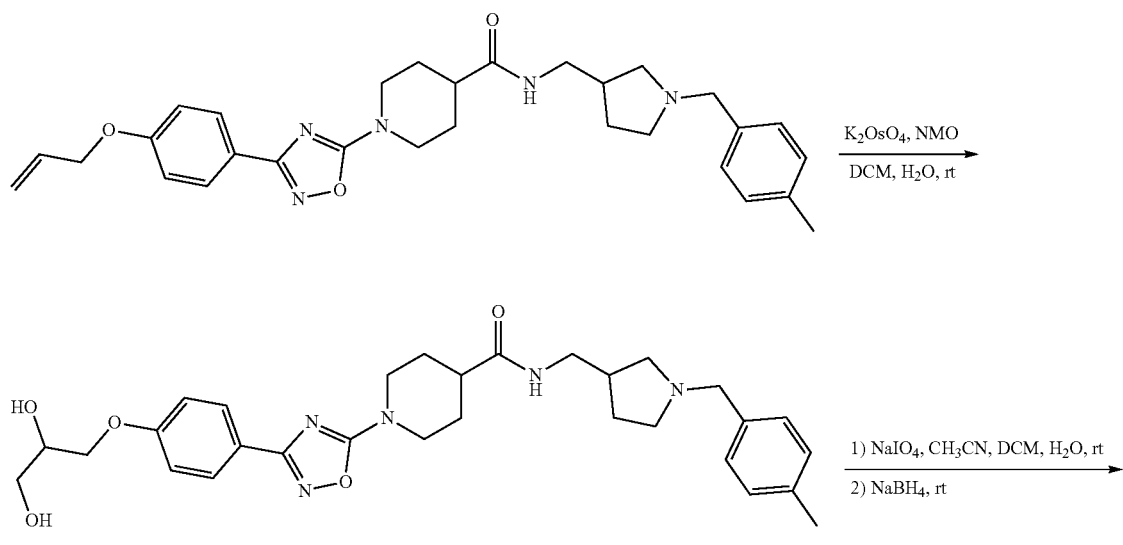

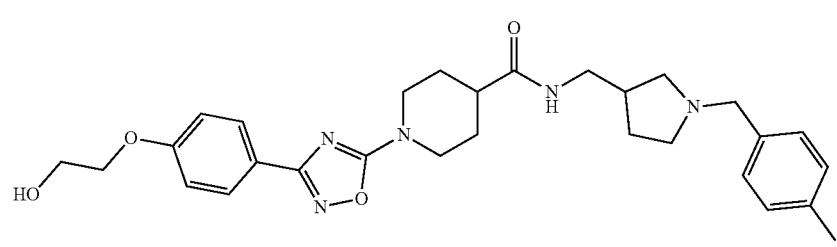

Compound 463

2H), 7.11 (d, J=8.0 Hz, 2H), 7.05 (d, J=8.8 Hz, 2H), 4.99 (d, J=5.2 Hz, 1H), 4.69 (t, J=5.6 Hz, 1H), 4.13-3.99 (m, 3H), 3.93 (dd, J=6.0, 9.6 Hz, 1H), 3.86-3.75 (m, 1H), 3.48 (s, 2H), 3.46 (t, J=5.6 Hz, 2H), 3.25-3.13 (m, 2H), 3.11-2.91 (m, 2H), 2.50-2.30 (m, 4H), 2.27 (s, 3H), 2.26-2.13 (m, 2H), 1.90-1.70 (m, 3H), 1.68-1.53 (m, 2H), 1.44-1.30 (m, 1H). m/z: [ESI$^+$] 550 (M+H)$^+$, ($C_{30}H_{39}N_5O_5$).

The targets below were synthesized according to the procedure described above.

4-(3-(4-(2,3-Dihydroxypropoxy)phenyl)-1,2,4-oxadiazol-5-yl)-N-((1-(4-methylbenzyl)pyrrolidin-3-yl)methyl)piperazine-1-carboxamide (Compound 473): Using 4-(3-(4-(allyloxy)phenyl)-1,2,4-oxadiazol-5-yl)-N-((1-(4-methylbenzyl)pyrrolidin-3-yl)methyl)piperazine-1-carboxamide (0.50 g, 0.97 mmol).

Yield 29 mg (5%), as an off-white solid. $^1$H NMR (400 MHz, DMSO) δ 7.83 (d, J=8.8 Hz, 2H), 7.21 (d, J=7.6 Hz, 2H), 7.13 (d, J=7.6 Hz, 2H), 7.06 (d, J=8.8 Hz, 2H), 6.73 (t, J=5.6 Hz, 1H), 4.99 (dd, J=1.2, 5.2 Hz, 1H), 4.70 (dt, J=1.2, 5.6 Hz, 1H), 4.07 (dd, J=4.0, 9.6 Hz, 1H), 3.93 (dd, J=6.0, 9.6 Hz, 1H), 3.85-3.77 (m, 1H), 3.64-3.52 (m, 5H), 3.48-3.40 (m, 7H), 3.10-2.97 (m, 2H), 2.53-2.45 (m, 3H), 2.37-2.30 (m, 2H), 2.28 (s, 3H), 1.91-1.78 (m, 1H), 1.49-1.37 (m, 1H). m/z: [ESI$^+$] 551 (M+H)$^+$, ($C_{29}H_{38}N_6O_5$).

Step 2: 1-(3-(4-(2-hydroxyethoxy)phenyl)-1,2,4-oxadiazol-5-yl)-N-((1-(4-methylbenzyl)pyrrolidin-3-yl)methyl)piperidine-4-carboxamide (Compound 463)

To a stirred solution of 1-(3-(4-(2,3-dihydroxypropoxy)phenyl)-1,2,4-oxadiazol-5-yl)-N-((1-(4-methylbenzyl)pyrrolidin-3-yl)methyl)piperidine-4-carboxamide (250 mg, 0.455 mmol) in acetonitrile (250 mL), DCM (100 mL) and water (50 mL) was added portion-wise sodium metaperiodate (97 mg, 0.455 mmol), at room temperature under a nitrogen atmosphere. The reaction mixture was then stirred for 16 h at room temperature under a nitrogen atmosphere. After this time portion-wise sodium borohydride (86 mg, 2.273 mmol) was added at room temperature. The mixture was then stirred for additional 2 h at room temperature. The mixture was then quenched with acetone (50 mL) and concentrated under reduced pressure. The resulting residue was purified by reverse phase flash chromatography with the following conditions: Column: Spherical C18, 20-40 um, 120 g; Mobile Phase A: water (plus 10 mM $NH_4HCO_3$); Mobile Phase B: acetonitrile; Flow rate: 60 mL/min; Gradient: 20% B-40% B in 20 min; Detector: UV 220/254 nm. The fractions containing desired product were collected and concentrated under reduced pressure to afford 1-(3-(4-(2-hydroxyethoxy)phenyl)-1,2,4-oxadiazol-5-yl)-N-((1-(4-methylbenzyl)pyrrolidin-3-yl)methyl)piperidine-4-carboxamide as an off-white solid.

Yield: 40 mg (17%). $^1$H NMR (400 MHz, DMSO) δ 7.86 (t, J=5.6 Hz, 1H), 7.82 (d, J=8.8 Hz, 2H), 7.17 (d, J=8.0 Hz, 2H), 7.11 (d, J=8.0 Hz, 2H), 7.05 (d, J=8.8 Hz, 2H), 4.89 (t, J=5.6 Hz, 1H), 4.08-4.00 (m, 4H), 3.77-3.70 (m, 2H), 3.48 (s, 2H), 3.25-3.13 (m, 2H), 3.09-2.94 (m, 2H), 2.50-2.40 (m, 4H), 2.27 (s, 3H), 2.25-2.13 (m, 2H), 1.87-1.75 (m, 3H), 1.68-1.51 (m, 2H), 1.42-1.32 (m, 1H). m/z: [ESI$^+$] 520 (M+H)$^+$, ($C_{29}H_{37}N_5O_4$).

The targets below were synthesized according to the procedure described above.

4-(3-(4-(2-Hydroxyethoxy)phenyl)-1,2,4-oxadiazol-5-yl)-N-((1-(4-methylbenzyl)pyrrolidin-3-yl)methyl)piperazine-1-carboxamide (Compound 462): Using 4-(3-(4-(2,3-dihydroxypropoxy)phenyl)-1,2,4-oxadiazol-5-yl)-N-((1-(4-methylbenzyl)pyrrolidin-3-yl)methyl)piperazine-1-carboxamide (200 mg, 0.363 mmol).

Yield 21 mg (11%), as an off-white solid. $^1$H NMR (400 MHz, DMSO) δ 7.83 (d, J=8.8 Hz, 2H), 7.17 (d, J=8.0 Hz, 2H), 7.11 (d, J=8.0 Hz, 2H), 7.06 (d, J=8.8 Hz, 2H), 6.69 (t, J=5.4 Hz, 1H), 4.90 (t, J=5.6 Hz, 1H), 4.05 (t, J=5.2 Hz, 2H), 3.78-3.70 (m, 2H), 3.54 (dd, J=3.6, 6.8 Hz, 4H), 3.49 (d, J=4.0 Hz, 2H), 3.44 (dd, J=3.6, 6.8 Hz, 4H), 3.11-2.92 (m, 2H), 2.49-2.43 (m, 2H), 2.39 (dt, J=6.4, 8.4 Hz, 1H), 2.27 (s, 3H), 2.30-2.19 (m, 2H), 1.88-1.74 (m, 1H), 1.46-1.32 (m, 1H). m/z: [ESI$^+$] 521 (M+H)$^+$, ($C_{28}H_{36}N_6O_4$).

Synthesis of 1-(3-(4-chlorophenyl)-1,2,4-oxadiazol-5-yl)-N—(((S)-1-(((R)-1-methylpiperidin-3-yl)methyl)pyrrolidin-3-yl)methyl)piperidine-4-carboxamide (Compound 474) and 1-(3-(4-chlorophenyl)-1,2,4-oxadiazol-5-yl)-N—(((R)-1-(((R)-1-methylpiperidin-3-yl)methyl)pyrrolidin-3-yl)methyl)piperidine-4-carboxamide (Compound 475)

Compound 474

Compound 475

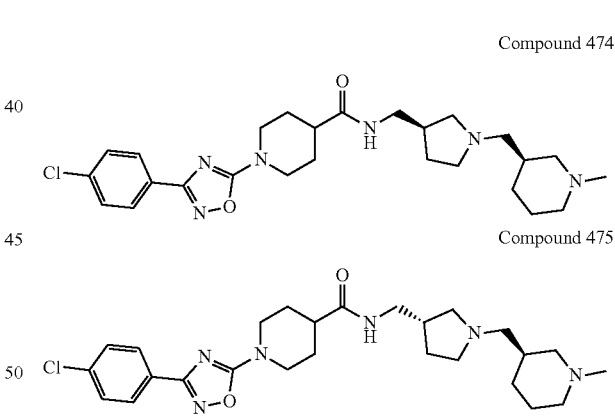

Scheme 24

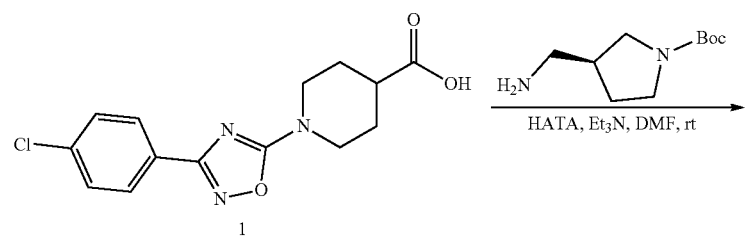

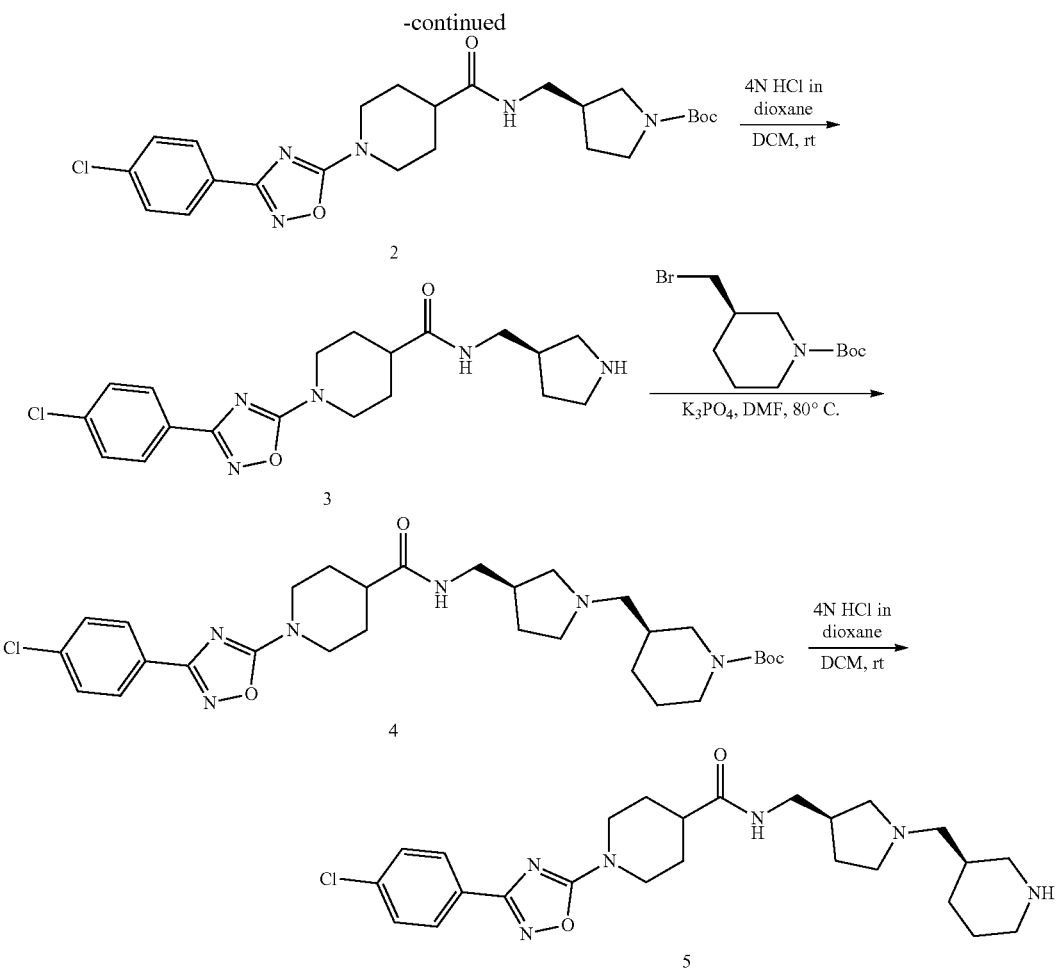

Synthesis of tert-butyl (S)-3-((1-(3-(4-chlorophenyl)-1,2,4-oxadiazol-5-yl)piperidine-4-carboxamido)methyl)pyrrolidine-1-carboxylate. (Intermediate 2, Scheme 24)

To a stirred solution of 1-(3-(4-chlorophenyl)-1,2,4-oxadiazol-5-yl)piperidine-4-carboxylic acid (2.00 g, 6.50 mmol) in N,N-dimethylformamide (30 mL) were added triethylamine (1.32 g, 13.04 mmol), O-(7-Azabenzotriazol-1-yl)-N,N,N',N'-tetramethyluronium hexafluorophosphate (3.71 g, 9.76 mmol) and tert-butyl (S)-3-(aminomethyl)pyrrolidine-1-carboxylate (1.56 g, 7.79 mmol) at room temperature. The resulting solution was stirred for 2 h at room temperature under a nitrogen atmosphere. The resulting solution was purified by reverse phase flash chromatography with the following conditions: Column: Spherical C18, 20-40 um, 330 g; Mobile Phase A: water (plus 10 mM NH$_4$HCO$_3$); Mobile Phase B: acetonitrile; Flow rate: 80 mL/min; Gradient: 60% B-80% B in 20 min; Detector: UV 220/254 nm. The fractions containing desired product were collected and concentrated under reduced pressure to afford tert-butyl (S)-3-((1-(3-(4-chlorophenyl)-1,2,4-oxadiazol-5-yl)piperidine-4-carboxamido)methyl)pyrrolidine-1-carboxylate as a white solid.

Yield 2.20 g (69%). $^1$H NMR (400 MHz, CDCl$_3$) δ 7.96 (d, J=8.8 Hz, 2H), 7.44 (d, J=8.8 Hz, 2H), 5.69-5.59 (m, 1H), 4.41-4.24 (m, 2H), 3.54-3.28 (m, 4H), 3.28-3.17 (m, 4H), 3.08-3.02 (m, 1H), 2.48-2.31 (m, 2H), 2.05-1.94 (m, 3H), 1.94-1.84 (m, 1H), 1.67-1.57 (m, 1H), 1.48 (s, 9H). m/z: [ESI$^+$] 490, 492 (M+H)$^+$.

Synthesis of (R)-1-(3-(4-chlorophenyl)-1,2,4-oxadiazol-5-yl)-N-(pyrrolidin-3-ylmethyl)piperidine-4-carboxamide hydrochloride (Intermediate 3, Scheme 24)

To a stirred solution of tert-butyl (S)-3-((1-(3-(4-chlorophenyl)-1,2,4-oxadiazol-5-yl)piperidine-4-carboxamido)methyl)pyrrolidine-1-carboxylate (2.20 g, 4.49 mmol) in dichloromethane (20 mL) was added a 4 N solution of HCl(g) in dioxane (20 mL) at room temperature. The resulting mixture was stirred for 2 h at room temperature under a nitrogen atmosphere. The resulting mixture was concentrated under reduced pressure to afford (R)-1-(3-(4-chlorophenyl)-1,2,4-oxadiazol-5-yl)-N-(pyrrolidin-3-ylmethyl)piperidine-4-carboxamide hydrochloride as a white solid.

Yield 1.84 g (96%). $^1$H NMR (400 MHz, CD$_3$OD) δ 7.95 (d, J=8.8 Hz, 2H), 7.51 (d, J=8.8 Hz, 2H), 4.31-4.21 (m, 2H), 3.46-3.35 (m, 2H), 3.32-3.21 (m, 5H), 3.04-2.92 (m, 1H), 2.71-2.44 (m, 2H), 2.26-2.09 (m, 1H), 1.98-1.89 (m, 2H), 1.87-1.66 (m, 3H). Active protons not observed. m/z: [ESI$^+$] 390, 392 (M+H)$^+$.

Synthesis of tert-butyl (S)-3-(((S)-3-((1-(3-(4-chlorophenyl)-1,2,4-oxadiazol-5-yl)piperidine-4-carboxamido)methyl)pyrrolidin-1-yl)methyl)piperidine-1-carboxylate (Intermediate 4, Scheme 24)

To a stirred solution of (R)-1-(3-(4-chlorophenyl)-1,2,4-oxadiazol-5-yl)-N-(pyrrolidin-3-ylmethyl)piperidine-4-carboxamide hydrochloride (460 mg, 1.079 mmol) in N,N-dimethylformamide (15 mL) were added potassium phosphate tribasic (700 mg, 3.298 mmol) and tert-butyl (R)-3-(bromomethyl)piperidine-1-carboxylate (360 mg, 1.294 mmol) at room temperature. The resulting mixture was stirred for 2 h at 80° C. under a nitrogen atmosphere. The resulting mixture was cooled down to room temperature and purified by reverse phase flash chromatography with the following conditions: Column: Spherical C18, 20-40 um, 330 g; Mobile Phase A: water (plus 10 mM $NH_4HCO_3$); Mobile Phase B: acetonitrile; Flow rate: 80 mL/min; Gradient: 60% B-80% B in 20 min; Detector: UV 220/254 nm. The fractions containing desired product were collected and concentrated under reduced pressure to afford tert-butyl (S)-3-(((S)-3-((1-(3-(4-chlorophenyl)-1,2,4-oxadiazol-5-yl)piperidine-4-carboxamido)methyl)pyrrolidin-1-yl)methyl)piperidine-1-carboxylate as a light yellow solid.

Yield 500 mg (79%). $^1$H NMR (400 MHz, $CDCl_3$) δ 7.95 (d, J=8.8 Hz, 2H), 7.43 (d, J=8.8 Hz, 2H), 4.59-4.50 (m, 1H), 4.31-4.21 (m, 2H), 4.11-3.95 (m, 1H), 3.93-3.73 (m, 1H), 3.49-3.29 (m, 2H), 3.27-3.14 (m, 2H), 3.00-2.86 (m, 1H), 2.84-2.47 (m, 7H), 2.20-2.18 (m, 1H), 2.05-1.79 (m, 8H), 1.72-1.60 (m, 3H), 1.47 (s, 9H), 1.42-1.20 (m, 1H). m/z: [ESI$^+$] 587, 589 (M+H)$^+$.

Synthesis of 1-(3-(4-chlorophenyl)-1,2,4-oxadiazol-5-yl)-N—(((S)-1-(((R)-piperidin-3-yl)methyl)pyrrolidin-3-yl)methyl)piperidine-4-carboxamide dihydrochloride (Intermediate 5, Scheme 24)

Compound 1-(3-(4-chlorophenyl)-1,2,4-oxadiazol-5-yl)-N—(((S)-1-(((R)-piperidin-3-yl)methyl)pyrrolidin-3-yl)methyl)piperidine-4-carboxamide dihydrochloride was prepared from tert-butyl (S)-3-(((S)-3-((1-(3-(4-chlorophenyl)-1,2,4-oxadiazol-5-yl)piperidine-4-carboxamido)methyl)pyrrolidin-1-yl)methyl)piperidine-1-carboxylate (500 mg, 0.852 mmol) following a similar procedure to that described for the synthesis of (R)-1-(3-(4-chlorophenyl)-1,2,4-oxadiazol-5-yl)-N-(pyrrolidin-3-ylmethyl)piperidine-4-carboxamide hydrochloride, and was isolated as a light yellow solid.

Yield 450 mg (94%). $^1$H NMR (400 MHz, $CD_3OD$) δ 7.93 (d, J=8.8 Hz, 2H), 7.49 (d, J=8.8 Hz, 2H), 4.31-4.20 (m, 2H), 3.92-3.71 (m, 1H), 3.64-3.48 (m, 1H), 3.46-3.13 (m, 9H), 3.06-2.76 (m, 3H), 2.76-2.52 (m, 2H), 2.41-2.15 (m, 2H), 2.14-1.71 (m, 8H), 1.52-1.33 (m, 1H). Active protons not observed. m/z: [ESI$^+$] 487, 489 (M+H)$^+$.

Scheme 25

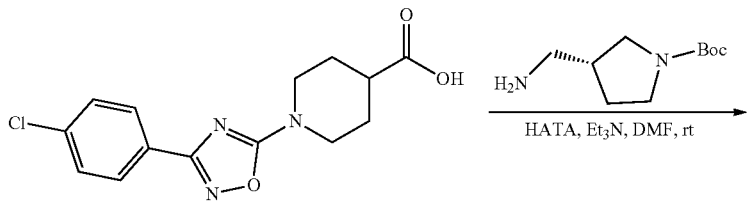

1

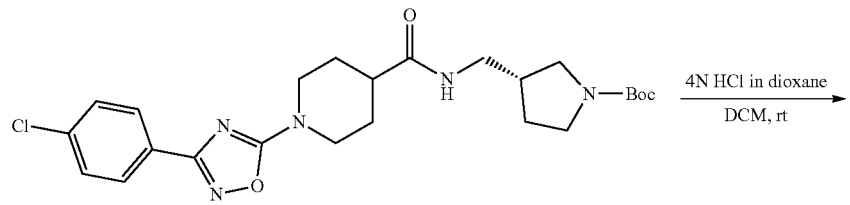

6

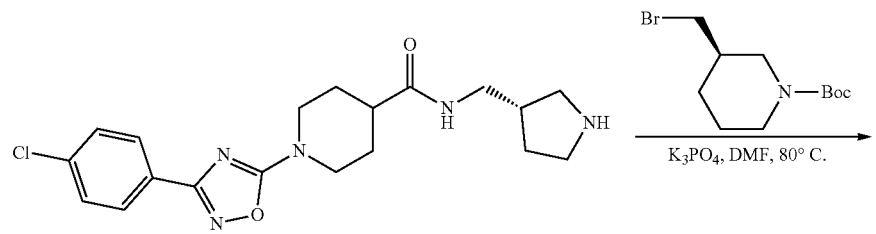

7

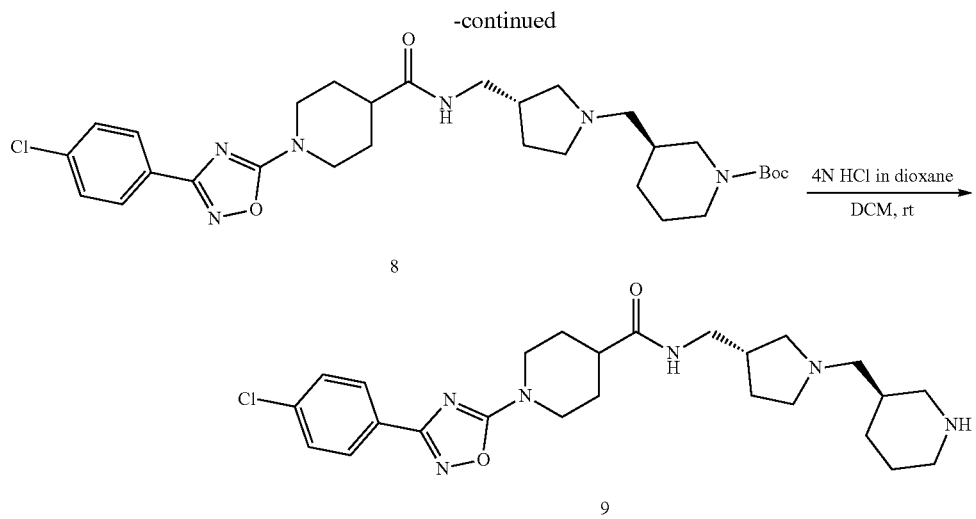

Synthesis of tert-butyl (R)-3-((1-(3-(4-chlorophenyl)-1,2,4-oxadiazol-5-yl)piperidine-4-carboxamido)methyl)pyrrolidine-1-carboxylate (Intermediate 6, Scheme 25)

Compound tert-butyl (R)-3-((1-(3-(4-chlorophenyl)-1,2,4-oxadiazol-5-yl)piperidine-4-carboxamido)methyl)pyrrolidine-1-carboxylate was prepared from 1-(3-(4-chlorophenyl)-1,2,4-oxadiazol-5-yl)piperidine-4-carboxylic acid (2.00 g, 6.50 mmol) and tert-butyl (R)-3-(aminomethyl)pyrrolidine-1-carboxylate (1.56 g, 7.79 mmol) following a similar procedure to that described for the synthesis of tert-butyl (S)-3-((1-(3-(4-chlorophenyl)-1,2,4-oxadiazol-5-yl)piperidine-4-carboxamido)methyl)pyrrolidine-1-carboxylate, and was isolated as a white solid.

Yield 2.73 g (86%). $^1$H NMR (400 MHz, DMSO) δ 8.00-7.94 (m, 1H), 7.90 (d, J=8.8 Hz, 2H), 7.59 (d, J=8.8 Hz, 2H), 4.13-4.02 (m, 2H), 3.42-2.99 (m, 6H), 2.96-2.87 (m, 1H), 2.45-2.20 (m, 2H), 1.94-1.72 (m, 4H), 1.70-1.56 (m, 3H), 1.39 (s, 9H). m/z: [ESI$^+$] 490, 492 (M+H)$^+$.

Synthesis of (S)-1-(3-(4-chlorophenyl)-1,2,4-oxadiazol-5-yl)-N-(pyrrolidin-3-ylmethyl)piperidine-4-carboxamide hydrochloride (Intermediate 7, Scheme 25)

Compound (S)-1-(3-(4-chlorophenyl)-1,2,4-oxadiazol-5-yl)-N-(pyrrolidin-3-ylmethyl)piperidine-4-carboxamide hydrochloride was prepared from tert-butyl (R)-3-((1-(3-(4-chlorophenyl)-1,2,4-oxadiazol-5-yl)piperidine-4-carboxamido)methyl)pyrrolidine-1-carboxylate (2.20 g, 4.49 mmol) following a similar procedure to that described for the synthesis of (R)-1-(3-(4-chlorophenyl)-1,2,4-oxadiazol-5-yl)-N-(pyrrolidin-3-ylmethyl)piperidine-4-carboxamide hydrochloride, and was isolated as a white solid.

Yield 1.80 g (94%). $^1$H NMR (400 MHz, DMSO) δ 9.28 (br s, 2H, NH$_2$+), 8.17 (t, J=5.6 Hz, 1H), 7.91 (d, J=8.8 Hz, 2H), 7.58 (dd, J=2.0, 8.8 Hz, 2H), 4.12-3.97 (m, 2H), 3.34-3.00 (m, 7H), 2.87-2.73 (m, 1H), 2.50-2.31 (m, 2H), 2.04-1.91 (m, 1H), 1.91-1.79 (m, 2H), 1.71-1.51 (m, 3H). m/z: [ESI$^+$] 390, 392 (M+H)$^+$.

Synthesis of tert-butyl (S)-3-(((R)-3-((1-(3-(4-chlorophenyl)-1,2,4-oxadiazol-5-yl)piperidine-4-carboxamido)methyl)pyrrolidin-1-yl)methyl)piperidine-1-carboxylate (Intermediate 8, Scheme 25)

Compound tert-butyl (S)-3-(((R)-3-((1-(3-(4-chlorophenyl)-1,2,4-oxadiazol-5-yl)piperidine-4-carboxamido)methyl)pyrrolidin-1-yl)methyl)piperidine-1-carboxylate was prepared from (S)-1-(3-(4-chlorophenyl)-1,2,4-oxadiazol-5-yl)-N-(pyrrolidin-3-ylmethyl)piperidine-4-carboxamide hydrochloride (460 mg, 1.079 mmol) and tert-butyl (R)-3-(bromomethyl)piperidine-1-carboxylate (360 mg, 1.294 mmol) following a similar procedure to that described for the synthesis of tert-butyl (S)-3-(((S)-3-((1-(3-(4-chlorophenyl)-1,2,4-oxadiazol-5-yl)piperidine-4-carboxamido)methyl)pyrrolidin-1-yl)methyl)piperidine-1-carboxylate, and was isolated as a light yellow solid.

Yield 500 mg (79%). $^1$H NMR (400 MHz, CDCl$_3$) δ 7.95 (d, J=8.8 Hz, 2H), 7.43 (d, J=8.8 Hz, 2H), 7.17 (br s, 1H), 4.32-4.20 (m, 2H), 4.19-3.99 (m, 1H), 3.99-3.73 (m, 1H), 3.47-2.99 (m, 4H), 2.99-2.79 (m, 1H), 2.79-2.65 (m, 1H), 2.69-2.36 (m, 5H), 2.41-2.13 (m, 2H), 2.13-1.80 (m, 6H), 1.82-1.57 (m, 5H), 1.46 (s, 9H), 1.25-1.09 (m, 1H). m/z: [ESI$^+$] 587, 589 (M+H)$^+$.

Synthesis of 1-(3-(4-chlorophenyl)-1,2,4-oxadiazol-5-yl)-N—(((R)-1-(((R)-piperidin-3-yl)methyl)pyrrolidin-3-yl)methyl)piperidine-4-carboxamide dihydrochloride (Intermediate 9, Scheme 25)

Compound 1-(3-(4-chlorophenyl)-1,2,4-oxadiazol-5-yl)-N—(((R)-1-(((R)-piperidin-3-yl)methyl)pyrrolidin-3-yl)methyl)piperidine-4-carboxamide dihydrochloride was prepared from tert-butyl (S)-3-(((R)-3-((1-(3-(4-chlorophenyl)-1,2,4-oxadiazol-5-yl)piperidine-4-carboxamido)methyl)pyrrolidin-1-yl)methyl)piperidine-1-carboxylate (500 mg, 0.852 mmol) following a similar procedure to that described for the synthesis of (R)-1-(3-(4-chlorophenyl)-1,2,4-oxadiazol-5-yl)-N-(pyrrolidin-3-ylmethyl)piperidine-4-carboxamide hydrochloride, and was isolated as a white solid.

Yield 450 mg (94%). $^1$H NMR (400 MHz, CD$_3$OD) δ 7.95 (d, J=8.8 Hz, 2H), 7.51 (d, J=8.8 Hz, 2H), 4.31-4.19 (m, 2H), 3.91-3.72 (m, 2H), 3.71-3.47 (m, 2H), 3.42-3.14 (m, 7H), 3.03-2.56 (m, 5H), 2.47-2.17 (m, 2H), 2.14-1.72 (m, 8H), 1.49-1.36 (m, 1H). Active protons not observed. m/z: [ESI$^+$] 487, 489 (M+H)$^+$.

Final Compounds

Synthesis of 1-(3-(4-chlorophenyl)-1,2,4-oxadiazol-5-yl)-N—(((S)-1-(((R)-1-methylpiperidin-3-yl)methyl)pyrrolidin-3-yl)methyl)piperidine-4-carboxamide (Compound 474)

To a stirred solution of 1-(3-(4-chlorophenyl)-1,2,4-oxadiazol-5-yl)-N—(((S)-1-(((R)-piperidin-3-yl)methyl)pyrrolidin-3-yl)methyl)piperidine-4-carboxamide dihydrochloride (450 mg, 0.804 mmol), sodium acetate (130 mg, 1.585 mmol) and paraformaldehyde (MW: 90.08, 50 mg, 0.555 mmol) in methanol (10 mL) and acetic acid (0.2 mL) was added sodium cyanoborohydride (100 mg, 1.591 mmol) in portions at room temperature under a nitrogen atmosphere. The resulting mixture was stirred for 16 h at room temperature. The resulting mixture was filtered. The filter cake was washed with methanol (3×10 mL). The filtrate was concentrated under reduced pressure. The residue was purified by reverse phase flash chromatography with the following conditions: Column: Spherical C18, 20-40 um, 120 g; Mobile Phase A: water (plus 10 mM $NH_4HCO_3$); Mobile Phase B: acetonitrile; How rate: 50 mL/min; Gradient: 25% B-45% B in 20 min; Detector: 254 nm. The fractions containing desired product were collected at 38% B and concentrated under reduced pressure to afford 1-(3-(4-chlorophenyl)-1,2,4-oxadiazol-5-yl)-N—(((S)-1-(((R)-1-methylpiperidin-3-yl)methyl)pyrrolidin-3-yl)methyl)piperidine-4-carboxamide as a white solid.

Yield 120 mg (30%). $^1$H NMR (400 MHz, DMSO) δ 7.91 (d, J=8.8 Hz, 2H), 7.90 (br s, 1H), 7.59 (d, J=8.8 Hz, 2H), 4.12-4.01 (m, 2H), 3.29-3.14 (m, 2H), 3.13-2.86 (m, 2H), 2.78-2.71 (m, 1H), 2.66-2.55 (m, 1H), 2.49-2.29 (m, 4H), 2.26-2.13 (m, 3H), 2.10-2.05 (m, 1H), 2.08 (s, 3H), 1.86-1.73 (m, 4H), 1.71-1.28 (m, 8H), 0.89-0.73 (m, 1H). m/z: [ESI$^+$] 501, 503 (M+H)$^+$ ($C_{26}H_{37}ClN_6O_2$).

Synthesis of 1-(3-(4-chlorophenyl)-1,2,4-oxadiazol-5-yl)-N—(((R)-1-(((R)-1-methylpiperidin-3-yl)methyl)pyrrolidin-3-yl)methyl)piperidine-4-carboxamide (Compound 475)

Compound 1-(3-(4-chlorophenyl)-1,2,4-oxadiazol-5-yl)-N—(((R)-1-(((R)-1-methylpiperidin-3-yl)methyl)pyrrolidin-3-yl)methyl)piperidine-4-carboxamide was prepared from 1-(3-(4-chlorophenyl)-1,2,4-oxadiazol-5-yl)-N—(((R)-1-(((R)-piperidin-3-yl)methyl)pyrrolidin-3-yl)methyl)piperidine-4-carboxamide dihydrochloride (450 mg, 0.804 mmol) following a similar procedure to that described for the synthesis of 1-(3-(4-chlorophenyl)-1,2,4-oxadiazol-5-yl)-N—(((S)-1-(((R)-1-methylpiperidin-3-yl)methyl)pyrrolidin-3-yl)methyl)piperidine-4-carboxamide, and was isolated as a white solid.

Yield 100 mg (25%). $^1$H NMR (400 MHz, DMSO) δ 7.91 (d, J=8.8 Hz, 2H), 7.90 (br s, 1H), 7.59 (d, J=8.8 Hz, 2H), 4.12-4.01 (m, 2H), 3.26-3.14 (m, 2H), 3.12-2.90 (m, 2H), 2.80-2.69 (m, 1H), 2.68-2.57 (m, 1H), 2.49-2.30 (m, 4H), 2.26-2.14 (m, 3H), 2.14-2.09 (m, 1H), 2.11 (s, 3H), 1.93-1.74 (m, 4H), 1.72-1.26 (m, 8H), 0.88-0.65 (m, 1H). m/z: [ESI$^+$] 501, 503 (M+H)$^+$ ($C_{26}H_{37}ClN_6O_2$).

Example 3

Biological Activity of Compounds of the Invention

The biological activity results of all compounds of the invention are summarized in Table 2.

TABLE 2

Cellular $LogEC_{120}$ values of compounds of the invention in the immunofluorescence assay.

| Compound Number | Myc Efficacy ($-LogEC_{50}$) |
|---|---|
| 101 | + |
| 102 | + |
| 103 | + |
| 104 | + |
| 105 | ++ |
| 106 | ++ |
| 107 | + |
| 109 | + |
| 110 | + |
| 111 | + |
| 112 | + |
| 113 | + |
| 114 | + |
| 115 | − |
| 116 | + |
| 117 | + |
| 119 | + |
| 120 | + |
| 121 | + |
| 122 | + |
| 123 | + |
| 124 | + |
| 125 | + |
| 126 | + |
| 127 | + |
| 128 | + |
| 129 | + |
| 130 | + |
| 131 | + |
| 132 | + |
| 133 | + |
| 134 | + |
| 135 | − |
| 136 | − |
| 137 | + |
| 138 | + |
| 139 | + |
| 140 | + |
| 141 | − |
| 142 | + |
| 143 | ++ |
| 144 | + |
| 145 | + |
| 146 | + |
| 147 | + |
| 148 | + |
| 149 | ++ |
| 150 | ++ |
| 151 | ++ |
| 152 | +++ |
| 153 | + |
| 154 | ++ |
| 155 | ++ |
| 156 | + |
| 157 | ++ |
| 158 | ++ |
| 159 | + |
| 160 | ++ |
| 161 | + |
| 162 | + |
| 163 | + |
| 164 | − |
| 165 | + |
| 166 | + |
| 167 | +++ |
| 168 | ++ |

TABLE 2-continued

Cellular LogEC$_{120}$ values of compounds of the invention in the immunofluorescence assay.

| Compound Number | Myc Efficacy (−LogEC$_{50}$) |
|---|---|
| 169 | + |
| 170 | + |
| 171 | ++ |
| 172 | ++ |
| 173 | + |
| 174 | ++ |
| 175 | + |
| 176 | + |
| 177 | ++ |
| 178 | + |
| 179 | + |
| 180 | + |
| 181 | + |
| 182 | + |
| 183 | + |
| 184 | + |
| 185 | ++ |
| 186 | ++ |
| 187 | ++ |
| 188 | ++ |
| 189 | + |
| 190 | + |
| 191 | + |
| 192 | + |
| 193 | ++ |
| 194 | + |
| 195 | + |
| 196 | ++ |
| 197 | + |
| 198 | ++ |
| 199 | + |
| 200 | + |
| 201 | + |
| 202 | + |
| 203 | + |
| 204 | + |
| 205 | + |
| 206 | + |
| 207 | +++ |
| 208 | ++ |
| 209 | + |
| 210 | + |
| 211 | + |
| 212 | + |
| 213 | + |
| 214 | + |
| 215 | + |
| 216 | + |
| 217 | − |
| 218 | − |
| 219 | − |
| 220 | + |
| 221 | + |
| 222 | ++ |
| 223 | ++ |
| 224 | + |
| 225 | − |
| 226 | + |
| 227 | + |
| 228 | + |
| 229 | + |
| 230 | + |
| 231 | ++ |
| 232 | + |
| 233 | + |
| 234 | + |
| 235 | + |
| 236 | ++ |
| 237 | ++ |
| 238 | +++ |
| 239 | +++ |
| 240 | +++ |
| 241 | +++ |
| 242 | + |
| 243 | +++ |
| 244 | + |
| 245 | +++ |
| 246 | + |
| 247 | + |
| 248 | +++ |
| 249 | + |
| 250 | + |
| 251 | − |
| 252 | + |
| 253 | + |
| 254 | + |
| 255 | + |
| 256 | + |
| 257 | + |
| 258 | + |
| 259 | + |
| 260 | + |
| 261 | + |
| 262 | + |
| 263 | − |
| 264 | + |
| 265 | + |
| 266 | + |
| 267 | ++ |
| 268 | ++ |
| 269 | + |
| 270 | + |
| 271 | + |
| 272 | + |
| 273 | − |
| 274 | + |
| 275 | + |
| 276 | + |
| 277 | + |
| 278 | + |
| 279 | + |
| 280 | + |
| 281 | + |
| 282 | + |
| 283 | + |
| 284 | + |
| 285 | ++ |
| 286 | ++ |
| 287 | +++ |
| 288 | ++ |
| 289 | + |
| 290 | + |
| 291 | + |
| 292 | + |
| 293 | + |
| 294 | + |
| 295 | + |
| 296 | + |
| 297 | + |
| 298 | + |
| 299 | + |
| 300 | ++ |
| 301 | + |
| 302 | + |
| 303 | + |
| 304 | + |
| 305 | + |
| 306 | + |
| 307 | + |
| 308 | + |
| 309 | − |
| 310 | + |
| 311 | − |
| 312 | + |
| 313 | − |
| 314 | + |
| 315 | + |
| 316 | + |
| 317 | ++ |
| 318 | + |

TABLE 2-continued

Cellular LogEC$_{120}$ values of compounds of the invention in the immunofluorescence assay.

| Compound Number | Myc Efficacy (−LogEC$_{50}$) |
|---|---|
| 319 | + |
| 320 | + |
| 321 | ++ |
| 322 | ++ |
| 323 | ++ |
| 324 | ++ |
| 325 | + |
| 326 | ++ |
| 327 | + |
| 328 | ++ |
| 329 | + |
| 330 | + |
| 331 | ++ |
| 332 | ++ |
| 333 | + |
| 334 | + |
| 335 | ++ |
| 336 | ++ |
| 337 | ++ |
| 338 | ++ |
| 339 | ++ |
| 340 | ++ |
| 341 | + |
| 342 | ++ |
| 343 | + |
| 344 | ++ |
| 345 | + |
| 346 | ++ |
| 347 | + |
| 348 | ++ |
| 349 | ++ |
| 350 | ++ |
| 351 | ++ |
| 352 | ++ |
| 353 | ++ |
| 354 | ++ |
| 355 | + |
| 356 | ++ |
| 357 | ++ |
| 358 | ++ |
| 359 | ++ |
| 360 | + |
| 361 | ++ |
| 362 | + |
| 363 | + |
| 364 | + |
| 365 | ++ |
| 366 | + |
| 367 | + |
| 368 | ++ |
| 369 | + |
| 370 | + |
| 371 | + |
| 372 | ++ |
| 373 | ++ |
| 374 | + |
| 375 | ++ |
| 376 | − |
| 377 | + |
| 378 | ++ |
| 379 | ++ |
| 380 | ++ |
| 381 | ++ |
| 382 | ++ |
| 383 | ++ |
| 384 | ++ |
| 385 | ++ |
| 386 | + |
| 387 | ++ |
| 388 | ++ |
| 389 | ++ |
| 390 | ++ |
| 391 | + |
| 392 | + |
| 393 | + |
| 394 | + |
| 395 | + |
| 396 | + |
| 397 | − |
| 398 | + |
| 399 | + |
| 400 | + |
| 401 | + |
| 402 | + |
| 403 | + |
| 404 | ++ |
| 405 | + |
| 406 | + |
| 407 | ++ |
| 408 | + |
| 409 | ++ |
| 410 | ++ |
| 411 | ++ |
| 412 | − |
| 413 | − |
| 414 | + |
| 415 | + |
| 416 | + |
| 417 | ++ |
| 418 | + |
| 419 | ++ |
| 420 | + |
| 421 | +++ |
| 422 | ++ |
| 428 | +++ |
| 429 | +++ |
| 430 | +++ |
| 433 | + |
| 434 | + |
| 435 | +++ |
| 436 | +++ |
| 438 | +++ |
| 450 | ++ |
| 453 | +++ |
| 458 | +++ |
| 459 | +++ |
| 460 | +++ |
| 462 | ++ |
| 463 | + |
| 464 | + |
| 465 | + |
| 466 | + |
| 467 | + |
| 468 | ++ |
| 470 | ++ |
| 471 | ++ |
| 473 | + |
| 474 | ++ |
| 475 | ++ |

Activity (−LogEC$_{50}$):
− ≤3
+ >3 and <5
++ ≥5 and <6
+++ ≥6

Compounds activity was tested in tumor cell lines expressing c-Myc by using high content image analysis. c-Myc mRNA rate of translation was assays using PSM assay, c-Myc protein levels and intracellular localization were assayed by immunofluorescence using a c-Myc specific antibody and c-Myc mRNA levels and intracellular localization was tested using specific fluorescent probes, as detailed in the Experimental Methods below (Example 4). The di-tRNA translation rate measurement specificity to c-Myc was shown by co-transfecting c-Myc specific siRNA. Transfection of labelled di-tRNA with c-Myc specific siRNA reduced the FRET signal originating from ribosome translating c-Myc, relative to cells transfected with nonrelevant siRNA (FIG. 1).

Figure 2:
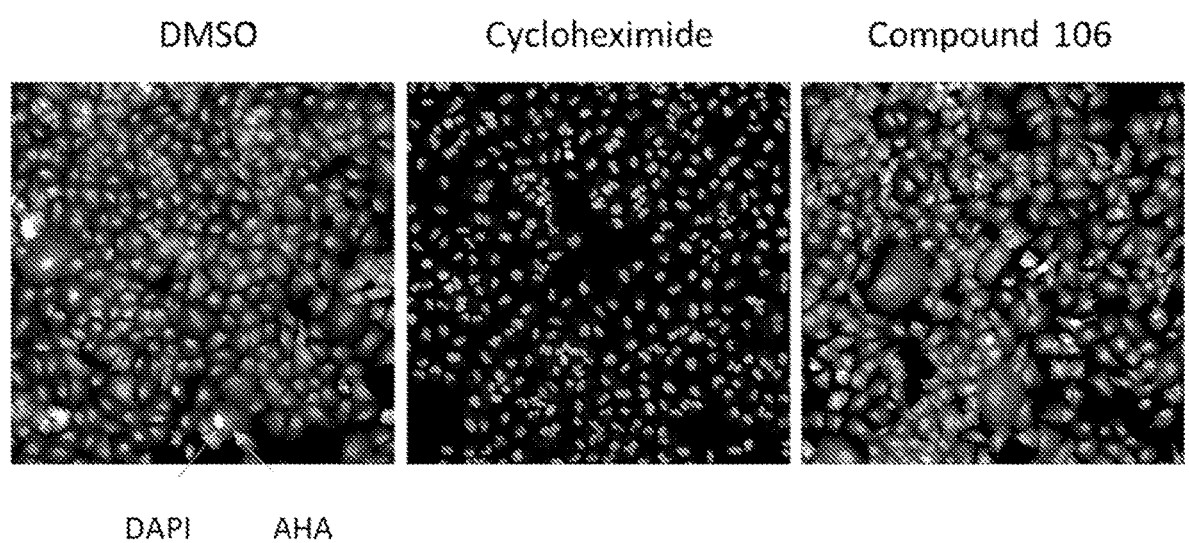
FIG. 2 depicts selective regulation of c-Myc translation. The panel demonstrates metabolic labeling in A549 cells, treated with vehicle, general translation inhibitor cycloheximide or anti-c-Myc compound. Treatment with cycloheximide resulted in total inhibition of global protein synthesis, while treatment with tested compound showed no significant effect. Cell nuclei stained with DAPI and AHA metabolic labeling are signed on the images.

Compounds did not affect global translation. A549 cells were incubated with active compounds and metabolically labelled with fluorescent methionine for a 4 hour pulse (click-chemistry modified methionine). Cells were fixed and newly synthesized proteins detected by using click-chemistry with a fluorescent detector (FIG. 2). Global ribosome inhibitor, cycloheximide (CHX) completely reduced incorporation of modified methionine (FIG. 2, compare middle and left panels). However, a representative compound did not inhibit incorporation of modified methionine, indicating that global translation is not affected by the compounds (FIG. 2, compare right and left panels, respectively).

Figure 3:
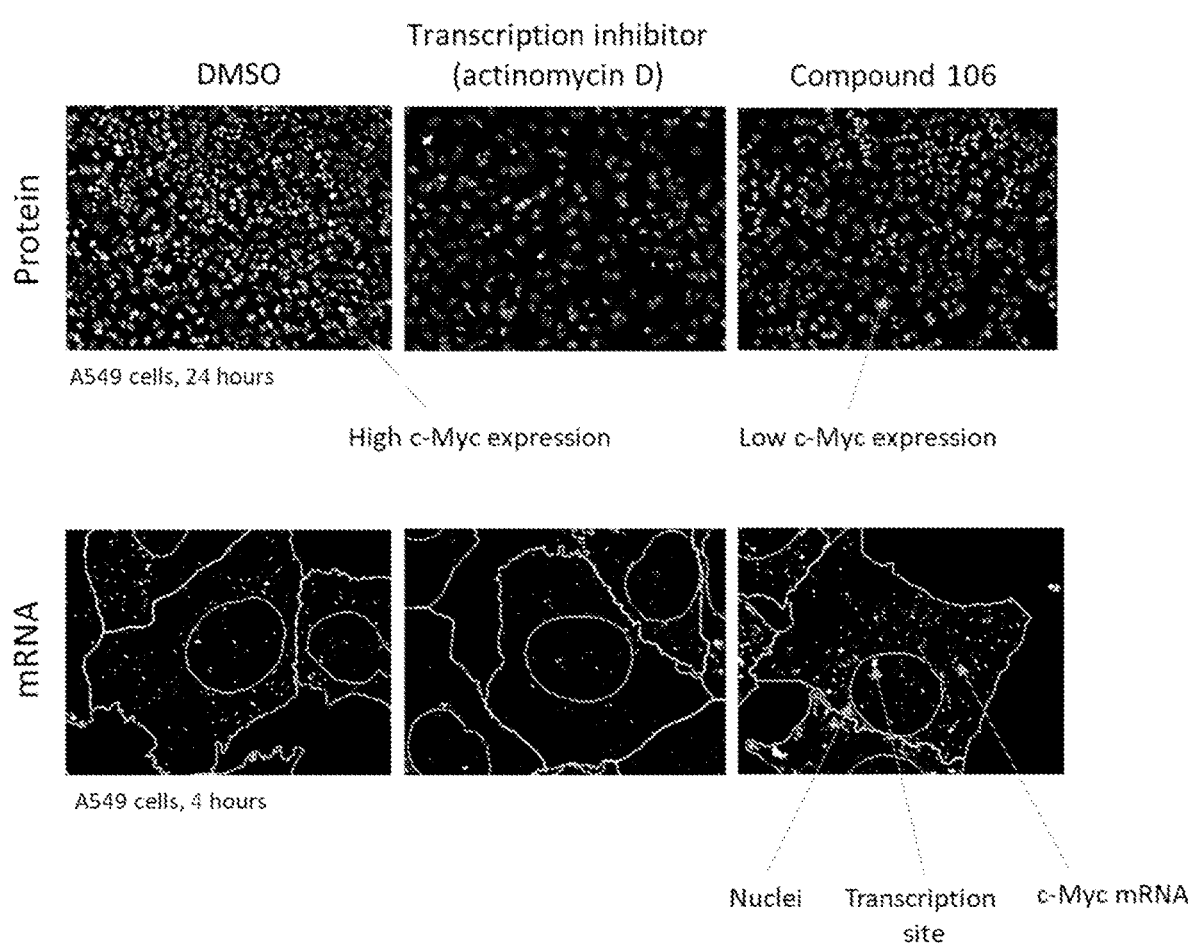
FIG. 3 demonstrates that compounds act at the level of translation. A549 cells were exposed to vehicle, general transcription inhibitor actinomycin D or anti-c-Myc compound. In the upper panel, significant decrease in c-Myc protein level was observed after treatment with either actinomycin D or tested compound. Lower panel shows complete reduction in c-Myc mRNA level as well as transcription sites after treatment with actinomycin D. Treatment with tested compound showed no effect on either c-Myc mRNA level or transcription sites. Cell nuclei stained with DAPI, c-Myc protein, c-Myc mRNA and transcription sites are signed on the images.
Figure 4A:
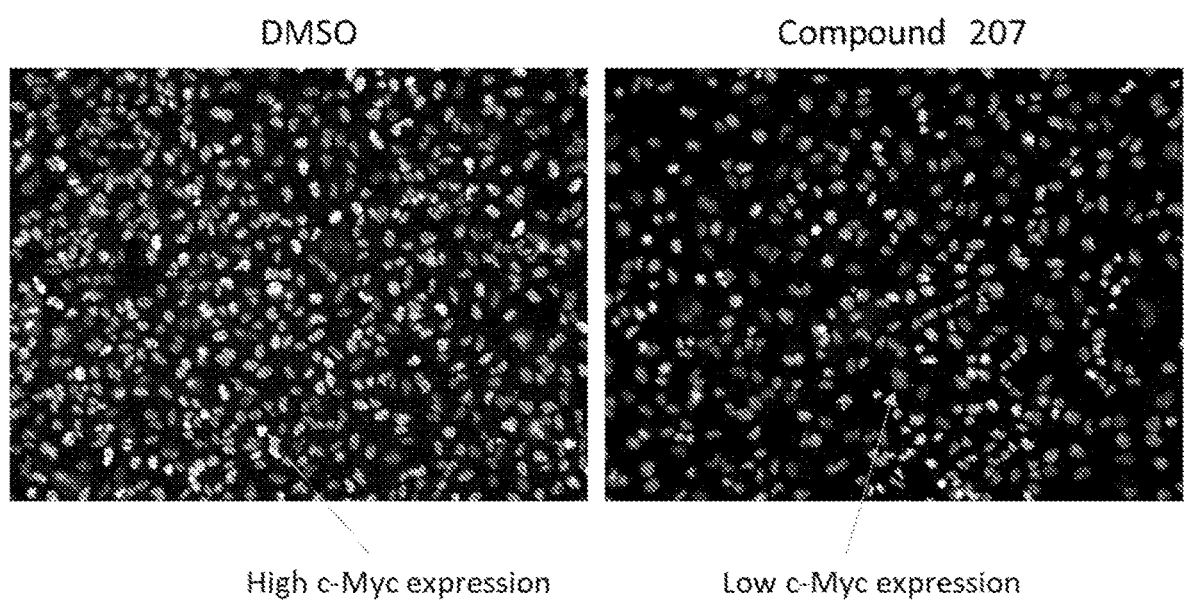
FIGS. 4A-4B demonstrate the efficacy and toxicity window of compounds.
Figure 4B:
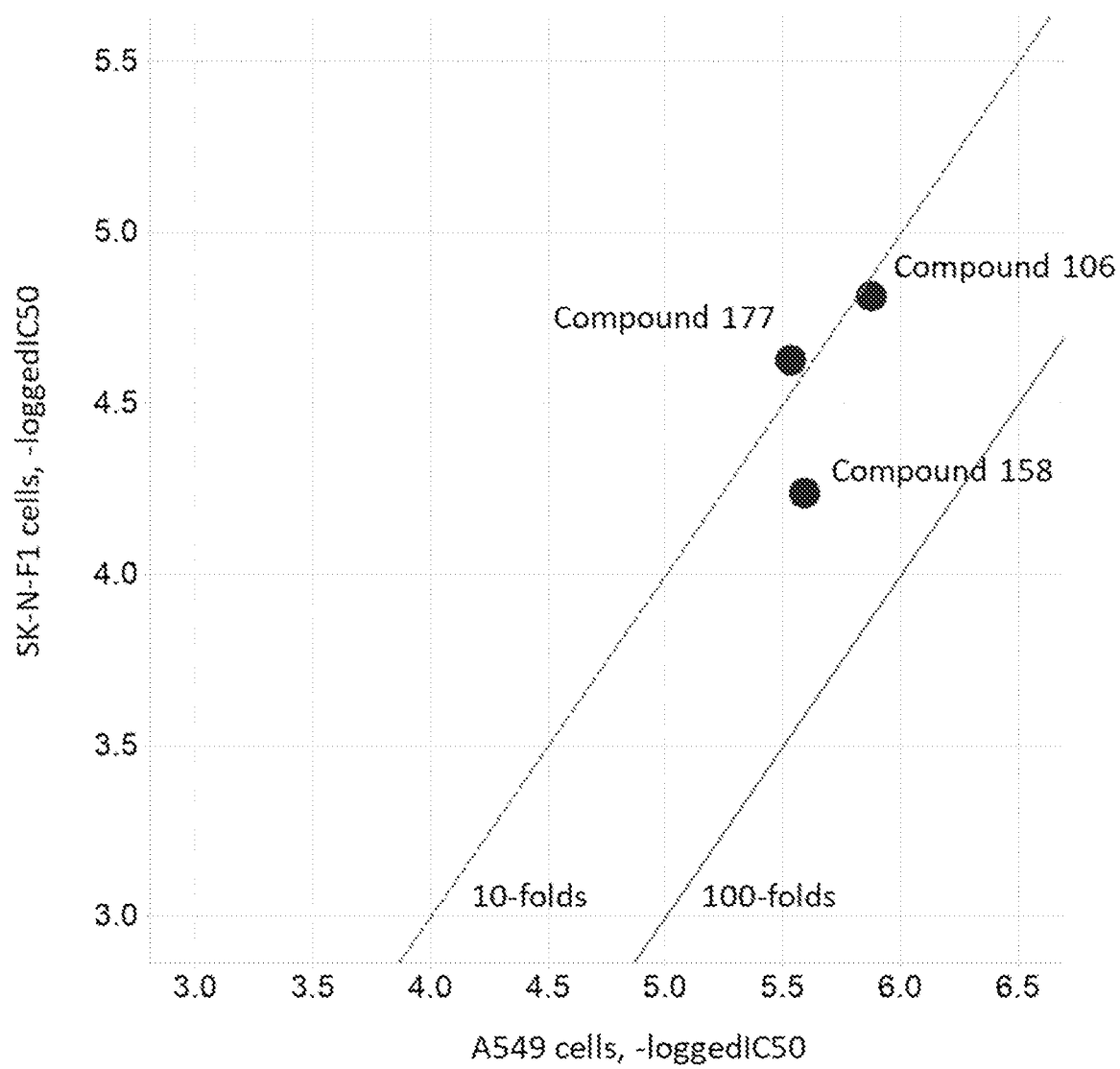

Compounds reduced c-Myc protein accumulation in A549 cells without affecting c-Myc transcription. A549 cells were incubated with compounds for 24 hours (FIG. 3, upper panel) and c-Myc protein detected by immunofluorescence. In parallel, A549 cells were incubated with compounds for 4 hours and c-Myc mRNA was visualized by microscopy using c-Myc mRNA specific fluorescent-tagged probes (FIG. 3, lower panel). Both a general transcription inhibitor, Actinomycin D, and compounds of the invention, reduced c-Myc protein (FIG. 3, upper panel). Actinomycin D inhibited transcription site (FIG. 3, middle lower panel, spots inside the nucleus) and mRNA accumulation in the cytoplasm (FIG. 3, middle lower panel, spots in the cytoplasm). However, compound treated cells did not affect transcription site intensity or number (FIG. 3, right lower panel, spots inside the nucleus are evident), but did affect steady state levels of mRNA in the cytoplasm (FIG. 3, right lower panel, reduction of spots in the cytoplasm relative to DMSO control). This indicates that compounds of the invention affect c-Myc steady state mRNA levels, either by affecting turn over rate of c-Myc mRNA, or by inhibiting its recruitment by ribosomes.

A549 human non-small cell lung carcinoma cells were treated for 24 hours with increasing compound concentration, cells were fixed and stained with a nuclei stain (DAPI) and anti-c-Myc fluorescent antibody. The c-Myc signal was quantified by image analysis, and data was exported and analyzed using TIBCO Spotfire® (TIBCO Corporation). Dose response curves were generated and fitted with logaristic regression to calculate potency ($EC_{50}$ values). Potency values are presented in Table 2 for all compounds and are shown for selected compounds (FIG. 3).

Example 4

Experimental Methods

High Content Screen for the Identification of c-Myc Modulators

Compound effect on translation of c-Myc in A549, human non-small cell lung carcinoma cell line, was conducted using specific PSM assay using tRNAgIn and tRNAser isoacceptors, as described below. A library of diverse small molecules, 90,000 compounds, was used at a final concentration of 30 µM. Image and data analyses were conducted using Anima's proprietary algorithms. False positive and toxic compounds were eliminated. A total of 3,307 compounds were identified as hits, compounds which increased or decreased the FRET signal generated by ribosomes during c-Myc translation.

Positive hits were re-screened in the specific PSM assay, using tRNAgIn and tRNAser. Hits were scored using Anima's proprietary algorithms, and 348 compounds, which selectively inhibited c-Myc synthesis in specific PSM assay, were selected as confirmed hits. These compounds were purchased as powder to confirm activity. Re-purchased hits were tested in the specific PSM assay (tRNAgIn-tRNAser) and anti-c-Myc immunofluorescence, and in counter assays to eliminate global translation modulators: (1) bulk tRNA and (2) metabolic labeling using Click-IT™ AHA (L-Azidohomoalanine).

Cell Culture

A549 cells (ATCC® CCL-185™) were maintained in DMEM low glucose medium (Biological Industries, Cat. 01-050-1A), containing 10% fetal bovine serum, 1% L-glutamine and 1% penicillin-streptomycin solution.

SK-N-F1 cells (ATCC® CRL-2142™) were maintained in DMEM high glucose medium (Biological Industries, Cat. 01-055-1A), containing 10% fetal bovine serum, 2% L-glutamine, 1% penicillin-streptomycin solution, 1% sodium pyruvate and 1% non-essential amino acids.

Specific tRNA (tRNA Isoacceptor) Isolation and Labeling

The specific tRNAgIn (TTG) and tRNAser (CGA) were isolated for from baker's yeast (Roche) using biotinylated oligos complimentary to sequences encompassing the D-loop and anti-codon. The biotinylated oligos were mixed with total yeast tRNA and heated up to 82° C. for 10 min, followed by addition of TMA buffer (20 mM Tris, pH 7.6, 1.8M tetramethylammonium chloride, 0.2 mM EDTA). The mixture was incubated at 68° C. for 10 min, and annealed by slow cooling to 37° C. tRNA:DNA oligo mixture then was incubated with streptavidin linked agarose beads at room temperature for 30 min while shaking. Unbound tRNA and tRNA:DNA complexes were removed by centrifugation and beads washed with 10 mM Tris-HCl (pH 7.6). The target tRNA was eluted from the resin by incubation at 45° C. or 55° C. for 7 min followed by centrifugation and collection of the supernatant to clean tubes.

The purity of the isolated tRNA isoacceptors was confirmed using fluorescent polarization assay. Purified tRNA was annealed to a complementary oligo tagged at the 3'-end with Cy3. The annealed purified tRNA isoacceptor FP signal was compared to the signal derived from annealing of a tRNA isoacceptor oligo annealed to the same Cy3-oligo. Samples with more than 80% purity were selected for labeling.

The dihydrouridines of the target tRNAs or total yeast tRNA were labeled as described in U.S. Pat. No. 8,785,119. Labeled tRNAs were purified by reverse phase HPLC and eluted with an ethanol gradient.

Protein Synthesis Monitoring (PSM) Assays

Cy3 and Cy5 Labeled tRNA, bulk or specific, were transfected with 0.4 µl HiPerFect (Qiagen) per 384 well. First, HiPerFect was mixed with DMEM and incubated for 5 min; next, 6 nanograms Cy3-labeled tRNAgIn and 6 ng Cy5-labled tRNAser (or 9 ng each Cy3 and Cy5-labelled bulk tRNA) were diluted in 1×PBS and then added to the HiPerFect:DMEM cocktail and incubated at room temperature for 10 min. The transfection mixture was dispersed automatically into 384-well black plates. Cells were then seeded at 3,500 cells per well in complete culture medium and incubated at 37° C., 5% $CO_2$. Forty-eight hours after transfection compounds were added at a final concentration of 30 µM. Four hours post-treatment, cells were fixed with 4% paraformaldehyde and images were captured with Operetta microscope (Perkin Elmer) using ×20 high NA objective lens.

Metabolic Labeling Assay

A549 cells were seeded at 3,200 cells per well in complete culture medium. Plates were incubated at 37° C., 5% $CO_2$ overnight. After 48 hours of incubation, the growth medium was aspirated, and cells were washed three times with HBSS. Metabolic labeling medium DMEM (-Cys -Met), containing 10% dialyzed FBS, 1% penicillin-streptomycin and 1% L-glutamine was added to the cells for 30 min. Then medium was replaced by metabolic labeling medium containing 25 μM L-Azidohomoalanine (AHA, ThermoFisher) and tested compounds at a final concentration of 30 μM, and cells were incubated for 4 hours at 37° C., 5% $CO_2$. Cells were washed by HBSS at 37° C. for 15 min before fixing with 4% paraformaldehyde. Cells were washed twice with 3% BSA in PBS before permeabilization with 0.5% Triton X-100 in PBS for 20 min. The AHA staining with Alexa Fluor™ 555 alkyne was performed according to the manufacturer protocol. Images were captured with Operetta microscope (Perkin Elmer) using ×20 high NA objective lens.

c-Myc Immunofluorescence Assay

A549 cells were grown in 384-wells plates (Perkin Elmer, Cat. 6057300) for 48 hours, treated with compounds and then fixed for 20 min in 4% paraformaldehyde. After that permeabilization was done using 0.1% Triton X-100 in PBS for 20 min. Primary anti-c-Myc antibody (Abcam, ab32072) staining was performed for 90 min at room temperature. Cells then were washed twice with PBS and incubated with secondary antibody (Abcam, ab150075) for 90 min at room temperature. Nuclei were stained with DAPI for 10 min and washed twice with PBS.

Cell images were taken with Operetta (Perkin Elmer, USA), a wide-field fluorescence microscope at 20× magnification. After acquisition, the images were transferred to Columbus software (Perkin-Elmer) for image analysis. In Columbus, cells were identified by their nucleus, using the "Find Nuceli" module and cytoplasm was detected based on the secondary antibody channel. Subsequently, the fluorescent signal was enumerated in the identified cell region. Then data was exported to a data analysis and visualization software, Tibco Spotfire, USA.

3'-Rapid Amplification of cDNA Ends (RACE) Assay

A549 cells were treated with compounds in 2-well dishes for 6 hours. Cells were washed with 1×PBS and pelleted by centrifugation. Total RNA was produced using Direct-zol RNA MiniPrep (Zymo research) and DNA was removed using Turbo-DNA free kit (Ambion). 3'-RACE was performed using RevertAid™ First Strand cDNA Synthesis Kit (Thermo) using an oligo-dT-adapter hybrid primer RTQt. The cDNA was used as a template for PCR using PCRBIO HS Taq Mix (PCRBIO). To perform the PCR, adapter-anti sense primer Qi and a forward Myc primer (gene-specific primer) were used. The amplified segment was excised from the agarose gel for sequencing using the Zymoclean™ Gel DNA Recovery Kit (Zymo research). The primers sequences are: cDNA RTqT: 5'-CCA GTG AGC AGA GTG ACG AGG ACT CGA GCT CAA GCT TTT TTT TTT TTT TTT T-3', PCR Qi (reverse primer): 5'-GAG GAC TCG AGC TCA AGC-3', Myc_RACE-F3 (Forward primer): 5'-TAG CAG TTA CAC AGA ATT TC-3'.

Fluorescent In Situ Hybridization (FISH) Assay

A549 cells were grown in 384-wells plates (Perkin Elmer, Cat. 6057300) for 48 hours, treated with compounds for 4 hours and then fixed for 20 min in 4% paraformaldehyde. Next day, permeabilization was done for 90 min at 4° C., using 70% ethanol. Then, the cells were incubated for 10 min with 10% formamide in 10% saline-sodium citrate. Fluorescently labeled customer DNA probes that target c-Myc (Cy3, BioSearch Technologies, Cat. SMF-1063-5) and GAPDH (Cy5, BioSearch Technologies, Cat. SMF-2019-1) mRNAs were hybridized overnight at 37° C. in a dark chamber in 10% formamide. The next day, cells were washed twice with 10% formamide for 30 min. Next, nuclei were counterstained with DAPI (SIGMA, Cat. 5MG-D9542) and then cells were washed twice with PBS. FISH experiments were performed according to the probes manufacturer's protocol for adherent cells.

Following RNA FISH experiments, images of cells were taken with Operetta (Perkin Elmer, USA), a wide-field fluorescence microscope at ×63 magnification. After acquisition, the images were transferred to Columbus software for image analysis. In Columbus, cells were identified by their nucleus, using the "Find Nuceli" module, cytoplasm was detected based on the FISH-channel, and single mRNAs in the cytoplasm and transcription sites in the nucleus were detected using "Find Spots" module. Subsequently, fluorescent signals were collected for each channel in the identified regions: nucleus, cytoplasm and spots. Data was exported to a data analysis and visualization software, Tibco Spotfire, USA.

What is claimed:

1. A compound represented by the structure of formula (I(a(ii))):

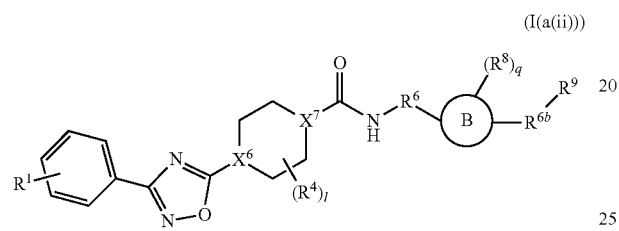

wherein
- $R^1$ is F, Cl, Br, I, OH, CF$_3$, OCH$_3$, CN, NO$_2$, —CH$_2$CN, C$_1$-C$_5$ linear or branched, substituted or unsubstituted alkyl, C$_1$-C$_5$ linear or branched, or C$_3$-C$_8$ cyclic haloalkyl, CHF$_2$, CF$_3$, substituted or unsubstituted C$_1$-C$_5$ linear or branched, or C$_3$-C$_8$ cyclic alkoxy, C$_1$-C$_5$ linear or branched haloalkoxy, NH—C(O)—R$^7$, NHC(O)—CH$_3$, C$_1$-C$_5$ linear or branched alkoxyalkyl;
- $R^6$ is [CH$_2$]$_p$, CH$_2$—CH$_2$—CH$_2$, [CH$_2$]$_{pa}$—O—[CH$_2$]$_{pb}$, or [CH$_2$]$_p$—O;
  wherein
  p is 1, 2 or 3; and
  each pa and pb is independently an integer between 1 and 5;
- $R^4$ is H, F, Cl, Br, I, OH, CF$_3$, CN, NO$_2$, C$_1$-C$_5$ linear or branched, substituted or unsubstituted alkyl, C$_1$-C$_5$ linear or branched, or C$_3$-C$_8$ cyclic haloalkyl;
- $R^{6b}$ is absent or O, C=O, [CH$_2$]$_p$, CH$_2$;
- $R^8$ is H, F, Cl, Br, I, OH, CF$_3$, CN, NO$_2$, C$_1$-C$_5$ linear or branched, substituted or unsubstituted alkyl, C$_1$-C$_5$ linear or branched, or C$_3$-C$_8$ cyclic haloalkyl;
- $R^9$ is substituted or unsubstituted saturated C$_3$-C$_8$ cycloalkyl, cyclohexyl, cyclopentyl, cyclopropyl, substituted or unsubstituted C$_3$-C$_8$ cycloalkenyl, cyclohexenyl, substituted or unsubstituted saturated or unsaturated 3-8 membered heterocyclic ring, methyl-piperidine, tetrahydropyran, tetrahydrothiopyran or R$^{20}$;
- B ring is a single or fused 3-12 membered heterocyclic ring, piperidine, pyrrolidine, C$_3$-C$_8$ saturated or unsaturated cycloalkyl or a spiro ring system;
- $X^6$ is N;
- $X^7$ is CH or N;
- I and q are each independently an integer between 0 and 4;
- wherein the term "substituted" refer to at least one substitution selected from: F, Cl, Br, I, CF$_3$, OH, SH, CN, NO$_2$, C$_1$-C$_5$ linear alkyne, acetylene, diazirine, C$_1$-C$_5$ linear, cyclic or branched alkyl, methyl, ethyl, propyl, isopropyl, cyclopropyl, benzyl, methylbenzyl, aryl, phenyl, fluorophenyl, heteroaryl, indole, tetrahydropyran, pyridine, C$_3$-C$_8$ cycloalkyl, cyclopropyl, C$_1$-C$_5$ linear or branched alkyl-OH, C(CH$_3$)$_2$CH$_2$—OH, CH$_2$CH$_2$—OH, 3-8 membered heterocyclic ring, piperidine, alkoxy, methoxy, ethoxy, propyloxy, isopropyloxy, NH$_2$, N(alkyl)$_2$, N(CH$_3$)$_2$, N(CH$_2$CH$_3$)$_2$, N(CH$_3$)(CH$_2$CH$_3$), NH(alkyl), NHCH$_3$, NHCH$_2$CH$_3$, NHCH$_2$CH$_2$CH$_3$, NH(cycloalkyl), NH(cyclohexyl), NH(cylopentyl), NH(aryl), NH(phenyl), NH(pyridiny), NH(benzyl), N(cycloalkyl)$_2$, N(cyclohexyl)$_2$, N(cylopentyl)$_2$, N(aryl)$_2$, N(phenyl)$_2$, N(pyridinyl)$_2$, N(alkyl)(aryl), N(methyl)(phenyl), N(methyl)(pyridinyl), N(alkyl)(cycloalkyl), N(methyl)(cyclopropyl), N(methyl)(cyclohexyl), N(methyl)(cyclopentyl), N(aryl)(cycloalkyl), N(phenyl)(cyclohexyl), N(pyridinyl)(cyclohexyl), NHC(O)(alkyl), NHC(O)CH$_3$, heteroaryl, halophenyl, and (benzyloxy) phenyl;

or its pharmaceutically acceptable salt, optical isomer, tautomer, hydrate, N-oxide, reverse amide analog, isotopic variant, or any combination thereof; wherein reverse amide analog does not include cyclic amides and amides of cyclic amines.

2. The compound according to claim 1,
wherein $R^1$ is Cl, O—R$^{20}$, OCH$_3$, —R$^3$CN, C$_1$-C$_5$ linear or branched, or C$_3$-C$_8$ cyclic haloalkyl, CF$_3$, C$_1$-C$_5$ linear or branched haloalkoxy, OCF$_3$, or OCHF$_2$;
wherein $R^{6b}$ is absent, O, C=O, [CH$_2$]$_p$ or CH$_2$;
wherein $R^9$ is R$^{20}$, substituted or unsubstituted heteroaryl, pyridine, 3-methyl-pyridine, thiazolyl, oxazolyl thiophenyl, furanyl, substituted or unsubstituted saturated C$_3$-C$_8$ cycloalkyl, cyclohexyl, cyclopentyl, cyclopropyl, substituted or unsubstituted C$_3$-C$_8$ cycloalkenyl, cyclohexenyl, substituted or unsubstituted 3-8 membered heterocyclic ring, tetrahydropyran, or tetrahydrothiopyran;

or any combination thereof.

3. The compound according to claim 1, represented by the structure of formula (I(a(iii))):

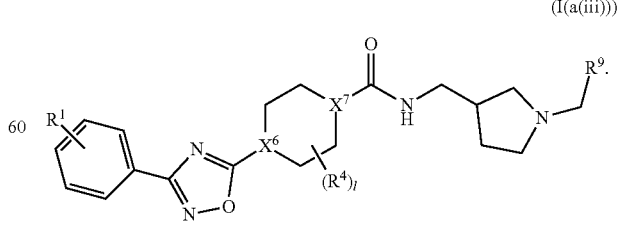

4. The compound according to claim 1, represented by the structure of formula (II):

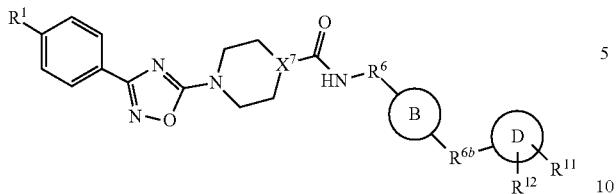

(II)

wherein
- $R^1$ is H, F, Cl, Br, I, OH, $CF_3$, $OCH_3$, CN, $NO_2$, $C_1$-$C_5$ linear or branched, substituted or unsubstituted alkyl, methyl, ethyl, $C_1$-$C_5$ linear or branched, or $C_3$-$C_8$ cyclic haloalkyl, $C_1$-$C_5$ substituted or unsubstituted, linear or branched, or $C_3$-$C_8$ cyclic alkoxy, methoxy, O—$(CH_2)_2$—OH, $C_1$-$C_5$ linear or branched haloalkoxy [(e.g.], $OCF_3$, $OCHF_2$, NH—C(O)—$R^7$, NHC(O)—$CH_3$, or $C_1$-$C_5$ linear or branched alkoxyalkyl;
  wherein
  - $R^7$ is H, $C_1$-$C_5$ substituted or unsubstituted linear or branched alkyl, methyl, ethyl, $CH_2$—$CH_2$—O—$CH_3$, $C_1$-$C_5$ linear or branched alkoxy, O—$CH_3$, C(O)R, or $S(O)_2R$;
- $R^6$ is absent or O, C=O, C(=O)—$[CH_2]_p$, $[CH_2]_p$—C(=O), $[CH_2]_p$, $CH_2$, $CH_2CH_2$, $CH_2CH_2CH_2$, $CH_2CH_2CH_2CH_2$, $[CHR^{21}]$, CHF, CH—$CH_3$, $[C(R^{21})_2]_p$, $CF_2$ or $[CH_2]_{pa}$—O—$[CH_2]_{pb}$, $CH_2OCH_2$, or $[CH_2]_p$—O, $CH_2CH_2O$;
- $R^{6b}$ is absent or O, C=O, C(=O)—$[CH_2]_p$, $[CH_2]_p$—C(=O), $[CH_2]_p$, $CH_2$, $CH_2CH_2$, $CH_2CH_2CH_2$, $CH_2CH_2CH_2CH_2$, $[CHR^{21}]$, CHF, CH—$CH_3$, $[C(R^{21})_2]_p$, $CF_2$ or $[CH_2]_{pa}$—O—$[CH_2]_{pb}$, $CH_2OCH_2$, or $[CH_2]_p$—O, $CH_2CH_2O$;
  wherein
  - p is an integer between 1 and 10; and
  - each pa and pb is independently an integer between 1 and 5;
- $R^{21}$ is H, F, Cl, Br, I, OH, $CF_3$, CN, $NO_2$, $C_1$-$C_5$ linear or branched, substituted or unsubstituted alkyl, methyl, ethyl, propyl, isopropyl, isobutyl, $C_1$-$C_5$ linear or branched alkoxy, methoxy, $C_1$-$C_5$ linear or branched haloalkyl, $CHF_2$, $CF_3$, $CH_2$-Ph, $CH_2$-Ph-ethyl, substituted or unsubstituted aryl, phenyl, ethylphenyl, substituted or unsubstituted heteroaryl, pyridine (2, 3, and 4-pyridine) benzimidazole, substituted or unsubstituted $C_3$-$C_8$ cycloalkyl, cyclopropyl, substituted or unsubstituted 3-8 membered heterocyclic ring, piperidine, pyrrolidine, $(CH_2)_3$-piperidine or C(O)-(alkyl), C(O)—$CH_3$;
- or wherein two geminal or vicinal $R^{21}$ substituents are joined to form a substituted or unsubstituted $C_3$-$C_8$ cycloalkyl, cyclopropyl;
- B ring is a substituted or unsubstituted saturated, unsaturated or aromatic, single, fused or spiro, 3-12 membered heterocyclic ring, piperidine, pyrrolidine, piperazine, 2-pyrrolidone, indole or substituted or unsubstituted saturated or unsaturated single, fused or spiro, 3-12 membered cycloalkyl ring;
- D ring is a saturated, unsaturated or aromatic, single, fused or spiro, heterocyclic 3-12 membered ring, 2, 3, or 4-pyridine, furan, thiophene, pyrrol, thiazole, isothiazole, tetrahydrofuran, piperidine, azepane, oxepane, 2-oxaspiro[3.3]heptane, azetidine, tetrahydro-2H-thiopyran 1,1-dioxide, tetrahydrothiopyran, tetrahydropyran, pyrrolidine, oxetane, diazirine or a saturated, unsaturated, single, fused or spiro, aliphatic carbocyclic 3-12 membered ring, cyclopropyl, cyclobutyl, cyclopentyl, cyclohexyl, cyclohexenyl;
- $R^{11}$ and $R^{12}$ are each independently H, F, Cl, Br, I, OH, $CF_3$, $OCH_3$, CN, $NO_2$, $C_1$-$C_5$ linear or branched, substituted or unsubstituted alkyl, methyl, ethyl, ethylacetylene, 1-butyne, $C_1$-$C_5$ linear or branched, or $C_3$-$C_8$ cyclic haloalkyl, $CHF_2$, $C_1$-$C_5$ substituted or unsubstituted, linear or branched, or $C_3$-$C_8$ cyclic alkoxy, methoxy, O—$(CH_2)_2$—OH, $C_1$-$C_5$ linear or branched haloalkoxy, $OCF_3$, $OCHF_2$, $C_1$-$C_5$ linear or branched alkoxyalkyl, $R^{20}$, $NH_2$, NHR, $NR_2$;
  wherein
  - R is H, F, Cl, Br, I, OH, $CF_3$, CN, $NO_2$, $C_1$-$C_5$ linear or branched, substituted or unsubstituted alkyl, $C_1$-$C_5$ linear or branched alkoxy, $C_1$-$C_5$ linear or branched haloalkyl, $R^6$-aryl, $R^6$—$N(alkyl)_2$, $R^6$—NH(alkyl), ($R^6$—NH(cycloalkyl), ($R^6$—NH(aryl), substituted or unsubstituted aryl, substituted or unsubstituted heteroaryl, substituted or unsubstituted $C_3$-$C_8$ cycloalkyl, substituted or unsubstituted 3-8 membered heterocyclic ring, $R^6$-(substituted or unsubstituted heterocycle) or C(O)-(alkyl);
- $X^7$ is CH or N;
- $R^{20}$ is represented by the following structure:

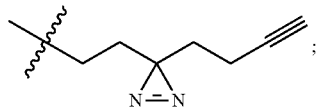 [SMILES: *CCC1(CCC#C)N=N1]

or its pharmaceutically acceptable salt, optical isomer, tautomer, hydrate, N-oxide, reverse amide analog, prodrug, isotopic variant, deuterated analog, pharmaceutical product or any combination thereof.

5. The compound according to claim 1, selected from the following:

| Compound number | Compound Name |
| --- | --- |
| 220 | N-((1-(cyclopropylmethyl)pyrrolidin-3-yl)methyl)-1-(3-(4-methoxyphenyl)-1,2,4-oxadiazol-5-yl)piperidine-4-carboxamide |
| 221 | N-((1-(cyclopropylmethyl)pyrrolidin-3-yl)methyl)-4-(3-(4-methoxyphenyl)-1,2,4-oxadiazol-5-yl)piperazine-1-carboxamide |
| 223 | 1-(3-(4-methoxyphenyl)-1,2,4-oxadiazol-5-yl)-N-((1-((5-methylpyridin-2-yl)methyl)pyrrolidin-3-yl)methyl)piperidine-4-carboxamide |
| 243 | 1-(3-(4-chlorophenyl)-1,2,4-oxadiazol-5-yl)-N-((1-((5-methylpyridin-2-yl)methyl)pyrrolidin-3-yl)methyl)piperidine-4-carboxamide |

-continued

| Compound number | Compound Name |
|---|---|
| 244 | 1-(3-(4-cyanophenyl)-1,2,4-oxadiazol-5-yl)-N-((1-((5-methylpyridin-2-yl)methyl)pyrrolidin-3-yl)methyl)piperidine-4-carboxamide |
| 248 | 4-(3-(4-methoxyphenyl)-1,2,4-oxadiazol-5-yl)-N-(3-(4-(pyridin-2-ylmethyl)piperidin-1-yl)propyl)piperazine-1-carboxamide |
| 286 | N-((1-(2-(3-(but-3-yn-1-yl)-3H-diazirin-3-yl)ethyl)pyrrolidin-3-yl)methyl)-1-(3-(4-methoxyphenyl)-1,2,4-oxadiazol-5-yl)piperidine-4-carboxamide |
| 320 | N-((1-(furan-2-ylmethyl)pyrrolidin-3-yl)methyl)-1-(3-(4-methoxyphenyl)-1,2,4-oxadiazol-5-yl)piperidine-4-carboxamide |
| 322 | 1-(3-(4-methoxyphenyl)-1,2,4-oxadiazol-5-yl)-N-((1-(pyridin-4-ylmethyl)pyrrolidin-3-yl)methyl)piperidine-4-carboxamide |
| 323 | N-((1-(cyclopentylmethyl)pyrrolidin-3-yl)methyl)-1-(3-(4-methoxyphenyl)-1,2,4-oxadiazol-5-yl)piperidine-4-carboxamide |
| 325 | N-((1-((1H-pyrrol-3-yl)methyl)pyrrolidin-3-yl)methyl)-1-(3-(4-methoxyphenyl)-1,2,4-oxadiazol-5-yl)piperidine-4-carboxamide |
| 326 | 1-(3-(4-methoxyphenyl)-1,2,4-oxadiazol-5-yl)-N-((1-((4-methylpyridin-2-yl)methyl)pyrrolidin-3-yl)methyl)piperidine-4-carboxamide |
| 329 | 1-(3-(4-methoxyphenyl)-1,2,4-oxadiazol-5-yl)-N-((1-((4-methylpyridin-3-yl)methyl)pyrrolidin-3-yl)methyl)piperidine-4-carboxamide |
| 330 | N-((1-(furan-3-ylmethyl)pyrrolidin-3-yl)methyl)-1-(3-(4-methoxyphenyl)-1,2,4-oxadiazol-5-yl)piperidine-4-carboxamide |
| 333 | N-((1-((5-fluoropyridin-3-yl)methyl)pyrrolidin-3-yl)methyl)-1-(3-(4-methoxyphenyl)-1,2,4-oxadiazol-5-yl)piperidine-4-carboxamide |
| 334 | N-((1-((3-fluoropyridin-2-yl)methyl)pyrrolidin-3-yl)methyl)-1-(3-(4-methoxyphenyl)-1,2,4-oxadiazol-5-yl)piperidine-4-carboxamide |
| 335 | N-((1-((5-fluoropyridin-2-yl)methyl)pyrrolidin-3-yl)methyl)-1-(3-(4-methoxyphenyl)-1,2,4-oxadiazol-5-yl)piperidine-4-carboxamide |
| 336 | N-((1-(cyclobutylmethyl)pyrrolidin-3-yl)methyl)-1-(3-(4-methoxyphenyl)-1,2,4-oxadiazol-5-yl)piperidine-4-carboxamide |
| 337 | N-((1-((2,2-dimethylcyclopropyl)methyl)pyrrolidin-3-yl)methyl)-1-(3-(4-methoxyphenyl)-1,2,4-oxadiazol-5-yl)piperidine-4-carboxamide |
| 338 | N-((1-(cyclohexylmethyl)pyrrolidin-3-yl)methyl)-1-(3-(4-methoxyphenyl)-1,2,4-oxadiazol-5-yl)piperidine-4-carboxamide |
| 340 | 1-(3-(4-methoxyphenyl)-1,2,4-oxadiazol-5-yl)-N-((1-(pyridin-2-ylmethyl)pyrrolidin-3-yl)methyl)piperidine-4-carboxamide |
| 341 | 1-(3-(4-methoxyphenyl)-1,2,4-oxadiazol-5-yl)-N-((1-(thiazol-5-ylmethyl)pyrrolidin-3-yl)methyl)piperidine-4-carboxamide |
| 347 | 1-(3-(4-methoxyphenyl)-1,2,4-oxadiazol-5-yl)-N-((1-((tetrahydrofuran-3-yl)methyl)pyrrolidin-3-yl)methyl)piperidine-4-carboxamide |
| 348 | 1-(3-(4-methoxyphenyl)-1,2,4-oxadiazol-5-yl)-N-((1-((3-methylpyridin-4-yl)methyl)pyrrolidin-3-yl)methyl)piperidine-4-carboxamide |
| 350 | 1-(3-(4-methoxyphenyl)-1,2,4-oxadiazol-5-yl)-N-((1-((3-methylpyridin-2-yl)methyl)pyrrolidin-3-yl)methyl)piperidine-4-carboxamide |
| 351 | 1-(3-(4-methoxyphenyl)-1,2,4-oxadiazol-5-yl)-N-((1-((6-methylpyridin-3-yl)methyl)pyrrolidin-3-yl)methyl)piperidine-4-carboxamide |
| 352 | N-((1-(isothiazol-5-ylmethyl)pyrrolidin-3-yl)methyl)-1-(3-(4-methoxyphenyl)-1,2,4-oxadiazol-5-yl)piperidine-4-carboxamide |
| 353 | 1-(3-(4-methoxyphenyl)-1,2,4-oxadiazol-5-yl)-N-((1-((1-methylpiperidin-4-yl)methyl)pyrrolidin-3-yl)methyl)piperidine-4-carboxamide |
| 354 | 1-(3-(4-methoxyphenyl)-1,2,4-oxadiazol-5-yl)-N-((1-((tetrahydro-2H-thiopyran-4-yl)methyl)pyrrolidin-3-yl)methyl)piperidine-4-carboxamide |
| 355 | 1-(3-(4-methoxyphenyl)-1,2,4-oxadiazol-5-yl)-N-((1-((tetrahydro-2H-pyran-4-yl)methyl)pyrrolidin-3-yl)methyl)piperidine-4-carboxamide |
| 356 | 1-(3-(4-methoxyphenyl)-1,2,4-oxadiazol-5-yl)-N-((1-(pyridin-3-ylmethyl)pyrrolidin-3-yl)methyl)piperidine-4-carboxamide |
| 357 | 1-(3-(4-methoxyphenyl)-1,2,4-oxadiazol-5-yl)-N-((1-(thiophen-3-ylmethyl)pyrrolidin-3-yl)methyl)piperidine-4-carboxamide |
| 359 | N-((1-((3-fluoropyridin-4-yl)methyl)pyrrolidin-3-yl)methyl)-1-(3-(4-methoxyphenyl)-1,2,4-oxadiazol-5-yl)piperidine-4-carboxamide |
| 360 | 1-(3-(4-methoxyphenyl)-1,2,4-oxadiazol-5-yl)-N-((1-(thiazol-4-ylmethyl)pyrrolidin-3-yl)methyl)piperidine-4-carboxamide |
| 361 | 1-(3-(4-methoxyphenyl)-1,2,4-oxadiazol-5-yl)-N-((1-((tetrahydro-2H-pyran-2-yl)methyl)pyrrolidin-3-yl)methyl)piperidine-4-carboxamide |
| 363 | 1-(3-(4-methoxyphenyl)-1,2,4-oxadiazol-5-yl)-N-((1-((1-methyl-1H-pyrrol-2-yl)methyl)pyrrolidin-3-yl)methyl)piperidine-4-carboxamide |
| 364 | 1-(3-(4-methoxyphenyl)-1,2,4-oxadiazol-5-yl)-N-((1-(thiazol-2-ylmethyl)pyrrolidin-3-yl)methyl)piperidine-4-carboxamide |
| 365 | 1-(3-(4-methoxyphenyl)-1,2,4-oxadiazol-5-yl)-N-((1-((5-methylpyridin-3-yl)methyl)pyrrolidin-3-yl)methyl)piperidine-4-carboxamide |
| 368 | 1-(3-(4-methoxyphenyl)-1,2,4-oxadiazol-5-yl)-N-((1-((2-methylcyclopropyl)methyl)pyrrolidin-3-yl)methyl)piperidine-4-carboxamide |
| 369 | 1-(3-(4-methoxyphenyl)-1,2,4-oxadiazol-5-yl)-N-((1-(((S)-1-methylpyrrolidin-2-yl)methyl)pyrrolidin-3-yl)methyl)piperidine-4-carboxamide |
| 370 | 1-(3-(4-methoxyphenyl)-1,2,4-oxadiazol-5-yl)-N-((1-(tetrahydrofuran-3-yl)pyrrolidin-3-yl)methyl)piperidine-4-carboxamide |
| 371 | 1-(3-(4-methoxyphenyl)-1,2,4-oxadiazol-5-yl)-N-((1-((3-methyloxetan-3-yl)methyl)pyrrolidin-3-yl)methyl)piperidine-4-carboxamide |

-continued

| Compound number | Compound Name |
|---|---|
| 372 | 1-(3-(4-methoxyphenyl)-1,2,4-oxadiazol-5-yl)-N-((1-(thiophen-2-ylmethyl)pyrrolidin-3-yl)methyl)piperidine-4-carboxamide |
| 373 | N-((1-(isothiazol-4-ylmethyl)pyrrolidin-3-yl)methyl)-1-(3-(4-methoxyphenyl)-1,2,4-oxadiazol-5-yl)piperidine-4-carboxamide |
| 375 | 1-(3-(4-methoxyphenyl)-1,2,4-oxadiazol-5-yl)-N-((1-(((tetrahydro-2H-pyran-3-yl)methyl)pyrrolidin-3-yl)methyl)piperidine-4-carboxamide |
| 377 | 1-(3-(4-methoxyphenyl)-1,2,4-oxadiazol-5-yl)-N-((1-((4-methyltetrahydro-2H-pyran-4-yl)methyl)pyrrolidin-3-yl)methyl)piperidine-4-carboxamide |
| 379 | 1-(3-(4-methoxyphenyl)-1,2,4-oxadiazol-5-yl)-N-((1-((5-methylfuran-2-yl)methyl)pyrrolidin-3-yl)methyl)piperidine-4-carboxamide |
| 380 | 1-(3-(4-methoxyphenyl)-1,2,4-oxadiazol-5-yl)-N-((1-((2-methylpyridin-3-yl)methyl)pyrrolidin-3-yl)methyl)piperidine-4-carboxamide |
| 381 | 1-(3-(4-methoxyphenyl)-1,2,4-oxadiazol-5-yl)-N-((1-((3-methylthiophen-2-yl)methyl)pyrrolidin-3-yl)methyl)piperidine-4-carboxamide |
| 382 | 1-(3-(4-methoxyphenyl)-1,2,4-oxadiazol-5-yl)-N-((1-((4-methylfuran-2-yl)methyl)pyrrolidin-3-yl)methyl)piperidine-4-carboxamide |
| 383 | 1-(3-(4-methoxyphenyl)-1,2,4-oxadiazol-5-yl)-N-((1-((2-methylthiazol-4-yl)methyl)pyrrolidin-3-yl)methyl)piperidine-4-carboxamide |
| 384 | 1-(3-(4-methoxyphenyl)-1,2,4-oxadiazol-5-yl)-N-((1-((4-methylthiazol-2-yl)methyl)pyrrolidin-3-yl)methyl)piperidine-4-carboxamide |
| 385 | 1-(3-(4-methoxyphenyl)-1,2,4-oxadiazol-5-yl)-N-((1-((5-methylthiophen-2-yl)methyl)pyrrolidin-3-yl)methyl)piperidine-4-carboxamide |
| 387 | 1-(3-(4-methoxyphenyl)-1,2,4-oxadiazol-5-yl)-N-((1-((6-methylpyridin-2-yl)methyl)pyrrolidin-3-yl)methyl)piperidine-4-carboxamide |
| 388 | 1-(3-(4-methoxyphenyl)-1,2,4-oxadiazol-5-yl)-N-((1-((2-methylthiazol-5-yl)methyl)pyrrolidin-3-yl)methyl)piperidine-4-carboxamide |
| 389 | N-((1-((1H-pyrrol-2-yl)methyl)pyrrolidin-3-yl)methyl)-1-(3-(4-methoxyphenyl)-1,2,4-oxadiazol-5-yl)piperidine-4-carboxamide |
| 391 | N-((1-(azepan-4-ylmethyl)pyrrolidin-3-yl)methyl)-1-(3-(4-methoxyphenyl)-1,2,4-oxadiazol-5-yl)piperidine-4-carboxamide |
| 392 | 1-(3-(4-methoxyphenyl)-1,2,4-oxadiazol-5-yl)-N-((1-(((S)-pyrrolidin-2-yl)methyl)pyrrolidin-3-yl)methyl)piperidine-4-carboxamide |
| 393 | N-((1-((3,3-difluorocyclobutyl)methyl)pyrrolidin-3-yl)methyl)-1-(3-(4-methoxyphenyl)-1,2,4-oxadiazol-5-yl)piperidine-4-carboxamide |
| 394 | N-((1-(((1s,3s)-3-aminocyclobutyl)methyl)pyrrolidin-3-yl)methyl)-1-(3-(4-methoxyphenyl)-1,2,4-oxadiazol-5-yl)piperidine-4-carboxamide |
| 395 | 1-(3-(4-methoxyphenyl)-1,2,4-oxadiazol-5-yl)-N-((1-(oxetan-2-ylmethyl)pyrrolidin-3-yl)methyl)piperidine-4-carboxamide |
| 396 | 1-(3-(4-methoxyphenyl)-1,2,4-oxadiazol-5-yl)-N-((1-(tetrahydro-2H-pyran-3-yl)pyrrolidin-3-yl)methyl)piperidine-4-carboxamide |
| 398 | 1-(3-(4-methoxyphenyl)-1,2,4-oxadiazol-5-yl)-N-((1-(tetrahydro-2H-pyran-4-yl)pyrrolidin-3-yl)methyl)piperidine-4-carboxamide |
| 399 | N-((1-(2-oxaspiro[3.3]heptan-6-yl)pyrrolidin-3-yl)methyl)-1-(3-(4-methoxyphenyl)-1,2,4-oxadiazol-5-yl)piperidine-4-carboxamide |
| 400 | 1-(3-(4-methoxyphenyl)-1,2,4-oxadiazol-5-yl)-N-((1-(oxepan-4-yl)pyrrolidin-3-yl)methyl)piperidine-4-carboxamide |
| 401 | 1-(3-(4-methoxyphenyl)-1,2,4-oxadiazol-5-yl)-N-((1-(oxetan-3-yl)pyrrolidin-3-yl)methyl)piperidine-4-carboxamide |
| 402 | 1-(3-(4-methoxyphenyl)-1,2,4-oxadiazol-5-yl)-N-((1-(2-methyltetrahydro-2H-pyran-4-yl)pyrrolidin-3-yl)methyl)piperidine-4-carboxamide |
| 404 | 1-(3-(4-methoxyphenyl)-1,2,4-oxadiazol-5-yl)-N-((1-((4-methylthiazol-5-yl)methyl)pyrrolidin-3-yl)methyl)piperidine-4-carboxamide |
| 405 | 1-(3-(4-methoxyphenyl)-1,2,4-oxadiazol-5-yl)-N-((1-((tetrahydrofuran-2-yl)methyl)pyrrolidin-3-yl)methyl)piperidine-4-carboxamide |
| 406 | 1-(3-(4-methoxyphenyl)-1,2,4-oxadiazol-5-yl)-N-((1-((3-methylfuran-2-yl)methyl)pyrrolidin-3-yl)methyl)piperidine-4-carboxamide |
| 407 | 1-(3-(4-methoxyphenyl)-1,2,4-oxadiazol-5-yl)-N-((1-((5-methylthiazol-2-yl)methyl)pyrrolidin-3-yl)methyl)piperidine-4-carboxamide |
| 408 | 1-(3-(4-methoxyphenyl)-1,2,4-oxadiazol-5-yl)-N-((1-(oxetan-3-ylmethyl)pyrrolidin-3-yl)methyl)piperidine-4-carboxamide |
| 409 | N-((1-(cyclohex-1-en-1-ylmethyl)pyrrolidin-3-yl)methyl)-1-(3-(4-methoxyphenyl)-1,2,4-oxadiazol-5-yl)piperidine-4-carboxamide |
| 412 | 1-(3-(4-methoxyphenyl)-1,2,4-oxadiazol-5-yl)-N-((1-(((R)-piperidin-3-yl)methyl)pyrrolidin-3-yl)methyl)piperidine-4-carboxamide |
| 413 | N-((1-(((R)-azetidin-2-yl)methyl)pyrrolidin-3-yl)methyl)-1-(3-(4-methoxyphenyl)-1,2,4-oxadiazol-5-yl)piperidine-4-carboxamide |
| 414 | 1-(3-(4-methoxyphenyl)-1,2,4-oxadiazol-5-yl)-N-((1-(((R)-1-methylpiperidin-2-yl)methyl)pyrrolidin-3-yl)methyl)piperidine-4-carboxamide |
| 415 | 1-(3-(4-methoxyphenyl)-1,2,4-oxadiazol-5-yl)-N-((1-(((R)-piperidin-2-yl)methyl)pyrrolidin-3-yl)methyl)piperidine-4-carboxamide |
| 416 | 1-(3-(4-methoxyphenyl)-1,2,4-oxadiazol-5-yl)-N-((1-(1-(tetrahydro-2H-pyran-4-yl)ethyl)pyrrolidin-3-yl)methyl)piperidine-4-carboxamide |
| 421 | N-((1-(cyclohexylmethyl)pyrrolidin-3-yl)methyl)-4-(3-(4-methoxyphenyl)-1,2,4-oxadiazol-5-yl)piperazine-1-carboxamide |
| 422 | 1-(3-(4-methoxyphenyl)-1,2,4-oxadiazol-5-yl)-N-((1-(((S)-1-methylpiperidin-3-yl)methyl)pyrrolidin-3-yl)methyl)piperidine-4-carboxamide |

| Compound number | Compound Name |
|---|---|
| 423 | N-((1-(((1s,4s)-4-aminocyclohexyl)methyl)pyrrolidin-3-yl)methyl)-1-(3-(4-methoxyphenyl)-1,2,4-oxadiazol-5-yl)piperidine-4-carboxamide |
| 425 | N-((1-(((1,1-dioxidotetrahydro-2H-thiopyran-4-yl)methyl)pyrrolidin-3-yl)methyl)-4-(3-(4-methoxyphenyl)-1,2,4-oxadiazol-5-yl)piperazine-1-carboxamide |
| 430 | 4-(3-(4-fluorophenyl)-1,2,4-oxadiazol-5-yl)-N-(3-(4-(pyridin-2-ylmethyl)piperidin-1-yl)propyl)piperazine-1-carboxamide |
| 431 | 4-(3-(4-cyanophenyl)-1,2,4-oxadiazol-5-yl)-N-(3-(4-(pyridin-2-ylmethyl)piperidin-1-yl)propyl)piperazine-1-carboxamide |
| 432 | 4-(3-(4-methoxyphenyl)-1,2,4-oxadiazol-5-yl)-N-((1-((tetrahydro-2H-pyran-4-yl)methyl)pyrrolidin-3-yl)methyl)piperazine-1-carboxamide |
| 433 | (R)-1-(3-(4-methoxyphenyl)-1,2,4-oxadiazol-5-yl)-N-((1-((1-methylpiperidin-4-yl)methyl)pyrrolidin-3-yl)methyl)piperidine-4-carboxamide |
| 434 | (S)-1-(3-(4-methoxyphenyl)-1,2,4-oxadiazol-5-yl)-N-((1-((1-methylpiperidin-4-yl)methyl)pyrrolidin-3-yl)methyl)piperidine-4-carboxamide |
| 435 | N-(3-(4-(pyridin-2-ylmethyl)piperidin-1-yl)propyl)-1-(3-(4-(trifluoromethoxy)phenyl)-1,2,4-oxadiazol-5-yl)piperidine-4-carboxamide |
| 436 | N-(3-(4-(pyridin-2-ylmethyl)piperidin-1-yl)propyl)-4-(3-(4-(trifluoromethoxy)phenyl)-1,2,4-oxadiazol-5-yl)piperazine-1-carboxamide |
| 437 | 4-(3-(4-(difluoromethoxy)phenyl)-1,2,4-oxadiazol-5-yl)-N-(3-(4-(pyridin-2-ylmethyl)piperidin-1-yl)propyl)piperazine-1-carboxamide |
| 440 | N-(3-(4-fluoro-4-(pyridin-2-yl)piperidin-1-yl)propyl)-4-(3-(4-methoxyphenyl)-1,2,4-oxadiazol-5-yl)piperazine-1-carboxamide |
| 441 | 4-(3-(4-methoxyphenyl)-1,2,4-oxadiazol-5-yl)-N-(3-(4-(pyridin-2-ylmethyl)piperazin-1-yl)propyl)piperazine-1-carboxamide |
| 451 | N-(((4-(pyridin-2-ylmethyl)piperidin-1-yl)methoxy)methyl)-4-(3-(4-(trifluoromethoxy)phenyl)-1,2,4-oxadiazol-5-yl)piperazine-1-carboxamide |
| 452 | N-(((4-(pyridin-2-yloxy)piperidin-1-yl)methoxy)methyl)-4-(3-(4-(trifluoromethoxy)phenyl)-1,2,4-oxadiazol-5-yl)piperazine-1-carboxamide |
| 453 | 1-(3-(4-(difluoromethoxy)phenyl)-1,2,4-oxadiazol-5-yl)-N-(3-(4-(pyridin-2-ylmethyl)piperidin-1-yl)propyl)piperidine-4-carboxamide |
| 456 | 1-(3-(4-methoxyphenyl)-1,2,4-oxadiazol-5-yl)-N-(2-((1-(pyridin-2-ylmethyl)piperidin-4-yl)oxy)ethyl)piperidine-4-carboxamide |
| 457 | 4-(3-(4-methoxyphenyl)-1,2,4-oxadiazol-5-yl)-N-(2-((1-(pyridin-2-ylmethyl)piperidin-4-yl)oxy)ethyl)piperazine-1-carboxamide |
| 458 | 4-(3-(4-chlorophenyl)-1,2,4-oxadiazol-5-yl)-N-(3-(4-(pyridin-2-ylmethyl)piperidin-1-yl)propyl)piperazine-1-carboxamide |
| 459 | N-(3-(4-(pyridin-2-ylmethyl)piperidin-1-yl)propyl)-4-(3-(4-(trifluoromethyl)phenyl)-1,2,4-oxadiazol-5-yl)piperazine-1-carboxamide |
| 460 | 4-(3-(4-(difluoromethyl)phenyl)-1,2,4-oxadiazol-5-yl)-N-(3-(4-(pyridin-2-ylmethyl)piperidin-1-yl)propyl)piperazine-1-carboxamide |
| 461 | N-(3-(4-fluoro-4-(pyridin-2-ylmethyl)piperidin-1-yl)propyl)-4-(3-(4-methoxyphenyl)-1,2,4-oxadiazol-5-yl)piperazine-1-carboxamide |
| 464 | 1-(3-(4-methoxyphenyl)-1,2,4-oxadiazol-5-yl)-N-((1-(((R)-1-methylpiperidin-3-yl)methyl)pyrrolidin-3-yl)methyl)piperidine-4-carboxamide |
| 465 | 1-(3-(4-methoxyphenyl)-1,2,4-oxadiazol-5-yl)-N-(((R)-1-(((S)-1-methylpiperidin-3-yl)methyl)pyrrolidin-3-yl)methyl)piperidine-4-carboxamide |
| 466 | 1-(3-(4-methoxyphenyl)-1,2,4-oxadiazol-5-yl)-N-(((S)-1-(((S)-1-methylpiperidin-3-yl)methyl)pyrrolidin-3-yl)methyl)piperidine-4-carboxamide |
| 467 | 1-(3-(4-cyanophenyl)-1,2,4-oxadiazol-5-yl)-N-((1-(((S)-1-methylpiperidin-3-yl)methyl)pyrrolidin-3-yl)methyl)piperidine-4-carboxamide |
| 468 | 1-(3-(4-chlorophenyl)-1,2,4-oxadiazol-5-yl)-N-((1-(((S)-1-methylpiperidin-3-yl)methyl)pyrrolidin-3-yl)methyl)piperidine-4-carboxamide |
| 470 | 1-(3-(4-chlorophenyl)-1,2,4-oxadiazol-5-yl)-N-(((S)-1-(((S)-1-methylpiperidin-3-yl)methyl)pyrrolidin-3-yl)methyl)piperidine-4-carboxamide |
| 471 | 1-(3-(4-chlorophenyl)-1,2,4-oxadiazol-5-yl)-N-(((R)-1-(((S)-1-methylpiperidin-3-yl)methyl)pyrrolidin-3-yl)methyl)piperidine-4-carboxamide |
| 474 | 1-(3-(4-chlorophenyl)-1,2,4-oxadiazol-5-yl)-N-(((S)-1-(((R)-1-methylpiperidin-3-yl)methyl)pyrrolidin-3-yl)methyl)piperidine-4-carboxamide |
| 475 | 1-(3-(4-chlorophenyl)-1,2,4-oxadiazol-5-yl)-N-(((R)-1-(((R)-1-methylpiperidin-3-yl)methyl)pyrrolidin-3-yl)methyl)piperidine-4-carboxamide. |

6. The compound according to claim 1, wherein the compound is a c-Myc mRNA translation modulator, a c-Myc mRNA transcription regulator, a c-Myc inhibitor or any combination thereof.

7. A pharmaceutical composition comprising the compound of claim 1 and a pharmaceutically acceptable carrier.

8. A method of treating, suppressing, reducing the severity, reducing the risk of developing or inhibiting cancer in a subject, comprising administering a compound according to claim 1, to a subject suffering from cancer, under conditions effective to treat, suppress, reduce the severity, reduce the risk of developing, or inhibit cancer in said subject.

9. The method of claim 8, wherein the cancer is selected from the list of: breast cancer, ovarian carcinoma, acute myeloid leukemia, chronic myelogenous leukemia, Hodgkin's and Burkitt's lymphoma, diffuse large Bcell lymphoma, prostate cancer, colon cancer, gastric cancer, primary central nervous system lymphoma, glioblastoma, medulloblastoma, melanoma, non-small cell lung carcinoma, germinal center-derived lymphomas, esophageal squamous cell carcinoma, osteosarcoma, bladder cancer, pancreatic cancer, lung adenocarcinoma, BRAF V600E thyroid cancer, choroid plexus carcinoma, colitis-associated cancer, epithelial ovarian cancer, colorectal cancer, pancreatic cancer and uterine cancer.

10. The method of claim 8, wherein the cancer is early cancer, advanced cancer, invasive cancer, metastatic cancer, drug resistant cancer or any combination thereof.

11. The method of claim 8, wherein the subject has been previously treated with chemotherapy, immunotherapy, radiotherapy, biological therapy, surgical intervention, or any combination thereof.

12. The method of claim 8, wherein the compound is administered in combination with an anti-cancer therapy.

13. The method of claim 12, wherein the anti-cancer therapy is chemotherapy, immunotherapy, radiotherapy, biological therapy, surgical intervention, or any combination thereof.

14. A method of suppressing, reducing or inhibiting tumor growth in a subject, comprising administering a compound according to claim 1, to a subject suffering from cancer, under conditions effective to suppress, reduce, or inhibit the growth of the tumor in said subject.

15. An in vitro method of modulating c-Myc mRNA translation in a cell, comprising contacting a compound according to claim 1 with a cell, thereby modulating c-Myc mRNA translation in said cell.

16. An in vitro method of regulating c-Myc mRNA transcription in a cell, comprising contacting a compound according to claim 1 with a cell, thereby regulating c-Myc mRNA transcription in said cell.

17. The method of claim 15, wherein said method is carried out
 (a) by regulating c-Myc mRNA splicing (inclusion or exclusion of untranslated region or alternative usage of exons);
 (b) by regulation of c-Myc mRNA modifications;
 (c) by regulation of the interaction of RNA binding protein with c-Myc mRNA thereby changing mRNA localization;
 (d) by regulating c-Myc mRNA localization in the cytoplasm;
 (e) by regulating ribosomes or ribosome accessory factor to c-Myc mRNA;
 (f) by reducing the amount of c-Myc protein in the cell; or any combination thereof.

* * * * *